United States Patent [19]

Moorman et al.

[11] Patent Number: 5,610,967

[45] Date of Patent: Mar. 11, 1997

[54] X-RAY GRID ASSEMBLY

[75] Inventors: Jack W. Moorman, Los Gatos; Brian Skillicorn, Saratoga; John W. Wilent, deceased, late of Aptos, by Virginia B. Wilent, heiress; Alan C. Abel, San Jose, all of Calif.

[73] Assignee: Cardiac Mariners, Incorporated, Los Gatos, Calif.

[21] Appl. No.: 419,740

[22] Filed: Apr. 10, 1995

Related U.S. Application Data

[63] Continuation of Ser. No. 386,861, Feb. 10, 1995, which is a continuation-in-part of Ser. No. 375,501, Jan. 17, 1995, abandoned, and Ser. No. 342,641, filed as PCT/US94/03737 Apr. 5, 1994, abandoned, which is a continuation of Ser. No. 8,455, Jan. 25, 1993, abandoned, said Ser. No. 375,501, is a continuation of Ser. No. 42,742, Apr. 5, 1993, abandoned.

[51] Int. Cl.$^6$ ........................................... G21K 1/10
[52] U.S. Cl. ........................ 378/154; 378/147; 378/149; 378/141
[58] Field of Search ................................ 378/147, 149, 378/145, 148, 154, 155, 119, 130, 140, 141, 142, 143

[56] References Cited

U.S. PATENT DOCUMENTS

| 2,730,566 | 1/1956 | Bartow et al. | 378/146 |
| 3,114,832 | 12/1963 | Alvarez. | |
| 3,593,243 | 7/1971 | Trump et al. | 336/70 |
| 3,605,750 | 9/1971 | Sheridan et al. | 128/658 |
| 3,611,032 | 10/1971 | Skillicorn | 317/14 |

(List continued on next page.)

OTHER PUBLICATIONS

Swinth et al., "Biomedical Probe Using a Fiber-optic Coupled Scintillator", Medical Physics, vol. 3, 1976, pp. 109–112.

W.C. Nixon, "High–resolution X–ray Projection Microscopy", vol. 232, *Proceedings of the Royal Society of London*, Nov., 1995, pp. 475–484.

George L. Clark, "The Encyclopedia of X–rays and Gamma Rays", 1963, pp. 608–610, 617.

V.E. Cosslett et al., "X–ray Microscopy", 1960, pp. 216–219, 296–303, 350–355, 368–369.

B. Skillicorn, "Insulators and X-ray Tube Longevity: Some Theory and a Few Practical Hints", 1983, pp. 2–6.

Howard H. Pattee, Jr., "The Scanning X–ray Microscope", 1953, pp. 61–62.

Lewis Etter, "The Science of Ionizing Radiation", 1965, pp. 546–548.

R.M. Dolby et al., "A Spectrometer System for Long Wavelength X–ray Emission Microanalysis", *X–ray Microscopy and X–ray Microanalysis*, 1960, pp. 351–357.

Russell H. Morgan et al., "Clinical Potentialities of Screen Intensifying Systems", Nov., 1949, pp. 635–644.

Robert J. Moon, "Amplifying and Intensifying the Fluoroscopic image by Means of a Scanning X –Ray Tube", Oct. 6, 1950, pp. 389–395.

Howard H. Pattee, Jr., "Possibilities of the Scanning X–Ray Microscope", 1957; *X–Ray Microscopy and Microradiography*, pp. 367–375.

(List continued on next page.)

Primary Examiner—Don Wong
Attorney, Agent, or Firm—Lyon & Lyon

[57] ABSTRACT

An x-ray imaging system according to the present invention comprising a stepped scanning-beam x-ray source and a multi-detector array. The output of the multi-detector array is input to an image reconstruction engine which combines the outputs of the multiple detectors over selected steps of the x-ray beam to generate an x-ray image of the object. A collimating element, preferably in the form of a perforated grid containing an array of apertures, interposed between the x-ray source and an object to be x-rayed. A maneuverable positioner incorporating an x-ray sensitive marker allowing the determination of the precise position coordinates of the maneuverable positioner.

24 Claims, 149 Drawing Sheets

U.S. PATENT DOCUMENTS

| | | | |
|---|---|---|---|
| 3,617,740 | 11/1971 | Skillicorn | 250/49.5 |
| 3,684,991 | 8/1972 | Trump et al. | 336/70 |
| 3,890,521 | 6/1975 | Shroff | 313/55 |
| 3,925,660 | 12/1975 | Albert | 250/272 |
| 3,949,229 | 4/1976 | Albert | 250/401 |
| 3,983,397 | 9/1976 | Albert | 250/406 |
| 3,992,631 | 11/1976 | Harte | 250/302 |
| 4,007,375 | 2/1977 | Albert | 250/404 |
| 4,032,787 | 6/1977 | Albert | 250/402 |
| 4,048,496 | 9/1977 | Albert | 250/272 |
| 4,057,745 | 11/1977 | Albert | 313/55 |
| 4,104,526 | 8/1978 | Albert | 250/403 |
| 4,144,457 | 3/1979 | Albert | 250/445 T |
| 4,149,076 | 4/1979 | Albert | 250/402 |
| 4,196,351 | 4/1980 | Albert | 250/416 TV |
| 4,234,794 | 11/1980 | Voinea et al. | 378/146 |
| 4,259,582 | 3/1981 | Albert | 250/402 |
| 4,259,583 | 3/1981 | Albert | 250/416 TV |
| 4,260,885 | 4/1981 | Albert | 250/277 |
| 4,288,697 | 9/1981 | Albert | 250/505 |
| 4,321,473 | 3/1982 | Albert | 250/505 |
| 4,323,779 | 4/1982 | Albert | 250/401 |
| 4,383,327 | 5/1983 | Kruger | 378/146 |
| 4,419,585 | 12/1983 | Strauss et al. | 378/149 |
| 4,465,540 | 8/1984 | Albert | 156/252 |
| 4,519,092 | 5/1985 | Albert | 378/45 |
| 4,573,183 | 2/1986 | Relihan | 378/108 |
| 4,577,637 | 3/1986 | Mueller, Jr. | 128/658 |
| 4,646,338 | 2/1987 | Skillicorn | 378/110 |
| 4,694,480 | 9/1987 | Skillicorn | 378/119 |
| 4,730,350 | 3/1988 | Albert | 378/10 |
| 4,796,637 | 1/1989 | Mascuch et al. | 128/658 |
| 4,873,708 | 10/1989 | Cusano et al. | 378/62 |
| 4,945,894 | 8/1990 | Kawashima | 128/658 |
| 4,967,121 | 10/1990 | Nero | 315/411 |
| 4,974,929 | 12/1990 | Curry | 128/658 |
| 5,029,338 | 7/1991 | Aichinger et al. | 378/108 |
| 5,132,539 | 7/1992 | Kwasnick et al. | 250/361 |
| 5,140,162 | 8/1992 | Stettner | 250/370.09 |
| 5,153,438 | 10/1992 | Kingsley et al. | 250/370 |
| 5,171,232 | 12/1992 | Castillo et al. | 128/658 |
| 5,185,773 | 2/1993 | Blossfeld et al. | 378/53 |
| 5,187,369 | 2/1993 | Kingsley et al. | 250/370 |
| 5,198,673 | 3/1993 | Rougeot et al. | 250/370 |
| 5,203,777 | 4/1993 | Lee | 128/658 |
| 5,231,654 | 7/1993 | Kwasnick et al. | 378/147 |
| 5,231,655 | 7/1993 | Wei et al. | 378/149 |
| 5,237,598 | 8/1993 | Albert | 378/146 |
| 5,267,296 | 11/1993 | Albert | 378/113 |
| 5,276,604 | 1/1994 | Messman | 363/65 |
| 5,293,417 | 3/1994 | Wei et al. | 378/149 |
| 5,303,282 | 4/1994 | Kwasnick et al. | 378/147 |
| 5,304,898 | 4/1994 | Kataoka et al. | 315/411 |

OTHER PUBLICATIONS

Center for Devices and Radiological Health, Radiological Health Bulletin, "FDA Draws Attention to Concerns about Radiation Risk from Fluoroscopy", Aug., 1992, pp. 1–3, 5.

Philips Photonics, "xP1700 Multichannel Photomultipliers", 1993, pp. 1–15.

Digiray, "Digiray's Reverse Geometry X-ray System", 1992 (?), pp. 1–2.

Thomas S. Curry, III, "Christensen's Physics of Diagnostic Radiology," Fourth Edition, Lea & Febiger, pp. 1–521.

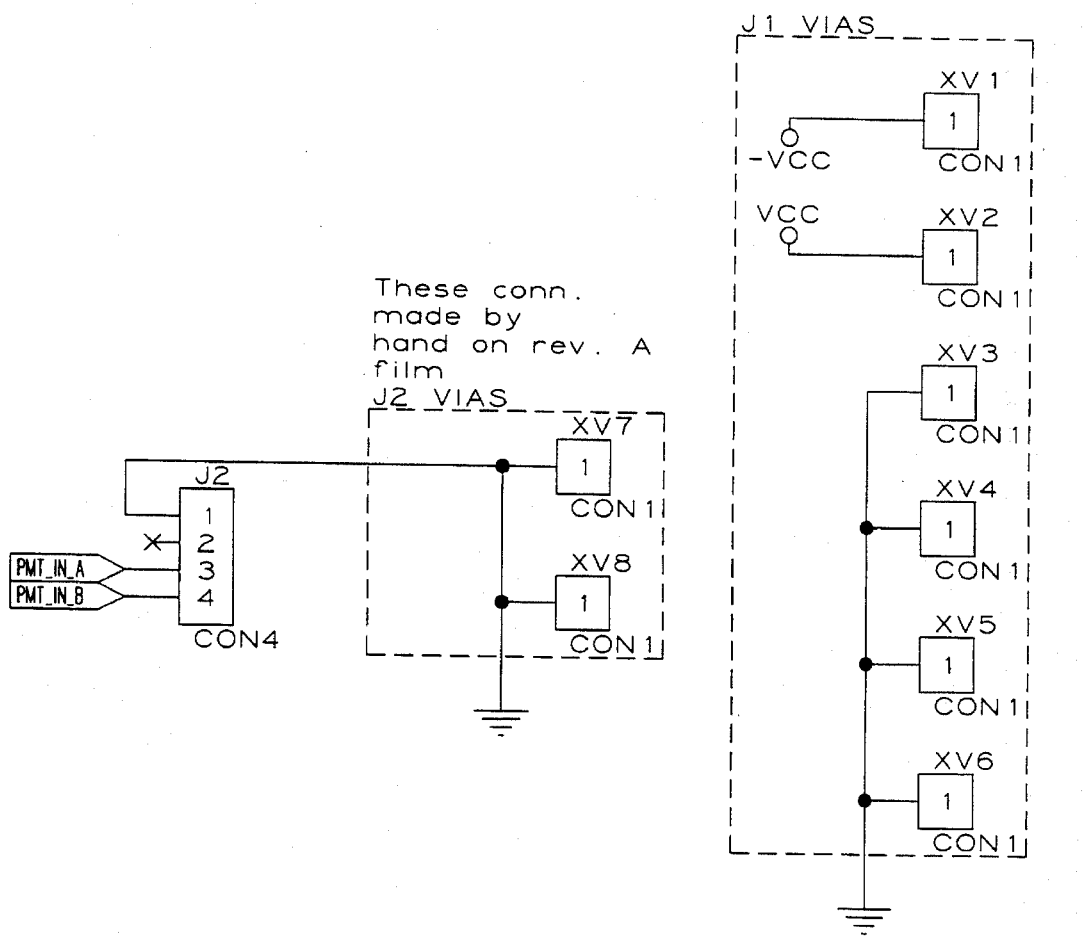
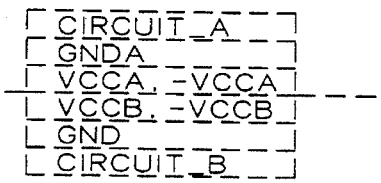
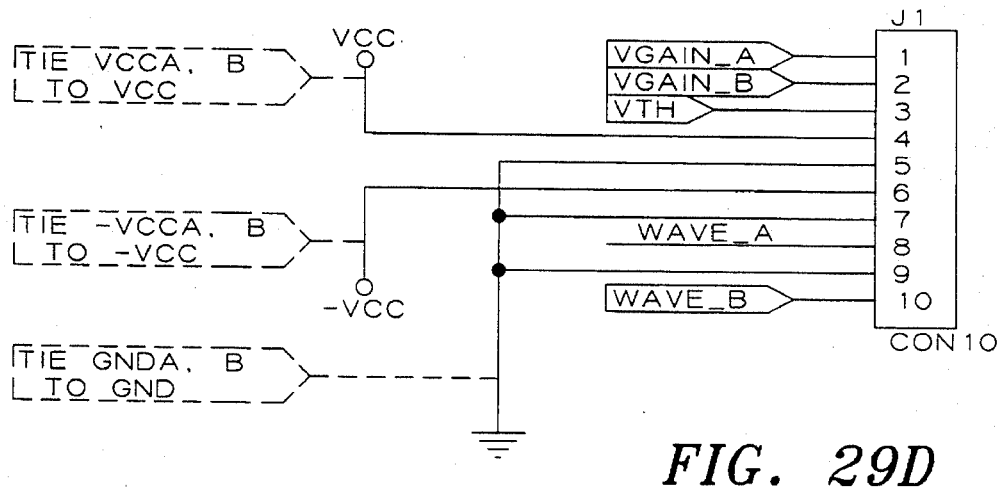
FIG. 29D

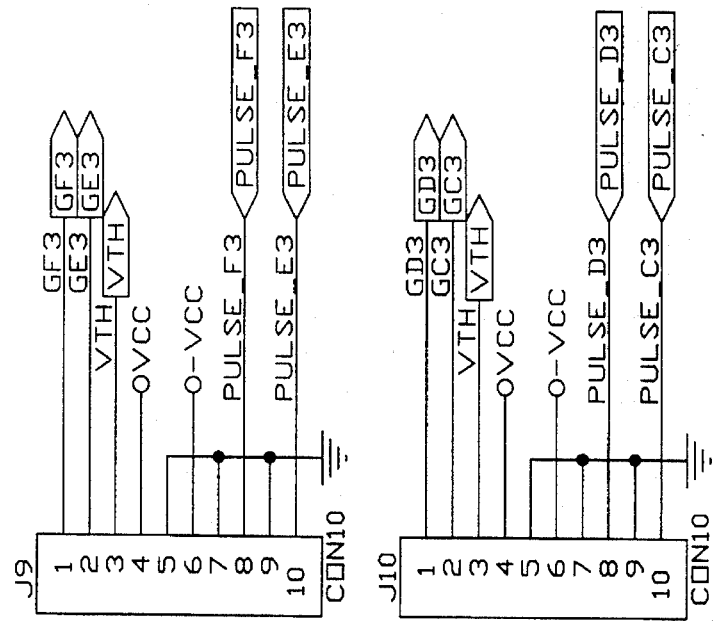
FIG. 33
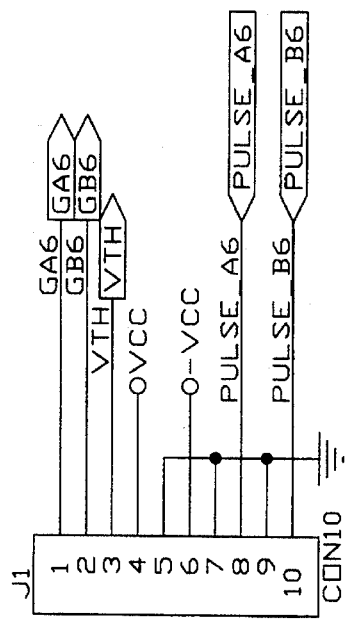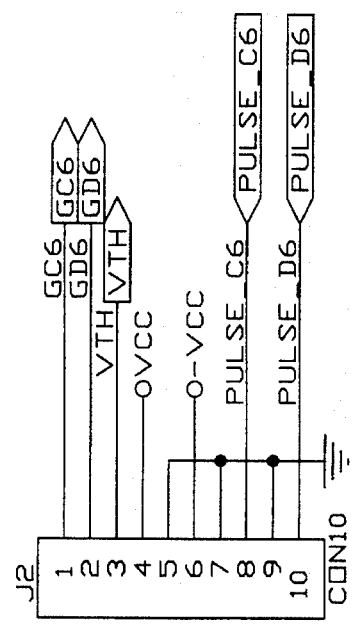
FIG. 33A

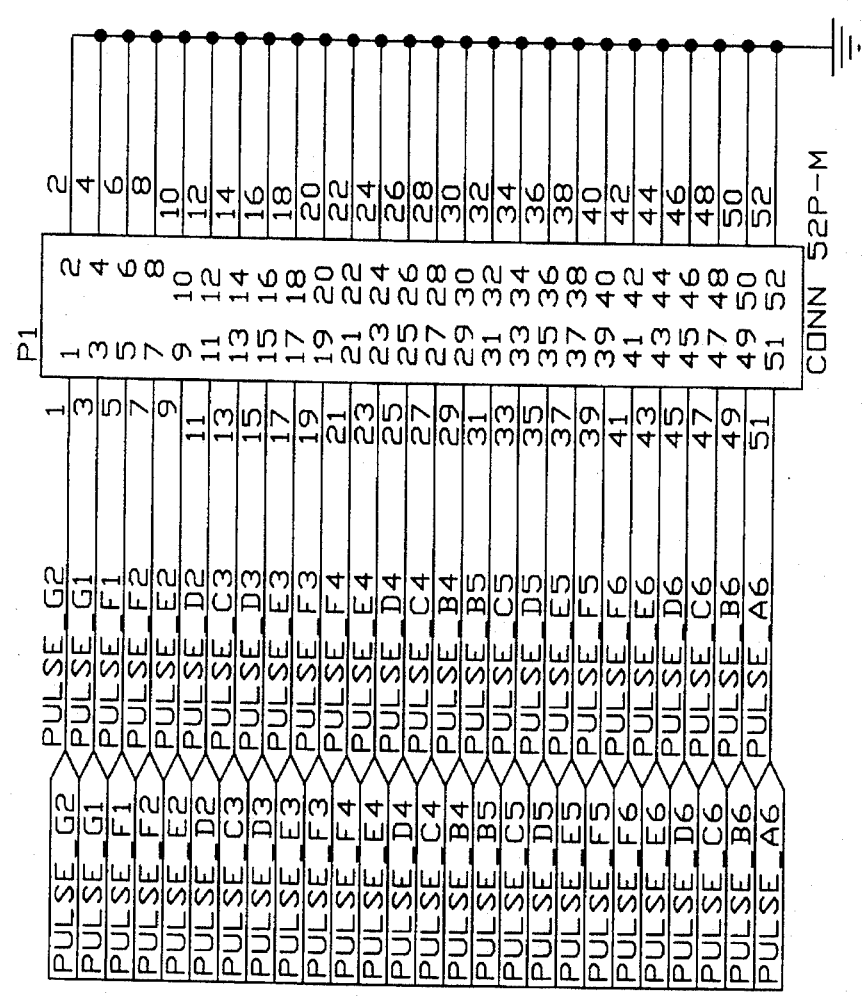

|   | A | B | C | D | E | F | G | H | J | K | L | M |   |
|---|---|---|---|---|---|---|---|---|---|---|---|---|---|
| 1 | 3 | 2 | 1 | 3 | 2 | 1 | 3 | 2 | 1 | 3 | 2 | 1 | 1 |
| 2 | 6 | 5 | 4 | 6 | 5 | 4 | 6 | 5 | 4 | 6 | 5 | 4 | 2 |
| 3 | 9 | 8 | 7 | 9 | 8 | 7 | 9 | 8 | 7 | 9 | 8 | 7 | 3 |
| 4 | 3 | 2 | 1 | 3 | 2 | 1 | 3 | 2 | 1 | 3 | 2 | 1 | 4 |
| 5 | 6 | 5 | 4 | 6 | 5 | 4 | 6 | 5 | 4 | 6 | 5 | 4 | 5 |
| 6 | 9 | 8 | 7 | 9 | 8 | 7 | 9 | 8 | 7 | 9 | 8 | 7 | 6 |
| 7 | 3 | 2 | 1 | 3 | 2 | 1 | 3 | 2 | 1 | 3 | 2 | 1 | 7 |
| 8 | 6 | 5 | 4 | 6 | 5 | 4 | 6 | 5 | 4 | 6 | 5 | 4 | 8 |
| 9 | 9 | 8 | 7 | 9 | 8 | 7 | 9 | 8 | 7 | 9 | 8 | 7 | 9 |
| 10 | 3 | 2 | 1 | 3 | 2 | 1 | 3 | 2 | 1 | 3 | 2 | 1 | 10 |
| 11 | 6 | 5 | 4 | 6 | 5 | 4 | 6 | 5 | 4 | 6 | 5 | 4 | 11 |
| 12 | 9 | 8 | 7 | 9 | 8 | 7 | 9 | 8 | 7 | 9 | 8 | 7 | 12 |
|   | A | B | C | D | E | F | G | H | J | K | L | M |   |

*FIG. 36*

|   | M | L | K | J | H | G | F | E | D | C | B | A |   |
|---|---|---|---|---|---|---|---|---|---|---|---|---|---|
| 1 |   |   |   |   |   | TLO | TRO |   |   |   |   |   | 1 |
| 2 |   |   |   | TLO | TLO | TLO | TRO | TRO | TRO |   |   |   | 2 |
| 3 |   |   | TLO | TLO | TLI | TLI | TRI | TRI | TRO | TRO |   |   | 3 |
| 4 |   | TLO | TLO | TLO | TLI | TLI | TRI | TRI | TRO | TRO | TRO |   | 4 |
| 5 |   | TLO | TLI | TLI | TLI | TLI | TRI | TRI | TRI | TRI | TRO |   | 5 |
| 6 | TLO | TLO | TLI | TLI | TLI | TLI | TRI | TRI | TRI | TRI | TRO | TRO | 6 |
| 7 | BLO | BLO | BLI | BLI | BLI | BLI | BRI | BRI | BRI | BRI | BRO | BRO | 7 |
| 8 |   | BLO | BLI | BLI | BLI | BLI | BRI | BRI | BRI | BRI | BRO |   | 8 |
| 9 |   | BLO | BLO | BLO | BLI | BLI | BRI | BRI | BRO | BRO | BRO |   | 9 |
| 10 |   |   | BLO | BLO | BLI | BLI | BRI | BRI | BRO | BRO |   |   | 10 |
| 11 |   |   |   | BLO | BLO | BLO | BRO | BRO | BRO |   |   |   | 11 |
| 12 |   |   |   |   |   | BLO | BRO |   |   |   |   |   | 12 |
|   | M | L | K | J | H | G | F | E | D | C | B | A |   |

*FIG. 38*

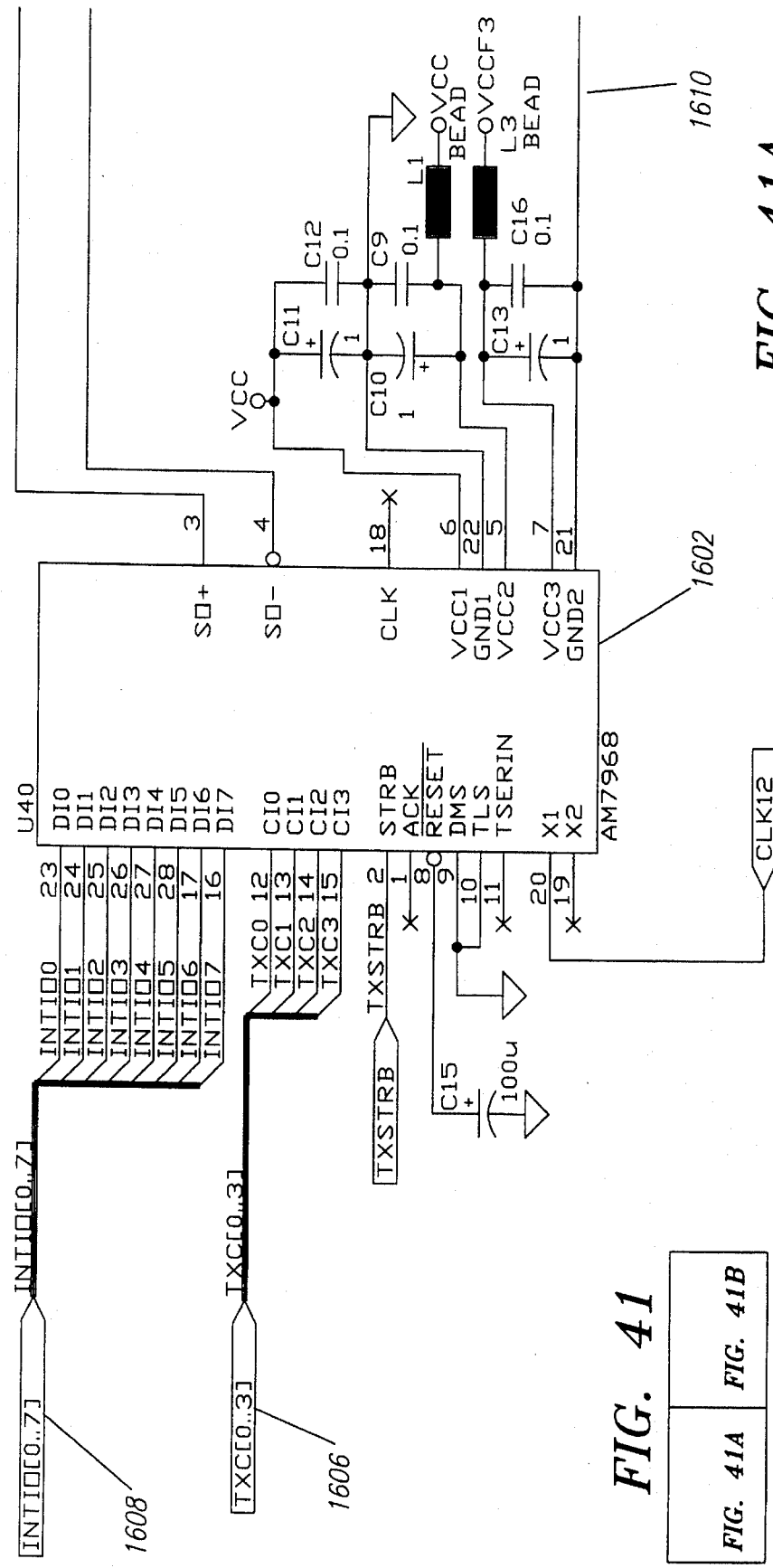

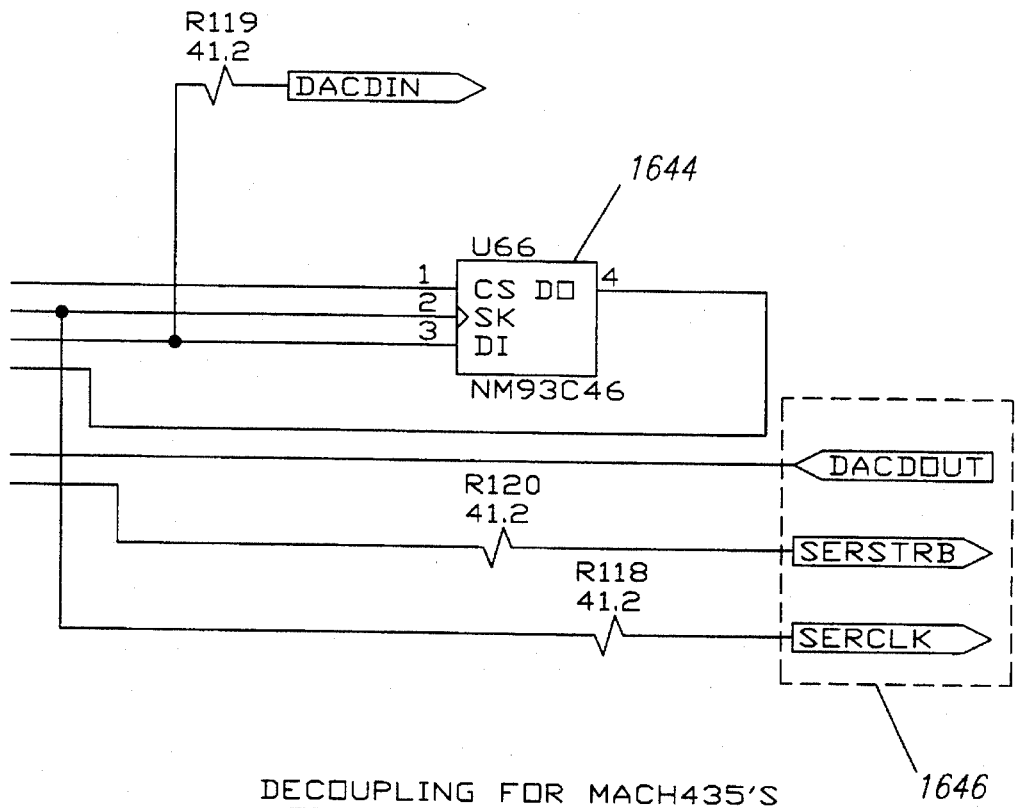
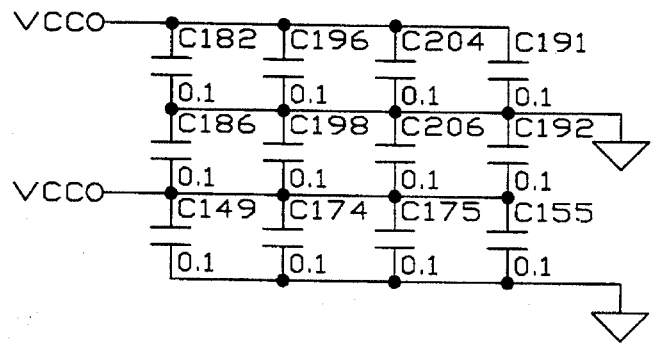
DECOUPLING FOR MACH435'S
FOR PINS 2,21,42,63
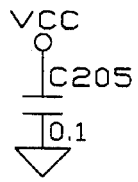
DECOUPLING FOR NM93C46
FOR PIN 8
*FIG. 42E*

FIG. 47A
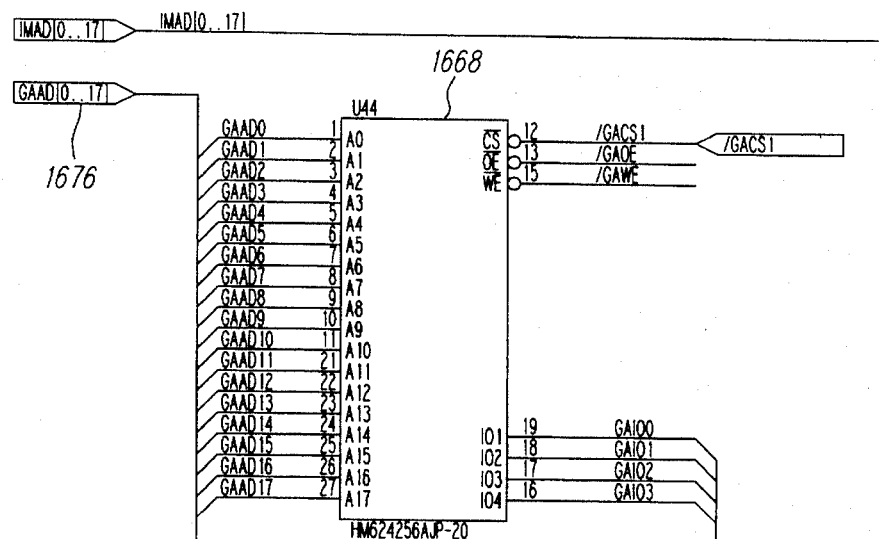
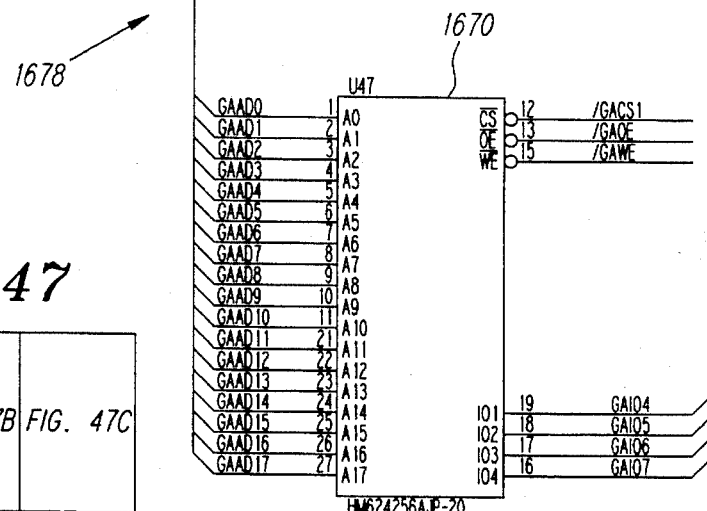
FIG. 47
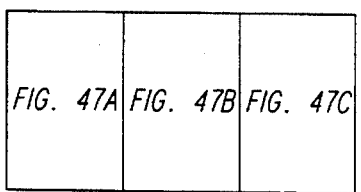

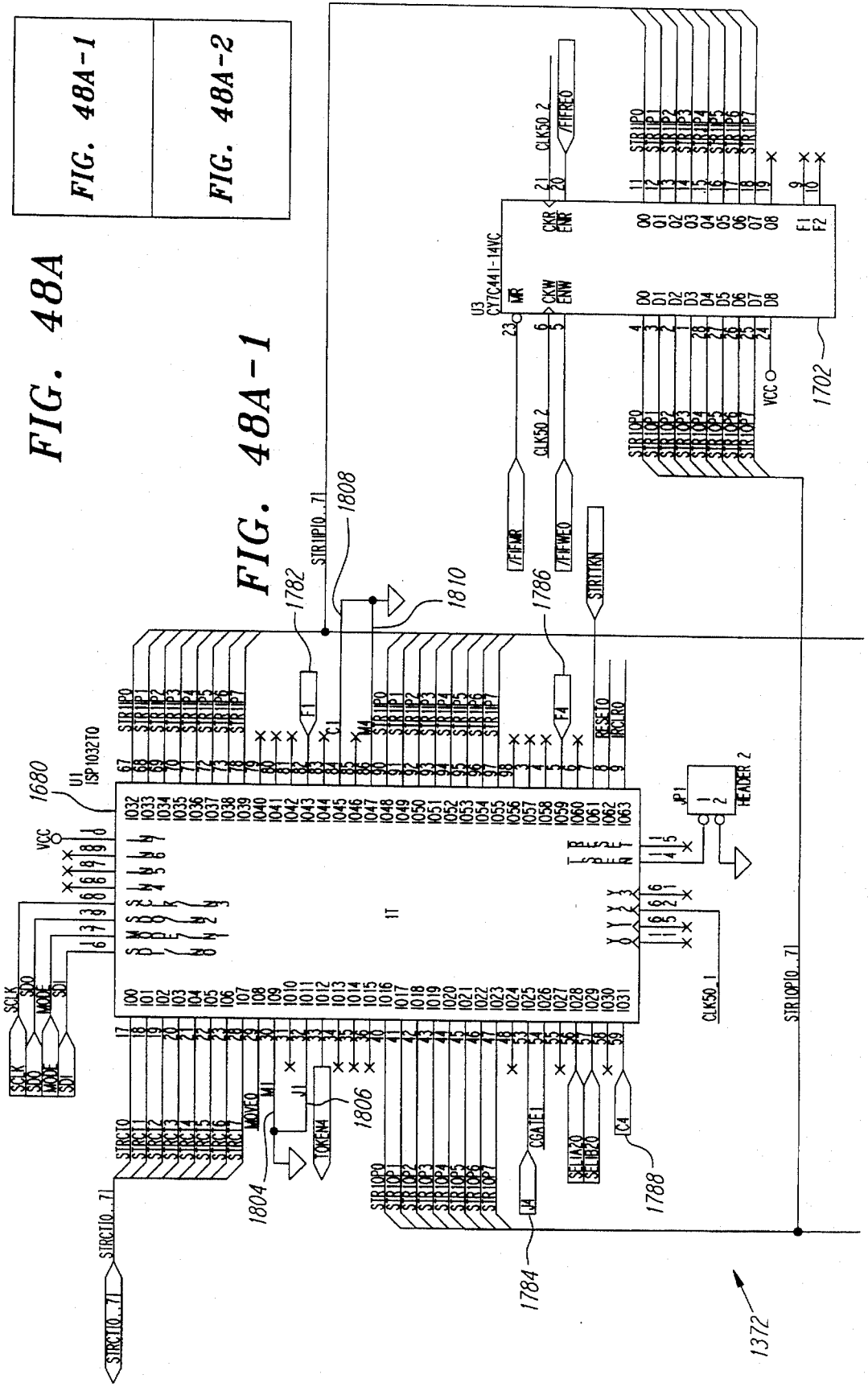

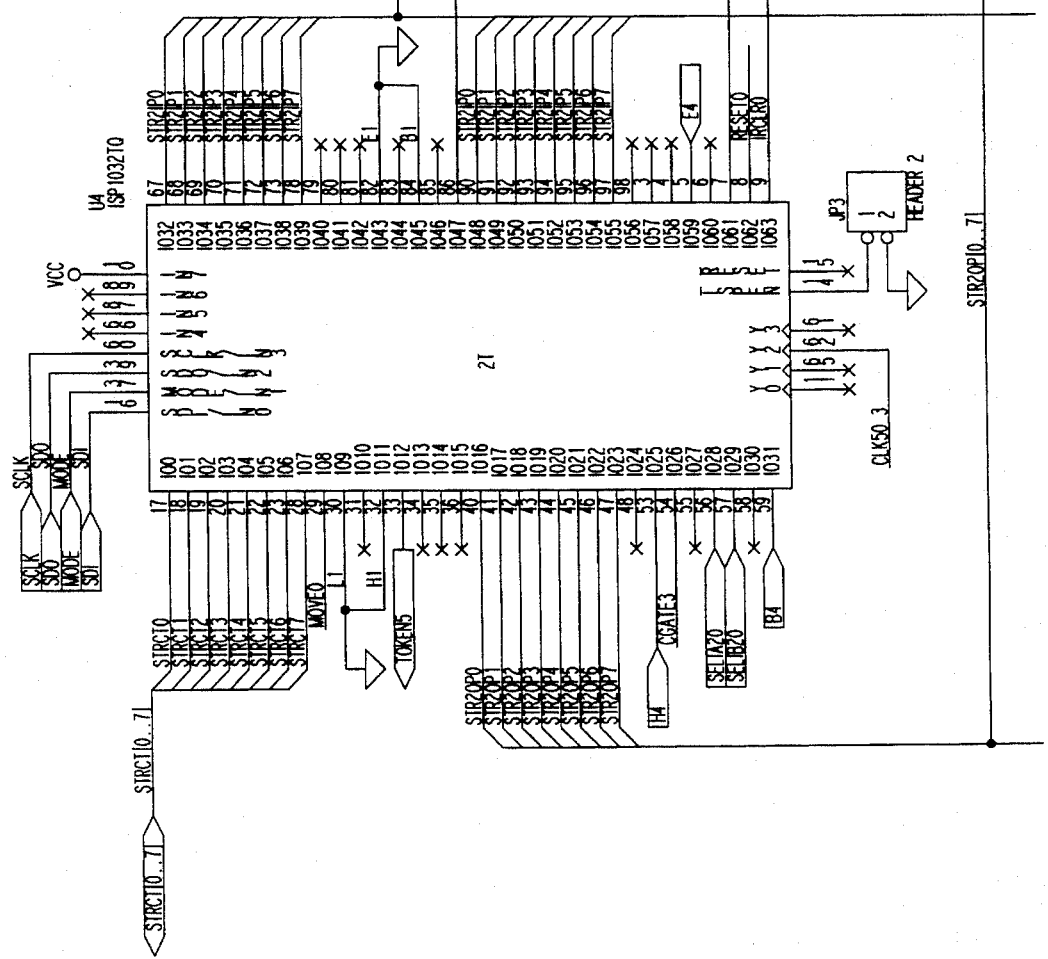

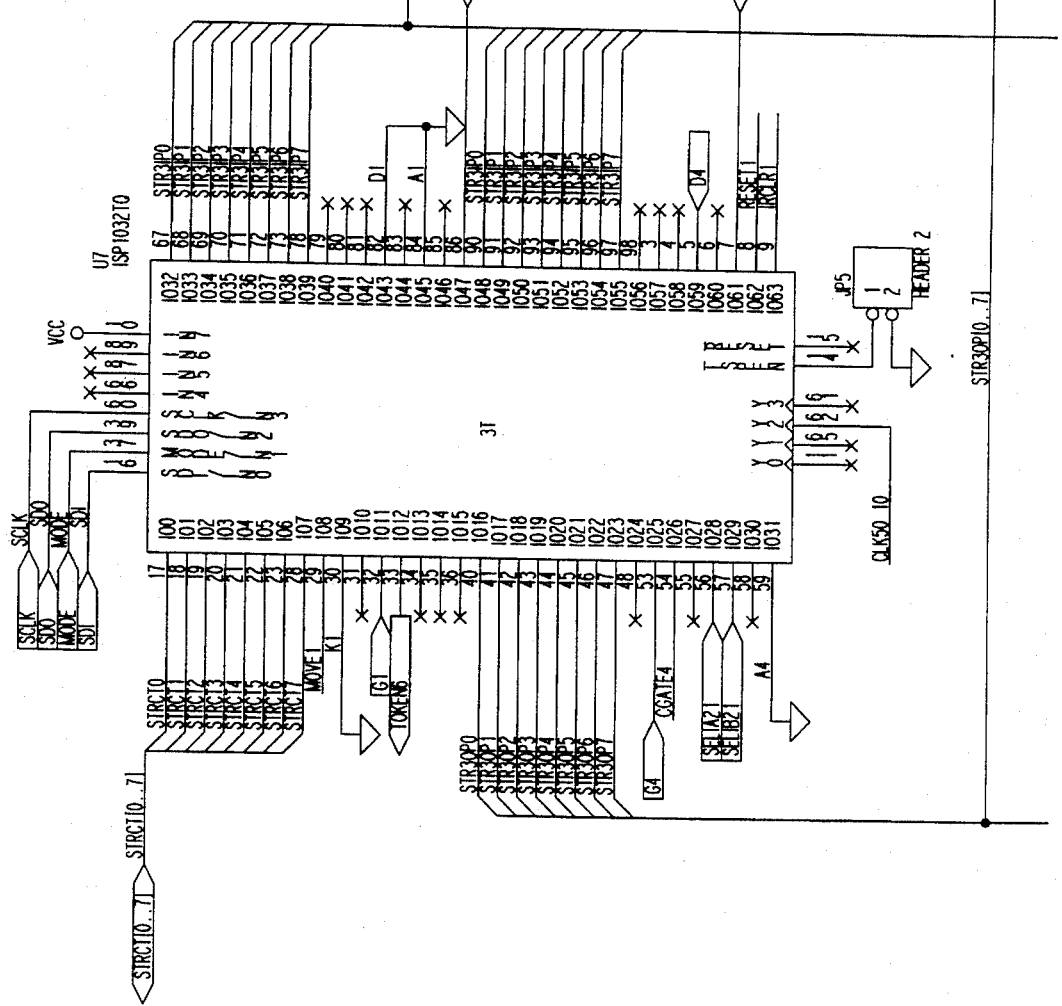

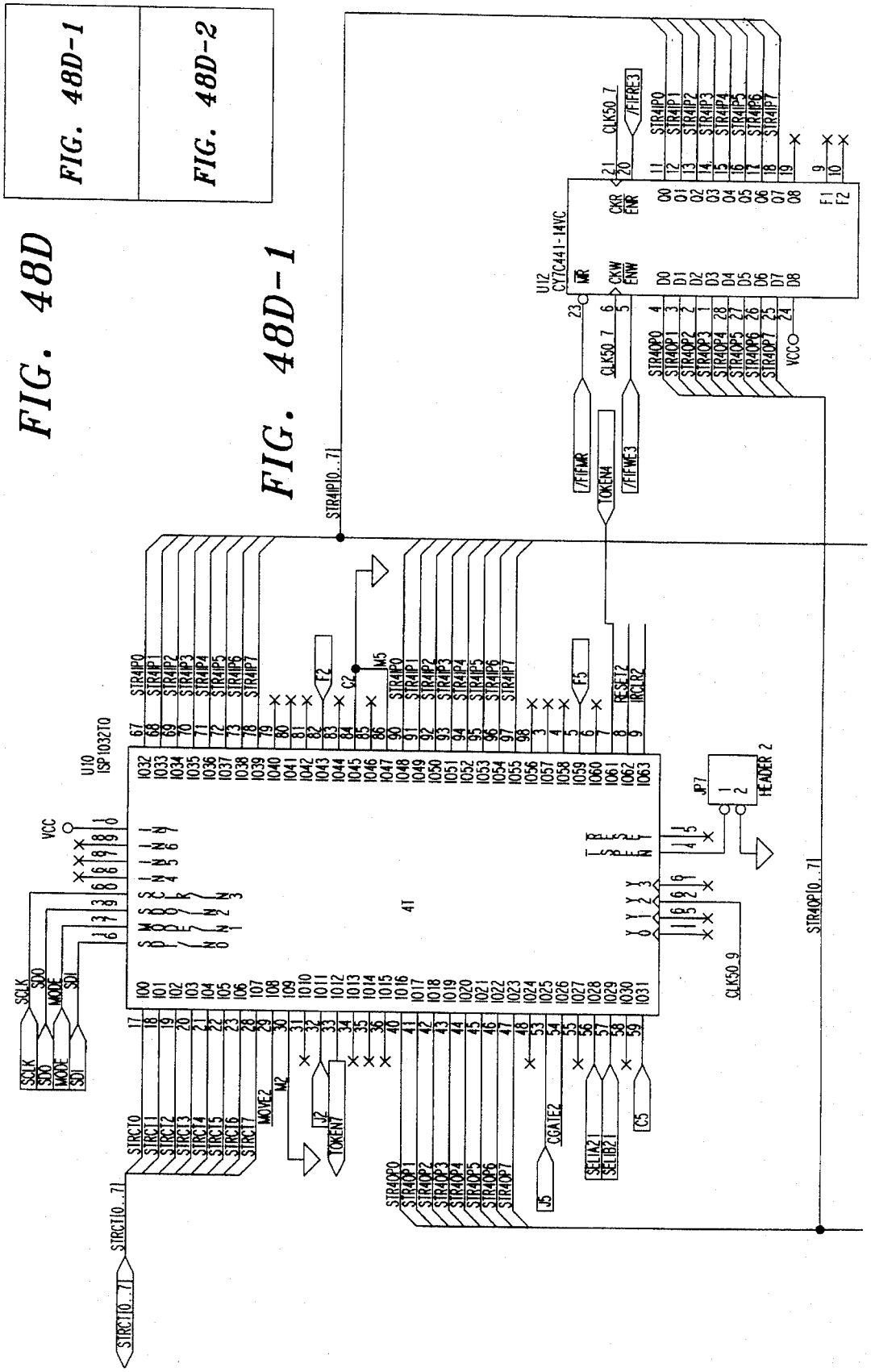

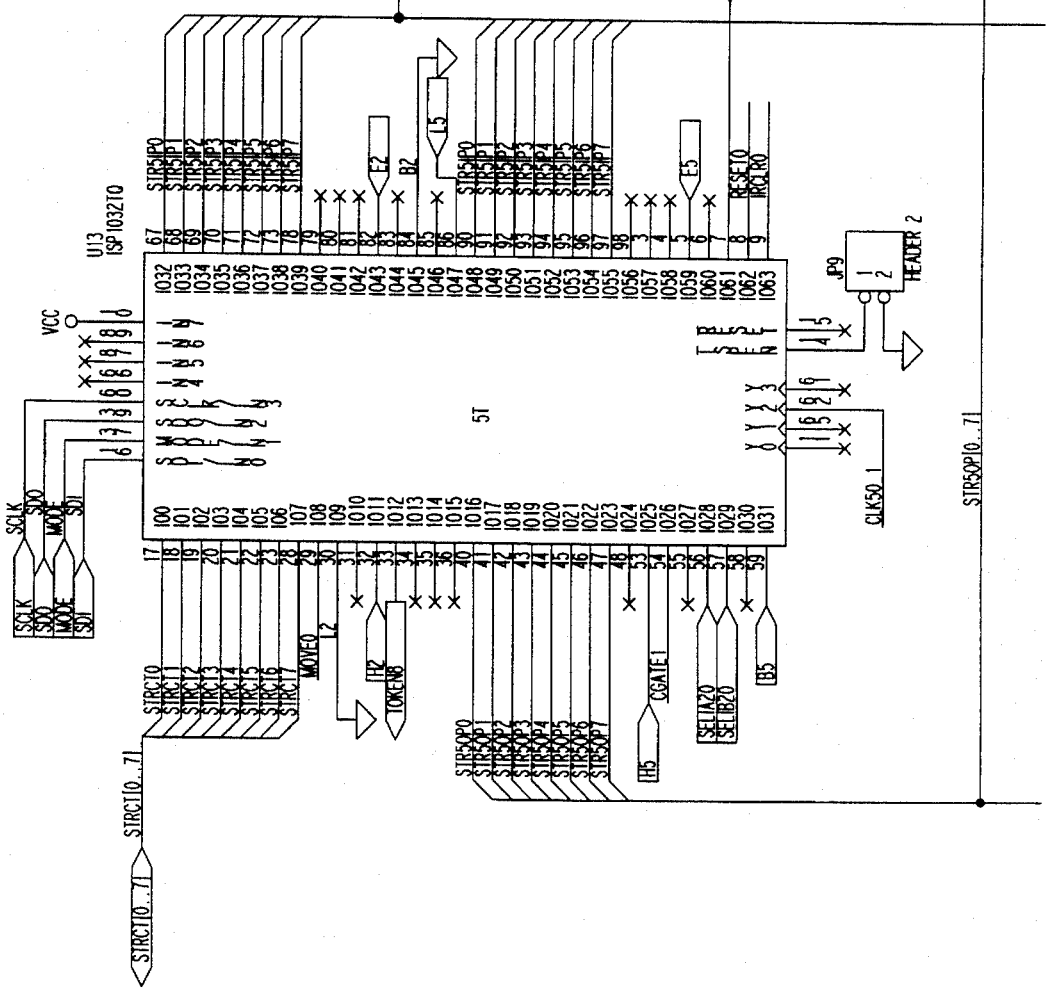

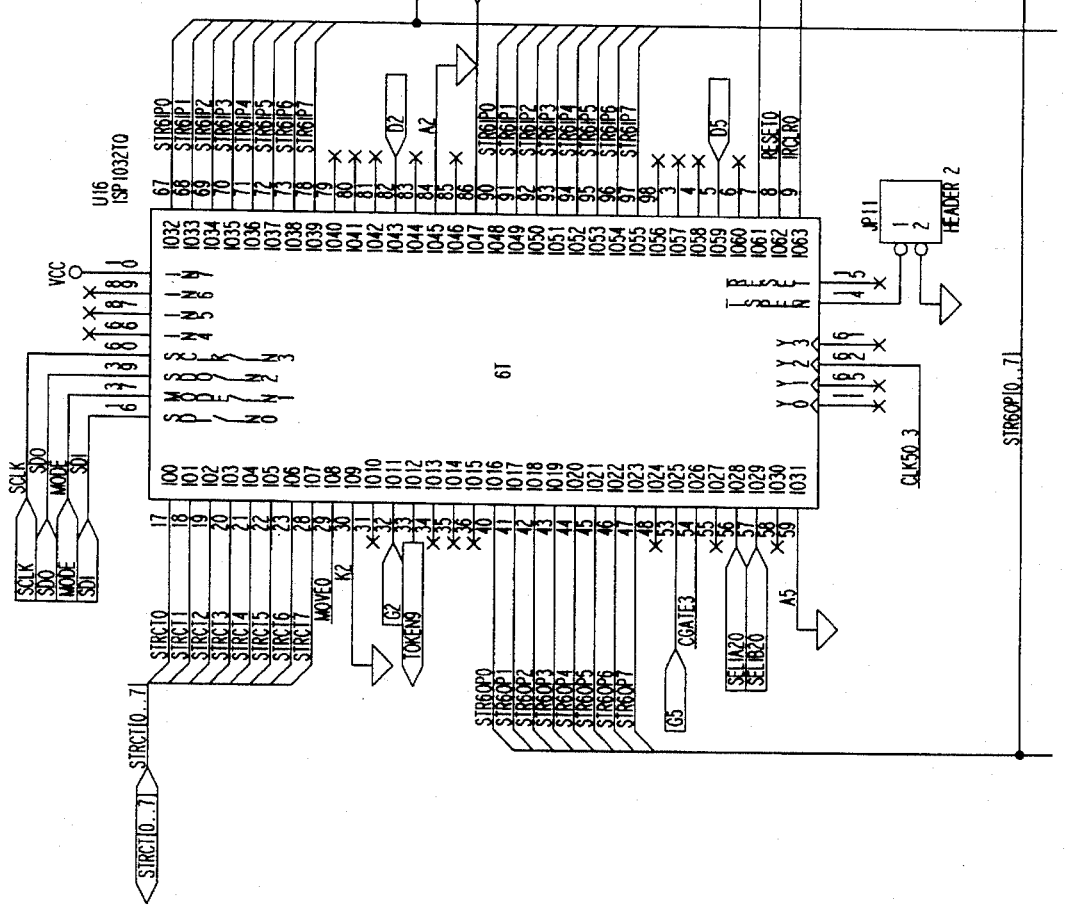

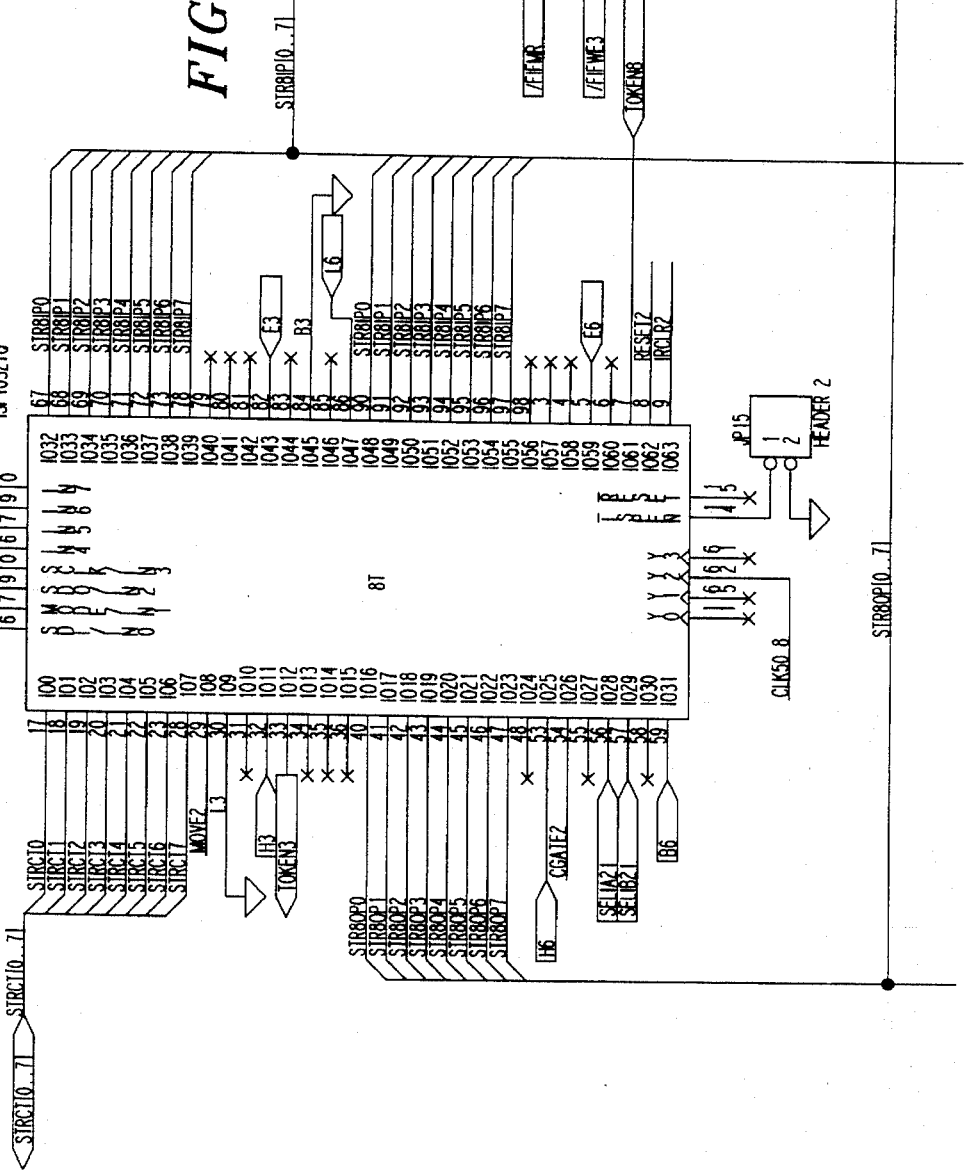
FIG. 48H
FIG. 48H-1
FIG. 48H-2
FIG. 48H-1

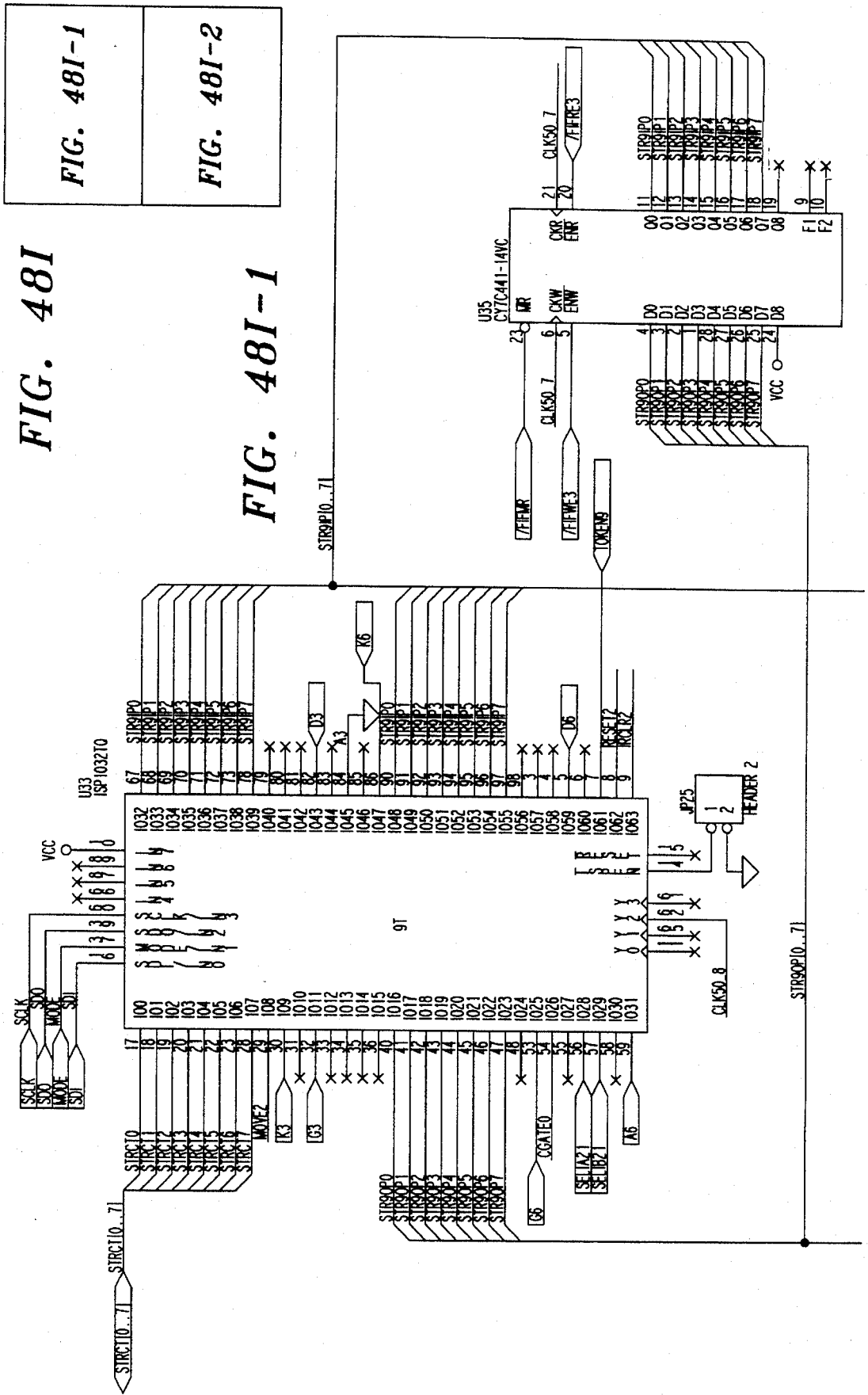

NORMALIZATION PROM

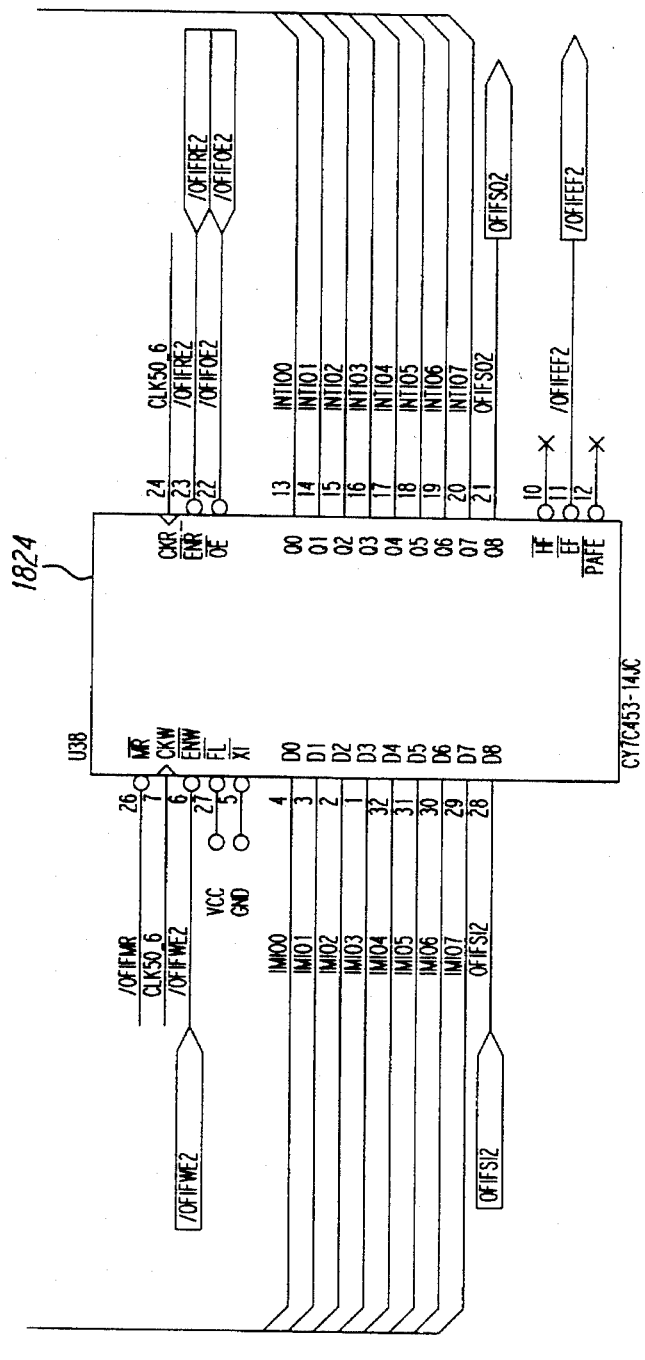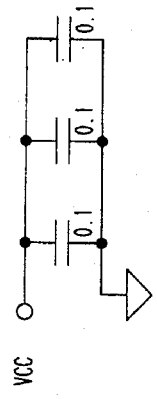
FIG. 51C

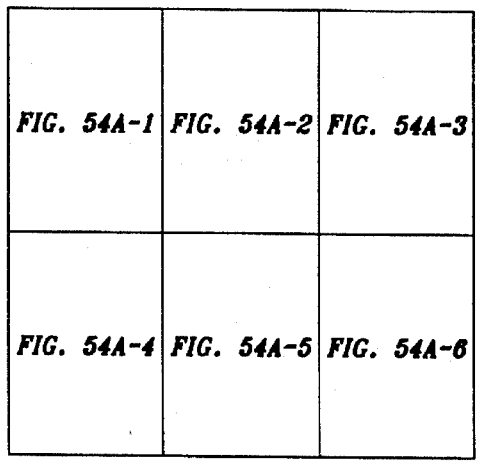
*FIG. 54A*
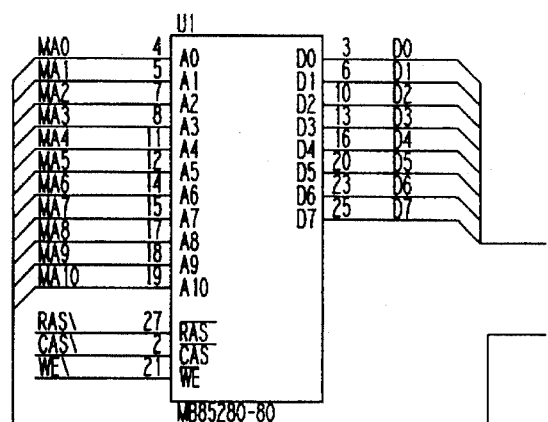
*FIG. 54A-1*
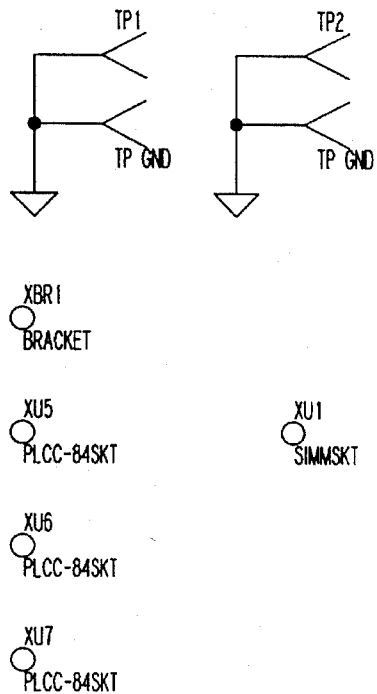

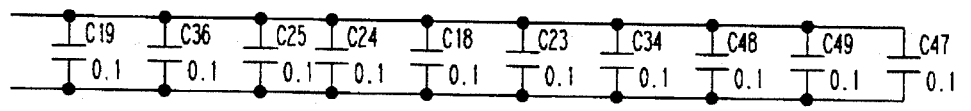
FIG. 54A-3
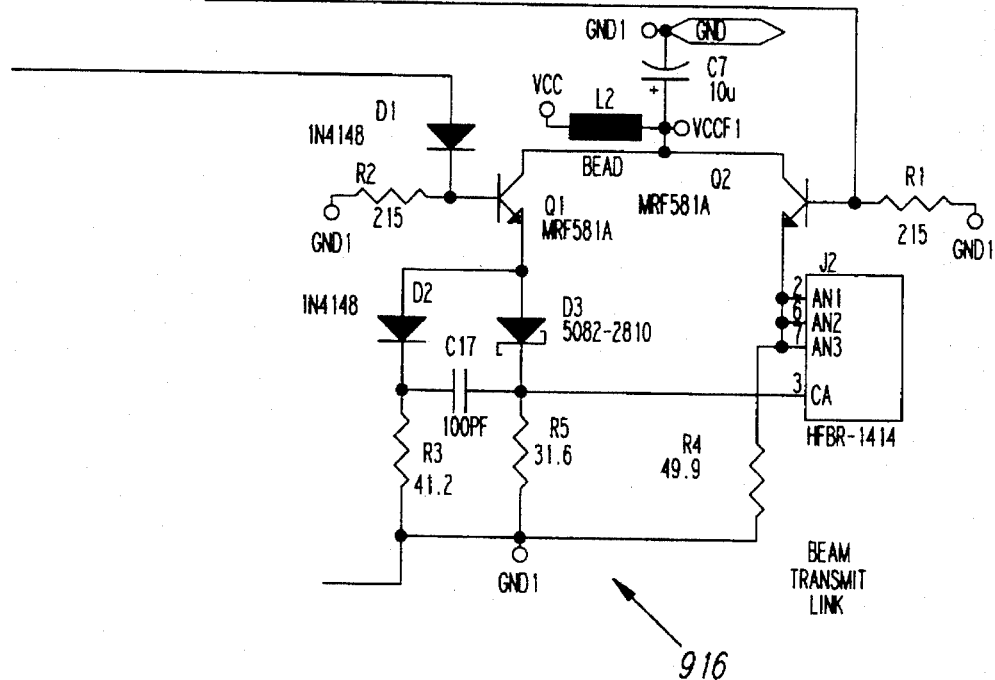

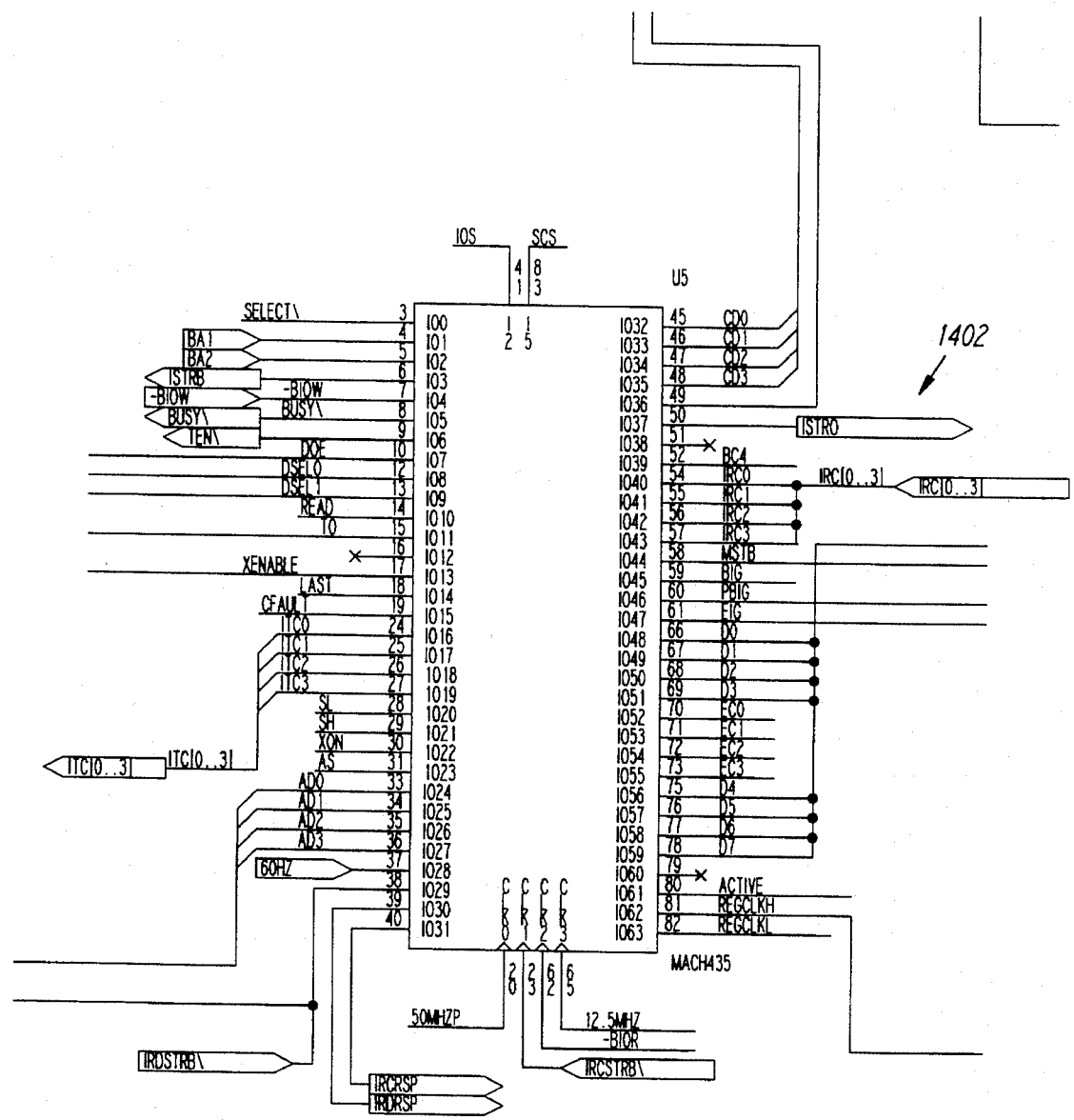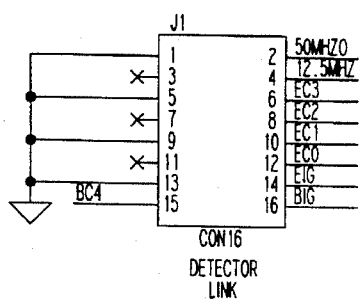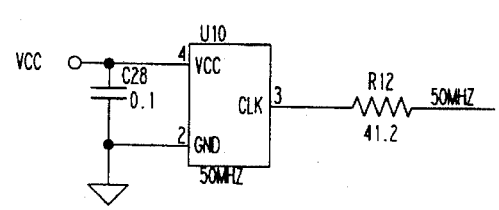
FIG. 54A-5

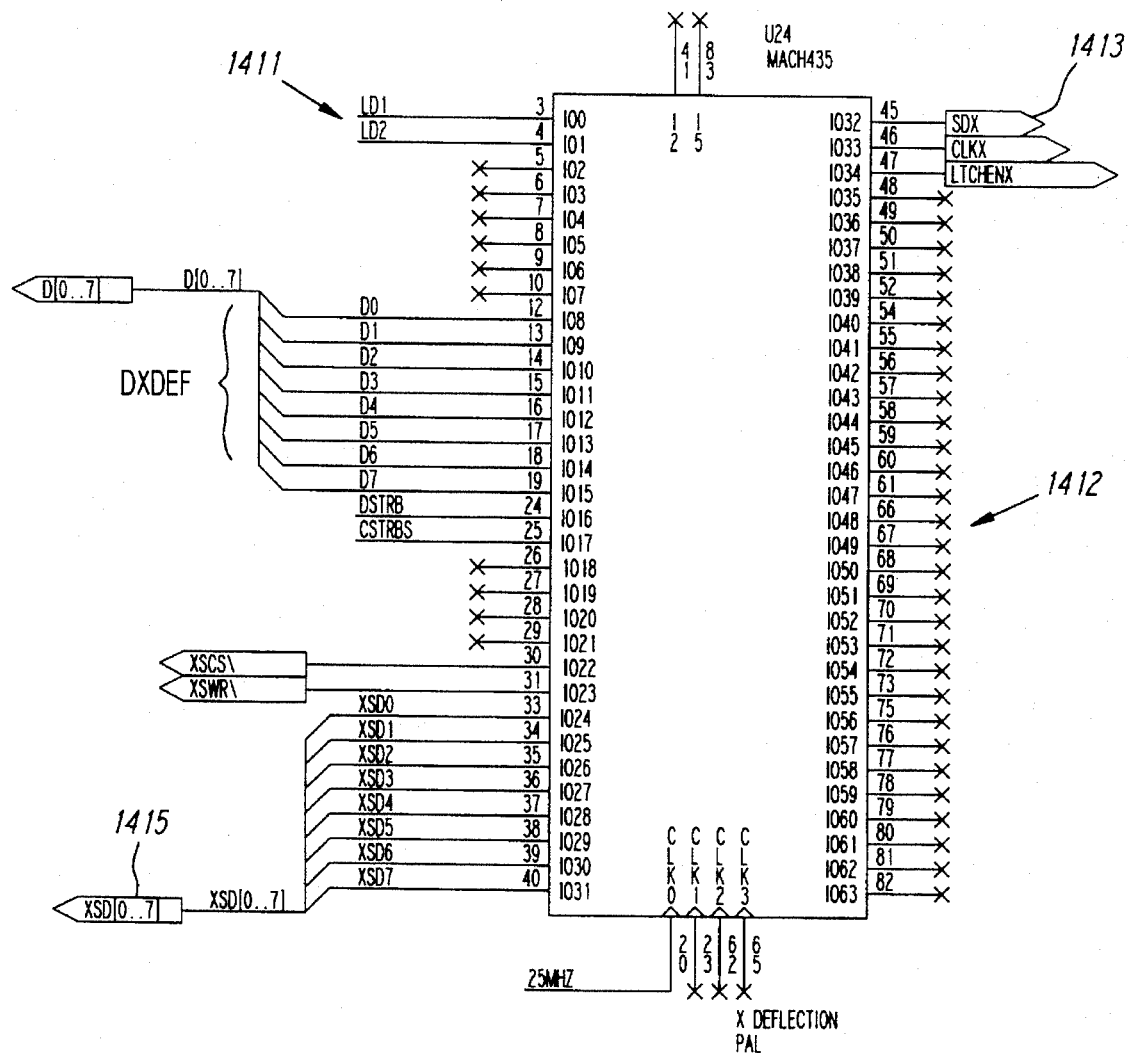
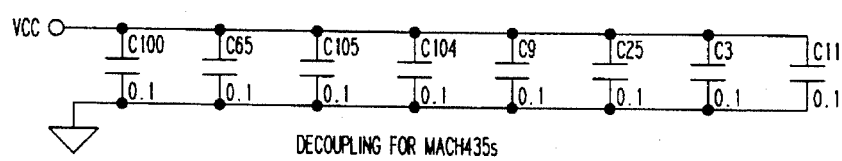
FIG. 55B

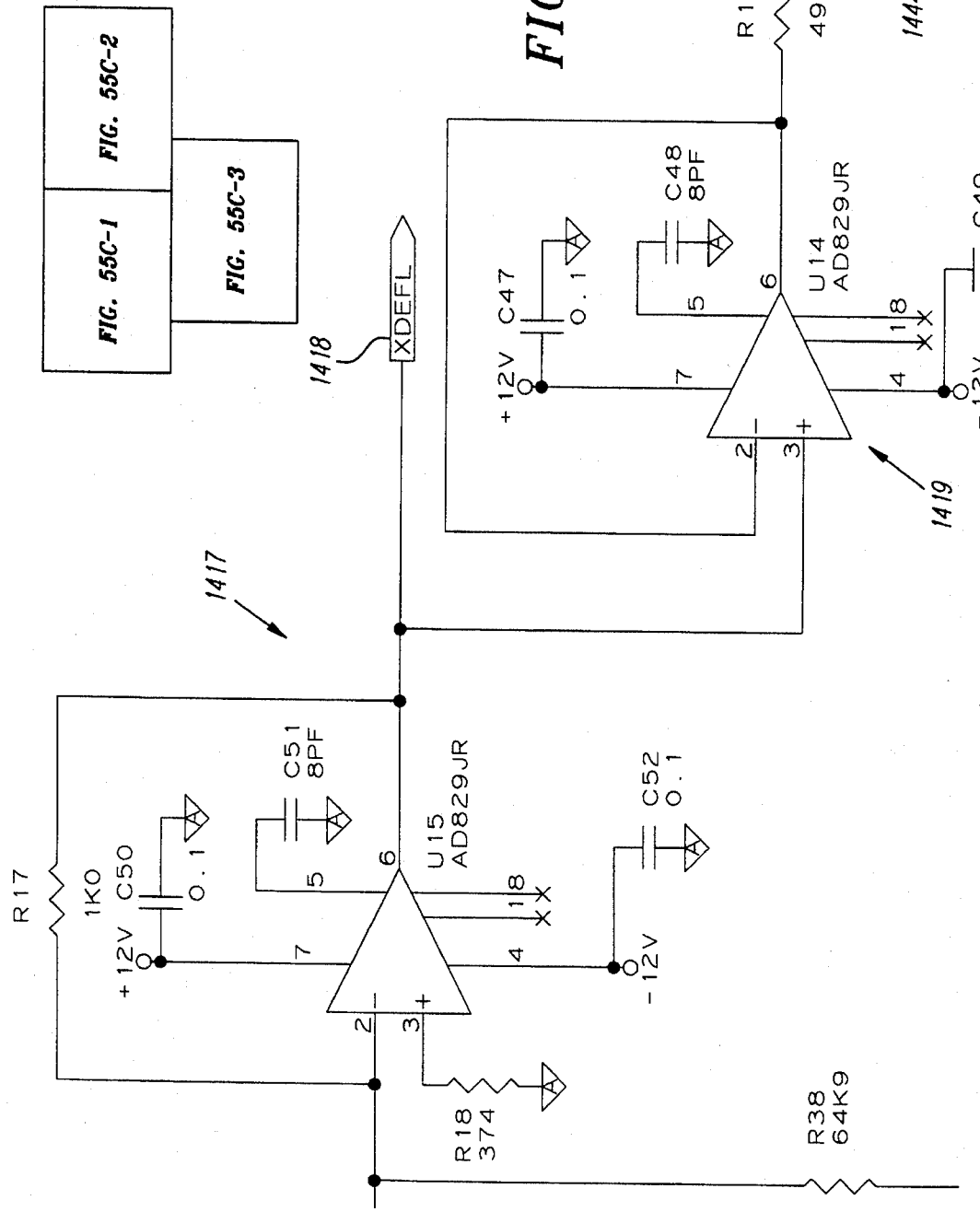

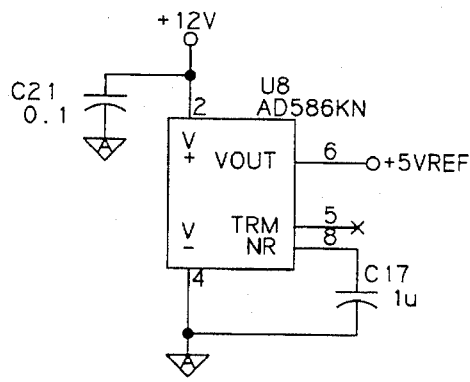
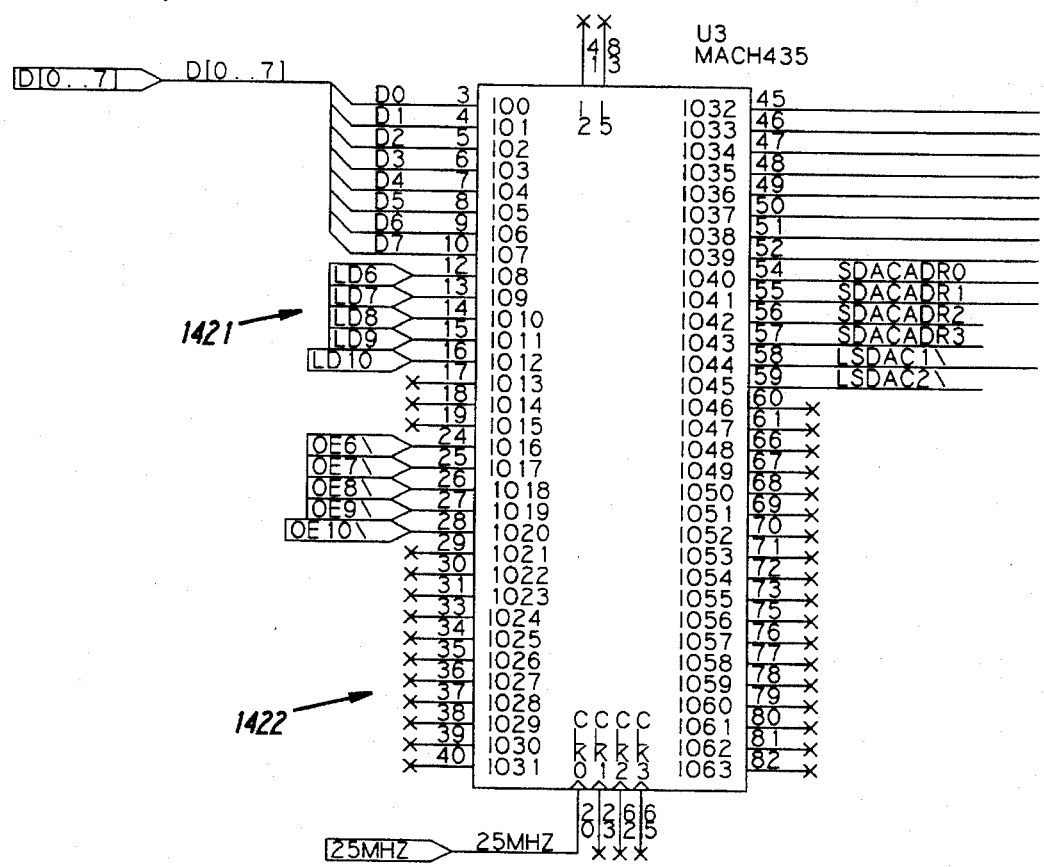
*FIG. 55D-1*
SMALL DAC CONTROL PAL
| FIG. 55D-1 | FIG. 55D-2 | FIG. 55D-3 |
*FIG. 55D*

SERIAL DATA
PAL

| FIG. 55E-1 | FIG. 55E-2 | FIG. 55E-3 |

X-RAY GRID ASSEMBLY

CROSS-REFERENCE TO RELATED APPLICATIONS

This application is a continuation of U.S. patent application Ser. No. 08/386,861, Lyon and Lyon Docket No. 209/151, filed Feb. 10, 1995, which is expressly incorporated herein by reference in its entirety. U.S. application Ser. No. 08/386,861 is a continuation-in-part of U.S. patent application Ser. No. 08/375,501, now abandoned filed on Jan. 17, 1995, which is a continuation of U.S. patent application Ser. No. 08/042,742, filed Apr. 5, 1993, now abandoned; which is a continuation-in-part of U.S. patent application Ser. No. 08/342,641, filed Nov. 21, 1994, now abandoned which is a continuation of U.S. patent application Ser. No. 08/008,455, filed Jan. 25, 1993, now abandoned; and, a continuation-in-part of International Patent Application Serial No. PCT/US94/03737, filed Apr. 5, 1994, which designated the United States from which priority is claimed under the provisions of 35 U.S.C. § § 120 and 365, all of which are incorporated herein by reference in their entirety. The reader is referred to copending U.S. patent application Ser. No. 08/387,292, Lyon & Lyon Docket No. 210/205, filed Feb. 10, 1995 and copending U.S. patent application Ser. No. 08/386,884, Lyon & Lyon Docket No. 210/204, both filed Feb. 10, 1995, the disclosures of which are incorporated herein by reference in their entirety.

APPENDIX

Attached hereto is APPENDIX A, which contains the program listings for the preferred software modules for the programmable logic devices employed in an embodiment of the present invention. The contents of APPENDIX A are hereby incorporated by reference in its entirety.

BACKGROUND OF THE INVENTION

1. Field of the Invention

The field of the present invention pertains to diagnostic x-ray imaging equipment. More particularly, the present invention pertains to real-time scanning-beam x-ray imaging systems and to devices incorporating a marker, such as a medical catheter incorporating an x-ray sensor, which allows the determination of the device's precise position within another object.

2. Description of Related Art

Real-time x-ray imaging is increasingly being required by medical procedures as therapeutic technologies advance. For example, many electro-physiologic cardiac procedures, peripheral vascular procedures, PTCA procedures (percutaneous transluminal catheter angioplasty), urological procedures, and orthopedic procedures rely on real-time x-ray imaging. In addition, modern medical procedures often require the use of instruments, such as catheters, that are inserted into the human body. These medical procedures often require the ability to discern the exact location of instruments that are inserted within the human body, often in conjunction with an accurate image of the surrounding body through the use of x-ray imaging.

Current clinical real-time x-ray equipment produces high levels of x-ray exposure to both patients and attending staff. The United States Food and Drug Administration (F.D.A.) has reported anecdotal evidence of acute radiation sickness in patients, and concern among physicians of excessive occupational exposure. (Radiological Health Bulletin, Vol. XXVl, No. 8, August 1992).

A number of real-time x-ray imaging systems are known. These include fluoroscope-based systems where x-rays are projected into an object to be x-rayed and shadows caused by relatively x-ray opaque matter within the object are displayed on the fluoroscope located on the opposite side of the object from the x-ray source. Scanning x-ray tubes have been known in conjunction with the fluoroscopy art since at least the early 1950s. Moon, *Amplifying and Intensifying the Fluoroscopic Image by Means of a Scanning X-ray Tube*, Science, Oct. 6, 1950, pp. 389–395.

Reverse-geometry scanning-beam x-ray imaging systems are also known. In such systems, an x-ray tube is employed to generate x-ray radiation. Within the x-ray tube, an electron beam is generated and focussed upon a small spot on the relatively large anode (transmission target) of the tube, inducing x-ray radiation emission from that spot. The electron beam is deflected (electromagnetically or electrostatically) in a raster scan pattern over the anode target. A small x-ray detector is placed at a distance from the anode target of the x-ray tube. The detector typically converts x-rays which strike it into an electrical signal in proportion to the detected x-ray flux. When an object is placed between the x-ray tube and the detector, x-rays are attenuated and scattered by the object in proportion to the x-ray density of the object. While the x-ray tube is in the scanning mode, the signal from the detector is inversely proportional to the x-ray density of the object.

Examples of known reverse-geometry scanning-beam x-ray systems include those described in U.S. Pat. No. 3,949,229 to Albert; U.S. Pat. No. 4,032,787 to Albert; U.S. Pat. No. 4,057,745 to Albert; U.S. Pat. No. 4,144,457 to Albert; U.S. Pat. No. 4,149,076 to Albert; U.S. Pat. No. 4,196,351 to Albert; U.S. Pat. No. 4,259,582 to Albert; U.S. Pat. No. 4,259,583 to Albert; U.S. Pat. No. 4,288,697 to Albert; U.S. Pat. No. 4,321,473 to Albert; U.S. Pat. No. 4,323,779 to Albert; U.S. Pat. No. 4,465,540 to Albert; U.S. Pat. No. 4,519,092 to Albert; and U.S. Pat. No. 4,730,350 to Albert.

In a typical known embodiment of a reverse-geometry scanning-beam system, an output signal from the detector is applied to the z-axis (luminance) input of a video monitor. This signal modulates the brightness of the viewing screen. The x and y inputs to the video monitor are typically derived from the signal that effects deflection of the electron beam of the x-ray tube. Therefore, the luminance of a point on the viewing screen is inversely proportional to the absorption of x-rays passing from the source, through the object, to the detector.

Medical x-ray systems are usually operated at the lowest possible x-ray exposure level at the entrance of the patient that is consistent with the image quality requirements (particularly contrast resolution and spatial resolution requirements) for the procedure and the system. Typical patient entrance exposure in conventional 9" field of view image intensifier systems used in cardiac procedures, in the AP (anterior posterior) view with a standard adult chest, is approximately 2.0 to 2.8 R/min. The term "low dosage" used herein refers to a factor of 2 to 20 less than this.

Time and area distributions of x-ray flux follow a Poisson distribution and have an associated randomness which is unavoidable. The randomness is typically expressed as the standard deviation of the mean flux, and equals its square root. The signal-to-noise ratio of an x-ray image under these conditions is equal to the mean flux divided by the square root of the mean flux. i.e., for a mean flux of 100 photons, the noise is +/−10 photons, and the signal-to-noise ratio is 10.

Accordingly, the spatial resolution and the signal-to-noise ratio of x-ray images formed by known reverse-geometry scanning x-ray imaging systems are dependent, to a large extent, upon the size of the sensitive area of the detector. If the detector aperture is increased in area, more of the diverging rays are detected, effectively increasing sensitivity and improving the signal-to-noise ratio. At the same time, however, the larger detector aperture reduces attainable spatial resolution as the "pixel" size (measured at the plane of the object to be imaged) becomes larger. This is necessarily so because most objects to be imaged in medical applications (e.g., structures internal to the human body) are some distance from the x-ray source. In the known systems, therefore, the detector aperture size has been selected so as to effect a compromise between resolution and sensitivity, it not being previously possible to maximize both resolution and sensitivity simultaneously.

In the medical field, several conflicting factors, among them patient dosage, frame rate (the number of times per second that the object is scanned and the image refreshed), and resolution of the image of the object, often work to limit the usefulness of an x-ray imaging system. For example, a high x-ray flux may easily yield high resolution and a high frame rate, yet result in an unacceptably high x-ray dosage to the patient and -attending staff.

Similarly, lower dosages may be achieved from the known systems at the cost of a low resolution image or an inadequate refresh rate. A preferred medical imaging system should provide low patient dosage, high resolution and an adequate refresh rate of up to at least about 15 images per second—all at the same time. Therefore, systems such as the known reverse-geometry scanning-beam x-ray imaging systems described above are not acceptable for diagnostic medical procedures where exposure times are relatively long and where, as is always the case with live patients, the x-ray dose received by the patient should be kept to a minimum.

Minimally invasive procedures in medicine are typically characterized by access to areas inside the body using existing orifices such as the ureter or by percutaneous entry such as a puncture of the femoral vein. In such procedures, various tools and catheters may then be progressed into the body and maneuvered using a real-time x-ray imaging system for guidance. An estimated 3,000,000 medical procedures of this type were performed in 1993 under x-ray fluoroscopy guidance. Many of these procedures involve the introduction of a catheter into the coronary arteries and the heart, and the evaluation of cardiac function by inspection of images taken when contrast media is introduced via a lumen in the catheter. Some of the tools that may be inserted in this manner include lasers where the laser device is located outside the body and the laser light delivered to the site of interest with a fiber-optic wave guide disposed in a catheter, drug delivery systems adapted to deliver precisely measured quantities of a specific drug or radiological material to the site of interest, ultrasound systems in which a transducer on the tip is used to view a site of interest by delivering the image over to a video system which can then display and record images of the site of interest, and other tools known to the art. It is also possible to adapt such procedures to non-medical applications where access is difficult and the value of the procedure high, e.g., engine diagnosis and repair.

As used herein, the term "maneuverable positioner" is meant to collectively include and refer to, for example, catheters, probes, endoscopes, and other maneuverable positioners and tools.

The known medical x-ray imaging devices do not provide a highly-accurate determination of location for maneuverable positioners with a precise image of the patient's internal structure. Generally, the physician using known systems can roughly ascertain the position of maneuverable positioners relative to body features within the patient, but precision and repeatability, the ability to return to the exact same place, especially in the axis parallel to the x-ray beam, is lacking. Thus the distance between the x-ray emitting source and the maneuverable positioner within the body may not be readily or accurately determined with the precision useful in today's advanced medical procedures, which may require, among other things, the ability to determine a position with the maneuverable positioner, move the maneuverable positioner, and return the maneuverable positioner to the exact same place.

For example, since 1982 there has been increasing use of catheter ablation to cure certain types of arrhythmia. In these types of arrhythmia, such as Wolff-Parkinson-White syndrome, the conductive congenital muscle fibers can be made nonconductive by heating them locally to a sufficient temperature to cause scar tissue to form. Most of these ablations are done with radio-frequency energy but the emitting electrode must be placed within one to three millimeters of the muscle fiber location and it must stay in intimate contact with it for a number of heartbeats and respiratory cycles.

Although the treatment of arrhythmia through catheter ablation has some advantages, there are also some problems. The advantages of the procedure are that it has a very high success rate, it is minimally invasive, it can be performed in a few hours in a procedure room, and it is considerably less expensive than open chest surgery or a lifetime of drug therapy. The major disadvantage is that the length of the procedure is uncertain and typically long. This leads to difficulty in scheduling physicians and facilities, fatigue for both patient and staff, and high-radiation dosages for patient and physician.

Attempts to solve these problems have focused mainly on providing more steerable catheters to reduce the time to find the precise location of the ablation site and to position the catheter for remaining in contact with the substrate during the ablation time, which is typically five to ninety seconds. Having more steerable catheters has not yet reduced the time or uncertainty of time because the location of the catheter is generally determined by looking at an x-ray image projected on a monitor and by analyzing the electrocardiogram. Both of these actions must be done in real time in order to know whether to move the catheter and in which direction to move it. The actual direction of movement may be uncertain due to the nature of an x-ray image of soft tissue and blood, the poor control and feedback of the catheter, the movement of the heart, and the difficulty of determining direction from the electrocardiogram analysis.

In the U.S., there are currently 300,000 to 500,000 people who die each year due to arrhythmia that is a result of a myocardial infarction. However, it is believed that if the slow-conduction zone around the infarct could be electrically mapped and selectively ablated, that a cure could be obtained. Tests on animals and some humans have demonstrated the possibility of such a procedure but the success rate has been low. The reason for the low success is thought to be the need to map the entire area of the infarct and slow conduction zone and then to be able to ablate multiple sites without depending on acquiring a characteristic electrogram once the ablation has begun. Current investigations attempting to solve the problem utilizing a catheter network array of nodes suffers from the problem of extracting the catheter network array from inside the heart without damaging the internal structure of the heart.

For various reasons, the imaging modalities of MRI, CT, and ultrasound are not normally suitable when anatomical markers are needed during cardiac diagnostic and treatment procedures. In addition, the use of known methods employing x-ray fluoroscopes for imaging typically has the serious disadvantage of not being able to distinguish anatomical detail inside the heart. The physician relies on the shadows generated, his or her intimate knowledge of the anatomy, the characteristic movement of the image and catheters caused by the cardiac cycle and the respiratory cycle, and for fine positioning, the electrocardiogram.

Accordingly, there is a need for devices and methods to provide a precise determination of the coordinates of a maneuverable positioner within a human patient during a medical procedure. The same techniques and apparatus can also be used to advantage in any x-ray procedure which requires accurate determination of the X, Y and Z coordinates of the position of a maneuverable positioner which may be adapted to sense x-rays.

SUMMARY OF THE INVENTION

An x-ray imaging system according to the present invention comprises a scanning-beam x-ray source and a multi-detector array. The output of the multi-detector array is input to an image reconstruction engine which combines the outputs of the multiple detectors over selected positions of the x-ray beam to generate a real-time x-ray image of the object.

An embodiment of an aspect of the invention includes an x-ray tube including a charged particle beam source and an anode target. Beam control circuitry focusses the charged particle beam and directs or scans the beam across the anode target in a predetermined pattern. For example, the predetermined pattern may be a raster scan pattern, a serpentine or "S" shaped pattern, a spiral pattern, a random pattern, a gaussian distribution pattern centered on a predetermined point of the anode, or such other pattern as may be useful to the task at hand.

A collimating element, preferably in the form of a grid, may be interposed between the x-ray tube and an object to be x-rayed. In one preferred embodiment, the collimating element is composed of a round metal plate having a diameter of about 25.4 cm (10 in) and includes a staggered array of apertures numbering 500 by 500 at the center row and column of the collimating element. The collimating element is preferably placed immediately in front of the emitting face of the x-ray tube. Other collimating element configurations may also be used. In one preferred embodiment, each of the apertures in the collimating element is constructed so that each of the axes of each of the apertures is directed toward (or points at) a detection point, e.g., the center of a multi-detector array, located a selected distance from the collimating element. That distance is selected to allow placement of the object to be x-rayed between the collimating element and the multi-detector array. In the preferred embodiment, the function of the collimating element is to form thin pencil beams of x-rays, all directed from a focal spot on the anode target of the x-ray tube toward the multi-detector array.

A multi-detector array, preferably containing an array of detector elements (preferably an area array such as a $DET_x$ by $DET_y$ rectangle or square, or, more preferably, a pseudo-round array), is centered at the detection point. The multi-detector array preferably comprises a plurality of densely packed x-ray detectors. The multi-detector array is designed, positioned and applied, according to the present invention, in a manner that yields high sensitivity without loss of resolution. This results in an x-ray system having a resolution comparable to or better than that of known conventional x-ray systems at an exposure at least an order of magnitude less than that of the known x-ray systems. This aspect of the present invention provides important benefits in medical and other applications. X-ray dosage to patients and attending medical staff is reduced when using this aspect to perform current medical procedures. Procedures now believed to have too high a radiation exposure risk may become acceptable.

The output of the multi-detector array is preferably an intensity value for each detector of the multi-detector array for each x-ray beam emitted through an aperture in the collimating element. Because each aperture is located at a different point in space relative to the multi-detector array and the object under investigation, different outputs will be available from each detector of the multi-detector array for each aperture that the x-ray beam travels through. The multi-detector array output may be converted into an image in a number of ways.

The imaging system of the present invention is also capable of use in stereo imaging. In one embodiment, the collimation element contains two groups of apertures. For stereo imaging, the axes of one group of apertures is constructed to point to a first detection point on a first multi-detector array and the axes of a second group of apertures is constructed to point to a second detection point on a second multi-detector array. By constructing two images from the outputs of the multi-detector array and using conventional stereoscopic display methods, a stereo image may be produced.

An imaging system of the present invention is also capable of highlighted imaging of materials which exhibit different x-ray transmissivities at different x-ray photon energies. Accordingly, for example, microcalcification, which is associated with approximately 60% of the breast cancer diagnosed, may be imaged. Calcium is also typically associated with heart disease when found in the coronary arteries. In one embodiment, by constructing the collimation element and/or anode target to sequentially emit two or more groups of x-rays beams each having different x-ray energy spectra, and directing each group to the multi-detector array (more than one multi-detector arrays could also be used), the difference of transmissivities of the object under investigation at the various x-ray photon energies can be used to create an image, thus highlighting only those materials within the object under investigation which exhibit differential x-ray transmissivity. Optimized for the detection of calcium, for example, such an imaging system is a powerful tool for use in the early detection of breast cancer and other anomalies.

Utilizing a multi-detector array which intercepts the entire x-ray beam emitted from each aperture of the collimator element and image processing the array output is the preferred embodiment of the detector. It provides a maximum sensitivity without sacrificing the resolution provided by using a single small area detector. While a single detector of the same area as the multi-detector array would provide the same sensitivity, it would do so at the cost of a loss of resolution.

Additionally, sampling techniques utilizing information from less than a 1:1 image pixel to aperture ratio may be used for generating data from the multi-detector array which can reduce the complexity of the system, required processing speed, and energy consumption while providing virtually the same image quality.

An aspect of the present invention can also be used to identify the unique location of a marker transported within another object by a maneuverable positioner. In its most general sense, this would be accomplished by an x-ray sensitive marker disposed in a body and includes the transmission of an indication of the presence of x-ray radiation outside of the body in which it is disposed.

According to one embodiment of this aspect of the invention useful in medical applications, a catheter comprises an elongated body having a distal end adapted to be inserted into a body cavity, blood vessel, digestive tract, or the like and a proximal end available to a person performing a medical procedure. The catheter includes at least one lumen running therethrough. An optical fiber is disposed in the lumen and extends from the distal end to the proximal thereof. A miniaturized ("mini") x-ray sensor comprised of an x-ray sensitive material is disposed at the end of the optical fiber positioned at the distal end of the catheter. The end of the optical fiber at the proximal end of the catheter is coupled to a photodetector. The reaction of the sensor material of the mini x-ray sensor to an x-ray beam sequentially transmitted through a collimator, coupled with the transmission of that reaction to the photodetector, allows the determination of the precise position of the sensor material. Embodiments of the techniques to determine this precise position from the mini x-ray sensor reaction is discussed in detail below.

Another aspect of the present invention is the ability to determine the distance of a maneuverable positioner containing a mini x-ray sensor from a known reference plane. Each x-ray beam emitted through a collimation grid aperture of the present invention is shaped like a diverging cone with its apex at the anode target and its divergence angle determined by electron beam spot size on the anode target and the geometry of the collimation grid apertures with respect to the anode target. The divergent beams are designed to overlap more and more the farther you get from the x-ray source. The mini x-ray sensor in this aspect is preferably disposed in a maneuverable positioner and may have (but is not required to have) a size smaller than the spacing between the apertures of the collimation grid. When such a sensor is disposed in the x-ray field it will detect, during a complete scan cycle, x-rays from only a certain number of apertures, the number depending upon the mini x-ray sensor's distance from the output face of the collimation grid. When the mini x-ray sensor is located close to the output face of the collimation grid, it will react to x-ray pulses from a first number of apertures per scan cycle. At a greater distance from the output face, it will react to x-ray pulses from a second number of apertures greater than the first number. When the mini x-ray sensor is near the x-ray multi-detector array, it will react to x-ray pulses from an even greater number of apertures per scan cycle. By calibrating the number of apertures per scan cycle to which the mini x-ray sensors reacts with the mini x-ray sensor's distance from a known reference, the distance of the mini x-ray sensor from the reference may be determined by consulting a look-up table and/or by interpolation.

When used as described herein, the above-described embodiment of the present invention answers the long felt need for anatomical markers during cardiac diagnostic and treatment procedures. Since typical reference positions for electrocardiograms are the high right atrium, the bundle of HIS, the apex of the right ventricle, and the coronary sinus, there is an opportunity to have at least three points located in the x-ray image during the cardiac cycle. These three points can precisely locate the coordinates of the ablation catheter. Knowing the coordinates of these points, the physician can then map an area with the catheter and correlate its position with the electrocardiograms. He can then return to the same spot after leaving it and can measure bounce or other movement, he can also measure internal dimensions of the heart mapping points, determine wall thicknesses, build 3D images from the data and overlay cardiac action potentials. In addition, in a subsequent procedure the same locations may be found from overlaying the maps of anatomy and cardiac potentials.

The initial work performed with this aspect of the invention was to analyze the images from a biplane x-ray system when it was gated to the cardiac cycle. In some cases this positioning using image analysis is adequate but the precision can be greatly improved if an x-ray marker is included in the catheter. With conventional image intensifier technology, such a point sensor would not be useful since the entire field of view is irradiated simultaneously. However, in a scanning-beam x-ray system, the beam irradiates only a small field of view at a given time and therefore the location of the sensor in each individual catheter can be uniquely identified. By utilizing a stereo or biplane scanning-beam system, the sensor can be located in three dimensions provided that the two beams are synchronized. The advantage of the above described medical catheter embodiment of the invention is that it permits existing catheters inside the patient to now also function as anatomical markers when a mini x-ray sensor is employed, significantly reducing the time to map and ablate. Additional advantages are more detailed mapping of the cardiac substrate, correlation of the intercardiac electrodes with anatomical location, display in three dimensions of the intercardiac electrodes on an image of the heart, and comparison of electrograms from studies done at different times by overlaying.

It is an object of one aspect of the present invention to provide a scanning-beam x-ray imaging system capable of use in medical diagnostic procedures undertaken on living human patients.

It is also an object of another aspect of the present invention to provide a scanning-beam x-ray imaging system which provides high resolution images at adequate frame rates while minimally exposing the object under investigation to x-ray radiation.

It is a further object of another aspect of the present invention to provide a scanning-beam x-ray imaging system having improved resolution at a distance from the plane of the source of the x-rays while maintaining decreased x-ray flux levels.

It is also a further object of an aspect of the present invention to provide a method and apparatus for precisely determining the position of a maneuverable positioner within an object undergoing an x-ray procedure.

It is yet a further object of an aspect of the present invention to provide a method and apparatus for precisely and simultaneously determining and displaying information related to the X, Y and Z coordinates of a maneuverable positioner within an object undergoing an x-ray procedure.

It is also a further object of an aspect of the present invention to provide an electronic glove and other improvements in safety for medical applications by feedback of position from a mini x-ray sensor.

It is an object of another aspect of the present invention to provide for improved image quality by employing region of interest scanning.

It is a further object of an aspect of the present invention to provide a scanning beam x-ray imaging system for non-medical applications where scatter may degrade image quality, e.g., to image or inspect honeycomb airplane structures, corrosion, and printed circuit boards.

An advantage of an aspect of the present invention is that it can provide a method and apparatus for generating a "road map." For example, once a maneuverable positioner incorporating a mini x-ray sensor in accordance with the present invention has been threaded to a particular location of interest within the body or object, it can be removed and then re-threaded along the same path by generating waypoints, e.g., by determining X, Y and Z coordinates of various locations passed through during the first insertion. These waypoints may be obtained as frequently as desired along the first path taken to the location of interest to facilitate retracing the same path on subsequent occasions. This aspect of the present invention may have important application in intravascular and intracardiac ultra sound procedures.

Another advantage of an aspect of the present invention is that it can provide a method and apparatus to precisely locate and monitor the shape or position of stents. The precise location of the surface of a stent can be obtained through use of an x-ray sensing maneuverable positioner in accordance with the present invention by defining points along the surface of the stent, determining the X, Y and Z coordinates of those points and recording them. Subsequently, X, Y, and Z coordinates for those defined points can be redetermined and recorded over time and changes in shape or position of the stent can be observed and plotted.

Another advantage of an aspect of the present invention is that it can provide a method and apparatus for repeatable delivery of drugs, radiologic and similar materials to a specific site in the body.

These and many other objects and advantages of the present invention will become apparent to those of ordinary skill in the art from a consideration of the drawings and the description of the invention contained herein. The principles of the present invention may be employed in any application, medical or industrial. Principles or aspects of the present invention can be applied for example where location of internal features of an object is desired and insertion of an x-ray sensitive device is feasible. Industrial applications are variously called x-ray inspection, x-ray analysis, failure analysis, non-destructive testing, and in-situ testing.

BRIEF DESCRIPTION OF THE DRAWINGS

FIGS. 18 and 19 are partial functional block diagrams comprising a preferred x-ray source for a scanning-beam imaging system.

FIG. 20 is a partial functional block diagram comprising a preferred dual multi-detector array for a scanning-beam imaging system.

FIGS. 21 and 22 are partial functional block diagrams comprising a preferred monitor for a scanning-beam imaging system.

FIG. 23 is partial functional block diagrams comprising a preferred scan generator for an scanning-beam imaging system.

FIG. 24 is a cross-sectional view through a two-dimensional array of regularly-spaced x-ray sources and a two-dimensional array of regularly-spaced detectors.

FIG. 25 is a diagram showing focal plane location for one embodiment of a scanning beam x-ray imaging system.

FIG. 36 diagrammatically depicts a preferred detector arrangement of 144 logical detector elements in the presently preferred image reconstruction engine.

FIG. 38 is a diagram showing the preferred beam alignment octant arrangement.

FIGS. 48A–I are schematics of string counters for strings one through nine for a preferred image reconstruction engine.

FIGS. 55A–E comprise schematics of the preferred beam controller interface.

DESCRIPTION OF THE PREFERRED EMBODIMENTS

The following description of the aspects of the present invention is illustrative only and not to be construed as in any way limiting to the inventive concepts disclosed and claimed herein.

System Overview

Figure 1:
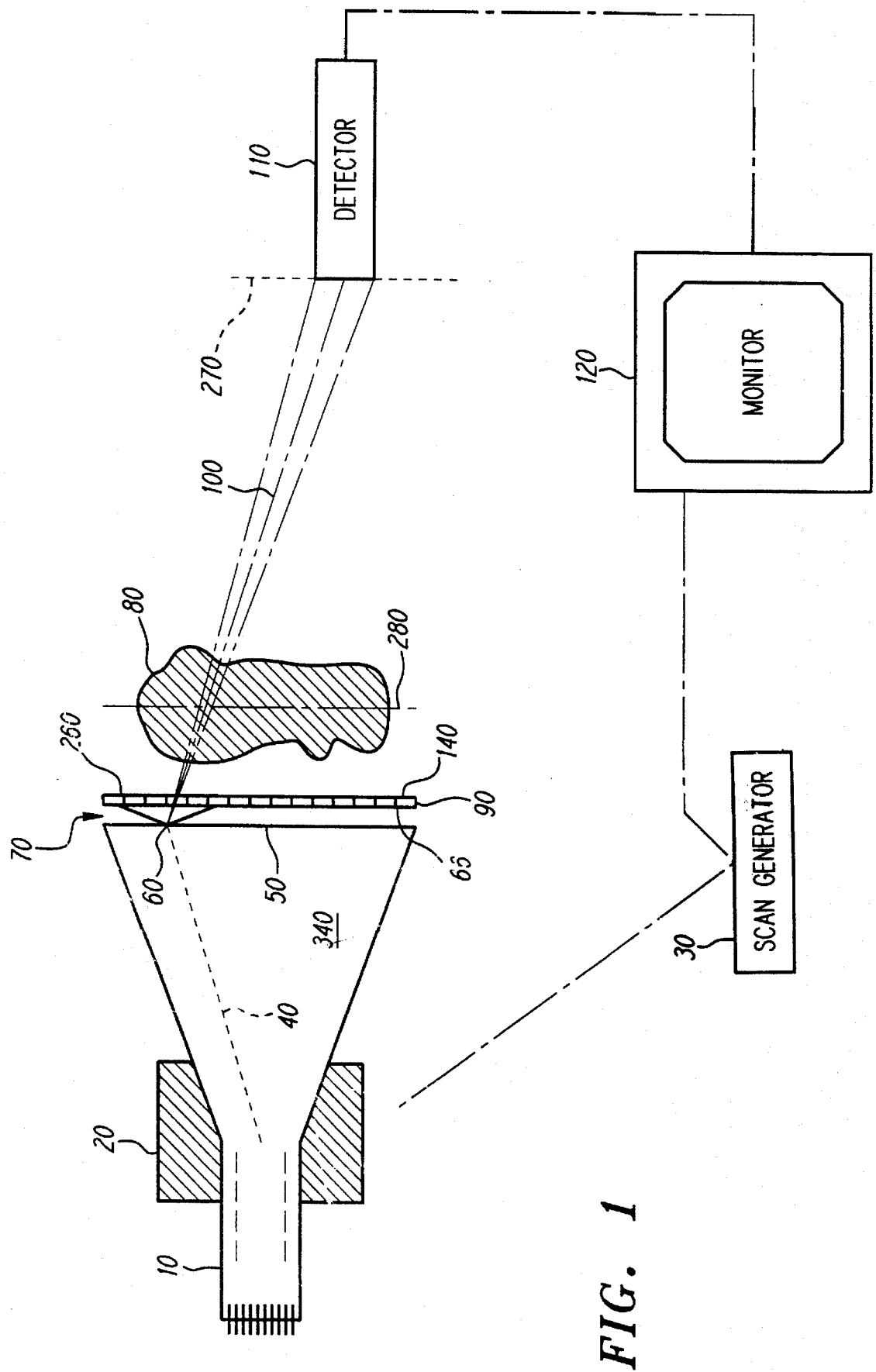
FIG. 1 is a diagram showing the basic components of a preferred low dosage scanning-beam x-ray imaging system.

Turning to FIG. 1, a scanning-beam x-ray imaging system according to a preferred embodiment of the present invention is diagrammed. The x-ray source is preferably a scanning x-ray source 10 preferably comprising a power supply capable of generating approximately −100 kV to −120 kV, which can operate x-ray tube 10 at about −70 kV to −100 kV. At this voltage level, x-ray source 10 produces a spectrum of x-rays ranging to 100 keV. As used herein, the term 100 keV x-rays refers to this spectrum. X-ray source 10 includes deflection yoke 20 under the control of scan generator 30. An electron beam 40 generated within x-ray source 10 is scanned across a grounded anode target 50 within x-ray source 10 in a predetermined pattern. Hereinafter, for simplicity, anode target 50 is referred to as target 50. For example, the predetermined pattern may be a raster scan pattern, a serpentine (or "S" shaped) pattern, a spiral pattern, a random pattern, a gaussian distribution pattern centered on a predetermined point of the target, or such other pattern as may be useful to the task at hand. Presently preferred is the serpentine (or "S" shaped) pattern which eliminates the need in a raster scan pattern for horizontal "fly back."

As electron beam 40 strikes target 50 at focal spot 60, a cascade of x-rays 70 is emitted and travel outside of x-ray source 10 toward the object 80 to be investigated. To optimize system performance of the presently preferred embodiment, a cone of x-ray photons should be generated that will diverge in a manner that will just cover the multi-detector array 110.

Figure 2:
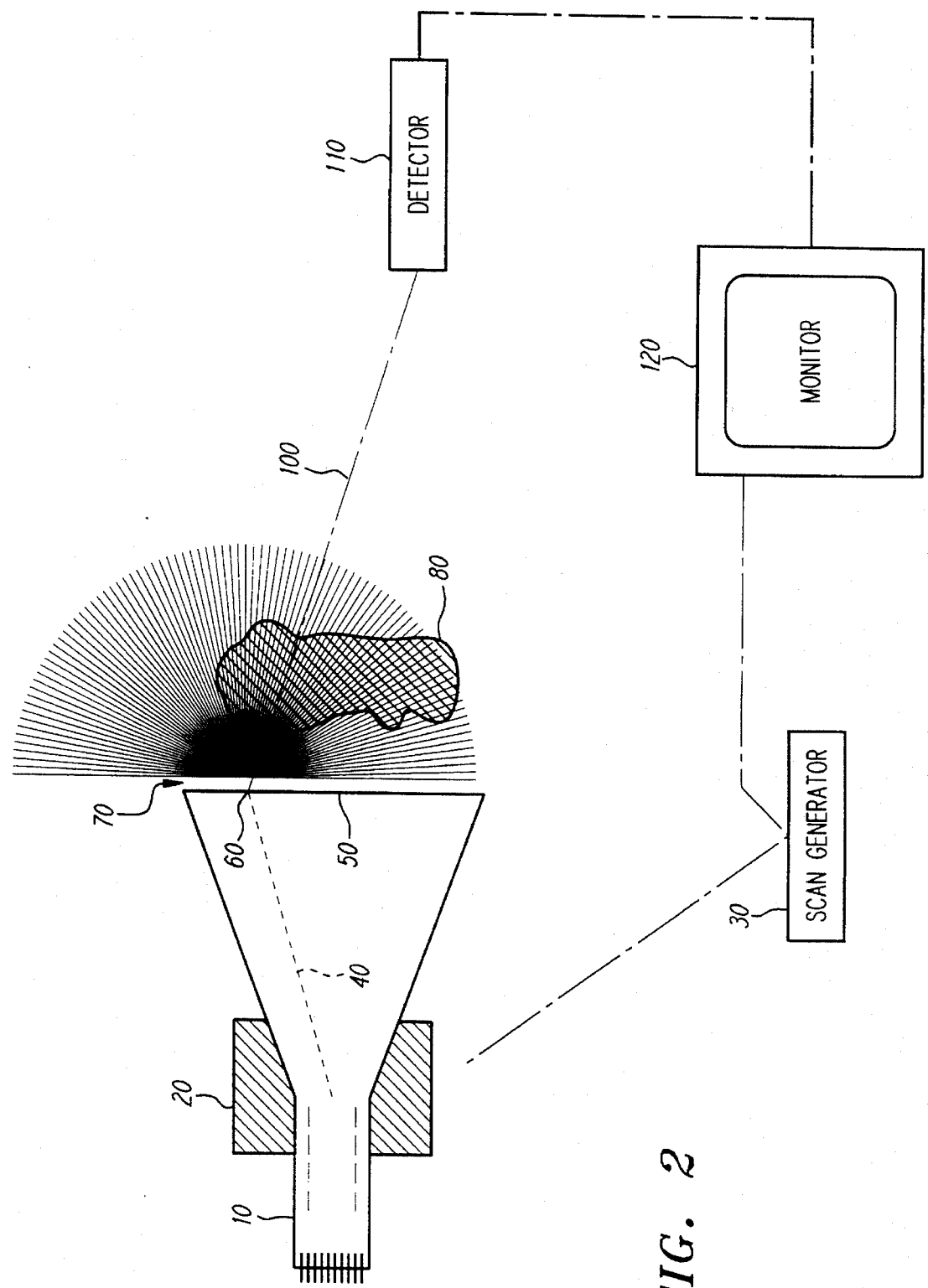
FIG. 2 is a diagram showing the distribution of x-rays in the forward direction from a scanning-beam x-ray imaging system in the absence of a collimation grid.

This is preferably accomplished by placing a collimating assembly between the target 50 of the scanning x-ray source 10 and the multi-detector array 110, and more preferably between the target 50 and the object to be imaged. The presently preferred collimating assembly is a collimation grid 90, containing a grid of x-ray transmissive apertures 140. Collimation grid 90 is designed to permit passage of only those x-ray pencil beams 100 whose axes lie in a path that directly intercepts multi-detector array 110. Collimation grid 90 does not move with respect to multi-detector array 110 while the system is in operation. Thus, as electron beam 40 is scanned across target 50, at any given moment there is only a single x-ray pencil beam 100 which passes through object 80 to multi-detector array 110. This preferred result is in contrast to the result in FIG. 2, which depicts the distribution of x-rays 70 from a scanning-beam x-ray source in the absence of a collimator assembly. For purpose of illustration only, the scatter from x-rays 70 which strike multi-detector array 110 is not shown in FIG. 2.

The output of multi-detector array 110 is processed and displayed on monitor 120 as luminance values. Image processing techniques can be used to produce a computer driven image on an appropriate display or photographic or other medium.

The embodiment of the inventive system disclosed herein is a low exposure system in that it typically exposes the cardiology patient at a rate of about 0.09 to 0.33 R/min with a 30 frame/sec refresh rate measured at the entrance to the patient, which in conventional systems under the same conditions would typically be between 2.0 to 2.8 R/min. Whole body exposure with a 30 frame/sec refresh rate with the present inventive system will be lower than that for conventional systems as well.

The X-Ray Tube

Figure 3:
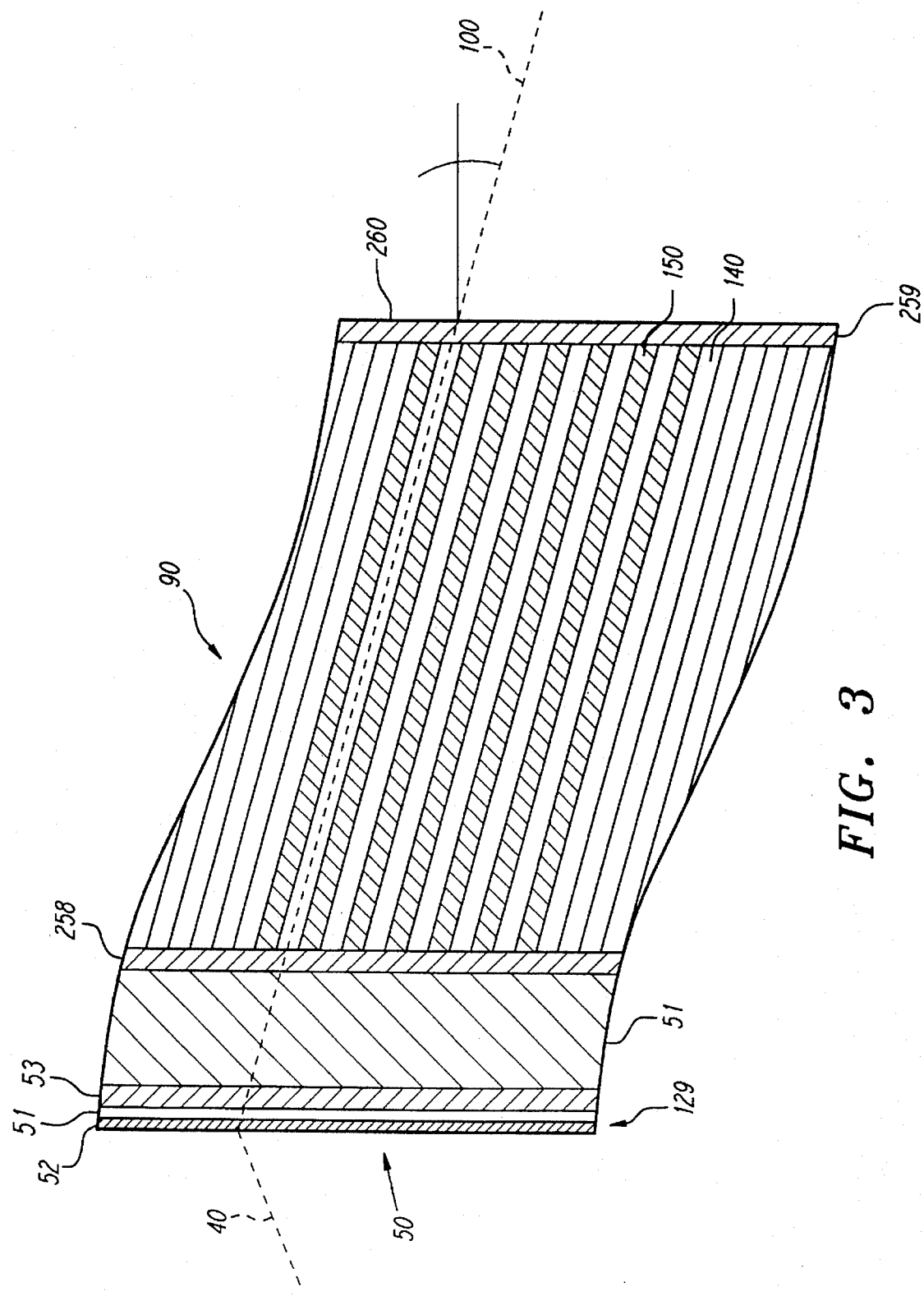
FIG. 3 is an enlarged cross sectional representation of a portion of a preferred collimation grid and target of an x-ray tube for use in a preferred low dosage scanning-beam x-ray imaging system.

FIG. 3 depicts a magnified diagrammatic view of a preferred collimation grid and target structure. Target 50 is preferably comprised of a target layer 129 of a material having good vacuum characteristics and the ability to withstand high heat and electron bombardment, which is then formed upon a beryllium target support 53. Aluminum or other relatively x-ray transparent materials can be used to fabricate the target support 53 as well. A preferred construction of the target layer 129 is a first layer of niobium 51 approximately 1 micron thick sputter-deposited upon the beryllium target support 53 to which is then sputter-deposited a second layer of tantalum 52 approximately 5 microns thick. This structure is presently preferred because niobium has a thermal coefficient of expansion intermediate to the coefficients of thermal expansion of tantalum and beryllium, thus reducing or preventing microcracking due to thermal cycling of the target as the electron beam 40 scans across the target. Another embodiment is a layer of tantalum approximately 5 microns thick sputter deposited directly on the beryllium target support 53. Yet another embodiment is a layer of tungsten-rhenium approximately 5 microns thick sputter-deposited on the beryllium target support 53. Still another embodiment is a layer of tungsten approximately 5 to 7 microns thick sputter deposited on the beryllium target support 53. Tantalum, tungsten and tungsten-rhenium are presently preferred for use in target layer 129 because they have relatively high atomic numbers and densities and readily emit x-rays when bombarded by an electron beam. Tungsten's high melting point of 3370° C. and good vacuum characteristics make it suitable for the high temperature and hard vacuum conditions within the x-ray source. Tantalum and tungsten-rhenium have similar characteristics as known to those of skill in the art. The thicknesses of the target layers are preferably selected so that they are approximately equivalent to the distance necessary to efficiently convert 100 keV electrons to x-rays.

Beryllium is presently preferred for target support 53 because it is strong and does not significantly attenuate or scatter the x-rays emitted from target layer 129. The thickness of beryllium target support 53 is preferably about 0.5 cm. In the presently preferred embodiment of the present invention, target support 53 should be constructed as thin as possible subject to the physical constraint that it must be strong enough to withstand the pressure gradient of one atmosphere across it.

A cooling chamber 54 is preferably located between the target support 53 and collimation grid 90.

Collimation grid 90 preferably consists of an array of apertures 140, the axes of each, according to one preferred embodiment of the present invention, are oriented or pointed toward multi-detector array 110. That is to say that the axes of apertures within the collimation grid 90 are not parallel to each other and form an acute to the line perpendicular to the output face 260 of the collimation grid 90. For example, a collimation grid for a chest x-ray application may comprise apertures forming an angle with a line perpendicular to the output face 260 of the collimation grid 90 of between 0° at the center of the collimation grid 90 to as much as 20° at the edge of the grid 90. A mammogram application on the other hand may have a collimation grid 90 comprising apertures forming an angle with a line perpendicular to the output face 260 ranging to 45° at the edge of the grid. Thus, a different collimation grid 90 may be selected and inserted for use in different medical applications.

The number of apertures 140 in collimation grid 90 may correspond to the number of image pixels to be generated on the monitor. For example, 500 by 500 to 1024 by 1024. Alternatively, the image pixel to aperture ratio may be increased, i.e., fewer apertures than image pixels may be used, in conjunction with the technique of "sub-sampling" discussed below. The system spatial resolution may be determined, in part, by the pitch of the apertures in collimation grid 90. The precise number of apertures suggested above is illustrative only, and is not intended in any way to be limiting.

Some of the factors preferably used to determine the thickness of collimation grid 90 and the diameter of apertures 140 are the distance of the multi-detector array 110 from target 50, which is presently preferably 94.5 cm (37.2 in), the desire to significantly attenuate all x-rays 70 not aimed at the multi-detector array 110, and the size of the multi-detector array 110 (not shown in this figure). Apertures 140, as viewed from output face 260, are preferably laid out in a rectangular row and column pattern containing a substantially circular boundary 25.4 cm (10 in). in diameter forming a circular active array. The aperture array may, however, be of any convenient layout to resolve the image of object 80. Further, the electron beam 40 may be scanned in a pattern which employs only a portion of the apertures 140. The circular active area according to one preferred embodiment of the present invention has a diameter of approximately 500 apertures.

The x-ray absorbent portion 150 of preferred collimation grid 90 is designed to absorb errant x-rays so that they do not illuminate object 80. This is accomplished by fabricating the preferred collimation grid 90 with sufficient thickness so that the x-ray radiation passing through an aperture 140 towards the multi-detector array 110 is substantially greater than the cumulative x-ray radiation passing through x-ray absorbent portion 150 in all directions other than toward multi-detector array 110. Such errant x-rays would provide the object 80 and attending staff with x-ray dosage but contribute no meaningful information to the image.

Figure 3A:
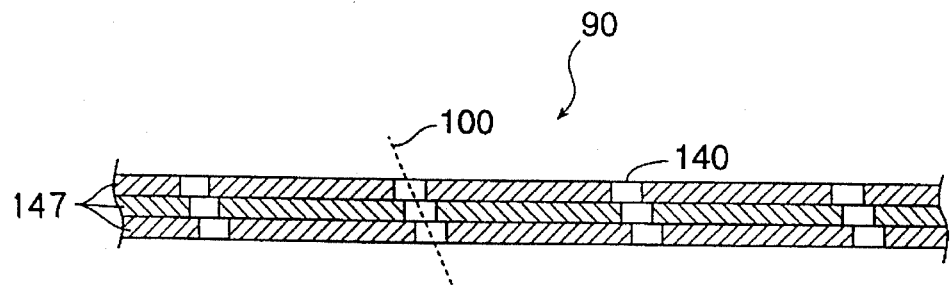
FIGS. 3A, 3B, 3C, and 3D are partial cross-sectional representations of collimation grids useful in the inventive device.

Collimation grid 90, as shown in FIG. 3A, is preferably fabricated from a number of sheets 147 of x-ray absorbing materials having apertures 140 therethrough to form an x-ray pencil beam 100 as the x-rays pass through the collimation grid to the multi-detector array 110. The material used for the sheets 147 can be formed from x-ray opaque materials such as molybdenum, brass, lead, copper, tungsten, tantalum, gold or any of these used in combination. The collimation grid 90 is preferably fabricated of 50 thin sheets of 0.0254 cm (0.010 in) thick molybdenum which are stacked and held together by end plates 258 and 259. Molybdenum is a preferred material for sheets 147 because it readily absorbs x-rays so that x-rays generated by x-ray source 10 which are not directed to multi-detector array 110 will be absorbed before they impinge upon object 80, which, of course, may be a human patient. The end plates 258 and 259 are constructed from an x-ray transmissive material, preferably aluminum. Aluminum is a preferred material for plate 259 to minimize x-ray generation in molybdenum collimation sheets 147.

Alternatively, collimation grid 90 can be formed of sheets 147 fabricated out of both high atomic number materials and low atomic number materials to minimize the amount of fluorescent K x-rays which emanate to the patient. Fluorescent K x-rays, which are generated by the interaction of the x-rays emanating from the target 50 with the materials of the collimator sheets 147, are typically undesirable because they increase patient exposure without contributing to the formation of an x-ray image. The K x-rays can be attenuated by plate 259, but plate 259 should also be transparent to pencil beam 100. This is preferably accomplished by using materials of low atomic number for sheets 137, preferably brass, since low atomic number materials produce low energy K x-rays which can be strongly attenuated by plate 259. For example, a sheet of aluminum 1 mm thick for plate 259 will typically reduce the K x-ray intensity of brass by approximately 99.9%, while being relatively transparent to the higher energy x-rays of pencil beam 100. Brass is therefore a superior material for sheets 137 from the point of view of stopping K x-rays but, by itself, provides inadequate attenuation for the x-rays emanating from target 50 which do not pass through collimator aperture 140. Therefore collimator sheets 137 preferably comprise a combination of materials, with higher atomic number materials such as tungsten, lead or molybdenum at the side of collimation grid 90 closest to the target 50 and low atomic number material such as brass on the side closest to the object 80 to be imaged. Presently preferred is a combination of molybdenum and brass, which provides for high collimation grid efficiency while producing low energy K x-rays which are strongly attenuated by plate 259.

The apertures 140 of collimation grid 90 are preferably either round or square in cross section. Other shapes could also be used, particularly hexagons, although the shape of the aperture holes should preferably match the shape of the multi-detector array, since the aperture shape affects the shape that x-ray beams will tend to diverge into. For example, the presently most preferred round aperture hole will tend to produce an x-ray beam that diverges into a circular shaped beam at the multi-detector array. Therefore, if round apertures are used, the multi-detector array is preferably circular to maximize its exposure and coverage to the circular x-ray beams.

If square apertures 140 are used they should preferably be 0.0381 cm (0.015 in) by 0.0381 cm in dimension while round apertures are preferably 0.015 in (0.038 cm) in diameter. Both square and round apertures yield a cross sectional area at multi-detector 110 that is about 1/100 the cross sectional area of detectors of known x-ray fluoroscopes. The cross sectional area of the face of the multi-detector array 110 is much smaller than in known conventional systems. As a result, x-rays scattered at the object miss the multi-detector array and do not tend to fog the image as they do in conventional systems which typically utilize relatively large surface area detectors.

Figure 3B:
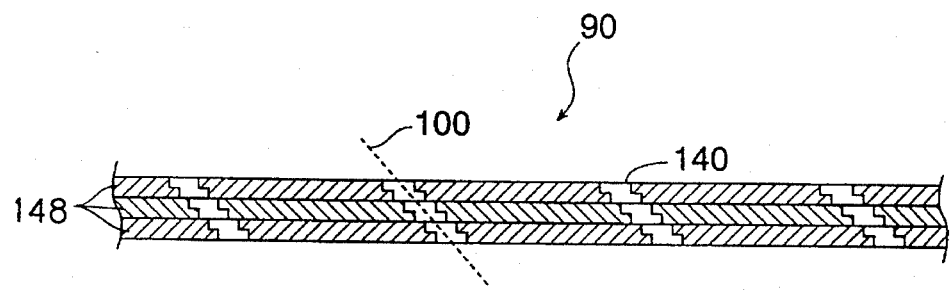

The presently preferred method for fabricating the collimation grid 90 is by photo-chemical milling or etching. Photo-chemical milling is presently preferred because it is cost effective and accurate. According to one embodiment of this method, a set of 50 photo masks is created to etch holes or interstices into 50 thin sheets of 0.0254 cm (0.010 in) thick material. In an alternate embodiment, a set of 100 photo masks is created to etch holes or interstices into each side of the 50 thin sheets of 0.0254 cm (0.010 in) thick material. The etched sheets are then preferably stacked, aligned and held together to form a grid assembly having a plurality of stepped apertures, each of a predetermined angular relationship with respect to the sheets. FIG. 3A shows an embodiment of the preferred collimation grid 90. This variation includes a number of x-ray absorbing sheets 147 having individual apertures with a constant cross-section (however, the cross-section need not be constant). The resulting aperture 140 has a stepped configuration, as shown, while allowing the x-ray pencil beam 100 to pass through to the multi-detector array 110. The variation shown in FIG. 3B is quite similar to that shown in FIG. 3A except that the individual apertures formed in x-ray absorbing sheets 146 are themselves stepped. These stepped apertures may be made by milling or chemical etching from each side of sheet 146 with a slight offset as described above so as to result in the configuration shown. The FIG. 3B configuration is highly desirable because less x-ray energy need be absorbed within the stepped apertures 140 of collimation grid 90 and consequently, the x-ray flux at the edge of the x-ray beam 100 is not attenuated as much as in the variation shown in FIG. 3A. X-rays are generally unaffected by the roughness of the channels due to the stepped surface, and even if they are scattered within the aperture, the scattering will not measurably affect the resultant beam. The stepped apertures shown in FIGS. 3A and 3B can also be beneficial in controlling the K x-ray intensity as discussed in U.S. Pat. No. 2,638,554, issued to Bartow et. al., entitled "Directivity Control of X-rays."

Figure 4:
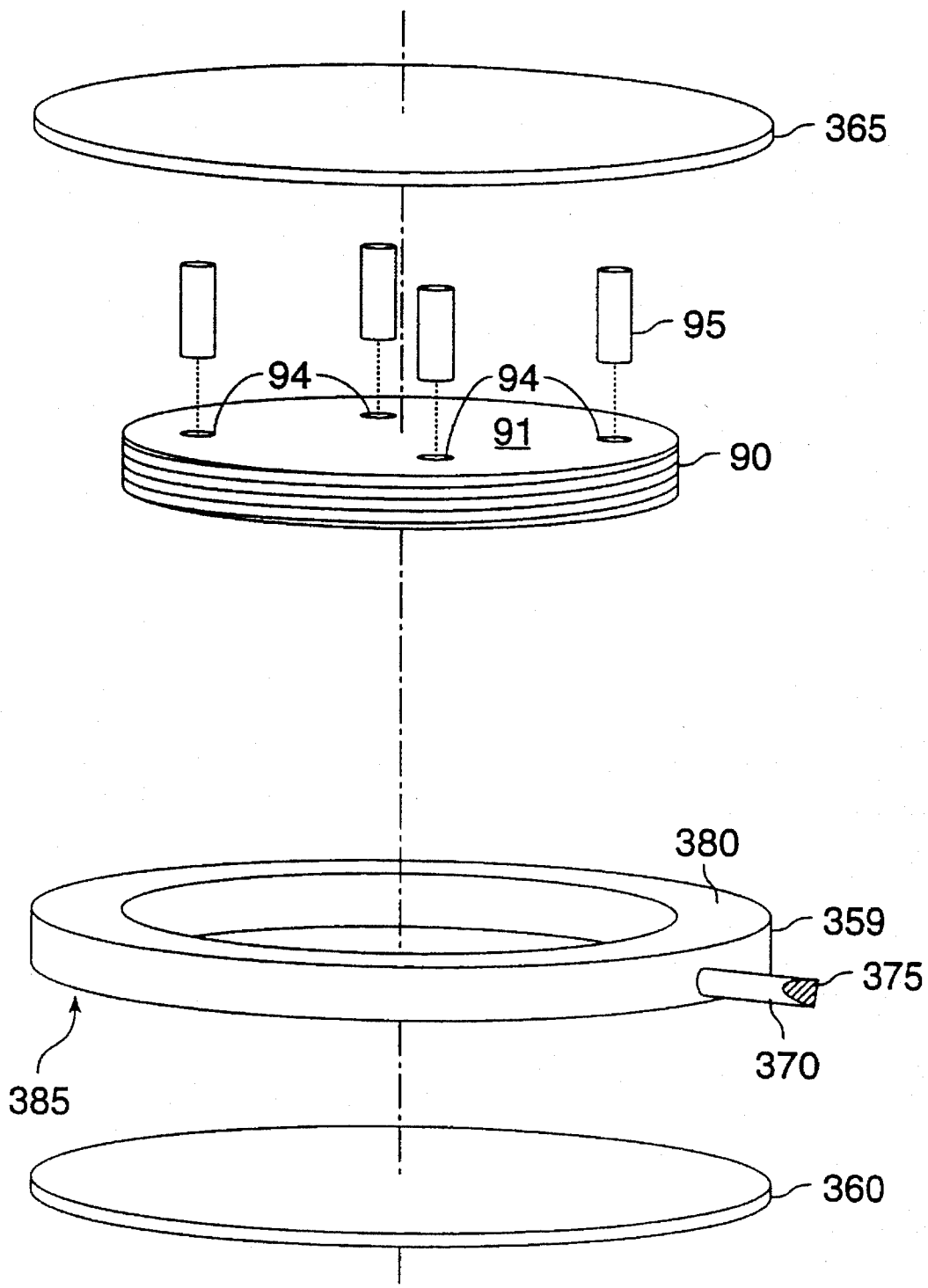
FIG. 4 is a perspective exploded diagram showing assembly for a preferred embodiment of a collimator grid.

FIG. 4 shows a preferred method for assembling the preferred collimation grid assembly 90 from etched sheets 91. Preferably 50 etched sheets 91 are each provided with alignment holes or alignment apertures 94. Alignment pegs 95 are placed in each alignment aperture 94 to align the etched sheets 91. The assembled sheets 91 and pegs 95 are placed in aluminum ring 359. Aluminum ring 359 is provided with a vacuum port 370 which may, after assembly, be sealed with pinch off 375. Aluminum sheet 365 which is preferably 0.1 cm in thickness is bonded and sealed with a vacuum adhesive to upper surface 380 of ring 359. Aluminum sheet 360 is similarly bonded to a lower surface 385 of ring 359. A partial vacuum is then pulled through port 370 and the port 370 is then sealed at pinch off 375. The partial vacuum causes relatively x-ray transparent aluminum sheets 360 and 365 to provide a clamping action tending to hold etched sheets 91 together and in alignment to form a collimation grid 90. The presently preferred tolerance for the aperture center-to-center distance is +/−0.00127 cm (0.0005 in) without cumulative error. The presently preferred tolerance on the aperture sizes is +/−0.00254 cm (0.001 in). For ease in assembly the diameters of apertures in every other sheet may be fabricated to be larger than the diameter at the output face of the collimator. Thus, only every other sheet need be carefully aligned. The material used for the sheets 91 as discussed above can be molybdenum, brass, lead, copper, tungsten, tantalum, gold or any of these used in combination. Molybdenum is a preferred material for use in the sheets 91, but more preferred at present is a combination of molybdenum and brass.

In an alternate method to fabricate collimator grid 90, the alignment holes 94 are etched along with the apertures 140. However, due to the differential between the sizes of the apertures 140 and the alignment holes 94, undercutting of the apertures 140 occurs because the time for etching is governed by the time it takes to etch the large holes. In a presently preferred alternative method, pilot alignment holes smaller than the final size of the alignment pegs are etched into the sheets 91. The etched sheets 91 then undergo an additional procedure such as reaming to enlarge the pilot alignment holes to the desired diameter. The finished sheets are aligned and clamped together as previously described.

Alternative methods for fabricating collimation grid 90 include electron beam machining, drilling, mini-machining, and laser drilling. Drilling and laser drilling are useful for generating round holes, but a drawback is the relative difficulty in generating square holes with either method. In addition, these non-etch methods typically require greater time and costs when compared to the above described etching methods.

Figure 5:
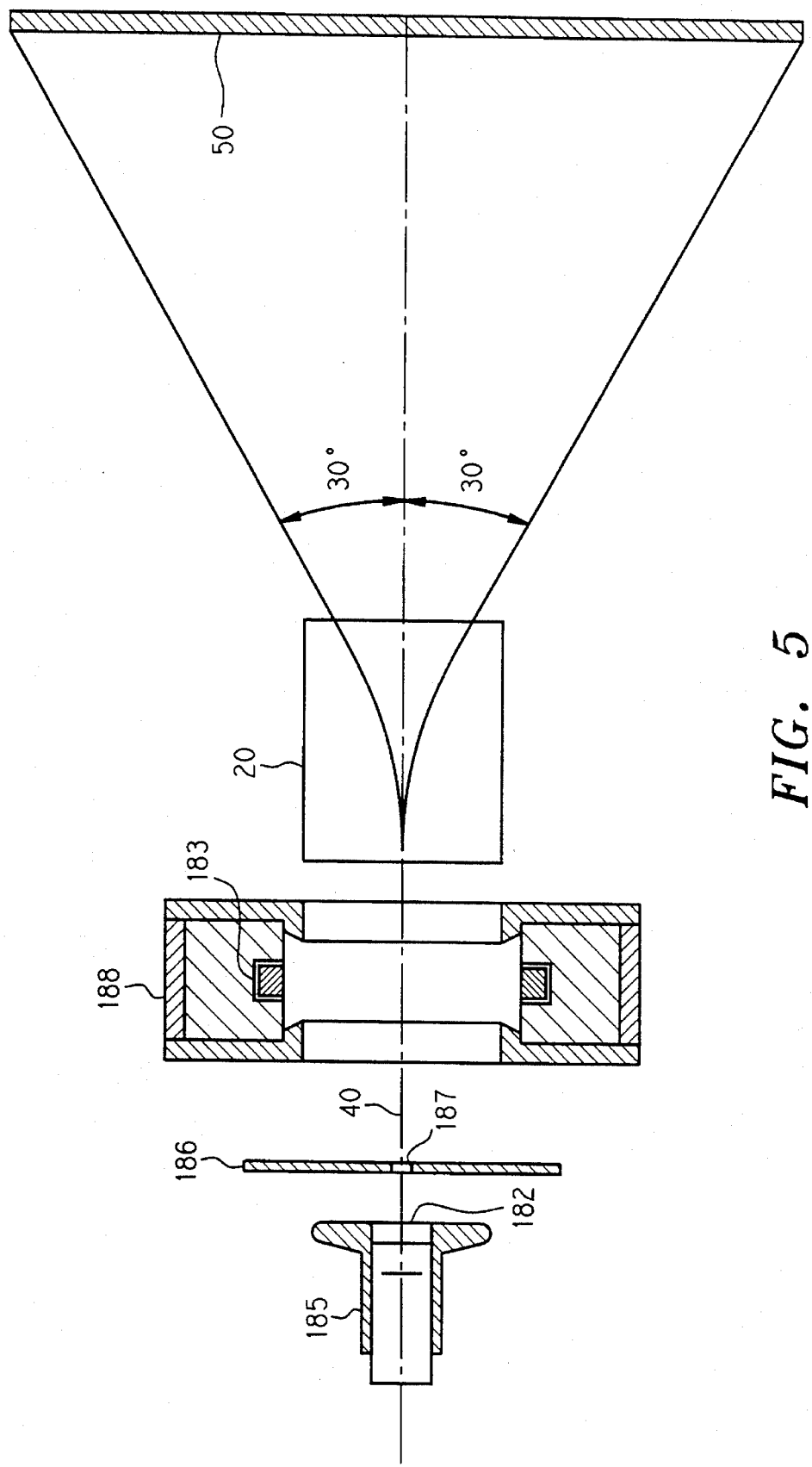
FIG. 5 is a functional representation of components of an x-ray tube for a scanning-beam x-ray imaging system.
Figure 6:
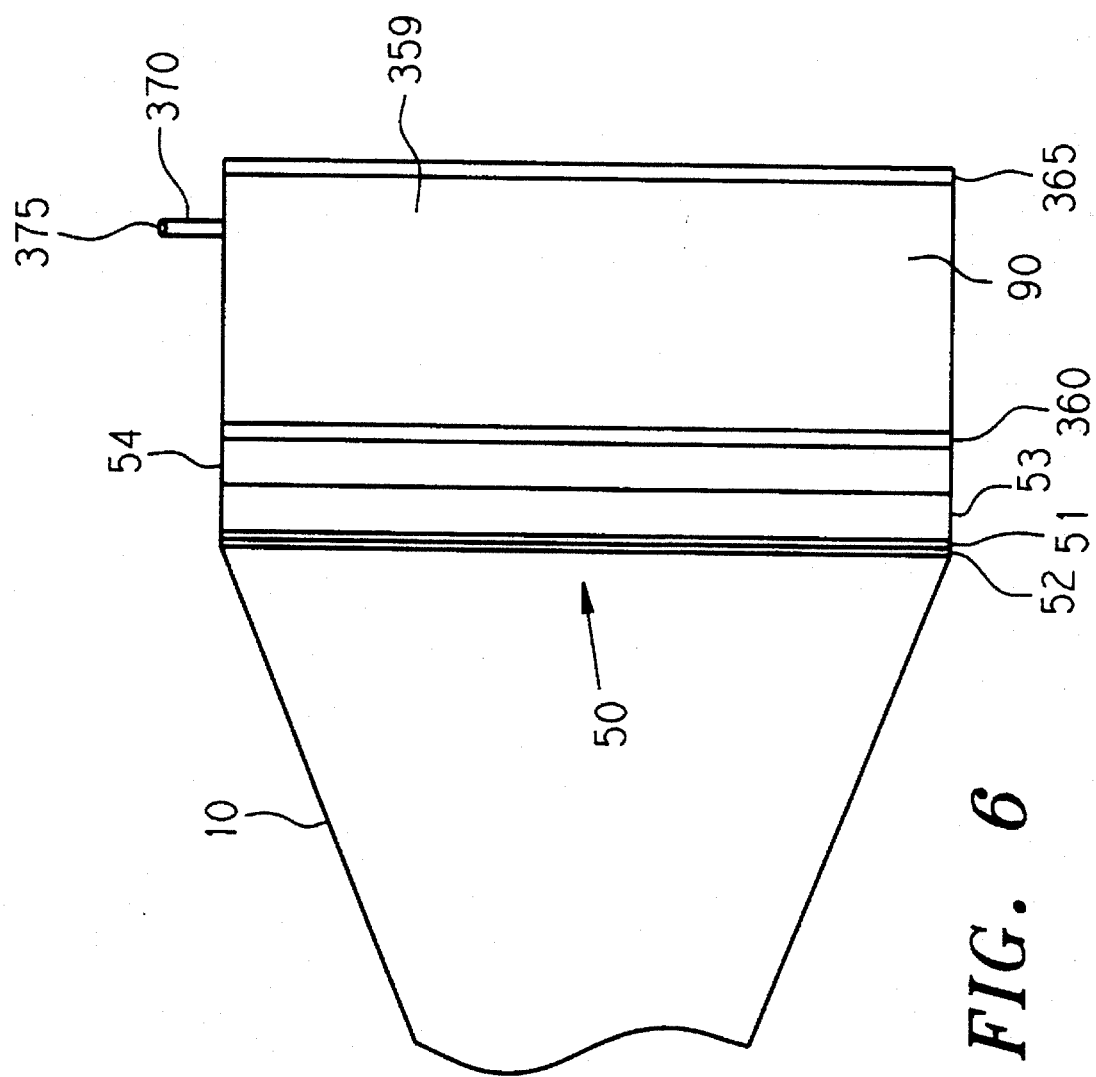
FIG. 6 is a diagram showing the target end of a preferred x-ray tube for a low dosage scanning-beam x-ray imaging system.

More details of the preferred scanning x-ray source 10 are shown in FIGS. 5 and 6. Grid controlled electron gun 185 is preferably located opposite the face of x-ray tube 10 and is operated at a potential between −70 kV to −120 kV. The electron beam 40 emanating from electron gun 185 can be controlled in amplitude and can be rapidly reduced to zero by the application of an appropriate voltage to a control grid 182. Grounded target 50 is preferably located at the face of the tube and electron beam 40 is preferably emitted from electron gun 185 towards target 50. A grounded anode 186 is preferably located near electron gun 185 and includes an aperture 187 at its center for electron beam 40 to accelerate the electrons as they pass through. Divergent electron beam 40 is accelerated towards anode 186 and passes through aperture 187. Magnetic focus lens 188, preferably of fixed power, causes the electron beam 40 to become convergent so that it strikes target 50 at focal spot 60. Focal spot 60 preferably has a diameter of 0.3 mm. Varying currents flowing in the coils of magnetic deflection yoke 20 preferably deflect the electron beam 40 so that focal spot 60 moves over the surface of target 50 in the previously mentioned preferred serpentine pattern. Dynamic focus coil 183 is energized by a current which varies in synchronism with the varying current in deflection yoke 20 to maintain the preferred 0.3 mm diameter for focal spot 60 as the electron beam 40 is scanned over the surface of target 50. The tube is preferably fabricated to have a 25.4 cm (10 in) diameter sweep area to correspond with the circular active area of the collimator grid 90. Electron beam 40 intersects target 50 at an angle of up to about 30° at the extremities of the circular active area. When the x-ray source 10 is in use, no more than one aperture 140 (possibly two for stereo) of collimation grid 90 will be passing an x-ray pencil beam 100 at any given instant. According to one preferred embodiment, the electron beam 40 may be shut off by application of a short rise voltage pulse to control grid 182 when focal spot 60 is not positioned directly in front of an aperture 140. Thus the x-ray tube may be operated effectively in a scanned-pulsed mode to reduce power consumption approximately 25% and heating of the target 50.

Turning to FIG. 6, a cross-sectional view of the front portion of the preferred x-ray source 10 is depicted. The interior of the x-ray source 10 is maintained at a vacuum. Target 50 as discussed above is comprised of a suitable target material deposited on beryllium target support 53 which is 0.5 cm thick. Forward of beryllium target support 53 is cooling jacket 54 which is preferably 0.2 cm thick and may be adapted to carry water, forced air or preferably Fluorinert™. Aluminum grid supports 360 and 365 are each preferably 0.1 cm thick and help support collimation grid 90 which is preferably 1.27 cm (0.5 in) thick. Aluminum grid supports 360 and 365 together with the beryllium target support 53 and the coolant in cooling jacket 54 preferably form an x-ray filter which filters out low energy x-rays. The presently preferred x-ray source is described more fully in copending U.S. patent application Ser. No. , Lyon & Lyon Docket No. 210/204, which has been incorporated herein by reference in its entirety.

Stereoscopic X-ray Imaging

Figure 7:
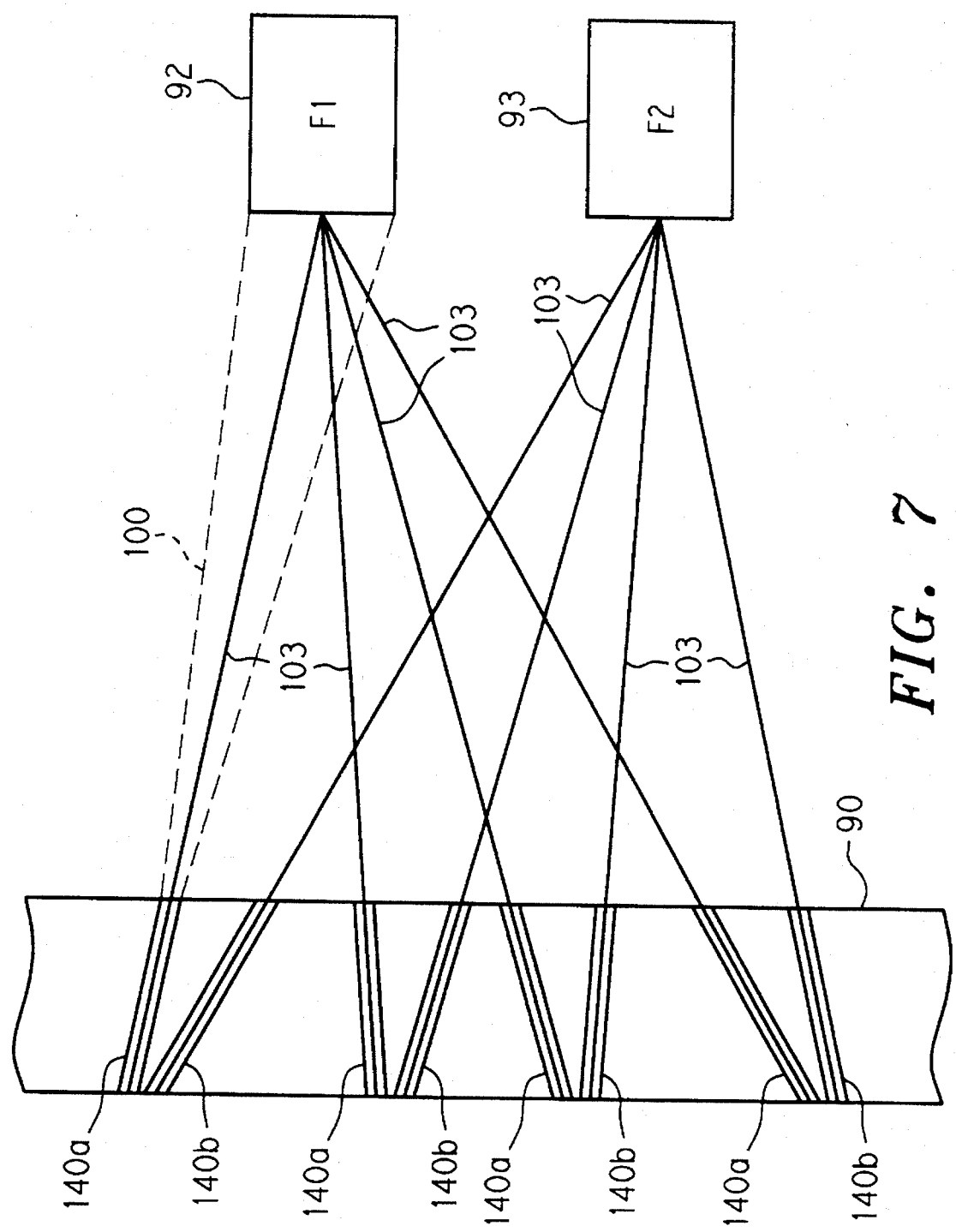
FIG. 7 is a diagram showing the axes of x-ray beams for a stereoscopic scanning-beam x-ray imaging system.

Turning now to FIG. 7, a collimation grid having more than one focal point may be provided so that stereoscopic x-ray images may be obtained. If, for example, the axes 101 of the x-ray pencil beams 100, corresponding to the aperture axes of every other row of apertures 140a in grid 90 are pointed at focal point F1 at the center of multi-detector array 92 and the aperture axes of the remaining apertures are pointed at focal point F2 at the center of multi-detector array 93, one can scan the apertures in a raster or serpentine pattern and create a "line" of data from the first multi-detector array, and a line of data from the second multi-detector array. Repeating this, it is possible to build up two complete images, as seen from two distinct angles and thereby display them with conventional stereoscopic imaging display systems to provide a stereoscopic x-ray image.

Figure 3C:
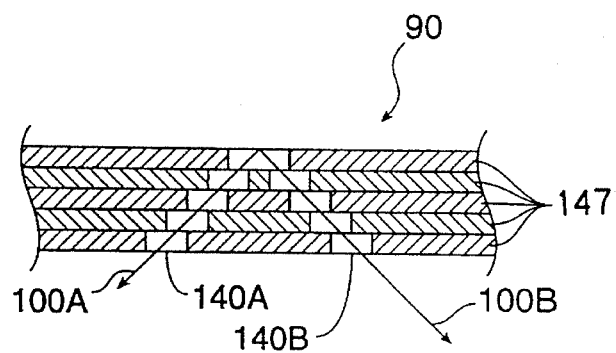

FIG. 3C depicts how one may construct such a stereoscopic collimation grid out of layers 147 of x-ray absorptive material. In this embodiment apertures 140A, 140B may diverge from a common first aperture 140 to form a "V" as shown providing separate paths along the "legs" of the "V" for x-ray pencil beams 100A, 100B. There is no requirement, however, that apertures 140A, 140B diverge from a common aperture as shown, but an advantage of the "V"-shaped aperture where the x-rays enter at the common aperture or apex of the "V" is that both multi-detector arrays 92 and 93 will be illuminated simultaneously, the "V" acting as an x-ray splitter with some of the x-rays going to multi-detector array 92 and some to multi-detector array 93. This decreases by 50% the power required for the beam current.

Figure 3D:
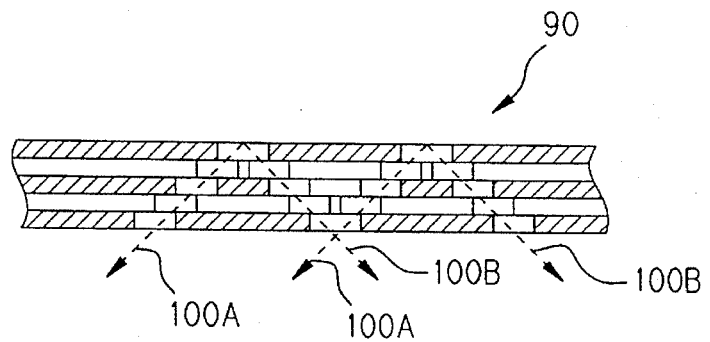

Additionally, the system may be designed to such that the common adjacent holes in the first sheet share common holes in the last sheet last two sheets as shown in FIG. 3D.

The Multi-Detector Array

To achieve resolutions of several line pairs per millimeter or more at the object plane, as are required in some medical applications, the spatial resolution limit in known reverse-geometry systems is in large part determined by the size of the single nonsegmented detector. Generally speaking, a small non-segmented detector can provide high spatial resolution while a large non-segmented detector provides high collection efficiency. It has in part been this trade-off that has been a problem in developing low dosage x-ray imaging systems. Other parts have been the inability to fabricate a suitable collimator and the lack of a high efficiency x-ray scintillator also having a fast decay time.

Figure 8A:
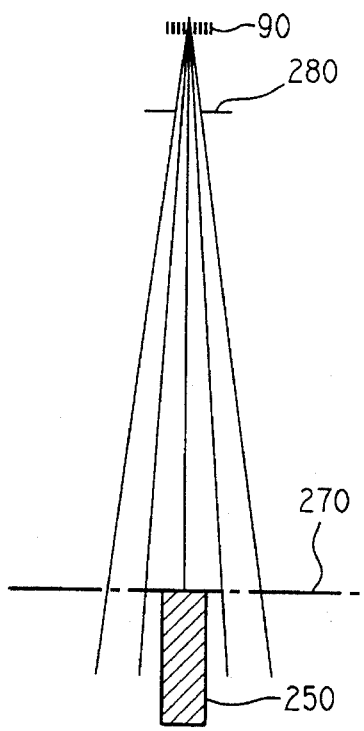
FIG. 8A depicts a single nonsegmented detector that is smaller in width than the x-ray beam emitted from an apertured x-ray source.
Figure 9:
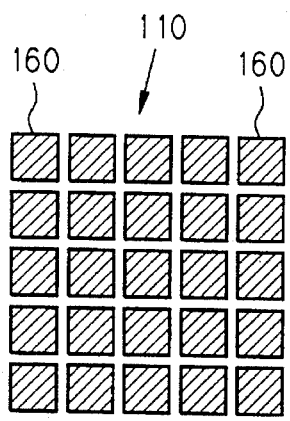
FIG. 9 is a front view of a 5×5 detector array.

When such a detector is small to increase resolution, a large proportion of the x-rays emitted by target 50 are unused by the single detector 250, as shown in FIG. 8A even when a collimator grid 90 is used. This is, in fact, how industrial reverse-geometry scanning-beam x-ray inspection systems are designed, where dose is usually not a consideration. Accordingly, while one can decrease the size of a detector by placing, for example, a lead washer in front of the single detector 250 and thereby increase spatial resolution, the x-ray intensity and/or exposure time would have to be increased to maintain contrast resolution By fabricating a multi-detector array having a large area subdivided into multiple smaller detector array elements (e.g., as shown by the front view of the multi-detector array 110 in FIG. 9) a large capture area is achieved, while simultaneously through image reconstruction techniques described herein retaining an image resolution that is comparable to the size of a single small detector element without increasing x-ray intensity an/or exposure time.

Figure 8B:
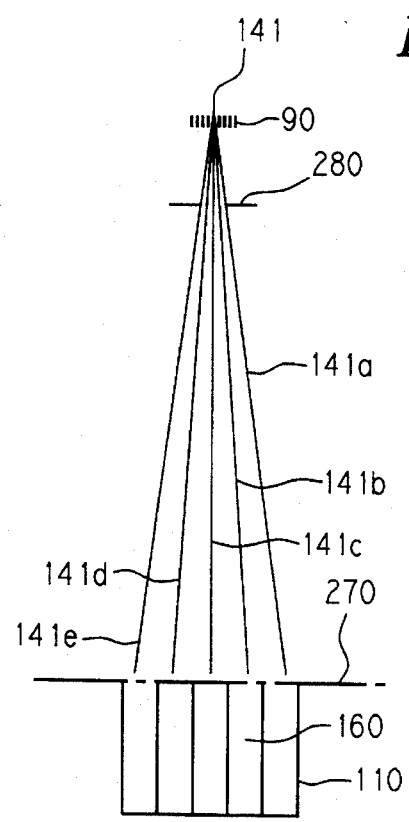
FIG. 8B depicts an x-ray beam from a single aperture of an apertured x-ray source interacting with a multi-detector array.
Figure 8C:
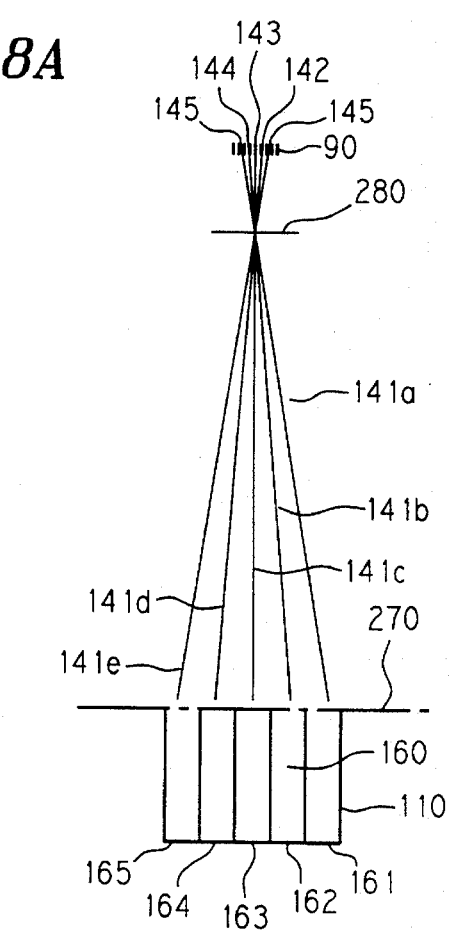
FIG. 8C depicts the axes for x-ray beams from a number of apertures of an apertured x-ray source passing through the same image pixel interacting with a segmented detector array.

The resolution defined by the individual detector elements 160 is maintained by distributing and summing the outputs from the individual detector elements 160 into a memory buffer in which each address, i.e., image pixel, corresponds to a specific location in the object plane 280. As an electron beam 40 is moved discretely across the target 50, illuminating the area behind selected apertures 140 of the collimation grid 90, the address, to which the output of a given individual detector element 160 is added, changes. The imaging geometry is shown in FIGS. 8B and 8C. In FIG. 8B a single x-ray beam 100 is shown along with how it generates information for 5 image pixels. Effectively, the single x-ray pencil beam 100 emanating from individual aperture 141 is divided into x-ray micro-beams, the number of x-ray micro-beams created corresponding to the number of individual detector elements 160 which comprise the multi-detector array 110. In the case shown in FIG. 8B. The axes of five x-ray micro-beams 141a, 141b, 141c, 141d and 141e are shown. In FIG. 8C the sequential positions of the axes of the x-ray micro-beams from x-ray pencil beams 100 emanating from five consecutive apertures 141 through 145 illuminating a single image pixel ("IP") are shown. The outputs from the five individual detector elements 161, 162, 163, 164 and 165 receiving the x-ray flux from the five x-ray microbeams, 145a, 144b, 143c, 142d and 141e respectfully, are added together to provide the luminance for the single pixel IP.

Stated differently, the output for each of the individual detector elements 160 is stored for later summation in an image buffer, at a memory address that corresponds to a very small specific region in the object plane 280, e.g., a single image pixel.

Accordingly, in one embodiment the memory storage address for the output of each individual detector element 160 changes with the position of the scanning x-ray beam 40 in an ordered fashion such that each memory address contains the sum of the radiation passing through a specific image pixel or spot in the object plane 280. In this way the spatial resolution of the system is determined by the size of a single individual detector element 160, while the contrast resolution of the system is determined by the area of all of the individual detector elements comprising the multi-detector array 110.

Figure 8D:
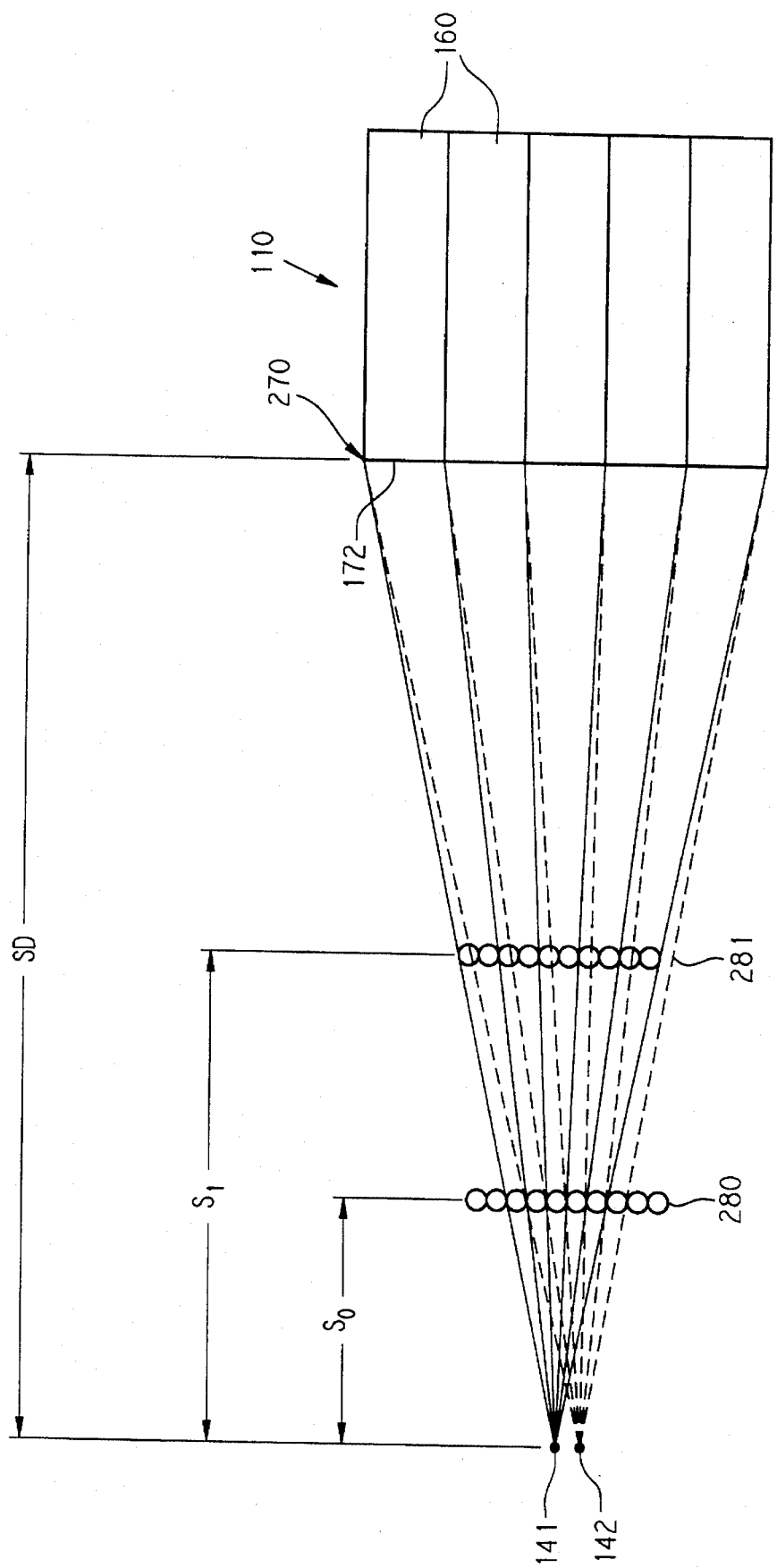
FIG. 8D is a diagram of x-ray beams from two apertures of an x-ray collimation grid interacting with an object under investigation at various distances from the x-ray source.

An additional benefit of this multi-detector array imaging geometry is that the depth of field of the object plane 280 is narrowly defined. Structures lying in front of or behind it will be blurred (out of focus). X-ray pencil beams from a first aperture 141 and a second aperture 142 are depicted in FIG. 8D passing through an object plane 280 a distance $S_0$ from apertures 141, 142 and passing through a plane 281 a distance $S_1$ from apertures 141, 142 where $S_1 > S_0$. The bubbles represent image pixels $IP_1$ through $IP_{10}$. As can be readily seen, the resolution at $S_1$ is less than that available at $S_0$. This feature provides for improved localization and visualization of detailed structures in the plane of interest 280, while providing an adequate depth of field that may be modified by the system geometry.

The multi-detector array 110 of the presently preferred embodiment comprises 96 individual detector elements 160 arranged in a pseudo-round array of square scintillator elements 0.135 cm on a side disposed within a circle of diameter about 1.93 cm (0.72 in). This number of individual detector elements is merely illustrative. The preferred multi-detector array 110 is described more fully in co-pending patent application Ser. No. 08/387,292, Lyon and Lyon Docket No. 210/205, which has been incorporated herein by reference in its entirety.

The Detector Elements

Conventional image intensifier technology typically has basic constraints that limit a system's sensitivity. One of the objects of the present invention is to provide a scanning-beam x-ray imaging system which will result in the subject under examination being exposed to the lowest possible level of x-rays commensurate with achieving image quality adequate to meet the requirements of the procedure being performed. This means that the system used to detect the x.-ray photons emerging from the subject preferably has the highest possible detective quantum efficiency. To achieve this, the scintillating material used in the individual detector elements preferably has a length in the direction in which the x-ray photons travel that is sufficient to ensure that no x-ray photons emerge from the end opposite the incident x-rays, i.e., the x-ray photon energy should be adequately dissipated in the material to maximize the output of the detector.

There are several types of individual detector elements which can be used in the presently described scanning-beam x-ray imaging system. That which is currently preferred comprises a scintillator in which x-ray photon energy is converted to visible light energy and the light intensity is then converted to an electrical signal by means of a photomultiplier, photo diode, CCD or similar device. Because the information from each aperture must be obtained in a very short time period, the scintillating material should have a fast response and a minimum afterglow time. Afterglow is the phenomenon wherein the scintillator continues to emit light after the stimulating incident x-rays have ceased. Even faster response and shorter afterglow times are required if x-ray intensity measurements are obtained using the preferred x-ray photon counting technique.

Plastic scintillators, such as organic loaded polystyrene, are suitable from a standpoint of speed in that they have the required fast response and minimum afterglow characteristics. However, plastic scintillators have a relatively small x-ray photon interaction cross section so that their linear x-ray absorption coefficients are also small in value. The consequence is that a considerable thickness is required to absorb x-ray photons. For 100 kV x-rays, a typical plastic scintillator should be about 28 cm (11 in) thick to capture 99% of the incident x-rays. More preferred materials at present (and in order of preference) are: (1) YSO (cerium doped yttrium oxy-orthosilicate) available from Airtron (Litton) of Charlotte, N.C.); (2) LSO (cerium doped lutetium oxyorthosilicate) available from Schlumberger, Inc.); and (3) BGO (bismuth germanate, available from Rexon Components, Inc. of Beachwood, Ohio). YSO and LSO are advantageous in that they may be used at room temperature. BGO must be heated to about 100° C. in order to achieve a suitable light output decay period of the order of 50 nanoseconds. These scintillating materials need not be as long as the plastic scintillator and are typically effective at a length of 0.10 cm, and preferably at a length of several millimeters.

According to one embodiment of the present invention, multi-detector array 110 comprises at its input face a pseudo-round array of 96 densely packed scintillators including two rows of 12 and two columns of 12 at its horizontal and vertical midplanes spaced a distance of preferably 91.4 cm (36 in), and more preferably 94.5 cm (37.2 in), from the x-ray source 50. (FIG. 15) A square 5 by 5 and a square 3 by 3 array are also contemplated as is a non-square array of scintillators square cross sections filling a circle about the center of the multi-detector array. If scintillators 170 have parallel sides, x-rays entering near the edges may strike the scintillator walls and pass through to a neighboring scintillator of an adjacent detector element causing the detected element to generate an output seemingly from the wrong spatial position in the subject with consequent degradation of the image quality. This problem is addressed by placing shielding material between the neighboring scintillators. While some x-ray photons are lost, in that they may not generate a light photon, due to the image reconstruction method employed, the resultant image is not affected to any substantial degree.

Figure 10:
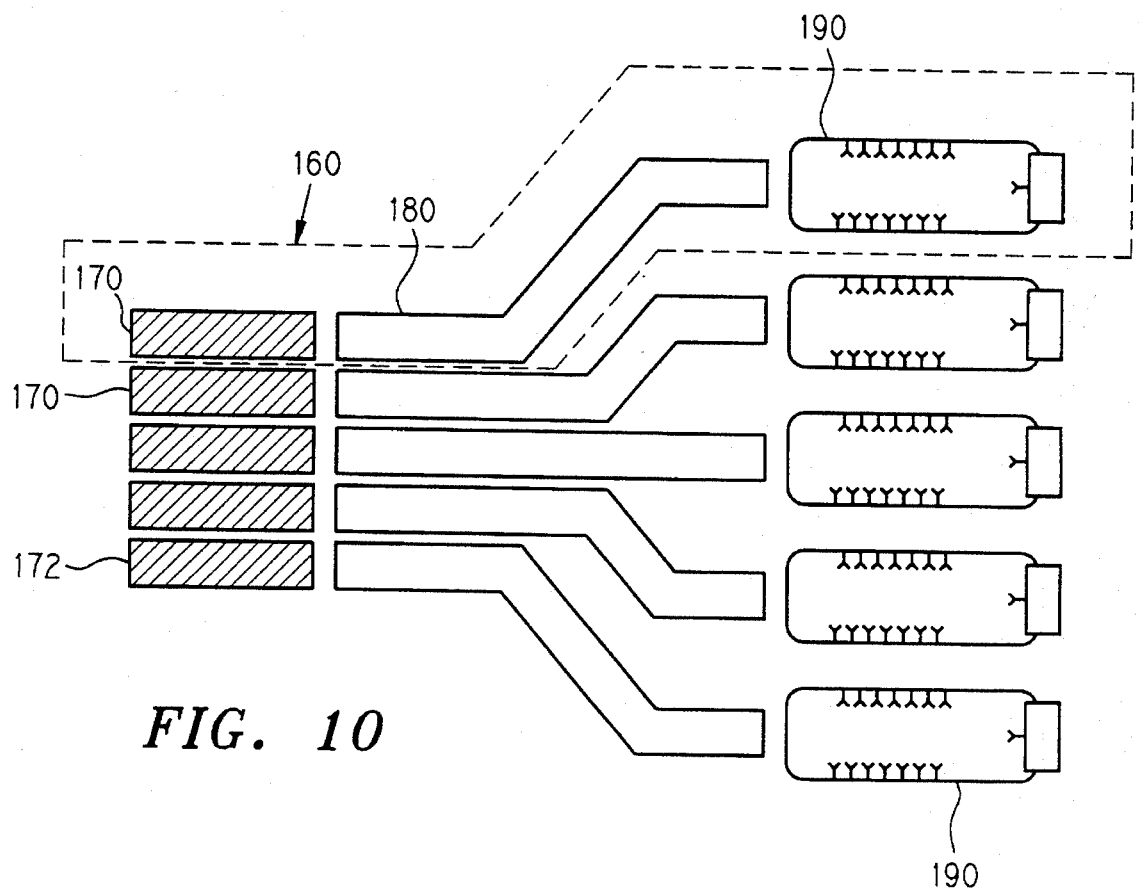
FIG. 10 is a functional representation of one row or column of detector elements for a 5×5 detector array for an embodiment of a low dosage scanning-beam x-ray imaging system.

Referring now to FIG. 10, according to one presently preferred embodiment of the detector element 160, each scintillator element 170 is preferably in Contact with a light pipe or fiber-optic coupler 180 which optically couples each scintillator element 170 with a corresponding photomultiplier tube 190 or solid state detector. A coupling oil is preferably used between each end of the fiber optic coupler to ensure proper transmission at the interfaces. Alternatively, scintillators 170 may be located in close physical proximity to their corresponding photodetectors, eliminating the fiber optic coupler.

Figure 11:
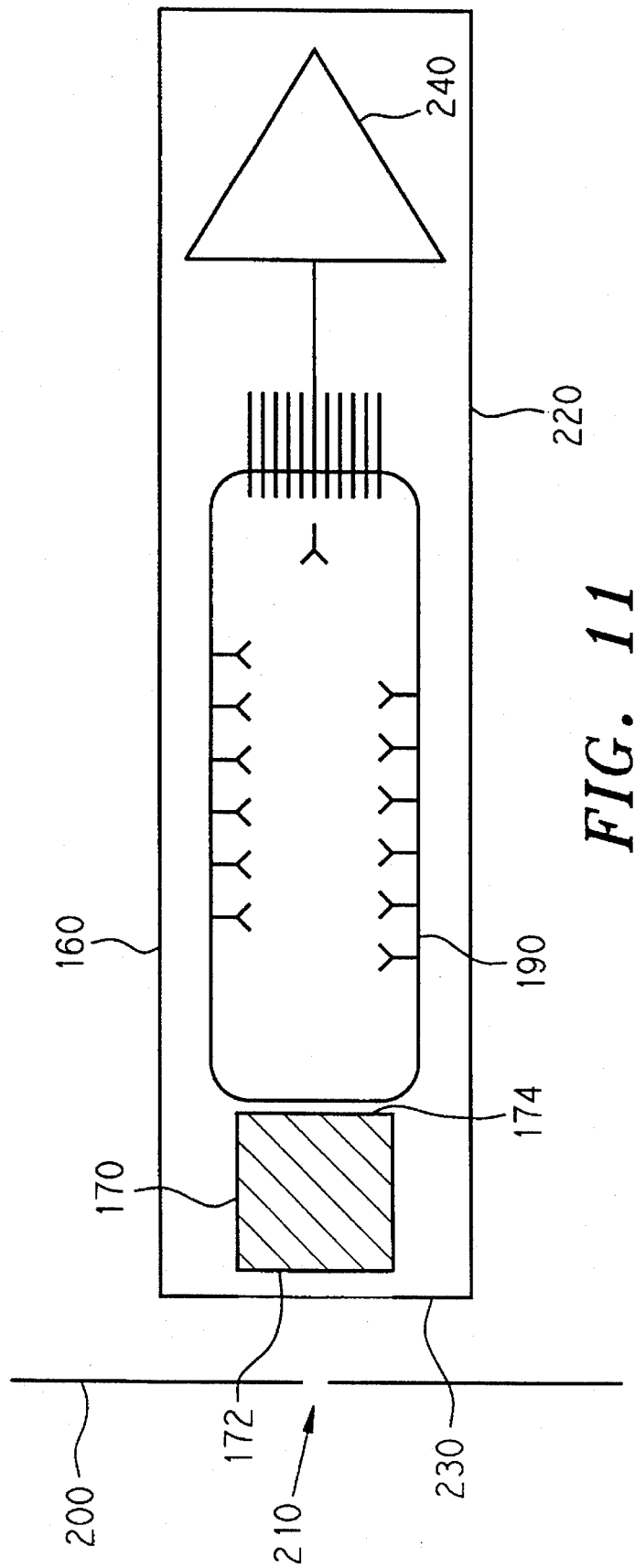
FIG. 11 depicts an embodiment of a detector element for a low dosage scanning-beam x-ray imaging system.

FIG. 11 shows an alternative configuration of a detector element 160 without the optical coupler. An x-ray opaque sheet 200 with apertures 210 corresponding to each detector element 160 is disposed in front of multi-detector array 110. Each detector element 160 is enclosed in a light tight enclosure 220 which may also be x-ray opaque. A light blocking window 230, preferably made of thin aluminum sheet is located at the front of light tight enclosure 220. Light blocking-window 230 is x-ray transmissive. Within light tight enclosure 220 is a scintillator element 170 in close proximity to a photomultiplier tube 190 which is preferably electrically connected to a pre-amplifier 240.

Alternatively, scintillators could be placed in direct or close contact with an array of photo diodes, photo transistors or charge coupled devices (CCDs) to achieve a rugged and compact detector. Where solid state devices, particularly CCDs, are used, cooling, such as with a Peltier-type cooler, or the like, may be employed to increase the signal-to-noise ratio of the device. Alternatively, the scintillator array could be placed in direct or close contact with one or more position sensitive photomultiplier tubes which provide an output signal which identifies the position coordinates of the light source as well as its amplitude.

According to a presently preferred embodiment of the present invention, the scintillators are coated along their lengths and the input face with a material which reflects light, such as preferably titanium dioxide, to prevent light from escaping from or entering the scintillators and to aid in internal reflection within the scintillators.

Figure 12:
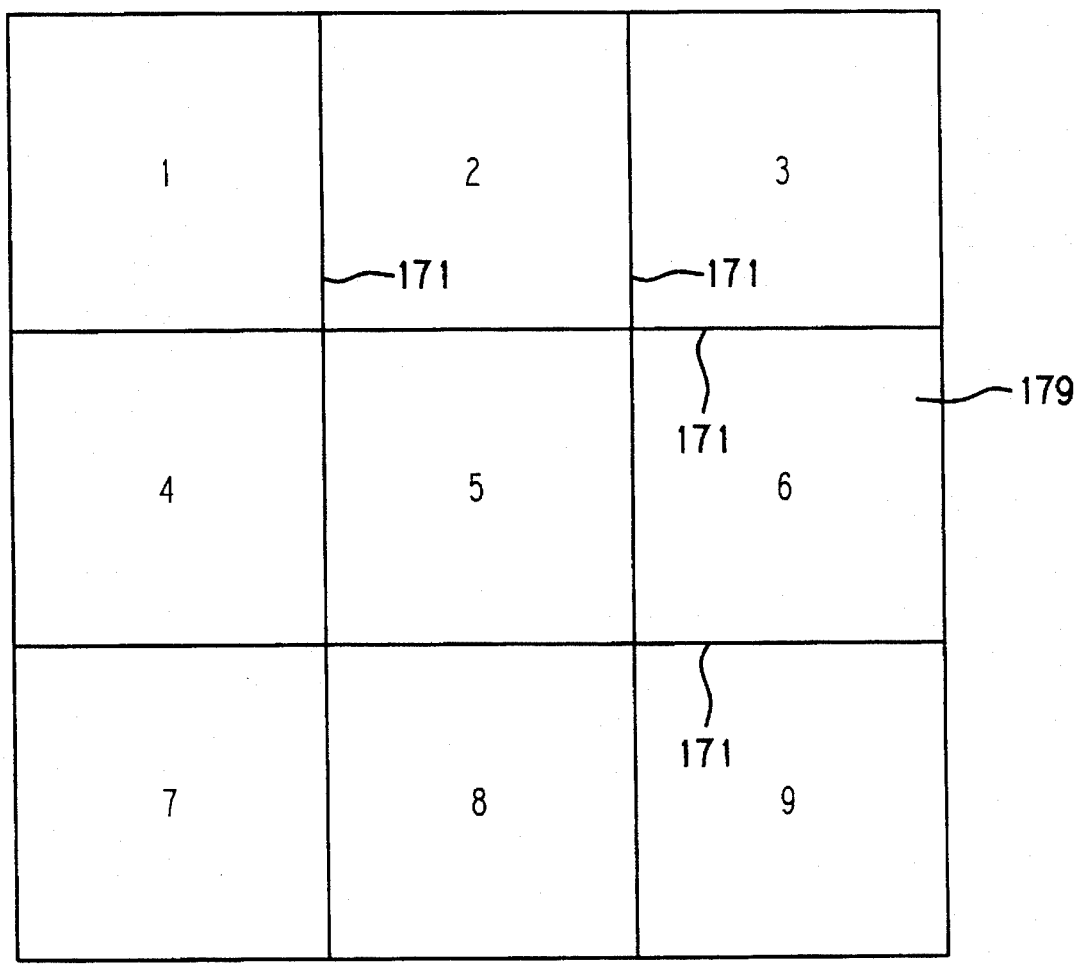
FIG. 12 is a diagram of a front view of a 3×3 multi-detector array for an embodiment of a low dosage scanning-beam x-ray imaging system.

According to a preferred embodiment of the present invention, each scintillator element 170 is isolated from its adjacent scintillator elements 170 by a thin sheet 171 of a highly x-ray opaque material such as, for example, gold or lead. Sheets 171 may be about 0.0102 cm (0.004 in) to 0.0127 cm (0.005 in) thick and is most preferably 0.0051 cm (0.002 in) to 0.0127 cm (0.005 in). An example of the position of sheets 171 between the scintillators 170 is shown in FIG. 12.

The area of the circular active area of collimation grid 90 is preferably larger than the area of multi-detector array 110. Thus the axes of the x-ray pencil beams 100 emitted from the respective apertures 140 of collimation grid 90 all converge toward the multi-detector array 110 while each individual x-ray pencil beam 100 diverges, or spreads, as would a flashlight beam to cover the face of the multi-detector array 110.

Image Reconstruction

An important advancement of the present invention concerns the application of an image reconstruction system to obtain high quality x-ray images. The output of the multi-detector array is preferably not applied directly to the luminance input of a video monitor. Instead, digitized intensity data for each image pixel are stored in a discrete address in a "frame store buffer". More than one such buffer may be used in certain applications. Pixel addresses within the buffer can be randomly accessed and the intensity value can be manipulated mathematically. This function has application in applying various image enhancement algorithms and it allows for pixel assignment of the data from discrete segments of the detector array.

Figure 13:
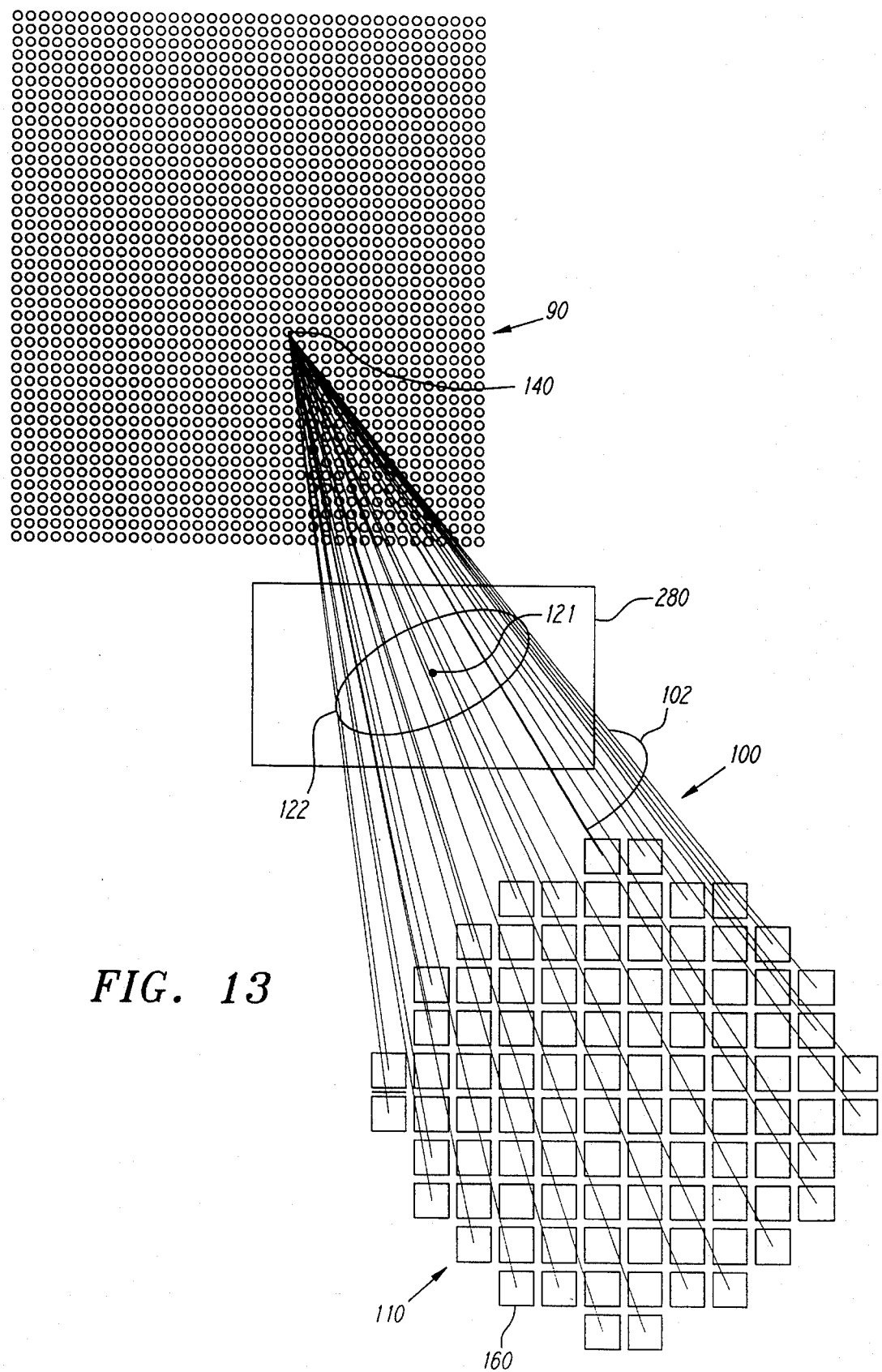
FIG. 13 depicts x-ray paths of an x-ray beam emanating from a single collimator aperture passing through an object plane to a multi-detector array.

Referring to FIG. 13, this diagram illustrates the divergence of a single x-ray pencil beam 100 from aperture 140 to the multi-detector array and how it intersects an object 80 (not shown) at object plane 280. Image pixel 121 is just one of the image pixels comprising the x-ray pencil beam intersection area 122 of object plane 280. A representative sample of the axes 102 of the x-ray micro-beams created by having a segmented array are also shown. In FIG. 13, x-ray pencil beam 100 is shown emitted through a single aperture 140 of collimator grid 90. X-ray pencil beam 100 as it exits aperture 40 will diverge forming a cone having a cross section the size of the aperture as it exits the aperture to a cross section covering the scintillators of the detector elements of the multi-detector array by the time it reaches the 96 element multi-detector array 110. The 96 element multi-detector array 110 is preferably positioned and designed such that the area of the cone of the x-ray beam 100 just covers the surface area of the multi-detector array 160 when the x-ray pencil beam 100 intersects the face of the multi-detector array.

As x-ray pencil beam 100 passes through an object 80, information about object 80 will be detected by the multi-detector array 110 as x-ray intensity values. Because multi-detector array 110 is composed of 96 separate detector elements, each detector element 160 will detect only the intensity value for the particular x-ray micro-beam 101 of a segment of x-ray pencil beam 100 that it intersects with. The cross sectional shape and area of the x-ray micro-beams will correspond to the cross sectional area and shape as the input face of the detector elements. For example, if the input faces are square, the x-ray micro-beam will have a square cross section. The x-ray pencil beam 100 emitted from each aperture 140 on collimator grid 90 will therefore generate one group of 96 separate or discrete pieces of information (the intensity value at each detector element) about 96 areas of object 80 in the x-ray pencil beam's 100 path 122. The intensity information from each of the x-ray micro-beams provide partial image pixel information which can be used to compile complete image pixel information for each image pixel in a desired plane of object 80.

Figure 14:
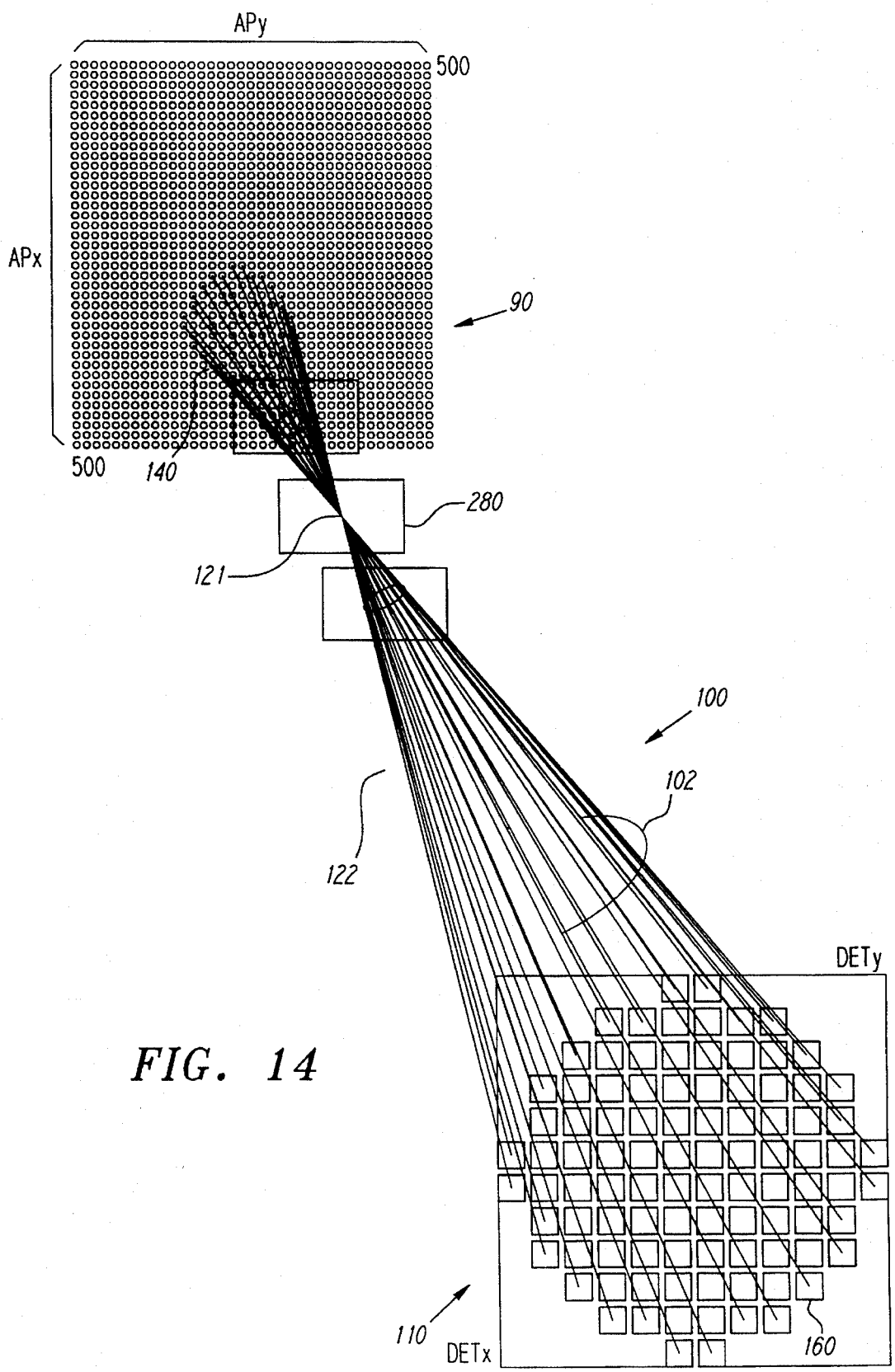
FIG. 14 depicts x-ray paths of multiple x-ray sub-beams emanating from multiple apertures passing through a single pixel to a multi-detector array.

FIG. 14 illustrates the axes 102 of all of the x-ray micro-beams from all of the apertures 140 that intersect a single image pixel 121 in object plane 280 as they travel to the multi-detector array 110. This image pixel group of x-ray micro-beams is ultimately processed to generate an image pixel on a video monitor. In a preferred embodiment of the scanning-beam x-ray system, the apertures 140 on collimator grid 90 will generate x-ray pencil beams 100 in a predetermined pattern. As x-ray pencil beams 100 pass through an object, x-ray micro-beams 101 from adjacent and nearby apertures will intersect at, for example, point 121 (e.g. an image pixel) in the object. The intensity of each of these x-ray micro-beams 101 from these x-ray pencil beams 100 after they pass through the object provide information about these intersecting points in the object. In this preferred embodiment, each intersecting point on the object can therefore be considered a single-image "pixel" 121. In accordance with the techniques explained in more detail herein, each image pixel 121 is preferably mathematically reconstructed from the intensity information of the separate x-ray micro-beams 101 that were generated by the detector elements 160 for each of the emitted x-ray pencil beams 100 from, for example, the image pixel group of apertures that generated x-ray micro-beams whose axes passed through the object at that point, image pixel 121.

According to a preferred embodiment of the present invention, the output image would preferably consist of up to about 250,000 pixels, arranged in 500 rows and 500 columns. For the purpose of the explanatory example below, it is assumed that the scanning x-ray source is momentarily centered upon the point, P, located at row 100 and column 100 of collimation grid 90. It is further assumed in regard to this embodiment that the detector array 110 consists of a square 3-by-3 multi-detector array 110 containing 9 detectors 179 (FIG. 12) and that each detector 179 is sized so as to intercept all of the x-ray emissions associated with a single image pixel. Other array configurations obviously may be used as are detailed herein.

The resulting intensity values, preferably digitized from the individual detectors of the multi-detector array 110, may be assigned to pixel buffer addresses as follows:

detector 1—row 99, column 99 detector 2—row 99, column 100 detector 3—row 99, column 101 detector 4—row 100, column 99 detector 5—row 100, column 100 detector 6—row 100, column 101 detector 7—row 101, column 99 detector 8—row 101, column 100 detector 9—row 101, column 101

In this example, a corresponding pattern of data assignment is repeated as the scanning x-ray beam passes behind all of the pixels.

In the displayed image, with a sub-sampling ratio of 1:1, the numerical value of each image pixel is equal to the sum of "n" parts where "n" is the number of detectors 179 in the multi-detector array 110 (in this example, n=9).

When constructed as shown in this example, the multi-detector array 110 together with the image reconstruction method selected, has the effect of fixing the working distance at which optimum focus is obtained and providing a plane of optimum focus not available in prior art non-segmented detector scanning-beam imaging systems.

The following parameters must be taken into consideration in design of the multi-detector array:

1. The size and shape of the collimated beam from the x-ray source (target 50);

2. The distance between the target 50 and the multi-detector array 110, "SD" (FIG. 8);

3. The distance between the source 50 and the center of the object of interest 280, "SO";

4. The desired resolution, or pixel size at the object of interest 80; and,

5. In medical applications, the total area of the multi-detector array 110 must be large enough to intercept all of the x-rays in x-ray pencil beam 100 emanating from the collimation grid 90, to avoid exposing the patient to x-ray radiation which does not contribute to the image.

In a preferred embodiment of the invention, the distance between the target 50 and the exit side 260 of collimation grid 90 is about 2.271 cm (0.894 in), and more preferably 2.54 cm (1.00 in) (see FIGS. 3 and 6). Apertures 140 are preferably round with a diameter of 0.0381 cm (0.015 in). If the apertures are square they are preferably 0.0381 cm on a side. The spot size of electron beam 40 on target 50 is preferably about 0.0254 cm (0.010 in) in diameter. The multi-detector array 110 is preferably about 91.4 cm (36 in), and more preferably about 94.5 cm (37.2 in), from target 50. The preferred beam divergence angle of x-ray pencil beam 100 is calculated by 2*ARCTAN((spot diameter/2)/((aperture width/2)+(spot diameter/2))* (spot diameter). The projected x-ray pencil beam 100 diameter is SD * TAN(divergence angle). It has been determined that the preferred size of the multi-detector array 110 should be about 2.54 cm (1 in) in diameter for the more preferred embodiment.

For example, with a multi-detector array size of 2.54 cm (1 in) square, if the object plane to be imaged is 22.86 cm (9 in) from target 50 and the desired image pixel size is 0.0508 cm (0.020 in) at the object plane, and the distance from the target 50 to the multi-detector array is 91.4 cm (36 in), the projected size of image pixels at the detector plane 270 is (SD/SO)*pixel size at object, or 0.2032 cm (0.080 in). The desired resolution may be obtained by dividing 2.54 cm (1 in) by 0.2032 cm (0.080 in) yielding a square multi-detector array having 12 to 13 detector elements on a side. Other configurations are possible depending upon the circumstances in which the invention is to be used.

Outside of the plane of optimum spatial resolution, SO (280 in FIG. 8D and FIG. 14), spatial resolution will degrade. In some applications, such as imaging of the human heart, degraded spatial resolution outside of the depth of field of the system may be seen as being advantageous because blurring of detail outside of the area of interest may tend to increase the perception of details within the area of interest.

A number of methods can be used to obtain a useable image from the data obtained as described above. As described above, a simple convolution method may be used. Two additional methods are presently preferred for obtaining maximal resolution and sensitivity from the captured data. These are called the multi-image convolution method and the multi-output convolution method. For both cases, the following is assumed:

Assume there are $AP_x$ rows of apertures and $AP_y$ columns of apertures in collimation grid 90 (FIG. 14). Each intersection of a column and row is an "aperture point." Those aperture points outside of the circular active area of collimation grid 90 are treated as if they contribute no measured intensity to the image, i.e., they are treated as if they are "dark". Aperture points not illuminated by electron beam 40 during a scan are similarly treated as if they contribute no measured intensity to the image, i.e., they are also treated as if they are "dark".

Figure 15:
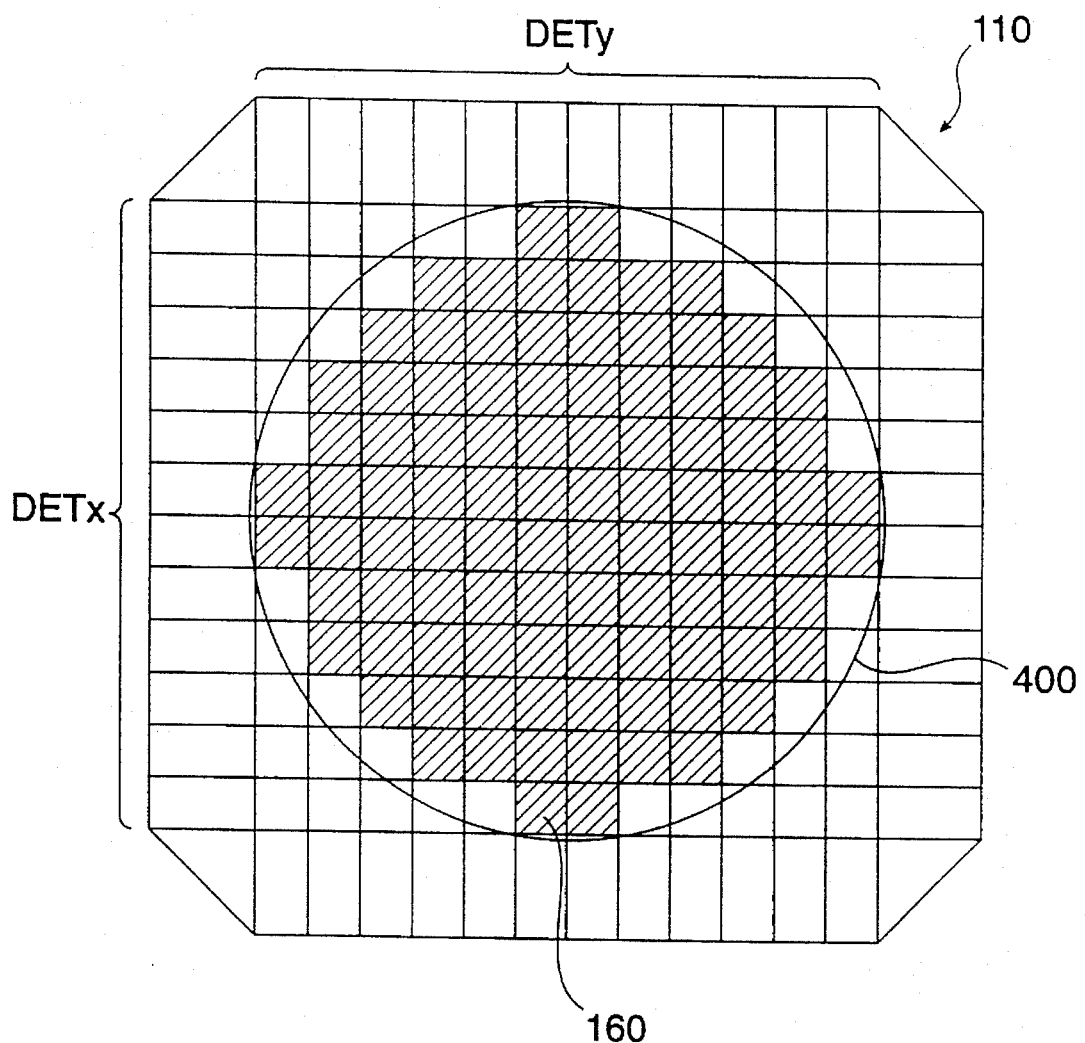
FIG. 15 is a front view of the presently preferred embodiment of a 96 element scintillator array.

Turning now to FIGS. 14 and 15, in multi-detector array 110 assume there are a maximum of $DET_x$ rows of detector elements 160 and a maximum of $DET_y$ columns of detector elements 160 in a pseudo-round arrangement.

ZRATIO is a real number between 0 and 1. If ZRATIO=1, the focus will be at the detector plane 270 and if ZRATIO=0, the focus will be at the target 50 plane. If ZRATIO=0.5, then the focus is half way between the target 50 and the detector plane 270, and so on. PIXELRATIO is the number of image pixels per physical distance between adjacent detectors in a column or row. For example, if the spacing between image pixel centers at object plane 280 is 0.01 cm, and the spacing between the centers of the detector elements at detector plane 270 is 0.1 cm, then PIXELRATIO=10. FOCUS= ZRATIO*PIXELRATIO. Focus is typically in the range of 0.5 to 2.0 and is usually 1.0.

IMAGE is a data array of size $DET_x$ by $DET_y$ containing the intensity information for a particular scan and corresponding to a particular aperture point. PIXEL is a 4-dimensional array of size $DET_x \times DET_y \times AP_x \times AP_y$, which contains the IMAGE data arrays obtained by scanning all (or part of) the apertures. PIXEL is refreshed after each scan according to one preferred embodiment of the present invention.

As the electron beam 40 is scanned across the target 50 surface, it is, in effect, positioned at the center of selected apertures 140, "fired," and then repositioned. Thus for each firing or pulse an IMAGE array of data will be acquired. While these arrays of data could be constructed into a displayable image having some use directly, more resolution and sensitivity at lower dosage is obtained by combining them.

The first preferred method for combining the images is called the multi-image convolution method. In the multi-image convolution method, an OUTIMAGE array of intensities of size $AP_x \times AP_y$, which can be displayed on a CRT or like display means, is formed by assigning to OUTIMAGE(y,x) the value of:

$$\frac{\sum_{j=1}^{j=DET_y} \sum_{i=1}^{i=DET_x} PIXEL(j,i,y+j*FOCUS,x+i*FOCUS)}{DET_x*DET_y} \quad (EQ. 1)$$

The second presently preferred method for combining the $AP_x \times AP_y$ number of IMAGE data arrays into a useful picture is called the multi-output convolution method. In this case, with a sensor array of $DET_x \times DET_y$ sensors there will be $DET_x \times DET_y$ digitizers (or their equivalents, multiplexed) and the same number of pixel summing circuits. The digitized values from each sensor are called SENSOR(j,i). The final OUTIMAGE array is computed as follows—for each pixel in the output image array OUTIMAGE(y,x) [for y=1 to $AP_y$ and x=1 to $AP_x$] one pixel from each of the $DET_x \times DET_y$ source images SENSOR(j,i) is summed [for j=1 to $DET_y$ and ii to $DET_x$] into destination image pixel OUTIMAGE(y-j*FOCUS,x-i*FOCUS). Normalization is then carried out over the OUTIMAGE array by dividing each element thereof by $DET_x*DET_y$.

A further improvement upon these techniques may be obtained by performing linear interpolation based upon the fractional part of the FOCUS factor.

An advantage of the multi-image convolution method over the multi-output convolution method is that the former allows the plane of optimum focus to be selected in software after the data is captured while the latter does not. The latter method, however, may be performed quicker where timing is a limitation.

Three Dimensional Image Reconstruction

The scanning-beam imaging system described herein may be used to generate a set of sequential planar images which can then be used to form a tomograph or a three dimensional display of the object 80. An image set can be analyzed to produce a 3D image consisting of a series of images at various depths by re-analyzing the data set with various values of FOCUS. The natural FOCUS values to use are $n/DET_x$ or $n/DET_y$ where n is an integer from 0 to $DET_x$ or $DET_y$, respectively. Normally, only the focus values corresponding to planes of interest in the object 80 would be analyzed. For example, in the scanning-beam imaging system described in TABLE I (below), the planes of focus would be spaced at approximately 2.54 cm (1 in) intervals around the normal object plane of 22.86 cm (9 in) (plane of optimum focus).

The following preferred formula shows where the sequential planar images are located in terms of distance from the target 50.

$$F_i(FOCUS) = \frac{F_d * \lambda_s * FOCUS}{\lambda_d} \quad EQ. 6$$

Where $F_i(FOCUS)$=Distance from the target to the particular focal plane of interest $F_d$=Distance from the detector to focal plane (distance from the target to the detector less $F_1$)

$\lambda_s$=Center-to-center spacing between adjacent collimation grid apertures $\lambda_d$=Spacing between centers of adjacent detectors 160 within detector array 110.

When using the sub-sampling method, the basic method of computation does not change—only the data from the collimation grid apertures which are not "skipped" need be processed. Note that $\lambda_s$ remains the same even if intervening collimation grid holes are skipped.

Negative Feedback X-Ray Flux Control

Figure 16:
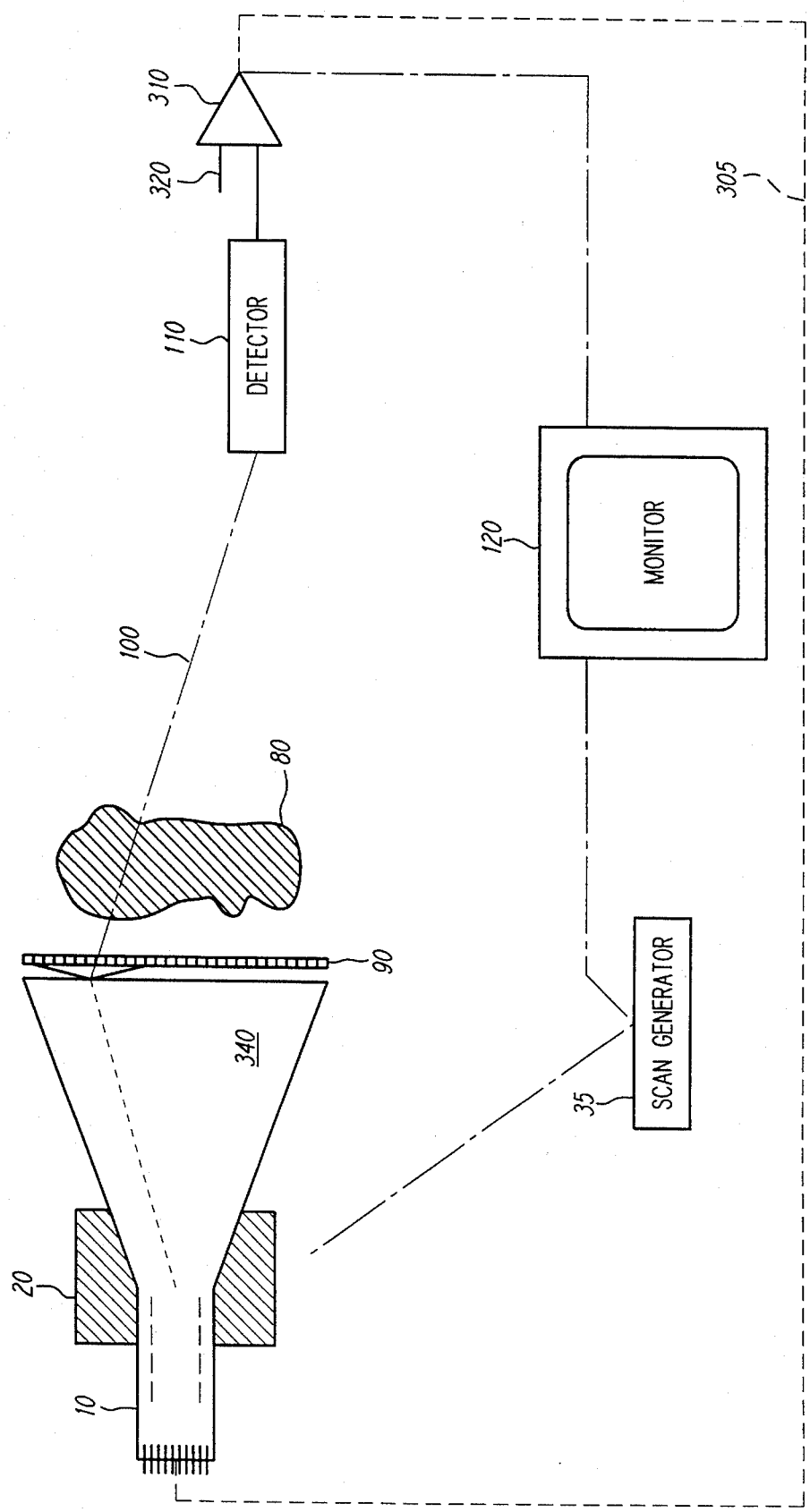
FIG. 16 is a diagram showing a preferred low dosage scanning-beam x-ray imaging system utilizing negative feedback to control x-ray flux.

Turning now to FIG. 16 an embodiment of the preferred scanning-beam imaging system employing a negative feedback path 305 to control the x-ray flux of x-ray pencil beams 100 is depicted. Negative feedback from the multi-detector array 110 can be utilized to control x-ray flux so that the multi-detector array 110 always sees approximately the same flux level. In this way when soft tissue (which is relatively transparent to x-rays) is being scanned, the x-ray flux can be lowered, without degrading the image reducing the overall dosage to the patient (or object). Improved contrast and dynamic range are provided by using negative feedback flux control. According to this embodiment, differential amplifier 310 has an adjustable reference level 320 which may be set by the user. Negative feedback loop 305 feeds back to x-ray tube 10 to control the x-ray flux.

Time Domain Scanning Mode

A time domain x-ray imaging system may also be implemented using the principles disclosed herein. In such a system, the time to reach a predetermined measured x-ray flux from the various pixels could be computed and mapped. Negative feedback control could then be employed to turn off or reduce x-ray flux from apertures corresponding to pixels which had reached the predetermined flux level for the scan period in question. In this case, the information gathered would be time to flux level and the mapped or imaged information would correspond to time rather than intensity. Such a system has the potential to provide much higher signal-to-noise ratios, improved contrast, drastically reduced x-ray dosage to the object under investigation, and improved dynamic range.

Multiple Energy X-ray Imaging Mode

According to one preferred embodiment of the present invention, two or more groups of x-ray pencil beams 100 are directed toward one or more detector arrays through two or more groups of aperture 40. A first group of x-ray pencil beams 100 has a first characteristic x-ray energy spectrum. A second group of x-ray pencil beams 100 has a different second characteristic x-ray energy spectrum. By comparing the measured transmissivities of the first and second group of x-ray pencil beams 100, the presence of certain materials in the object under investigation may be detected. The basic concept of use of differential x-ray imaging in known imaging systems is disclosed, for example, in U.S. Pat. No. 5,185,773 entitled "Method and Apparatus for Nondestructive Selective Determination of a Metal" which is hereby incorporated herein by reference.

The two groups of x-rays may be generated in a number of ways. One such way is by fabrication of a special target 50 having a first material or first thickness of a material adjacent to the apertures of the first group of apertures and a second material or second thickness of material adjacent to the apertures of the second group of apertures. In this manner, the apertures associated with the first group will preferably emit x-rays having a first characteristic energy spectrum and the apertures associated with the second group will preferably emit x-rays having a second characteristic energy spectrum.

Alternatively, K-filtering (or K-edge filtering) can be used by placing filter material (such as, for example, molybdenum) within a portion of the apertures 140 to produce a similar effect. In this case, a first group of apertures would comprise a first filter inserted therein and a second group of apertures would comprise a second filter inserted therein. The second filter could be no filter at all. As in the previous case, two groups of x-rays having different characteristic energy spectra would be associated with the two groups of apertures.

Once at least two groups of apertures are associated with different characteristic x-ray spectra, it is now easier to detect micro-calcification (associated with breast cancer and coronary artery diseases) and other abnormalities not normally visible with broadband x-rays. For example, by performing a scan of the first group of apertures to form a first image, then performing a scan of the second group of apertures to form a second image, and dividing the images to highlight their ratios, it is easier to detect micro-calcification and other such abnormalities with a low dosage scanning-beam x-ray imaging system—in real time. Similarly, a multiple detector array arrangement could be used with group 1 apertures directed toward a first detector array and group 2 apertures directed toward a second detector array, etc.

Another embodiment of multiple energy imaging uses an x-ray photon counting detector system in which the amplitude of the electrical pulse from a detected x-ray photon is proportional to the energy (keV) of the photon and the pulses coming from photons in two or more energy bands are counted separately. The pulses are separated by amplitude (i.e., x-ray photon energy) and then counted and processed separately, forming two or more separate images. Those images can be displayed as ratios. It is also possible to rapidly change the selected energy levels to distinguish different density regions in the object. The advantage of this embodiment is that it is more flexible than those described above, and does not require special collimation grids, target materials or dual detectors.

While a number of preferred embodiments have been discussed above for various configurations of the present invention, the following specifications are illustrative of a presently preferred scanning-beam imaging system according to the present invention:

TABLE I

| Grid | |
|---|---|
| Shape: | round |
| Diameter: | 25.4 cm (10 in) |
| Aperture Pitch: | 0.0508 cm (0.020 in), 0.152 cm (0.060 in for sub-sampling) |
| Max. No. of Apertures in a row or col: | 500 (166 for sub-sampling) |
| Cir. Active Area of grid: | 506.45 sq. cm (78.5 sq. in) |
| Number of apertures: | 196,350 approx. (approx. 21,630 for sub-sampling) |
| Aperture cross-section: | round |
| Aperture Diameter: | 0.0381 cm (0.015 in) |
| Space between apertures: | 0.0127 cm (0.005 in) (0.045 in for sub-sampling) |
| Grid Output Face to target surface Dist: | 2.54 cm (1.0 in) |

TABLE I-continued

| General System Config. | |
|---|---|
| Source-Detector Distance: | 94.5 cm (37.2 in) |
| Location of Object Plane: | 23.6 cm (9.3 in) from Source |
| Scan Frequency: | Adjustable to 30 Hz (Unless region of interest scanned) |
| Operating voltage on x-ray tube: | 70–120kV |
| Detector Array | |
| Overall shape: | pseudo-round (per FIG. 15) |
| Shape of input face of detector elements: | square |
| Size of input face of detector elements: | 0.142 cm × 0.142 cm |
| Number of detector elements: | 96 |
| Array diameter: | 1.83 cm (0.72 in) |
| Field of view at Plane of Optimum Focus: | 19.05 cm (7.5 in) |
| Pixel size at Plane of Optimum Focus: | 0.038 cm |
| Detector spacing: | 0.152 cm |
| Resolution: | approximately 20 line pairs/cm |

Accordingly, one embodiment of the scanning-beam imaging system utilizing a multi-detector array has been shown and described which simultaneously provides high resolution, high sensitivity, and low x-ray dosage to the object under investigation. The system also permits the plane of optimum focus to be varied between the target 50 and the multi-detector array 110, and provides an effective working depth of field.

Sub-Sampling Technique

The following relates to a particular preferred embodiment of the present invention which uses the technique of sub-sampling which reduces the computer processing overhead, and power consumption of the scanning-beam x-ray system.

Standard video quality images typically use 640×480 pixels and are updated at 30 Hz. This usually requires a pixel sample rate of about 12 Mhz. Positioning the high voltage electron beam of the x-ray tube accurately behind 250,000 different apertures at that rate typically requires high precision and relatively high power consumption. Digitization of signals from a large array of x-ray detectors at a 12 Mhz rate is similarly expensive and power intensive. Thus reduction of the pixel sample rate below 12 Mhz without significant reduction of the spatial or time resolution of a scanning-beam imaging system is useful in reducing initial unit costs, operating costs due to electronic power consumption, and cooling requirements for the waste heat developed by the x-ray tube.

Accordingly, a method for reducing the pixel sample rate while providing virtually the same spatial and time resolution has been developed. This method is referred to herein as "sub-sampling" and is best implemented with the embodiment of the scanning-beam imaging system described herein, although it could be adapted to be used with other configurations. Advantages of this embodiment include reduced power consumption and simpler circuitry for electron beam deflection within the x-ray tube 10, reduced cost of fabrication of the collimation grid 90, reduced complexity of the calculations needed to resolve an image of the object 80 and other advantages as would be obvious to those of skill in the art.

Pursuant to this embodiment a collimation grid 90 is fabricated having a number of apertures less than the number of desired image pixels. In other words, in sub-sampling the ratio of the number of apertures ("AP") to the number of Image Pixels ("IP") is less than one (Total AP/Total IP<1). Preferably, $AP_x=AP_y=166$ rather than 500, although other numbers are within the scope of the invention. The advantage of this reduction from a computational point of view will become apparent below. From a manufacturing point of view, it is a much simpler structure with approximately one-ninth the number of apertures which need to be fabricated. Because this sub-sampled system requires fewer apertures than a fully sampled system, it is easier to fabricate grids with higher deflection angles (i.e., the angle that the aperture makes with respect to the front face 260 of the collimation grid) without running into problems of having apertures 90 interfere with adjacent apertures. This is particularly useful when stereo grids are to be manufactured, since adjacent apertures in a stereo grid are directed to different detector arrays and hence may require more physical separation than non-stereo grids to avoid aperture interference.

In the presently preferred embodiment the apertures 140 of the collimator grid 90 preferably have a circular arrangement of maximum dimension $AP_x$ rows by $AP_y$ columns. For computational purposes in the presently preferred embodiment this arrangement is treated as a rectangle of dimension $AP_x$ rows by $AP_y$ columns with the apertures outside of the circular boundary contributing no information, i.e., never being used to pass x-ray pencil beams 100.

The input face of the detector elements 160 of the multi-detector array 110 are also preferably arranged in a circular array of maximum dimension $DET_x$ rows by $DET_y$ columns as shown in FIG. 15. For computational purposes, in the presently preferred embodiment this arrangement is treated as a rectangle of detector elements 160 of dimension $DET_x$ rows by $DET_y$ columns with the detectors outside of the circular boundary contributing no information, i.e., always being "dark", or non-illuminated by x-rays.

The pixel sample rate is reduced by illuminating less than all of the apertures 140 of the collimation grid, if the total number of apertures is equal to the number of image pixels, i.e., by sub-sampling. Preferably a collimation grid without the not-to-be-illuminated apertures is used, e.g. the collimation grid includes the number of apertures corresponding to the desired aperture to image pixel ratio. In a collimator grid 90 having more apertures than is necessary to achieve the desired aperture to image pixel ratio, an image is formed using the multi-detector array 110, by illuminating only the collimator holes in each row and only the collimator holes in each column that needs to be illuminated to achieve the desired aperture to image pixel ratio. Thus the image may be built up out of image tiles of pixels corresponding to the number of detector elements in a row in the multi-detector array 110 that provides information for a single image pixel ($VDET_x$) and the number of detector elements in a column of the multi-detector array 100 that provides information for that same image pixel ($VDET_y$) as the electron beam 40 is scanned across the target 50. This corresponds to a sub-sampling ratio of $(DET_x \times DET_y/VDET_x \times VDET_y):1$ which, for no sub-sampling, reduces to a sub-sampling ratio of 1:1. The sub-sampling ratio may thus be adjusted by changing the number of virtual detector elements from $DET_x$ to $VDET_x$ in the X-direction (rows) and from $DET_y$ to $VDET_y$ in the Y-direction (columns). In accordance with a preferred embodiment, $VDET_x=VDET_y=4$ as shown in FIG. 36, yielding an image to aperture pixel ratio of $(12 \times 12/4 \times 4):1$, i.e., 9:1.

Where a 12×12 detector is used and the sub-sampling ratio is 144:1, the image is fabricated from a plurality of non-overlapping images which are in effect "pasted" together—much like a photomosaic. Because real world scintillators and detectors are usually not all perfectly and identically responsive, the x-ray pencil beam 100 is usually not perfectly uniform, the collimation grid apertures are usually not all exactly identical with identical areas, and because a circular, rather than a square detector is used in the preferred embodiment, some degree of overlap is highly desirable in order to permit averaging out detector nonlinearities and noise.

If the sub-sampling ratio is less than the detector size in image pixels (that is, less than 144:1 in this embodiment), the image will be built up from overlapping "tiles", which are summed or averaged. If the sub-sampling ratios are not "even" multiples of the detector size (in image pixels) or if the multi-detector array 110 is not rectangular as in the preferred embodiment there will be different numbers of samples added to each image pixel. To obtain a more uniform picture the values from each of the virtual detectors is normalized using different divisors to average the resultant values to generate each image pixel.

In the calculations that follow, $VDET_x$ represents the sub-sampling value in the X direction (rows), and $VDET_y$ represents the sub-sampling value in the Y direction (columns). For example, if $VDET_x=VDET_y=12$, there is no sub-sampling. Similarly, if $VDET_x=VDET_y=1$, in this embodiment, the pixels are tiled. If every third aperture of the collimator grid 90 which has an array of apertures 500×500 is illuminated, then 166×166 apertures will be scanned, i.e., one-third in X and one-third in Y, reducing the data obtained by a factor of 9 with the 12×12 detector this will provide a sub-sampling ratio of $(12 \times 12/4 \times 4):1$ or 9:1. Note that if one is only going to use 166×166 apertures all of the time, there is no need for 500×500 apertures and only 166×166 need be included in the collimation grid.

In accordance with one embodiment, only 1/9 of the apertures in the collimation grid (500×500 apertures) are used or illuminated by the electron beam 40 to generate an image. If the frame rate is kept constant, e.g., 30 Hz, then the number of electron beam steps is reduced by 9, as is the frequency response of the circuit that drives the electron beam. The number of scan lines is reduced by 1/3, so that the average horizontal beam velocity across the target is reduced by 1/3. The image reconstruction pixel rate is the same as the collimation grid aperture rate (rate at which apertures are scanned or illuminated), and is also reduced by 1/9.

In accordance with this embodiment in which the collimator grid 90 includes a 500×500 array of apertures, and the multi-detector array 110 includes a 12×12 array of detector elements 160, arranged such that when each aperture is illuminated an image pixel to aperture ratio of 1:1 is achieved, the number of detector element outputs averaged into each image pixel is $VDET_x*VDET_y$. When using the sub-sampling ratio of 144:1 where $VDET_x$ and $VDET_y=1$, only one digitizer sample is used for each image pixel. The normalizing of the detector element outputs smooths out non-uniformities in the beam, the scintillators, the detectors, and the amplifiers. The sub-sampling ratio should be set to an appropriate level for the conditions presented in order to assure acceptable image quality. This may be adjusted in accordance with the user's preference for image quality and the conditions presented by a particular set of circumstances.

M,N Image Reconstruction

An alternatively preferred image reconstruction method can be employed to reconstruct images along multiple focal planes. This preferred image reconstruction method is referred to as m,n image reconstruction. FIG. 67 shows a cross-sectional view through a two-dimensional array of regularly-spaced x-ray sources and a two-dimensional array of regularly-spaced detectors. It will be noted that there are numerous planes parallel to the source plane 271 and detector plane 270 where multiple beams pass through regularly-spaced points in the plane. These planes are referred to as focal planes or image planes. The regularly-spaced points are referred to as image pixels. Each focal or image plane comprise characteristics which differ from other focal planes, including distance from the source, spacing of image pixels, and size of the image plane. In accordance with the present invention, a method is provided to reconstruct any of these image planes.

To illustrate an embodiment of this method, an array of sources, preferably a rectangular array of $SOURCE_x$ by $SOURCE_y$ sources on a pitch $\lambda_s$ in both the x- and y-directions, is employed with an array of detectors, preferably a rectangular array of $DET_x$ by $DET_y$ detectors on a pitch $\lambda_d$ in both the x- and y-directions. Each source produces a pencil beam of x-rays 100 which illuminates all the detectors in the array. Each x-ray pencil beam 100 is therefore segmented into an array of x-ray microbeams with one x-ray microbeam per detector. In this example, there are $DET_x*DET_y$ microbeams per pencil beam and $SOURCE_x*SOURCE_y$ pencil beams for a total of $DET_x*DET_y*SOURCE_x*SOURCE_y$ microbeams.

INTENSITY(i,j,k,l) is the intensity of the x-ray illumination detected at detector DET(i,j) when source SOURCE(k,l) is illuminated. For this example, i=[1,$DET_x$], j=[1,$DET_y$], k=[1,$SOURCE_x$], and l=[1,$SOURCE_y$].

Each focal plane can be described by a pair of natural numbers (integers≥1) m and n, where $m*\lambda_d$ and $n*\lambda_s$ are the baseline lengths of the similar triangles, shown in FIG. 68, which determine the location of the focal plane. For this example, $Z_d$ equals the distance from source to detector while $Z_{fp}$ equals the distance from source to focal plane. Therefore, the distance $Z_{fp}$ from the source plane 271 to a particular focal or image plane which is described by the values of m,n can be expressed as:

$$Z_{fp}(m,n) = Z_d \frac{n*\lambda_s}{n*\lambda_s + m*\lambda_d} \qquad \text{EQ. 2}$$

According to this method, reconstruction of an image at a particular focal plane m,n can be performed by creating the two-dimensional array $IMAGE_{m,n}$ by summing each value of INTENSITY(i,j,k,l) into image pixel $IMAGE_{m,n}$(i*n+k*m, j*n+l*m) respectively.

The maximum x- and y-indices of array $IMAGE_{m,n}$ can be expressed as: $DET_x*n+SOURCE_x*m$ and $DET_y*n+SOURCE_y*m$.

For the particular parameters of this embodiment, not all values of the natural numbers m and n are appropriate. For example, if m and n have a common factor (e.g. m=6, n=2) then the array $IMAGE_{m,n}$ will be sparsely filled. The image reconstructed using m=6, n=2 is equivalent to the image reconstructed using m=3, n=1. Although the array $IMAGE_{6,2}$ will have four times as many elements as $IMAGE_{3,1}$ only one-fourth of the elements in $IMAGE_{6,2}$ will be non-zero. Removing the all-zero rows and columns in $IMAGE_{6,2}$ yields $IMAGE_{3,1}$.

Referring to FIG. 68, in this example it will also be noted that, e.g., doubling or tripling both baselines of the similar triangles does not change the location of the resulting focal plane.

The pitch of the image pixels at the focal plane $\lambda_{fp}$ can be expressed as follows:

$$\lambda_{fp}(m,n) = \frac{\lambda_d}{n} * \frac{Z_{fp}(m,n)}{Z_d} \qquad \text{EQ. 3(a)}$$

$$= \frac{\lambda_d}{n} * \frac{n*\lambda_s}{n*\lambda_s + m*\lambda_d} \qquad \text{EQ. 3(b)}$$

$$= \frac{\lambda_d*\lambda_s}{n*\lambda_s + m*\lambda_d} \qquad \text{EQ. 3(c)}$$

Referring to FIG. 68, it will be noted that every mth detector in the x- and y-directions is used to reconstruct any particular image pixel. Therefore, there are, on average, $DET_x*DET_y/m^2$ microbeams per image pixel. Since the total number of microbeams in this example is $DET_x*DET_y*SOURCE_x*SOURCE_y$, the number of image pixels can be expressed as:

$$\frac{DET_x*DET_y*SOURCE_x*SOURCE_Y}{DET_x*DET_y/m^2} = \qquad \text{EQ. 4}$$

$$SOURCE_x*SOURCE_Y*m^2$$

Due to partial image reconstruction around the perimeter of the image, the number of fully reconstructed image pixels is slightly lower than the above number and the total number of fully and partially reconstructed image pixels is slightly higher than the above number.

In this example, when the size of the source array is $SOURCE_x*\lambda_s$ by $SOURCE_y*\lambda_s$, the size of the field of view (at the focal plane) can be expressed as:

$$SOURCE_x*\lambda_s*\left(1 - \frac{Z_{fp}}{Z_d}\right) \text{ by } SOURCE_y*\lambda_s*\left(1 - \frac{Z_{fp}}{Z_d}\right) \qquad \text{EQ. 5}$$

The m,n image reconstruction method is more flexible than the previously described reconstruction methods. As FIG. 67 shows, m,n image reconstruction can generate a wide variety of focal planes at numerous positions between the source and detector planes. Many of the focal planes have a small pitch between image pixels which can be used to produce images with high spatial resolution.

The ability to reconstruct a wide variety of focal planes can be used to move the focal plane with respect to the source and detector by simply selecting a suitable image plane near the region of interest of the object to be imaged.

The m,n image reconstruction method can also be used to increase the effective depth of field of an image by simultaneously reconstructing multiple focal planes around a region of interest. The reconstructed planes can be combined to produce a single image with high spatial resolution over a larger range of distances from the x-ray source plane. The multiple reconstructed planes can be combined, for example, by adding together only the high spatial frequency components from each reconstructed plane.

System Description

FIGS. 18–25 are functional block diagrams of a preferred stereoscopic scanning-beam x-ray imaging system according to the present invention. FIG. 17 depicts the manner in which FIGS. 18–25 can be arranged to create a single block diagram of this presently preferred system. For medical applications the x-ray source and the multi-detector arrays are preferably mounted on a movable C-arm with the x-ray source mounted above an adjustable patient table and the multi-detector arrays located below the table.

Figures 17, 18:
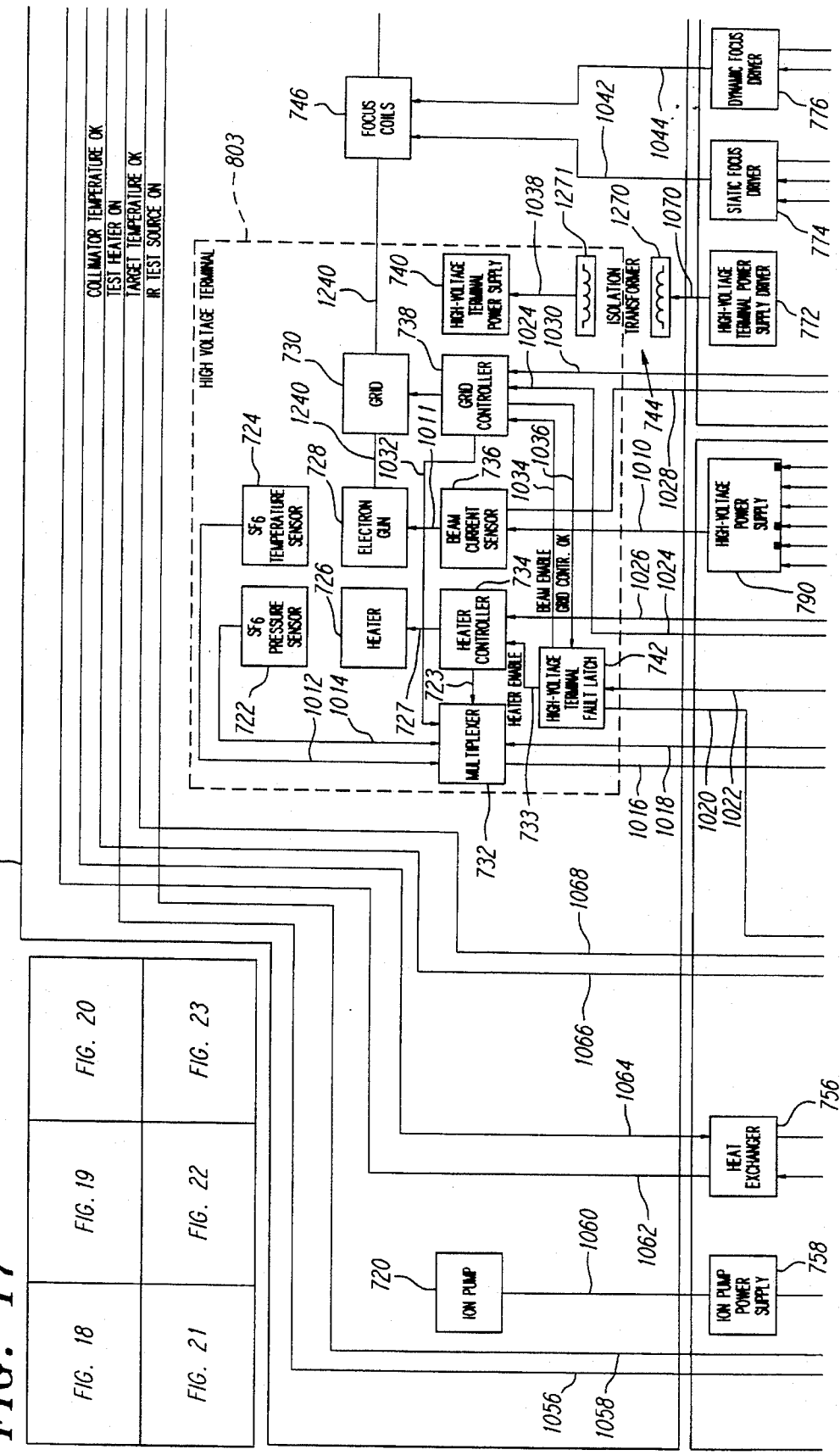
FIG. 17 is a layout arrangement plan for FIGS. 18–25.
FIGS. 18–25 provide a single functional block diagram of components of a preferred scanning-beam x-ray imaging system.

FIG. 18 includes a representative block diagram of high-voltage terminal 803, which is part of x-ray source 798. High-voltage terminal 803, which is preferably contained in a housing (not shown) includes electrical components for producing and controlling the electron beam 1240. The high voltage necessary to power the x-ray source is supplied to the high voltage terminal from an external adjustable high-voltage power supply 790 by a single cable 1010. All of the electronic components in the high voltage terminal 803 preferably float at the output potential of the high-voltage power supply. The unique construction of the high voltage terminal results in only this single electrical connection to the high voltage terminal. All other data and power transmission to and from the high voltage terminal is preferably accomplished via fiber optic links and via an isolation transformer. A more detailed description of the structure and operation of the presently preferred high voltage terminal is provided in copending U.S. patent application Ser. No. 08386,884, Lyon & Lyon Docket No. 210/204, which has been incorporated herein by reference in its entirety.

Because of the high operating voltages with respect to ground in the high-voltage terminal 803 (−100 kV to −120 kV), the housing is preferably filled with an electrically insulating medium preferably pressurized $SF_6$ (sulphur hexafluoride) gas to electrically isolate the high voltage terminal 803 from its surroundings.

High voltage isolation transformer 744 supplies power for the circuitry in the high-voltage terminal 803. The secondary winding 1271 of isolation transformer 744 is part of the high-voltage terminal 803, while the primary winding 1270 is separated from the terminal by a gap filled with the pressurized $SF_6$ gas. The primary winding 1270 preferably forms a part of the high voltage terminal housing and is supplied with power from the high voltage terminal power supply driver 772 located in the C-arm cart. The preferred construction of the isolation transformer is described more fully in copending U.S. patent application Ser. No. 08386,884, Lyon & Lyon Docket No. 210/204, which has been incorporated herein by reference in its entirety.

In addition to the components necessary for generating and controlling an electron beam, the high voltage terminal preferably includes components for monitoring certain parameters located within the high voltage terminal. The monitored information is preferably communicated outside the housing via fiber optic cables. The circuitry for converting the electrical signals to light signals and the light signals to electrical signals is described more fully in connection with the detailed description of FIGS. 40 and 41, and is enclosed within the high voltage terminal housing.

A pressure sensor 722 preferably monitors the pressure of the $SF_6$ gas in the housing to ensure adequate electrical isolation. Additionally, the temperature of the pressurized $SF_6$ gas is preferably monitored by temperature sensor 724. This information is transmitted via multiplexer 732 and I/O controller 762 to control computer 890. If the pressure drops below a predetermined threshold or the temperature increases above a predetermined threshold, the control computer will shut the system down.

The electric current from the high voltage power supply is preferably sensed by passing the current through a beam current sensor 736 which provides information to a current sense monitor 788 which is preferably located in the C-arm cart.

In addition the heater controller 734, which controls the heater 726 located in the electron gun 728, provides information concerning heater current and voltage to multiplexer 732 for transmission to the control computer 890.

The voltage of the electron grid 730, located in front of the emitting face of electron gun 728, is controlled by grid controller 738. The voltage level of electron grid 730 can preferably be varied between zero and −2000 V with respect to the cathode to adjust the current of the electron beam 1240, thereby controlling the x-ray flux emitted by target 1250. When the electron grid is at a potential of approximately −2000 V, the electron beam is effectively shut off. The beam-on control signal 1024 instructs the grid controller 738 to apply either −2000 V to the grid to turn the electron beam off, or to apply the beam-on grid voltage set via fiber optic link 1030 to the grid to turn the electron beam on to a preset current. The grid controller 738 also relays the beam-on and beam-off grid voltages to the multiplexer 732. Fault conditions in the grid controller will trip the high voltage terminal fault latch 742 which will shut the electron beam off by turning off heater 726 via heater controller 734 and setting the voltage of electron grid assembly 730 to −2000 V via grid controller 738. The entire x-ray source will also be shut down via fiber-optic cable 1020 and fail safe controller 760.

The status information from various components within high voltage terminal 803, which are input to multiplexer 732, are transmitted to I/O controller 762. Multiplexer 732 includes a voltage to frequency converter which drives an LED for conversion of the electrical status signals from a selected component into light pulses and transmits these signals to I/O controller 762 via fiber-optic cable 1016. I/O controller 762 controls the sequence of transmission of each component's status information sent via multiplexer 732 by sending a channel select signal to multiplexer 732 via fiber-optic cable 1018.

Ion pump 720 maintains the vacuum within the x-ray source 798. Ion pump 720 is powered by ion pump power supply 758, which in the preferred embodiment is located within C-arm cart 811. Ion pump power supply 758 also has an output which indicates the vacuum pressure to control computer 890 via I/O controller 762.

Figure 19:
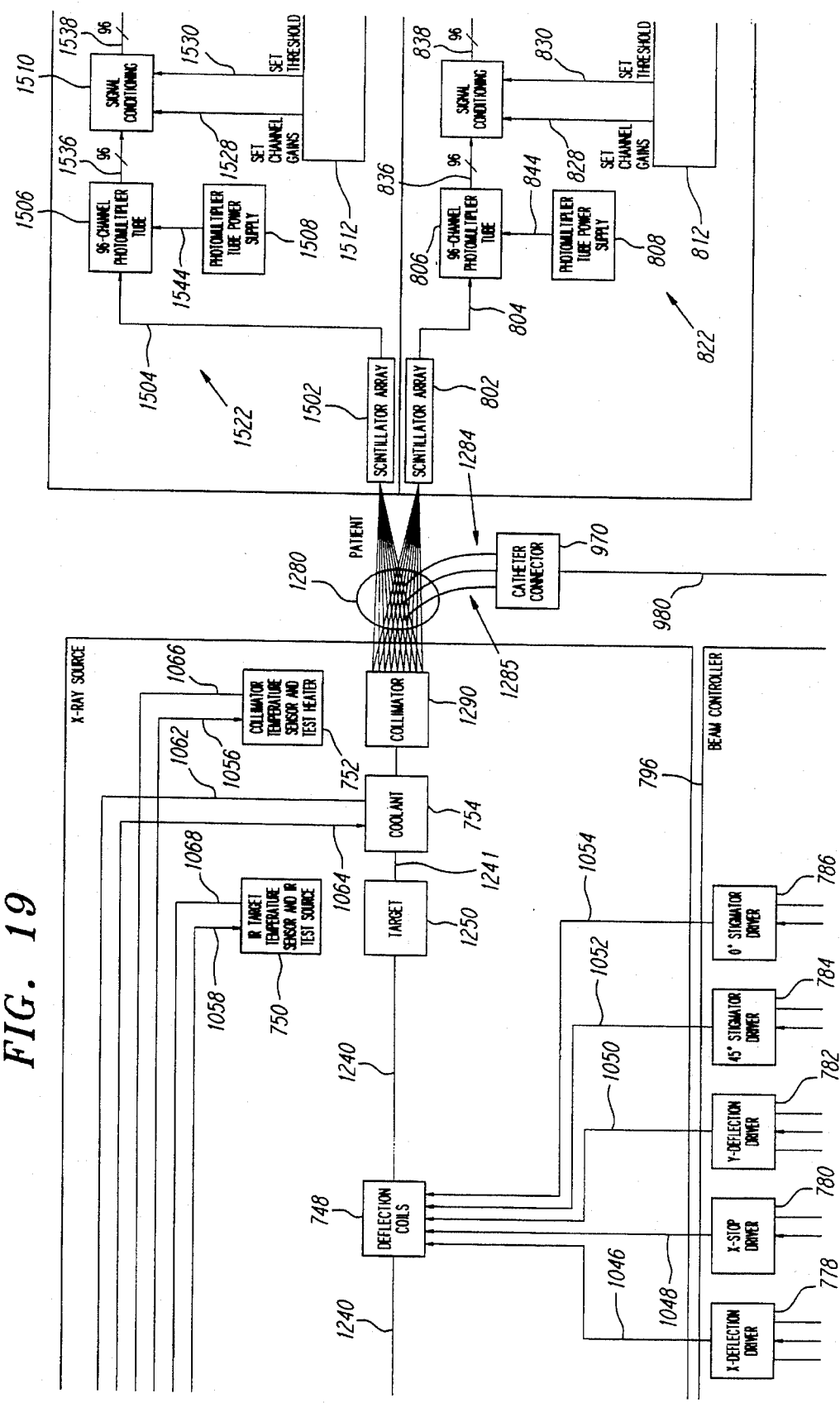

Referring now to FIG. 19, electron gun 728 emits a beam of electrons 1240 toward grounded target 1250 which preferably passes through focus coils 746 and deflection coils 748 to focus and position electron beam 1240 at a desired location on target 1250. The deflection coils 748 aim electron beam 1240 at a specific location on the surface of target 1250. Target 1250 emits x-rays 1241 at the spot illuminated by electron beam 1240. Infra-red temperature sensor 750 constantly monitors the temperature of target 1250 for abnormal increases in temperature caused by malfunctioning of the beam scanning. If infra-red temperature sensor 750 detects an over-temperature condition, it trips the fail-safe controller 760 to shut down the x-ray source. To verify proper operation of the temperature sensor, an infra-red test source is provided which can be activated by the control computer to simulate an over-temperature condition to verify that the infra-red temperature sensor will detect a fault and shutdown the x-ray source.

A cooling chamber 754 for cooling the target 1250 is preferably located between the target 1250 and the collimator 1290. The coolant from cooling chamber 754 is preferably circulated through a heat exchanger 756 (FIG. 24) preferably housed within the C-arm. Since the collimator 1290 may come in contact with the patient during imaging procedures, the collimator 1290 is preferably monitored for excessive temperatures by collimator temperature sensor 752. In this preferred embodiment, collimator temperature sensor 752 checks for temperatures in excess of 40° C. If the temperature exceeds this threshold, the fault is communicated to the fail-safe controller 760, which shuts down the x-ray source. To verify proper operation of the temperature sensor, a test heater is provided which can be activated by the control computer to simulate an over-temperature condition to verify that the temperature sensor will detect a fault and shutdown the x-ray source.

Figure 23:
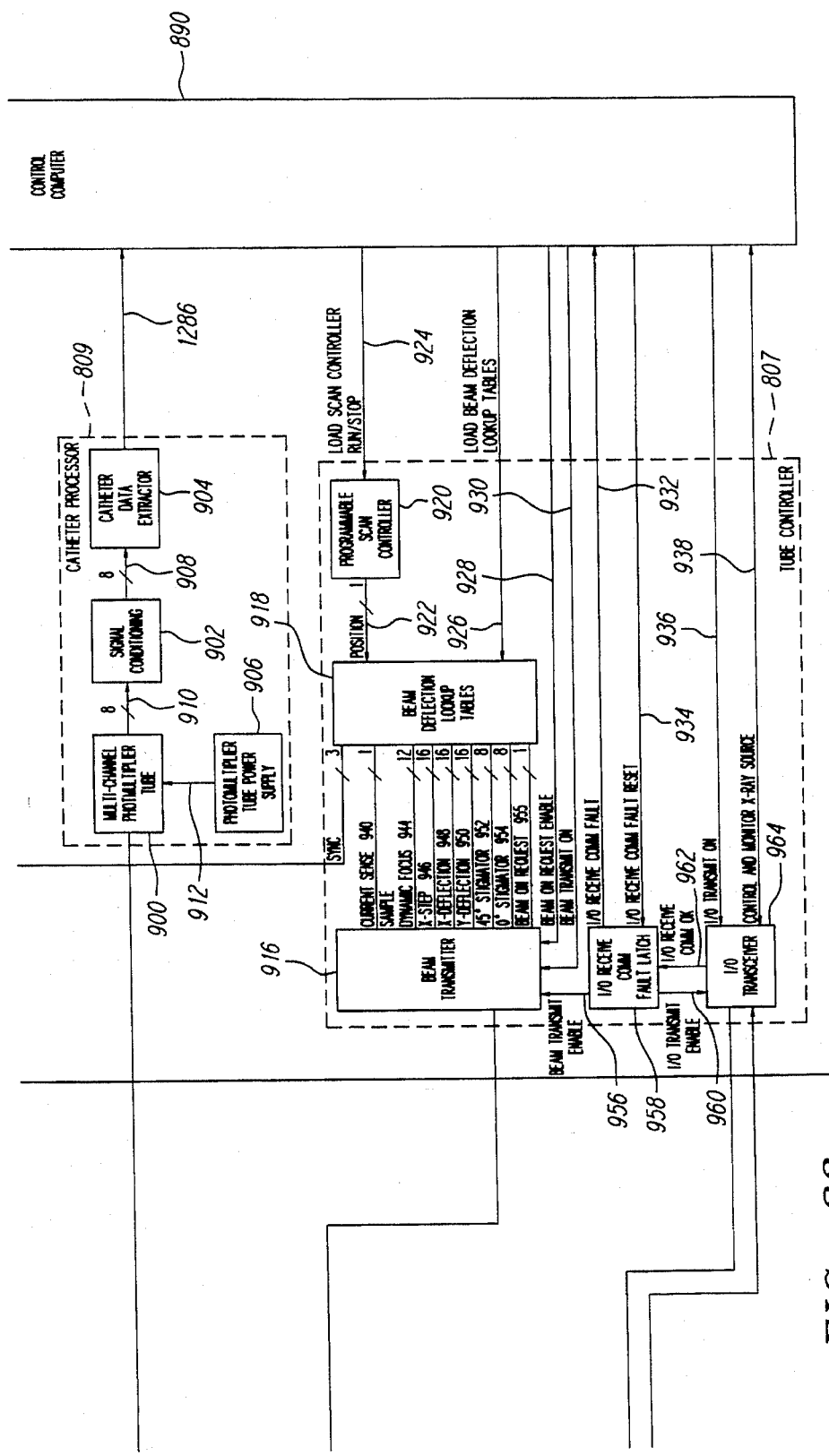

FIG. 23 is a block diagram comprising beam controller 796 and a portion of the C-arm cart. The beam controller interface 94 receives data from the tube controller via a high speed fiber optic link 1000. Consequently, beam controller interface 794 includes the light signal to electrical signal conversion circuitry described more fully in conjunction with FIGS. 40 and 41.

Beam controller 796 preferably controls the focus coils 746 through two separate drivers, a static focus driver 774 and a dynamic focus driver 776. Static focus driver 774 is preferably set only once for a given operating voltage of the high voltage power supply. The dynamic focus driver 776 adjusts the precise focussing of the electron beam 1240 as it scans across target 1250.

Beam controller 796 preferably controls the deflection coils 748 through five separate drivers: x-deflection driver 778, x-step driver 780, y-deflection driver 782, 45° stigmator driver 784, and 0° stigmator driver 786.

The x-deflection driver 778 communicates a conventional linear input pattern to the deflection coils via wires 1046 to drive the electron beam horizontally across the target whereas the x-step driver 780 communicates a novel sawtooth input signal to the deflection coils 748 via wires 1048. The net effect is a stepped movement of the electron beam across the target. The y-deflection driver 782 communicates a conventional y-deflection pattern to the deflection coils 748 via wires 1050 to drive the electron beam 1240 vertically across the face of the anode. The 45° stigmator driver 784 and the 0° stigmator driver 786 and their respective coils correct for aberrations in the electron beam spot to maintain a circular spot on the target. More detailed information about these circuits can be found in copending U.S. patent application Ser. No. 08/386884, Lyon and Lyon Docket No. 210/204, which has been incorporated herein by reference.

Current sense monitor 788 is preferably used to monitor the output of any of the beam controller drivers to verify their correct operation as well as to measure the electron beam current as previously discussed.

A failure in the deflection system could result in the electron beam not scanning across the target in the x direction or the y direction. This could result in thermal damage to the target. Deflection fault sensor 770 preferably receives x-scan and y-scan monitoring information from x-deflection driver 778 and y-deflection driver 782. Deflection fault sensor 770 preferably transmits a fault status signal to fail-safe controller 760 via fiber-optic cable 1072. If a deflection fault condition occurs, fail-safe controller 760 will shutdown the x-ray source.

Figure 24:
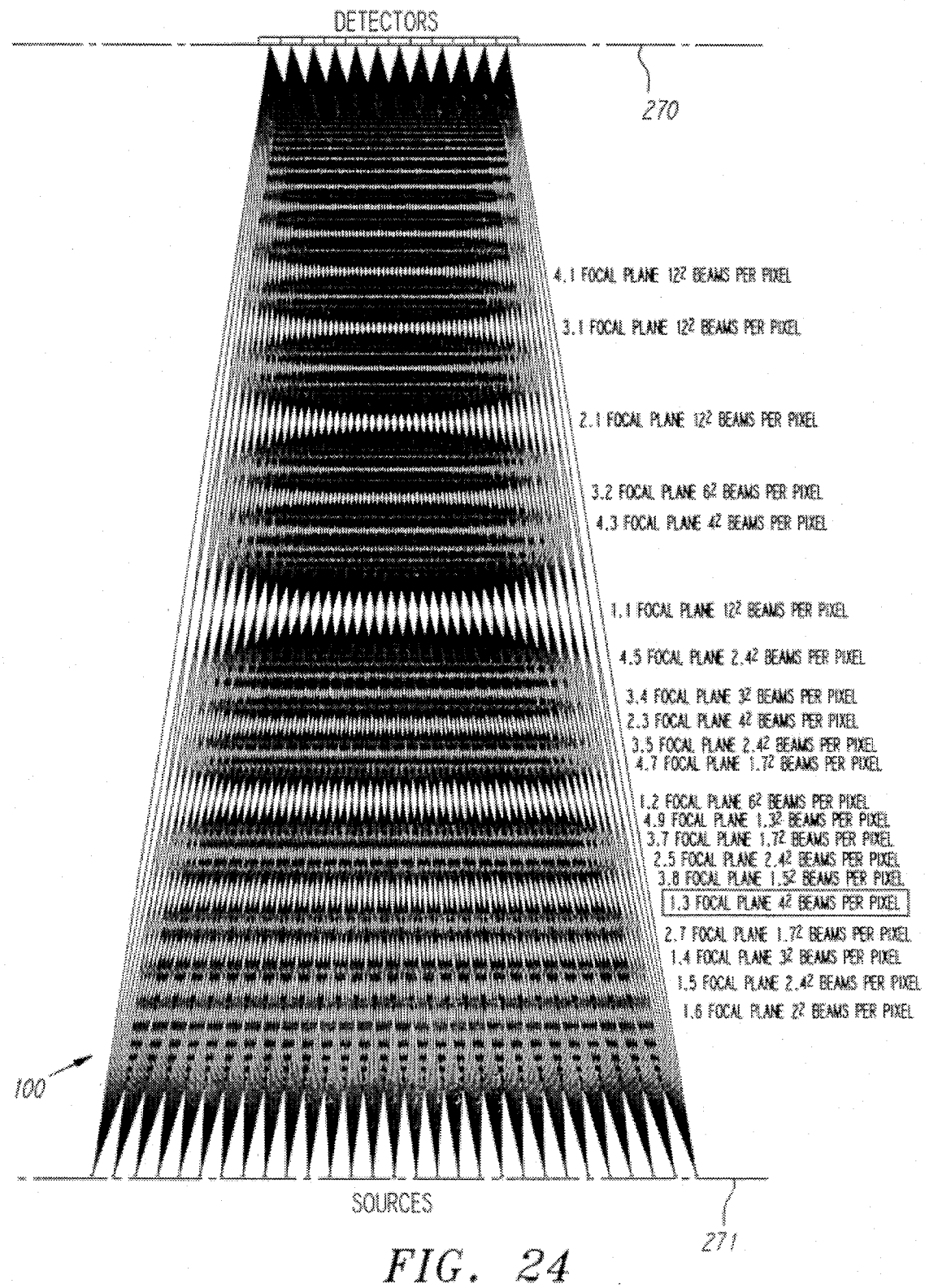

FIGS. 23 and 24 include a functional block diagram of the components preferably housed in the C-arm cart 811. Power is preferably supplied to the C-arm cart 811 from a 208 volt 3-phase AC power supply via cable 763. DC power is fed from the c-arm cart to the beam controller 796 via cable 1078.

Figure 40:
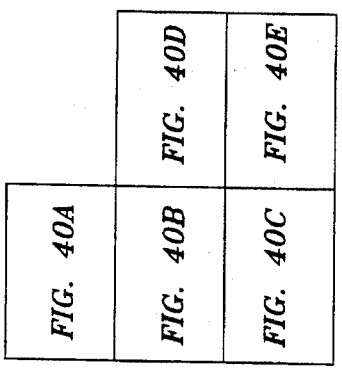
FIGS. 40 and 41 comprise schematics of the preferred real time eye optical to electrical and electrical to optical conversion circuitry.
Figure 40A:
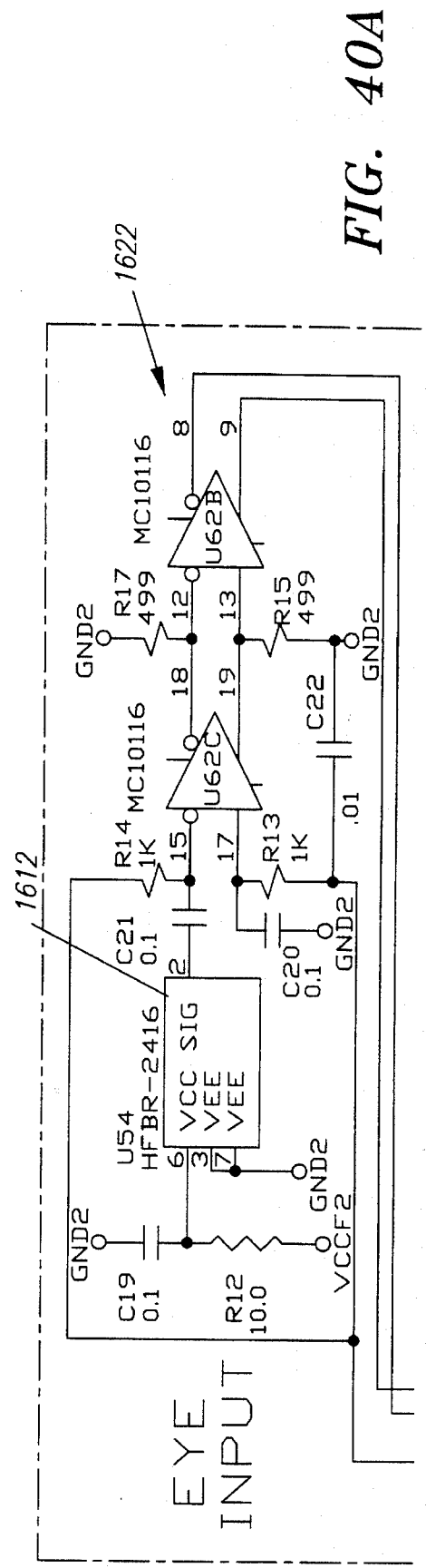
Figure 40B:
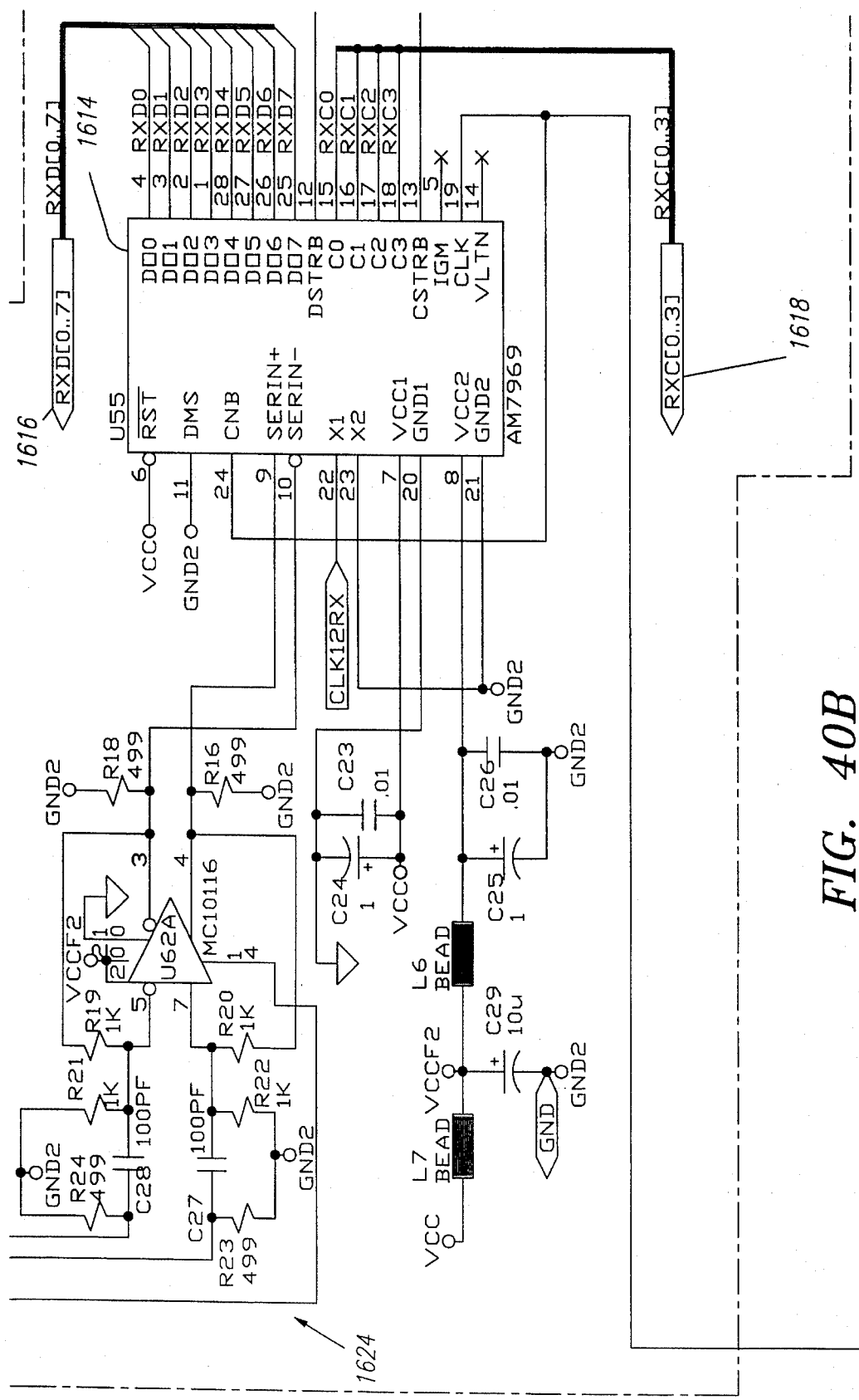
Figure 40C:
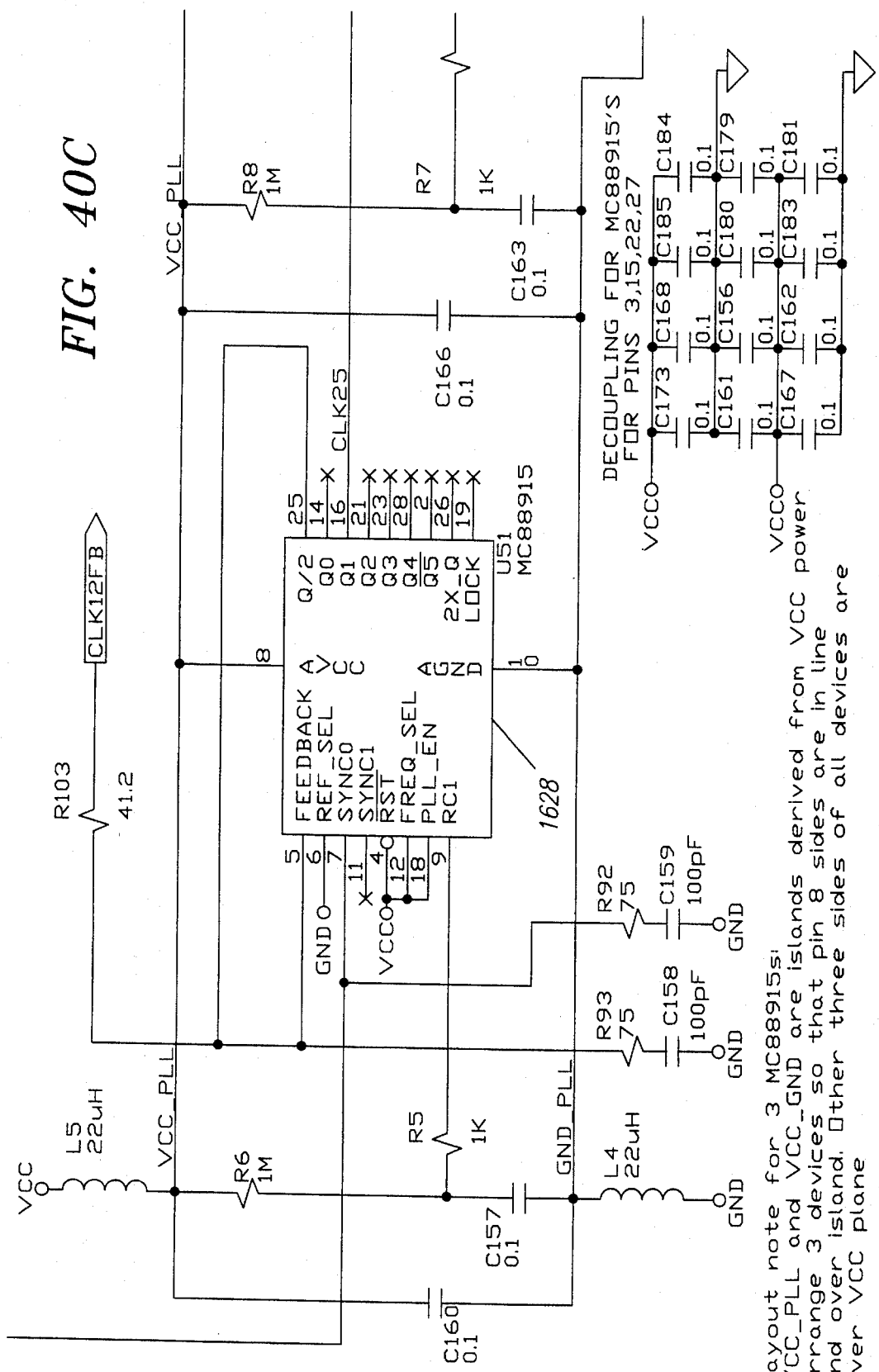
Figure 40D:
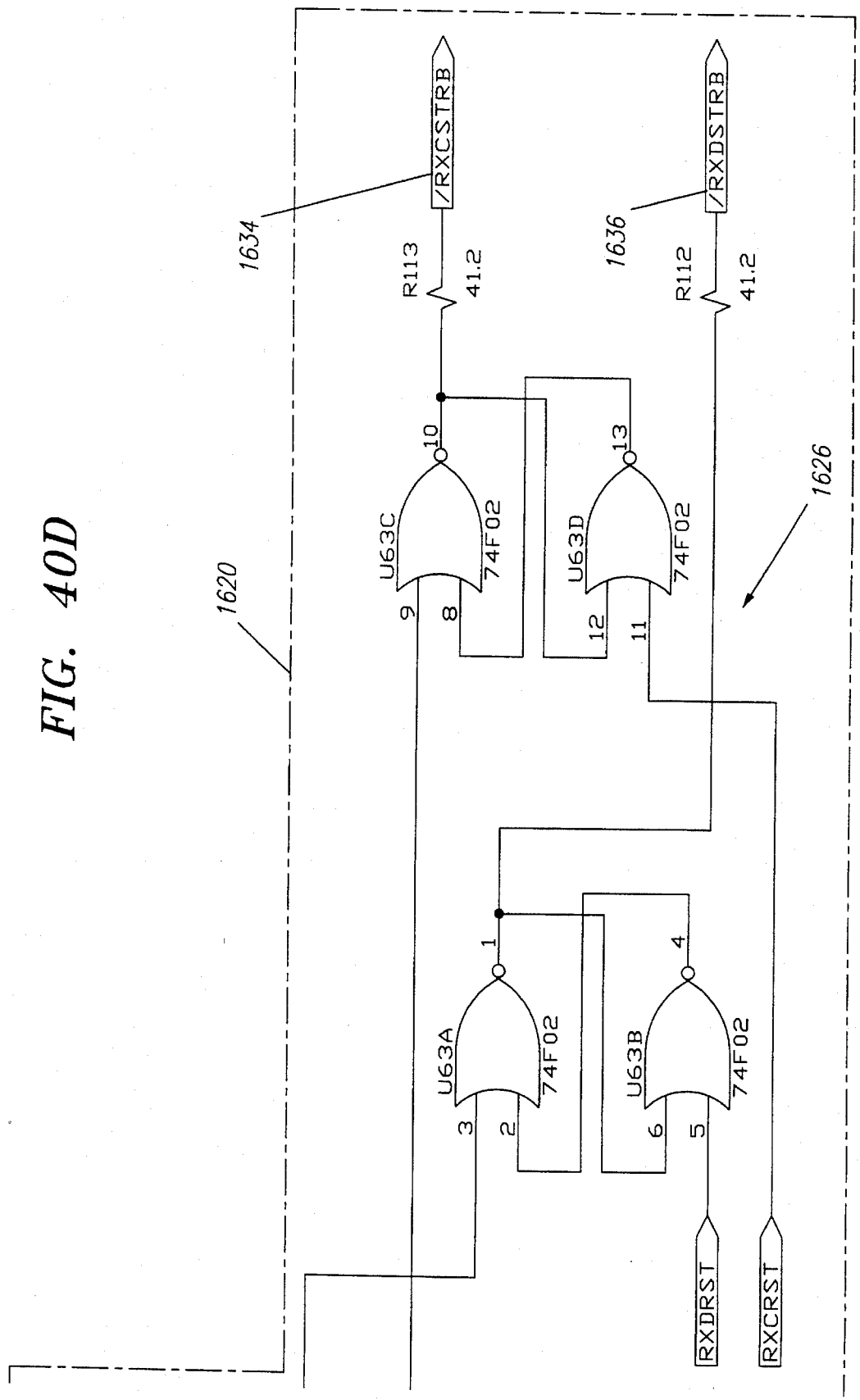
Figure 40E:
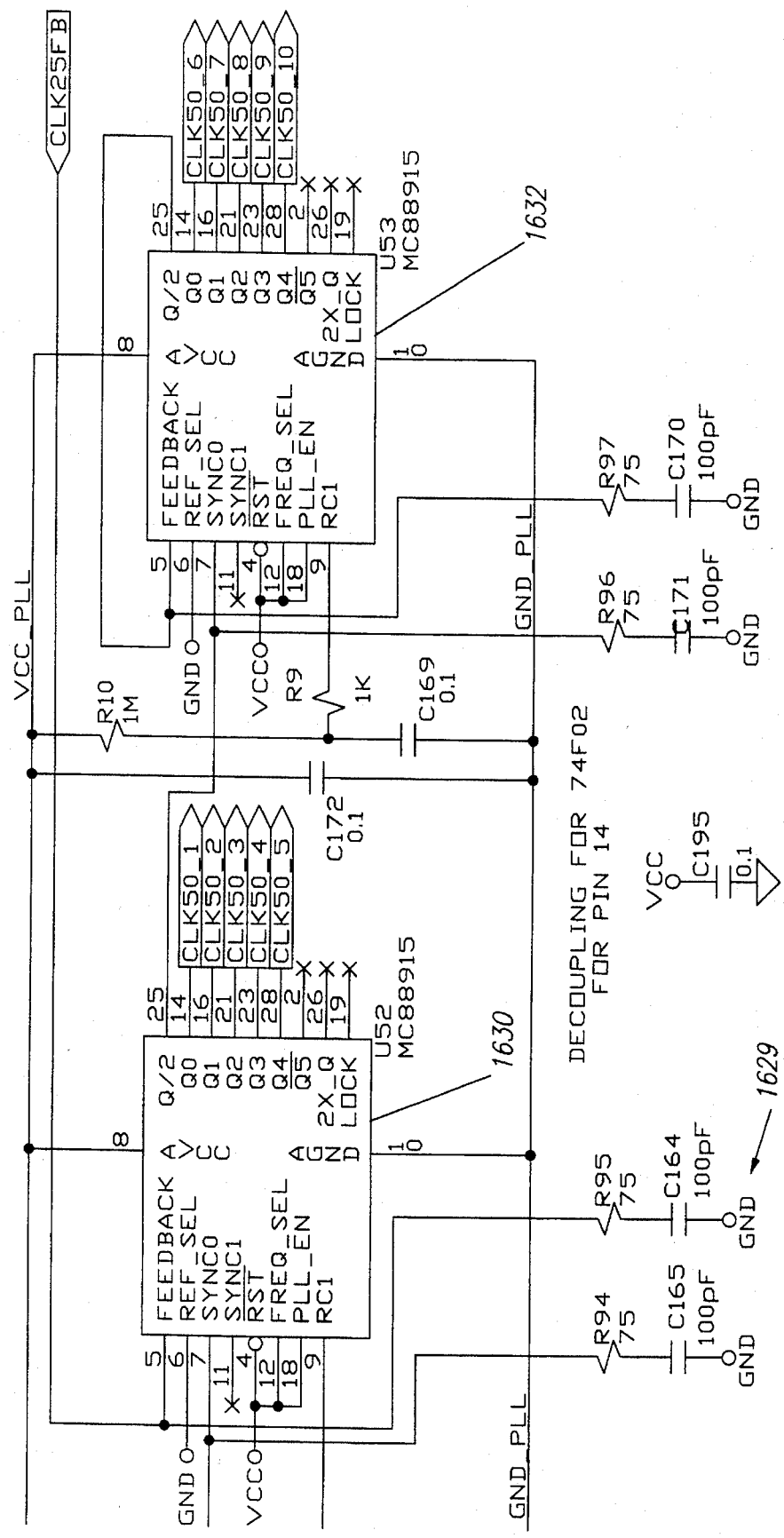
Figure 41B:
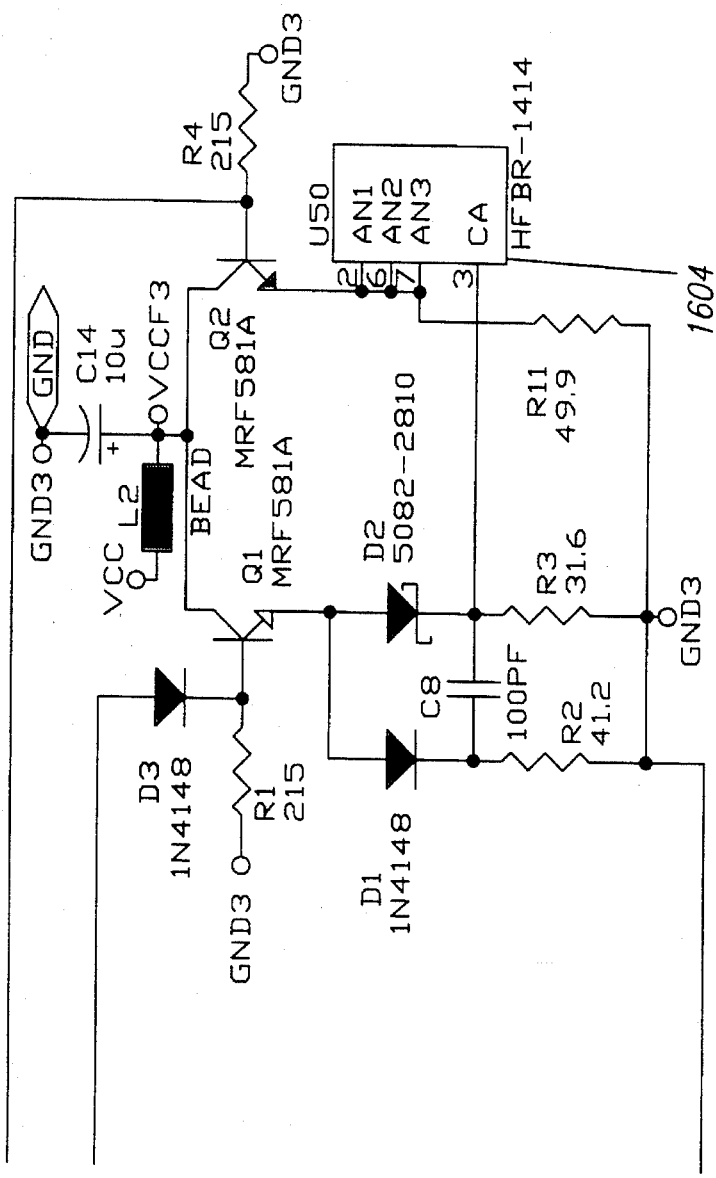

I/O controller 762 (FIGS. 23 and 24) preferably communicates with the control computer 890 via high speed fiber-optic cables 1002 and 1004 and includes the electrical to light and light signal to electrical signal conversion circuitry described more fully in conjunction with FIGS. 40 and 41. Beam controller interface information including grid voltage, static focus current, current sense select, current sense sample select information and current sense sample information, is transmitted to beam controller interface 794 from I/O controller 762 via cable 1080.

As discussed, fail-safe controller 760 preferably receives and monitors status information from various components of the system and is designed to disable the system upon detection of a potential safety problem. If the fail-safe controller 760 detects such a potential problem, it will preferably: (1) signal the grid controller 738 to disable (turn off) the electron beam; (2) shut down the high-voltage power supply 790; and (3) shut down the static focus driver 774 to defocus the electron beam.

In the preferred embodiment, fail-safe controller 760 receives fault status signals from: heat exchanger 756 via wire 1120; collimator temperature sensor 752 via wire 1066; IR target temperature sensor via wire 1068; high-voltage terminal fault latch 742 via fiber-optic cable 1020; and deflection fault sensor 770 via fiber-optic cable 1072. Fail-safe controller 760 also relays the fault status signals to the control computer via I/O controller 762 so that fault conditions may be displayed and logged by the control computer.

High-voltage power supply 790 is preferably located on C-arm cart 811. The signal to turn on the high-voltage power supply 790 is sent from the I/C controller 762 to the high voltage supply 790 via wire 1144. Voltage setpoint is sent to high-voltage power supply 790 via wire 1140, and current limit is sent via wire 1142. Voltage monitoring signal is sent to the I/O controller from the high voltage supply via wire 1146 and current monitoring signal is sent via wire 1148.

Figure 20:
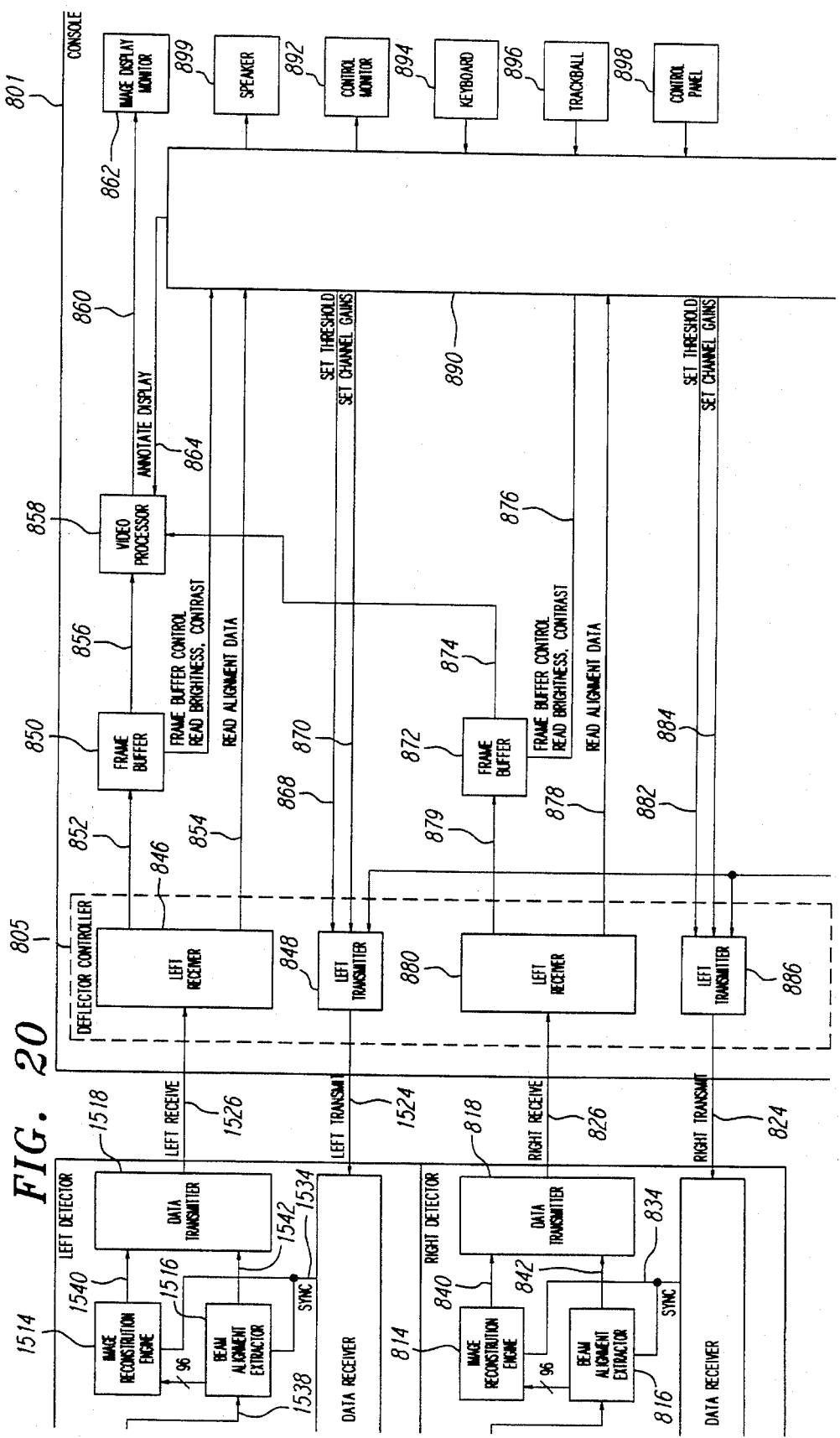

In FIG. 20, maneuverable and locatable catheters 1285 are shown inserted into patient 1280. The proximal end 1284 of catheters 1285 are preferably connected to catheter connector 970. Catheter connection 970 is preferably connected to a multi-channel photomultiplier tube 900 (FIG. 22) through fiber-optic cable 980.

FIG. 20 also functionally diagrams preferred right 822 and left 1522 detectors of the present invention. Since both detectors in FIG. 20 function in a similar fashion, only the right detector 822 will be discussed in detail. The components bearing a number having the same last two digits perform the same function.

Scintillator array 802 preferably comprises ninety-six elements and in response to x-ray photons generates visible light energy which is transmitted to photomultiplier tube 806 comprising ninety-six channels via a tapered fiber-optic bundle 804. The photomultiplier tube 806 converts the received light energy into electrical signals which are sent to signal conditioner 810 via 96 separate electrical connections 836. These signals are referred to herein as raw partial image pixel information. The multi-detector array preferably comprises a scintillator array 802, fiber-optic taper 804 and photomultiplier tube 806. It should be noted that while the preferred embodiment includes 96 channels, more or less than that number are within the spirit and scope of the present invention. Photomultiplier tube 806 is powered by photomultiplier tube power supply 808.

Signal conditioner 810 is preferably comprised of 48 circuit boards 1343. Each circuit board 1343 comprises two sets of signal conditioning amplifier circuits 1830, with each signal conditioning amplifier circuit 1830 feeding its output to a corresponding discriminator 1832. Thus 96 sets of signal conditioning amplifier circuits 1830 and discriminators 1832 are employed, with each set paired to a corresponding photomultiplier tube channel. The signal conditioner 810 outputs ninety-six separate signals for every step of the electron beam. This information is referred to as the partial image pixel information.

The outputs of the signal conditioners are preferably input into the beam alignment extractor 816. Beam alignment extractor 816 processes the information from each position of the electron beam on the target and sends processed alignment data to data transmitter 818. Clock signals are sent to the beam alignment extractor from data receiver 812.

Beam alignment extractor 816 sends the partial image pixel information from signal conditioner 810 to image reconstruction engine 814. For diagnostic purposes, the partial image pixel information sent from signal conditioner 810 may be modified by the beam alignment extractor 816 before it is sent to the image reconstruction engine 814. Image reconstruction engine 814 processes the partial image pixel information and sends image pixel data to data transmitter 818. The image reconstruction engine 814 receives clock signals from data receiver 812 via electrical connection 834.

The detector controller 805 (FIG. 21) for the detectors 822 and 1522 preferably transmits and receives optical signals to and from the detectors. Right receiver 880 receives image pixel data and beam alignment data from the right detector 822 through high-speed fiber-optic cable 826. Right detector 822 transmits this data through a data transmitter 818 (FIG. 20), which preferably includes circuitry for conversion of the signals from image reconstruction engine 814 and beam alignment extractor 816 into a serial signal. This serial signal is converted into light pulses using an LED. Right receiver 880 also comprises a light detector and related circuitry for receiving and decoding the light pulse from a serial signal into parallel signals. The beam alignment data is transmitted to control computer 890. The image pixel data is preferably transmitted to frame buffer 872. The left receiver 846 operates in a similar fashion to receive image pixel data and beam alignment data from the left detector 1522.

Figure 25:
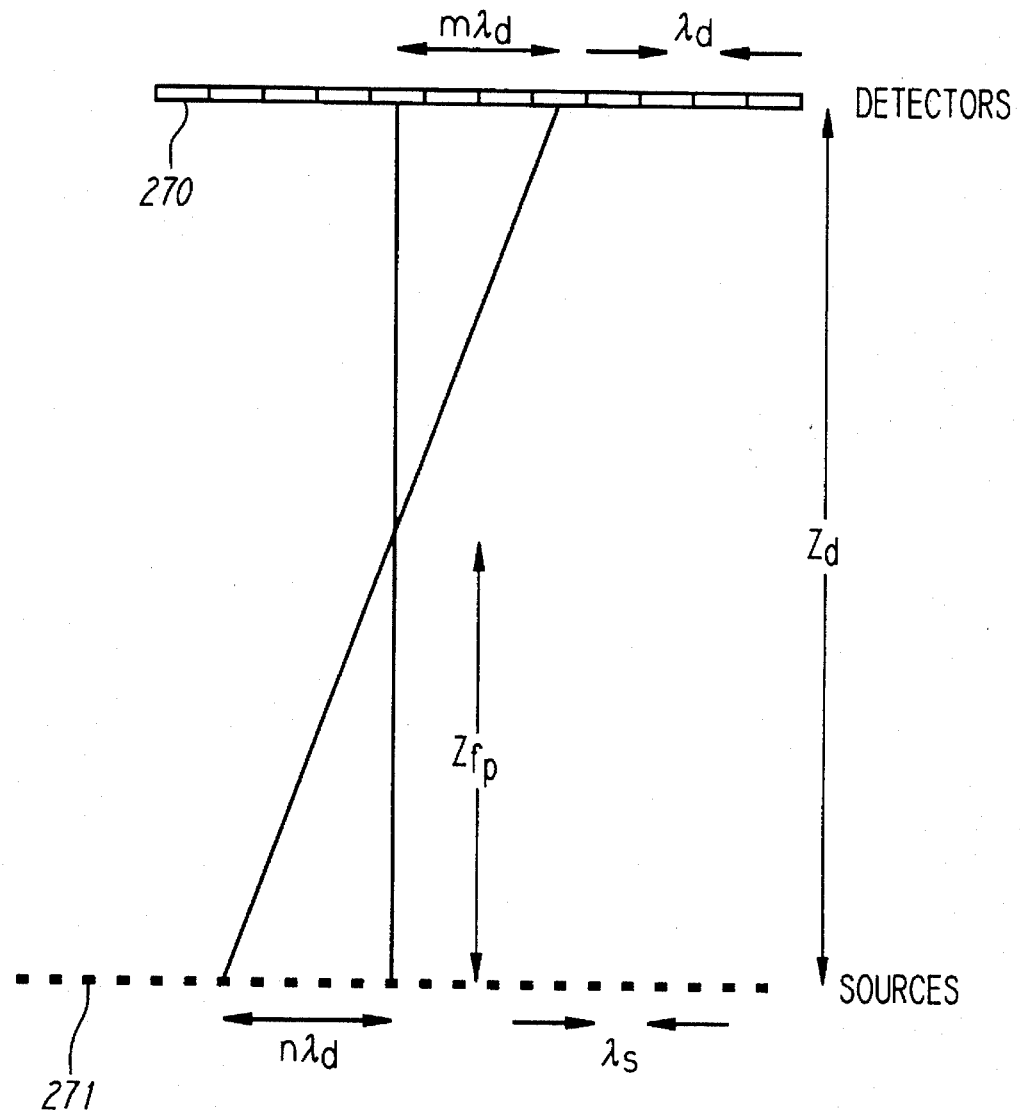

Right transmitter 886 comprises circuitry for converting parallel signals into serial signals. Right transmitter 886 receives, among other signals, signals to set channel gains and threshold levels from control computer 890. Right transmitter 886 also receives clock signals from beam deflection lookup table 918 (FIG. 25). These signals are converted into serial signals which are then transmitted as light pulses to the right detector 822 through high-speed fiber-optic cable 824. Right data receiver 812, which contains a light detector and circuitry to convert light pulses into parallel signals receives these signals. The signal to set channel gain is transmitted to the signal conditioner 810 through wire 828. The left transmitter 848 operates in a similar manner to communicate control signals to the left detector 1522.

Image pixel data transmitted to right frame buffer 872 is subsequently transmitted to video processor 858 where in a stereoscopic system, it is preferably combined with image pixel data from left frame buffer 850. Brightness and contrast information are transmitted from the right frame buffer 872 and from the left frame buffer 850 to control computer 890. This information is used to set the output of the x-ray source for optimal image quality and x-ray exposure control. Control computer 890 transmits information to the video processor 858 for annotation of the image display. The output of video processor 858 is preferably sent to image display monitor 862 where the image is displayed.

Control computer 890 preferably controls the operation of the system via detector controller 805, tube controller 807, and beam controller 796. Control computer 890 may receive operator instructions from input sources such as keyboard 894, trackball 896, and control panel 898. The operator receives system information from the control computer through control monitor 892 and speaker 899.

Figure 22:
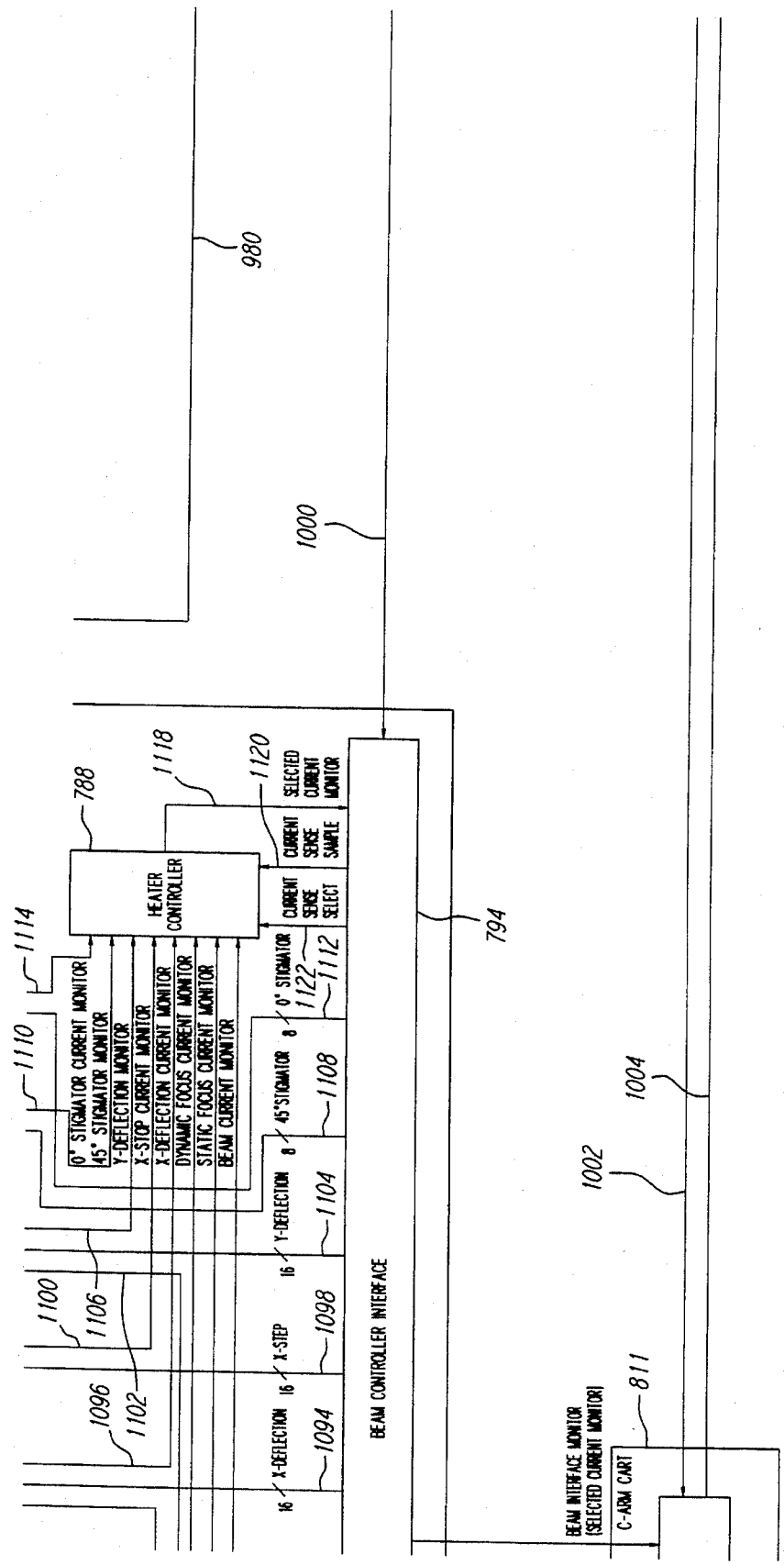

Referring to FIG. 22, catheter processor 809 preferably receives information from up to eight catheters 1285 via fiber-optic cables 980. The light pulses received through fiber-optic cables 980 are preferably detected by the catheter multi-channel photomultiplier tube 900. The catheter multi-channel photomultiplier tube 900 is powered by power supply 906. The information received by the catheter multi-channel photomultiplier tube 900 is preferably sent to catheter signal conditioning circuit 902 via electrical connection 910. The catheter signal conditioning circuit 902 outputs data to the catheter data extractor 904 via electrical connection 908. The catheter information from catheter data extractor 904 is transmitted to the control computer 890.

Tube controller 807 transmits data to and from the I/O controller 762 and the beam controller 796 to control the operation of x-ray source 798. Tube controller 807 preferably comprises beam deflection lookup table 918, programmable scan controller 920, beam transmitter 916, I/O transceiver 964, and I/O fault latch 958.

Programmable scan controller 920 is preferably set by control computer 890 to produce a particular scan. These setting may include, for example, scan rate, serpentine or raster scan, and round or square scan. Programmable scan controller 920 transmits a sequence of desired beam positions to beam deflection lookup table 918. For each desired location of the electron beam, the beam deflection lookup table preferably contains values for deflection and focus necessary to produce a well focused spot at the correct location on the target. The data in the beam deflection lookup table 918 is preferably programmed by control computer 890.

Data from the beam deflection lookup table 918 is preferably sent to beam controller interface 794 via beam transmitter 916 and high-speed fiber-optic link 1000. This data includes: (1) current sense sample signals; (2) dynamic focus; (3) x-step; (4) x-deflection; (5) y-deflection; (6) 45° stigmator; (7) 0° stigmator; and (8) "beam on request" signals. Preferably, approximately every 1.28 microseconds, a new set of data is sent from the beam deflection lookup table 918 to the beam controller interface 794.

I/O transceiver 964 provides the communications link between the control computer 890 and the I/O controller 762. Control computer 890 sends data and control signals to I/O controller 762. Information from the x-ray source 798 is sent to the control computer 890 via I/O transceiver 964.

If a fault condition occurs during the transmission of information from beam transmitter 916 to beam controller interface 794, deflection fault sensor will detect the fault and shut the x-ray source down via fail safe controller 760. If a fault condition occurs during the transmission of information from I/O transceiver 964 to I/O controller 762, the I/O controller will detect the fault and shut the x-ray source down via fail safe controller 760. If a fault condition occurs during the transmission of information from I/O controller 762 to I/O transceiver 964, I/O transceiver 964 will set the I/O fault latch 958 which will disable communications via fiber-optic cables 1000 and 1002. This will be detected as faults by the deflection fault sensor and by the I/O controller which will shut the x-ray source down as described above.

Real-Time Eye

Figure 26:
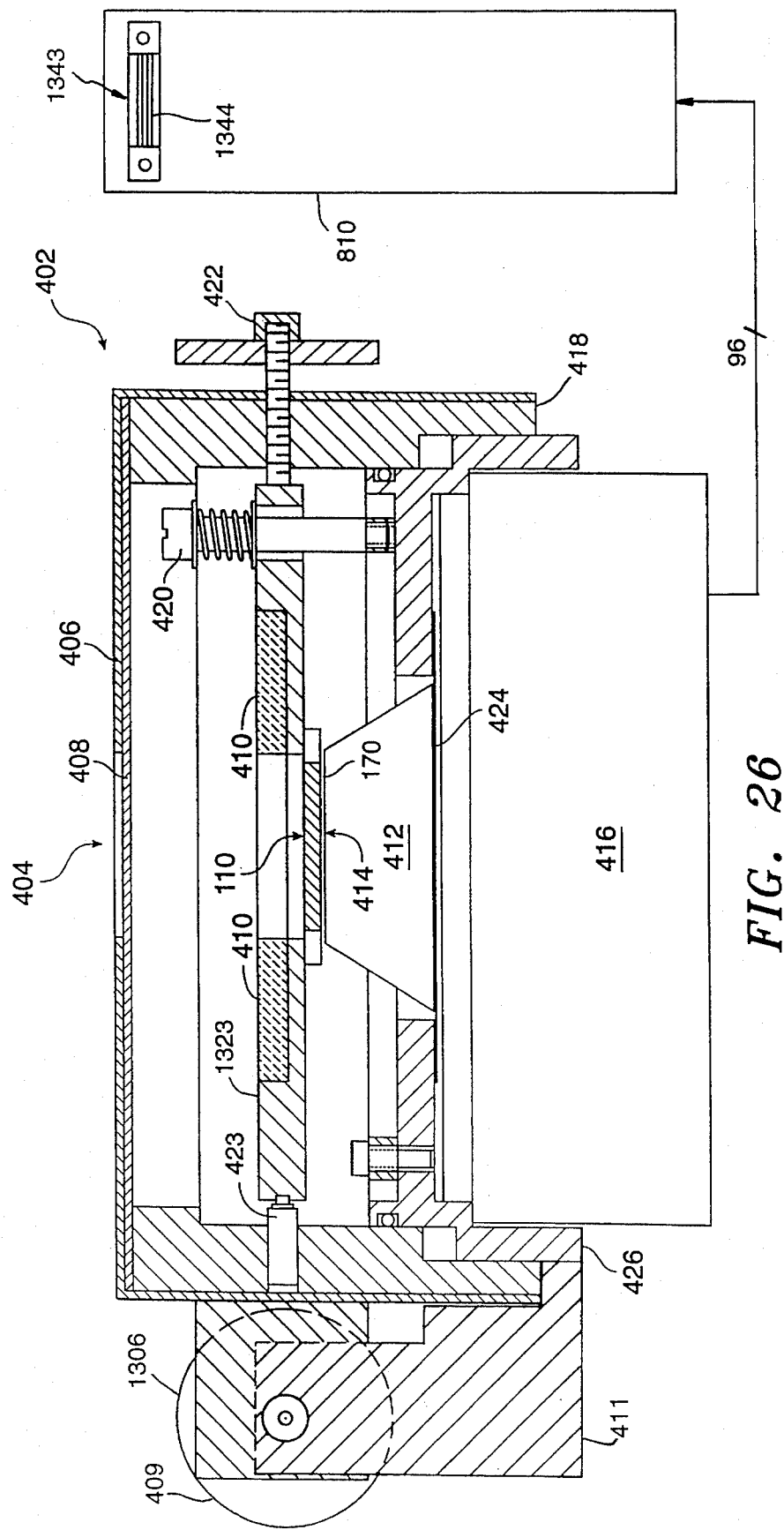
FIG. 26 is a partial cross-sectional representation of a preferred real-time eye assembly.

FIG. 26 depicts "real-time eye" assembly 402 which comprises the multi-detector array according to a presently preferred embodiment of the present invention. X-rays enter through x-ray window 404 in lead shield 406. X-ray window 404 is preferably circular and about 1.91 cm (0.75 in) in diameter to permit x-rays coming from the apertures 140 of the collimation grid 90 to strike the multi-detector array 110 while attenuating scattered x-rays. A light shield 408 is preferably provided to shield the eye from ambient light. The light shield 408 may be made of a thin sheet of aluminum or beryllium chosen to attenuate light without substantially attenuating the x-rays, and is preferably 0.0125 cm thick. The multi-detector array assembly 402 is preferably enclosed in a light-tight outer detector housing 418 to minimize stray light from generating noise. Three centering screws 422 are provided for planar and linear alignment. Rotational alignment in one embodiment is achieved by rotating outer detector housing 418 with respect to PMT mount 426.

Scintillator array 112 is preferably mounted beneath the x-ray window 404. Scintillator array 112 is preferably comprised of 96 scintillator elements 170 arranged in a pseudo-circle, with each scintillator element 170 preferably cut to a square horizontal cross-section. The length of the individual scintillator elements 170 are preferably about 0.50 cm and the front input faces are preferably 0.135 cm×0.135 cm. The scintillator elements 170 are preferably YSO, LSO or BGO but other scintillating materials may also be used.

For a suitably reduced decay time for its light output in this application (to about 50 nsec), BGO needs to be heated to approximately 100° C. When using BGO, the scintillator array is located near heating element 410 for use with a BGO scintillator. If a BGO scintillator is used heating element 410 may be a resistive heating element designed to keep the BGO scintillator crystal array 112 at an operating temperature of about 100° C. Accordingly a resistive heating element may be provided, as shown in FIG. 26. YSO is preferably used as the scintillator material, thereby avoiding the need for a heater.

A fiber-optic imaging taper 412 of the preferred multi-detector array 110 directs light photons emerging out of the bottom 414 of the scintillator crystal array 112 to a 96 channel photomultiplier tube (PMT) 416. A presently preferred fiber-optic imaging taper 412 is available from Collimated Holes of Campbell, Calif. and has a circular input aperture of diameter 2.03 cm (0.8 in) and a circular output aperture of diameter 3.38 cm (1.33 in). Taper 412 matches each scintillator crystal pitch dimension (0.06") to that of the PMT 416 (0.10"), i.e., it has a magnification of 1.667 times. High viscosity optical coupling fluid available from Dow Corning (Type 200) with a refractive index approximately matching that of the glass may be used at the two faces of the taper as an optical coupling medium to maximize the light transfer efficiency from the scintillator crystals 170 to the taper 412 and from the taper 412 to the PMT input face 424.

Photomultiplier tube 416 is preferably a 96 channel tube (one channel corresponding to each scintillator crystal 170) model number XP 1724A available from the Philips Corporation. Photomultiplier tube 416 preferably has a fiber-optic face plate so that the spatial arrangement of the scintillator crystal array 112 is accurately carried through to the PMT photocathode located in the PMT on the other face of the faceplate. An x-ray photon striking one of the scintillators 170 produces many light photons which are coupled to the PMT photocathode. This produces a corresponding electron pulse at the photocathode and the pulse is amplified in one channel of the PMT dynode structure up to 1,000,000 times.

Figure 27:
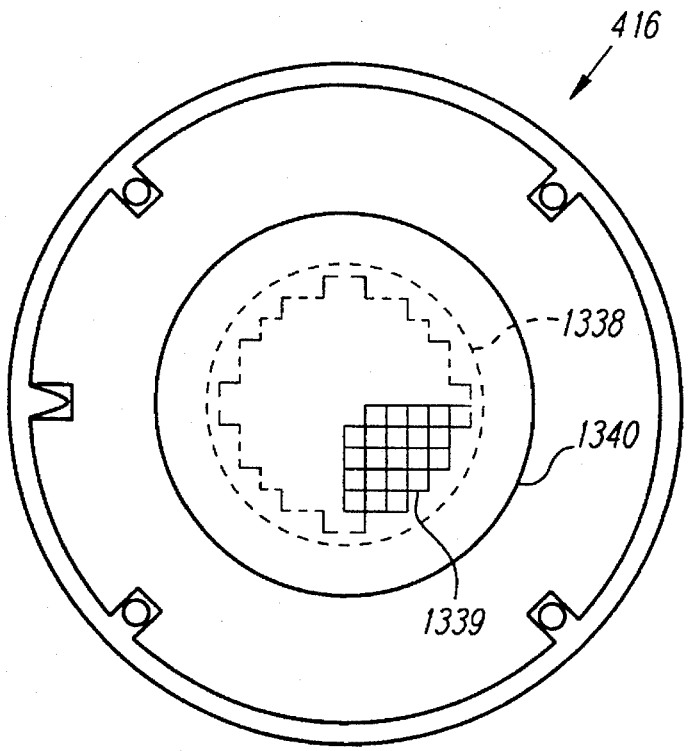
FIG. 27 is a diagram of a top view of a preferred 96-channel photomultiplier tube.
Figure 28:
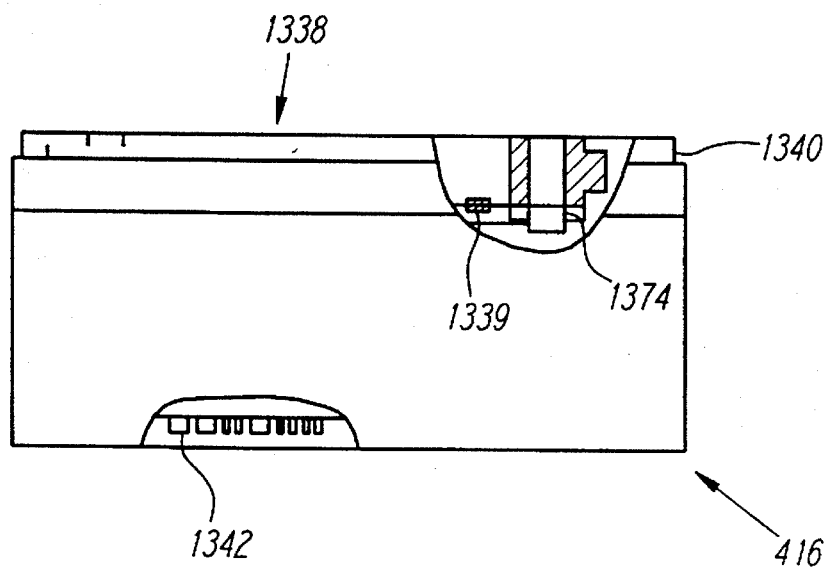
FIG. 28 is a partial cross-sectional side view of the photomultiplier tube of FIG. 27.

Referring to FIGS. 27 and 28, the front face of PMT 416 includes a glass window 1340 which extends beyond the PMT encapsulation by 0.1 mm. 96 photo-cathode elements 1339 are arranged in a pseudo-circular array in the center of the front face of PMT 416. Each photo-cathode element is square in shape with dimensions of 2.54 mm×2.54 mm. PMT 416 is attached to the PMT mount by means of attachment bolts set into PMT 416 at bolt holes 1374.

This pseudo-circular array of 96 photo-cathode elements creates a light-sensitive circular area 1338 on the PMT 416 with a diameter of 30.5 mm. It is this light sensitive area 1338 that interfaces with the tapered fiber-optic bundle 412. Each PMT photocathode element 1339 has a corresponding electrical output connector 1342. When light photons reach the PMT 416, the photocathode elements 1339 generates raw partial image pixel signals which is output at PMT connector 1342. The raw partial image pixel signals are transmitted via PMT connector 1342 to signal conditioner 810. Further details of a presently preferred real time eye assembly can be found in co-pending U.S. patent application Ser. No. 08/387,292, Lyon and Lyon Docket 210/205, which has been incorporated herein by reference in its entirety.

Signal Conditioner

Signal conditioner 810 preferably converts the 96 outputs of PMT 416 into 96 pulse trains with each pulse in the pulse train corresponding to a single x-ray photon arriving at the corresponding scintillator element 170. Signal conditioner 810 is preferably comprised of 48 circuit boards 1343. Each circuit board 1343 comprises two sets of signal conditioning amplifier circuits 1830, with each signal conditioning amplifier circuit 1830 feeding its output to a corresponding discriminator 1832. Thus 96 sets of signal conditioning amplifier circuits 1830 and discriminators 1832 are employed, with each set paired to a corresponding photomultiplier tube channel. The signal conditioner 810 outputs ninety-six separate pulse trains for every step of the electron beam. This information is referred to as the partial image pixel information.

The signal conditioning amplifiers 1344 shape and amplify the raw partial image pixel signals from the photomultiplier tube, and output a pulse train of partial image pixel signals to the beam alignment and image reconstruction boards. To even out any performance variations between the individual photomultiplier tube channels, a separate gain signal is sent to each of the signal conditioning amplifier circuits 1830. However, the same threshold signal is sent to each discriminator 1832.

Figures 29, 29A:
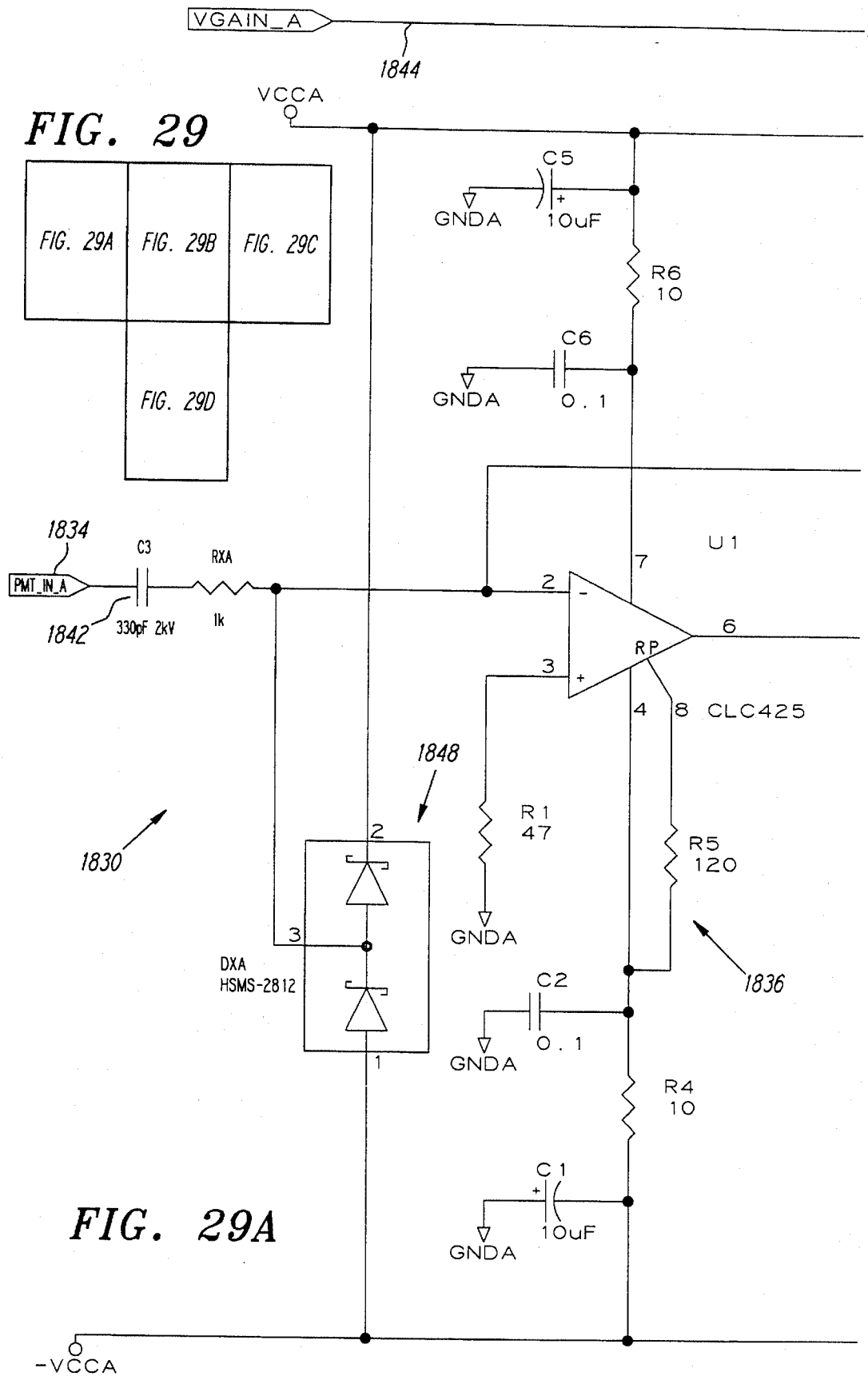
FIG. 29 is a schematic of a preferred signal conditioning amplifier.
Figure 29B:
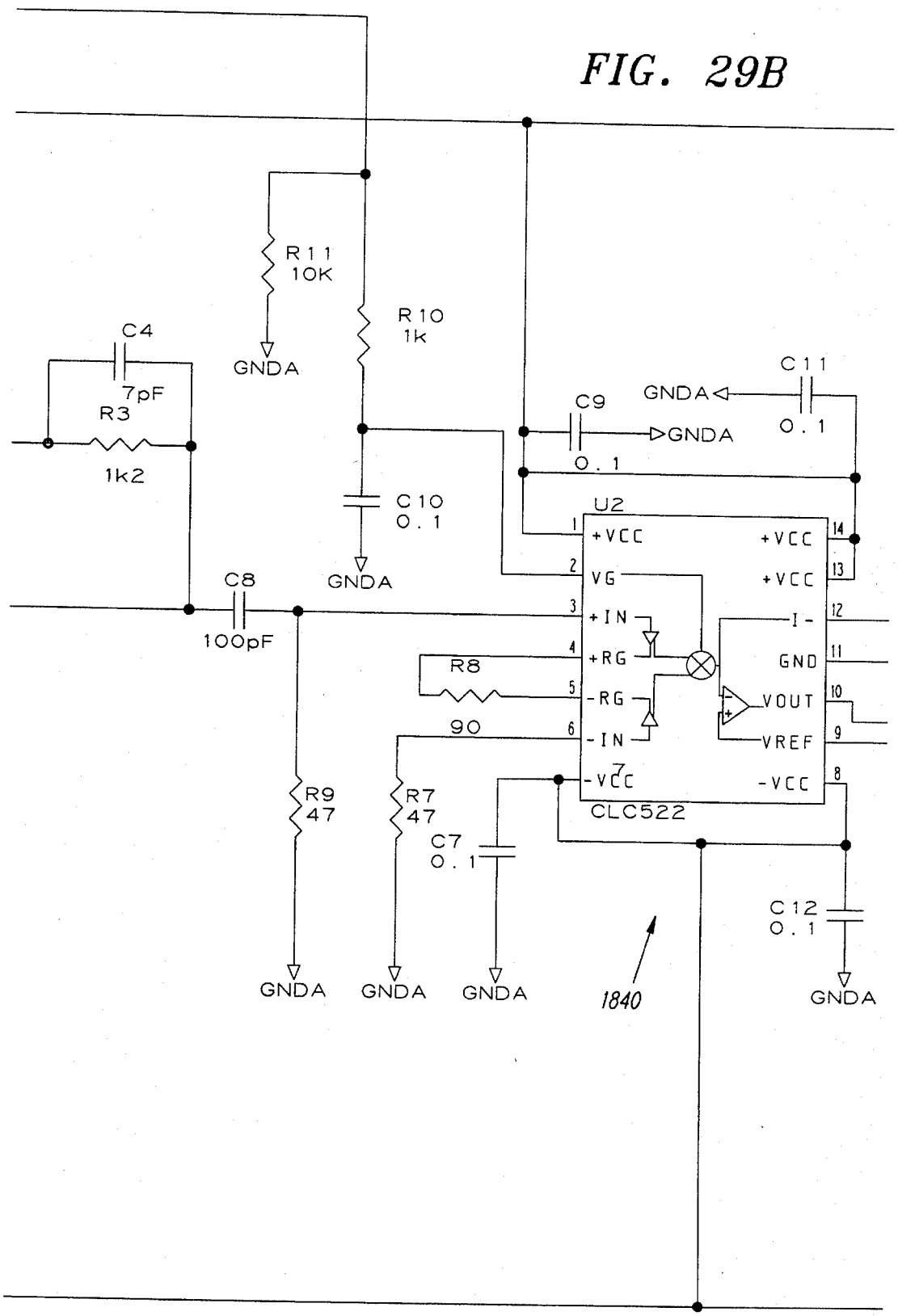
Figure 29C:
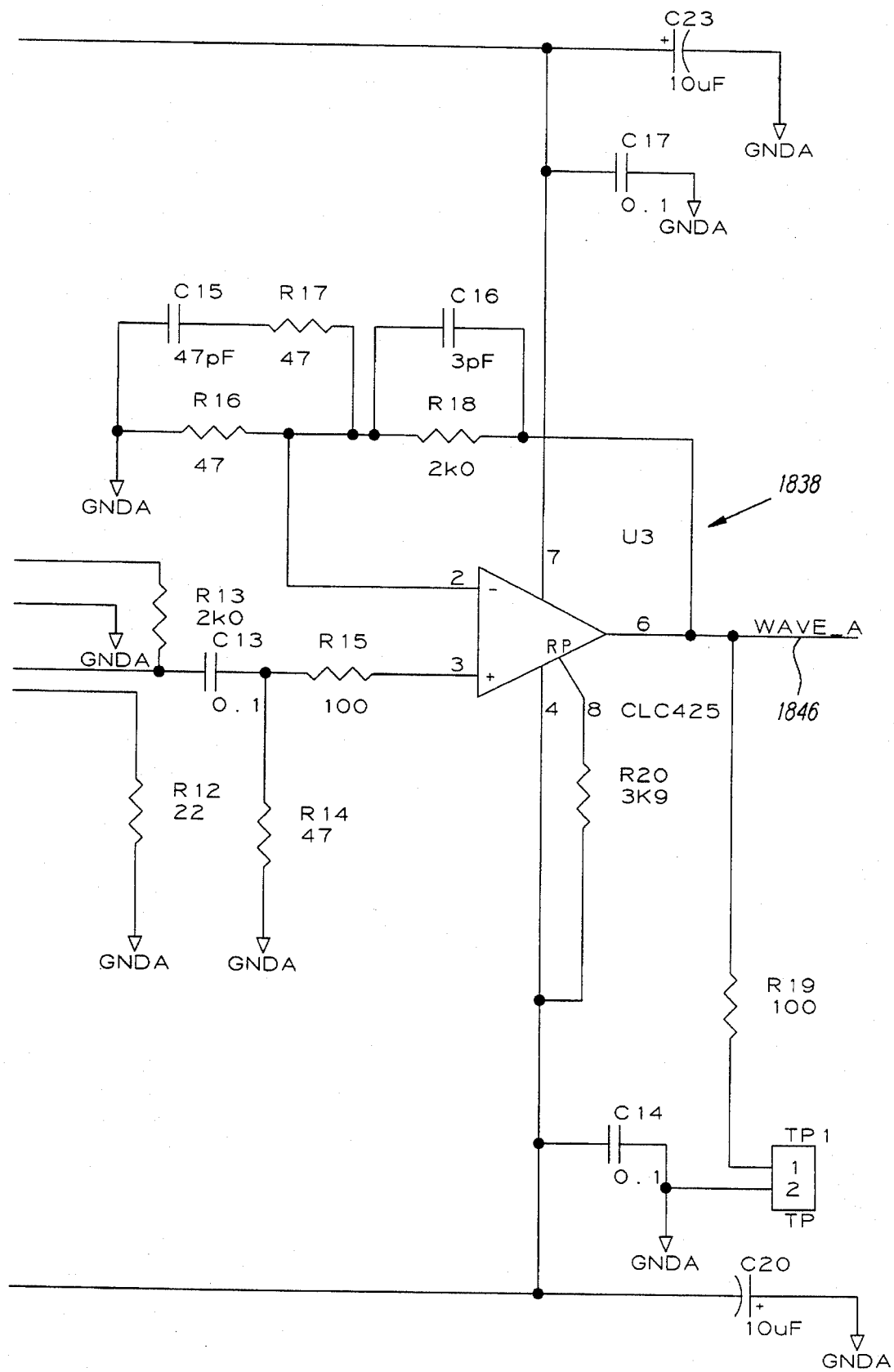

FIG. 29 is a circuit diagram of a preferred signal conditioning amplifier circuit 1830. Raw partial image pixel signals from a single photomultiplier tube channel are input to the signal conditioning amplifier circuit 1830 via input line 834. Signal conditioning amplifier circuit 1830 is preferably AC coupled to eliminate offset drift problems. The AC coupling low frequency cut-off is high, e.g., 30 Mhz, so that the pulse is differentiated. This eliminates the need for a DC restorer circuit to keep the baseline reference voltage constant as the pulse rate varies. Clamping diodes 1848 provide voltage protection for the amplifiers within the signal conditioning amplifier circuit 1830.

Signal conditioning amplifier circuit 1830 preferably comprises three stages of current amplification. The input partial image pixel signals are coupled through a coupling capacitor 1842 to a fixed gain first stage amplifier 1836. The output of the first stage amplifier is fed to a variable gain second stage amplifier 1840, which receives gain control signals applied over input line 1844. The output from the variable gain second stage amplifier 1840 is fed to a fixed gain third stage amplifier 1838, which sends an amplified partial image pixel waveform to the discriminator via line 1846. Supply voltages of SV and −SV are applied to the each amplifier stage within the signal conditioning amplifier circuit 1830. Each of the 96 signal conditioning amplifier circuits 1830 function similarly to process raw partial image pixel signals from its corresponding photomultiplier tube channel.

Figure 30:
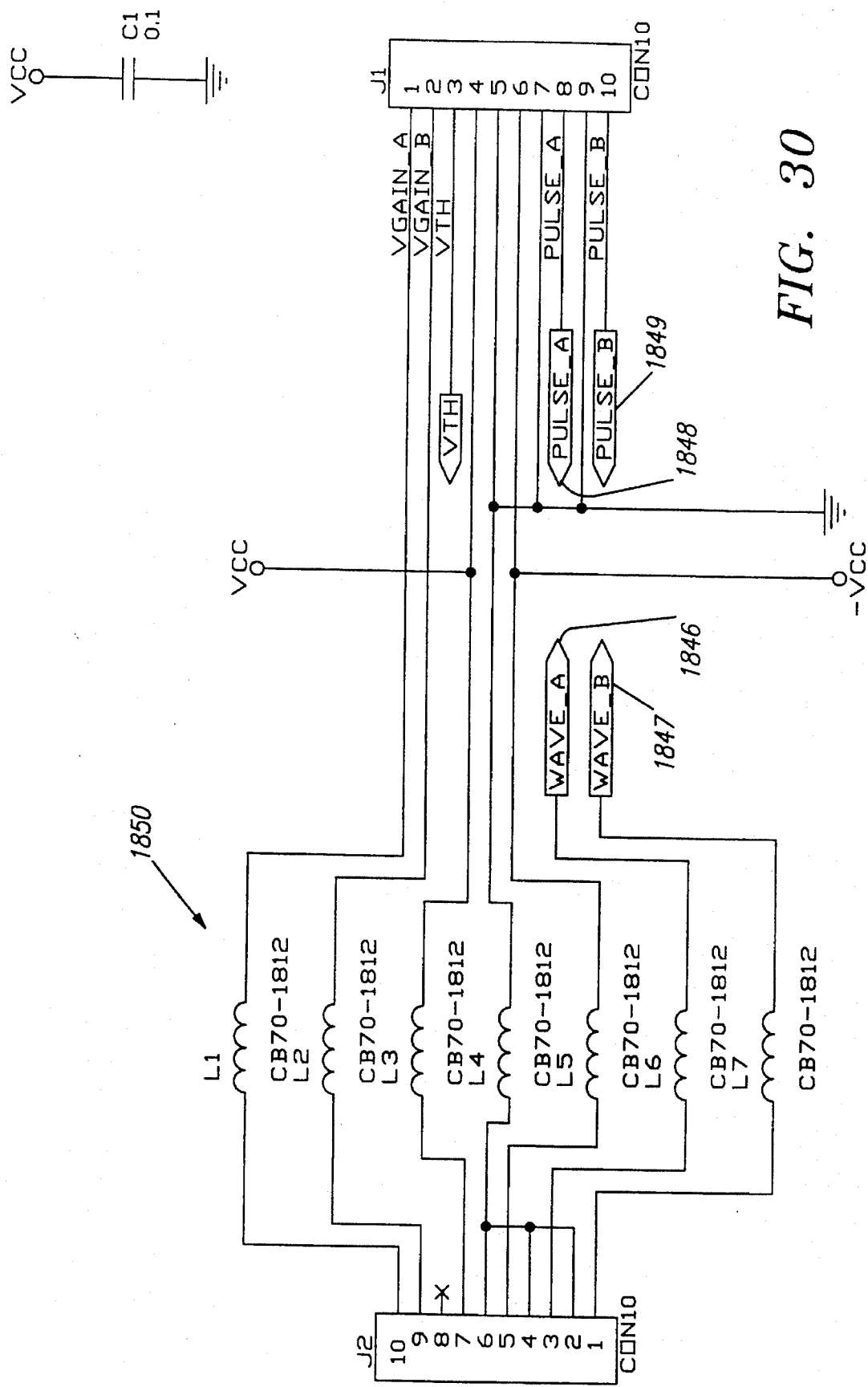
FIG. 30 is circuit diagram of the input and output connectors for a preferred discriminator.

Referring to FIG. 30, the discriminator 1832 essentially digitizes the partial pixel information by comparing the amplified partial image pixel waveform from a signal conditioning amplifier circuit 1830 with a threshold value and producing a high or low value depending on whether the threshold value is crossed. This high or low value corresponds to whether an x-ray photon was detected or not. FIG. 30 diagrams the preferred input and output connectors for each pair of discriminators 1832 located on a single circuit board 1343. The amplified partial image pixel waveforms from two sets of signal conditioning amplifier circuits 1830 are coupled to the discriminators 1832 via input lines 1846 and 1847. Surface mount ferrite bead inductor 1850 are preferably employed to filter noise from the input waveforms. Digitized output pulses from the discriminators 1832 are output via output lines 1848 and 1849.

Figure 31:
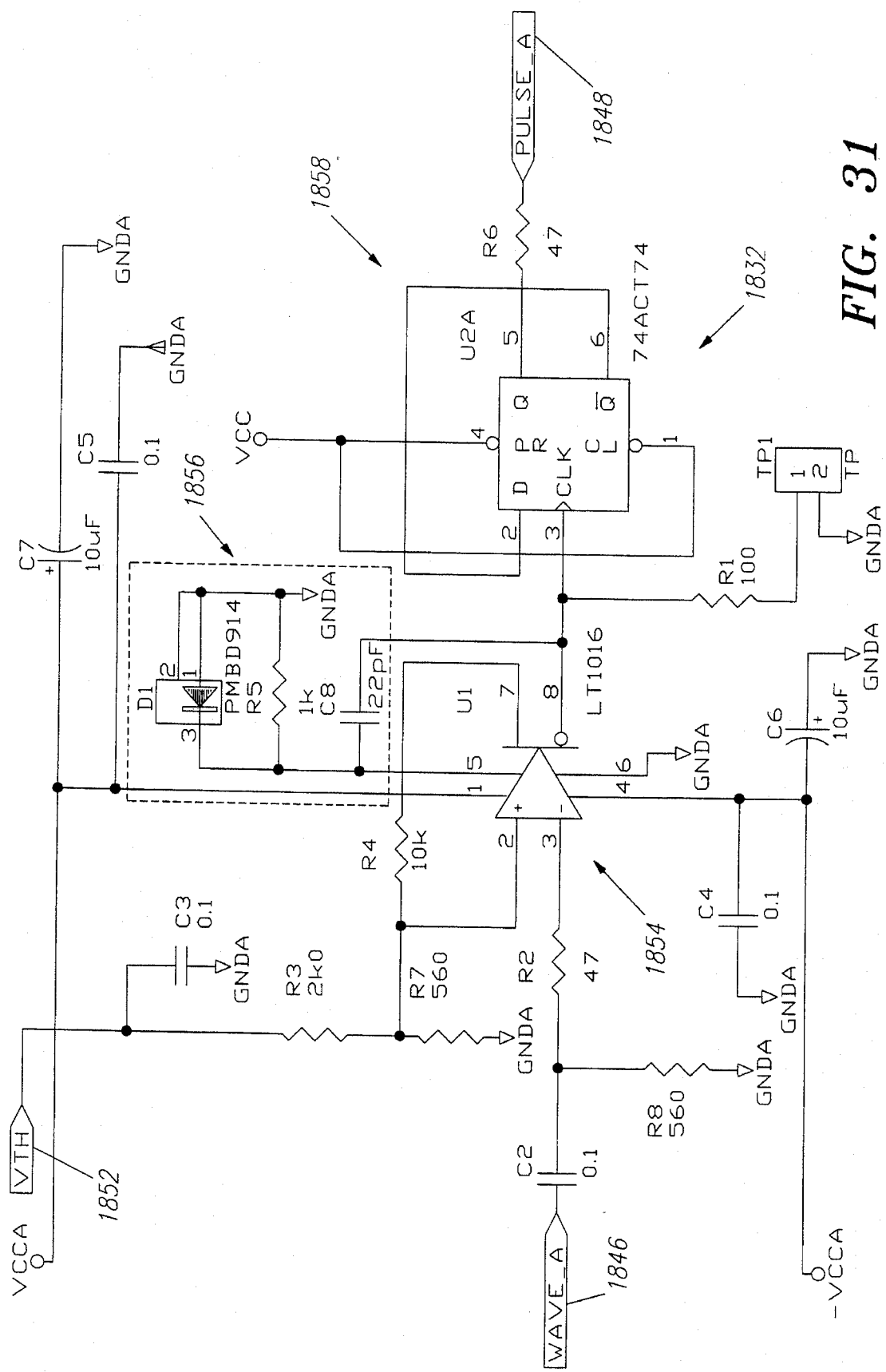
FIG. 31 is a schematic of a preferred discriminator.

FIG. 31 is a circuit diagram of a preferred discriminator 1832. The amplified partial image pixel waveforms from the signal conditioning amplifier circuit 1830 are input, via input line 1846, to a comparator 1854 which provides a constant amplitude output pulse regardless of the amplitude of its input. The threshold reference signal, applied to comparator 1854 via input line 1852, is preferably set to a value which is slightly higher than the amplifier noise output level so that it will not trigger on the noise level. The supply voltage inputs for the comparator 1854 are preferably set at +5 V and −5 V.

The preferred comparator 1854, a standard LT1016 comparator available from Linear Technology, functions as both a comparator and a register. Comparator 1854 generates a latched output which is preferably coupled to a pulse stretching circuit 1856, which is comprised of a circuitry diode, grounded resistor and a capacitor. The pulse stretching circuit 1856 allows the comparator 1854 to generate output pulses approximately 29 nanoseconds wide. The output pulse from the comparator is preferably fed to a divide-by-two counter 1858, to reduce the frequency of the output pulses. No information is lost since subsequent circuits count the edges of this pulsed output. The pulsed output, containing digitized partial image pixel signals, are output from the divide-by-two counter 1858 to the next processing stage via output line 1848. Each of the 96 discriminators 1832 function in a similar manner to process partial image pixel waveforms from its corresponding signal conditioning amplifier circuits 1830.

Figure 32:
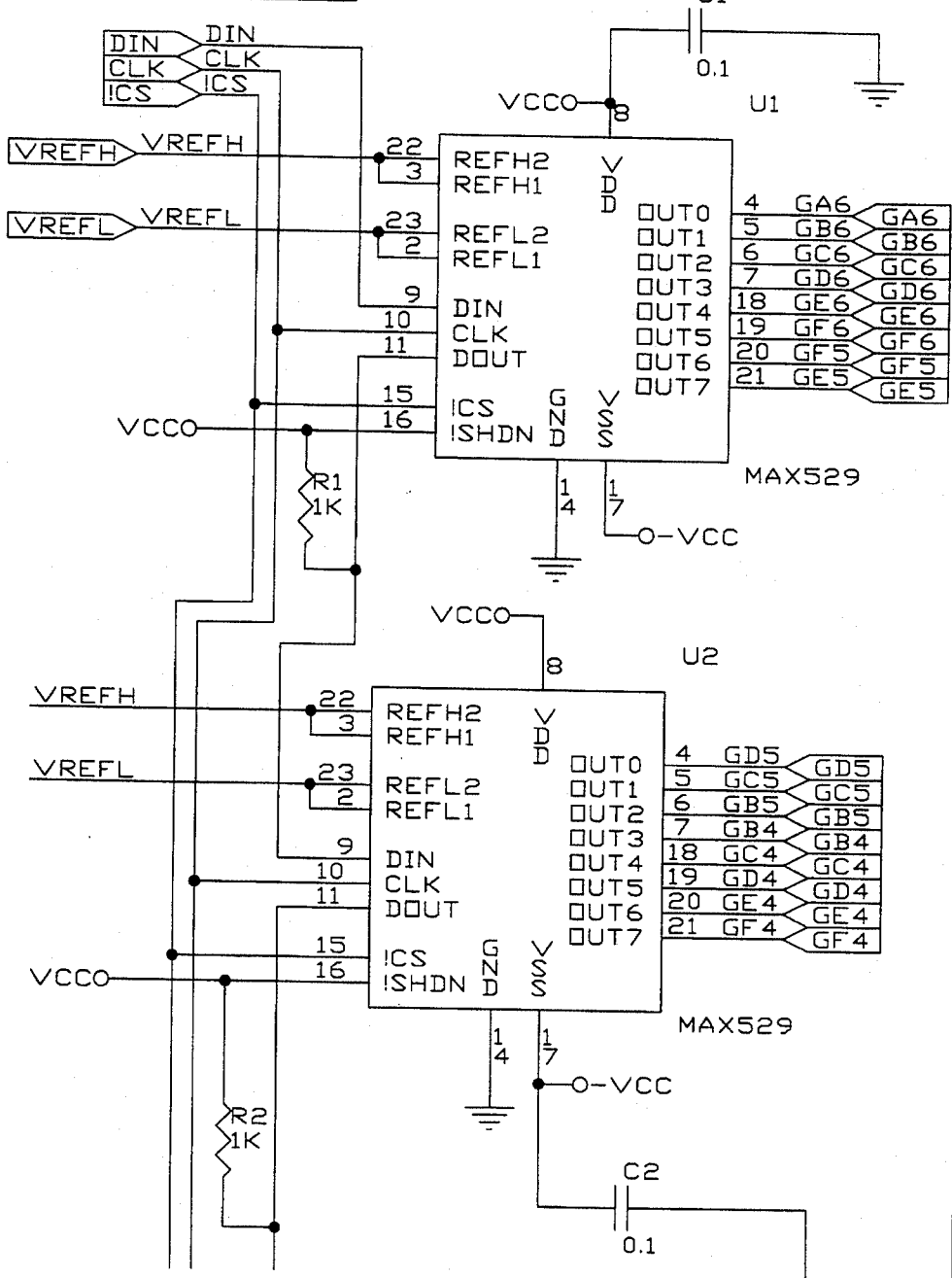
FIG. 32 is a schematic of preferred digital-to-analog converters which provide gain and threshold control signals to the signal conditioner.
Figure 32:
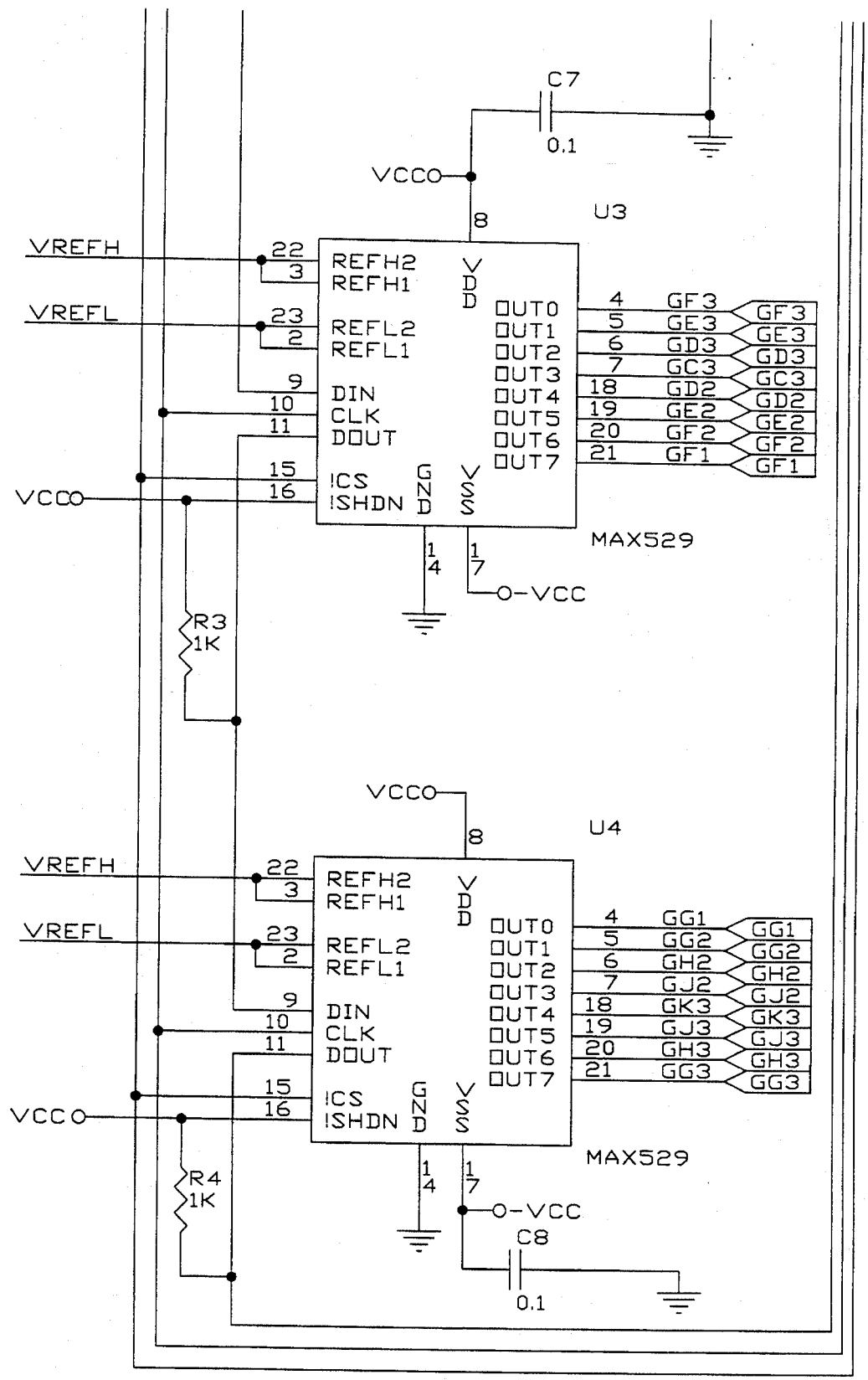
Figure 32:
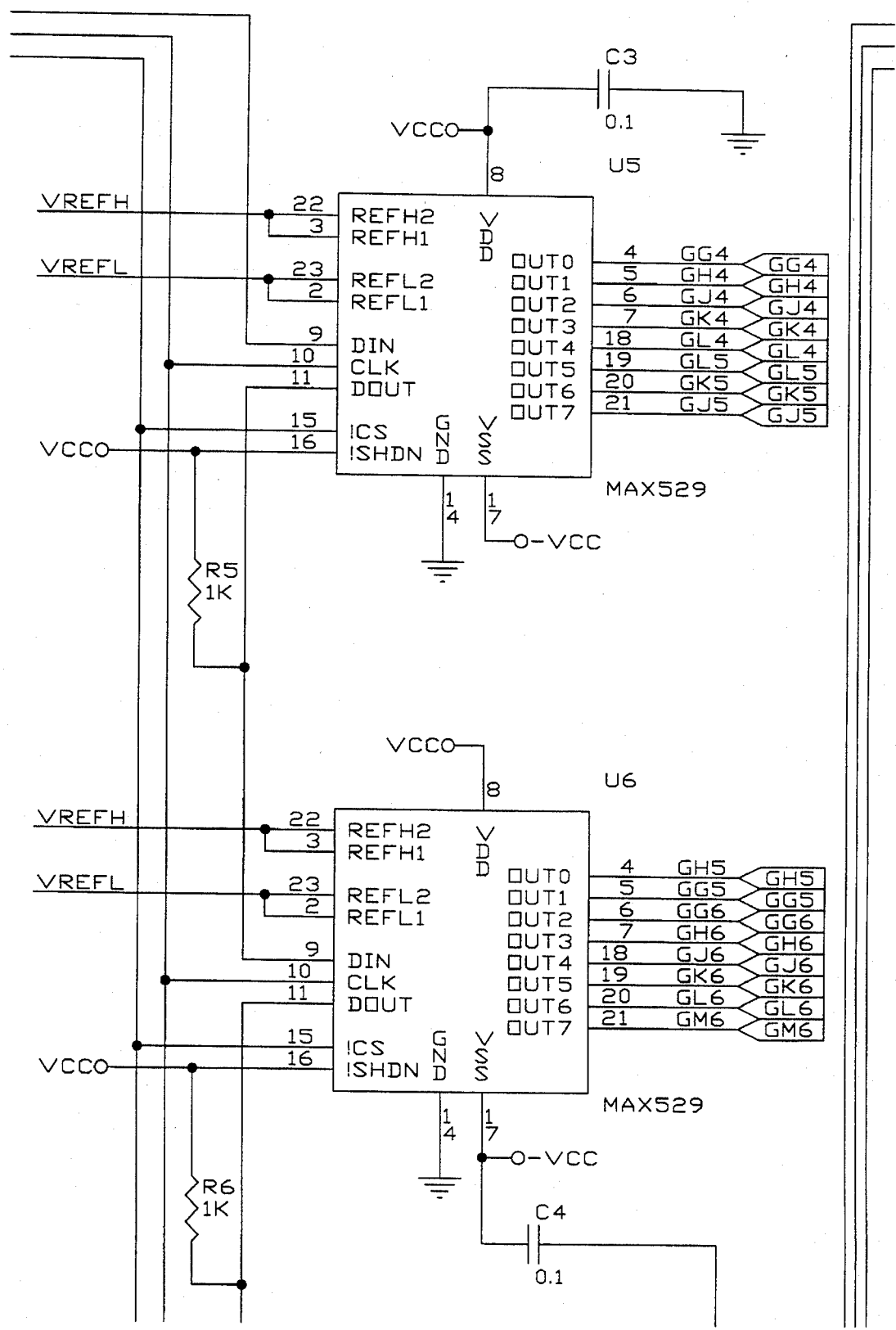
Figure 32:
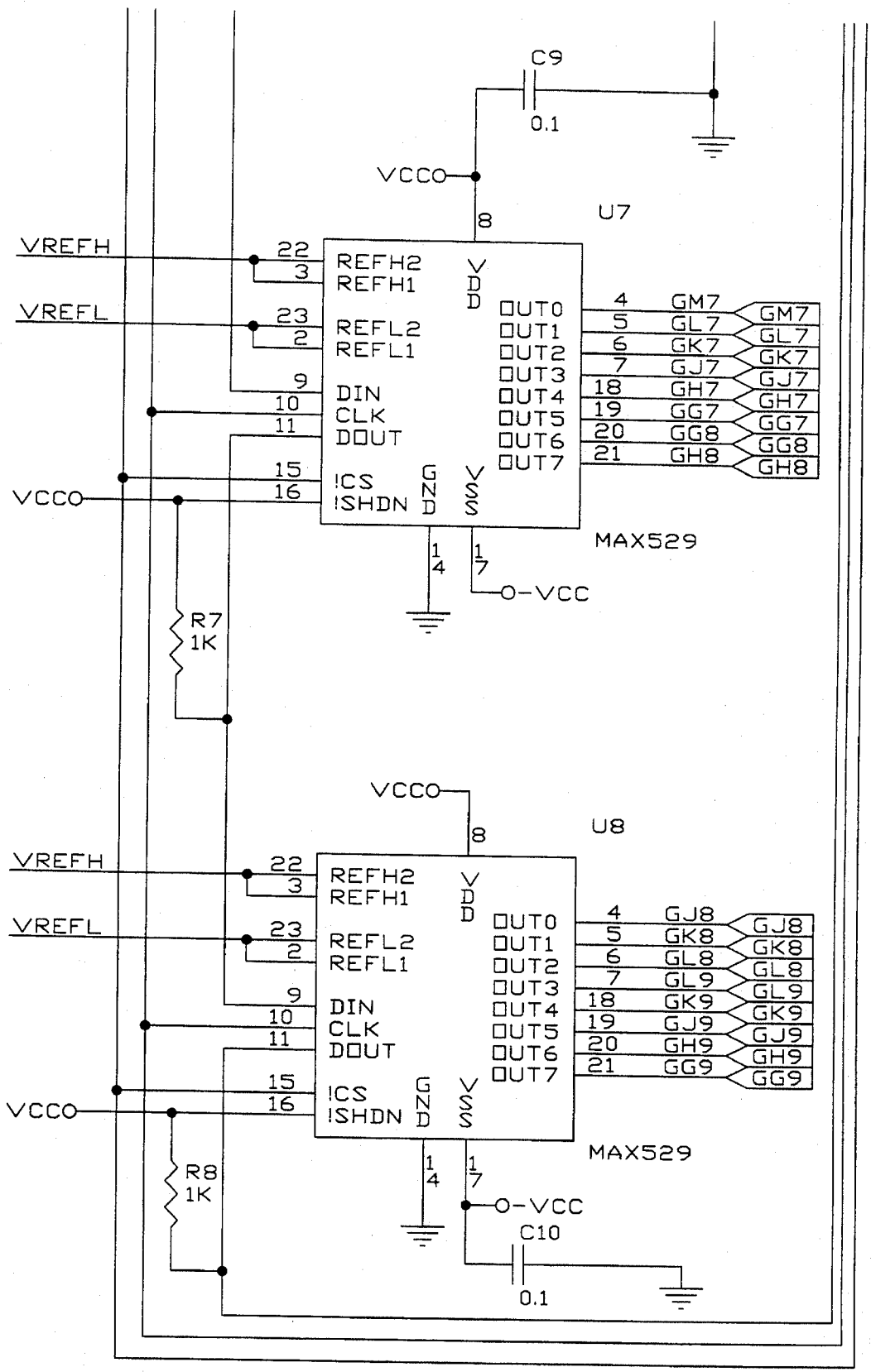
Figure 32:
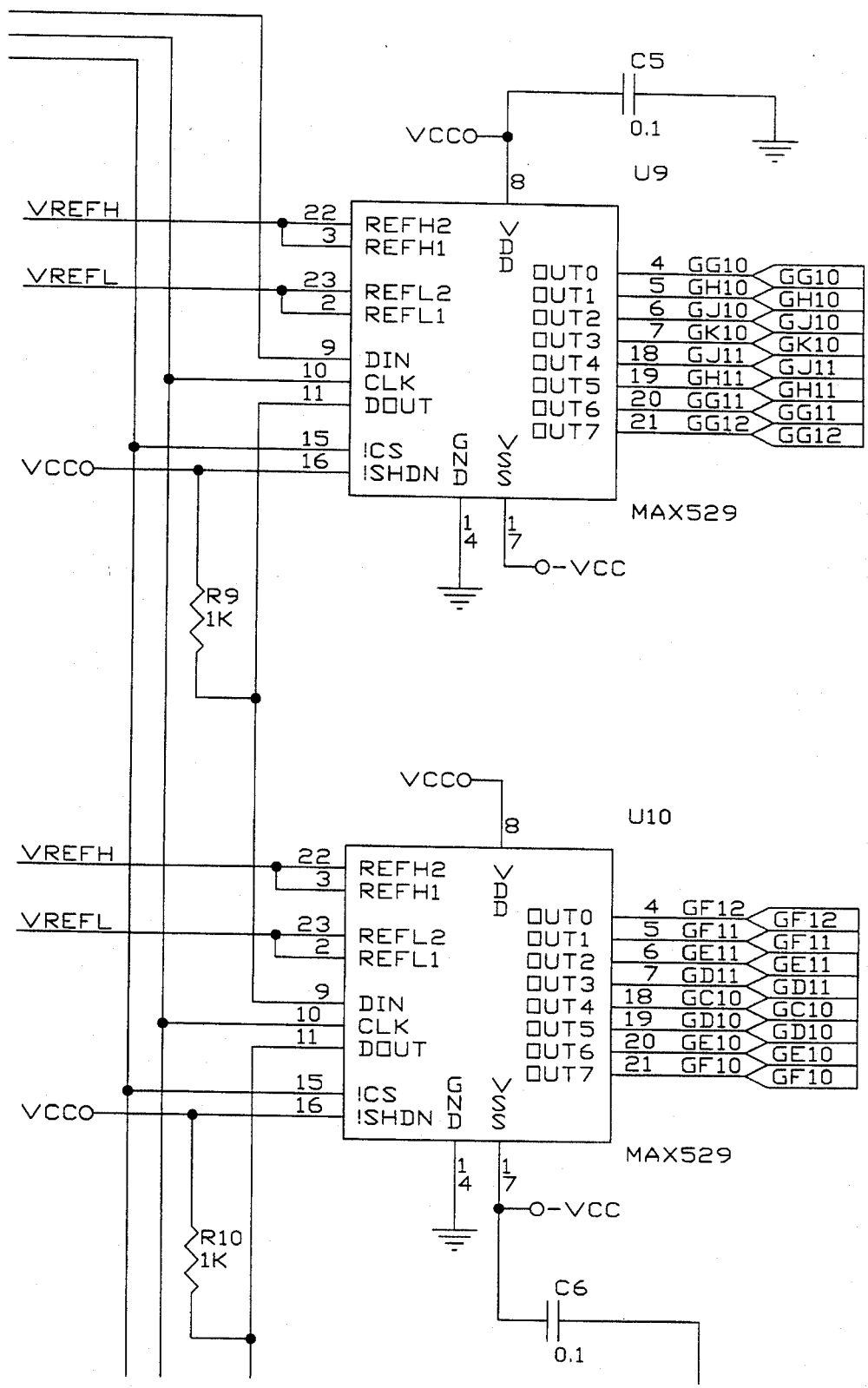
Figure 32:
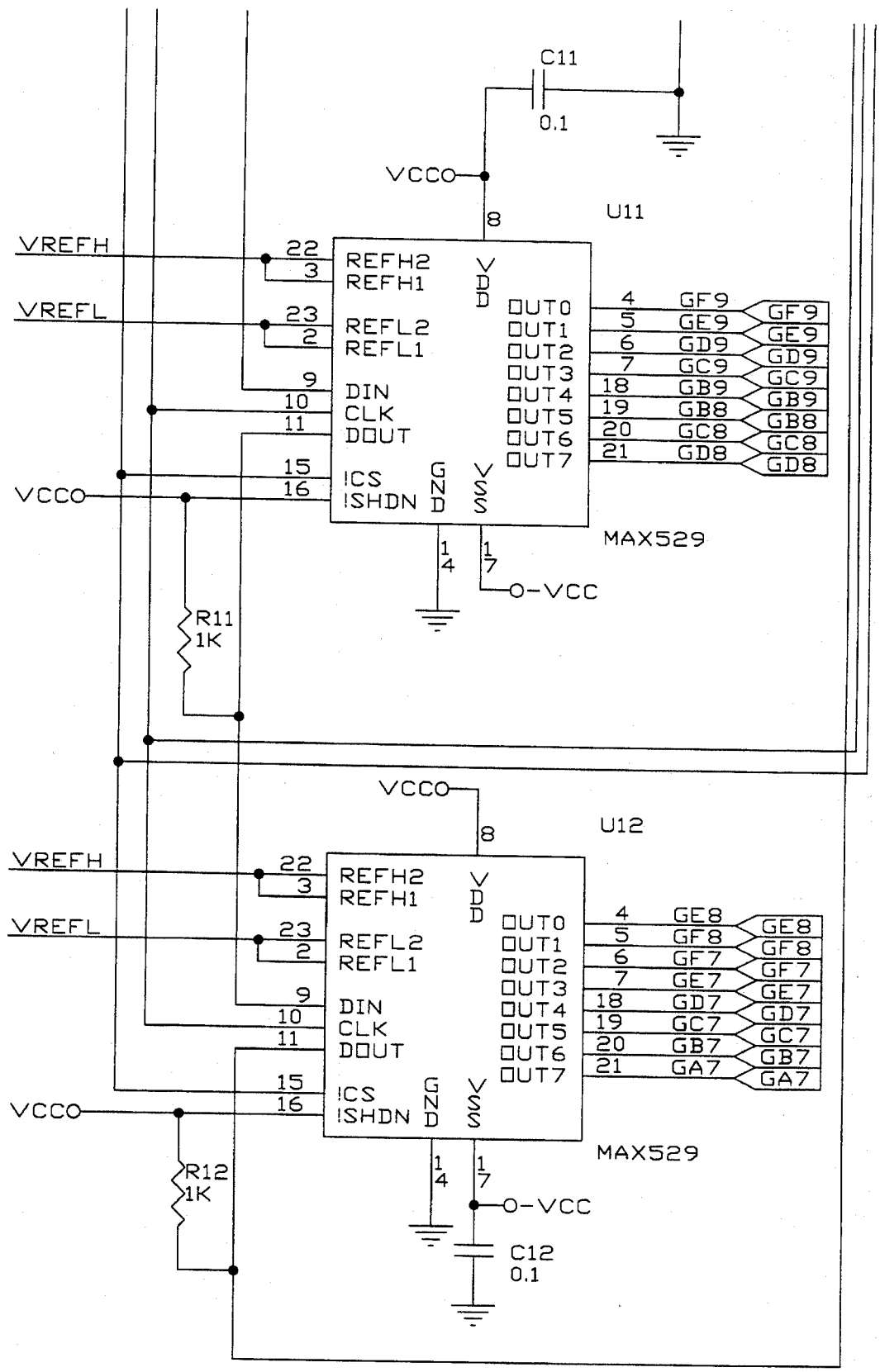
Figure 32:
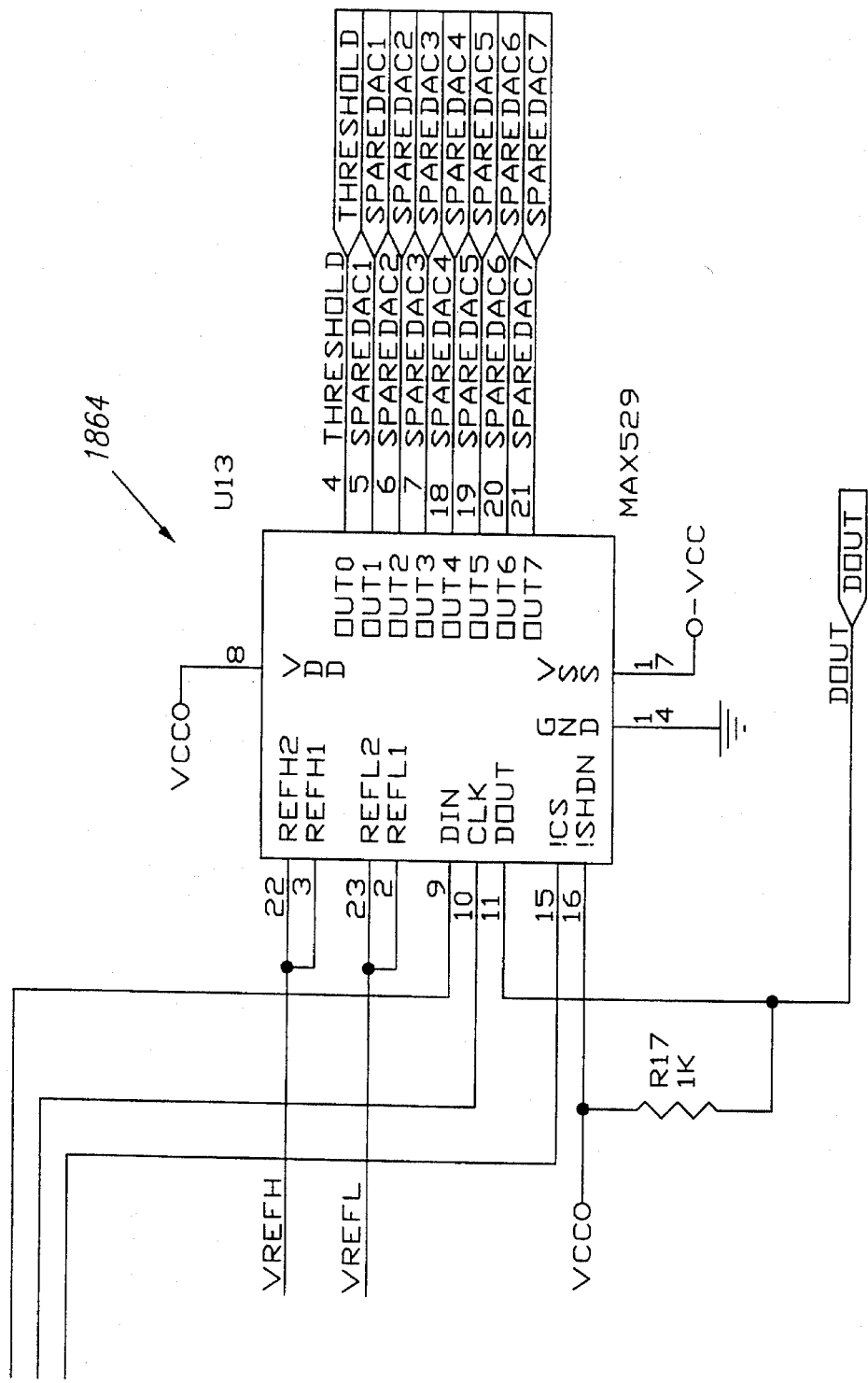
Figure 33B:
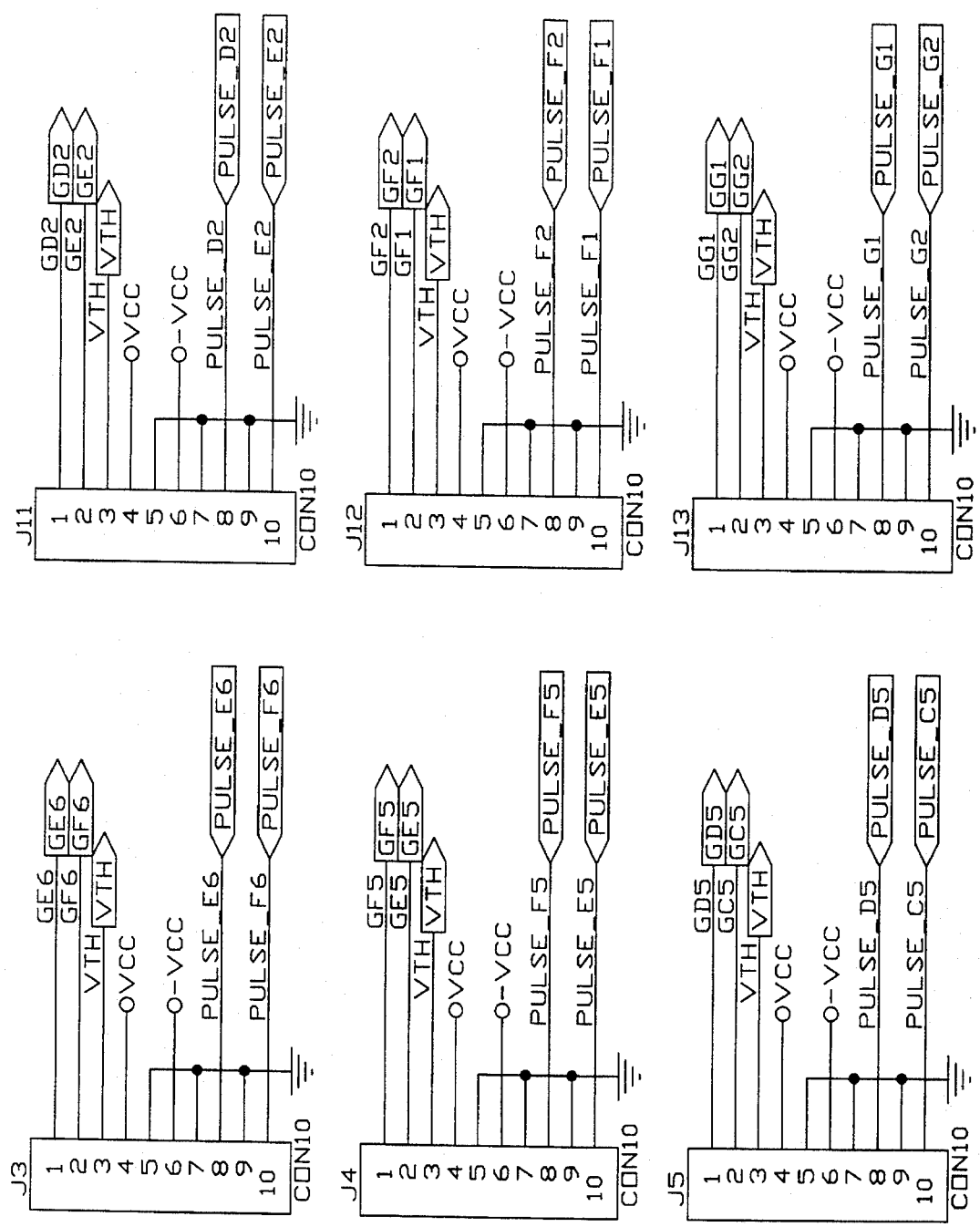
FIG. 33 is a circuit diagram of the preferred interface connectors between the DACs of FIG. 32 and the signal conditioning amplifier circuit of FIG. 29.
Figure 33C:
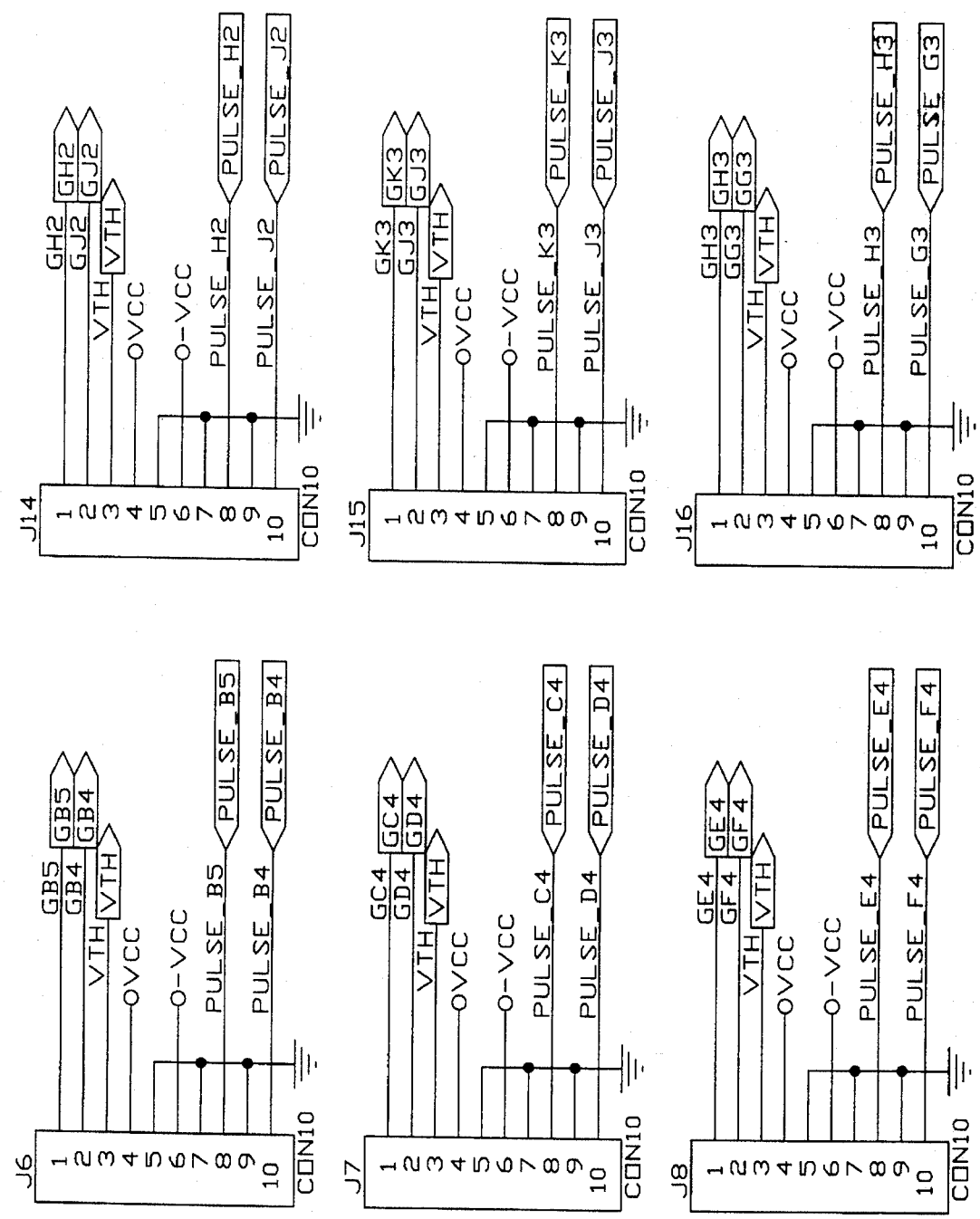
Figure 33D:
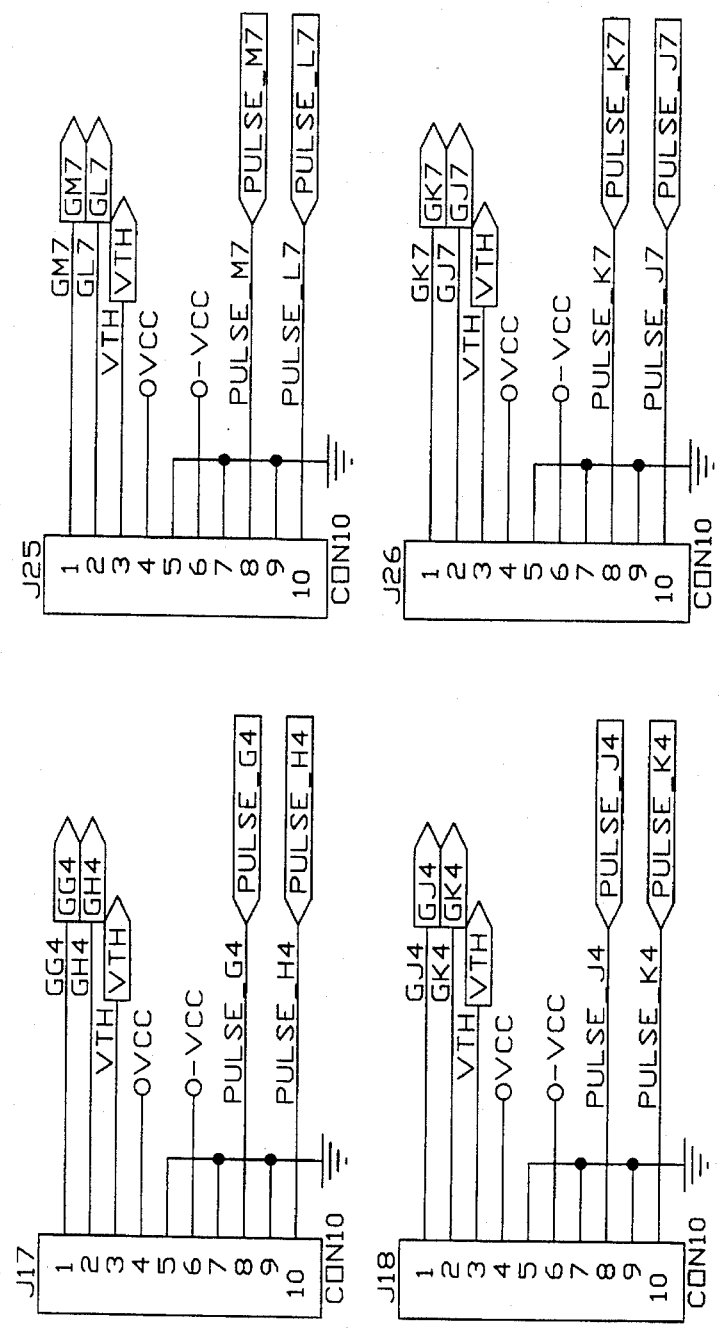
Figure 33E:
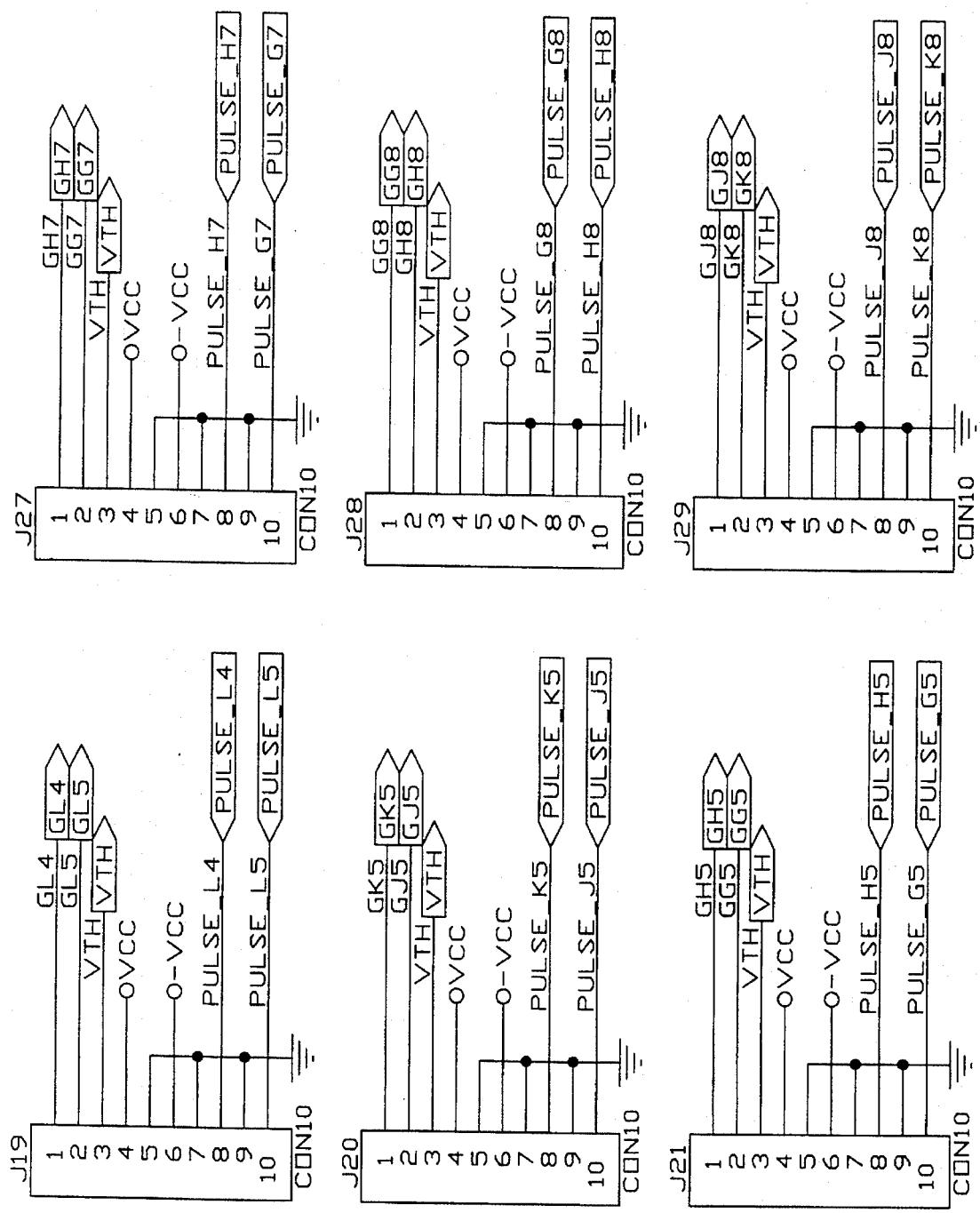
Figure 33F:
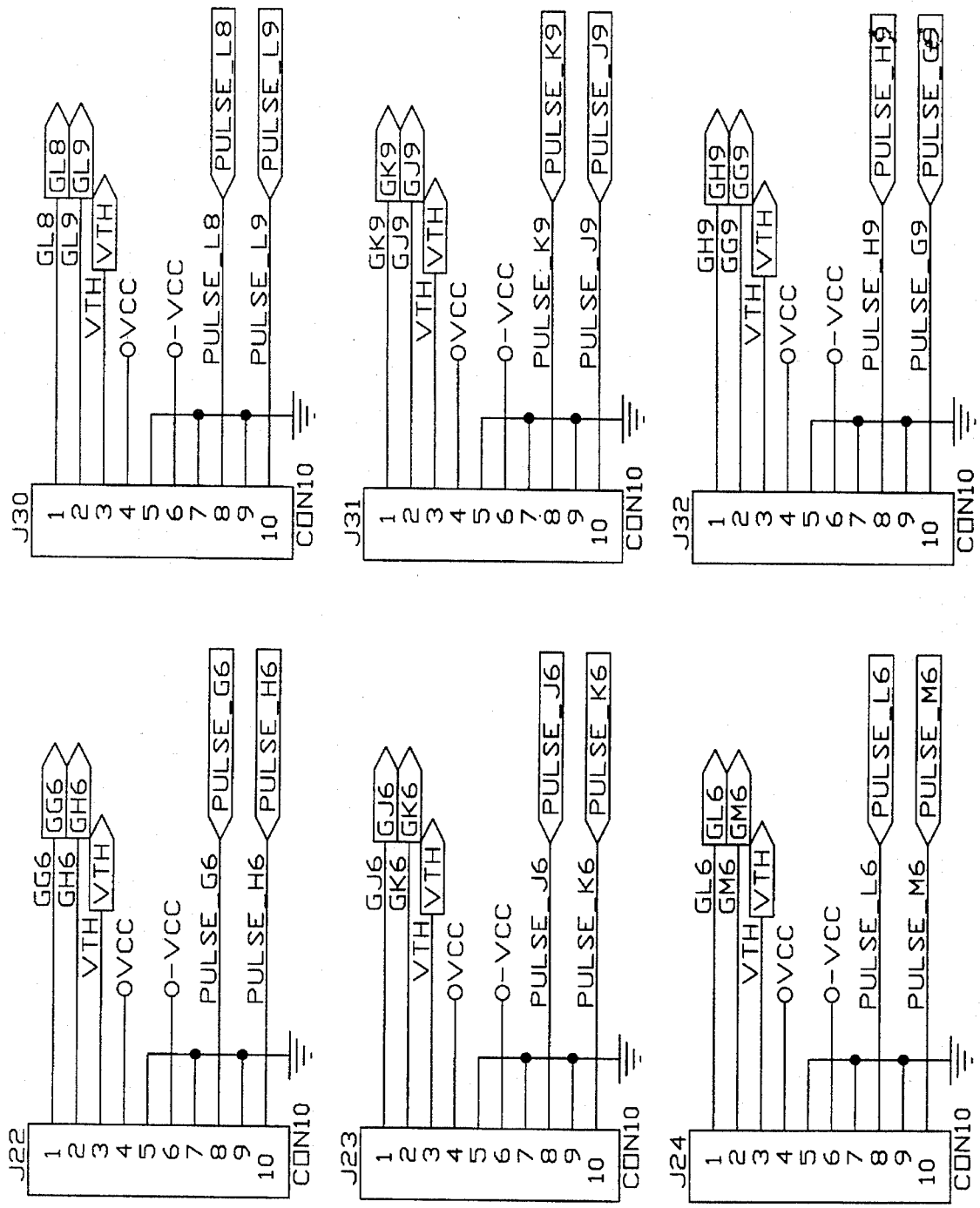
Figure 33G:
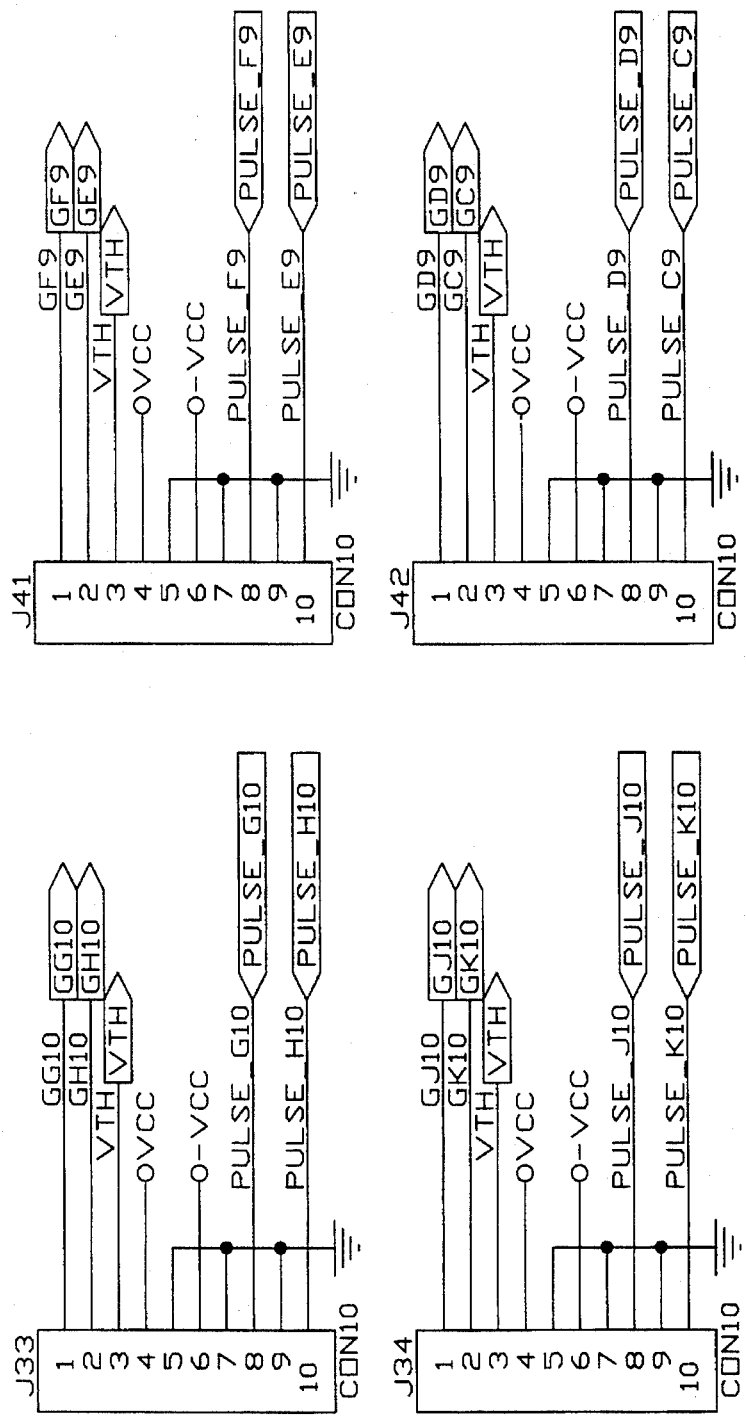
Figure 33H:
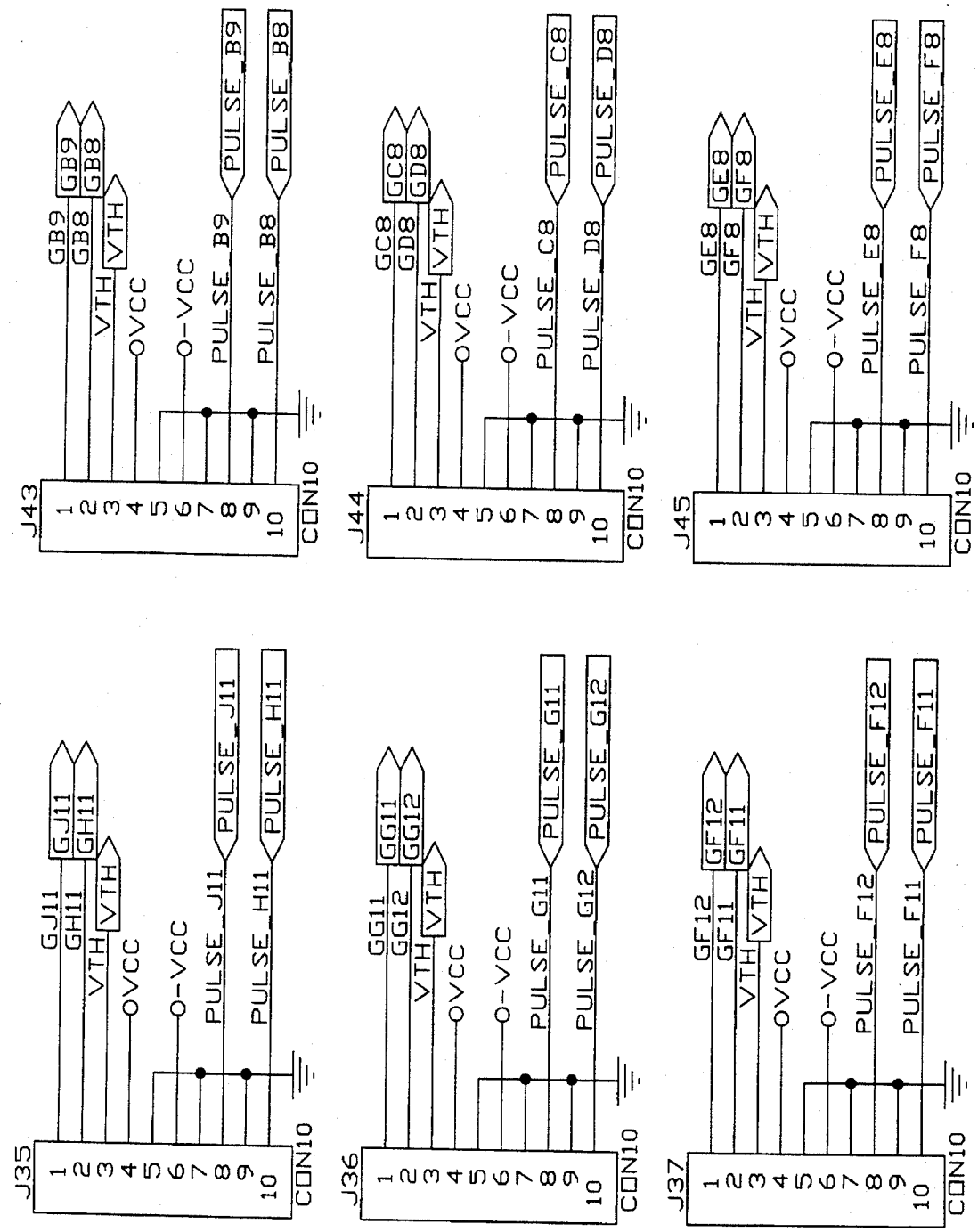
Figure 33I:
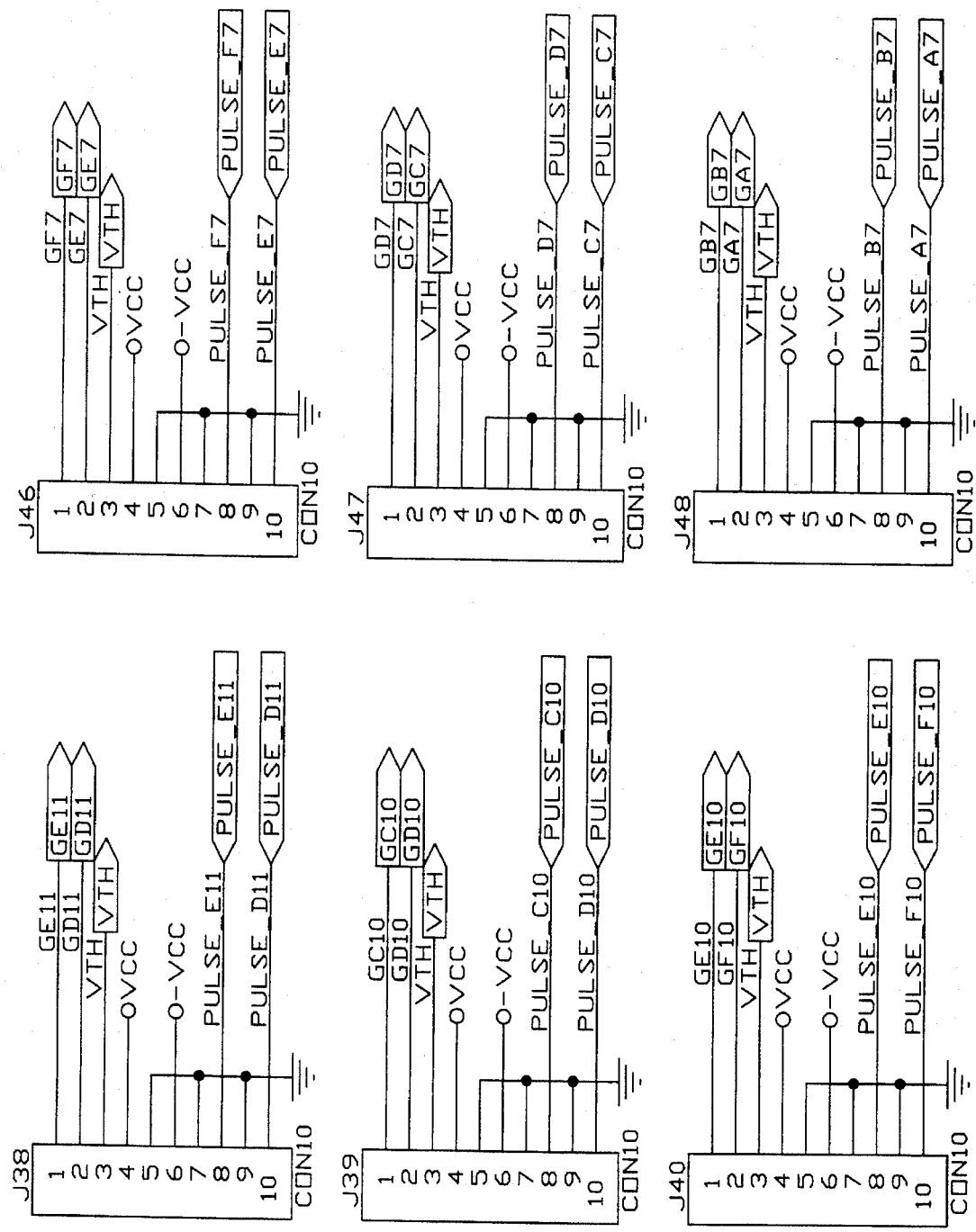
Figure 34:
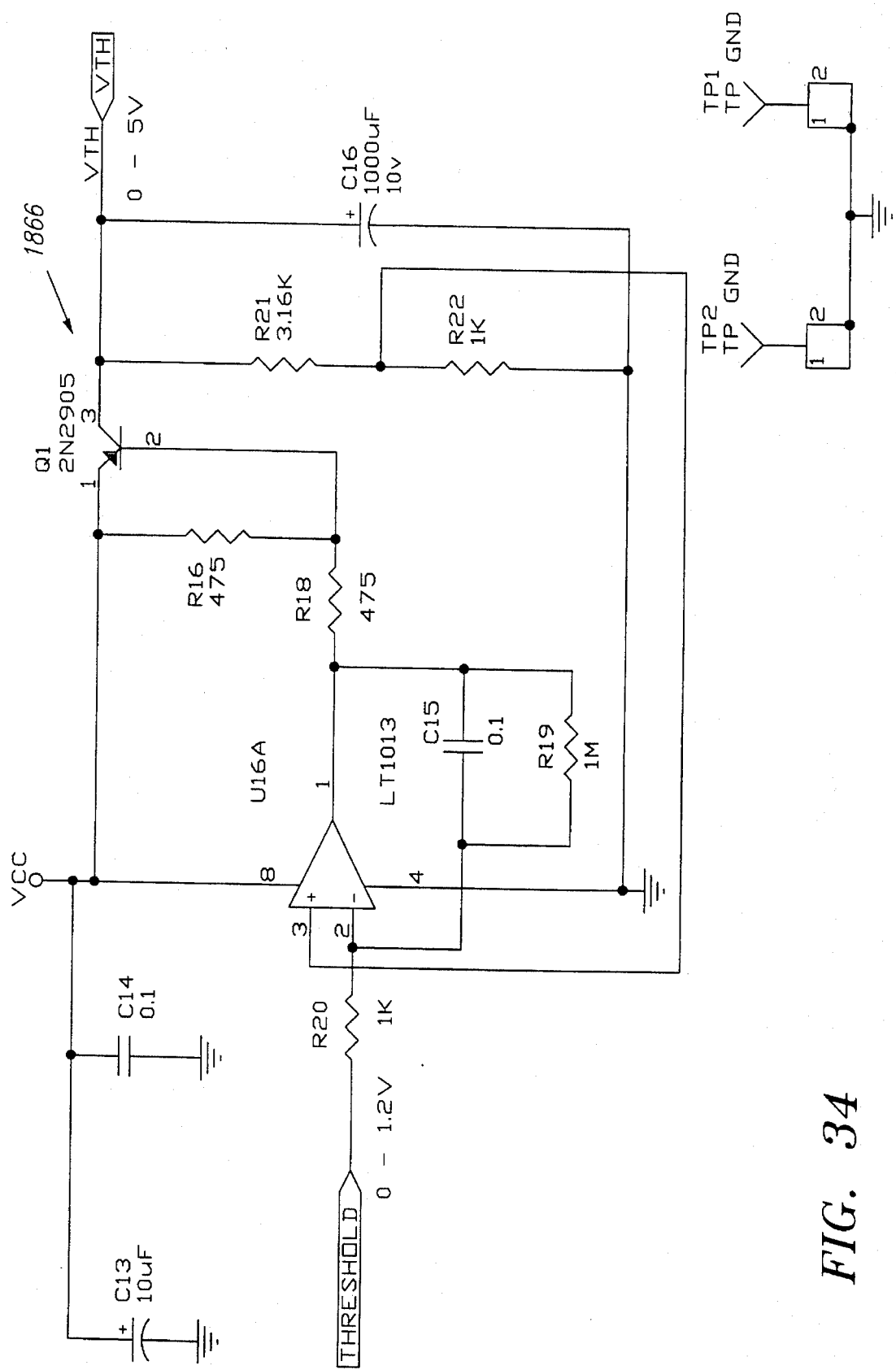
FIG. 34 is a circuit diagram of a preferred buffer amplifier for threshold control signals.

FIG. 32 diagrams the DACs (digital-analog converters) which preferably provide the gain and threshold control signals for the signal conditioner 810. The 12 gain control DACs 1860 each receive serial control data from the control computer, and output a total of 96 parallel analog gain control signals through 48 interface connectors 1862 (FIG. 33) to corresponding signal conditioning amplifier circuits 1830. A threshold control DAC 1864 receives digital control data from the control computer, and outputs a single threshold reference signal which is sent to all 96 discriminators 1832. Threshold control DAC 1864 feeds its output threshold reference signal to a buffer amplifier 1866 (FIG. 34), which provides the power to drive all 96 threshold reference inputs to the individual discriminators 1832.

Figure 35B:
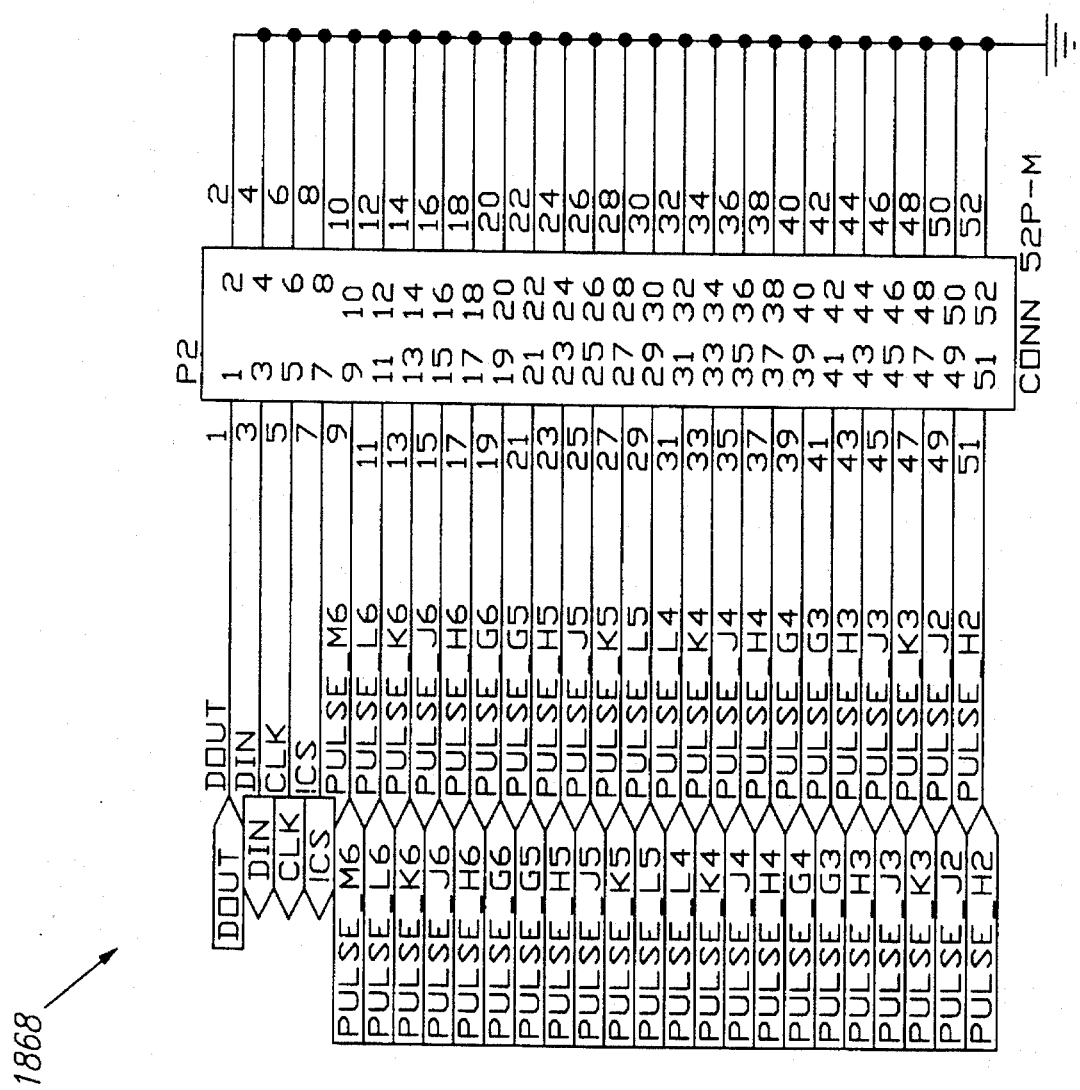
FIG. 35 is a circuit diagram of the preferred connectors between the discriminator of FIG. 31 and the preferred image reconstruction board.
Figure 35C:
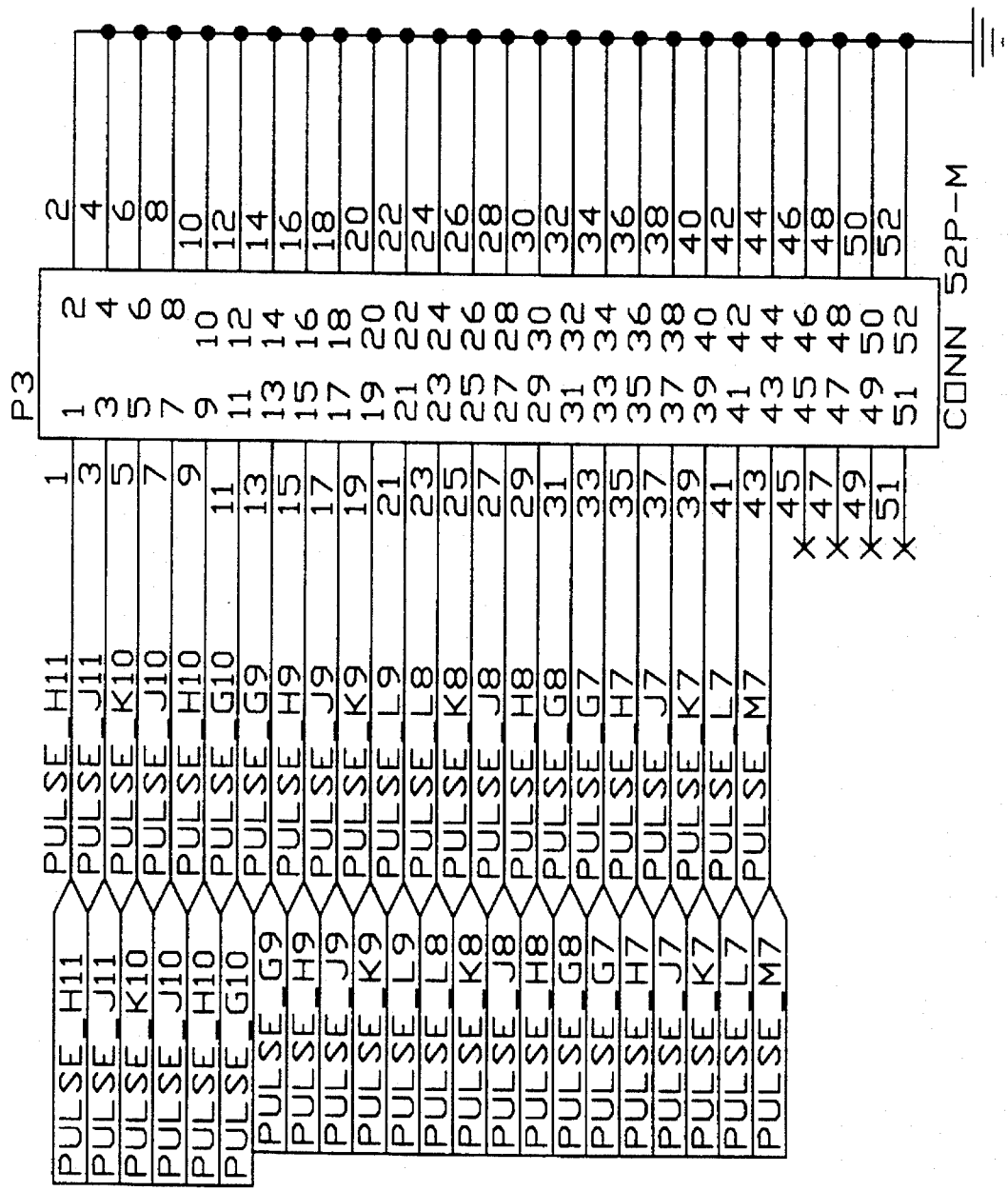
Figure 35D:
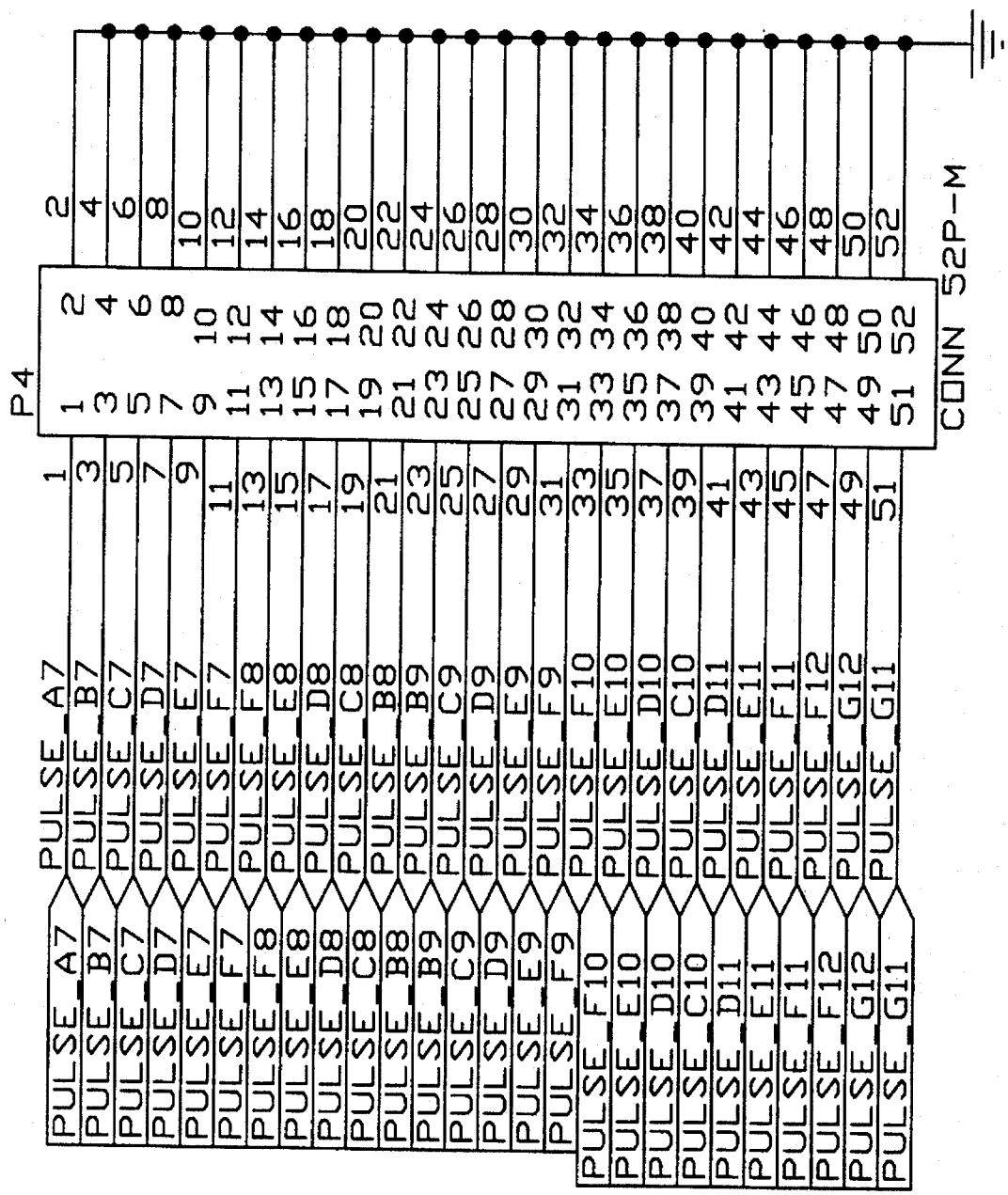

FIG. 35 diagrams the connectors 1868 between the output of the discriminators 1832 and the image reconstruction and beam alignment circuit boards.

Image Reconstruction with Sub-Sampling

The presently preferred image reconstruction method utilizes the sub-sampling method to process the detected information. Preferably the sub-sampling method is employed in a reverse geometry scanning beam x-ray system utilizing a sub-sampling ratio of 9:1 with a multi-detector array 822 including ninety-six detector elements arranged in a pseudo-circle.

FIG. 36 is a diagram of a 12 by 12 logical array 823 of detector elements. The logical array includes both active detector spaces 642 and inactive detector spaces 640. In the presently preferred image reconstruction method the 96 active detector element spaces each include a detector element and form an active logical array 822 which occupy the center spaces of a 12 by 12 logical array arranged in a symmetrical pattern about the horizontal midline and the vertical midline. The remaining 48 logical detector spaces of the array are inactive detectors and preferably do not include a detector element. In the preferred embodiment the inactive detector spaces do not output real information about the object.

To generate an image pixel, the processed x-ray intensity values detected by the multi-detector array 110 for each x-ray micro-beam passing through that image pixel IP are summed and output to a video monitor. For image reconstruction using a sub-sampling ratio of 1:1 each logical detector element of the logical array is capable of providing information about each image pixel in the object. For image reconstruction with a sub-sampling ratio of x:1, where x is a number greater than 1, less than all of the logical detector elements are capable of contributing information about a particular image pixel. The actual number capable of contributing information will depend on the particular sub-sampling ratio selected. With a presently preferred sub-sampling ratio of 9:1 in the presently preferred embodiment, only 16 logical detector elements of the 144 logical detector element logical array 823 will provide information about any particular image pixel.

In the sub-sampling method with a sub-sampling ratio of 9:1 the logical array 823 includes sixteen virtual detectors, e.g., 644, 646, 648 and 649. In this embodiment the virtual detectors each include 9 logical detectors arranged in a 3 by 3 array. Alternatively, if a sub-sampling ratio of 4:1 were used, there would be 36 virtual detectors, each including 4 logical detector elements. Using a sub-sampling ratio of 1:1 there would be 144 virtual detectors each including 1 logical detector element.

Each of the 16 logical detector elements used to reconstruct a single image pixel using a sub-sampling ratio of 9:1 are preferably situated in different virtual detectors. In this embodiment, each virtual detector contributes partial image pixel information for nine different image pixels. Complete image pixel information is obtained by combining the information from the logical detectors in the same virtual array location from all 16 virtual detectors.

The presently preferred image reconstruction method utilizes a novel string method. In the string method there is one string for each logical detector in a virtual detector. For example, using the preferred sub-sampling ratio of 9:1 there are nine strings. Referring to FIG. 36, each of the virtual array locations of the virtual detectors have been assigned numbers 1 through 9. String 1 includes all of the logical detectors assigned the number 1. String 2 includes all of the logical detectors assigned the number 2. And so on. Each row of the logical array 823 is assigned a number, 1 through 12, going from top to bottom. Each column of the logical array is assigned an alpha character, A through M, going from left to right. Naturally the use of right, left, top and down is relative and the particular orientation selected is merely to more easily explain the method of image reconstruction.

Figure 37:
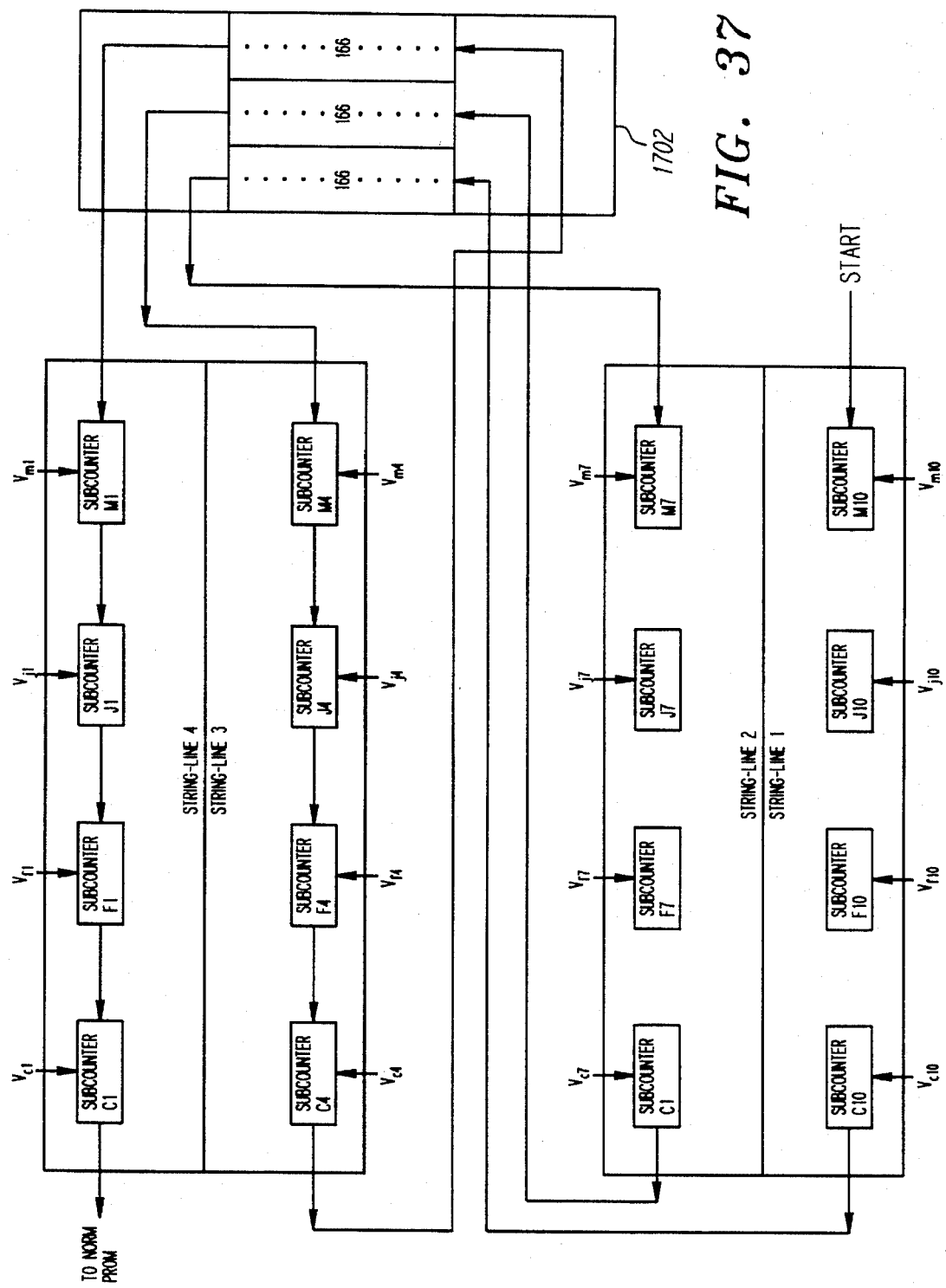
FIG. 37 comprises a partial functional diagram of a string counter in a preferred image reconstruction engine.

FIG. 37 is a diagram of the process flow used in the string method. Since the string method is the same for all strings, the method will be described in detail with regard to only string 1.

String 1 is comprised of the following logical detectors, M1, J1, F1, C1, M4, J4, F4, C4, M7, J7, F7, C7, M10, J10, F10 and C10. Assuming the electron beam moves from left to right for each row and top to bottom, and the sub-sampling ratio is 9:1, using the preferred multi-detector array 110, the first logical detector element that is capable of receiving information for a particular image pixel is M10 (FIG. 36). When the electron beam is positioned behind the next aperture (one hole to the right from the view of the output face of the collimator), the second logical detector capable of receiving information about that same image pixel is J10. And so on.

Referring back to FIG. 37, the partial pixel information for each image pixel is preferably processed for each string in accordance with the following method. The method will first be described in accordance with the embodiment in which each of the logical detectors are active and a sub-sampling ratio of 9:1 is selected resulting in a collimator including 167 rows and 167 columns. The description begins when the electron beam is positioned behind aperture $AP_{50,50}$. For purposes of this description image pixel $IP_1$ is located along the axes of the x-ray micro-beam detected by logical detector M10. Further, when the electron beam is described as being located behind a particle aperture, it means that the electron beam is aimed at the intersection of target layer and the axis of the x-ray pencil beam (which is aimed at the center of the multi-detector array) formed by that aperture.

As the electron beam is being positioned behind $AP_{50,50}$, subcounter M10 is reset to zero. While the electron beam is positioned behind $AP_{50,50}$ the partial image pixel information detected by logical detector M10 is input to subcounter M10. As the electron beam is positioned behind the next aperture in the same collimator row $AP_{50,51}$, the information contained in subcounter M10 is moved to subcounter J10. While the electron beam is positioned behind the next selected aperture $AP_{50,51}$ an x-ray micro-beam will pass through $IP_1$ and strike logical detector J10. The partial image pixel information detected by logical detector J10 will be input to and added to the contents of subcounter J10.

As the electron beam is positioned behind the next aperture in the same collimator row $AP_{50,52}$, the information contained in subcounter J10 is moved to subcounter F10. While the electron beam is positioned behind the next selected aperture $AP_{50,52}$, an x-ray micro-beam will pass through $IP_1$ and strike logical detector F10. The partial image pixel information detected by logical detector F10 will be input to and added to the contents of subcounter F10.

As the electron beam is positioned behind the next aperture in the same collimator row $AP_{50,53}$, the information contained in subcounter F10 is moved to subcounter C10. While the electron beam is positioned behind the next selected aperture $AP_{50,53}$, an x-ray micro-beam will pass through $IP_1$ and strike logical detector C10. The partial image pixel information detected by logical detector C10 will be input to and added to the contents of subcounter C10.

As the electron beam is positioned behind the next aperture in the same collimator row $AP_{50,54}$, the information contained in subcounter C10 is moved to a FIFO register. The reason for this is that because of the geometry of the preferred system, when the electron beam is positioned behind the next selected aperture $AP_{50,54}$, no x-ray micro-beam will pass through $IP_1$ and strike any logical detector in the array until the electron beam is moved to the next row. In accordance with this embodiment, no x-ray micro-beam will pass through $IP_1$ and strike any logical detector until the electron beam is positioned behind $AP_{51,50}$.

As the electron beam is being positioned behind $AP_{51,50}$, subcounter M7 is loaded with the partial image pixel information stored in the FIFO corresponding to the partial pixel information output from C10. While the electron beam is positioned behind $AP_{51,50}$ the partial image pixel information detected by logical detector M7 is added to the contents of subcounter M7.

As the electron beam is positioned behind the next aperture in the same collimator row $AP_{51,51}$, the information contained in subcounter M7 is moved to subcounter J7. While the electron beam is positioned behind the next selected aperture $AP_{51,51}$ an x-ray micro-beam will pass through $IP_1$ and strike logical detector J7. The partial image pixel information detected by logical detector J7 will be input to and added to the contents of subcounter J7.

As the electron beam is positioned behind the next aperture in the same collimator row $AP_{51,52}$, the information contained in subcounter J7 is moved to subcounter F7. While the electron beam is positioned behind the next selected aperture $AP_{51,52}$, an x-ray micro-beam will pass through $IP_1$ and strike logical detector F7. The partial image pixel information detected by logical detector F7 will be input to and added to the contents of subcounter F7.

As the electron beam is positioned behind the next aperture in the same collimator row $AP_{51,53}$, the information contained in subcounter F7 is moved to subcounter C7. While the electron beam is positioned behind the next selected aperture $AP_{51,53}$ an x-ray micro-beam will pass through $IP_1$ and strike logical detector C7. The partial image pixel information detected by logical detector C7 will be input to and added to the contents of subcounter C7.

As the electron beam is positioned behind the next aperture in the same collimator row $AP_{51,54}$, the information contained in subcounter C7 is moved to a FIFO register. Again, the reason for this is that because of the geometry of the preferred system, when the electron beam is positioned behind the next selected aperture $AP_{51,54}$, no x-ray micro-beam will pass through $IP_1$ and strike any logical detector in the array. In accordance with this embodiment, no x-ray micro-beam will pass through $IP_1$ and strike any logical detector until the electron beam is positioned behind $AP_{52,50}$.

As the electron beam is being positioned behind $AP_{52,50}$, subcounter M4 is loaded with the information stored in the FIFO corresponding to the partial pixel information output from subcounter C7. While the electron beam is positioned behind $AP_{52,50}$ the partial image pixel information detected by logical detector M4 is input to and added to the contents of subcounter M4.

As the electron beam is positioned behind the next aperture in the same collimator row $AP_{52,51}$, the information contained in subcounter M4 is input to subcounter J4. While the electron beam is positioned behind the next selected aperture $AP_{52,51}$ an x-ray micro-beam will pass through $IP_1$ and strike logical detector J4. The partial image pixel information detected by logical detector J4 will be input to and added to the contents of subcounter J4.

As the electron beam is positioned behind the next aperture in the same collimator row $AP_{52,52}$, the information contained in subcounter J4 is moved to subcounter F4. While the electron beam is positioned behind the next selected aperture $AP_{52,52}$, an x-ray micro-beam will pass through $IP_1$ and strike logical detector F4. The partial image pixel information detected by logical detector F4 will be input to and added to the contents of subcounter F4.

As the electron beam is positioned behind the next aperture in the same collimator row $AP_{52,53}$, the information contained in subcounter F4 is moved to subcounter C4. While the electron beam is positioned behind the next selected aperture $AP_{52,53}$, an x-ray micro-beam will pass through $IP_1$ and strike logical detector C4. The partial image pixel information detected by logical detector C4 will be input to and added to the contents of subcounter C4.

As the electron beam is positioned behind the next aperture in the same collimator row $AP_{52,54}$, the information contained in subcounter C4 is moved to a FIFO register. Again, the reason for this is that because of the geometry of the preferred system, when the electron beam is positioned behind the next selected aperture $AP_{52,54}$, no x-ray micro-beam will pass through $IP_1$ and strike any logical detector in the array. In accordance with this embodiment, no x-ray micro-beam will pass through $IP_1$ and strike any logical detector until the electron beam is positioned behind $AP_{53,50}$.

As the electron beam is being positioned behind $AP_{53,50}$, subcounter M1 is loaded with the information stored in the FIFO corresponding to the partial pixel information output from subcounter C4. While the electron beam is positioned behind $AP_{53,50}$ the partial image pixel information detected by logical detector M1 is input to and added to the contents of subcounter M1.

As the electron beam is positioned behind the next aperture in the same collimator row $AP_{53,51}$, the information contained in subcounter M1 is moved to subcounter J1. While the electron beam is positioned behind the next selected aperture $AP_{53,51}$ an x-ray micro-beam will pass through $IP_1$ and strike logical detector J1. The partial image pixel information detected by logical detector J1 will be input to and added to the contents of subcounter J1.

As the electron beam is positioned behind the next aperture in the same collimator row $AP_{53,52}$, the information contained in subcounter J1 is moved to subcounter F1. While the electron beam is positioned behind the next selected aperture $AP_{53,52}$, an x-ray micro-beam will pass through $IP_1$ and strike logical detector F1. The partial image pixel information detected by logical detector F1 will be input to and added to the contents of subcounter F1.

As the electron beam is positioned behind the next aperture in the same collimator row $AP_{53,53}$, the information contained in subcounter F1 is moved to subcounter C1. While the electron beam is positioned behind the next selected aperture $AP_{53,53}$, an x-ray micro-beam will pass through $IP_1$ and strike logical detector C1. The partial image pixel information detected by logical detector C1 will be input to and added to the contents of subcounter C1.

As the electron beam is positioned behind the next aperture in the same collimator row $AP_{53,54}$, the information contained in subcounter C1 is output to a monitor where the information can be processed for display. The output of C1 will contain complete image pixel information for pixel $IP_1$. The reason for this is that because of the geometry of the preferred system, no other apertures, other than those identified above will include an x-ray micro-beam that passes through $IP_1$.

In accordance with the string method, at the same time that information for $IP_1$ is being collected in string 1, information for $IP_2$ is being collected in string 2. The complete image pixel information for $IP_2$ is collected in accordance with the same method as with string 1 except that the logical detectors for string 2 (L10, H10, E10, B10, L7, H7, E7, B7, L4, H4, E4, B4, L1, H1, E1 and B1) collect the information and subcounters L10, H10, E10, B10, L7, H7, E7, B7, L4, H4, E4, B4, L1, H1, E1 and B1 combine the information as the electron beam is positioned behind $AP_{50,50}$, $AP_{50,51}$, etc. The same process is also used with the corresponding subcounters and logical detectors for strings 3, 4, 5, 6, 7, 8 and 9. Thus, after the electron beam has been positioned behind aperture $AP_{53,53}$ complete information for nine image pixels can be output to a video monitor for display. Also, a new string 1, string 2, . . . and string 9 are started every time the electron beam is positioned behind a new aperture. It should be noted that a FIFO may be replaced by any storage mechanism that can store the intermediate outputs of the strings until complete image pixel information has been collected.

As shown in FIG. 36, preferably only 96 of the 144 logical detectors are active. For example, string 1 is preferably mapped to 11 active (J10, F10, C10, M7, J7, F7, C7, J4, F4, C4 and F1) and 5 inactive detector elements (M10, M4, M1, J1 and C1). Since these inactive detector elements do not provide any information about the image pixel a zero value is input into the corresponding subcounters. Also, as noted, if it is determined that the inactive logical detectors will never be used to collect image pixel information, they need not have an actual detector associated with them. Similarly, for string 2, the inactive logical detectors (those outside the active detector array area 822) also input zero values to their corresponding subcounters, and so forth with the other strings.

When less than all of the logical detectors are active it is preferable to normalize the complete image pixel information to account for differences in the number of active detector elements for each string. As shown in Table II, the number of active detector elements providing input data vary between 10, 11 or 12 depending on the particular string. The complete image pixel information from each of the nine strings is preferably normalized by dividing the complete image pixel information by the number of active detectors in that string and then multiplying by 12.

TABLE II

| STRING | NUMBER OF ACTIVE ELEMENTS |
|---|---|
| 1 | 11 |
| 2 | 10 |
| 3 | 11 |
| 4 | 10 |
| 5 | 12 |
| 6 | 10 |
| 7 | 11 |
| 8 | 10 |
| 9 | 11 |

Alignment

The electron beam 40 in x-ray source 10 is preferably precisely aligned such that it will illuminate the area on the target layer at the exact point at which the axis of the collimator hole intersects the target layer. When no object is interposed between the target 50 and the multi-detector array 110, such a precisely aligned electron beam will result in a near symmetrical distribution of x-ray intensity across the face of detector elements 160 of the multi-detector array 110, within the pseudo-circle 400. An electron beam which is not so precisely aligned may create a non-symmetrical distribution of x-ray intensities across the face of the detector elements 160 of the multi-detector array 110.

Alignment of the electron beam behind the collimator holes is preferably accomplished with a 2-step process. An initial alignment procedure is preferably performed to approximate the correct positioning of the electron beam 40. The initial alignment procedure is preferably followed by a fine alignment procedure that optimizes the position of the center of the electron beam profile relative to the collimator holes.

The first step of the preferred initial alignment procedure is comprised of locating the electron beams using apriori knowledge related to the physical, electrical and magnetic properties of the scanning system. The relative spacing of the electron beam positions may be reasonably correct at this point, but the absolute positions of the electron beams may not be because of the difficulty in indexing the electron beam position array to the collimator holes, and because of small cumulative errors. Therefore, a "dithering" process is preferably employed whereby several measurements are made by making small adjustments of the index position for a whole array of electron beam positions. Typically, 25 measurements are made where the index point is moved in a 5 by 5 x-y grid. The total size of the grid is approximately the spacing of one collimator hole. The data collected for each measurement consists of the total intensity measured by the multi-detector array for each of the collimator holes.

The collected data for a give collimator hole will preferably be an array of 25 values. Many of the values will indicate that little or no x-ray flux impinged upon the multi-detector array, but several will indicate that at least part of the electron beam produced x-rays that impinge upon the multi-detector array. An approximate optimum beam position location is determined by mathematically fitting a multi-dimensional surface to the illuminated data.

Thus, approximate optimum beam positions are determined by this procedure. These positions are refined using the fine alignment method described below.

To initiate the fine alignment procedure, initial x-deflection values and y-deflection values are preferably computed for each collimator aperture, employing the initial alignment procedure described above. Using these computed initial deflection values the electron beam is scanned across the target, momentarily stopping at each of the computed locations corresponding to the computed x and y deflection values. The partial image pixel information obtained from each detector element for each x-ray pencil beam generated by stopping at each computed location is analyzed for even distribution of the x-ray intensity over several frames. (A complete scan of the target is referred to as a frame.) If the analysis results in a determination that the distribution of x-ray intensity is not even, new x-deflection values and/or y-deflection values are calculated and the alignment procedure is repeated to ensure optimal distribution.

The preferred way of analyzing the distribution of x-ray flux across the face of the multi-detector array is to compare the average intensity of the x-ray rays detected by selected areas of the face of the multi-detector array. This is preferably accomplished by dividing the preferred ninety-six detector element multi-detector array into eight areas comprising substantially the same number of detector elements.

FIG. 38 is a representational diagram of the face of a multi-detector array divided into eight areas. Each of the eight areas is referred to as an "octant." The eight octants are identified as the top right outer octant ("TRO") 1345, top right inner octant ("TRI") 1346, top left outer octant ("TLO") 1349, top left inner octant ("TLI") 1350, bottom right inner octant ("BRI") 1347, bottom right outer octant ("BRO") 1348, bottom left outer octant ("BLO") 1351, and bottom left inner octant ("BLI") 1352.

In the preferred embodiment, the 96 detector elements 1339 are evenly divided among the eight octants. Therefore each octant contains 12 detector elements 1339. However, it is contemplated that other arrangements may be used in the present invention. For example, an alternative arrangement could consist of 13 detector elements 1339 associated with each inner octant, with 11 detector elements 1339 associated with each outer octant.

The beam alignment calculations are preferably determined separately for the x-axis 1662 and the y-axis 1660.

The preferred sequence of steps to determine the proper beam alignment along the y-axis 1660 are as follows. The process begins when an x-ray pencil beam from a single collimator aperture strikes the scintillator elements of multi-detector array 110.

The total intensity values for each octant is summed by counting the number of x-ray photons which are received by each detector element 1339 associated with each octant. For example, arbitrarily selecting the variable V to refer to the sum of the photon counts in a particular area, $V_{TRO}$ is the sum of all the photon counts in the TRO octant 1345. Similarly, $V_{TRI}$ is the sum for the TRI octant 1346, $V_{TLO}$ for TLO octant 1349, $V_{TLI}$ for TLI octant 1350, $V_{BLO}$ for BLO octant 1351, $V_{BLI}$ for BLI octant 1352, $V_{BRI}$ for BRI octant 1347, and $V_{BLO}$ for BLO octant 1348. The intensity values for each octant, for each x-ray pencil beam from each collimator aperture for each of a predetermined number of succeeding frames, is accumulated. The presently preferred embodiment uses the octant values from 100–120 frames to perform the beam calculations. Thus, there are a total of eight octant values for each beam/aperture combination.

The accumulated values for the octants in the top and bottom halves of the PMT array are then separately summed. Thus the top octant accumulated value is $V_{top}=V_{TRO}+V_{TRI}+V_{TLI}+V_{TLO}$. The bottom octant accumulated is $V_{bottom}=V_{BRO}+V_{BRI}+V_{BLI}+V_{BLO}$.

Next the top octant accumulated value is compared to the bottom octant accumulated value. This comparison produces a y-axis alignment factor ($AF_{y\text{-}axis}$) which is a measure of the accuracy of the x-ray beam alignment with respect to a particular aperture along the y-axis. The formula to determine the $AF_{y\text{-}axis}$ is:

$$AF_{y\text{-}axis} = \frac{V_{top} - V_{bottom}}{V_{top} + V_{bottom}} \qquad \text{EQ. 7}$$

If the electron beam is properly aligned with the aperture under analysis along the y-axis, the accumulated intensity values for the top and the bottom octants should be the same. Thus when $V_{top}$ is equal to $V_{bottom}$, $AF_{y\text{-}axis}=0$ and the beam is properly aligned along the y-axis for the aperture under analysis.

If the electron beam was positioned to favor the top half of the multi-detector array, then $V_{top}$ will be greater than $V_{bottom}$. This results in $AF_{y\text{-}axis}>0$. If the electron beam is positioned to favor the bottom half of the multi-detector array, then $V_{top}$ will be less than $V_{bottom}$. This results in $AF_{y\text{-}axis}<0$. The value of $AF_{y\text{-}axis}$ generally indicates the amount the y-deflection value should change to optimize the alignment.

The method to determine the optimal electron beam alignment along the x-axis is similar. For this calculation, the accumulated values for the left and right octants are separately summed. Thus the right octant accumulated value is $V_{right}=V_{TRO}+V_{TRI}+V_{BRO}+V_{BRI}$. The left octant accumulated value is $V_{left}=V_{TLO}+V_{TLI}+V_{BLO}+V_{BLI}$. The formula to determine the x-axis alignment factor ($AF_{x\text{-}axis}$) is:

$$AF_{x\text{-}axis} = \frac{V_{right} - V_{left}}{V_{right} + V_{left}} \qquad \text{EQ. 8}$$

Calculations almost identical to those used for the y-axis alignment are used to determine the optimal alignment of the electron beam along the x-axis.

The x-axis and y-axis alignment factors are transmitted to the control computer 890. Control computer 890 processes these alignment factors to determine the amount of correction required at the x-ray source 798 to optimally align the x-ray pencil beam. The control computer 890 next updates the beam deflection lookup tables 918.

By adjusting the electron beam's positioning on the target 1250, x-rays are emitted from the target at a different position relative to the collimator grid aperture. The x-ray pencil beams passing through the collimator grid aperture would then illuminate the multi-detector array at a corrected optimally aligned position.

This alignment may be performed whenever the system is activated, at preset intervals or continuously.

While the previous discussion explores alignment calculations along the x and y axes, other octant calculation methods are also contemplated within the boundaries of this aspect of invention. For example, angular alignment calculations may be performed by comparing the accumulated value of the top right octants with the values of the bottom left octants and the top left octants with the bottom right octants.

Beam Alignment Extractor and Image Reconstruction Engine

Figure 39:
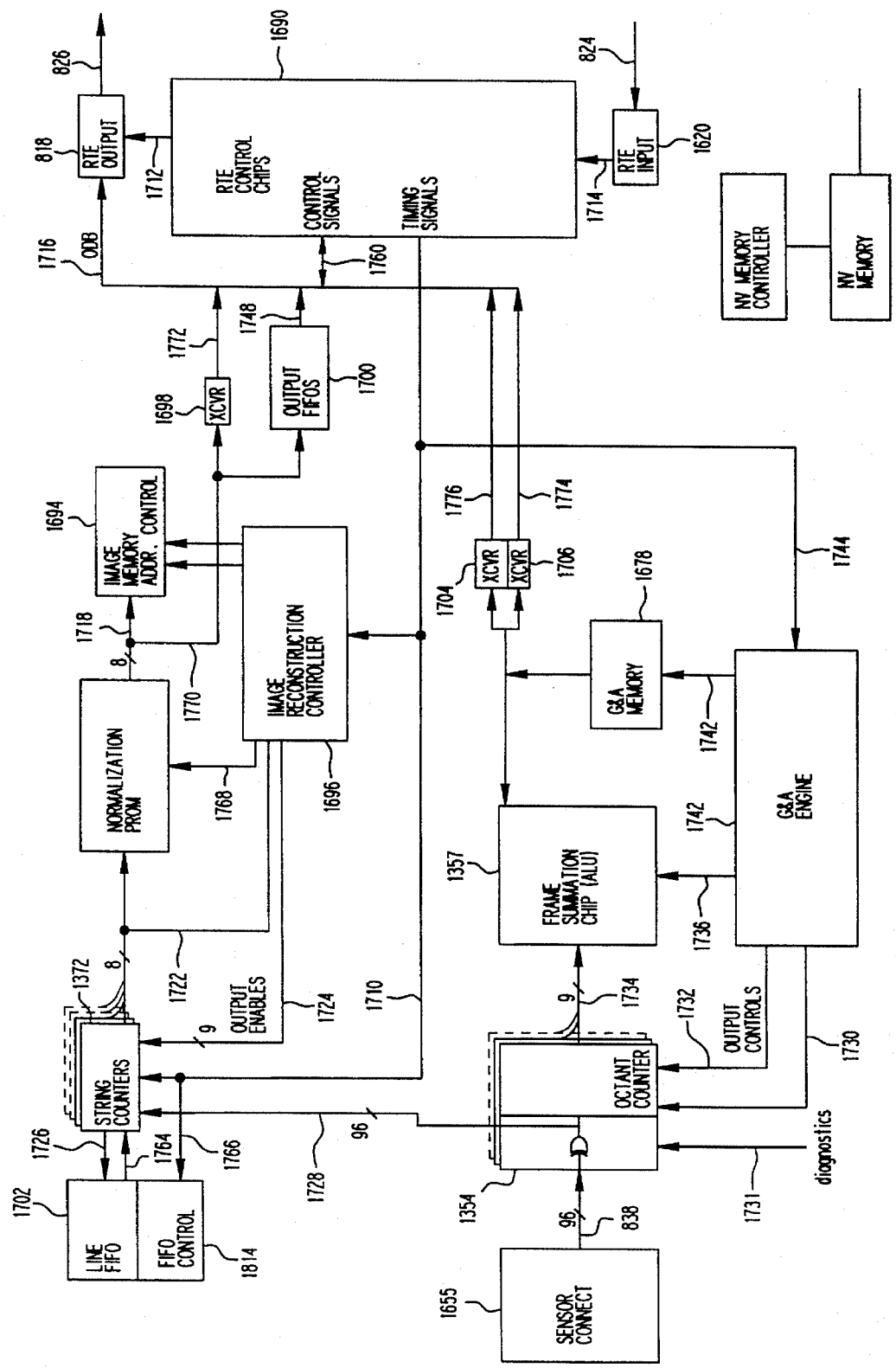
FIG. 39 comprises a partial functional block diagram of an image reconstruction engine.

FIG. 39 is a block diagram of the circuitry for the beam alignment extractor and image reconstruction engine. The output signals of the signal conditioner 810 are input, via connectors 1655, to the beam alignment extractor.

The conditioned partial image pixel signals from each detector element for each step of the electron beam are input to RTE octant counters 1354. There are preferably eight RTE octant counters. Each of the octant counters receives the conditioned partial image pixel signals from one of the eight octants. Each RTE octant counter 1354 splits the conditioned partial image pixel signals into two essentially identical signals. One set of the conditioned partial image pixel signals is used to analyze the optimal alignment of the electron beam. The other set is transmitted to the image reconstruction engine ultimately to be used to reconstruct the image of the object being investigated.

Each RTE octant counter 1354 then processes the input conditioned image pixel signals to obtain a total photon count for its corresponding octant. In sequential order, the RTE octant counters 1354 next transmit the total photon sum for each octant to the frame-summation chip 1357. This process is controlled and outputs to the frame summation chip are enabled by control signals communicated to the RTE octant counters 1354 from the gain & alignment engine 1674.

The frame-summation chip 1357 is an arithmetic logic unit ("ALU"). For each photon count input from a RTE octant counter 1354, the frame-summation chip 1357 also inputs an accumulated octant value from the gain & alignment memory 1678. This accumulated octant value corresponds to the sum of the photon counts from one or more previous frames for the same octant and for the same aperture on the collimator which was illuminated to produce the present photon count. The frame summation chip 1357 adds the photon count to the accumulated octant value to produce a new octant value, which is then stored at the gain & alignment memory 1678.

The gain & alignment engine 1674 controls the operation of the octant counters 1354, frame-summation chip 1357 and gain & alignment memory 1678. After approximately 100–120 frames of information have been collected at the gain & alignment memory 1678, the gain & alignment engine 1674 communicates instructions to the gain & alignment memory 1678 to output the beam alignment information, which is transmitted through transceivers 1704 and 1706 to the RTE output circuits 818.

The string counters 1372 input partial image pixel signals from the RTE octant counters 1354. The string counters 1372 process partial image pixel values to reconstruct data values for complete image pixels, as explained more fully in the detailed description of FIG. 37.

During the image reconstruction process, partially constructed image pixel values are stored by the string counters 1372 at the line FIFO ("first in first out") chips 1702. After 166 items of partial image pixel values are input into a line FIFO chip 1702, each successive item stored at that line FIFO chip 1702 will cause the line FIFO chip 1702 to transmit the then earliest stored string data value back to the string counters 1372. Line FIFO 1702 receives timing signals from the RTE control chips.

The string counters 1372 transmit data values for complete image pixels to the normalization PROM 1692. The normalization PROM adjusts this data value based upon the number of active detector elements which contribute partial image pixel information for that image pixel (this is explained in more detail in conjunction with the detailed discussion of FIG. 37). The normalization PROM 1692 receives control signals from the image reconstruction controller 1696 through electrical connection 1768.

Normalization PROM 1692 outputs normalized image pixel information to the output FIFOs 1700 through electrical connection 1746. Three lines of normalized image pixel information are stored at the output FIFOs 1700 before the normalized image pixel data is transmitted to the RTE output circuit.

The normalized image pixel information from the normalization PROM 1692 is also input to the image memory unit 1694. The normalized image pixel information for the entire image is stored and properly ordered at the image memory unit 1694. The control computer can access this image data through transceiver 1698.

The image reconstruction controller transmits the control signals which operate the components of the image reconstruction engine. Control and addressing signals are communicated to the image memory unit 1694 on electrical connections 1758 and 1756. Control signals are sent, via electrical connection 1768, to the normalization PROM. The image reconstruction controller 1696 communicates control signals, via electrical connection 1724, to the string counters 1372.

Control information from the control computer 890 are input to the real-time eye through RTE input circuit 1620, which receives light pulses from high-speed fiber-optic cable 824. The RTE input circuit 1620 comprises a light detector and circuitry which detects and demodulates the light pulses into electrical signals which contain the control information from the control computer 890. The control information is sent from RTE input circuit 1620 to the RTE control chips 1690 through electrical connection 1714.

The RTE control chips 1690 send timing signals to the RTE circuitry through electrical bus connection 1710. The RTE control chips 1690 send control signals to the RTE circuitry through electrical bus connection 1760.

RTE output circuit 818 sends image reconstruction and gain & alignment information to the control computer 890 through high-speed fiber-optic cable 826. RTE output circuit 818 comprises a high radiance LED and circuitry which converts electrical signals into light pulses.

Turning to FIG. 40, a detailed diagram is presented of the RTE input circuit 1620. RTE input circuit 1620 receives light pulses from right transmitter 880. Light pulses are detected and converted to an electrical signal by the fiber-optic receiver 1612. The electrical signal is filtered and shaped by circuits 1622 and 1624. The electrical signal is then input to the taxi chip 1614, a standard AM7969 chip available from AMD Corp, which functions as a serial to parallel converter. The electrical input signal was necessarily in a serial format because of its transmission through a fiber-optic cable. Four bits of control signals and eight bits of data signals are output from taxi chip 1614. While the present description of FIG. 40 is directed to the RTE input circuit 1620 of the data receiver 812, a similar circuit exists for other components of the present invention which receives light pulses through fiber-optic cables.

Phase locked loop (PLL) circuit 1629, located in data receiver 812, receives and locks onto a master 12.5 Mhz clock signal that is generated in the programmable scan controller 920 (FIG. 22). This master clock signal drives both the taxi chip 1614 in the data receiver 812 and the taxi chip 1602 in the data transmitter 818 to generate an output at a clock rate of 12.5 Mhz. MC88915 clock doublers 1628, 1630, and 1632 are used to quadruple the 12.5 Mhz clock signal to a 50 Mhz frequency. Timing circuit 1626 uses this 50 Mhz clock to synchronize taxi chip 1614 with the other components of the beam alignment extractor and image reconstruction circuitry. Timing circuit 1626 generates a data strobe signal which is transmitted via electrical connection 1636. Timing circuit 1626 generates a control strobe signal which is transmitted via electrical connection 1634.

FIG. 41 diagrams the RTE output circuit 818, which is also referred to as the right data transmitter. Taxi chip 1602 is another standard AM7968 chip available from AMD Corp. which also functions as a parallel to serial converter. Parallel data bits from the image reconstruction engine and the beam alignment extractor are input to the taxi chip 1602, which outputs a serial data signal. This serial data signal is then shaped by the conditioning circuitry 1610. The output signal from the conditioning circuit 1610 is sent to fiber-optic transmitter 1604, which transforms the serial data signal into light pulses through the use of a high-radiance LED. The light pulses are sent to a data receiver 880 through high-speed fiber-optic cable 826. While the present description of FIG. 41 is directed to the RTE output circuit 1620 of the real-time eye, a similar circuit exists for other components of the present invention which transmits light pulses through fiber-optic cables.

Figure 42:
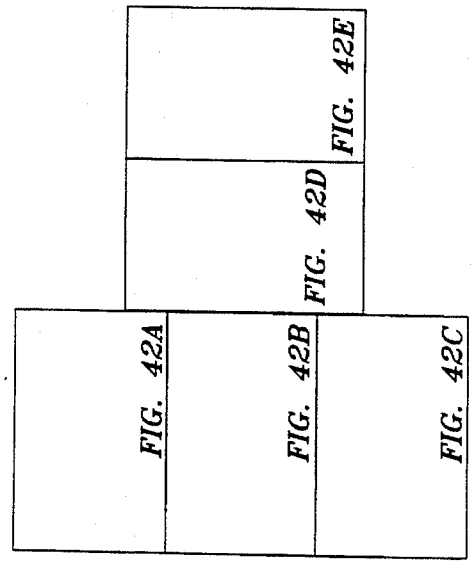
FIG. 42 is a schematic of the controller for the image reconstruction engine and gain & alignment circuitry.
Figure 42A:
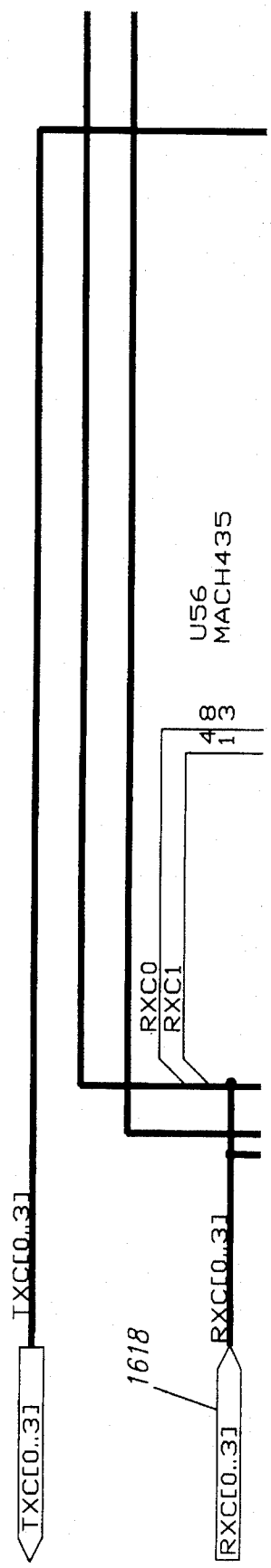
Figure 42B:
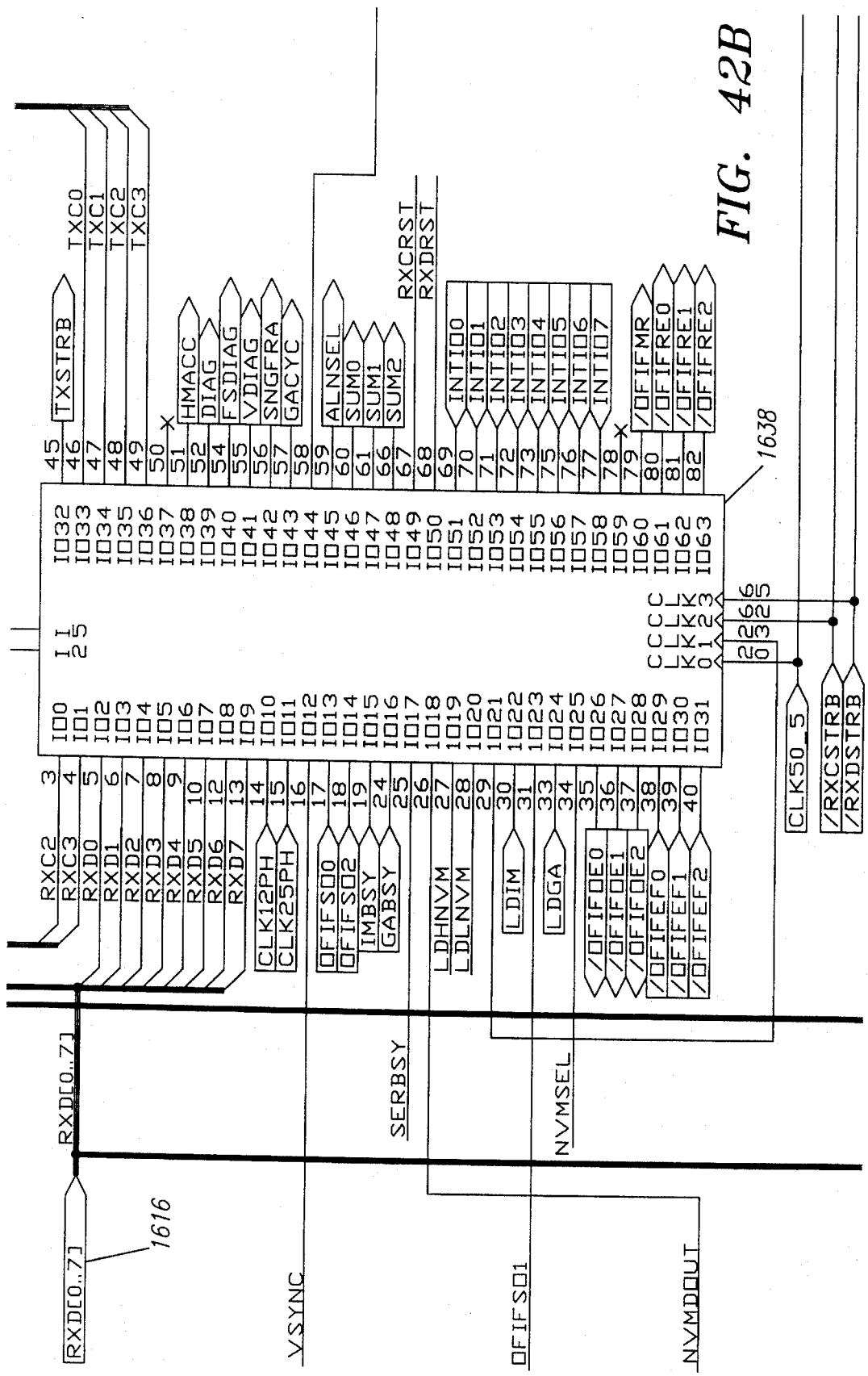
Figure 42C:
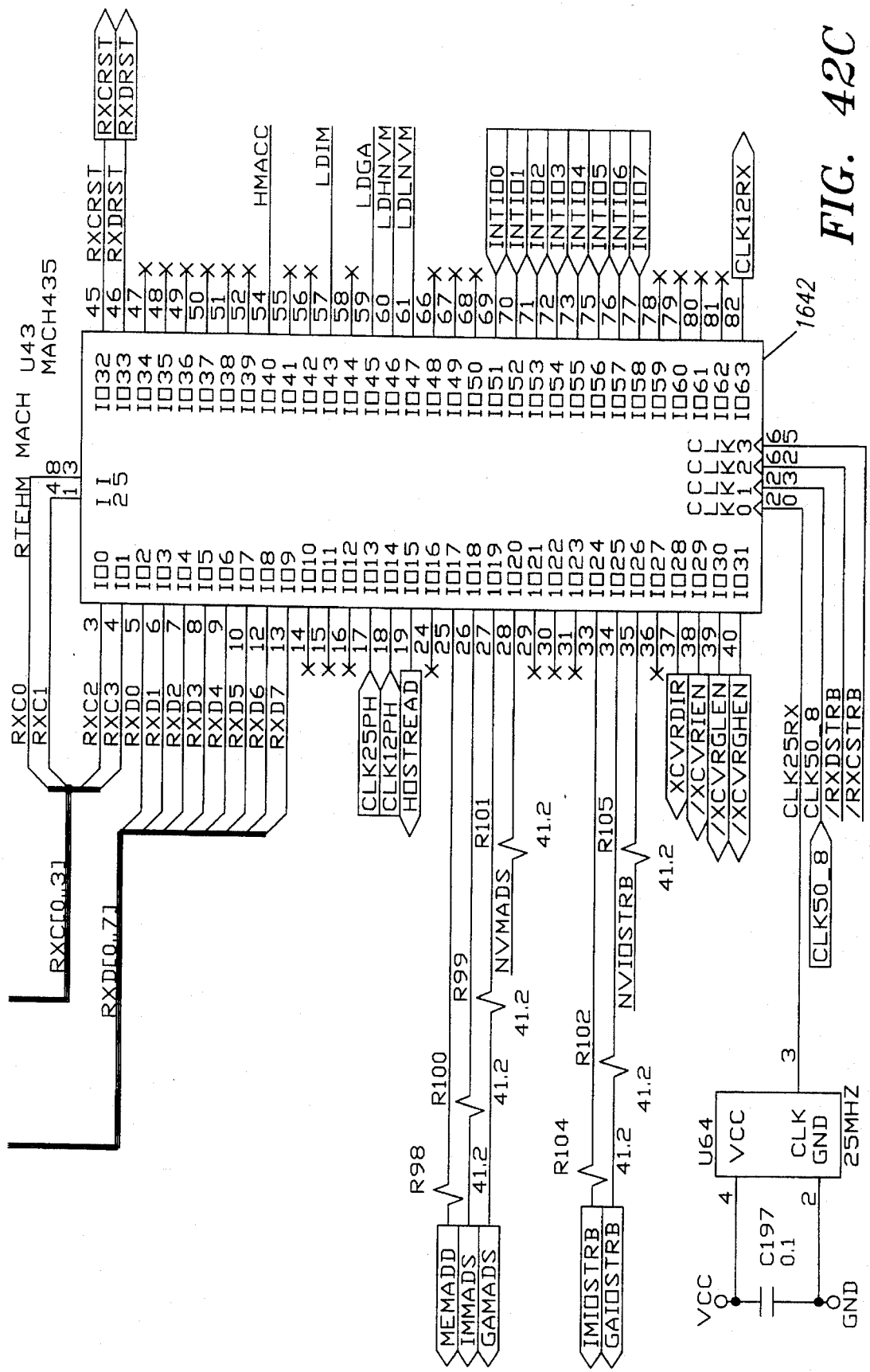
Figure 42D:
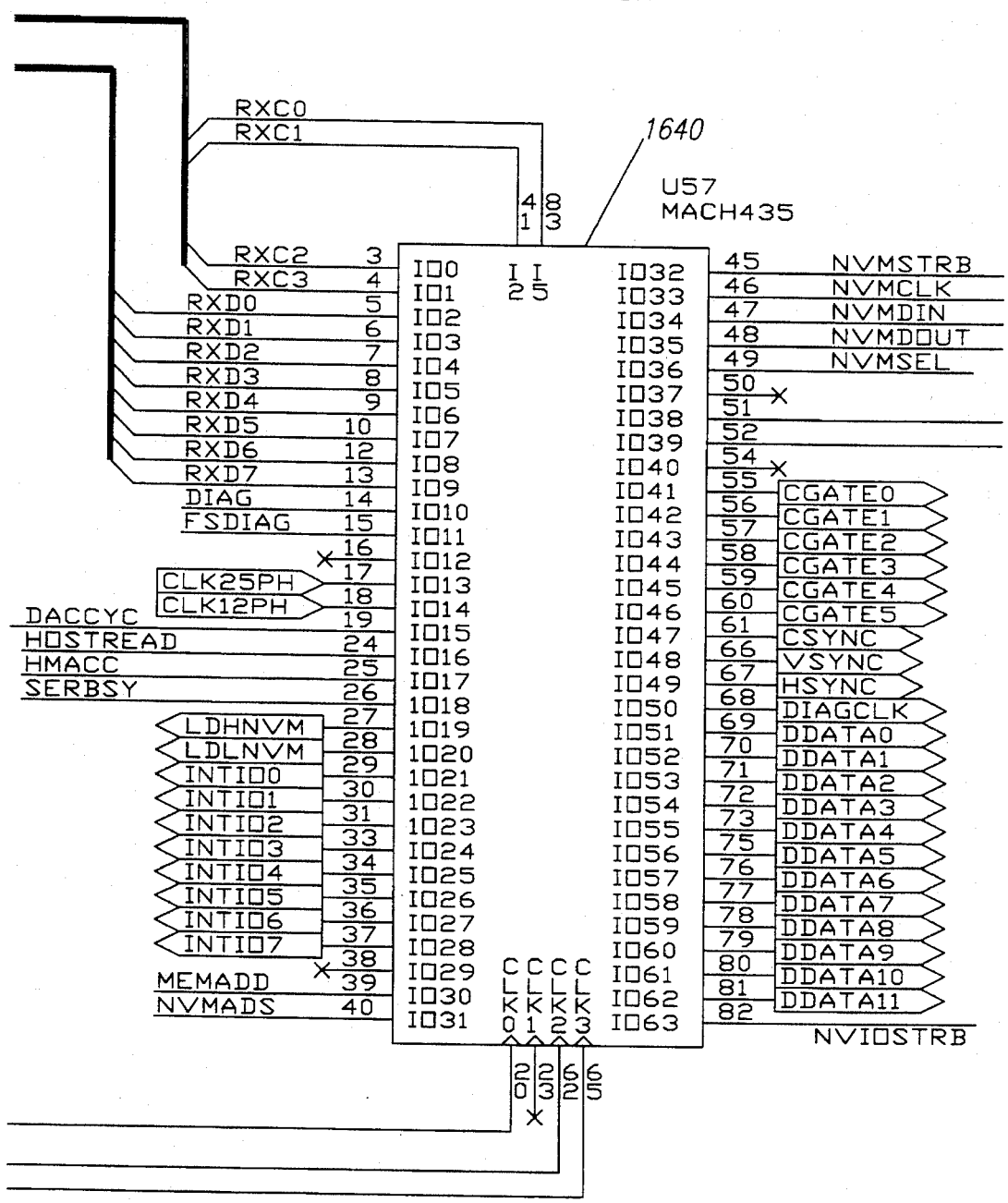

FIG. 42 is a circuit diagram of the RTE control chips 1690 which are located in the data receiver 812. Information from the control computer 890 that is acquired through the RTE input circuit 1620 is distributed to the various components of the multi-detector array through the RTE control chips 1690, each of which is a MACH435 programmable IC chip available from AMD Corp. Data outputs from the RTE input taxi chip 1614 are input to the RTE control chips via 8 bit electrical connection 1616. Control information outputs from the RTE input taxi chip 1614 are input to the RTE control chips via 4 bit electrical connection 1616.

Data acquisition control chip 1638 distributes control information relating to the selection of data that is acquired and processed by the components of the multi-detector array 822. Host memory control chip 1642 communicates instructions to the image memory unit 1694 and the gain & alignment memory unit 1678. Timing control chip 1640 communicates timing and diagnostic signals to the circuitry of the beam alignment extractor and the image reconstruction engine. The timing control signals for the signal conditioner 1510 (FIG. 33) is output from the timing control chip 1640 through connection 1646. 1 Kbyte of nonvolatile memory 1644 stores calibration information for the circuitry of the beam alignment extractor and the image reconstruction engine. The preferred software modules for data acquisition control chip 1638, host memory control chip 1642, and timing control chip 1640 are included in Appendix A.

Figures 43, 43A:
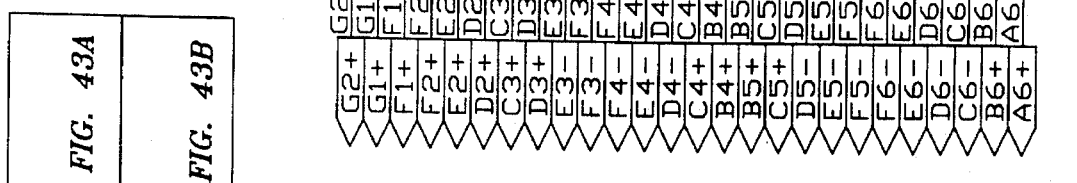
FIG. 43 is a diagram showing the preferred input sensor connectors between the photomultiplier tube and the signal conditioning circuits in the Real-time eye.
Figure 43B:
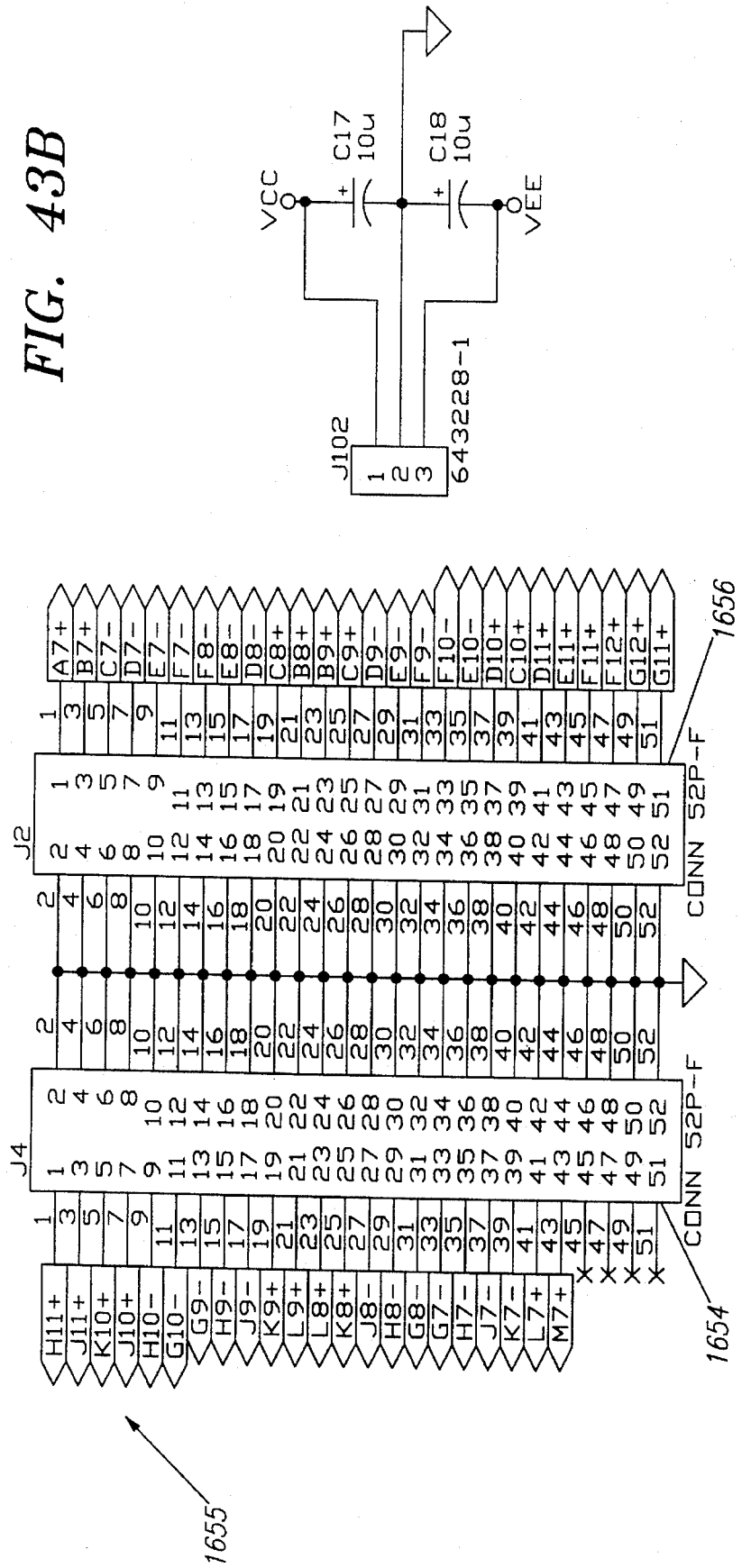

Referring to FIG. 43, four connectors 1650, 1652, 1654, and 1656 form the sensor connections 1655 between the signal conditioner 810 and the RTE octant counters 1354. After signal conditioning, signals from each of the 96 PMT detector elements 1339 connects the RTE octant counters 1354 through one of 96 electrical connections on the four connectors 1650, 1652, 1654, and 1656.

Figures 1, 44A:
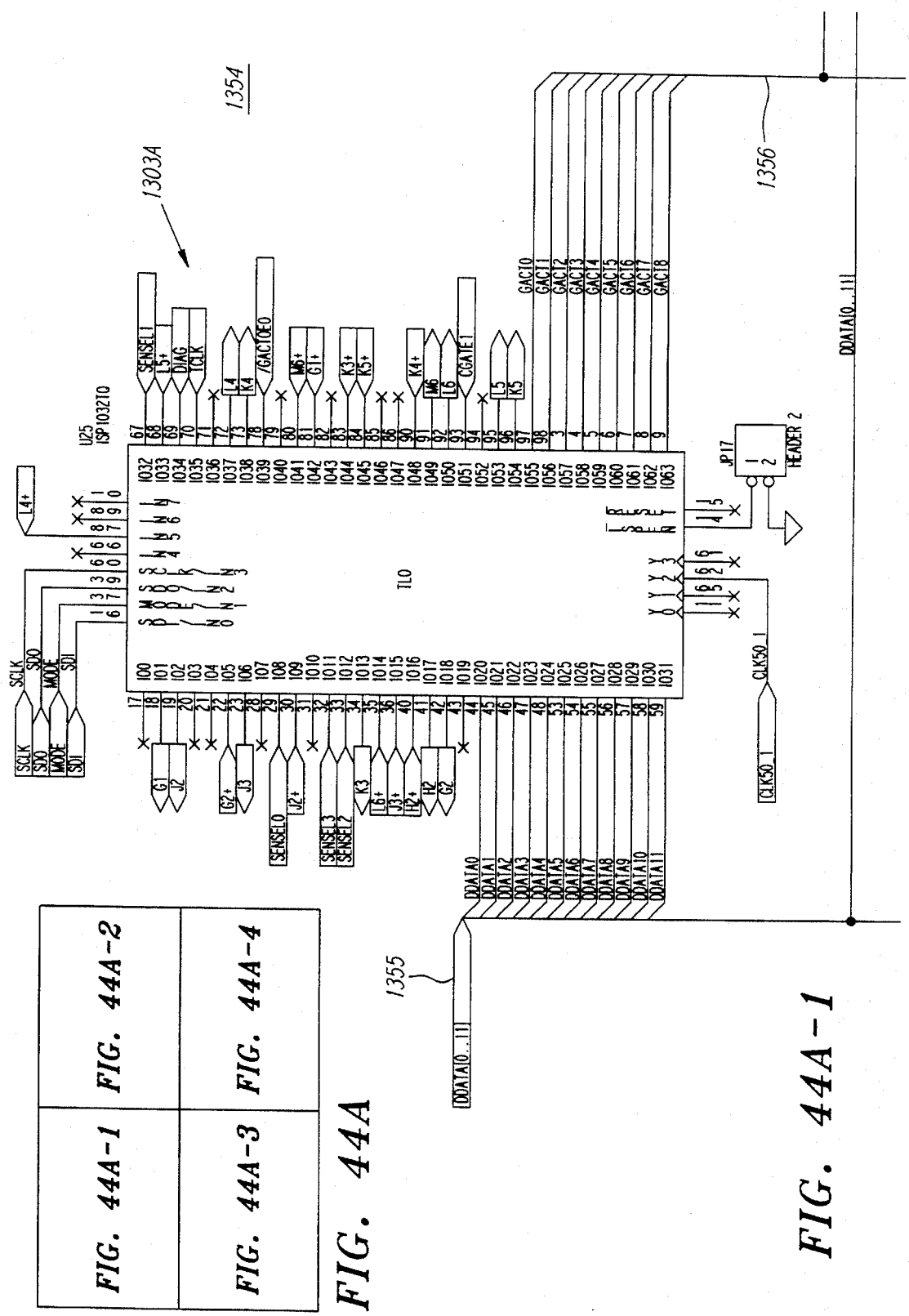
FIGS. 44A–B comprise schematics of the preferred octant counters.
Figures 2, 44A:
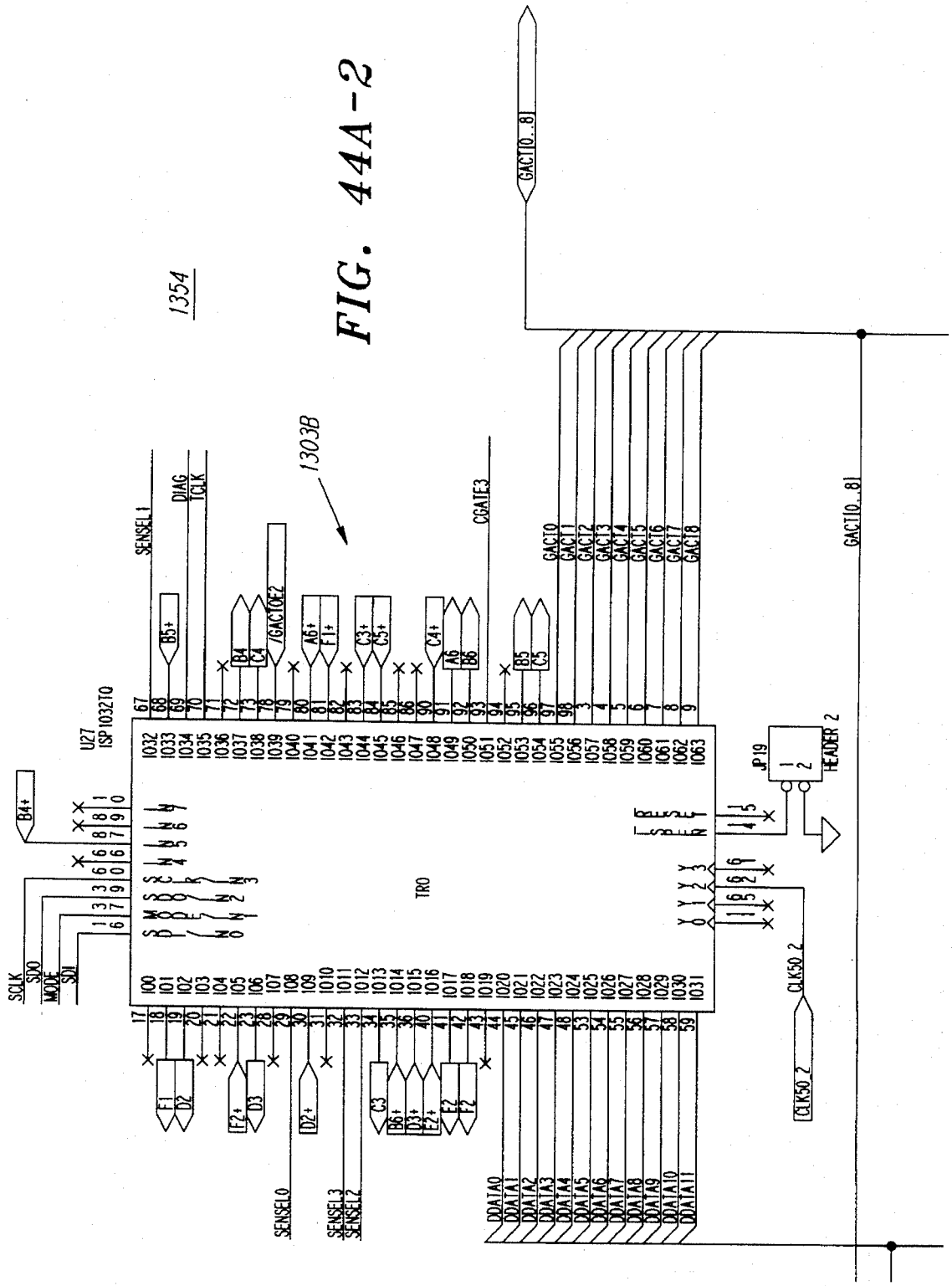
Figures 3, 44A:
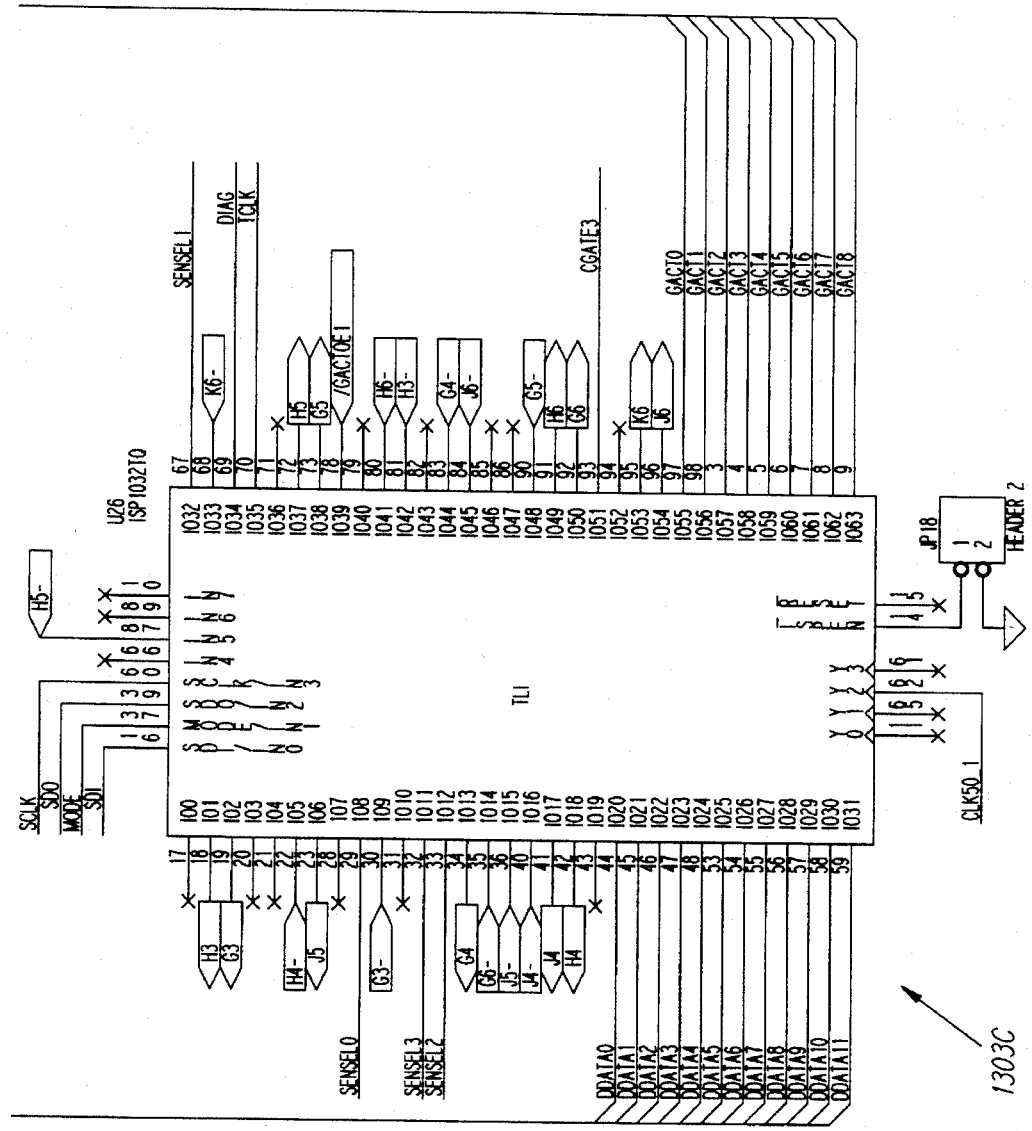
Figures 4, 44A:
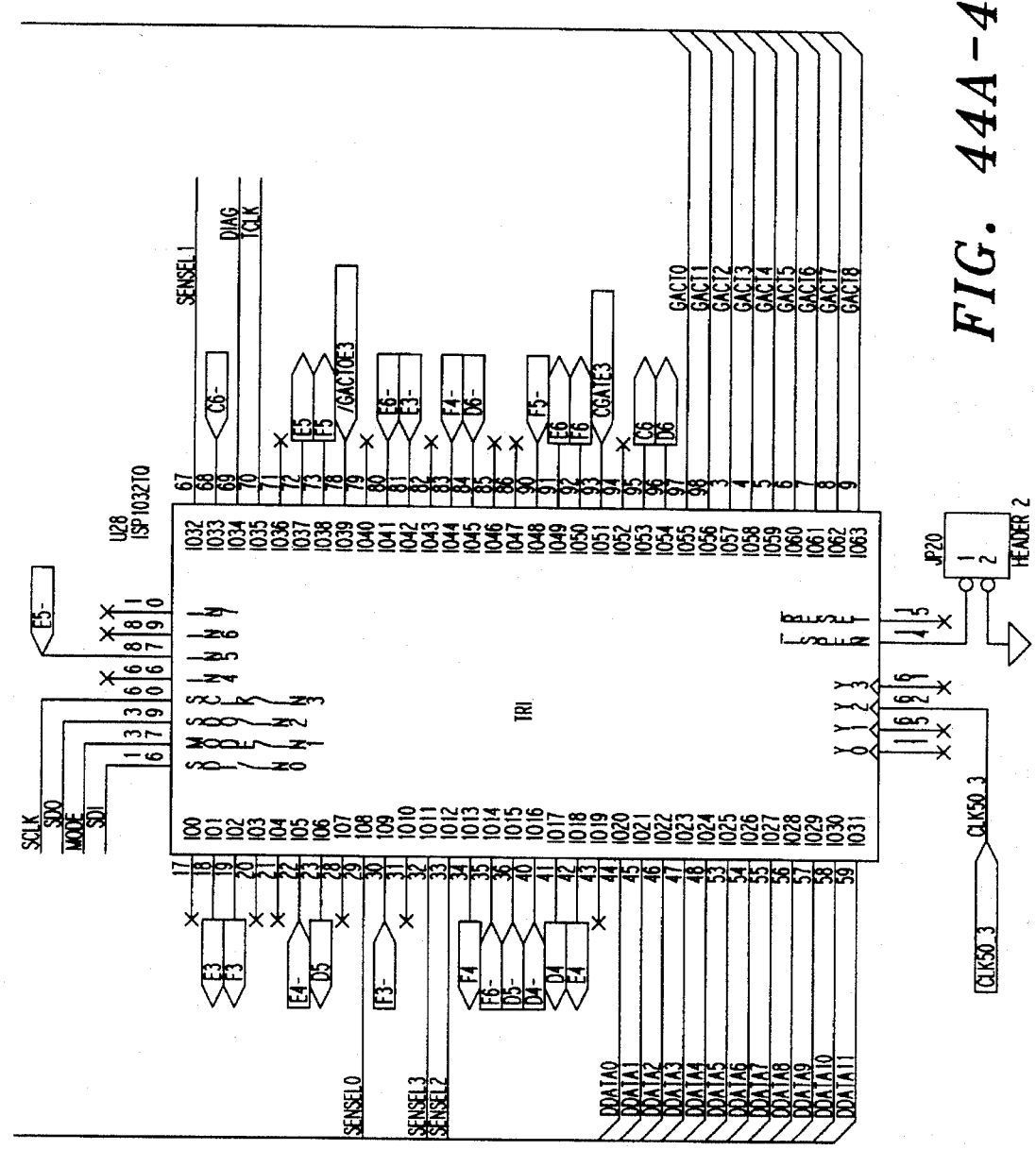
Figures 1, 44B:
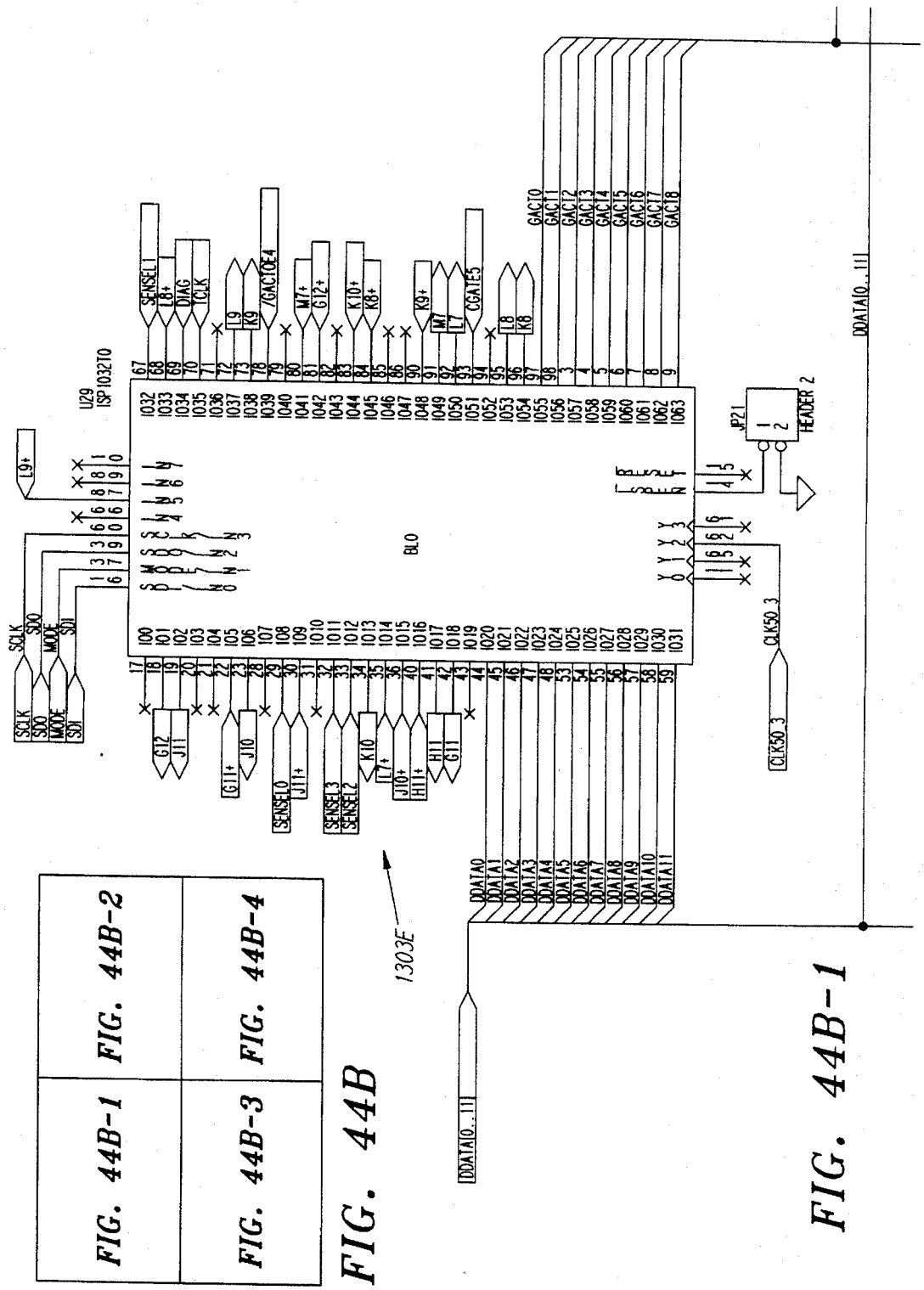
Figures 2, 44B:
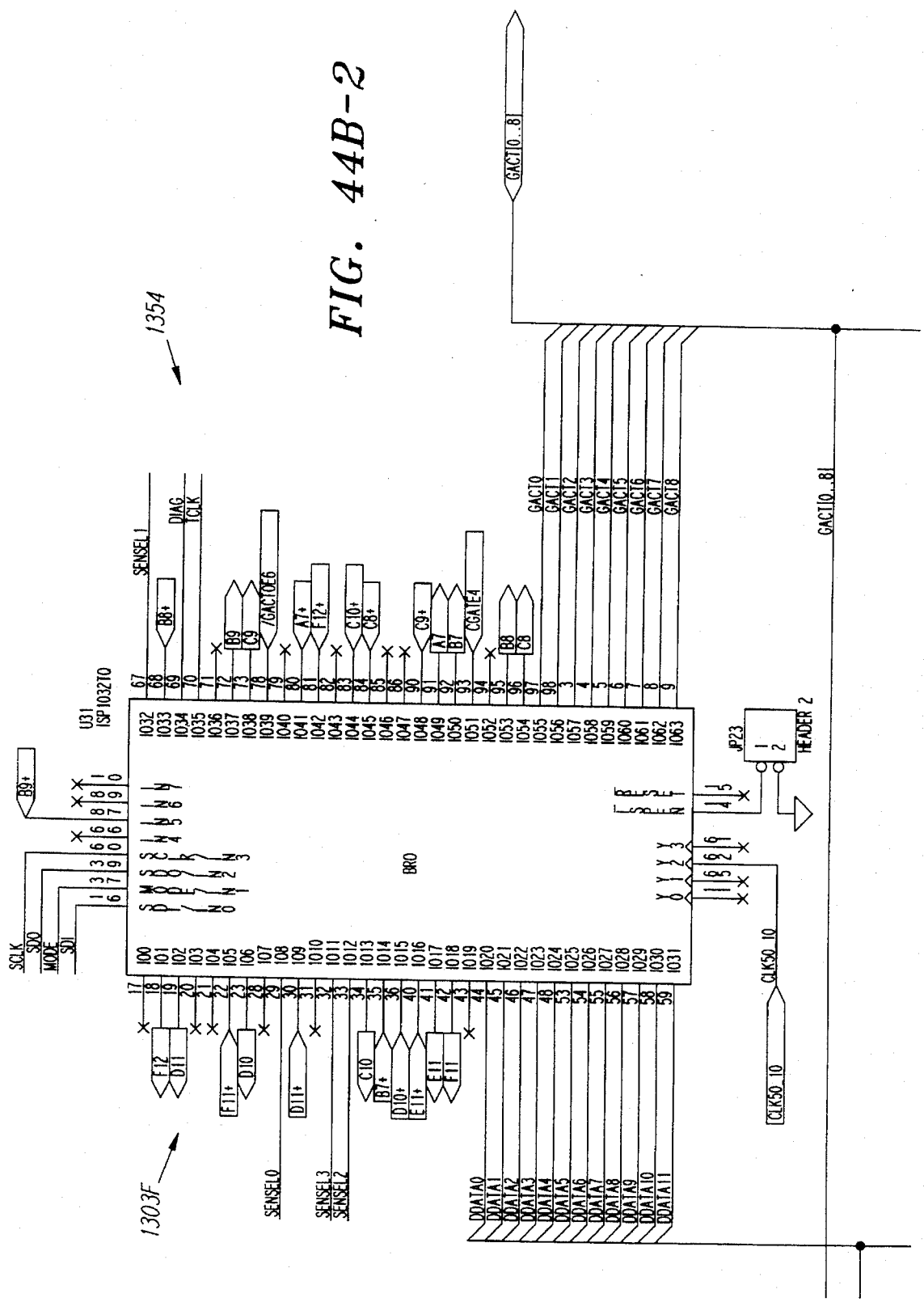
Figure 44B:
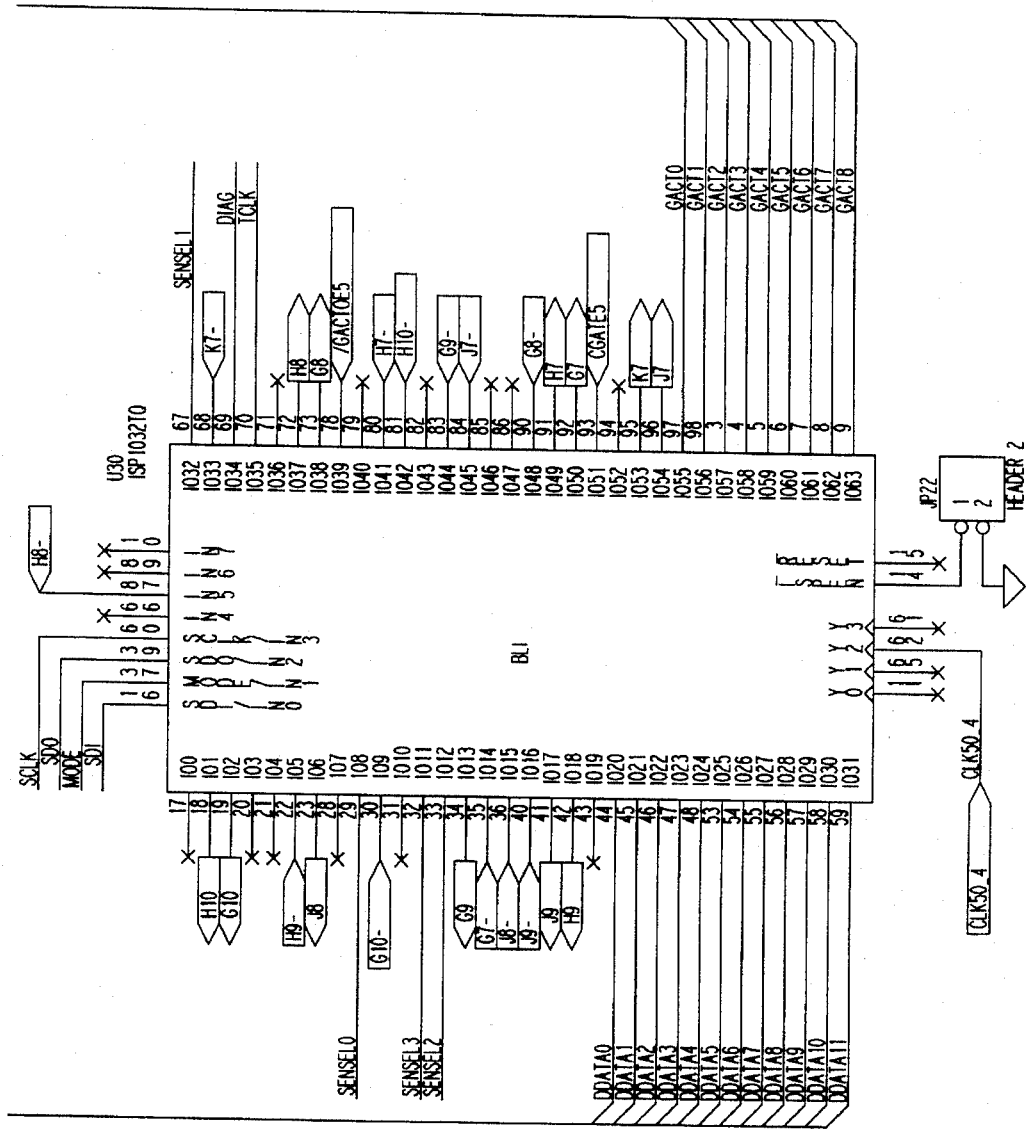
Figure 3:
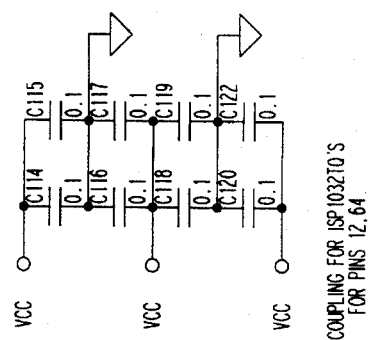
Figures 4, 44B:
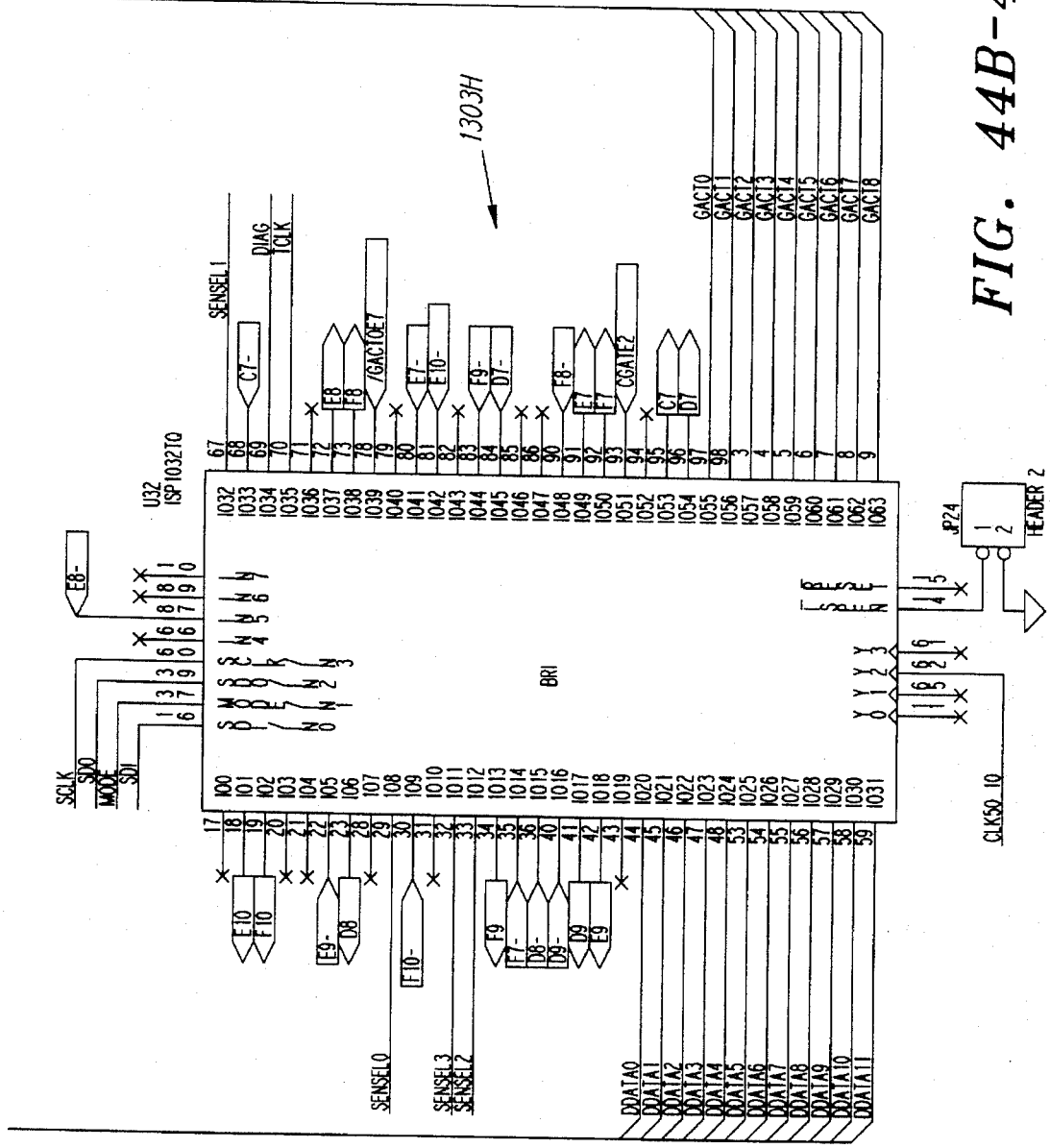

FIGS. 44A–B are diagrams of the preferred octant counters 1354. Eight such octant counters 1354 are used in the real-time eye. Each octant counter 1354 preferably comprises an ISP1032TQ lattice IC chip. Octant counter 1303A processes the inputs from the photocathode elements 1339 which is associated with the TLO octant. Similarly, octant counter 1303B processes the inputs for the TRO octant, octant counter 1303C for the TLI octant, octant counter 1303D for the TRI octant, octant counter 1303E for the BLO octant, octant counter 1303F for the BRO octant, octant counter 1303G for the BLI octant, and octant counter 1303H for the BRI octant. The preferred software modules for octant counters 1354 are included in Appendix A.

Each octant counter 1354 contains data input connections for each of the 12 PMT photo-cathode elements 1339 that is preferably associated with each octant. Upon detection of light photons by a PMT photo-cathode element 1339, an electrical signal is sent to its corresponding octant counter 1354. For the x-ray pencil beam which passes through a single collimator aperture, each of the eight octant counters 1354 produces a 9-bit value which contains the intensity data from all 12 of each octant's associated PMT photo-cathode elements 1339.

Figure 45:
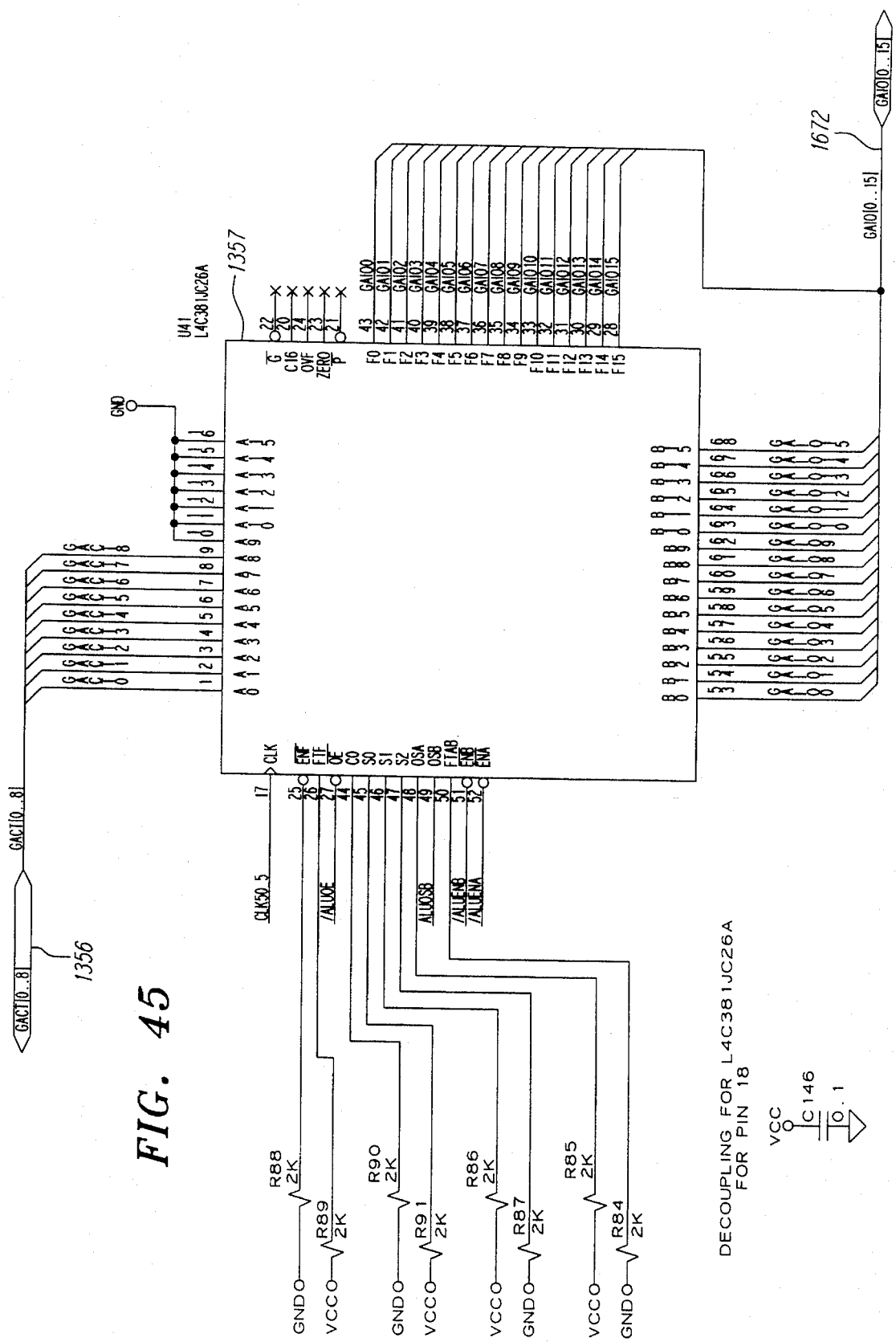
FIG. 45 is a schematic of a preferred gain & alignment ALU.

FIG. 45 diagrams the frame-summation chip 1357, which is an arithmetic logic unit ("ALU") and is preferably a L4C381JC26A IC chip available from Logic Devices, Inc. The 9 bit output from each octant counter 1354 is input to the frame-summation chip 1357 through connection 1356. The frame-summation chip 1357 processes eight numbers for each collimator aperture. For each succeeding frame, the frame-summation chip 1357 sums the corresponding values for the same octant for the same aperture from the previous frames. In the preferred embodiment, the octant values for 100–120 frames are added together to construct the data used for x-ray beam alignment.

Figure 46:
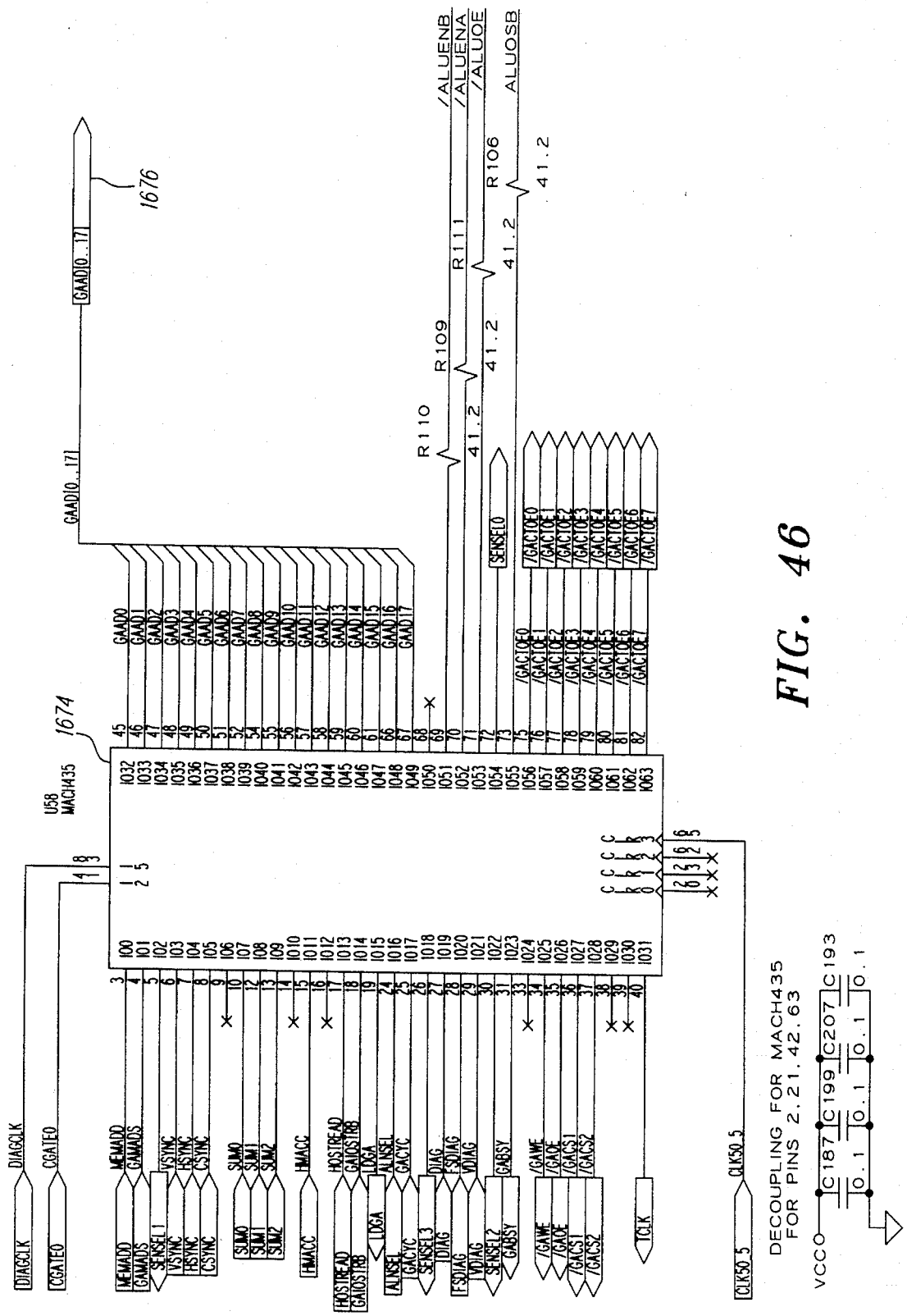
FIG. 46 is a schematic of a preferred gain & alignment engine.

FIG. 46 diagrams the gain & alignment engine 1674, which is preferably a MACH435 IC chip available from AMD Corp. The gain a alignment engine 1674 determines the items of beam alignment data which is to be processed and manner of processing intended for that item of data. Additionally, the gain & alignment engine 1674 controls the timing of the components within the beam alignment extractor 816. The preferred software modules for the gain a alignment engine 1674 are included in Appendix A.

Figure 47B:
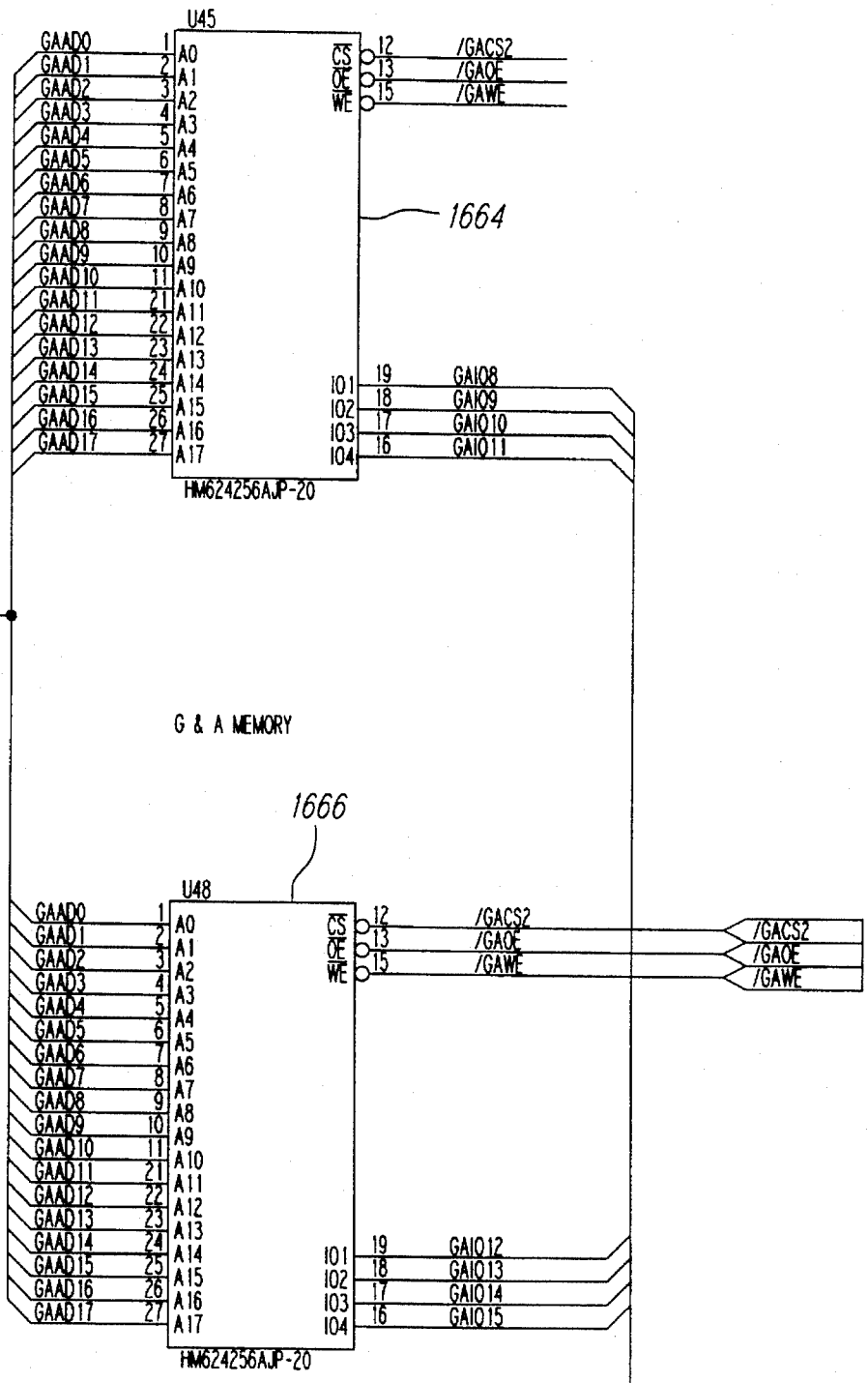
FIG. 47 is a schematic of the preferred memory for the preferred image reconstruction engine and gain & alignment circuitry.
Figure 47C:
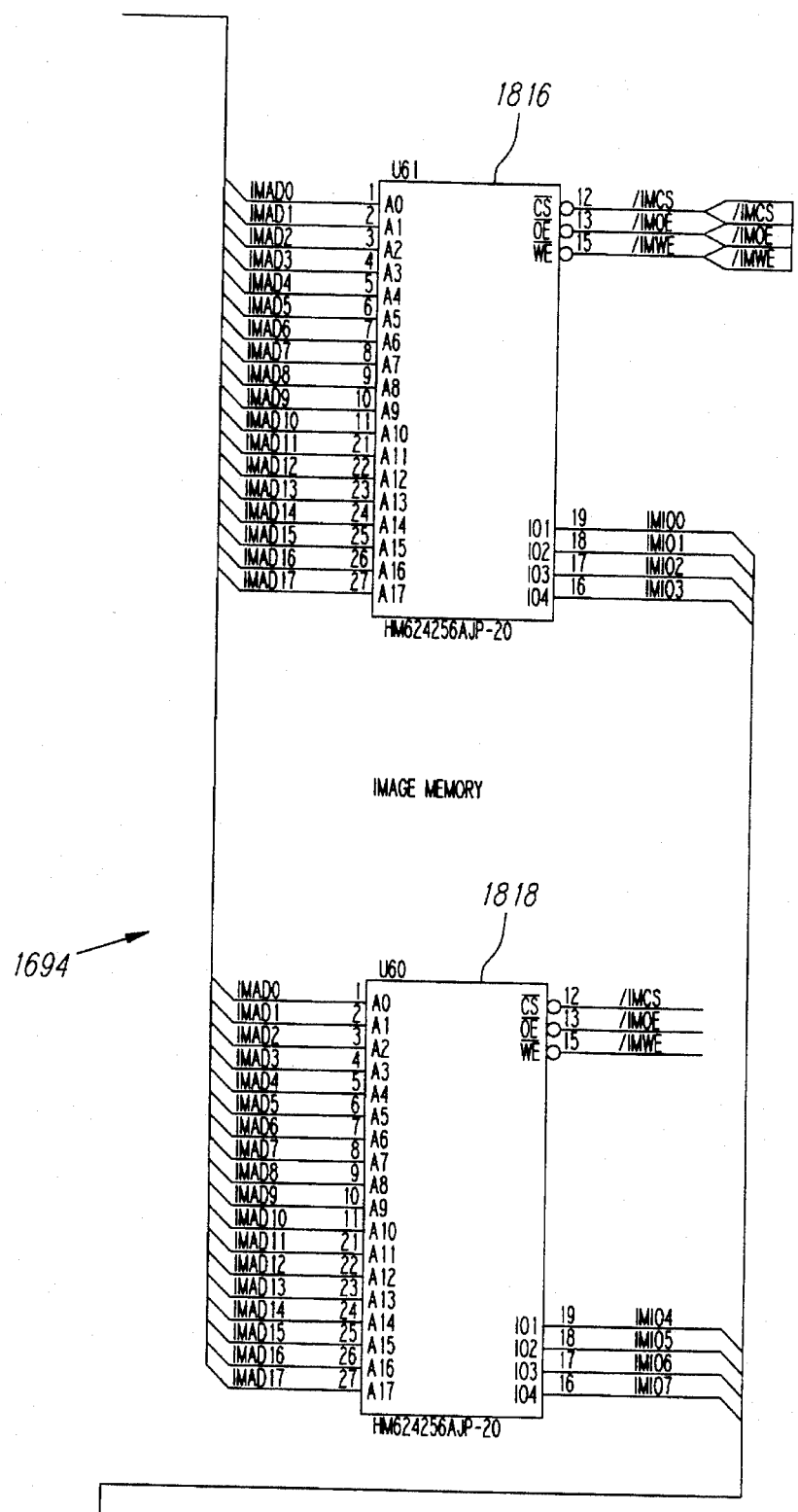
Figure 47D:
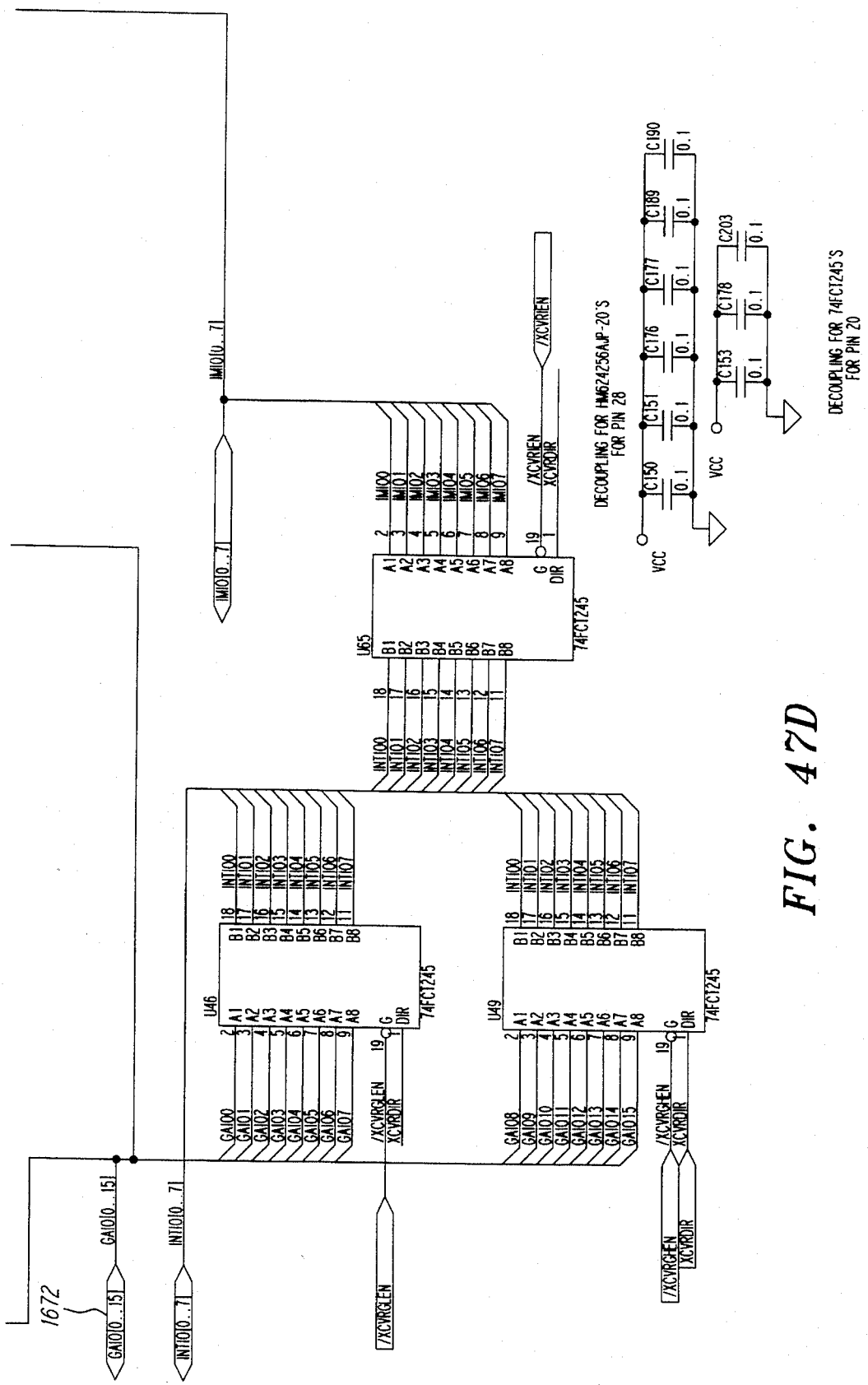

FIG. 47 is a diagram showing the gain & alignment memory chips 1678 which is comprised of four 1-Mbyte SRAM memory chips 1664, 1666, 1668, and 1670, each available under the model number MM624256AJP-20 from Hitachi Corporation. For each frame, eight values are collected for each collimator aperture. These values are stored in the gain a alignment memory 1678 after being processed through the frame-summation chip 1357. After 100–120 frames, the control computer will preferably access and process the data which is stored in the gain & alignment memory 1678 to correct the alignment of the x-ray beam.

FIGS. 48A–I are diagrams of string counters 1372 for strings one through nine. Nine such string counters are used in the image reconstruction circuitry, each of which is preferably comprised of two gate arrays 1680 and 1682, preferably IC part numbers ISP1032TQ available from Lattice Corp. Each string counter 1372 contains a total of 16 subcounters, with each gate array 1680 and 1682 containing 8 individual subcounters. Since there are a total of nine string counters 1372 and each string counter 1372 contains 8 individual subcounters, the total number of individual subcounters is 144. Since all nine string counters 1372 function similarly, only the string one string counter 47A will be discussed in detail. The preferred software modules for string counters 1372 are included in Appendix A.

Figures 2, 48A:
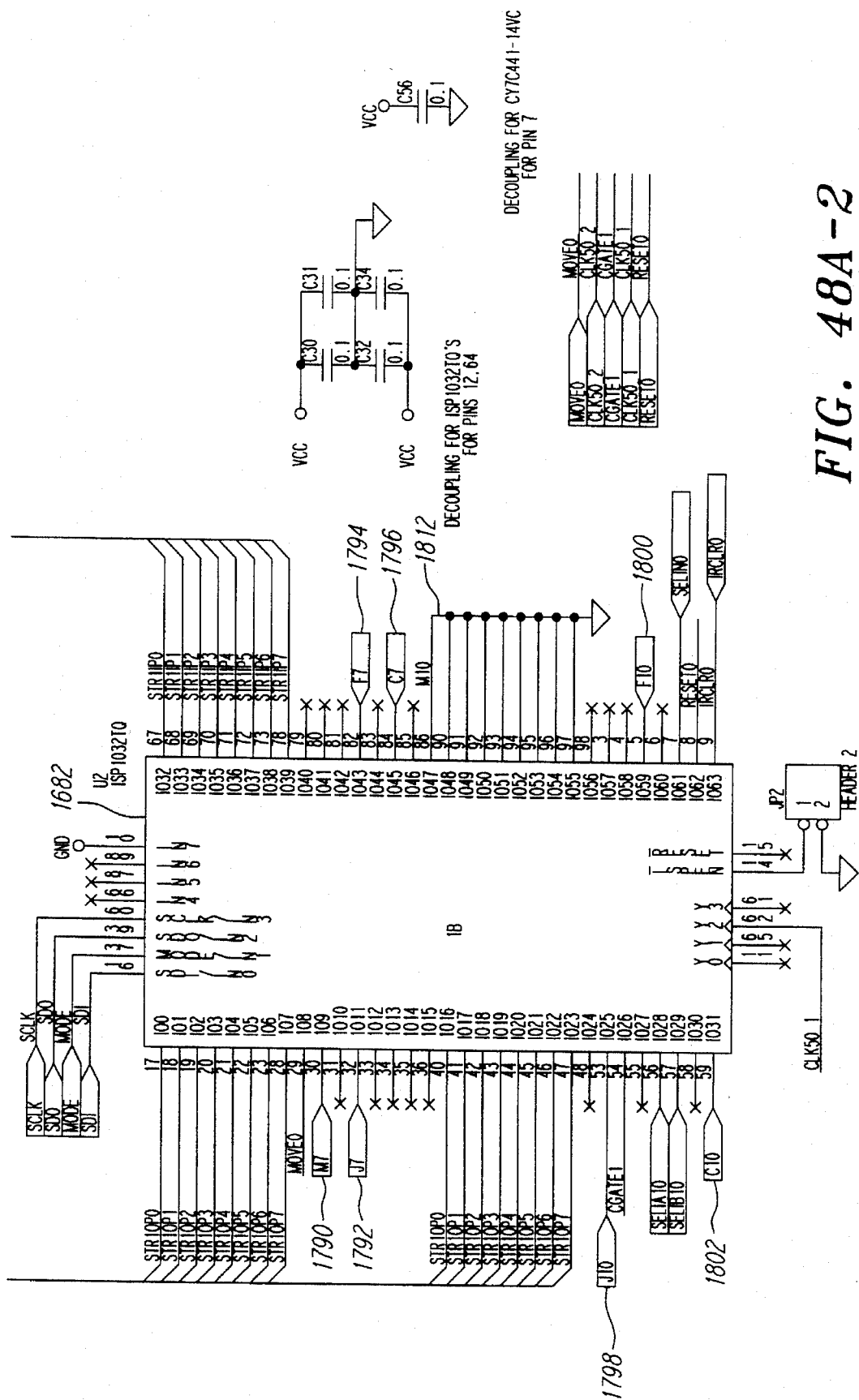
Figures 2, 48B:
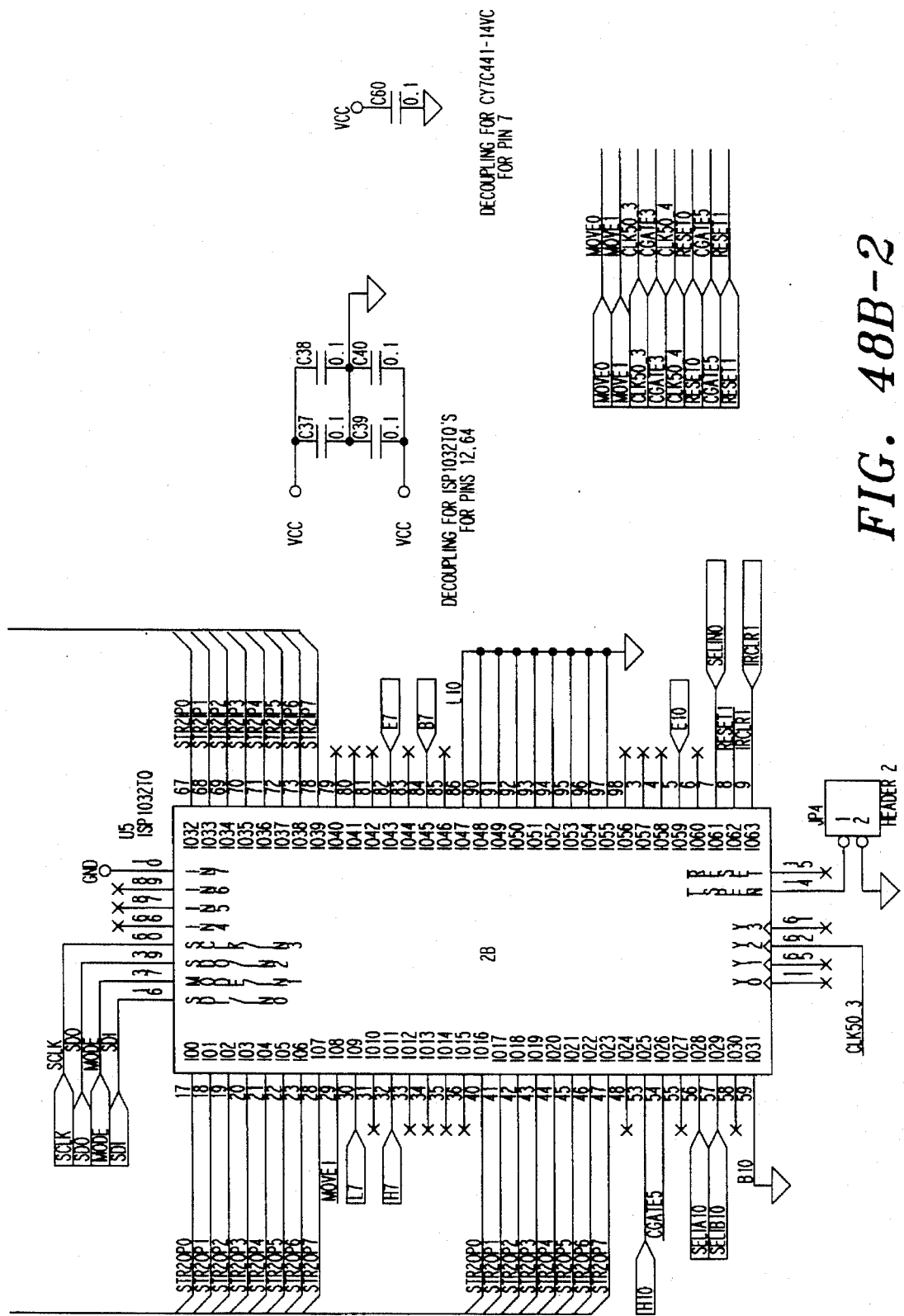
Figures 2, 48C:
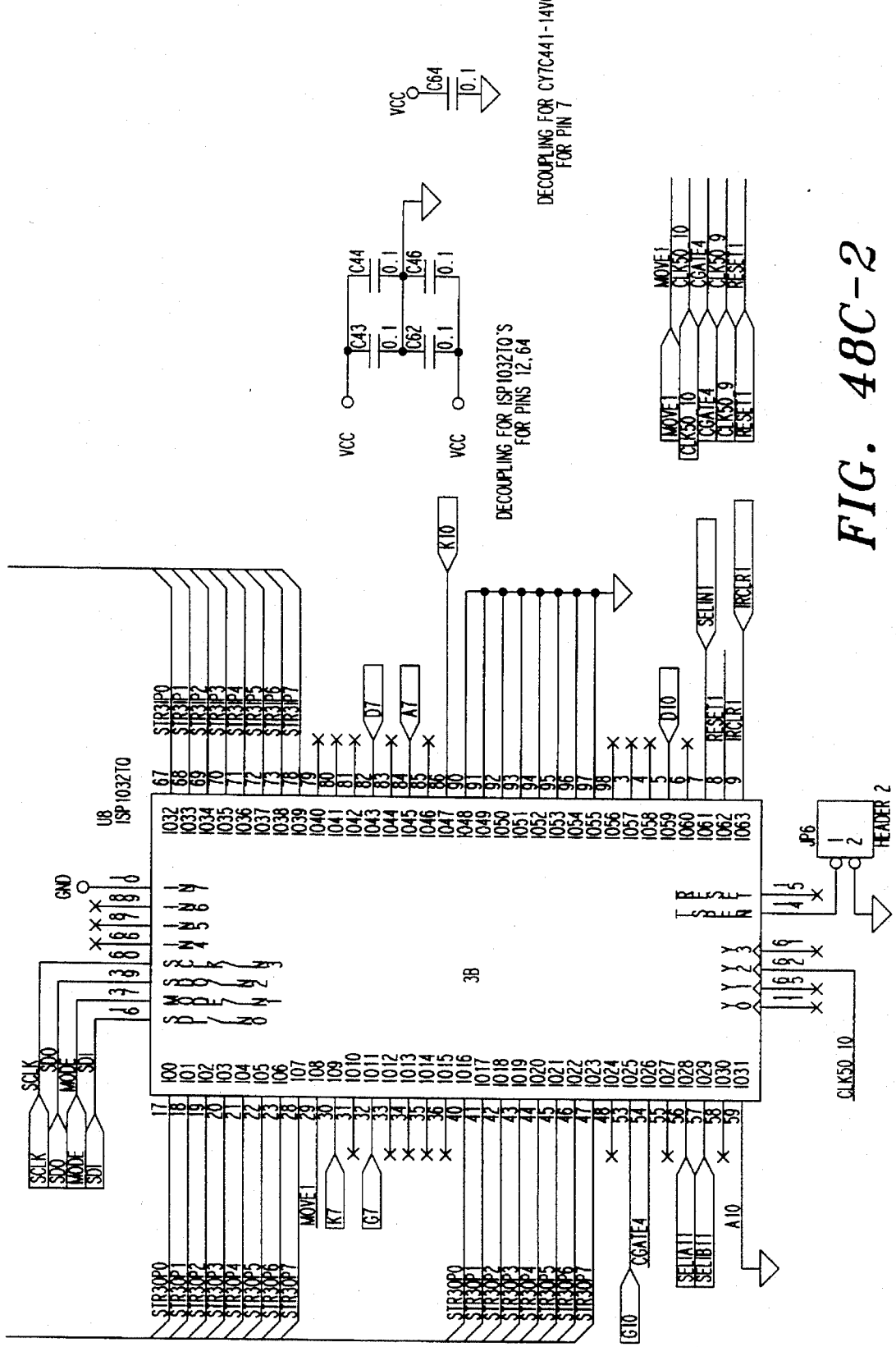
Figures 2, 48D:
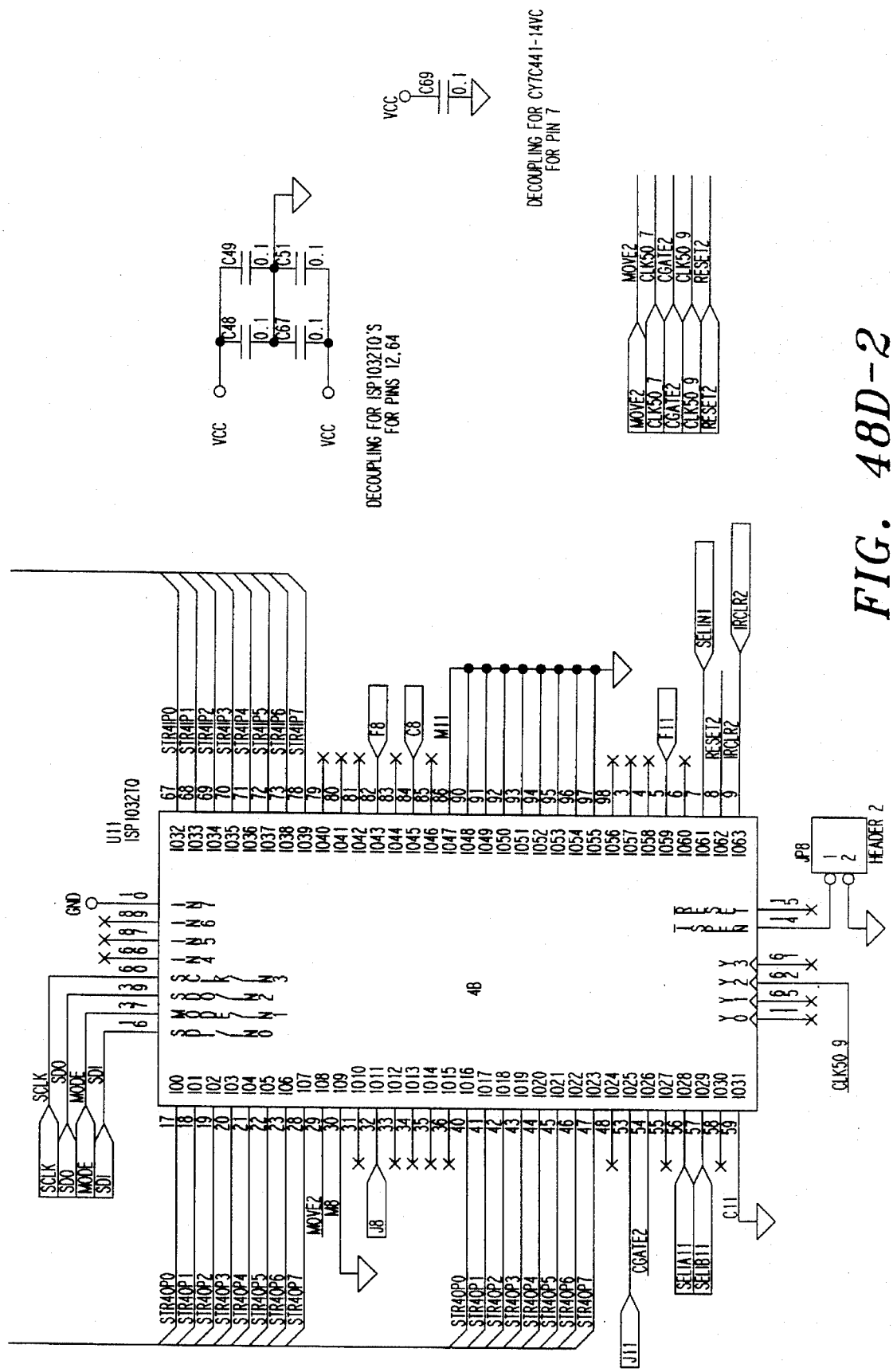
Figures 2, 48E:
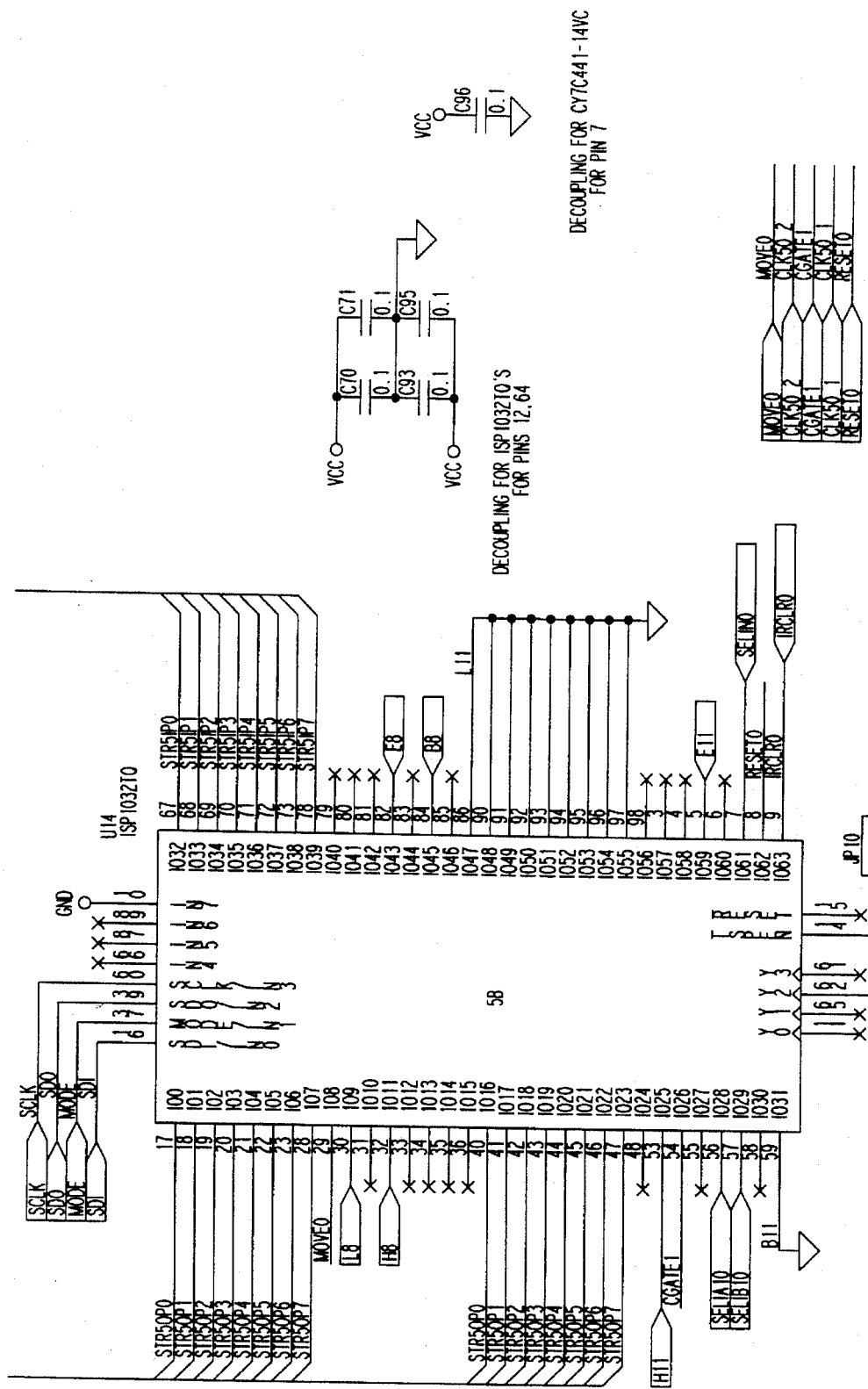
Figures 2, 48F:
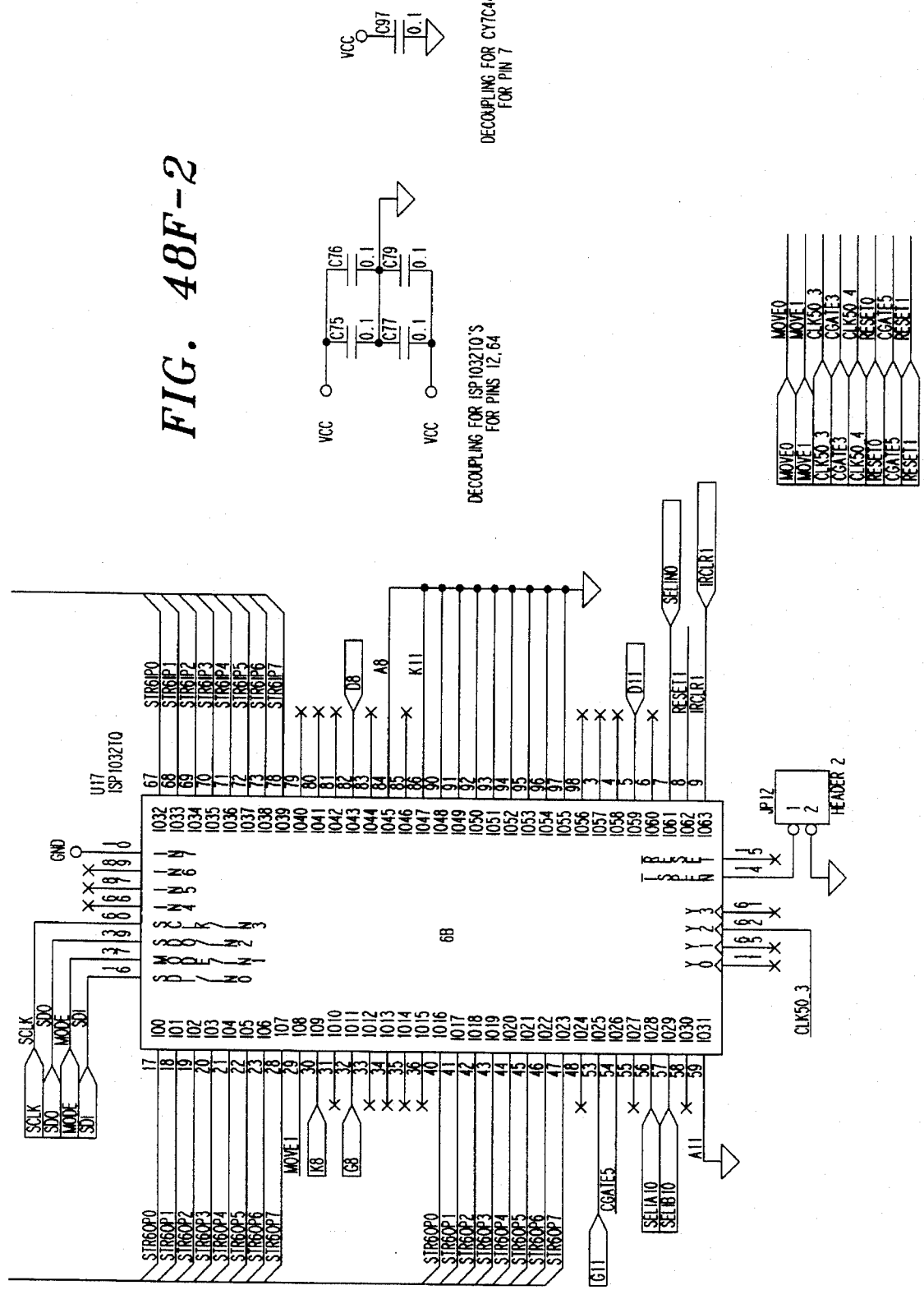
Figures 1, 2, 48G:
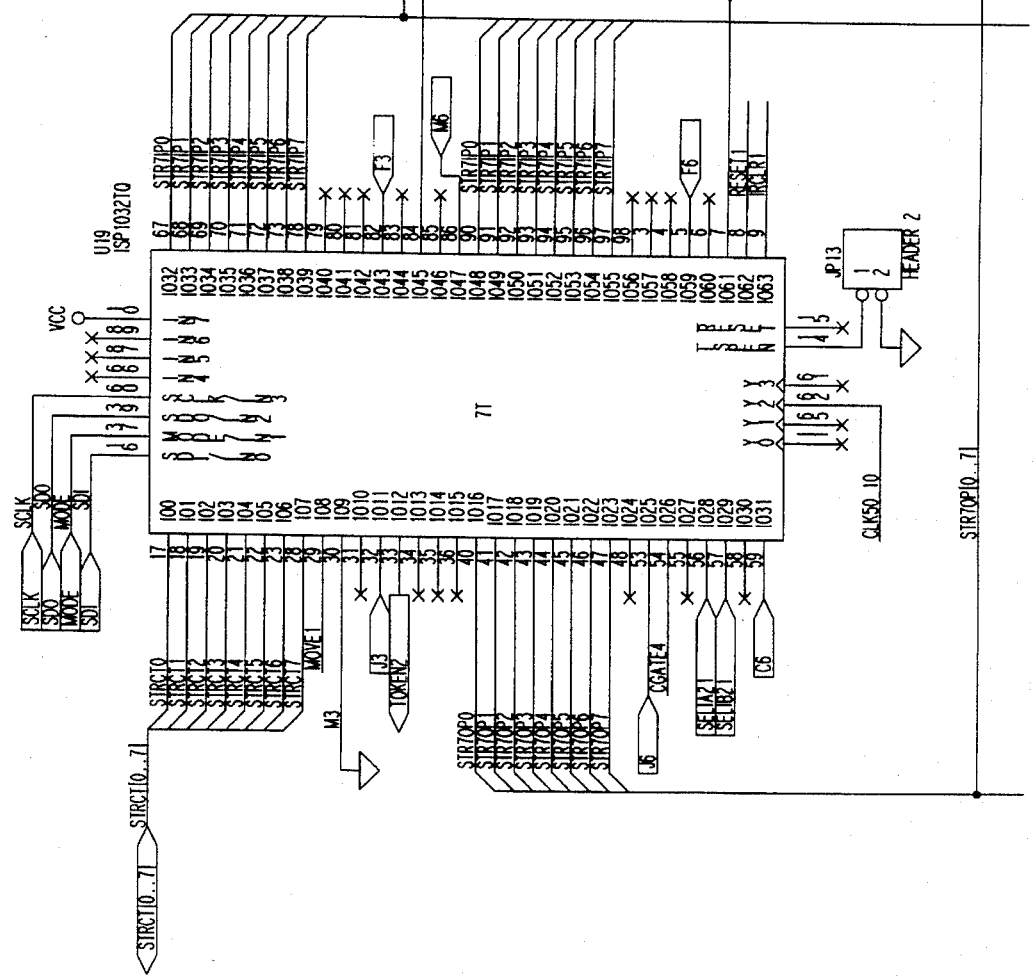
Figures 2, 48G:
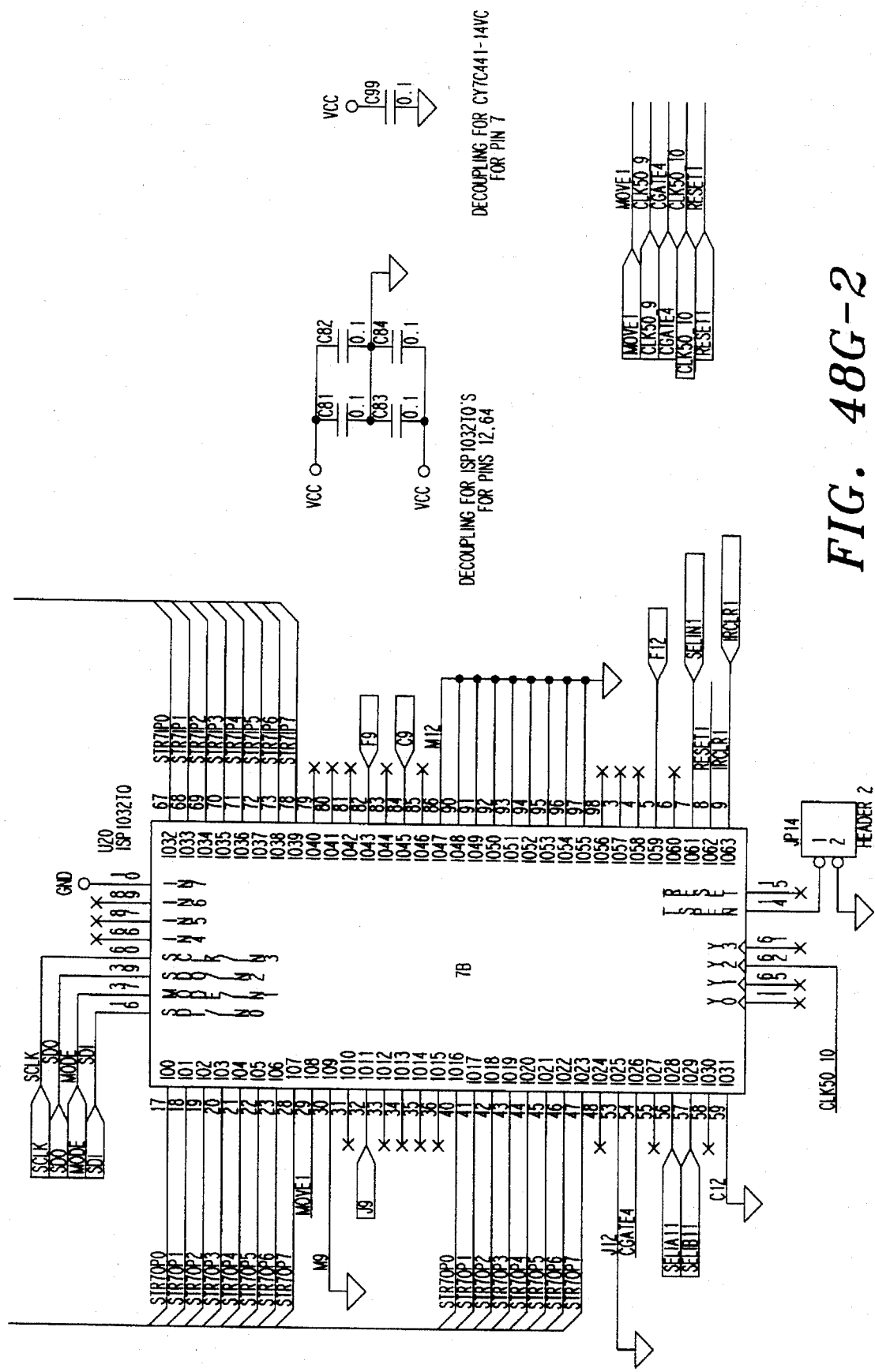
Figures 2, 48H:
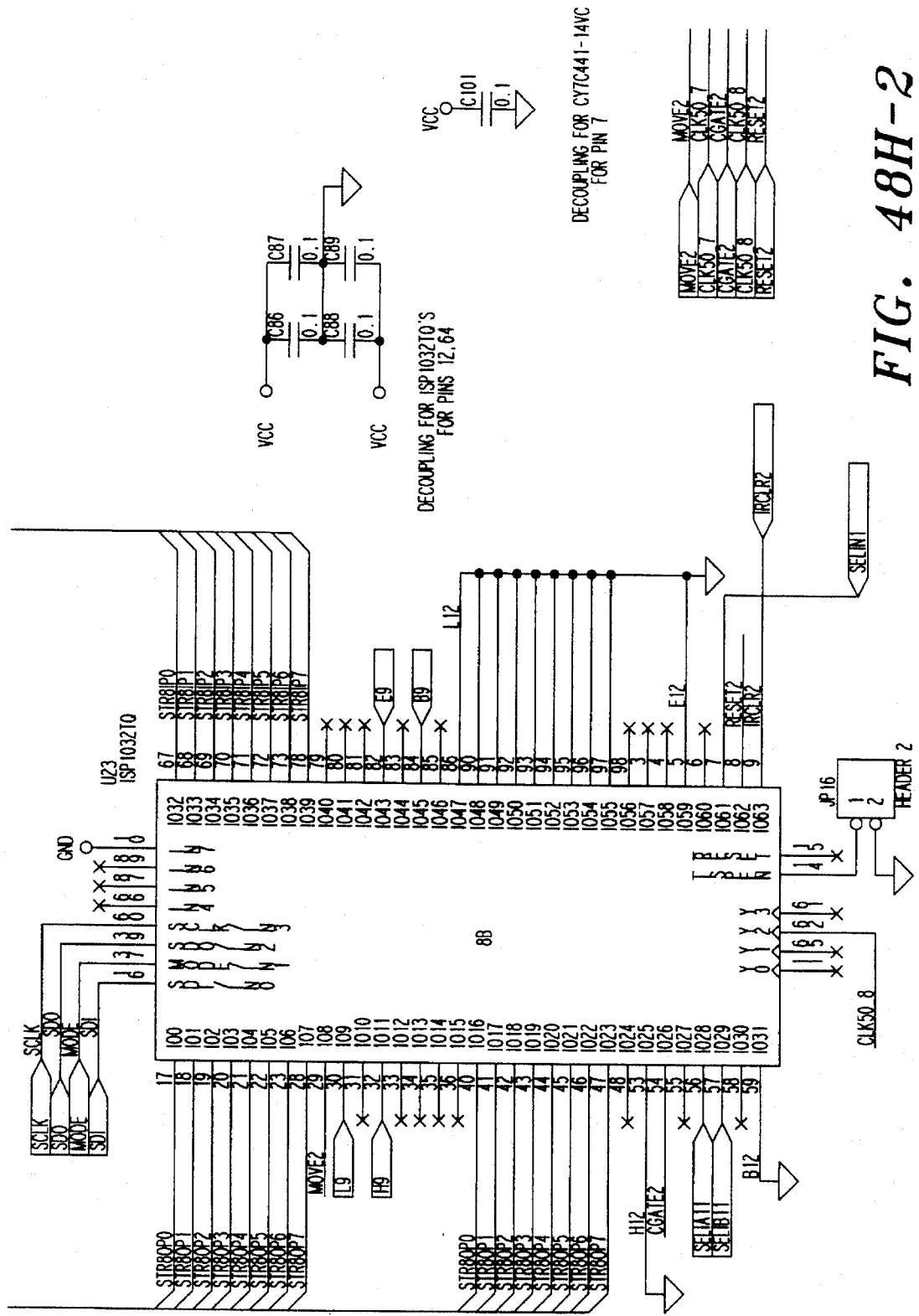
Figures 2, 481:
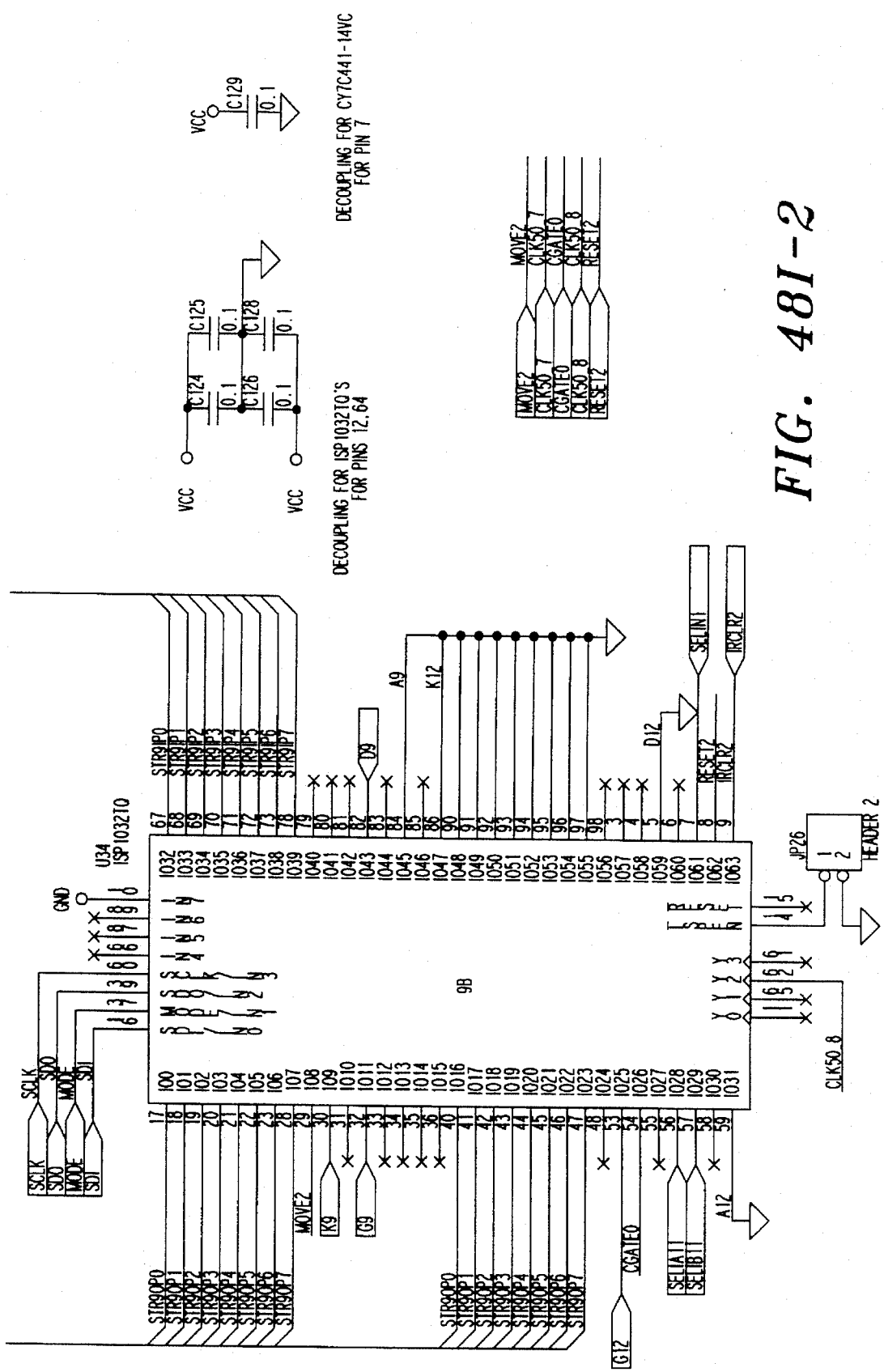

Referring back to FIG. 36, the detector element inputs for string one are marked with "1." Since only the 96 elements within the center pseudo circle 1780 correspond to active detector elements, the inputs mapped from active detector elements for string one are element F1, J4, F4, C4, M7, J7, F7, C7, J10, F10, and C10. Referring to FIG. 48A, data connection 1782 on string counter 1372 is mapped to the input from active detector element F1. Data connections 1784, 1786, 1788, 1790, 1792, 1794, 1796, 1798, 1800, and 1802 are mapped to active detector elements J4, F4, C4, M7, J7, F7, C7, J10, F10, C10 respectively. The inputs from elements M1, J1, C1, M4, and M10 correspond to the inactive detector elements for string counter one. Therefore, data connections 1804, 1806, 1808, 1810, and 1812 which correspond to inactive detector elements M1, J1, C1, M4, and M10 respectively, are all tied to ground.

Each of the other string counters are similarly mapped to their respective active and inactive detector elements. FIG. 36 diagrams the 144 logical detector elements and the string counter number that they are mapped to.

FIG. 48A also diagrams a line FIFO ("first in first out") chip 1702, preferably part no. CY7C441-14VC available from Cypress Semiconductor. The RTE image reconstruction circuitry consists of nine line FIFOs, with each line FIFO 1702 paired with a corresponding string counter 1372. Partial image pixel values from string counter 1372 are input into line FIFO 1702 as the string counter acquires data from the multi-detector array. After the 166th string counter data value is input into the line FIFO 1702, every succeeding data value will cause the line FIFO 1702 to return a data value that was stored 166 counts before to the its corresponding string counter 1372. The data values are returned to the string counter 1372 to be summed with new data values acquired for the same image pixel.

Figure 49:
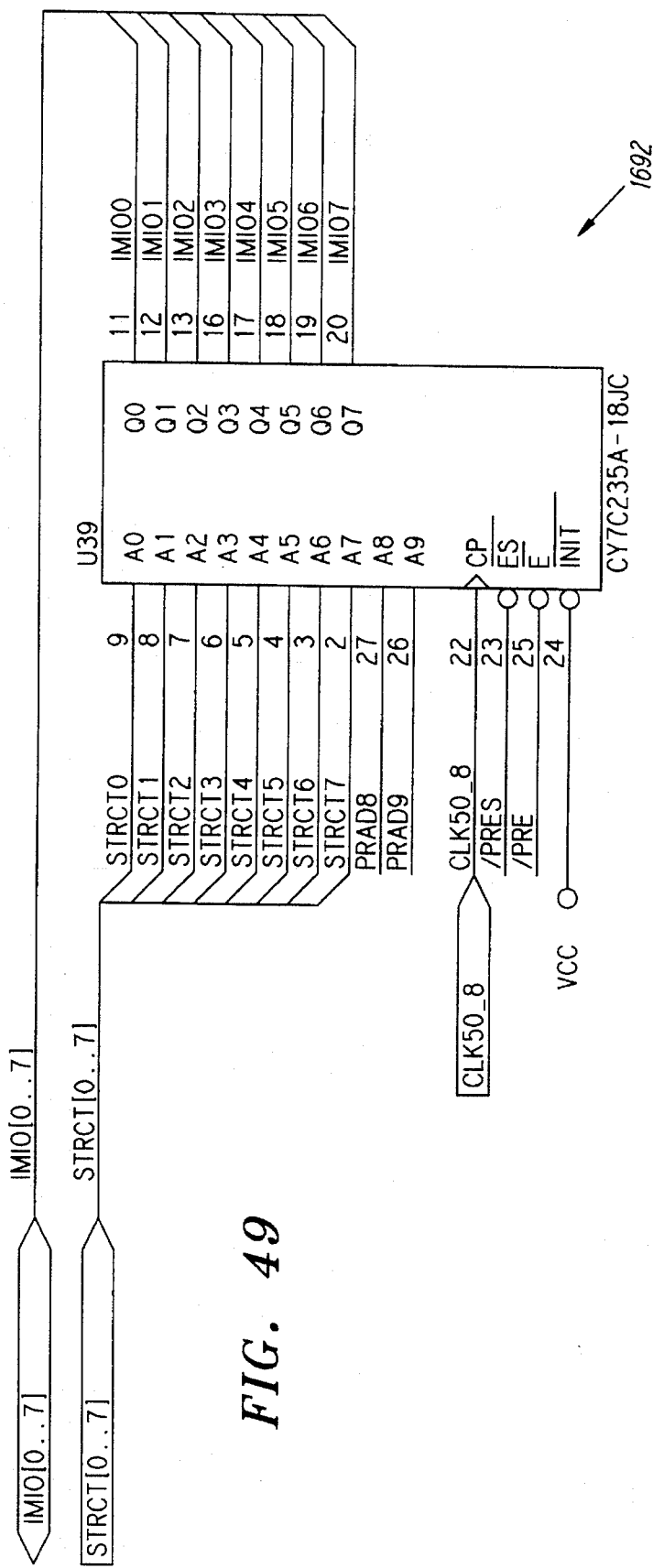
FIG. 49 is a schematic of a preferred normalization PROM for a preferred image reconstruction engine.

FIG. 49 diagrams the normalization PROM 1692, which is a CY7C235A-18JC Cypress Semiconductor unit. As explained previously, each string counter 1372 is mapped to 16 logical detector elements on a 12-by-12 array of logical detector elements. However, each string counter 1372 may receive meaningful input data from only among the 96 active detector elements which comprise the center pseudo-circular array. As shown in FIG. 36, the number of active detector elements providing input data may be 10, 11 or 12 depending on the particular string counter. The normalization PROM 1692 normalizes the outputs from the nine string counters 1372 by calculating the proper output levels based upon the number of active input detector elements for each string.

Figure 50:
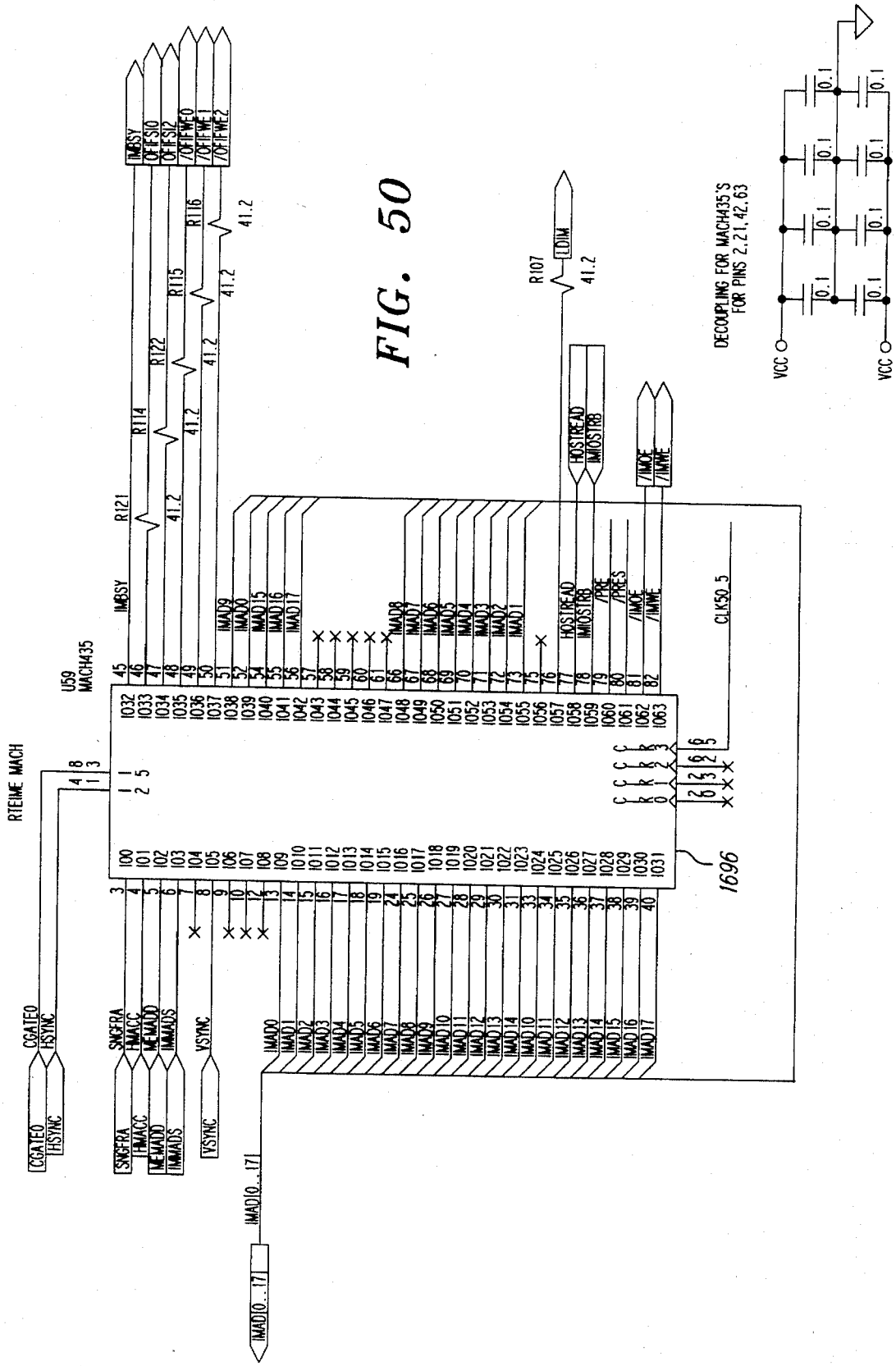
FIG. 50 is a schematic of the controller for the preferred image reconstruction engine.

FIG. 50 diagrams the image reconstruction controller 1696. Image reconstruction controller 1696 functions as the "engine" within the image reconstruction engine 814. Image reconstruction controller 1696 controls the timing and operation of the string counters 1372. The image reconstruction controller 1696 is the component which keeps track of both the strings and the individual image pixels which are reconstructed. Image reconstruction controller 1696 also controls the operation of the image memory unit 1694. The preferred software modules for the image reconstruction controller 1696 are included in Appendix A.

FIG. 47 diagrams the image memory unit 1694, which is preferably comprised of two conventional 1-Mbyte MM624256AJP-20 SRAM chips 1816 and 1818. The normalized pixel data output from the normalization PROM is input to the image memory unit 1694 through electrical connection 1718. The image memory unit 1694 combines and correctly orders the pixel data for the entire image.

Figures 51, 51A:
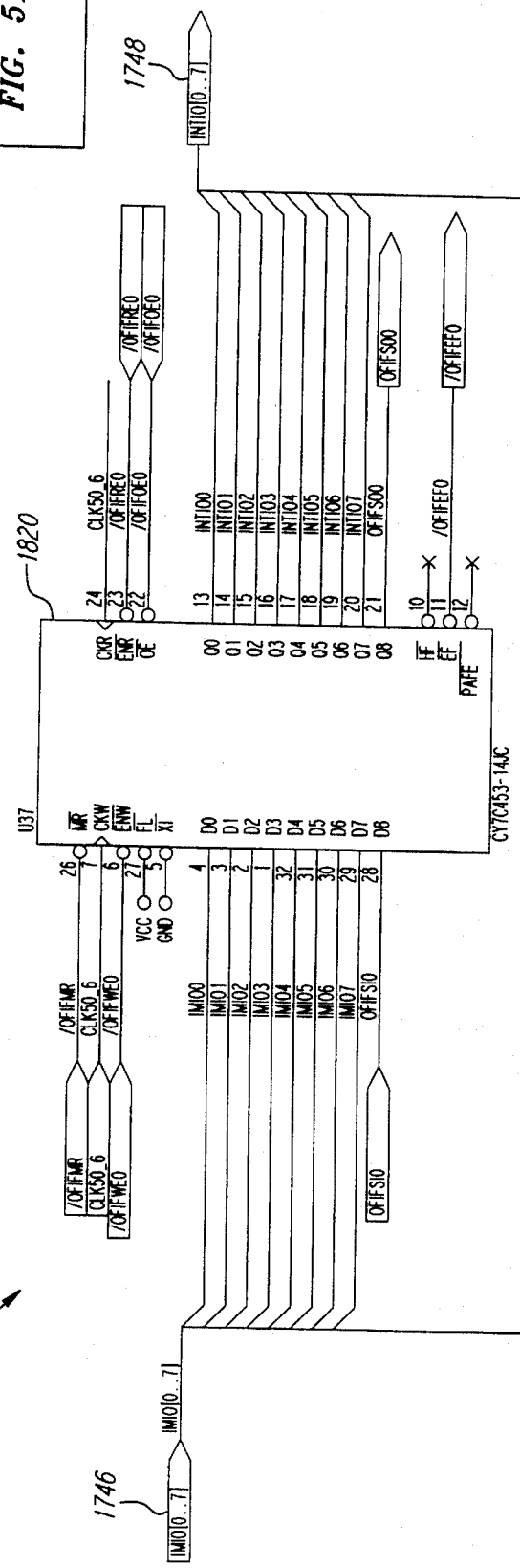
FIG. 51 is a schematic diagram of the preferred output FIFOs for the preferred image reconstruction engine.
Figure 51B:
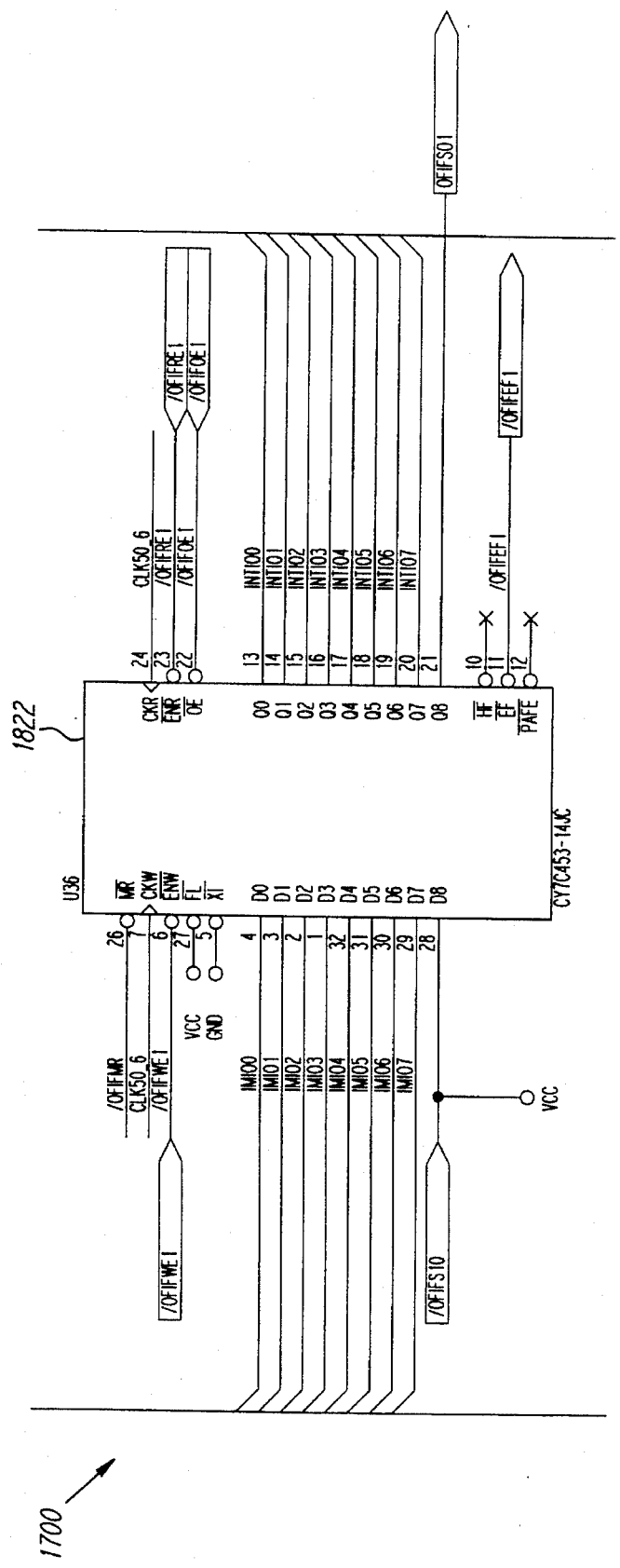

FIG. 51 is a diagram of the output FIFOs 1700. The output FIFOs 1700 preferably comprises three CY7C453-14JC devices 1820, 1822, and 1824. The output FIFOs 1700 store three lines of pixel data before outputting this data in frame order through RTE output circuit 818. The output FIFOs 1700 function in this manner because a completed scan of one collimator aperture row will result in the completion of three lines of image pixels. The pixel data is continually input from the normalization PROM 1692 until the three lines of pixel data are stored.

Figure 52:
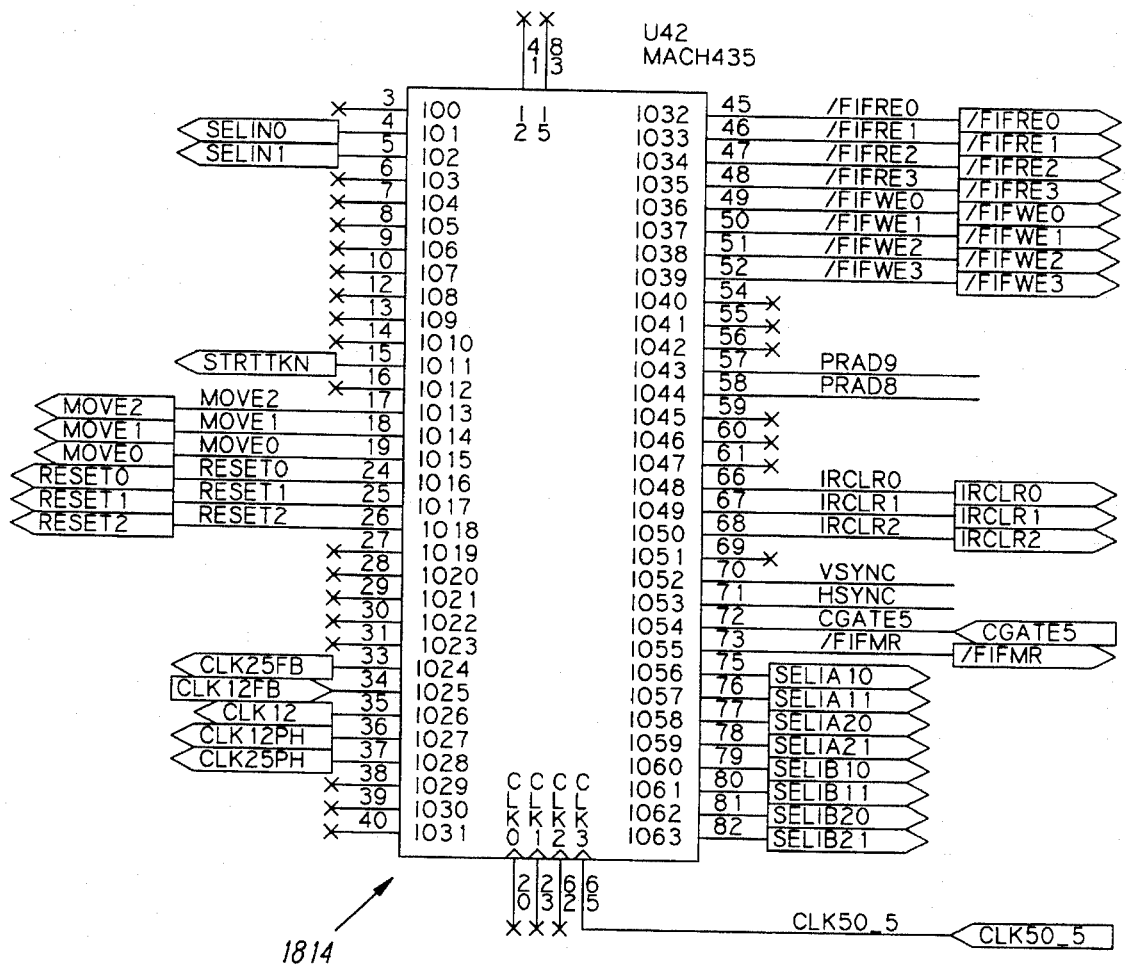
FIG. 52 is a schematic of the preferred output FIFO controller for the preferred image reconstruction image.

FIG. 52 diagrams the output FIFO controller 1814. Output FIFO controller 1814 consists of a lattice chip available under the model number MACH435 IC chip from AMD Corp. Output FIFO controller 1814 controls the operation of the three output FIFOs 1700. The preferred software modules for the output FIFO controller 1814 are included in Appendix A.

Detector Controller

The detector controller 805 (FIG. 21) for the detectors 822 and 1522 receives image pixel data and beam alignment data from the detectors and transmits control information to the detectors. Right receiver 880 optically receives image pixel data and beam alignment data from the right detector 822 through high-speed fiber-optic cable 826. Consequently, right receiver 880 includes the light signal to electrical signal conversion circuitry described more fully in conjunction with FIG. 40. The left receiver 846 operates in a similar fashion to receive image pixel data and beam alignment data from the left detector 1522.

Right transmitter 886 optically transmits threshold and gain control data to the right data receiver 812 though fiber-optic cable 824. Consequently, beam controller interface 794 includes the electrical to light conversion circuitry described more fully in conjunction with FIG. 41. Right transmitter 886 also receives synchronization signals from beam deflection lookup table 918 (FIG. 25). The left transmitter 848 operates in a similar manner to communicate control signals to the left detector 1522.

Figure 53:
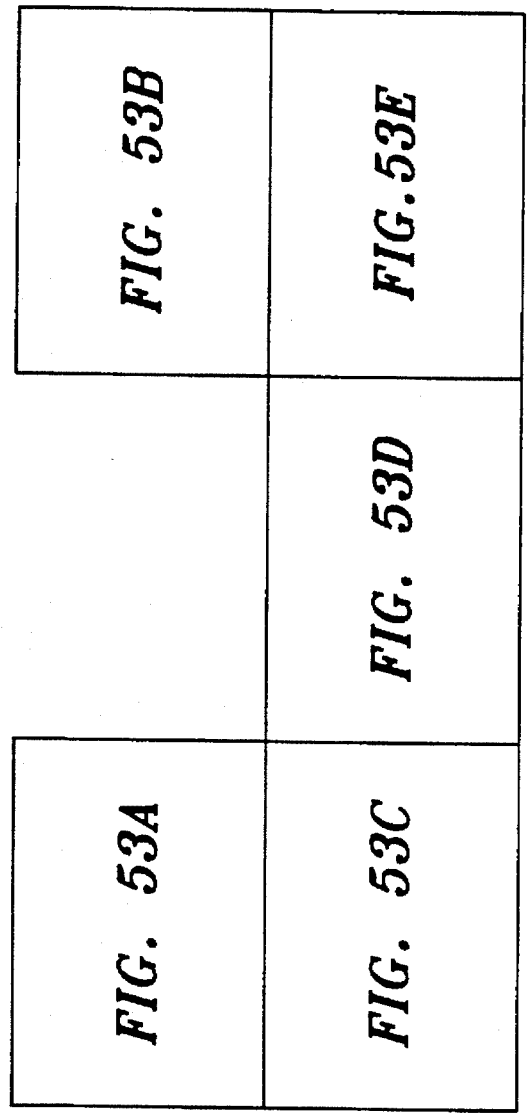
FIG. 53 is a circuit diagram of the preferred control logic for the detector controller.
Figure 53A:
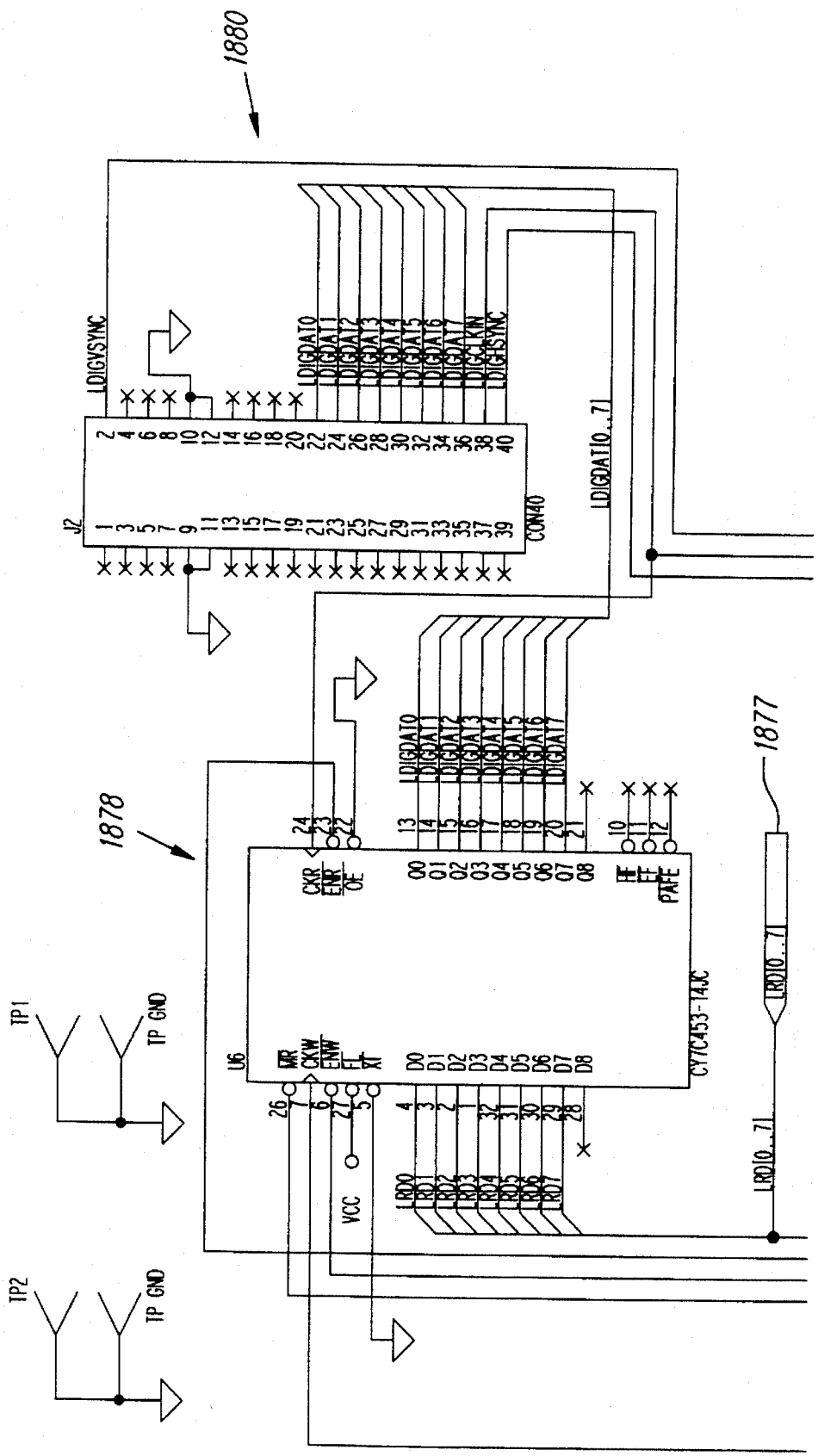
Figure 53B:
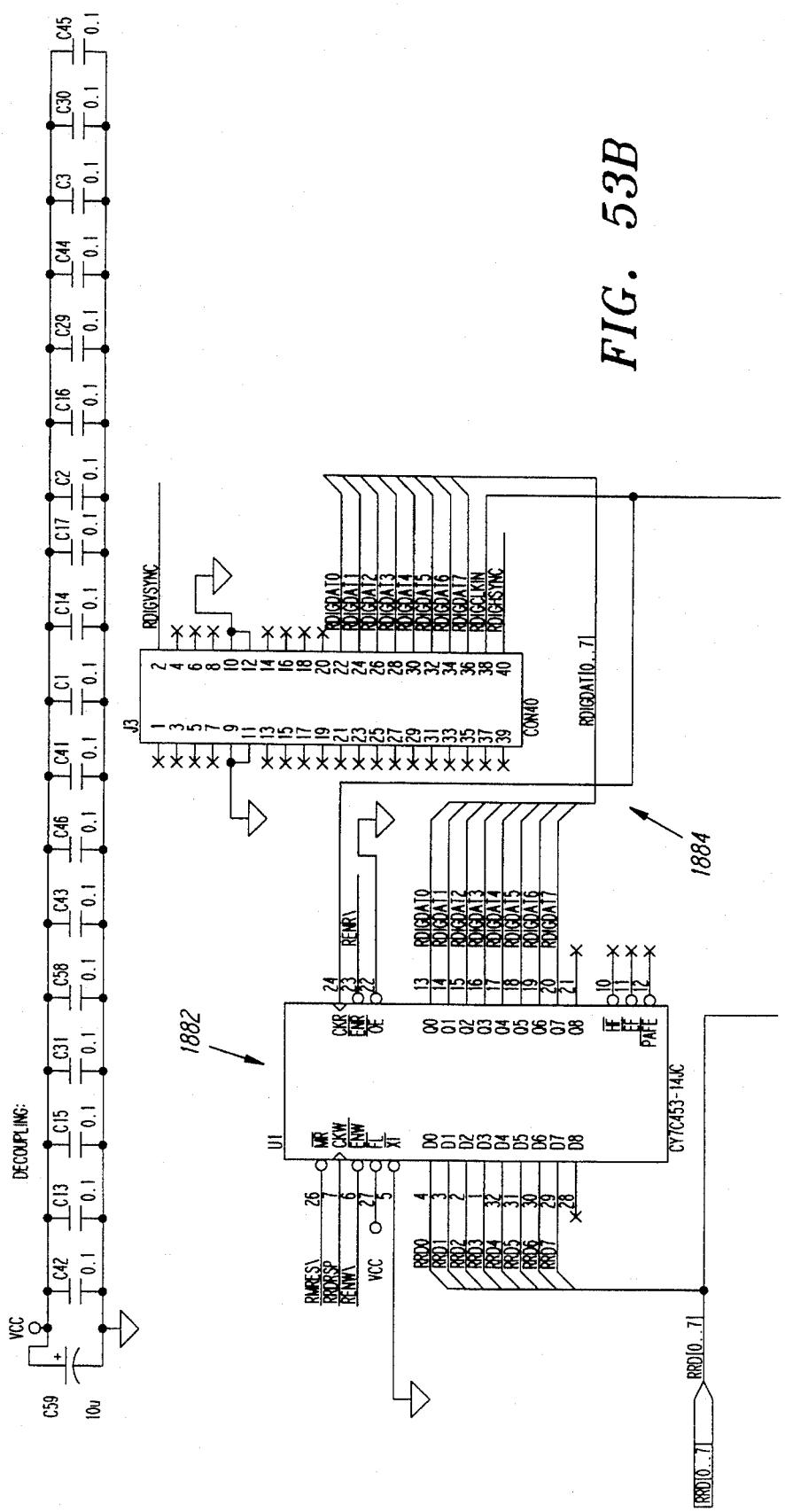
Figure 53C:
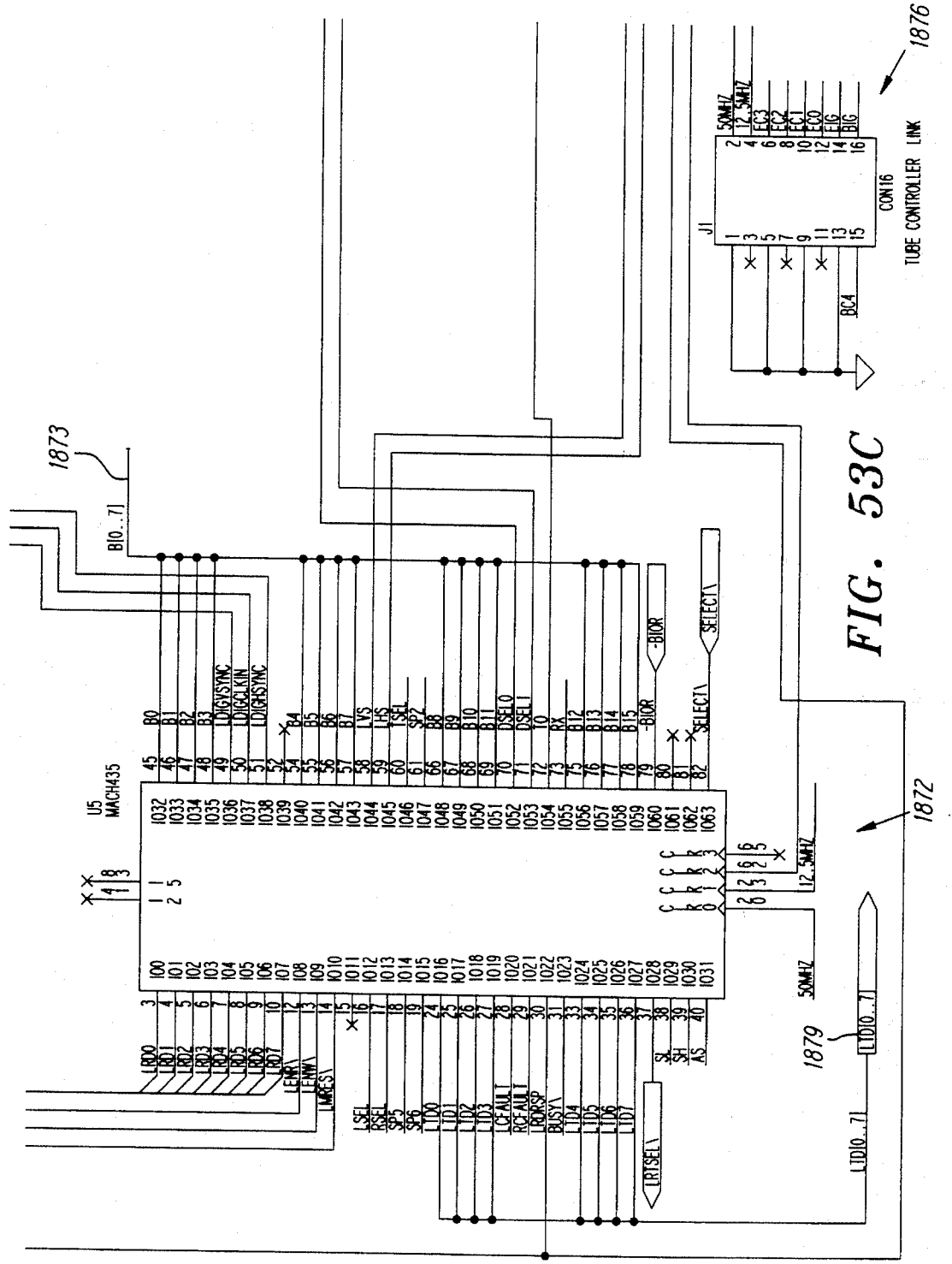
Figure 53D:
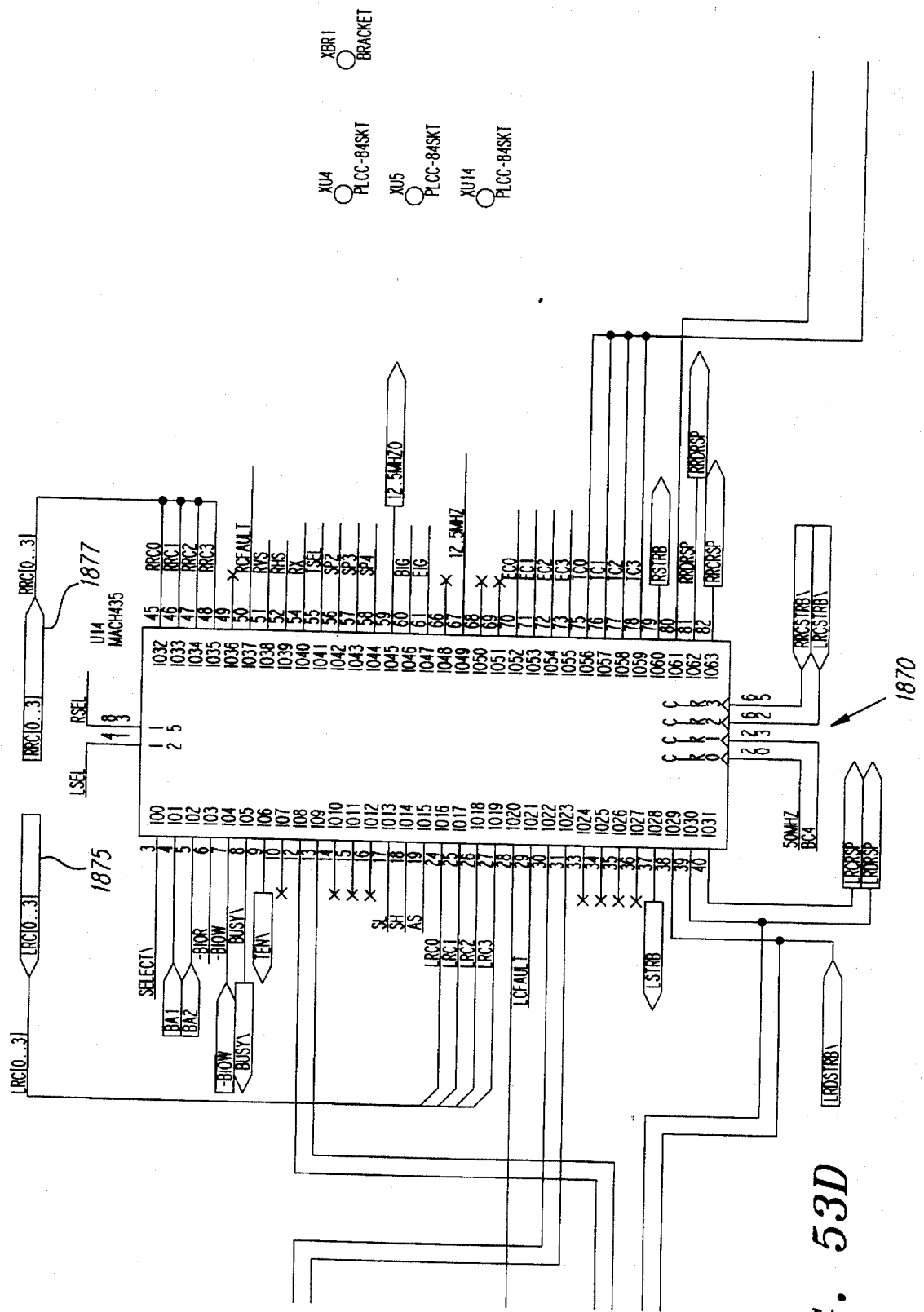
Figure 53E:
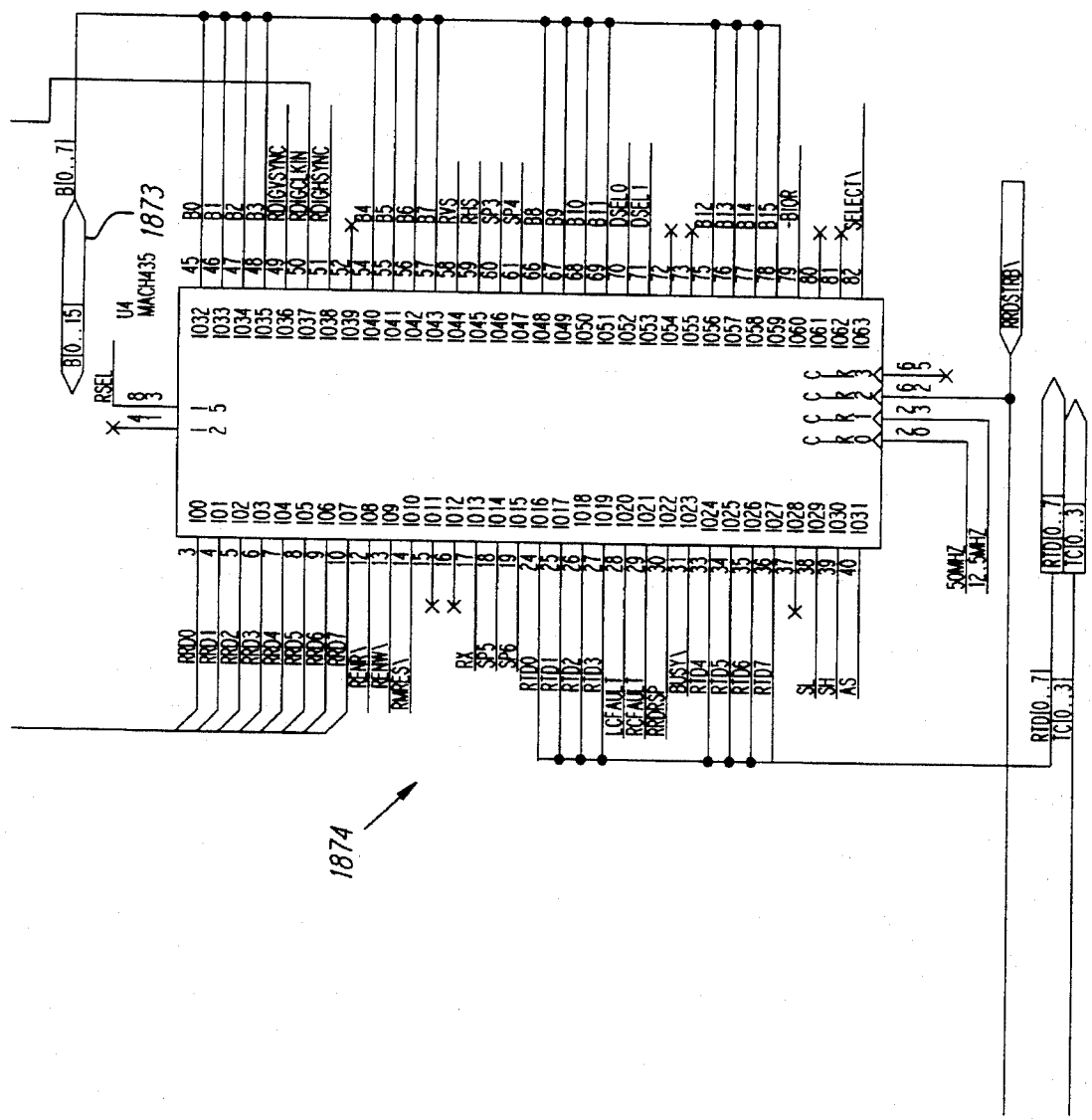

FIG. 53 is a circuit diagram of the preferred control logic for the detector controller 805. Control PAL 1870, preferably a conventional MACH435 programmable IC chip, provides the control signals to coordinate the activity of the detector controller 805 and the left and right multiplexer PALs 1872 and 1874. Control PAL 1870 receives left data control signals LRC from the left receiver 846 via leads 1875. Similarly, control PAL 1870 receives right data control signals from the right receiver via leads 1877. Control PAL 1870 receives timing input control signals through a tube controller link 1876. The software modules for the control PAL 1870 are included in Appendix A.

Left multiplexer PAL 1872 preferably functions as data multiplexers for the items of data which are received and transmitted by the left receiver 846 and the left transmitter 848. Left multiplexer PAL 1872 preferably loads gain and threshold control data from a bidirectional data bus via leads 1873. Left multiplexer PAL 1872 also preferably loads image pixel data and alignment data from the left receiver 846 via leads 1877.

Left multiplexer preferably transmits gain and threshold control signals, via leads 1879, to the left transmitter 848, which then optically transmits this data to the left detector 1522. The alignment data received by the left multiplexer PAL 1872 is redirected to the control computer via the bidirectional data bus via leads 1873. The image pixel data received by the left multiplexer PAL 1872 is sequentially redirected to a data FIFO 1878. Data FIFO 1878 and connector 1880 function as a data interface between the left multiplexer PAL 1872 and the left frame buffer 850. Right multiplexer PAL 1874 functions similarly to control and select the items of data which are received and transmitted by the right receiver 880 and right transmitter 886. Similarly, data FIFO 1882 and connector 1884 function as the data interface between the right multiplexer PAL 1874 and the right frame buffer 872. The preferred software modules for the left and right multiplexer PALs 1872 and 1874 are included in Appendix A.

In the preferred embodiment, detector controller 805 is fabricated as a PC module that plugs into the bus of the control computer 890. The preferred interface circuitry between detector controller 805 and the control computer 890 is described more fully in connection with the detailed description of FIG. 54B.

Tube Controller

Tube controller 807 generates scan control data which directs the operation of the beam controller 796, thereby controlling the scanning pattern of the x-ray source 798. Tube controller 807 functionally comprises a beam deflection lookup table 918 which stores beam deflection data for each point on the target anode, programmable scan controller 920, beam transmitter 916, I/O transceiver 964, and I/O latch 958.

Figures 2, 54A:
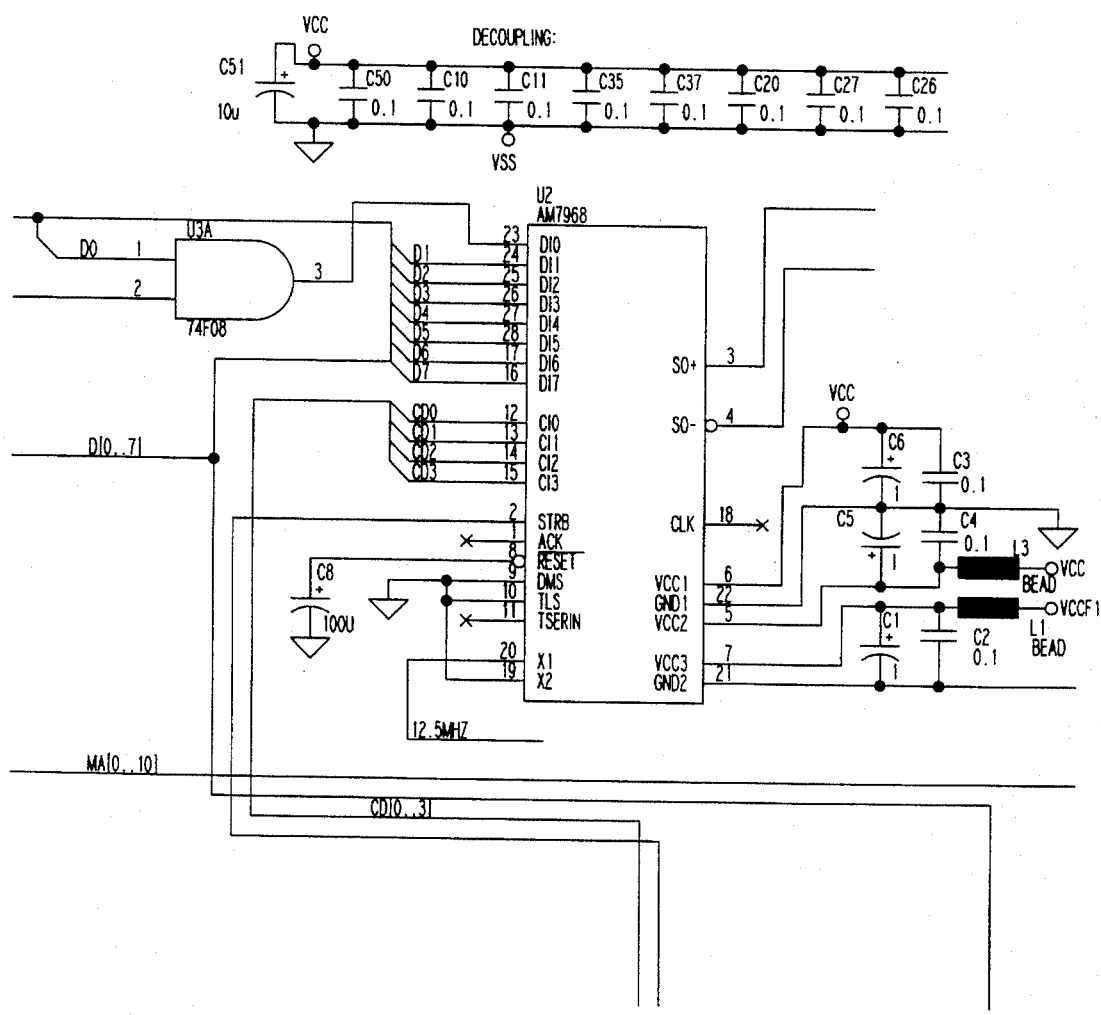
FIG. 54A is a circuit diagram of the control logic for the preferred tube controller.
Figures 4, 54A:
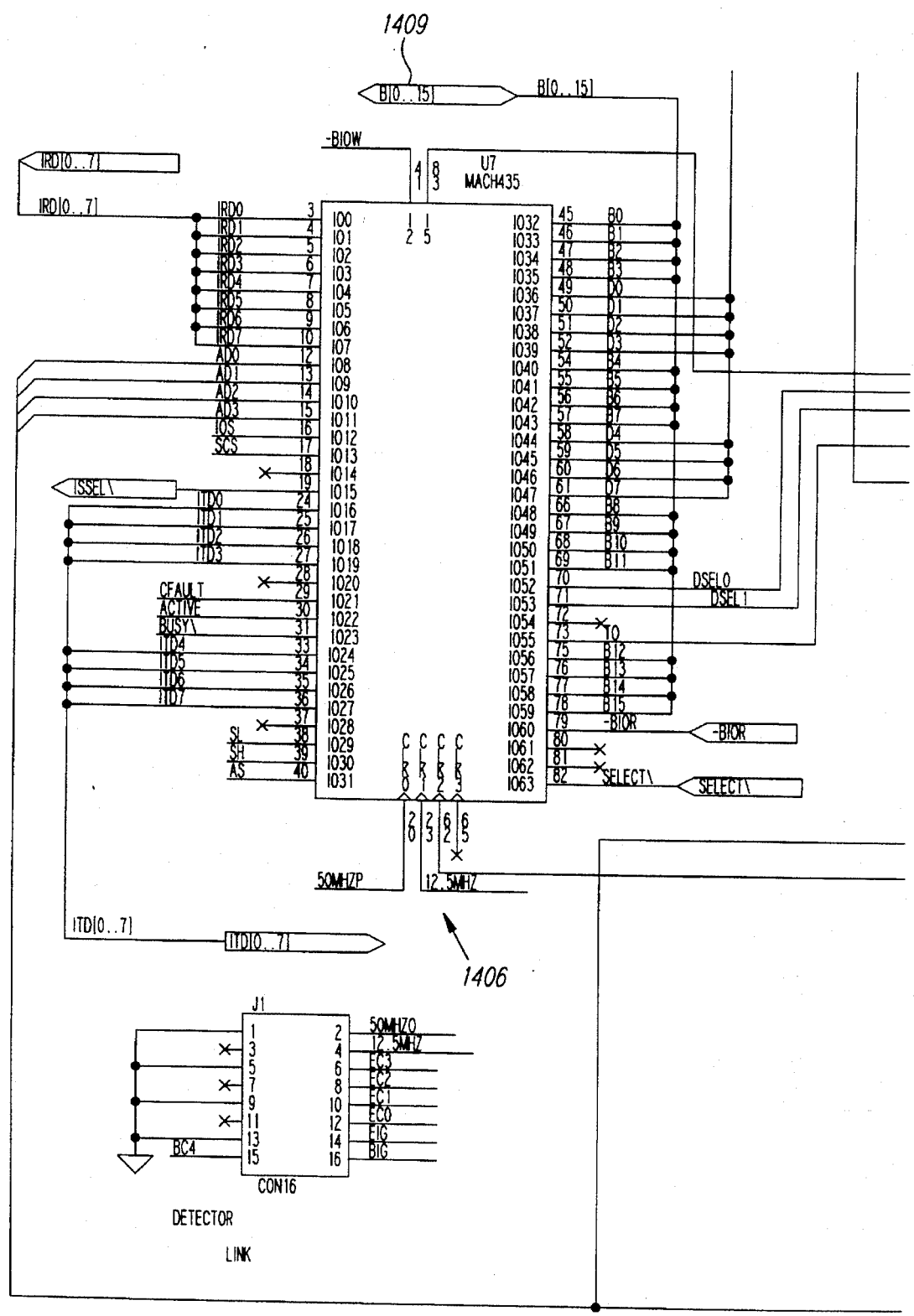
Figures 6, 54A:
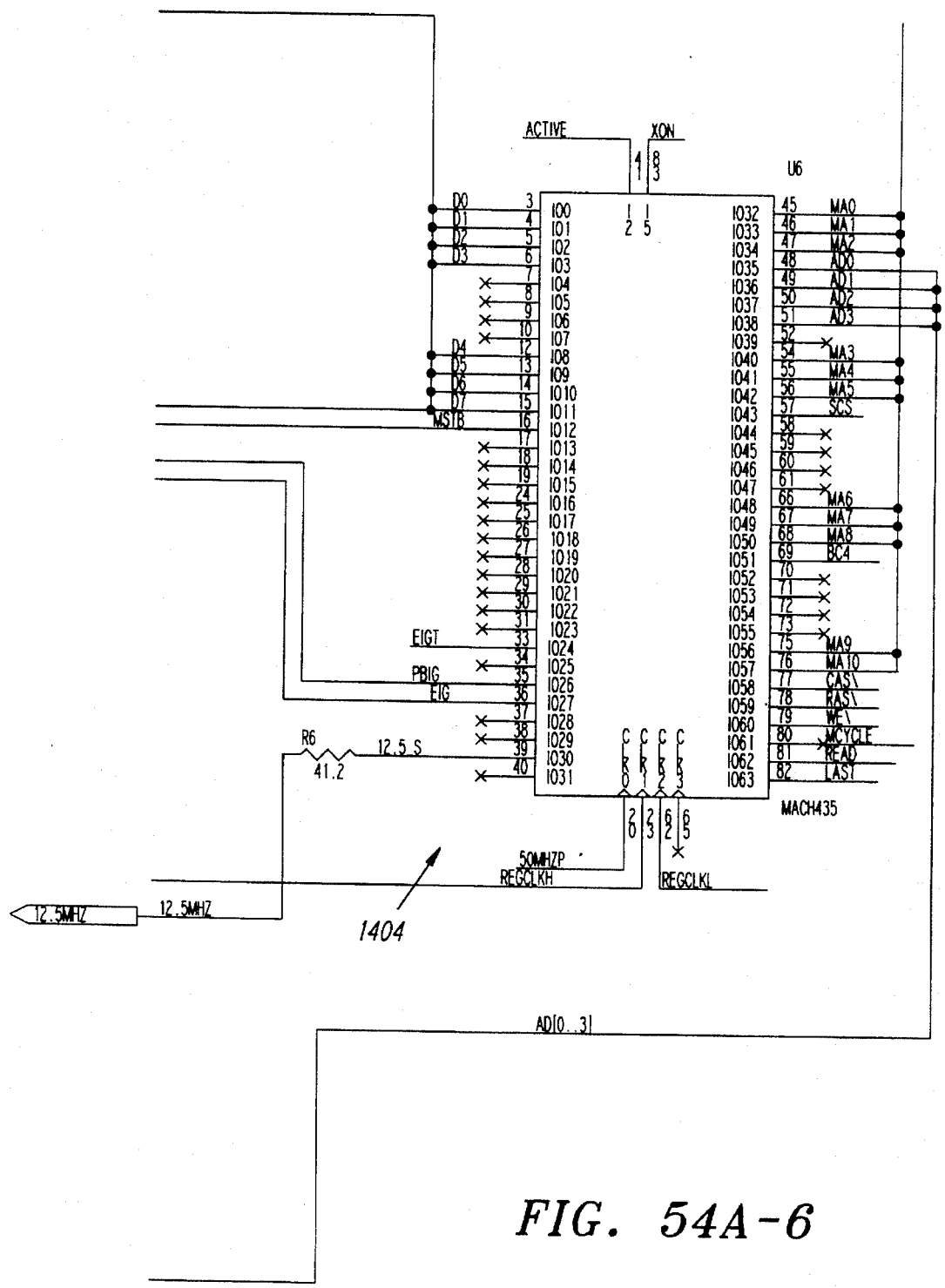

FIG. 54A is a circuit diagram of the control logic for the tube controller 807. Control PAL 1402 generally performs the functions of the programmable scan controller 920, by processing control instructions received from control computer 890, and distributing signals for loading, running or stopping the scan patterns to the memory control PAL 1404 and data PAL 1406. Control PAL 1402 provides control signals to direct the operation of the components within the tube controller 807. For example, control PAL 1402 is programmed to set the "measure and move" times for each collimator hole scanned. The preferred programming module for the control PAL 1402 is included in Appendix A.

Beam deflection lookup table 918 is preferably comprised of a memory control PAL 1404 and lookup table memory 1408. Memory control PAL 1404 generates control signals to direct the storage and retrieval of information in the lookup table memory 1408. At appropriate times, memory control PAL 1404 directs the retrieval of the beam deflection data from the lookup table memory 1408. The retrieved beam deflection data is sent to the beam transmitter 916 for transmission to the beam controller 796. Beam transmitter 916 is preferably a conventional optical transmission circuit, which is discussed more fully in connection with the detailed description of FIG. 41. The preferred programming module for memory control PAL 1404 is included in Appendix A.

Data PAL 1406 is programmed to function as the data multiplexer for the data which is received or transmitted by the tube controller 807. The preferred programming module for data PAL 1406 is included in Appendix A.

Figures 1, 54B:
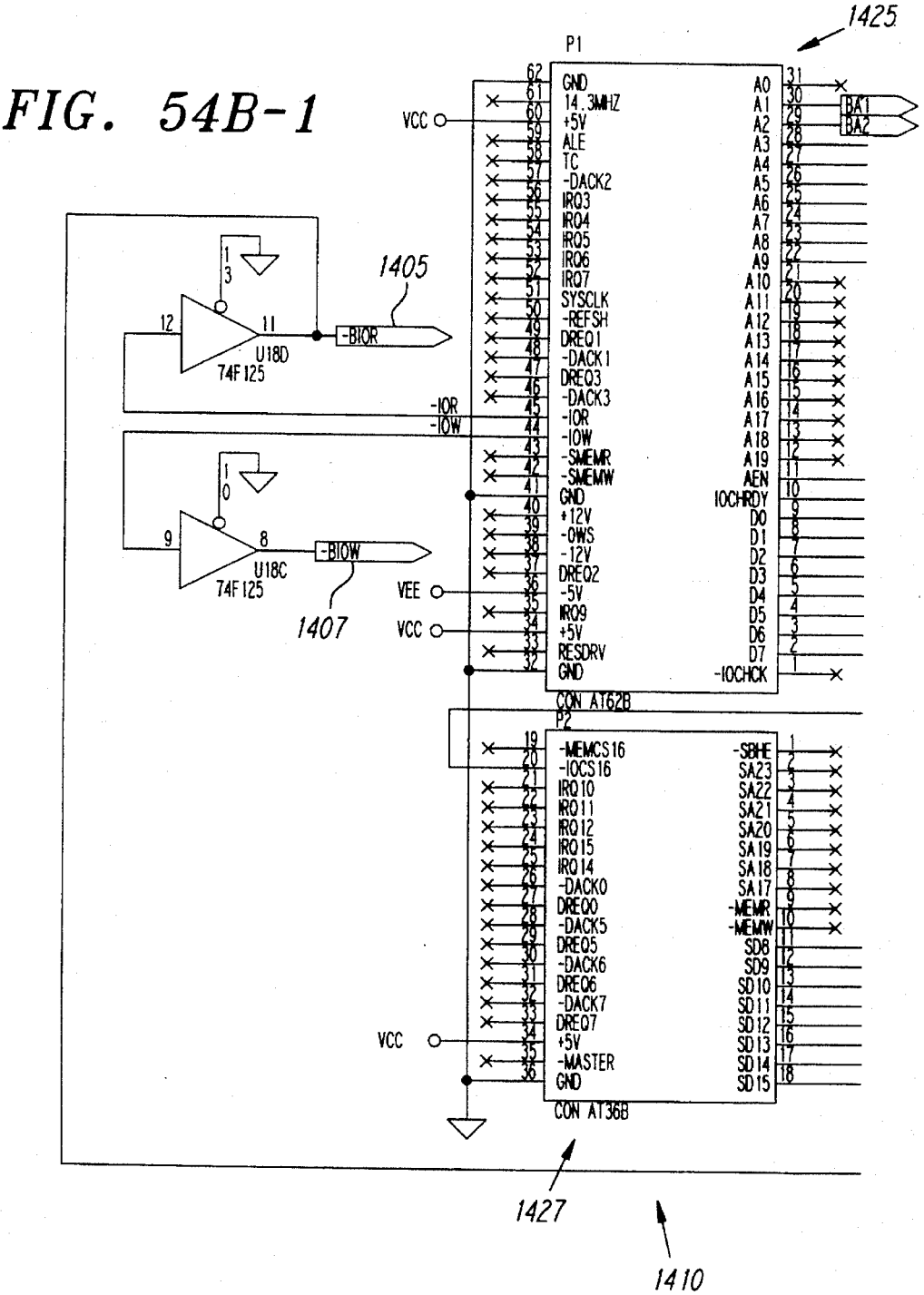
FIG. 54B is a diagram of the preferred interface circuitry connecting the tube controller circuits with the PC bus within the control computer.
Figures 2, 54B:
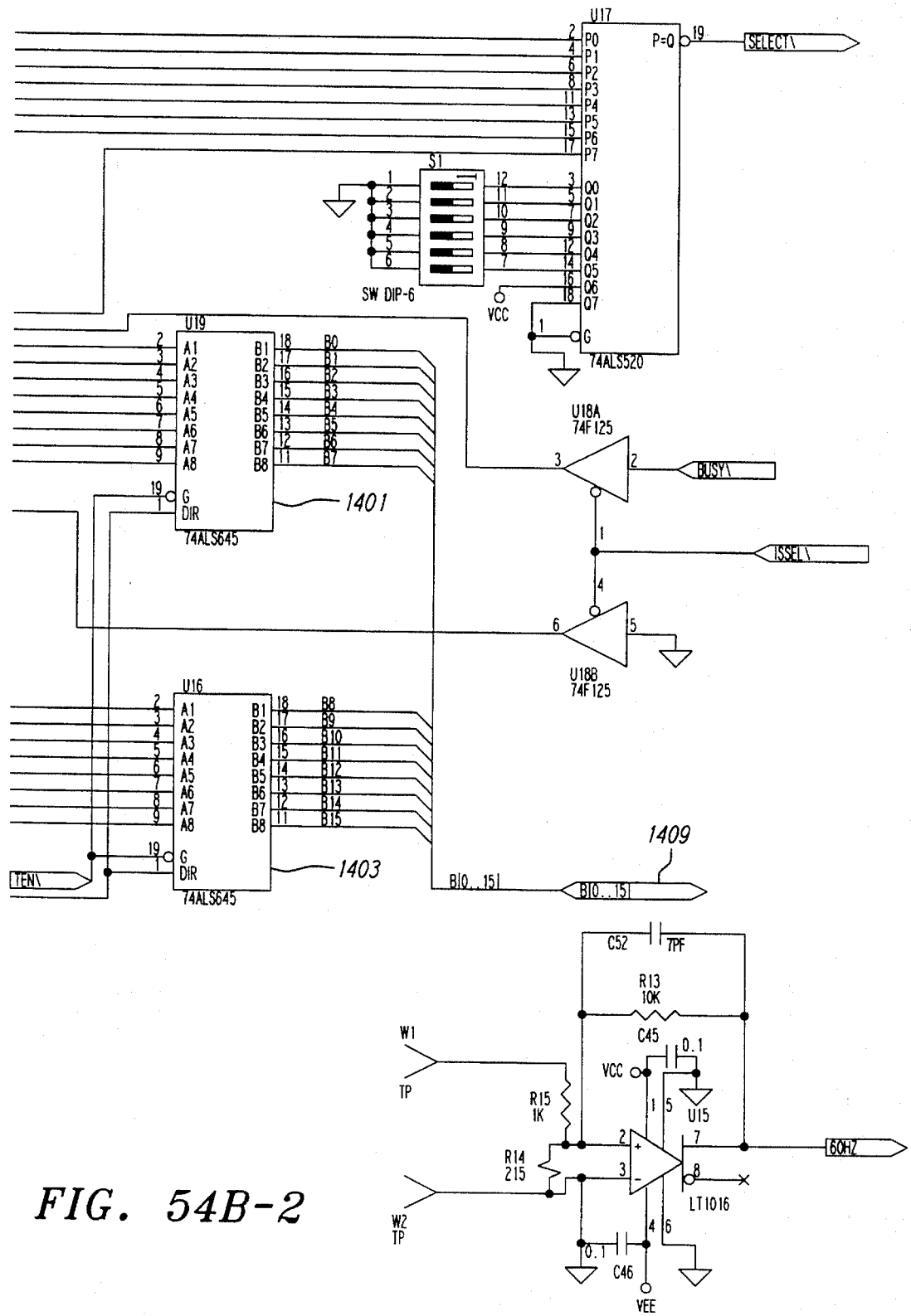

In the preferred embodiment, tube controller 807 is fabricated as a PC module that plugs into the bus of the control computer 890. FIG. 54B is a diagram of the preferred interface circuitry for connecting the tube controller 807 and the control computer 890. Connectors 1425 and 1427 interface the tube controller 807 with the bus of the control computer 890. Data transceivers 1401 and 1403 transfer binary information between the tube controller 807 and the control computer 890 on a three state bidirectional 16 bit data bus B[0..15] via leads 1409. I/O read control signals are applied via lead 1405 and I/O write control signals are applied via lead 1407.

The tube controller also controls the I/O transceiver 964 and the I/O latch 958. The tube controller 807 directs the various sets of control signals received from the control computer to the I/O transceiver 964 and the I/O latch 958 for further transmission of these control signals over an optical link to the I/O controller. I/O transceiver 964 preferably includes optical communications circuitry which is more fully discussed in connection with the detailed description of FIGS. 40 and 41.

Beam Controller

FIGS. 55A–E diagram the control logic within the beam controller interface 794, which processes and distributes analog coil current control signals to the various coil drivers. The digital scan control data generated by the tube controller 807 is optically coupled to the beam controller input circuit 1408, which preferably includes the optical communications circuit described more fully in connection with the detailed description of FIG. 40. Beam controller input circuit 1408 outputs eight parallel bits of digital scan control data to an eight-bit data bus D[0..7] and four parallel bits of control data CD to a control PAL 1410, which distributes and/or reformats the digital scan control data within the beam controller interface 794. The preferred software modules for control PAL 1410 are included in Appendix A.

Figures 1, 55A:
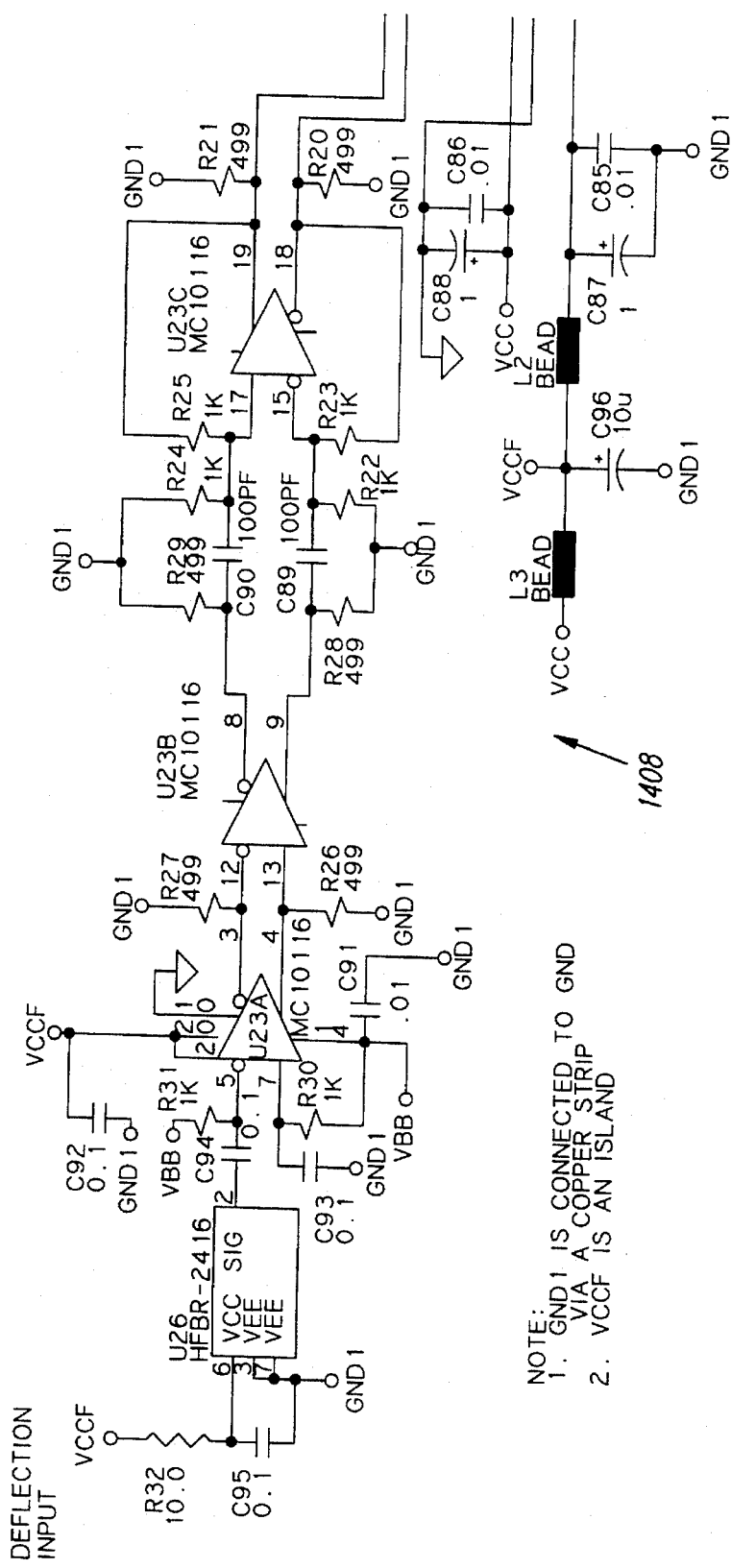
Figures 2, 55A:
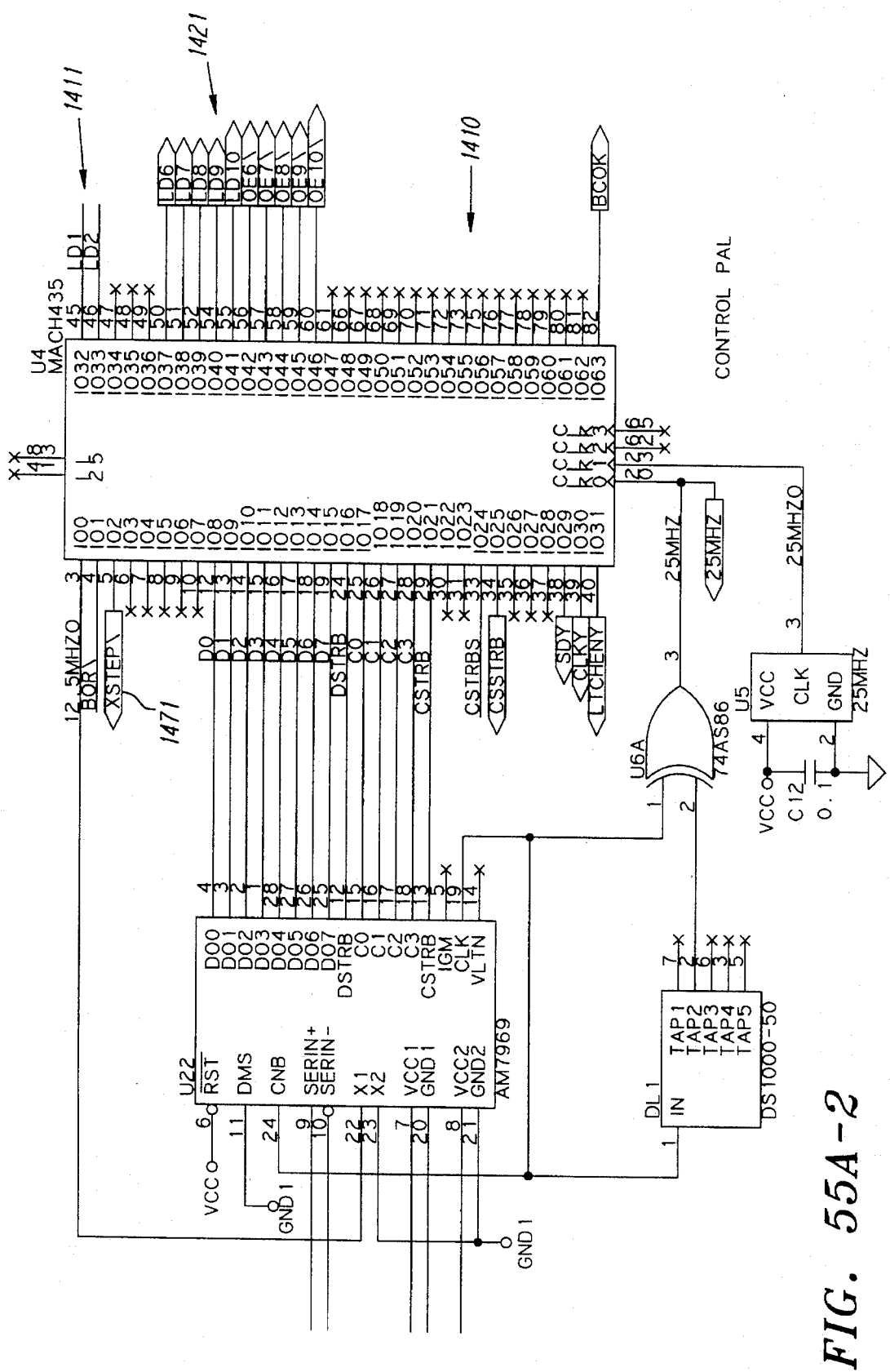
Figures 1, 55C:
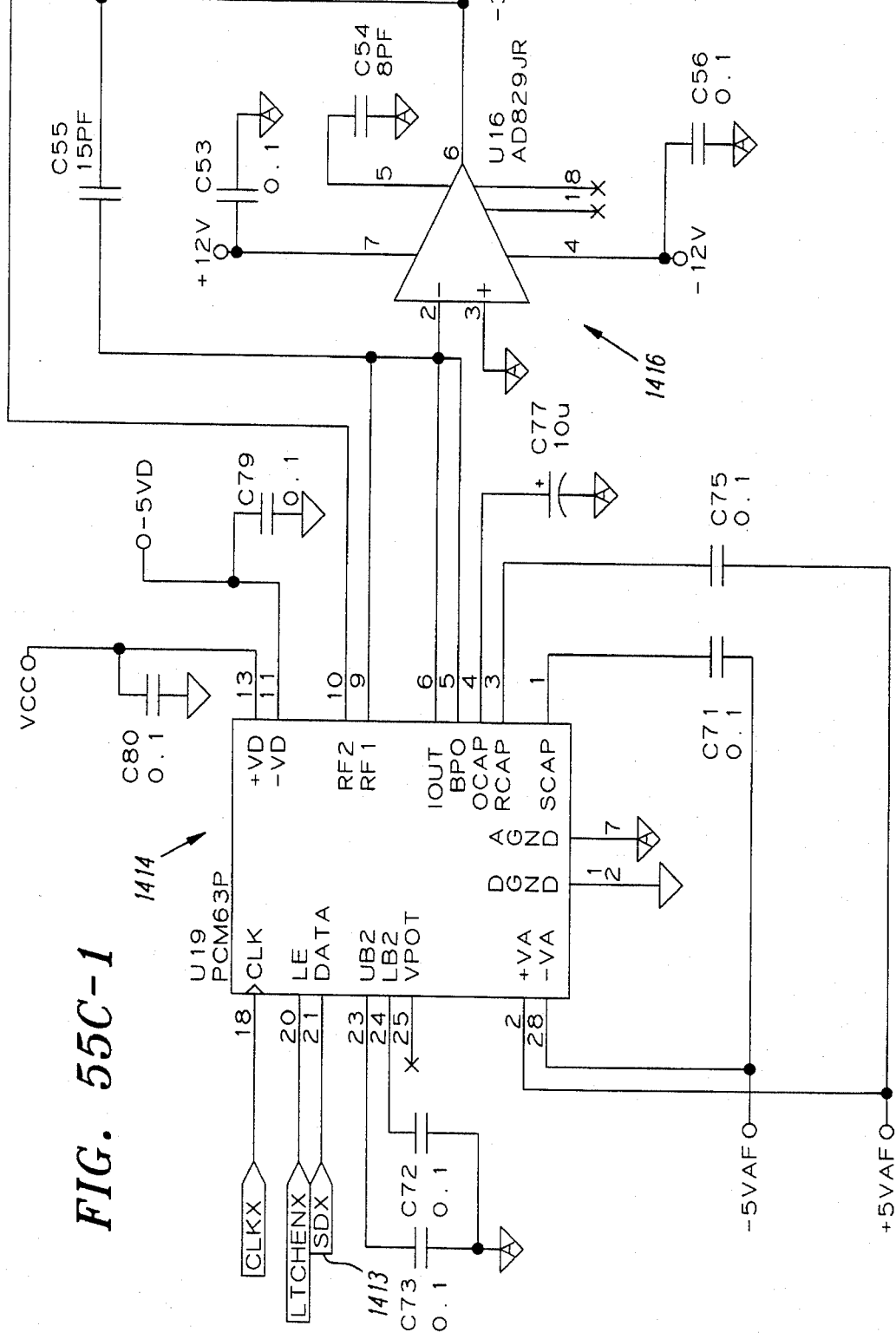
Figures 3, 55C:
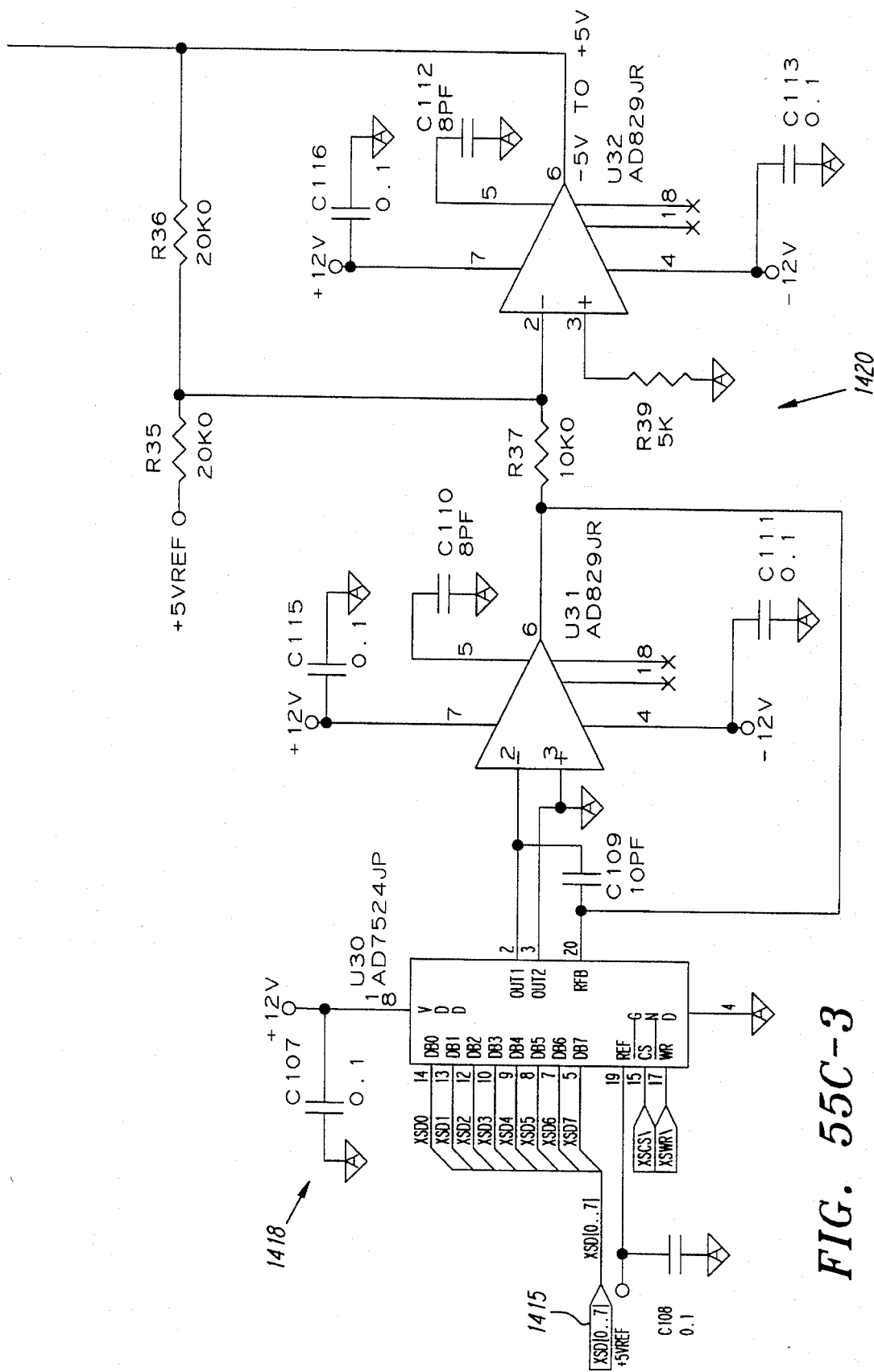
Figures 2, 55D:
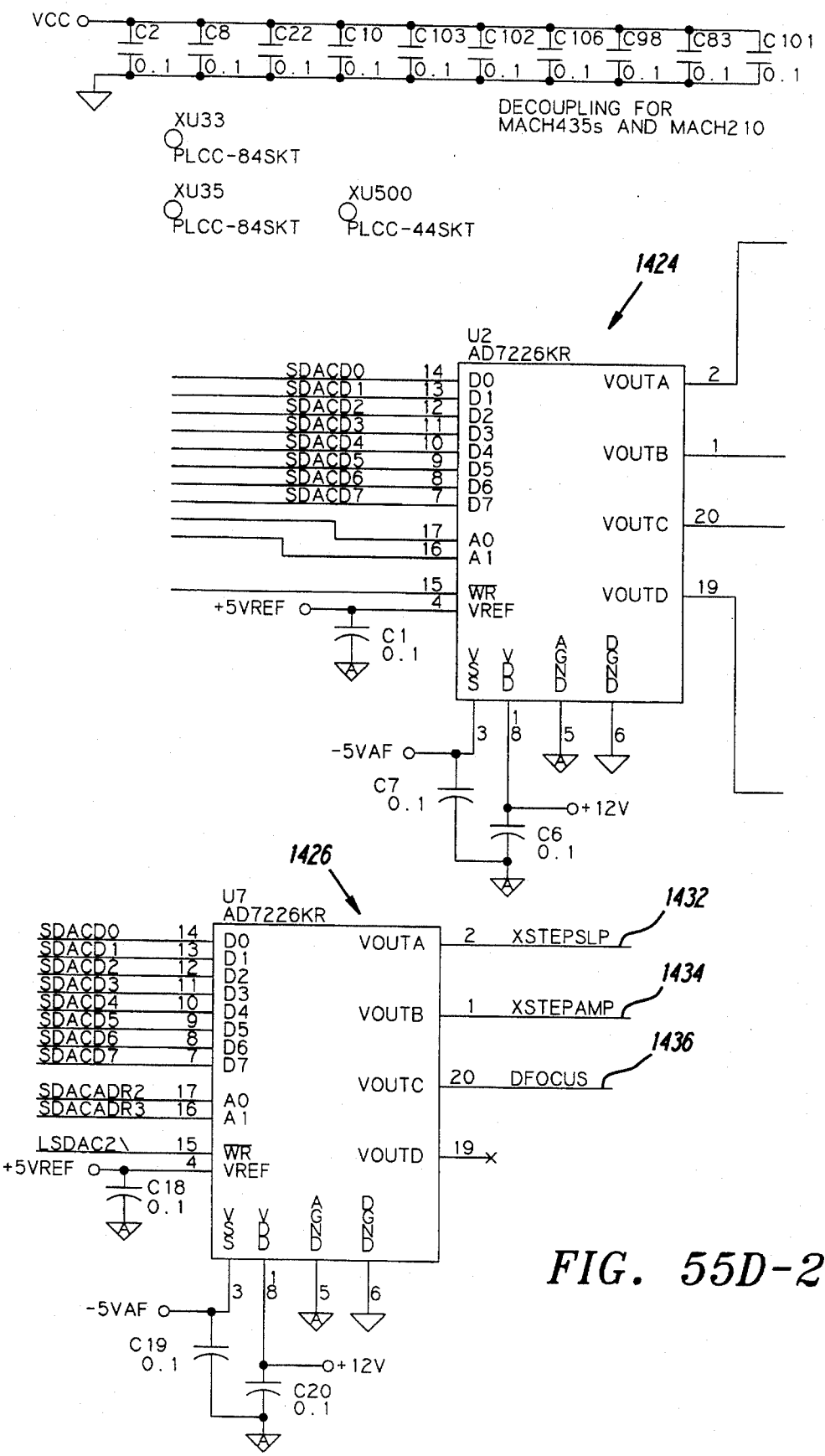
Figures 3, 55D:
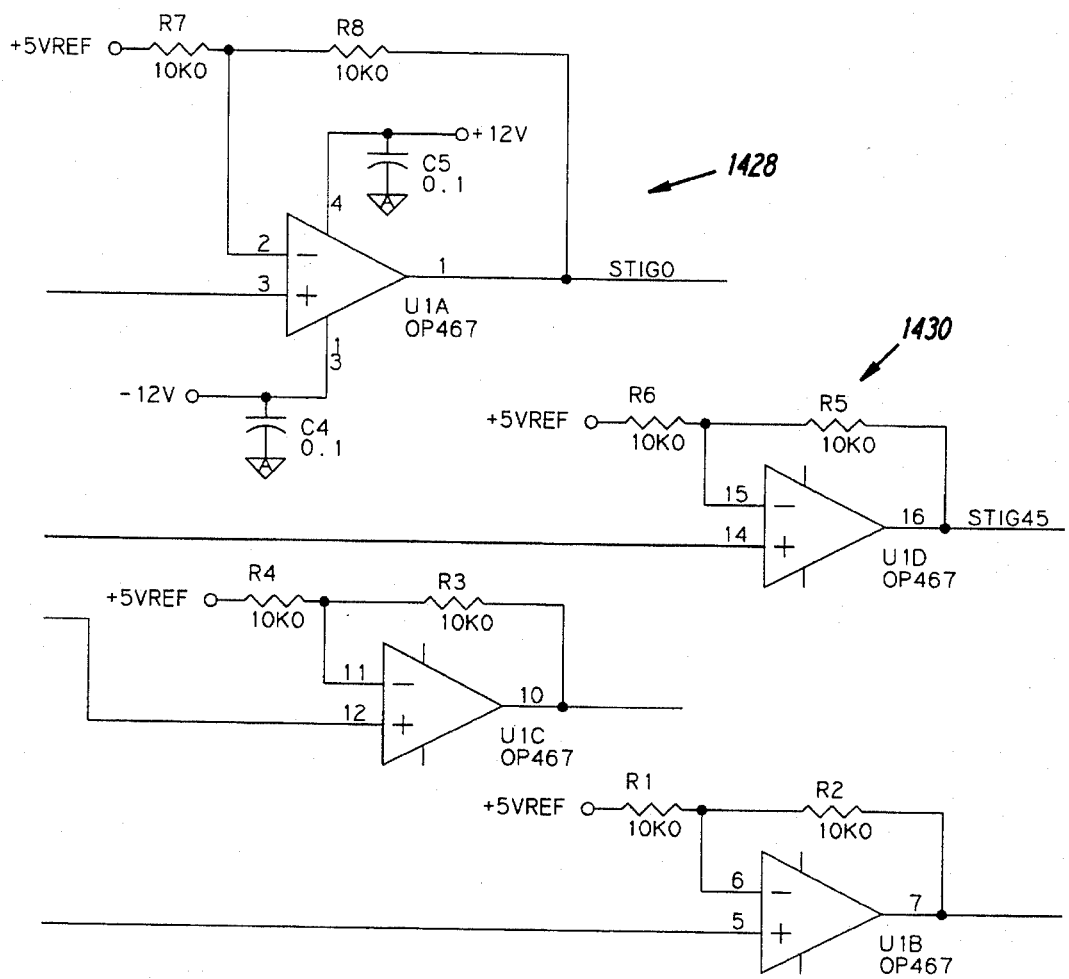
Figures 1, 55E:
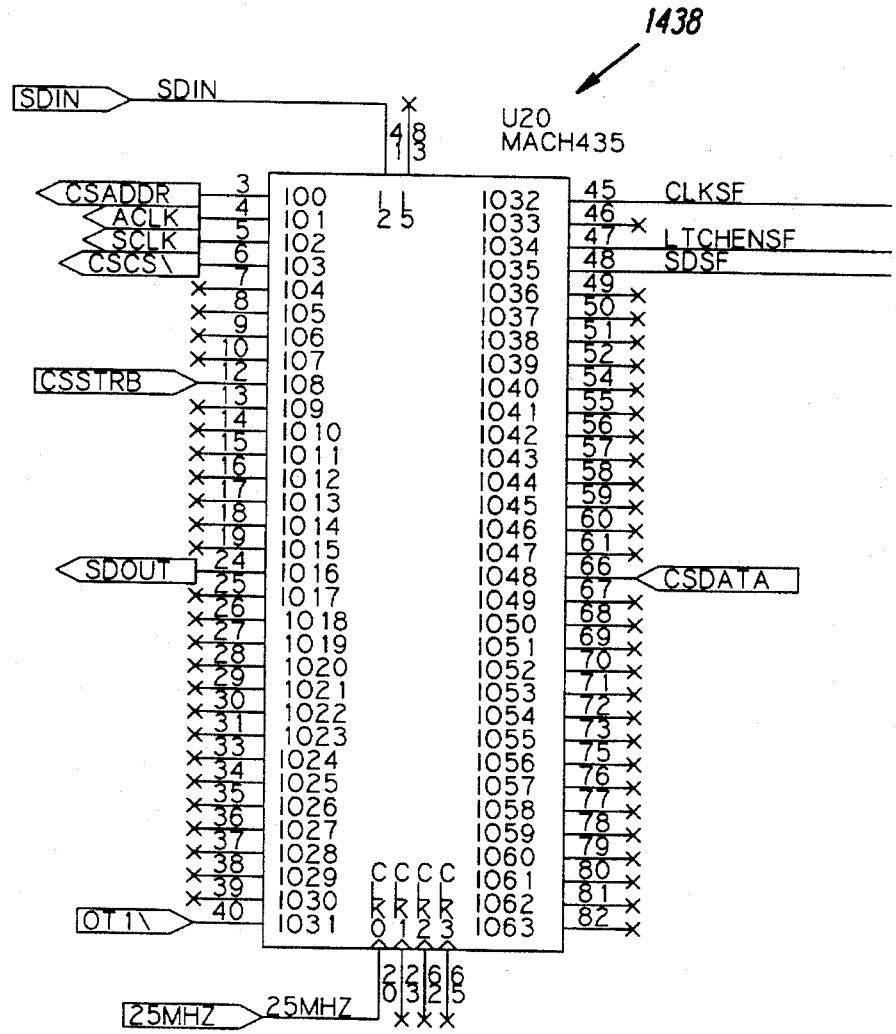
Figures 2, 55E:
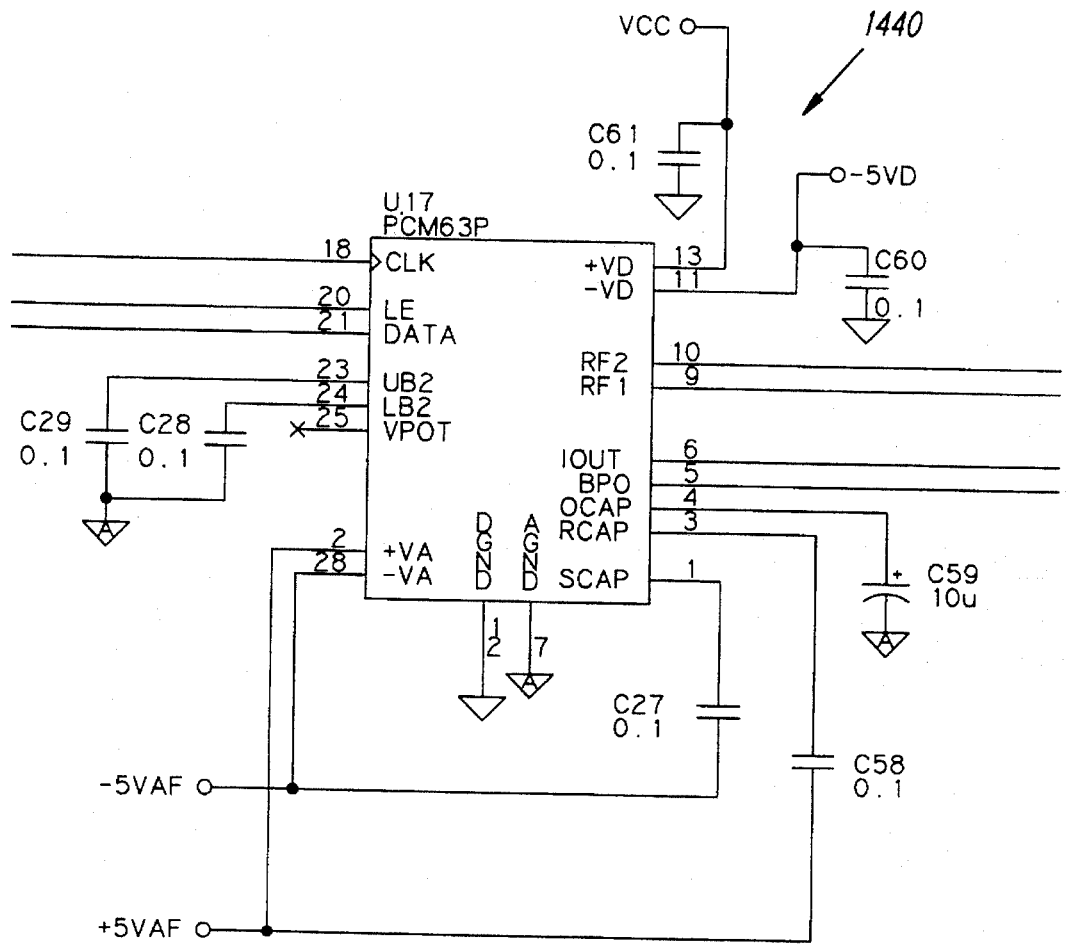
Figures 3, 55E:
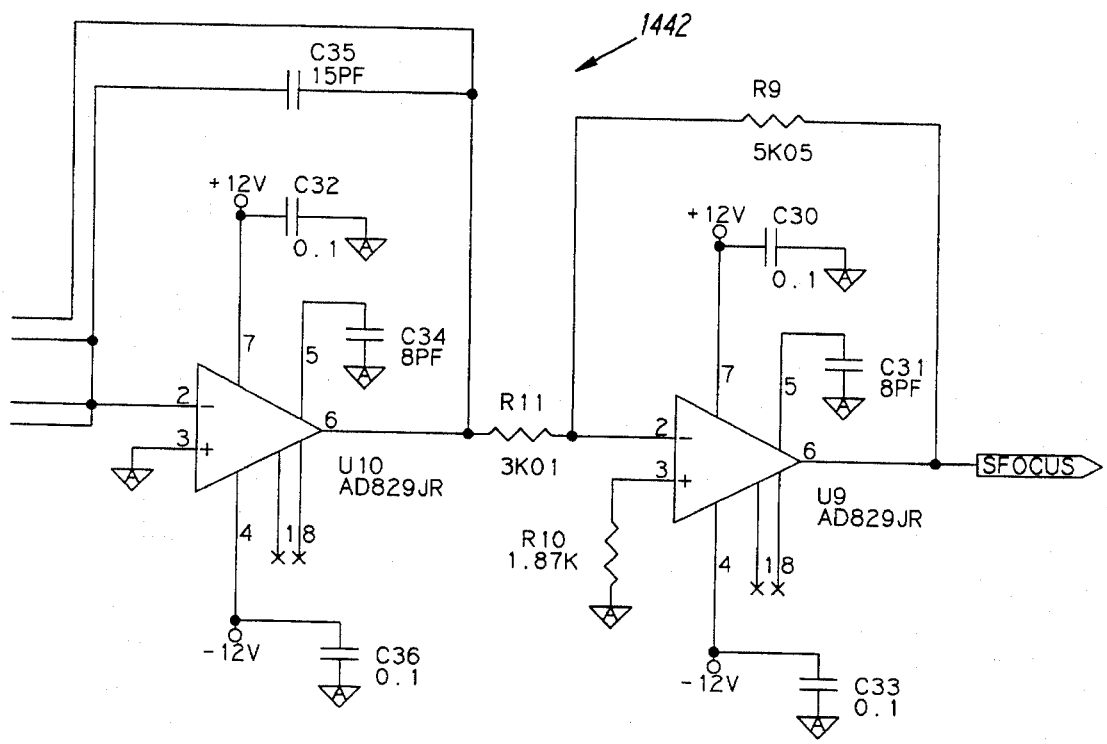

Referring to FIGS. 55B–C, control PAL 1410 preferably outputs control signals, via leads 1411 (LD1 and LD2), to instruct the x-deflection PAL 1412 to sequentially load parallel bits of digital x-deflection coil control data DXDEF from the eight-bit data bus D[0..7]. The x-deflection PAL 1412 essentially manipulates the digital x-deflection coil control data DXDEF to generate a smoothly ramping triangular waveform at the x-deflection driver 778. Approximately every 1.28 usec, the x-deflection PAL 1412 preferably converts the parallel bits of digital x-deflection coil control data DXDEF to serial bits of digital x-deflection coil control data SDX. The serial x-deflection coil control data SDX is coupled, via output line 1413, to a twenty-bit serial DAC 1414 which converts the information to an analog signal that is preferably applied to an intermediate x-deflection amplifier 1416. The preferred software modules for x-deflection PAL 1412 are included in Appendix A.

Approximately every 80 nsec, the x-deflection PAL 1412 mathematically manipulates the sequentially acquired items of digital x-deflection coil control data DXDEF to calculate an eight-bit x-slope value, which is referred to as the x-slope control data XSD. The x-slope control data XSD is transmitted to DAC 1418 for conversion to an analog signal, and its analog output signal is preferably coupled to a series of intermediate x-slope amplifiers 1420. The amplified analog x-slope control signals XSD is preferably summed with the amplified analog x-deflection coil control data SDX to generate a smoothly ramping output waveform, which is amplified by intermediate amplifier 1417 to produce the x-deflection coil control signal XDEFL. The x-deflection coil control signal XDEFL is preferably output, via output line 1418, to a preferred x-deflection driver 778, which is described more fully in connection with the detailed description of FIG. 56. Alternatively, the x-deflection coil control signal XDEFL can be coupled, through an amplifier 1419 and a BNC connector 1444, to a commercially available amplifier, for example a Centronics amplifier, which then drives the current in the x-deflection coil.

Analog y-deflection coil control signals are generated in the same fashion and output to a y-deflection driver 782. However, if a raster scan pattern is employed, then the serial y-deflection coil control data SDY is directly generated by the control PAL 1410, therefore a y-deflection PAL, y-slope control data YSD, and related circuitry are not required.

Control PAL 1410 also outputs control signals, via leads 1421 (LD6, LD7, LD8, LD9, and LD10), to instruct the small DAC control PAL 1422 to sequentially load x-step control data (XCD), dynamic focus coil control data (DFCD), and stigmator control data (SCD) from the data bus D[0..7]. Small DAC control PAL 1422 redistributes the XCD and DFCD control signals to multi-channel DAC 1426 and redistributes SCD control signals to multi-channel DAC 1424. DAC 1424 preferably outputs analog 0° stigmator coil control signals to the 0° stigmator driver 786 through an intermediate 0° amplifier 1428. Analog 45° stigmator coil control signals are similarly output to the 45° stigmator driver through an intermediate 0° amplifier 1430. DAC 1426 preferably outputs analog x-step slope control signals XSTEPSLP to the x-step driver 780 via output line 1432. Similarly, analog x-step amplitude control signals XSTEPAMP are preferably output to the x-step driver 780 via output line 1434 and analog dynamic focus coil control signals DFOCUS are preferably output to the dynamic focus driver 776 via output line 1436. The preferred software modules for small DAC control PAL 1422 are included in Appendix A.

Serial data PAL 1438 preferably receives static focus coil control data SDIN from the I/O controller 762. Serial data PAL 1438 couples control data SDIN to a DAC 1440, which converts this information to analog static focus coil control signals which are sent to the static focus driver 774 through intermediate focus amplifiers 1442. The preferred software modules for serial data PAL 1438 are included in Appendix A.

Figure 56:
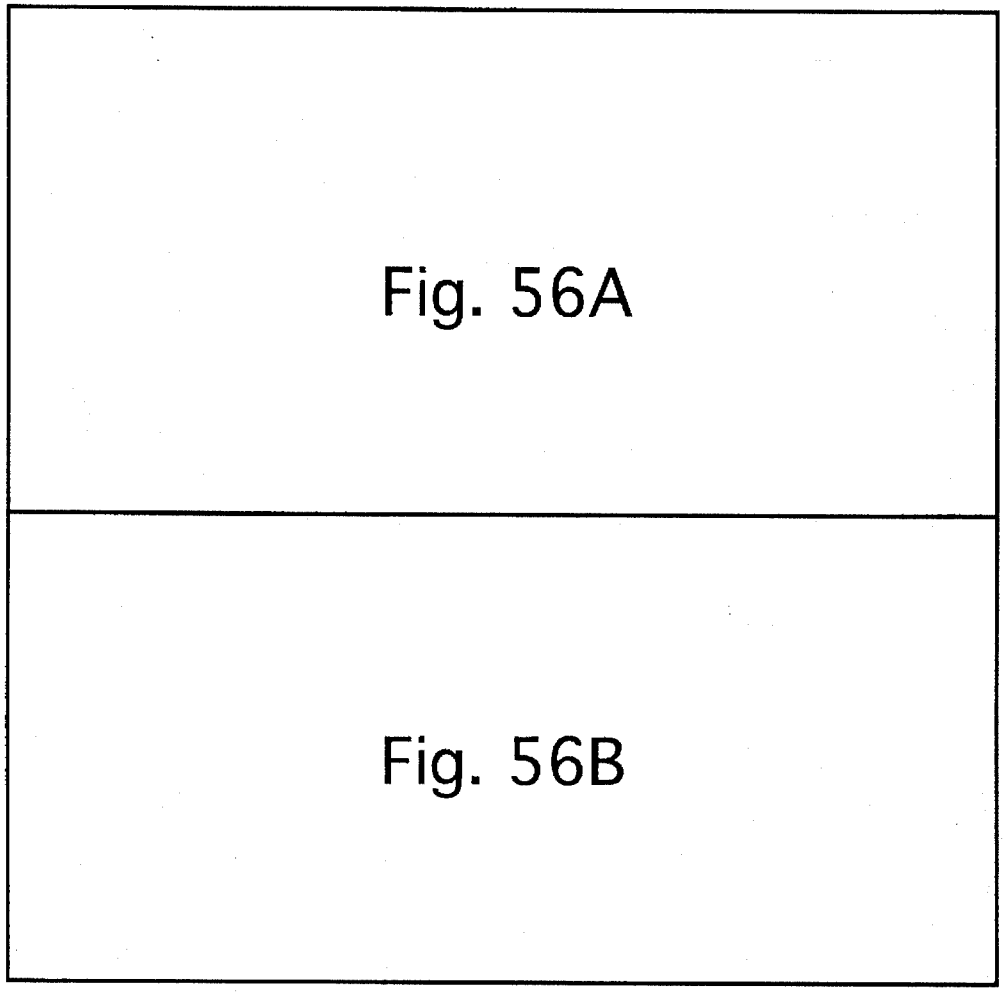
FIGS. 56A–B comprise schematics of the preferred x-deflection driver.
Figures 1, 56A:
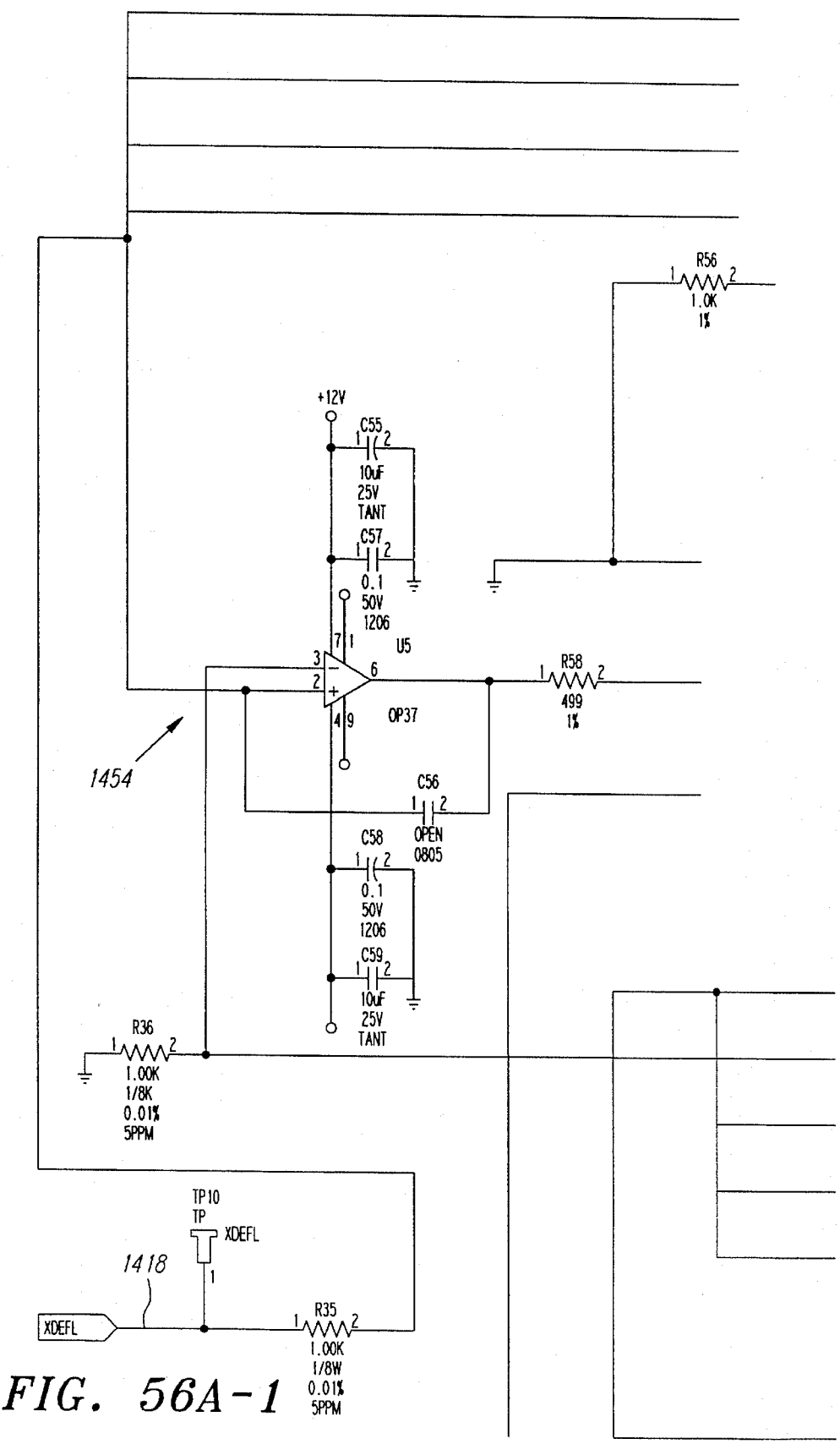
Figures 2, 56A:
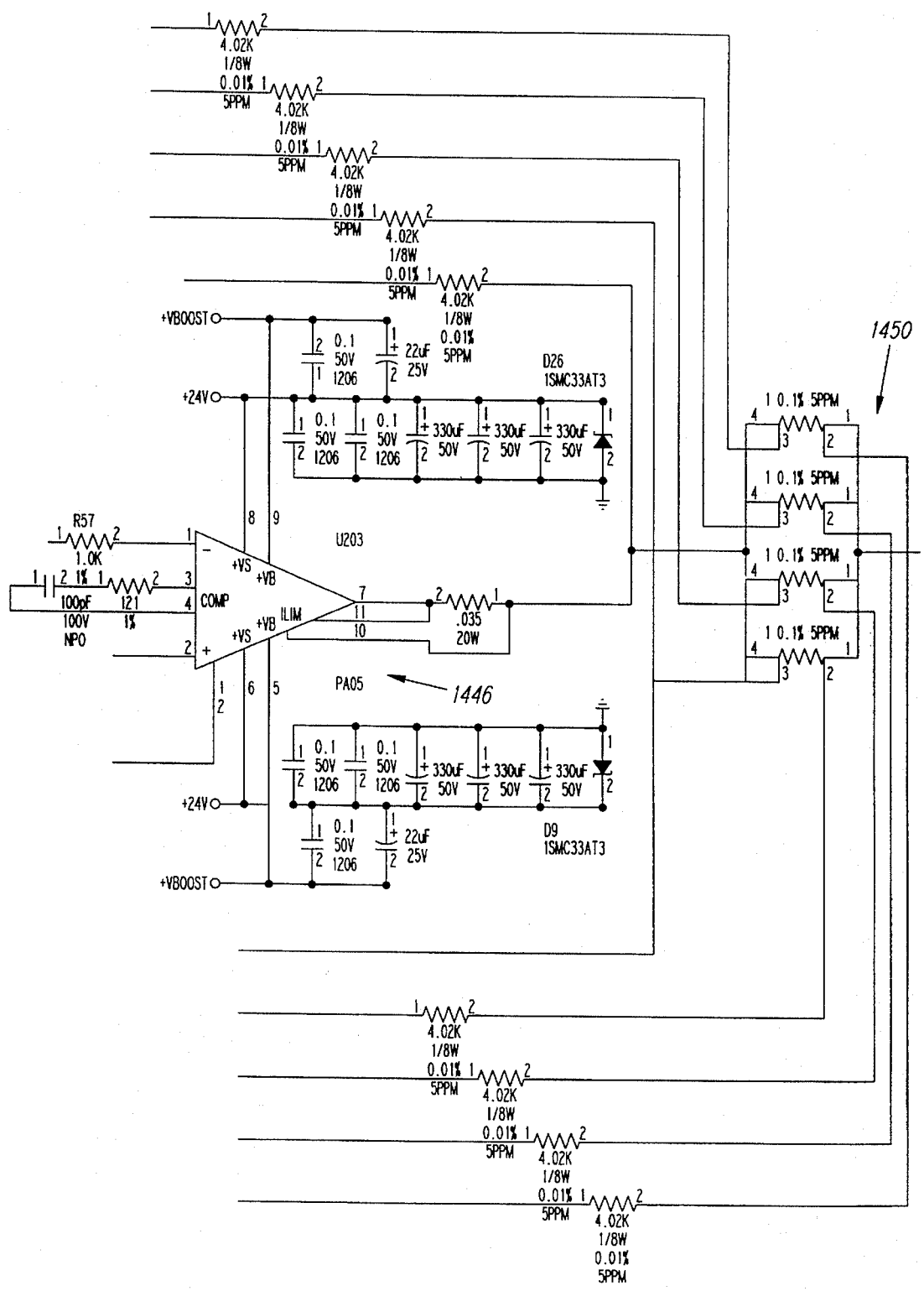
Figures 3, 56A:
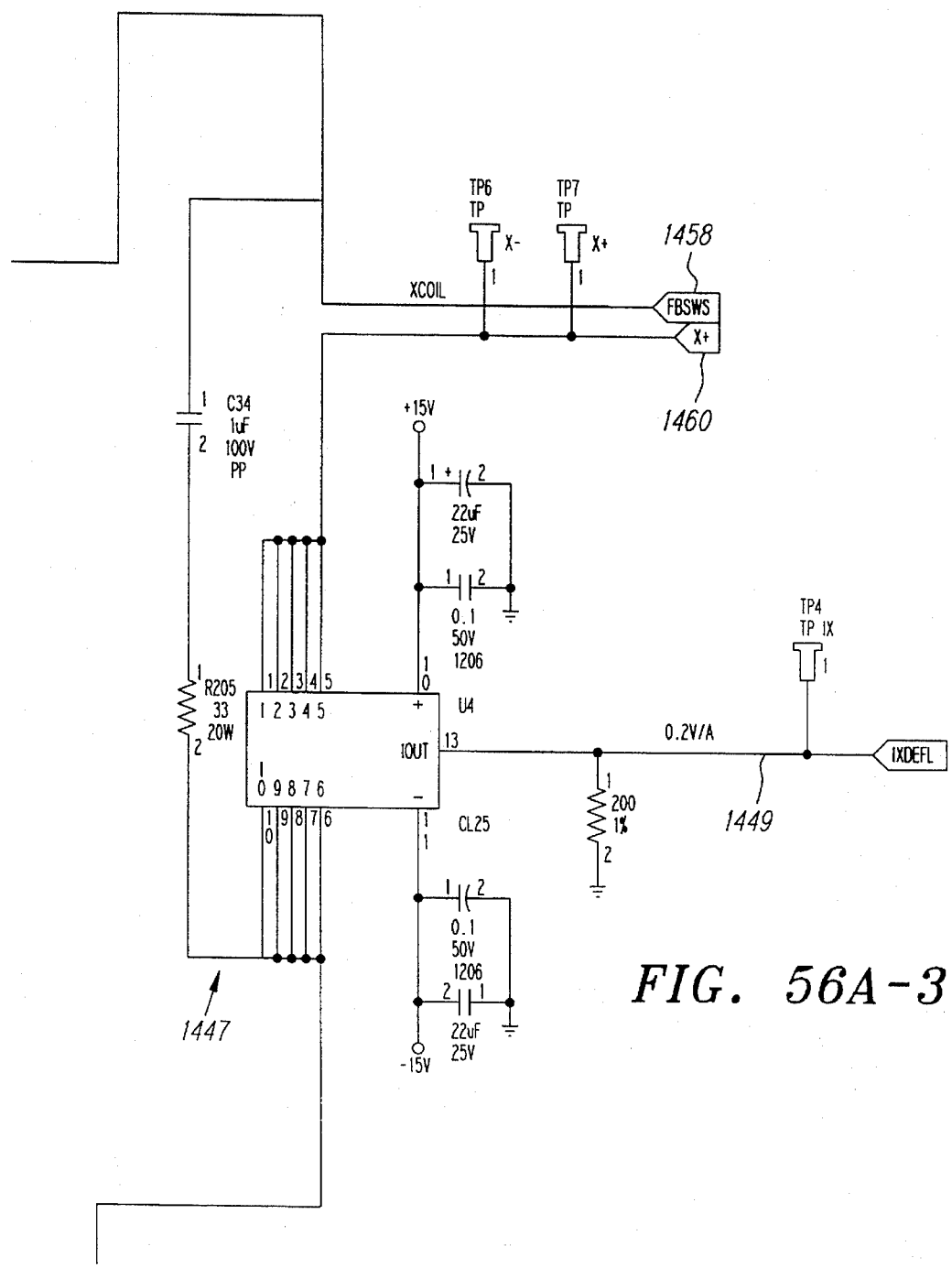
Figures 1, 56B:
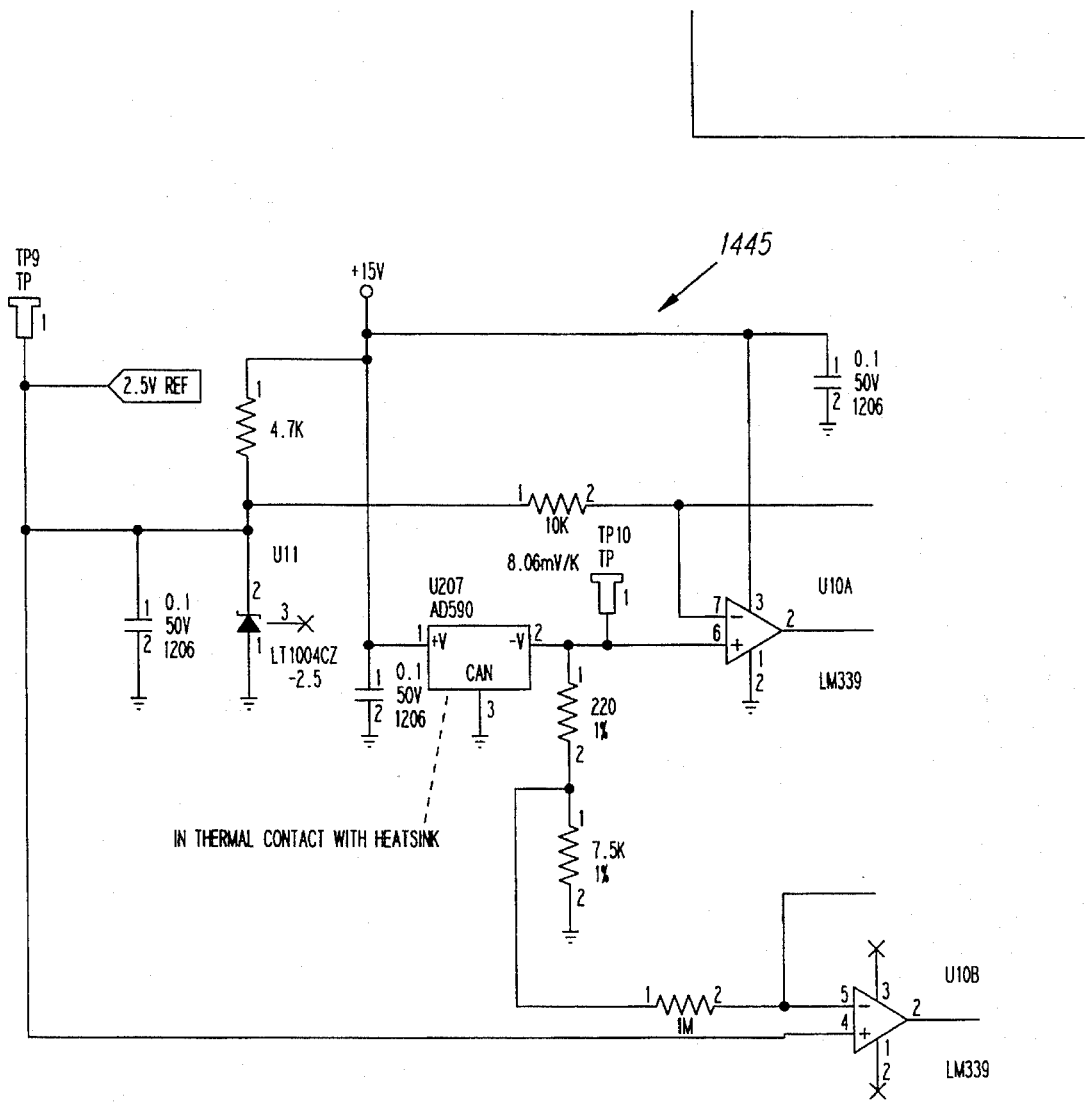
Figures 2, 56B:
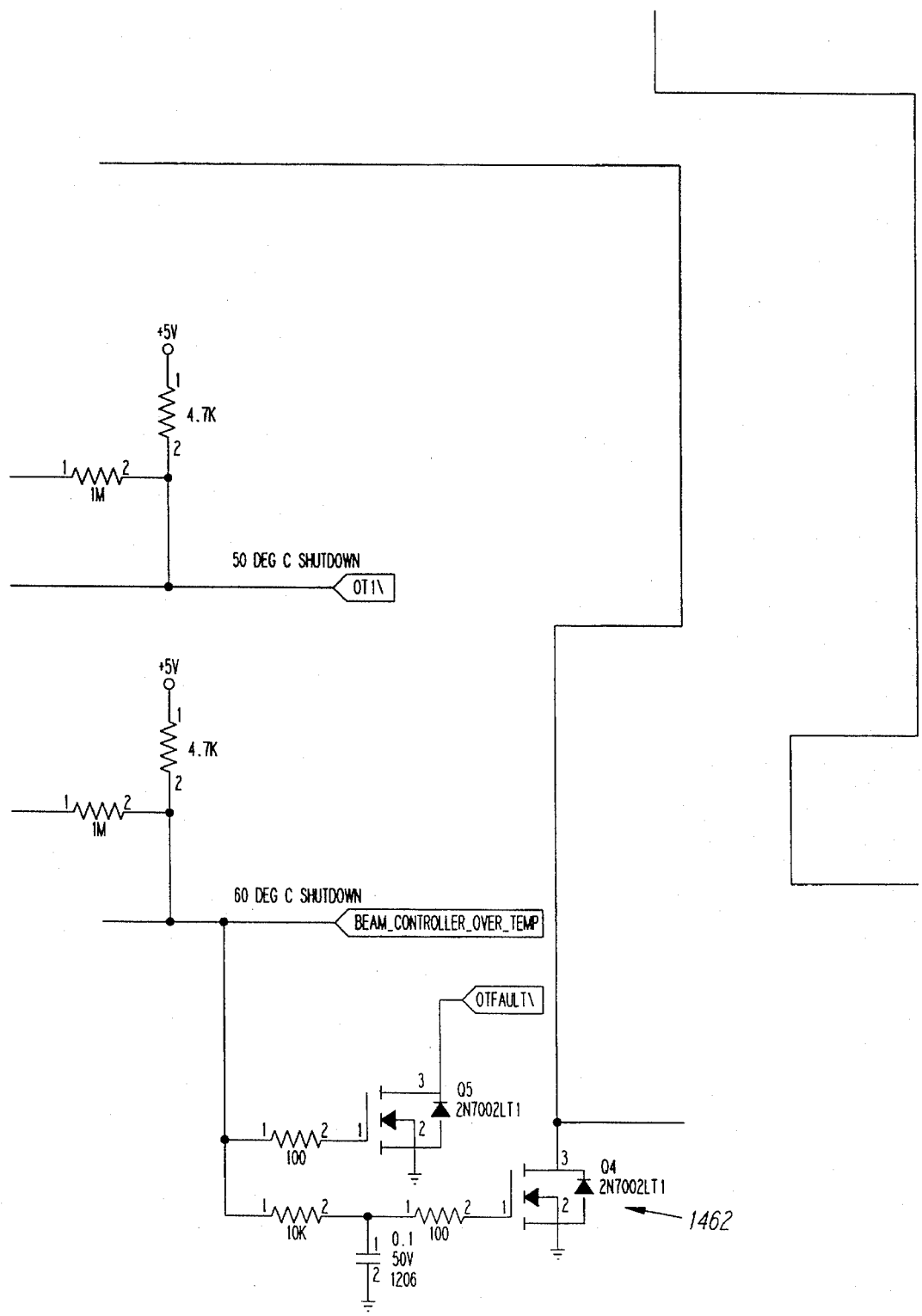
Figures 3, 56B:
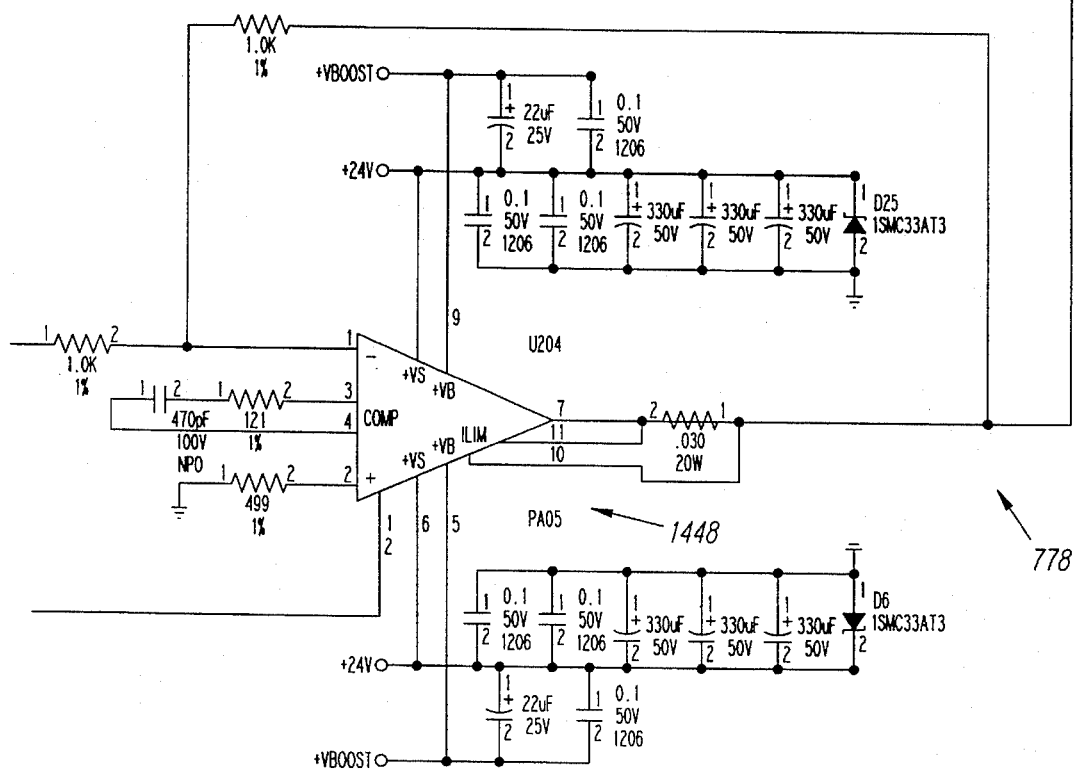

The analog coil control signals from the beam controller interface 794 are preferably transmitted to suitable power amplifier circuits within the coil drivers to drive the current patterns in their corresponding focus or deflection coils. For example, the analog x-deflection coil control signals XDEFL from the beam controller interface 794 are preferably coupled, via input line 1418, to a preferred x-deflection driver 778 (FIG. 56). The XDEFL control signals are applied to a control amplifier 1454, which regulates the activity of power amplifiers 1446 and 1448. The x-deflection driver 778 is preferably a circle bridge circuit in which power amplifiers 1446 and 1448 differentially drive both ends of the x-deflection coil. The output voltages of the power amplifiers 1446 and 1448 are coupled, through current sense resistors 1450 and current sensor 1447, to the x-deflection coil via output lines 1458 and 1460. Resistors 1450 sense the current in the x-deflection coil and preferably feeds the current information back to regulate the control amplifier 1454. The current in the x-deflection coil is also monitored by a current sensor 1447, which transmits the measured current, via output line 1449, to the current sense monitor 788. Temperature sensor 1445, which measures the temperature at the x-deflection driver 778, employs a temperature switch 1462 to disable the x-deflection driver 778 if a temperature fault condition occurs. The y-deflection driver 782 preferably includes a similar circuit to drive the current in the y-deflection coil.

Figure 57A:
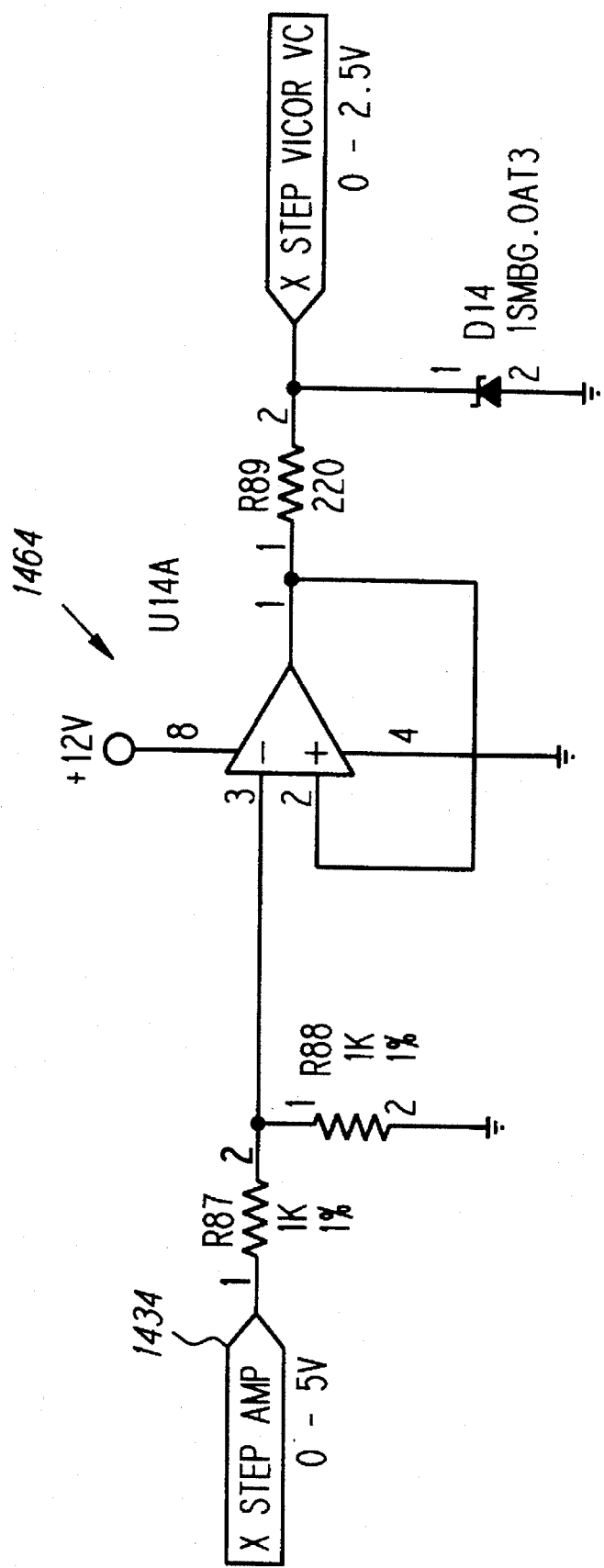
FIGS. 57A–B comprise schematics of the preferred x-step driver.

X-step driver 780, which preferably comprises x-step ramp control switch 1462, x-step voltage control circuit 1464, and decay control circuit 1468 (FIGS. 57A–B), is preferably employed to generate a sawtooth current wave form in the x-step coil. The x-step driver 780 is connected across the x-step coil via output leads 1472 and 1474. Referring to FIG. 57A, x-step amplitude control signals XSTEPAMP from the beam controller interface 794 are preferably applied to x-step voltage control circuit 1464 to control the voltage level of a VICOR multi-output switching power supply (not shown), which supplies an input voltage to the x-step driver 780 via input line 1470.

Ramp switch control signals XSTEP\ are preferably applied from the control PAL 1410, via input line 1471, to control the operation of the x-step ramp control switch 1462. When the x-step ramp control switch 1462 is switched on, voltage from the VICOR multi-output power supply is applied to the x-step coil, allowing the current in the x-step coil to ramp up for a specified time period, preferably 1 to 200 nsec. The amplitude of the current pattern is determined by the voltage level of the VICOR multi-output power supply, which is preferably set by the x-step voltage control circuit 1464.

Figures 1, 57B:
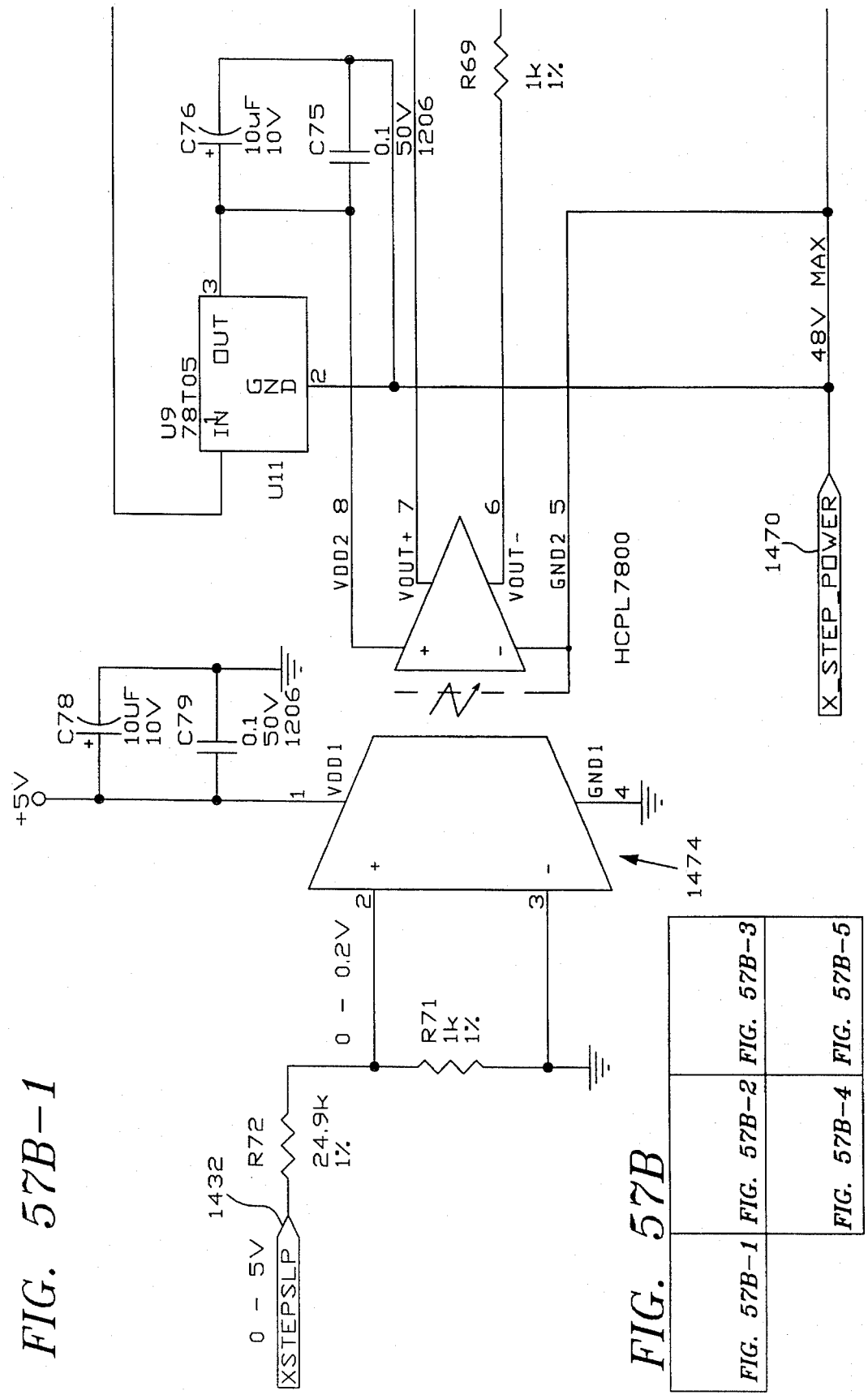
Figures 2, 57B:
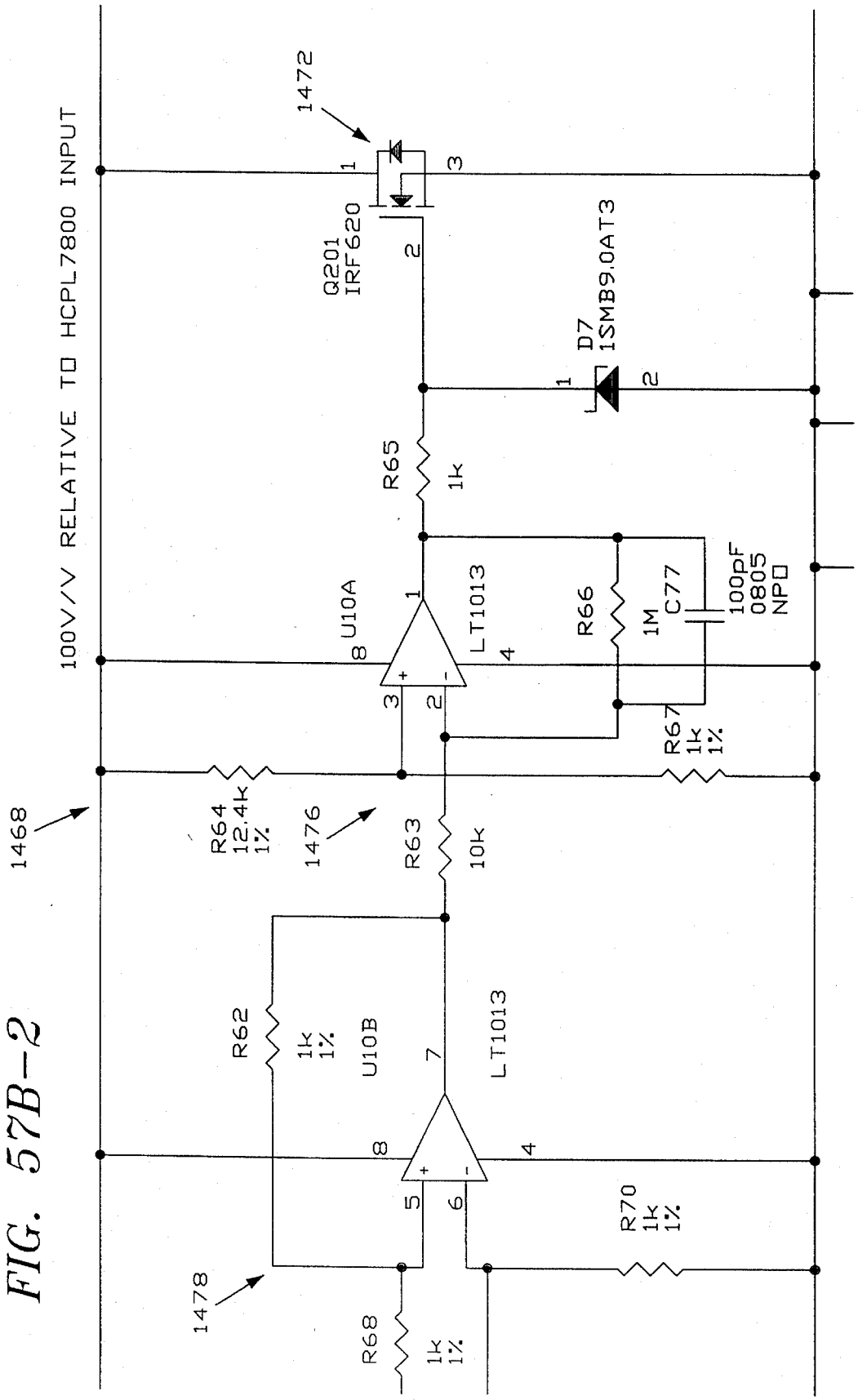
Figures 3, 57B:
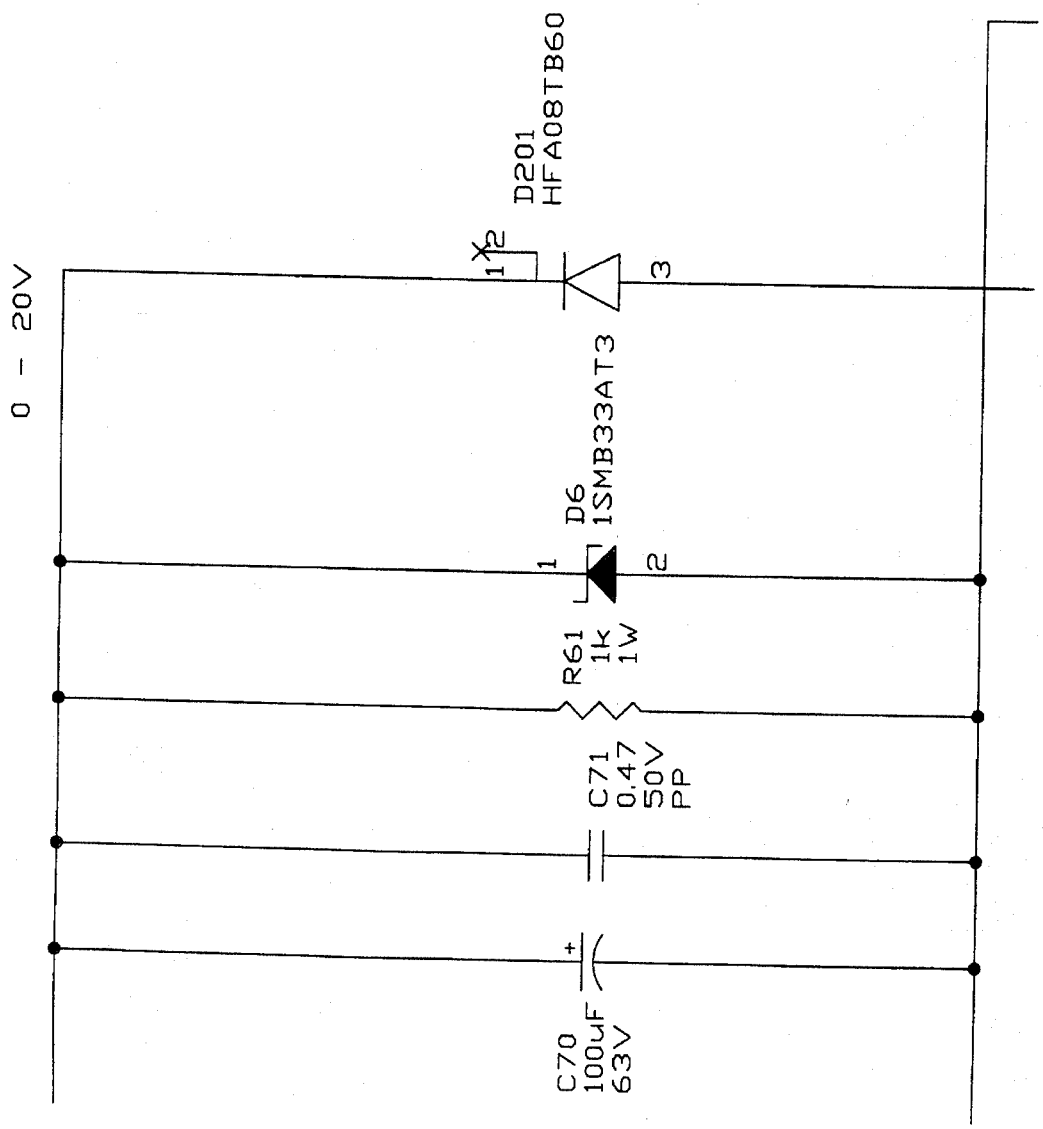
Figures 4, 57B:
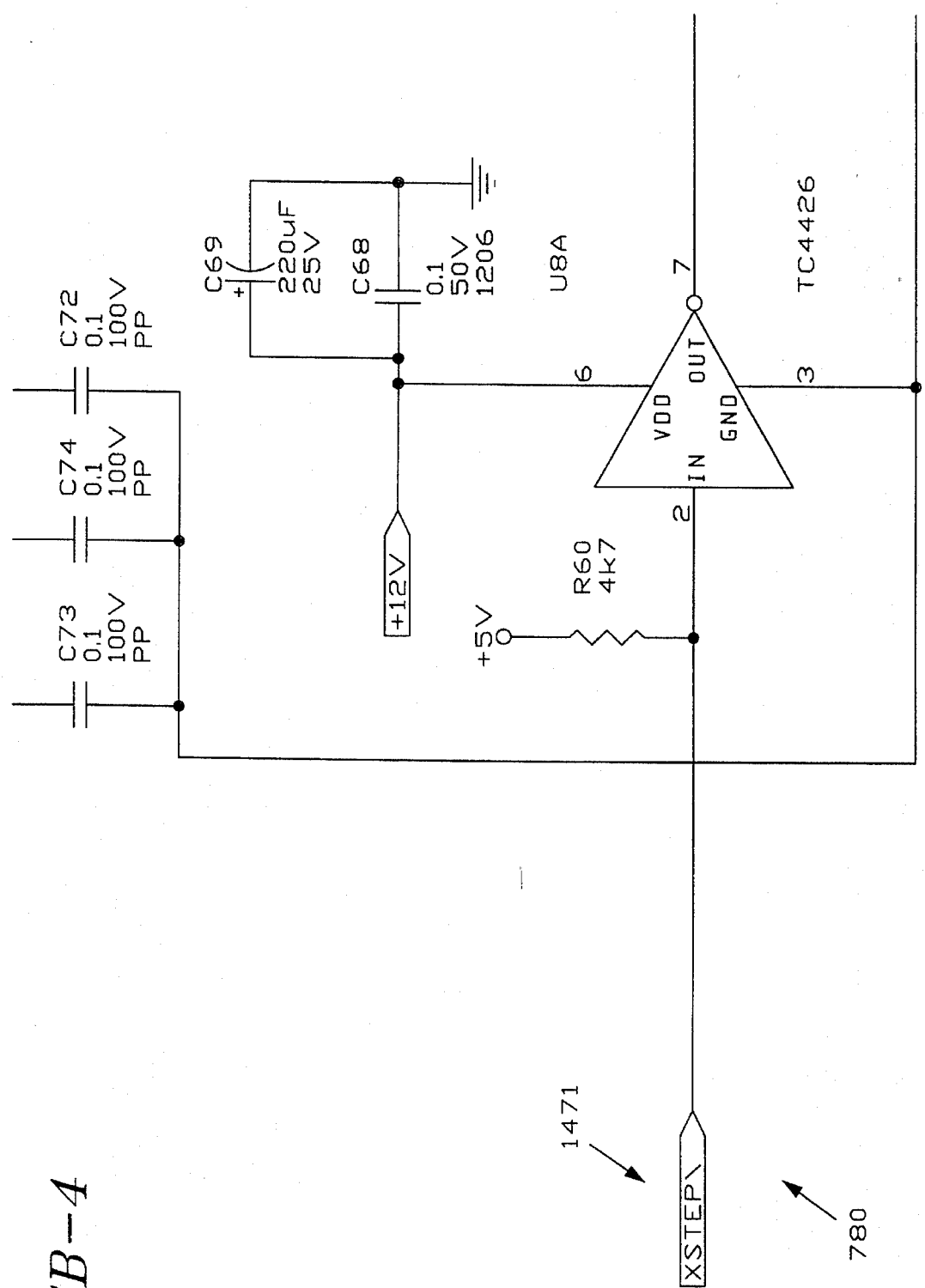
Figures 5, 57B:
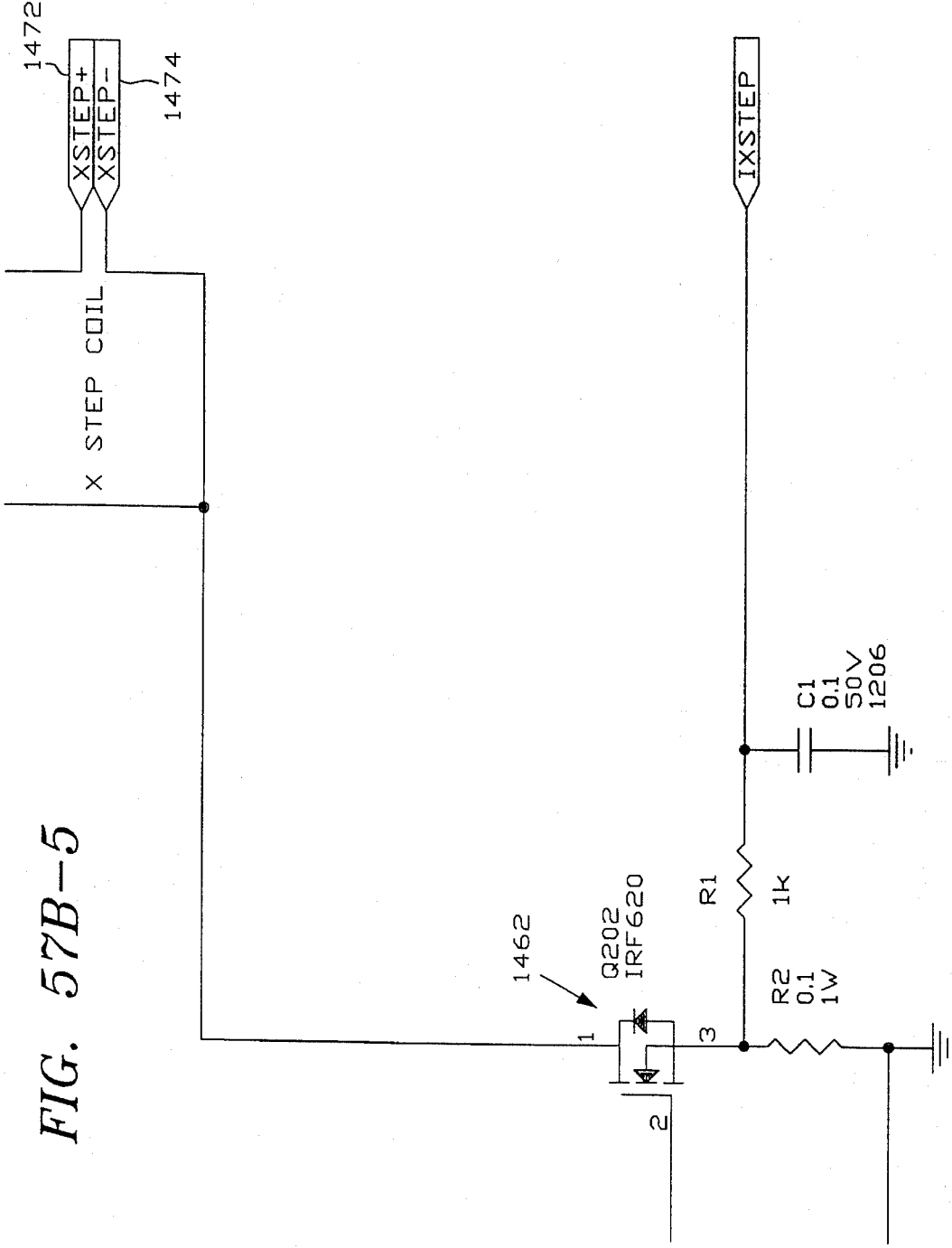

When the x-step ramp control switch 1462 is switched off, decay control circuit 1468 applies a voltage to the x-step coil to control and shape the slope of the current decay in the x-step coil. X-step slope control signals XSTEPSLP are preferably applied to the decay control circuit 1468 via input line 1432. An isolation amplifier 1474 is preferably employed to optically couple the x-step slope control signals XSTEPSLP to the decay control circuit 1468, to avoid potential problems relating to high voltages applied to the circuit by the VICOR power supply. The output of the isolation amplifier 1474 is preferably coupled to an intermediate x-step amplifier 1478. Intermediate x-step amplifier 1478 preferably converts the differential output from isolation amplifier 1474 into a single ended signal, which is coupled to the inverting input of a control amplifier 1476. Control amplifier 1476 manages the voltage across transistor 1472, which functions as a variable load, such that the voltage applied to the x-step coil during the current decay period produces an optimal current decay rate in the x-step coil. If a particular x-ray imaging application requires the use of a y-step coil, then a y-step driver similar to the x-step driver of FIGS. 57A–B is preferably employed.

While embodiments, applications and advantages of the invention have been shown and described with sufficient clarity to enable one skilled in the art to make and use the invention, it would be equally apparent to those skilled in the art that many more embodiments, applications and advantages are possible without deviating from the inventive concepts disclosed and described herein. The invention therefore should only be restricted in accordance with the spirit of the claims appended hereto and is not to be restricted by the preferred embodiments, specification or drawings.

APPENDIX A

This document is an appendix to the U.S. patent application entitled "Scanning Beam X-Ray Imaging System". This appendix contains the program listings for the preferred software modules for the programmable logic devices employed in the above-identified invention. These software modules are written in ABEL V. 5.1, from DATAIO Corp., for x86 based IBM PC-compatible computers.

PATENT
209/151

APPENDIX A

TABLE OF CONTENTS FOR SOFTWARE MODULES

| Programmable Logic Device | Section |
|---|---|
| Data Acquisition Control Chip 1638 (Fig. 42) | 1 |
| Timing Control Chip 1640 (Fig. 42) | 2 |
| Host Memory Control Chip 1642 (Fig. 42) | 3 |
| Octant Counters 1354 (Figs. 44A-B) | 4 |
| Gain & Alignment Engine 1674 (Fig. 46) | 5 |
| String Counters 1372 (Figs. 48A-I) | 6 |
| Image Reconstruction Controller 1696 (Fig. 50) | 7 |
| Output FIFO Controller 1814 (Fig. 52) | 8 |
| Detector Controller Control PAL 1870 (Fig. 53) | 9 |
| Detector Controller Left Multiplexer PAL 1872 (Fig. 53) | 10 |
| Detector Controller Right Multiplexer PAL 1874 (Fig. 53) | 11 |
| Tube Controller Control PAL 1402 (Fig. 54A) | 12 |
| Tube Controller Memory Control PAL 1404 (Fig. 54A) | 13 |
| Tube Controller Data PAL 1406 (Fig. 54A) | 14 |
| Beam Controller Control PAL 1410 (Fig. 55A) | 15 |
| Beam Controller X-Deflection PAL 1412 (Fig. 55B) | 16 |
| Beam Controller Small DAC Control PAL 1422 (Fig. 55D) | 17 |
| Beam Controller Serial Data PAL 1438 (Fig. 55E) | 18 |

```
module rteda title 'RTE Data Acquisition Mode MACH (RTEDA)
       Ver. 0; 8/10/94'
       R1U56R0 device 'MACH435A';

" On-board registers in this device:

"  Command Address 33

"  bit 0        SNGFRA    RW
"  bit 1        GACYC     RW
"  bit 2        DACCYC    RW " ControlStatus Address 34

"  bit 0        ALMSEL    RW
"  bit 1        BMACC     RW
"  bit 2        DIAG      RW
"  bit 3        FSDIAG    RW
"  bit 4        VDIAG     RW
"  bit 5        NVMSEL    RW
"  bit 8        IMBSY     R
"  bit 9        GABSY     R
"  bit 10       SERBSY    R
"  bit 11       NVMDOUT   R " Sum Address 35
"  bit 0        SUM0      RW
"  bit 1        SUM1      RW
"  bit 2        SUM2      RW " Test Address 40 (uses DOR)

"  bit 0        TEST0     RW
"  bit 1        TEST1     RW
"  bit 2        TEST2     RW
"  bit 3        TEST3     RW
"  bit 4        TEST4     RW
"  bit 5        TEST5     RW
"  bit 6        TEST6     RW
"  bit 7        TEST7     RW
"  bit 8        TEST8     RW
"  bit 9        TEST9     RW
"  bit 10       TEST10    RW
"  bit 11       TEST11    RW
"  bit 12       TEST12    RW
"  bit 13       TEST13    RW
"  bit 14       TEST14    RW
"  bit 15       TEST15    RW "inputs
     CLK50 pin 20;
     RXD0,RXD1,RXD2,RXD3,RXD4,RXD5,RXD6,RXD7 pin 5,6,7,8,9,10,12,13;
     RXC0,RXC1,RXC2,RXC3 pin 33,41,3,4;
     !RXCSTRB pin 62;
     !RXDSTRB pin 65;
     RXCRST,RXDRST pin 67,68;
     IMBSY, GABSY, NVBSY pin 19,24,25;
     NVMDOUT pin 26;
```

```
        !OFIFEF0, !OFIFEF1, !OFIFEF pin 38,39,40;
        OFIFSO0 pin 17;
        OFIFSO1 pin 31;
        OFIFSO2 pin 18;
        CLK12PE, CLK25PE pin 14, 15;
        LDIM, LDCA, LDENVM, LDLNVM pin 30,33,27,28;
        VSYNC pin 16;

"outputs
        TXC0,TXC1,TXC2,TXC3 pin 46,47,48,49 istype 'reg_D,buffer';
        TXSTRB pin 45 istype 'reg_D,buffer';
        SNGFRA,ALNSEL pin 56, 59, istype 'reg_D,buffer';
        NVMSEL pin 34 istype 'reg_D,buffer';
        EHACC,CACYC,DACCYC pin 51, 57, 58 istype 'reg_D,buffer';
        SUM0,SUM1,SUM2 pin 60, 61, 66 istype 'reg_D,buffer';
        DIAG,FSDIAG,VDIAG pin 52, 54, 55 istype 'reg_D,buffer';
        !OFIFOE0,!OFIFOE1,!OFIFOE2 pin 35, 36, 37 istype 'reg_D,buffer';
        !OFIFRE0,!OFIFRE1,!OFIFRE2 pin 80, 81, 82 istype 'reg_D,buffer';
        !OFIFWR pin 79 istype 'reg_D, buffer';

OUTCCK pin 29 istype 'buffer';
        INCCK pin 23;

"I/Os
        INTIO0,INTIO1,INTIO2,INTIO3 pin 69,70,71,72;
        INTIO4,INTIO5,INTIO6,INTIO7 pin 73,75,76,77;

"nodes
    "incoming address buffer
        ADD0, ADD1, ADD2, ADD3 node istype 'reg_D';
        ADD4, ADD5, ADD6, ADD7 node istype 'reg_D';
    "incoming command buffer
        BUC0,BUC1,BUC2,BUC3 node istype 'reg_D';
    "decode lines
        TESTPEND1, TESTPEND2, CTRLPEND, CMDPEND, SUMPEND node istype 'reg_D';
    "DCR
        DOR0, DOR1, DOR2, DOR3 node istype 'reg_D';
        DOR4, DOR5, DOR6, DOR7 node istype 'reg_D';
        DOR8, DOR9, DOR10,DOR11 node istype 'reg_D';
        DOR12,DOR13,DOR14,DOR15 node istype 'reg_D';
        LDDOR,LDCS,LDCMD,LDSUM node istype 'reg_D';
        DORRDY node istype 'reg_D,buffer';
        DOROE,OUTEI node istype 'reg_D,buffer';
    "other
        READ node istype 'reg_D';
        RXS2,RXS1,RXS0 node istype 'reg_D';
        TXS2,TXS1,TXS0 node istype 'reg_D';
        LINCT2..LINCT0 node istype 'reg_T';
        CGA1..CGA0 node istype 'reg_D';
        DLDCA node istype 'reg_D';
        DVSYNC node istype 'reg_D';
        FLGSVLD node istype 'reg_D,buffer';
        SFRAME node istype 'reg_T,buffer';
        BELEF2 node istype 'reg_D,buffer';

ADMACH PROPERTY 'GROUP B DOR0 DOR1 DOR2 DOR6 DOR7';
ADMACH PROPERTY 'GROUP C DOR3 DOR4 DOR5 DOR8 DOR9';
ADMACH PROPERTY 'GROUP F DOR10 DOR11 DOR12';
ADMACH PROPERTY 'GROUP G DOR13';
ADMACH PROPERTY 'GROUP H DOR14';
```

```
AMDMACH PROPERTY  'GROUP E DOR15';

"constants
        H,L,X,C,Z = 1,0,.X.,.C.,.Z.;
        INTIO = [INTIO7..INTIO0];
        RXD = [RXD7..RXD0];
        RXC = [RXC3..RXC0];
        TXC = [TXC3..TXC0];
        ADD = [ADD7..ADD0];
        BUC = [BUC3..BUC0];
        DORL = [DOR7..DOR0];
        DORH = [DOR15..DOR8];
        SUM_R = [SUM2..SUM0];
        SUM_8 = [0,0,0,0,0,SUM2..SUM0];
        CMD_R = [DACCYC,GACYC,SNGFRA];
        CMD_8 = [0,0,0,0,0,DACCYC,GACYC,SNGFRA];
        CTRL_R = [NVMSEL,VDIAG,FSDIAG,DIAG,EMACC,ALNSEL];
        CTRL_8 = [0,0,NVMSEL,VDIAG,FSDIAG,DIAG,EMACC,ALNSEL];
        MOD_8 = [0,0,0,0,0,0,0,1];
        STAT_8 = [0,0,0,0,NVMDOUT,NVBSY,GABSY,IMBSY];
        LS3BS = [RXD2..RXD0];
        LS6BS = [RXD5..RXD0];
        RX_STATE = [RXS2..RXS0];
        TX_STATE = [TXS2..TXS0];
        LINCT = [LINCT2..LINCT0];
        CGA   = [CGA1..CGA0];

Declarations

WAIT_FOR_CMD = [0,0,0];  " 0
        WAIT_FOR_ADD = [0,0,1];  " 1
        WAIT_FOR_DB0 = [0,1,1];  " 3
        WAIT_FOR_DB1 = [1,1,1];  " 7
        LOAD_DOR     = [0,1,0];  " 2
        UNUSED_1     = [1,0,0];  " 4
        UNUSED_2     = [1,0,1];  " 5
        UNUSED_3     = [1,1,0];  " 6 equations

" ******************* DATA OUT REGISTER (DOR) HANDLING *************

DORH.clk = CLK50;
        DORL.clk = CLK50;
        LDDOR.clk = CLK50;
"       LDMOD.clk = CLK50;
        LDCS.clk = CLK50;
        LDCMD.clk = CLK50;
        LDSUM.clk = CLK50;
        DORRDY.clk = CLK50;
        OUTHI.clk = CLK50;
        DOROE.clk = CLK50;
        CGA.clk  = CLK50;

" Data for the DOR is from an Image or GA memory read (managed by RTEEM),
" or an NV memory read, managed by RTETIM.

" ++++++ Image Memory Reads
" One byte transferred. HOSTREAD true. IMIOSTRB and LDIM are interlocked.
" This MACHs cycle is complete when byte is strobed into DOR by LDIM
```

```
"  CLK50    | | | | | | | | | | | | | | |
"  XCVRIEN  _____--------------------_____
"  INTIOEN  _____-_____
"  IHIOSTRB _____--------------------_____
"  INTIO    IIIIIIIIIIIIIIIIIIIIIIIIII-IIIIVVVVVVVIIIIIIIIII
"  LDIH     _____-____----_____
"                                     ^
"                     INTIO data to DOR (RTEDA MACH)
" ++++++ GA Memory Reads
" Two bytes transferred. HOSTREAD true. GAIOSTRB and LDGA are interlocked.
" This MACHs cycle is complete when bytes are strobed into DOR by LDGA
"
"  CLK50    | | | | -| | | | | | | | | | |
"  XCVRGLEN _____-- -------_____
"  XCVRGHEN _____-_____--------_____
"  INTIOEN  _____-_____
"  GAIOSTRB _____-- -------------------_____
"  INTIO    ZZZZZZZZZZZZZLL -LLLLLLZZZZHHHHHHHZZZZZZZZZZZZZ
"  CGA0     _____--------_____
"  CGA1     _____--------_____
"  LDGA     _____-_--------------------_____
"  DLDGA    _____-____--------------------_____
"                      ^    ^
"              L then H byte INTIO data to DOR (RTEDA MACH)
"              (timed from LDGA goes high).
"
        DLDGA.clk = CLK50;
        DLDGA := LDGA;

CGA0 := LDGA & DLDGA & !CGA1;
        CGA1 := CGA0;
        DORH := INTIO & LDGA & CGA0
              # INTIO & LDENVH
              # STAT_8 & LDCS
              # RXD & TESTPEND2&RXDRST
  # DORH & !(LDGA & CGA0 # LDENVH # LDCS # LDIH # LDCMD # LDSUM # TESTPEND2&RXDRST);

DORL := INTIO & LDGA & !DLDGA
              # INTIO & LDLNVH
              # INTIO & LDIH
              # CTRL_8 & LDCS
              # CMD_8 & LDCMD
              # SUM_8 & LDSUM
              # MOD_8 & LDMOD
              # DORL & !(LDGA & !DLDGA # LDLNVH # LDIH # LDCS
                            # LDCMD # LDSUM);

INTIO = DORH &  OUTHI
            # DORL & !OUTHI;

INTIO.oe = DOROE;

" ********************** RX TAXI STATE MACHINE **************************

" This MACH decodes Taxi input commands
"    1 = WRITE REGISTER
"    2 = READ REGISTER
```

```
" for addresses
"     32 = ModuleID (Read only)
"     33 = Command (Read/write)
"     34 = ControlStatus (Read/write)
"     35 = Sum (Read/write)
"     40 = Test (DOR) (Read/write)

" Use the edge of the strobe to clock the Taxi command or data
" into a local buffer " The command data is always strobed into the BCC buffer. When it is a
" command appropriate to us (READ or WRITE REGISTER commands) it
" will kick off the state machine. Subsequent commands may overwrite BCC
" even if the state machine has not finished, however they will be
" timing commands, not read or writes, and therefore ignored here.
"
" The data is strobed into the address buffer if the state machine
" is waiting for an address.
" The data is strobed into the CTRL, CMD and SUM registers if the
" state machine is waiting for data for that register.

ADD.clk = RXDSTRB;
        BCC.clk = RXCSTRB;

ADD  :=  (RXD  & (RX_STATE == WAIT_FOR_ADD))
               # (ADD  & (RX_STATE != WAIT_FOR_ADD));
        BCC := RXC;

" Use the strobe resets to flag when command or data is received

" The RX state machine decodes the Taxi command and data inputs
" It controls the READ, SUMPEND, CMDPEND, CTRLPEND, LDCS, LDCMS
" LDSUM and LDMOD outputs.

RX_STATE.clk = CLK50;
        READ.clk = CLK50;
        SUMPEND.clk  = CLK50;
        CMDPEND.clk  = CLK50;
        CTRLPEND.clk = CLK50;
        TESTPEND1.clk = CLK50;
        TESTPEND2.clk = CLK50;

CMD_R.clk  = RXDSTRB;
        SUM_R.clk  = RXDSTRB;
        CTRL_R.clk = RXDSTRB & CTRLPEND;
*       CTRL_R.clk = INCCK;

OUTCCK = RXDSTRB & CTRLPEND;

SUM_R := LS3BS &  SUMPEND
               # SUM_R & !SUMPEND;

CMD_R := LS3BS &  CMDPEND
               # CMD_R & !CMDPEND;

CTRL_R := LS6BS;

State_diagram [RXS2,RXS1,RXS0]
```

```
state WAIT_FOR_CMD:
    if (RXCRST & (BUC == 1)) " Write reg
        then WAIT_FOR_ADD
            with READ := 0;
                CTRLPEND := 0;
                CMDPEND := 0;
                SUMPEND := 0;
                TESTPEND1 := 0;
                TESTPEND2 := 0;
                LDMOD := 0;
                LDDOR := 0;
                LDCMD := 0;
                LDSUM := 0;
                LDCS := 0;
            endwith;
    else if (RXCRST & (BUC == 2)) " Read reg
        then WAIT_FOR_ADD
            with READ := 1;
                CTRLPEND := 0;
                CMDPEND := 0;
                SUMPEND := 0;
                TESTPEND1 := 0;
                TESTPEND2 := 0;
                LDMOD := 0;
                LDDOR := 0;
                LDCMD := 0;
                LDSUM := 0;
                LDCS := 0;
            endwith;
    else WAIT_FOR_CMD
            with READ := 0;
                CTRLPEND := 0;
                CMDPEND := 0;
                SUMPEND := 0;
                TESTPEND1 := 0;
                TESTPEND2 := 0;
                LDMOD := 0;
                LDDOR := 0;
                LDCMD := 0;
                LDSUM := 0;
                LDCS := 0;
            endwith;
state WAIT_FOR_ADD:
    if (RXDRST & (ADD == 33) & !READ) " Command reg write
        then WAIT_FOR_DB0
            with READ := 0;
                CTRLPEND := 0;
                CMDPEND := 1;
                SUMPEND := 0;
                TESTPEND1 := 0;
                TESTPEND2 := 0;
                LDMOD := 0;
                LDDOR := 0;
                LDCMD := 0;
                LDSUM := 0;
                LDCS := 0;
            endwith;
    else if (RXDRST & (ADD == 34) & !READ) " Control reg write
        then WAIT_FOR_DB0
```

```
                with READ := 0;
                     CTRLPEND := 1;
                     CMDPEND := 0;
                     SUMPEND := 0;
                     TESTPEND1 := 0;
                     TESTPEND2 := 0;
                     LDMOD := 0;
                     LDDOR := 0;
                     LDCMD := 0;
                     LDSUM := 0;
                     LDCS  := 0;
                endwith;
           else if (RXDRST & (ADD == 35) & !READ) * Sum reg write
              then WAIT_FOR_DB0
                with READ := 0;
                     CTRLPEND := 0;
                     CMDPEND := 0;
                     SUMPEND := 1;
                     TESTPEND1 := 0;
                     TESTPEND2 := 0;
                     LDMOD := 0;
                     LDDOR := 0;
                     LDCMD := 0;
                     LDSUM := 0;
                     LDCS  := 0;
                endwith;
           else if (RXDRST & (ADD == 40) & !READ) * Test reg write
              then WAIT_FOR_DB0
                with READ := 0;
                     CTRLPEND := 0;
                     CMDPEND := 0;
                     SUMPEND := 0;
                     TESTPEND1 := 1;
                     TESTPEND2 := 0;
                     LDMOD := 0;
                     LDDOR := 0;
                     LDCMD := 0;
                     LDSUM := 0;
                     LDCS  := 0;
                endwith;
           else if (RXDRST & (ADD == 32) & READ) * Modid read
              then LOAD_DOR
                with READ := 1;
                     CTRLPEND := 0;
                     CMDPEND := 0;
                     SUMPEND := 0;
                     TESTPEND1 := 0;
                     TESTPEND2 := 0;
                     LDMOD := 1;
                     LDDOR := 0;
                     LDCMD := 0;
                     LDSUM := 0;
                     LDCS  := 0;
                endwith;
           else if (RXDRST & (ADD == 40) & READ) * DOR read
              then LOAD_DOR
                with READ := 1;
                     CTRLPEND := 0;
                     CMDPEND := 0;
                     SUMPEND := 0;
```

```
                    TESTPEND1 :=   1;
                    TESTPEND2 := 0;
                     LDMOD := 0;
                    LDDOR := 1;
                    LDCMD := 0;
                    LDSUM := 0;
                    LDCS  := 0;
            endwith;
        else if (RXDRST & (ADD == 33) & READ)  " Cmd reg read
           then LOAD_DOR
                with READ := 1;
                     CTRLPEND := 0;
                     CMDPEND := 0;
                     SUMPEND := 0;
                     TESTPEND1 := 0;
                     TESTPEND2 := 0;
                      LDMOD := 0;
                     LDCMD := 1;
                     LDSUM := 0;
                     LDCS  := 0;
            endwith;
        else if (RXDRST & (ADD == 34) & READ)  " Ctrl/stat reg read
           then LOAD_DOR
                with READ := 1;
                     CTRLPEND := 0;
                     CMDPEND := 0;
                     SUMPEND := 0;
                     TESTPEND1 := 0;
                     TESTPEND2 := 0;
                      LDMOD := 0;
                     LDDOR := 0;
                     LDCMD := 0;
                     LDSUM := 0;
                     LDCS  := 1;
            endwith;
        else if (RXDRST & (ADD == 35) & READ)  " Sum reg read
           then LOAD_DOR
                with READ := 1;
                     CTRLPEND := 0;
                     CMDPEND := 0;
                     SUMPEND := 0;
                     TESTPEND1 := 0;
                     TESTPEND2 := 0;
                      LDMOD := 0;
                     LDDOR := 0;
                     LDCMD := 0;
                     LDSUM := 1;
                     LDCS  := 0;
            endwith;
        else if (RXDRST)       " Address not for us
           then goto WAIT_FOR_CMD
                with READ := 0;
                     CTRLPEND := 0;
                     CMDPEND := 0;
                     SUMPEND := 0;
                     TESTPEND1 := 0;
                     TESTPEND2 := 0;
                      LDMOD := 0;
                     LDDOR := 0;
                     LDCMD := 0;
```

```
                              LDSUM := 0;
                              LDCS  := 0;
                        endwith;
                  else WAIT_FOR_ADD
                        with READ := READ;
                              CTRLPEND := 0;
                              CMDPEND := 0;
                              SUMPEND := 0;
                              TESTPEND1 := 0;
                              TESTPEND2 := 0;
                              LDMOD := 0;
                              LDDOR := 0;
                              LDCMD := 0;
                              LDSUM := 0;
                              LDCS  := 0;
                        endwith;
            state WAIT_FOR_DB0:
                  if RXDRST & TESTPEND1
                        then WAIT_FOR_DB1
                              with READ := 0;
                                    CTRLPEND := 0;
                                    CMDPEND := 0;
                                    SUMPEND := 0;
                                    TESTPEND1 := 0;
                                    TESTPEND2 := 1;
                                    LDMOD := 0;
                                    LDDOR := 0;
                                    LDCMD := 0;
                                    LDSUM := 0;
                                    LDCS  := 0;
                              endwith;
                  else if RXDRST
                        then WAIT_FOR_CMD
                              with READ := 0;
                                    CTRLPEND := 0;
                                    CMDPEND := 0;
                                    SUMPEND := 0;
                                    TESTPEND1 := 0;
                                    TESTPEND2 := 0;
                                    LDMOD := 0;
                                    LDDOR := 0;
                                    LDCMD := 0;
                                    LDSUM := 0;
                                    LDCS  := 0;
                              endwith;
                  else WAIT_FOR_DB0
                        with READ := 0;
                              CTRLPEND := CTRLPEND;
                              CMDPEND := CMDPEND;
                              SUMPEND := SUMPEND;
                              TESTPEND1 := TESTPEND1;
                              TESTPEND2 := TESTPEND2;
                              LDMOD := 0;
                              LDDOR := 0;
                              LDCMD := 0;
                              LDSUM := 0;
                              LDCS  := 0;
                        endwith;
            state WAIT_FOR_DB1:
                  if RXDRST
```

```
                        then WAIT_FOR_CMD         ' Done
                            with READ := 0;
                                 CTRLPEND := 0;
                                 CMDPEND := 0;
                                 SUMPEND := 0;
                                 TESTPEND1 := 0;
                                 TESTPEND2 := 0;
                                 LDMOD := 0;
                                 LDDOR := 0;
                                 LDCMD := 0;
                                 LDSUM := 0;
                                 LDCS  := 0;
                            endwith;
                        else WAIT_FOR_DB1
                            with READ := 0;
                                 CTRLPEND := 0;
                                 CMDPEND := 0;
                                 SUMPEND := 0;
                                 TESTPEND1 := 0;
                                 TESTPEND2 := 1;
                                 LDMOD := 0;
                                 LDDOR := 0;
                                 LDCMD := 0;
                                 LDSUM := 0;
                                 LDCS  := 0;
                            endwith;
            state LOAD_DOR:
                goto WAIT_FOR_CMD
                            with READ := 0;
                                 CTRLPEND := 0;
                                 CMDPEND := 0;
                                 SUMPEND := 0;
                                 TESTPEND1 := 0;
                                 TESTPEND2 := 0;
                                 LDMOD := 0;
                                 LDDOR := 0;
                                 LDCMD := 0;
                                 LDSUM := 0;
                                 LDCS  := 0;
                            endwith;
            state UNUSED_1:
                goto WAIT_FOR_CMD
                            with READ := 0;
                                 CTRLPEND := 0;
                                 CMDPEND := 0;
                                 SUMPEND := 0;
                                 TESTPEND1 := 0;
                                 TESTPEND2 := 0;
                                 LDMOD := 0;
                                 LDDOR := 0;
                                 LDCMD := 0;
                                 LDSUM := 0;
                                 LDCS  := 0;
                            endwith;
            state UNUSED_2:
                goto WAIT_FOR_CMD
                            with READ := 0;
                                 CTRLPEND := 0;
                                 CMDPEND := 0;
                                 SUMPEND := 0;
```

```
                        TESTPEND1 := 0;
                        TESTPEND2 := 0;
                          LDMOD := 0;
                          LDDOR := 0;
                          LDCMD := 0;
                          LDSUM := 0;
                          LDCS  := 0;
                endwith;
    state UNUSED_3:
        goto WAIT_FOR_CMD
                with READ := 0;
                        CTRLPEND := 0;
                        CMDPEND := 0;
                        SUMPEND := 0;
                        TESTPEND1 := 0;
                        TESTPEND2 := 0;
                          LDMOD := 0;
                          LDDOR := 0;
                          LDCMD := 0;
                          LDSUM := 0;
                          LDCS  := 0;
                endwith;
```

" ****************** TX TAXI STATE MACHINE **********************

" The TX Taxi is controlled by a state machine. Transmissions occur
" if there is data to go in the DOR or the OFIFO. The DOR has priority.
" DORRDY flags data ready to go in the DOR, DORRDY is set when
" one of the strobes is detected and cleared by this state machine.

" OFIFO data is taken out 489 bytes from each of 3 lines in turn.
" When each byte is taken out, if the sync bit is high that indicates
" end of line. This is checked in TX state STR_DATA and causes a branch
" to state SEND_SL. In SEND_SL a START LINE message is sent and
" LINCT is incremented.
" The three LINCT lines indicate which is the currently active line.
" Everything is reset on the trailing edge of VSYNC, which indicates
" the start of an active frame. The reset includes a FIFO reset and
" LINCT reset. Also, VSYNC trailing edge sets the send start of frame
" bit and causes a START FRAME message to be sent.

"
" CLK12PH and CLK25PH are decoded to indicate the phase of the Taxi
" transmission (the Taxi is clocked by CLK12 which is identical to
" CLK12PH).
"
" The Taxi requires a data strobe and four command inputs, TXCSTRB
" and TXC3..TXC0. The strobe is decoded from the state and phase.

Declarations

```
        WAIT_SEND = [0,0,0];
        SET_READ  = [0,0,1];
        SEND_DB0  = [0,1,0];
        SEND_DB1  = [0,1,1];
        RD_FIFO   = [1,0,0];
        STR_DATA  = [1,0,1];
        SEND_SF   = [1,1,0];
        SEND_SL   = [1,1,1];
```

Equations

```
    TXC.clk = CLK50;
    TX_STATE.clk = CLK50;
    OFIFOE0.clk = CLK50;
    OFIFOE1.clk = CLK50;
    OFIFOE2.clk = CLK50;
    OFIFRE0.clk = CLK50;
    OFIFRE1.clk = CLK50;
    OFIFRE2.clk = CLK50;

DVSYNC.clk = CLK50;
 DVSYNC := VSYNC;

SFRAME.clk  = CLK50;
 FLGSVLD.clk = CLK50;
 DELEF2.clk  = CLK50;

"          |   |   |   |   |   |
" VSYNC   -------_____
" DVSYNC  -----------_____
" OFIFMR              -----_____
" FLGSVLD ------------_____-----

OFIFMR.clk = CLK50;

OFIFMR := !VSYNC & DVSYNC;
 FLGSVLD := (!EMACC # EMACC&SNGFRA) & !(!VSYNC & DVSYNC) & !OFIFMR;
 DELEF2 := OFIFEF2;
```

" SFRAME causes a start frame message to be transmitted, used as
" VSYNC at the receiver
" The act of sending the message causes SFRAME to be reset
" Two of these messages are sent. The decoded conditions are
" 1:
" VSYNC AND the third OFIFO empty flag leading edge (ie the final line
" FIFO is emptied at the end of frame)
" 2:
" VSYNC going false causes a one-cycle OFIFO master reset. This
" sets SFRAME.

```
   SFRAME.t = OFIFMR & !SFRAME
            # OFIFEF2 & !DELEF2 & VSYNC & !SFRAME
            # (TX_STATE == SEND_SF) & CLK25PH & CLK12PH & SFRAME;
```

" Line flags
" Data on a line is sent when the LINCT bit is set and the associated
" FIFO has data in it.

```
LINCT.clk = CLK50;

LINCT0.t = !LINCT0 & !VSYNC & DVSYNC              " Reset to 1 at EOF
         # LINCT0 & (TX_STATE == SEND_SL) & CLK25PH & CLK12PH
         # !LINCT0 & LINCT2 & (TX_STATE == SEND_SL) & CLK25PH & CLK12PH;
                                                  " Change at EOL LINCT1.t = LINCT1 & !VSYNC & DVSYNC               " Reset at EOF
         # LINCT1 & (TX_STATE == SEND_SL) & CLK25PH & CLK12PH
         # !LINCT1 & LINCT0 & (TX_STATE == SEND_SL) & CLK25PH & CLK12PH;
```

```
LINCT2.t = LINCT2 & !VSYNC & DVSYNC              " Reset at EOF
         # LINCT2 & (TX_STATE == SEND_SL) & CLK25PH & CLK12PH
         # !LINCT2 & LINCT1 & (TX_STATE == SEND_SL) & CLK25PH & CLK12PH;

TXSTRB.clk = CLK50;

TXSTRB := ((TX_STATE==SET_READ)& !CLK25PH & !CLK12PH) # "send READ msg
          ((TX_STATE==SEND_DB0)& !CLK25PH & !CLK12PH) # "send read databyte 0
          ((TX_STATE==SEND_DB1)& !CLK25PH & !CLK12PH) # "send read databyte 1
          ((TX_STATE==STR_DATA)& !CLK25PH & !CLK12PH) # "send data
          ((TX_STATE==SEND_SF )& !CLK25PH & !CLK12PH) # "send start frame msg
          ((TX_STATE==SEND_SL )& !CLK25PH & !CLK12PH);  "send start line msg DORRDY := LDIM # (LDGA & CGA1) # LDHNVH # LDDOR
                    # LDCS # LDCMD # LDSUH  "  # LDMOD
                    # DORRDY & !(TX_STATE == SET_READ);

State_diagram [TXS2,TXS1,TXS0]

" Send something if DORRDY                (data in DOR to go)
"               or (LINECT0 and OFIFEF0)  (line data ready)
"               or (LINECT1 and OFIFEF1)       "
"               or (LINECT2 and OFIFEF2)       "
"
" Also send START FRAME and START LINE messages when necessary " The following are state machine outputs. Use the 'with' syntax
" to avoid the one-clock delay.
" TXC, OFIFRE[2..0], OFIFOE[2..0], OUTHI, DOROE STATE WAIT_SEND:
          " Use CLK25PH and CLK12PH to phase align as
          " we start the send sequence.

if (DORRDY & !CLK25PH & CLK12PH) then SET_READ
               with TXC := 3 ;
                    OFIFRE0 := 0;
                    OFIFRE1 := 0;
                    OFIFRE2 := 0;
                    OFIFOE0 := 0;
                    OFIFOE1 := 0;
                    OFIFOE2 := 0;
                    OUTHI   := 0;
                    DOROE   := 0;
               endwith;
          else if (SFRAME & !CLK25PH & CLK12PH) then SEND_SF
               with TXC := 13 ;
                    OFIFRE0 := 0;
                    OFIFRE1 := 0;
                    OFIFRE2 := 0;
                    OFIFOE0 := 0;
                    OFIFOE1 := 0;
                    OFIFOE2 := 0;
                    OUTHI   := 0;
                    DOROE   := 0;
               endwith;
          else if   (LINCT0 & !OFIFEF0 & !CLK25PH & CLK12PH & FLGSVLD)
                  # (LINCT1 & !OFIFEF1 & !CLK25PH & CLK12PH & FLGSVLD)
```

```
                        | (LINCT2 & !OFXBX2 & !CLK25PH & CLK12PH & FLGSVLD)
                    then RD_FIFO
                        with TXC := 0;
                            OFIFRE0 := LINCT0;
                            OFIFOE0 := LINCT0;
                            OFIFRE1 := LINCT1;
                            OFIFOE1 := LINCT1;
                            OFIFRE2 := LINCT2;
                            OFIFOE2 := LINCT2;
                            OUTHI   := 0;
                            DOROE   := 0;
                        endwith;
                else WAIT_SEND
                        with TXC := 0 ;
                            OFIFRE0 := 0;
                            OFIFRE1 := 0;
                            OFIFRE2 := 0;
                            OFIFOE0 := 0;
                            OFIFOE1 := 0;
                            OFIFOE2 := 0;
                            OUTHI   := 0;
                            DOROE   := 0;
                        endwith;
        STATE SET_READ:
                if (CLK12PH & CLK25PH) then SEND_DB0
                        with TXC := 0 ;
                            OFIFRE0 := 0;
                            OFIFRE1 := 0;
                            OFIFRE2 := 0;
                            OFIFOE0 := 0;
                            OFIFOE1 := 0;
                            OFIFOE2 := 0;
                            OUTHI   := 0;
                            DOROE   := 1;
                        endwith;
                else SET_READ
                        with TXC := 3 ;
                            OFIFRE0 := 0;
                            OFIFRE1 := 0;
                            OFIFRE2 := 0;
                            OFIFOE0 := 0;
                            OFIFOE1 := 0;
                            OFIFOE2 := 0;
                            OUTHI   := 0;
                            DOROE   := 0;
                        endwith;
        STATE SEND_DB0:
                if (CLK12PH & CLK25PH) then SEND_DB1
                        with TXC := 0;
                            OFIFRE0 := 0;
                            OFIFRE1 := 0;
                            OFIFRE2 := 0;
                            OFIFOE0 := 0;
                            OFIFOE1 := 0;
                            OFIFOE2 := 0;
                            OUTHI   := 1;
                            DOROE   := 1;
                        endwith;
                else SEND_DB0
                        with TXC := 0;
```

```
                        OFIFRE0 := 0;
                        OFIFRE1 := 0;
                        OFIFRE2 := 0;
                        OFIFOE0 := 0;
                        OFIFOE1 := 0;
                        OFIFOE2 := 0;
                        OUTHI   := 0;
                        DOROE   := 1;
                    endwith;
        STATE SEND_DB1:
            if (CLK25PH & CLK12PH) then WAIT_SEND
                    with TXC := 0;
                        OFIFRE0 := 0;
                        OFIFRE1 := 0;
                        OFIFRE2 := 0;
                        OFIFOE0 := 0;
                        OFIFOE1 := 0;
                        OFIFOE2 := 0;
                        OUTHI   := 0;
                        DOROE   := 0;
                    endwith;
                else SEND_DB1
                    with TXC := 0;
                        OFIFRE0 := 0;
                        OFIFRE1 := 0;
                        OFIFRE2 := 0;
                        OFIFOE0 := 0;
                        OFIFOE1 := 0;
                        OFIFOE2 := 0;
                        OUTHI   := 1;
                        DOROE   := 1;
                    endwith;
        STATE RD_FIFO:                  " FIFOs read enabled one clock
            goto STR_DATA
                    with TXC := 0;
                        OFIFRE0 := 0;
                        OFIFRE1 := 0;
                        OFIFRE2 := 0;
                        OFIFOE0 := LINCT0;
                        OFIFOE1 := LINCT1;
                        OFIFOE2 := LINCT2;
                        OUTHI   := 0;
                        DOROE   := 0;
                    endwith;
        STATE STR_DATA:
            if (CLK25PH & CLK12PH &
            (LINCT0&OFIFSO0 # LINCT1&OFIFSO1 # LINCT2&OFIFSO2))
                                then SEND_SL
                    with TXC := 14;
                        OFIFRE0 := 0;
                        OFIFRE1 := 0;
                        OFIFRE2 := 0;
                        OFIFOE0 := 0;
                        OFIFOE1 := 0;
                        OFIFOE2 := 0;
                        OUTHI   := 0;
                        DOROE   := 0;
                    endwith;
                else if (CLK25PH & CLK12PH) then WAIT_SEND
                    with TXC := 0;
```

```
                        OFIFRE0 := 0;
                        OFIFRE1 := 0;
                        OFIFRE2 := 0;
                        OFIFOE0 := 0;
                        OFIFOE1 := 0;
                        OFIFOE2 := 0;
                        OUTHI   := 0;
                        DOROE   := 0;
                    endwith;
            else STR_DATA
                    with TXC := 0;
                        OFIFRE0 := 0;
                        OFIFRE1 := 0;
                        OFIFRE2 := 0;
                        OFIFOE0 := LINCT0;
                        OFIFOE1 := LINCT1;
                        OFIFOE2 := LINCT2;
                        OUTHI   := 0;
                        DOROE   := 0;
                    endwith;
        STATE SEND_SF:
            if (CLK25PH & CLK12PH) then WAIT_SEND
                    with TXC := 0;
                        OFIFRE0 := 0;
                        OFIFRE1 := 0;
                        OFIFRE2 := 0;
                        OFIFOE0 := 0;
                        OFIFOE1 := 0;
                        OFIFOE2 := 0;
                        OUTHI   := 0;
                        DOROE   := 0;
                    endwith;
            else SEND_SF
                    with TXC := 13;
                        OFIFRE0 := 0;
                        OFIFRE1 := 0;
                        OFIFRE2 := 0;
                        OFIFOE0 := 0;
                        OFIFOE1 := 0;
                        OFIFOE2 := 0;
                        OUTHI   := 0;
                        DOROE   := 0;
                    endwith;
        STATE SEND_SL:
            if (CLK25PH & CLK12PH) then WAIT_SEND
                    with TXC := 0;
                        OFIFRE0 := 0;
                        OFIFRE1 := 0;
                        OFIFRE2 := 0;
                        OFIFOE0 := 0;
                        OFIFOE1 := 0;
                        OFIFOE2 := 0;
                        OUTHI   := 0;
                        DOROE   := 0;
                    endwith;
            else SEND_SL
                    with TXC := 14;
                        OFIFRE0 := 0;
                        OFIFRE1 := 0;
                        OFIFRE2 := 0;
```

```
        OFIFOE0 := 0;
        OFIFOE1 := 0;
        OFIFOE2 := 0;
        OUTHI   := 0;
        DOROE   := 0;
     endwith;
END
```

```
module rtetim title 'RTE Timing, Diagnostic and NVM MACH (RTETIM)
        Ver. 0; 8/15/94'
        R1U57R0 device 'MACH435A';

" Handles serial register IO
" Handles diagnostic register writes
" Decodes timing messages (or diagnostics) into sync signals
" This device uses the INTIO bus only to return read NVM data
" because it decodes SerialData register writes for itself
" to the NVM and DAC.

" to go back and solve if possible:
" SERBSY uses SERBS node in order to get a fit.
" READ and WRITE use .T when .D would be better.
" Had to take timing delays out of this device because
" needed the nodes for Serial Register Read storage.

"inputs
        CLK50 pin 20;
        CLK25PH pin 17;
        RXD0,RXD1,RXD2,RXD3,RXD4,RXD5,RXD6,RXD7 pin 5,6,7,8,9,10,12,13;
        RXC0,RXC1,RXC2,RXC3 pin 83,41,3,4;
        !RXDSTRB pin 65;
        !RXCSTRB pin 62;
        HMACC, DACCYC, NVMSEL pin 25,19,49;
        DIAG, FSDIAG, NVMDOUT, DACDOUT pin 14,15,48,51;
"       !PURST pin 82;

"unused pins but wired on board.
        MEMADD pin 39;
        HOSTREAD pin 24;
        NVIOSTRB pin 82;
        CLK12PH pin 18;
"outputs
        LDENVM, LDLNVM pin 27,28 istype 'reg_D,buffer';
        NVMCLK pin 46 istype 'reg_T,buffer';
        NVMDIN pin 47 istype 'reg_D,buffer';
        DDATA11..DDATA6 pin 81,80,79,78,77,76 istype 'reg_D,buffer';
        DDATA5..DDATA0  pin 75,73,72,71,70,69 istype 'reg_D,buffer';
        CGATE5..CGATE0  pin 60,59,58,57,56,55 istype 'reg_D,buffer';
        VSYNC pin 66 istype 'reg_D,buffer';
        HSYNC pin 67 istype 'reg_D,buffer';
        CSYNC pin 61 istype 'reg_D,buffer';
        SERBSY pin 26 istype 'buffer';
        DIAGCLK1 pin 68 istype 'reg_D,buffer';
        NVMSTRB, !SERSTRB pin 45, 52;

"Tristate outputs
        INTIO0,INTIO1,INTIO2,INTIO3 pin 29,30,31,33 istype 'reg_D,buffer';
        INTIO4,INTIO5,INTIO6,INTIO7 pin 34,35,36,37 istype 'reg_D,buffer';

"nodes
    "incoming command buffer
        BUC0,BUC1,BUC2,BUC3 node istype 'reg_D';
        ADD7,ADD6,ADD5,ADD4,ADD3,ADD2,ADD1,ADD0 node istype 'reg_D';
    "state machine state bits
        RXS1,RXS0 node istype 'reg_D';
        RXDRST node istype 'reg_D';
```

```
        RXCRST node istype 'reg_D';
    "serial data register
        SREG15,SREG14,SREG13,SREG12 node istype 'reg_T';
        SREG11,SREG10,SREG9, SREG8  node istype 'reg_T';
        SREG7, SREG6, SREG5, SREG4  node istype 'reg_T';
        SREG3, SREG2, SREG1, SREG0  node istype 'reg_T';
    "serial holding register
        SHR15,SHR14,SHR13,SHR12 node istype 'reg_T';
        SHR11,SHR10,SHR9, SHR8  node istype 'reg_T';
        SHR7, SHR6, SHR5, SHR4  node istype 'reg_T';
        SHR3, SHR2, SHR1, SHR0  node istype 'reg_T';
    "other
        INTIOEN node istype 'reg_D';
        DCTRL3,DCTRL2,DCTRL1,DCTRL0 node istype 'reg_D';
        DIAGCLK0 node istype 'reg_D';
        CGATE node istype 'reg_T';
        SHIFTING node istype 'reg_D';
        SHFTTIM4..SHFTTIM0, SHFTCT3..SHFTCT0  node istype 'reg_T';
        READ, WRITE, SERBS node istype 'reg_T';
        SERIO, WRSREGH, WRSREGL node istype 'reg_D';
        USEDIAG node;

VSDELAY0,HSDELAY0,CSDELAY0 node istype 'reg_T';
"       CGDELAY4..CGDELAY0 node istype 'reg_D';
"       VSDELAY5..VSDELAY1 node istype 'reg_D';
"       HSDELAY5..HSDELAY1 node istype 'reg_D';
"       CSDELAY5..CSDELAY1 node istype 'reg_D';

"constants
        H,L,X,C,Z = 1,0,.X.,.C.,.Z.;
        INTIO = [INTIO7..INTIO0];
        DREGL = [DDATA7..DDATA0];                       "Diagnostic reg
        DREGH = [DCTRL3..DCTRL0, DDATA11..DDATA8];
        SREGL = [SREG7..SREG0];                         "Serial reg
        SREGH = [SREG15..SREG8];
        SHFTOUTH = [SREG14..SREG7];         "Serial shifting (write)
        SHFTOUTL = [SREG6..SREG0,SREG15];   "Serial shifting (write)
        SHR      = [SHR15..SHR0];
        SHRIN    = [SHR14..SHR0,NVMDOUT];
        SHRH     = [SHR15..SHR8];
        SHRL     = [SHR7..SHR0];
        DCTRL = [DCTRL3..DCTRL0];
        DDATA = [DDATA11..DDATA0];
        RXD = [RXD7..RXD0];
        RXC = [RXC3..RXC0];
        BUC = [BUC3..BUC0];
        ADD = [ADD7..ADD0];
        RX_STATE = [RXS1..RXS0];
        SHFTTIM = [NVMCLK,SHFTTIM4..SHFTTIM0];
        SHFTCT = [SHFTCT3..SHFTCT0];
TIMSIGS=[VSYNC,HSYNC,CSYNC,CGATE,CGATE0..CGATE5,VSDELAY0,HSDELAY0,CSDELAY0];

"       CGDEL0 = [CGDELAY4..CGDELAY0];
"       CGDELI = [CGDELAY3..CGDELAY0,CGATE];
"       VSDEL0 = [VSYNC,VSDELAY5..VSDELAY1];
"       VSDELI = [VSDELAY5..VSDELAY0];
"       HSDEL0 = [HSYNC,HSDELAY5..HSDELAY1];
"       HSDELI = [HSDELAY5..HSDELAY0];
"       CSDEL0 = [CSYNC,CSDELAY5..CSDELAY1];
```

```
"       CSDELL = [CSDELAY5..CSDELAY];

Declarations
        WAIT_FOR_CMD = [0,0];
        WAIT_FOR_ADD = [0,1];
        WAIT_FOR_DB0 = [1,1];
        WAIT_FOR_DB1 = [1,0];

START_LINE   = [0,1,0,0];
        START_FRAME  = [0,1,0,1];
        START_COUNT  = [0,1,1,0];
        STOP_COUNT   = [0,1,1,1];
        END_FRAME    = [1,0,0,0];
        END_LINE     = [1,0,1,0];
        START_GAIN   = [1,1,1,1];

equations

" CLK12PH and CLK25PH are in phase with the RX Taxi output.
" Use the strobes and phase clocks to indicate when a message received
" Incoming data is valid when the RST is true and one clock cycle after " Tristate unused signals CLK12PH.oe = 0;
MEMADD.oe  = 0;
HOSTREAD.oe = 0;
NVIOSTRB.oe = 0;

RXCRST.clk = CLK50;
        RXDRST.clk = CLK50;
        RXCRST := RXCSTRB & !RXCRST & !CLK25PH;
        RXDRST := RXDSTRB & !RXDRST & !CLK25PH;

" This MACH decodes Taxi input commands
"       1 = WRITE REGISTER
"       2 = READ REGISTER
" for address 38 = DiagnosticControl register
" and address 39 = SerialData register
" and
"       4 = START IMAGE LINE
"       5 = START IMAGE FRAME
"       6 = START IMAGE COUNT
"       7 = STOP COUNT
"       8 = END IMAGE FRAME
"      10 = END IMAGE LINE
"      15 = START GAIN COUNT " The reads and writes are handled by a state machine
" The timing messages are decoded directly ADD.clk   = RXDSTRB;
        DREGL.clk = RXDSTRB;
        DREGH.clk = RXDSTRB;
        SREGL.clk = CLK50;
        SREGH.clk = CLK50;
        BUC.clk   = RXCSTRB;

" Address lines change for every READ or WRITE command detected,
" even if not our address.
```

```
" This is 'transparent latch' syntax. ADD = RXD when state WAIT_FOR_ADD
" but is latched when state changes.

ADD   :=   RXD   & (RX_STATE == WAIT_FOR_ADD)
                # ADD   & (RX_STATE != WAIT_FOR_ADD);

" Address 38 is the diagnostic register. Latch the low and high
" bytes separately as they are sent.

DREGH :=   RXD   & (RX_STATE == WAIT_FOR_DB1) & (ADD == 38)
                # DREGH & !((RX_STATE == WAIT_FOR_DB1) & (ADD == 38));
      DREGL :=   RXD   & (RX_STATE == WAIT_FOR_DB0) & (ADD == 38)
                # DREGL & !((RX_STATE == WAIT_FOR_DB0) & (ADD == 38));

BUC := RXC;

" Use the strobe resets to flag when command or data is received

" A state machine decodes the Taxi write diagnostic register
" New data in the diagnostic register is flagged by state
" WAIT_FOR_DB1 & RXDRST & (ADD == 38)
" This condition is decoded to generate the diagnostic clock DIAGCLK
" and the diagnostic timing replacement in the appropriate modes.

RX_STATE.clk = CLK50;
"     RX_STATE.ar  = PURST;

State_diagram [RXS1,RXS0]

state WAIT_FOR_CMD:
          if (RXCRST & ((BUC == 1) # (BUC == 2))) " Reg read or write
             then WAIT_FOR_ADD;
          else
             WAIT_FOR_CMD;
   state WAIT_FOR_ADD:
          if RXDRST & WRITE & ((ADD == 38) # (ADD == 39))
             then WAIT_FOR_DB0;
          else if RXDRST
             then WAIT_FOR_CMD;
          else
             WAIT_FOR_ADD;
   state WAIT_FOR_DB0:
          if RXDRST
             then WAIT_FOR_DB1;
          else
             WAIT_FOR_DB0;
   state WAIT_FOR_DB1:
          if RXDRST
             then WAIT_FOR_CMD
          else
             WAIT_FOR_DB1;

Equations

" ********************* Decode the timing signals *************************
" OK to use combinational logic for USEDIAG, its inputs are
" effectively DC.

USEDIAG = DIAG & !FSDIAG;
```

```
     TIMSIGS.clk    = CLK50;
"    TIMSIGS.ar     = PURST;

VSDELAY0.t = RXCRST & (BUC == START_FRAME) & !USEDIAG & VSDELAY0
              # RXCRST & (BUC == END_FRAME)   & !USEDIAG & !VSDELAY0
              # DIAGCLKO & (DCTRL == START_FRAME) & USEDIAG & VSDELAY0
              # DIAGCLKO & (DCTRL == END_FRAME) & USEDIAG & !VSDELAY0;

HSDELAY0.t = RXCRST & (BUC == START_FRAME) & !USEDIAG & HSDELAY0
              # RXCRST & (BUC == START_LINE)  & !USEDIAG & HSDELAY0
              # RXCRST & (BUC == END_FRAME)   & !USEDIAG & !HSDELAY0
              # RXCRST & (BUC == END_LINE)    & !USEDIAG & !HSDELAY0
              # DIAGCLKO & (DCTRL == START_FRAME) & USEDIAG & HSDELAY0
              # DIAGCLKO & (DCTRL == START_LINE)  & USEDIAG & HSDELAY0
              # DIAGCLKO & (DCTRL == END_FRAME) & USEDIAG & !HSDELAY0
              # DIAGCLKO & (DCTRL == END_LINE)  & USEDIAG & !HSDELAY0;

CGATE.t = RXCRST & (BUC == START_FRAME) & !USEDIAG & !CGATE
             # RXCRST & (BUC == START_LINE)  & !USEDIAG & !CGATE
             # RXCRST & (BUC == START_COUNT) & !USEDIAG & !CGATE
             # RXCRST & (BUC == START_GAIN)  & !USEDIAG & !CGATE
             # RXCRST & (BUC == END_FRAME)   & !USEDIAG & !CGATE
             # RXCRST & (BUC == END_LINE)    & !USEDIAG & !CGATE
             # RXCRST & (BUC == STOP_COUNT)  & !USEDIAG & CGATE
             # DIAGCLKO & (DCTRL == START_FRAME) & USEDIAG & !CGATE
             # DIAGCLKO & (DCTRL == START_LINE)  & USEDIAG & !CGATE
             # DIAGCLKO & (DCTRL == START_COUNT) & USEDIAG & !CGATE
             # DIAGCLKO & (DCTRL == START_GAIN)  & USEDIAG & !CGATE
             # DIAGCLKO & (DCTRL == END_FRAME) & USEDIAG & !CGATE
             # DIAGCLKO & (DCTRL == END_LINE)  & USEDIAG & !CGATE
             # DIAGCLKO & (DCTRL == STOP_COUNT)& USEDIAG & CGATE;

CSDELAY0.t = RXCRST & (BUC == START_GAIN) & !USEDIAG & !CSDELAY0
              # RXCRST & (BUC == STOP_COUNT) & !USEDIAG & CSDELAY0
              # DIAGCLKO & (DCTRL == START_GAIN) & USEDIAG & !CSDELAY0
              # DIAGCLKO & (DCTRL == STOP_COUNT) & USEDIAG & CSDELAY0;

"********************* Timing signal delays *******************************

"       CGDEL0.clk = CLK50;
"       VSDEL0.clk = CLK50;
"       HSDEL0.clk = CLK50;
"       CSDEL0.clk = CLK50;
"
"       CGDEL0 := CGDELI;
"       VSDEL0 := VSDELI;
"       HSDEL0 := HSDELI;
"       CSDEL0 := CSDELI;
"
"       CGATE0 := CGDELAY4;
"       CGATE1 := CGDELAY4;
"       CGATE2 := CGDELAY4;
"       CGATE3 := CGDELAY4;
"       CGATE4 := CGDELAY4;
"       CGATE5 := CGDELAY4;
"
        VSYNC := VSDELAY0;
        HSYNC := HSDELAY0;
```

```
       CSYNC   := CSDELAY0;
       CGATE0  := CGATE;
       CGATE1  := CGATE;
       CGATE2  := CGATE;
       CGATE3  := CGATE;
       CGATE4  := CGATE;
       CGATE5  := CGATE;
```

"********************* Diagnostic data out *******************************

" Decode the data written to the diagnostic register

```
       DIAGCLK0.clk = CLK50; " DIAGCLK0 flags new diagnostic data
       DIAGCLK1.clk = CLK50;

DIAGCLK0 := (RX_STATE == WAIT_FOR_DB1) & (ADD == 38)
                   & RXDRST & USEDIAG;
```

" Toggle DIAGLCK1 once only, if the diagnostic control bits are 0
" indicating that this is a diagnostic data strobe

```
       DIAGCLK1 := DIAGCLK0 & (DCTRL == 0);
```

" *********************** Shift serial data *******************************

" Data clock is 50/64 MHz (slowest device max. speed is 1 MHz)
" SHFTTIM is clock divider to match speed of device
" SHFTCT is counter for serial 16-bit shift, 1 bit shifted
" and output every 50/64 MHz count
" Everything starts when SERIO goes true with READ or WRITE set
" NVMSEL line is used to decode whether NVM or DAC is active " If NVM, then NVMSTRB is true for the duration of READ or WRITE
" whether read or write we clock the NVM 16 times.
" If NVM WRITE -
" shift out of SREG through NVMDIN and into SREGO from NVMDIN (so
" SREG is unaltered)
" If NVM READ -
" send what is already in SREG to DOR
" shift into SREG from NVMDOUT " If DAC, then SERSTRB is true for the duration of DACCYC (which
" is a bit written by the host, not controlled here).

" Decode both SHFTTIM and SHFTCT to
"  - shift data to serial output pin NVMDIN (write)
"  - shift data in from serial input pin NVMDOUT (read)
"  - generate clock to serial device
"  - keep SERBSY true till operation complete
"  - reset READ and WRITE lines when complete " Msb of SHFTTIM is NVMCLK SHFTTIM.clk  = CLK50;
       SHFTCT.clk   = CLK50;
       SHIFTING.clk = CLK50;
       READ.clk     = CLK50;
       WRITE.clk    = CLK50;
```

```
"       SHFTTIM.ar  = PURST;
"       SHFTCT.ar   = PURST;
"       SHIFTING.ar = PURST;
"       READ.ar     = PURST;
"       WRITE.ar    = PURST;

SHFTTIM.t = (SHFTTIM $ (SHFTTIM+1)) & SERIO & (READ # WRITE) " Count
                  # (SHFTTIM $ (0))  & SERIO & !(READ # WRITE);    " Reset to 0

SHIFTING := (SHFTTIM == 32) & WRITE
                  # (SHFTTIM == 57) & READ;

SHFTCT.t  = (SHFTCT $ (SHFTCT+1)) & SHIFTING        " Count shifts
                  # (SHFTCT $ (15)) & !(READ # WRITE);      " Reset to -1

" READ and WRITE are set when a read or write register command is decoded
" They are cleared either by an address other than 39 (SerialData register)
" or when the IO to address 39 is complete.

" This is D-logic but alas it does not fit in D

"       READ := RXCRST & (BUC == 1)
"            # READ & !((RXDRST & (RX_STATE == WAIT_FOR_ADD) & (ADD != 39))
"                      #((SHFTCT == 15) & (SHFTTIM == 63)));
"       WRITE := RXCRST & (BUC == 2)
"            # WRITE & !((RXDRST & (RX_STATE == WAIT_FOR_ADD) & (ADD != 39))
"                      #((SHFTCT == 15) & (SHFTTIM == 63)));
"
" so we have to use T WRITE.t = RXCRST & (BUC == 1) & !WRITE

RXDRST & (RX_STATE == WAIT_FOR_ADD) & (ADD != 39) & WRITE

(SHFTCT == 15) & (SHFTTIM == 63) & WRITE;
        READ.t  = RXCRST & (BUC == 2) & !READ
                # RXDRST & (RX_STATE == WAIT_FOR_ADD) & (ADD != 39) & READ
                # (SHFTCT == 15) & (SHFTTIM == 63) & READ;

SERBS.t = RXDRST & (RX_STATE==WAIT_FOR_ADD) & (ADD==39) & !SERBS
                # (SHFTCT == 15) & (SHFTTIM == 63) & SERBS;

" SERBSY gross timing not critical, this dissociates the node from the pin
" and gives a better chance of fitting

SERBSY = SERBS;

" Serial register data changes when written to from host during a
" WRITE operation, or when shifted out as the write is executed,
" or when shifted in during a READ operation " WRSREGx (Write Serial Register) lines are transparent while
" the state machine is waiting for the databyte after receiving
" the WRITE SERIAL REGISTER sequence. It latches as soon as the
" data is received, signalled by the state machine state changing.
" This happens as a result of a RXDRST pulse. The RXD data is
" guaranteed one cycle after RXDRST. Hence pre-decoding of the
" WRSREGx lines is OK, and it saves routing resources.
" SERIO (Serial IO in progress) is set true when there is an IO access
" to address 39, and cleared when the read or write completes.
```

```
        SERBS.clk   = CLK50;
        NVMDIN.clk  = CLK50;
        SERIO.clk   = CLK50;
        WRSREGH.clk = CLK50;
        WRSREGL.clk = CLK50;
        SHR.clk     = CLK50;

"       SERBS.ar    = PURST;
"       NVMDIN.ar   = PURST;
"       SERIO.ar    = PURST;
"       WRSREGH.ar  = PURST;
"       WRSREGL.ar  = PURST;
"       SHR.ar      = PURST;

SERIO   := RXDRST & WRITE & (ADD == 39) & (RX_STATE == WAIT_FOR_DB1)
                 # RXDRST & READ  & (ADD == 39) & (RX_STATE == WAIT_FOR_ADD)
                 # SERIO & !((SHFTCT == 15) & (SHFTTIM == 63));
        WRSREGH := (RX_STATE == WAIT_FOR_DB1) & (ADD == 39);
        WRSREGL := (RX_STATE == WAIT_FOR_DB0) & (ADD == 39);

SREGH.t = (SREGH $ RXD) & WRSREGH
                # (SREGH $ SHFTOUTH) & SHIFTING & WRITE;

SREGL.t = (SREGL $ RXD) & WRSREGL
                # (SREGL $ SHFTOUTL) & SHIFTING & WRITE;

SHR.t   = (SHR $ SHRIN) & SHIFTING & READ;

NVMDIN  := SREG15 & WRITE;

NVMSTRB = DACCYC & NVMSEL;
        SERSTRB = DACCYC & !NVMSEL;

" ********************** Serial read - data to host cycle **************

" The dataword in the SHR is sent to the host when a read is
" received. The read loads the SHR with new data immediately afterwards.
" Hence the host is reading data one cycle behind.
" The serial shift counters are convenient to decode to do this. Note that
" no serial shift occurs until the timing counter reaches 63 so the data
" is available for sending for plenty of time.

" 50MHz   |||||||||||||||||||||||||||||||||||||||||||||
" READ         ---------------------------------------
" SERIO         --------------------------------------
" SHFTTIM 000000000000123456789
" SHFTCT  000000000000000000000
" INTIO   ZZZZZZZZZZZZLLLHHHHZZZ
" LDLNVM                -___
" LDHNVM                 -__

INTIO.clk   = CLK50;
        INTIOEN.clk = CLK50;
        LDLNVM.clk  = CLK50;
        LDHNVM.clk  = CLK50;

"       INTIO.ar    = PURST;
"       INTIOEN.ar  = PURST;
```

```
"       LDLNVH.ar  = PURST;
"       LDENVH.ar  = PURST;

INTIO.oe   = INTIOEN;

INTIO := SHRH & SHFTTIM2
              # SHRL & !SHFTTIM2;
        LDLNVH := EMACC & READ & (SHFTTIM == 2) & (SHFTCT == 15);
        LDENVH := EMACC & READ & (SHFTTIM == 5) & (SHFTCT == 15);
        INTIOEN := EMACC & READ & (SHFTTIM<9)&(SHFTTIM>0) & (SHFTCT == 15);
" INTIOEN := 0;  For testing
END
```

```
module rtehm title 'RTE Host Memory Mode MACH (RTEHM)
       Ver. 0; 8/3/94'
       R1U43R0 device 'MACH435A';

"inputs
       CLK50 pin 23;
       CLK25RX pin 20;
       RXD0,RXD1,RXD2,RXD3,RXD4,RXD5,RXD6,RXD7 pin 5,6,7,8,9,10,12,13;
       RXC0,RXC1,RXC2,RXC3 pin 63,41,3,4;
       !RXDSTRB pin 62;
       !RXCSTRB pin 65;
       CLK25PH pin 17;
       EMACC pin 54;
       LDIH, LDGA pin 57,59;
       !PURST pin 50;
       SNGFRA pin 29;

"outputs
       CLK12RX   pin 82 istype 'reg_D, buffer';
       RXCRST pin 45 istype 'reg_D, buffer';
       RXDRST pin 46 istype 'reg_D, buffer';
       HEMADD, IMMADS, GAMADS, NVMADS pin 25,26,27,28 istype 'reg_D, buffer';
       !XCVRIEN pin 38 istype 'reg_T, buffer';
       XCVRDIR pin 37 istype 'reg_D, buffer';
       !XCVRGHEN, !XCVRGLEN pin 40, 39 istype 'reg_T, buffer';
       HOSTREAD pin 19 istype 'reg_T, buffer';
       IHIOSTRB, GAIOSTRB pin 33,34 istype 'reg_T, buffer';

"I/Os
       INTIO0,INTIO1,INTIO2,INTIO3 pin 69,70,71,72 istype 'reg_D,buffer';
       INTIO4,INTIO5,INTIO6,INTIO7 pin 73,75,76,77 istype 'reg_D,buffer';

"wired on board but not used
       NVIOSTRB pin 35;
       CLK12PH pin 18;
       LDLNVH pin 61;
       LDENVH pin 60;

"nodes
     "incoming data buffer
       BUD0, BUD1, BUD2, BUD3  pin istype 'reg_D, buffer';
       BUD4, BUD5, BUD6, BUD7  node istype 'reg_D';
       BUD8, BUD9, BUD10,BUD11 pin istype 'reg_D, buffer';
       BUD12,BUD13,BUD14,BUD15 node istype 'reg_D';
     "incoming register address
       RAD0, RAD1, RAD2, RAD3 node istype 'reg_D';
       RAD4, RAD5, RAD6, RAD7 node istype 'reg_D';
     "incoming memory select buffer
       ADD0, ADD1, ADD2, ADD3  node istype 'reg_D';
       ADD4, ADD5, ADD6, ADD7  node istype 'reg_D';
       ADD8, ADD9, ADD10,ADD11 node istype 'reg_D';
     "incoming command buffer
       BUC0,BUC1,BUC2,BUC3 node istype 'reg_D';
     "state machine state bits
       RXS1,RXS0 pin istype 'reg_D,buffer';
       IOS4,IOS3,IOS2,IOS1,IOS0 pin istype 'reg_D,buffer';
     "flags
       HEMADDR, HEMDATA, GOWRITE pin istype 'reg_T,buffer';
```

```
"other
    INTIOEN, OUTHI node istype 'reg_T';
    DGEN node istype 'reg_D';

"constants
    H,L,X,C,Z = 1,0,.X.,.C.,.Z.;
"   INCMD  = [RXC3..RXC0];
"   OUTCMD = [TXC3..TXC0];
"   INDATA = [RXD7..RXD0];
    INTIO  = [INTIO7..INTIO0];
    RXD    = [RXD7..RXD0];
    RXC    = [RXC3..RXC0];
    BUDL   = [BUD7..BUD0];
    BUDH   = [BUD15..BUD8];
    RAD    = [RAD7..RAD0];
    ADD    = [ADD11..ADD0];
    ADDBITS = [0,BUD10..BUD0];
    SHFADDIN  = [ADD10..ADD0,HEMADD];
    SHFADDOUT = [HEMADD,ADD10..ADD0];
    BUC = [BUC3..BUC0];
    RX_STATE = [RXS1..RXS0];
    IO_STATE = [IOS4..IOS0];

" T/D flip-flop rules.
" T flip-flop logic may only be used if all the inputs to the T are
" internal feedback lines, or guaranteed to be set up several clock
" cycles ahead of the switch (eq a DC control line like EMACC).

Declarations

WAIT_FOR_CMD = [0,0];
    WAIT_FOR_ADD = [0,1];
    WAIT_FOR_DB0 = [1,1];
    WAIT_FOR_DB1 = [1,0];

Equations

"CLOCK GENERATION

CLK12PH.oe = 0;

"CLK12RX is CLK25RX divide-by-2

CLK12RX.clk = CLK25RX;
    CLK12RX := !CLK12RX;

" CLK12PH and CLK25PH are in phase with the RX Taxi output.
" Generate the external flip-flop resets RXCRST.clk = CLK50;
    RXDRST.clk = CLK50;
    RXCRST := RXCSTRB & !RXCRST & !CLK25PH;
    RXDRST := RXDSTRB & !RXDRST & !CLK25PH;

" ******************* Taxi Input Command State Machine ***************

" This MACH decodes Taxi input commands
"     1 = WRITE REGISTER
"     2 = READ REGISTER
" for addresses
```

```
"    36 = MemoryAddress register
"    37 = MemoryData register

" Use the edge of the strobe to clock the Taxi command or data
" into a local buffer " Command data is used to start off state machine, after that it
" may be overwritten by the next command.

" Taxi data may also be overwritten by the next data. However timing
" messages have no data, so it won't be overwritten until the next
" read or write request BUDH.clk  = RXDSTRB;
      BUDL.clk  = RXDSTRB;
      RAD.clk   = RXDSTRB;
      BUC.clk   = RXCSTRB;

BUDH :=  (RXD & (RX_STATE == WAIT_FOR_DB1))
             # (BUDH & (RX_STATE != WAIT_FOR_DB1));
      BUDL :=  (RXD & (RX_STATE == WAIT_FOR_DB0))
             # (BUDL & (RX_STATE != WAIT_FOR_DB0));
      RAD  :=  (RXD & (RX_STATE == WAIT_FOR_ADD))
             # (RAD & (RX_STATE != WAIT_FOR_ADD));
      BUC  := RXC;

" Use the strobe resets to flag when command or data is received

" A state machine decodes the Taxi command and data inputs
" It sets flags for other state machines to handle the received data RX_STATE.clk = CLK50;
      HOSTREAD.clk = CLK50;
      MEMADDR.clk  = CLK50;
      MEMDATA.clk  = CLK50;
      GOWRITE.clk  = CLK50;

State_diagram [RXS1,RXS0]

state WAIT_FOR_CMD:
         if (RXCRST & (BUC == 1) & HMACC & !SNGFRA) " Write req
            then WAIT_FOR_ADD;
         else if (RXCRST & (BUC == 2) & HMACC & !SNGFRA) " Read req
            then WAIT_FOR_ADD;
         else WAIT_FOR_CMD;

state WAIT_FOR_ADD:
         if (RXDRST & (RAD == 36) & !HOSTREAD) " Mem addr write
            then WAIT_FOR_DB0;
         else if (RXDRST & (RAD == 37) & !HOSTREAD) " Mem data write
            then WAIT_FOR_DB0;
         else if RXDRST    " (Decode read addresses in flag logic)
            then WAIT_FOR_CMD;
         else WAIT_FOR_ADD;

state WAIT_FOR_DB0:     " DB0 data buffer loaded in this state
         if RXDRST
            then WAIT_FOR_DB1;
```

```
            else
                WAIT_FOR_DB0;

state WAIT_FOR_DB1:      " DB1 data buffer loaded in this state
            if RXDRST        " Decode this transition to set GOWRITE
                then WAIT_FOR_CMD;
            else
                WAIT_FOR_DB1;

" ***************** IO State Machine **********************************

" This state machine watches for the MEMADDR, MEMDATA and GOWRITE flags
" HOSTREAD indicates the action to be taken. The flags are cleared
" when the read or write is complete (see flag decode logic).
" MEMADDR, MEMDATA and HOSTREAD are set as the information comes in
" from the Taxilink. GOWRITE is set when all the necessary information
" is latched and the write operation can be performed.

Declarations
        WAIT_FOR_FLG   = [0,0,0,0,0];
        WRITE_ADDRESS  = [0,0,0,0,1];
        WRITE_DATA     = [0,0,0,1,1];
        READ_ADDRESS   = [0,0,0,1,0];
        READ_DATA      = [0,0,1,1,0];
        MEMOUT_01      = [1,0,0,0,0];
        MEMOUT_02      = [1,0,0,0,1];
        MEMOUT_03      = [1,0,0,1,1];
        MEMOUT_04      = [1,0,0,1,0];
        MEMOUT_05      = [1,0,1,1,0];
        MEMOUT_06      = [1,0,1,1,1];
        MEMOUT_07      = [1,0,1,0,1];
        MEMOUT_08      = [1,0,1,0,0];
        MEMOUT_09      = [1,1,1,0,0];
        MEMOUT_10      = [1,1,1,1,1];
        MEMOUT_11      = [1,1,1,1,0];
        WRDATA_01      = [0,0,1,1,1];
        WRDATA_02      = [0,0,1,0,1];
        WRDATA_03      = [0,0,1,0,0];
        WRDATA_04      = [0,1,1,0,0];
        WRDATA_05      = [0,1,1,0,1];
        WRDATA_06      = [0,1,1,1,1];
        WRDATA_07      = [0,1,1,1,0];

Equations

IO_STATE.clk  = CLK50;
        MEMADD.clk    = CLK50;
        GAMADS.clk    = CLK50;
        IMMADS.clk    = CLK50;
        NVMADS.clk    = CLK50;
        XCVRDIR.clk   = CLK50;    " A -> B = read, B -> A = write
        XCVRIEN.clk   = CLK50;
        XCVRGHEN.clk  = CLK50;
        XCVRGLEN.clk  = CLK50;
        IMIOSTRB.clk  = CLK50;
        GAIOSTRB.clk  = CLK50;
        INTIO.clk     = CLK50;
        INTIOEN.clk   = CLK50;
        OUTHI.clk     = CLK50;
        ADD.clk       = CLK50;
```

```
       DGEEN.clk    = CLK50;

GAMADS  := IOS4 & GOWRITE & (EMACC&!SNGFRA) &  ADD11;
       IMMADS  := IOS4 & GOWRITE & (EMACC&!SNGFRA) & !ADD11;

INTIO.oe = INTIOEN;
       INTIO   := BUDL & !OUTHI
                # BUDH &  OUTHI;

State_diagram [IOS4,IOS3,IOS2,IOS1,IOS0]

state WAIT_FOR_FLG:
           if (GOWRITE & MEMADDR & !HOSTREAD ) " Write address
              then WRITE_ADDRESS;
           else if (MEMADDR &  HOSTREAD ) " Read address
              then READ_ADDRESS;
           else if (GOWRITE & MEMDATA & !HOSTREAD ) " Write data
              then WRDATA_01
           else if (MEMDATA &  HOSTREAD ) " Read data
              then READ_DATA;
           else WAIT_FOR_FLG;
    state WRITE_ADDRESS:
           goto MEMOUT_01;
    state MEMOUT_01:
           goto MEMOUT_02;
    state MEMOUT_02:
           goto MEMOUT_03;
    state MEMOUT_03:
           goto MEMOUT_04;
    state MEMOUT_04:
           goto MEMOUT_05;
    state MEMOUT_05:
           goto MEMOUT_06;
    state MEMOUT_06:
           goto MEMOUT_07;
    state MEMOUT_07:
           goto MEMOUT_08;
    state MEMOUT_08:
           goto MEMOUT_09;
    state MEMOUT_09:
           goto MEMOUT_10;
    state MEMOUT_10:
           goto MEMOUT_11;
    state MEMOUT_11:
           goto WAIT_FOR_FLG;
    state WRDATA_01:
           goto WRDATA_02;
    state WRDATA_02:
           goto WRDATA_03;
    state WRDATA_03:
           goto WRDATA_04;
    state WRDATA_04:
           goto WRDATA_05;
    state WRDATA_05:
           goto WRDATA_06;
    state WRDATA_06:
           goto WRDATA_07;
    state WRDATA_07:
" write data is complete (no handshake required) so reset everything
```

```
          goto WAIT_FOR_FLG;
    state READ_ADDRESS:
          goto WAIT_FOR_FLG;
" state READ_DATA initiates all the reads but control then transfers
" to the return data strobes, LDIM, LDGA,
" which disable the transceivers when received.
    state READ_DATA:
          goto WAIT_FOR_FLG;

" ************* Control Line Decoding from State Machines ************
"
" Flags.
" MEMADDR, MEMDATA, GOWRITE are used for communication between
" the state machines.
" The flag transitions are decoded from state machine states,
" hence will lag the states by one clock cycle.

Equations

MEMADDR.t = (RX_STATE == WAIT_FOR_ADD) & (RAD == 36) & RXDRST & !MEMADDR
          # (IO_STATE == MEMOUT_11) & MEMADDR
          # (IO_STATE == READ_ADDRESS) & MEMADDR;
MEMDATA.t = (RX_STATE == WAIT_FOR_ADD) & (RAD == 37) & RXDRST & !MEMDATA
          # (IO_STATE == WRDATA_07) & MEMDATA
          # (IO_STATE == READ_DATA) & MEMDATA;
GOWRITE.t = (RX_STATE == WAIT_FOR_DB1) & RXDRST & !GOWRITE
          # (IO_STATE == WRDATA_07) & GOWRITE
          # (IO_STATE == MEMOUT_11) & GOWRITE;

" If it is a memory address register write, catch it and shift it out

ADD11 := BUD11 & (IO_STATE == WRITE_ADDRESS)
              # ADD11 & (IO_STATE != WRITE_ADDRESS);

SHFADDOUT := ADDBITS & (IO_STATE == WRITE_ADDRESS)
                  # SHFADDIN & IOS4 & GOWRITE
                  # SHFADDOUT & !((IO_STATE == WRITE_ADDRESS) # IOS4 & GOWRITE);

" HOSTREAD
" HOSTREAD is used in this device and is also an output to the memory
" controllers to indicate IO direction.

HOSTREAD.t = (RX_STATE == WAIT_FOR_CMD) & (BUC == 2) & RXCRST & !HOSTREAD
              # (RX_STATE == WAIT_FOR_CMD) & (BUC == 1) & RXCRST & HOSTREAD;

"********************** Memory Handshaking ****************************

" Transceiver, strobes and INTIO enable control (memory data IO)
" XCVRDIR, XCVRIEN, XCVRGHEN, XCVRGLEN, INTIOEN, OUTHI
" IMIOSTRB, GAIOSTRB
" There are four cases to consider (read or write to either memory):
"
" ++++++ Image Memory Writes
" One byte transferred. HOSTREAD false. No interlock between strobes.
"
" CLK50   | | | | | | | | | | | | | | | | |
" state   WFF    X 1 X 2 X 3 X 4 X 5 X 6 X 7 X WFF
" XCVRIEN        _____
" INTIOEN        _____
```

```
" INTIO    IIIIIIIIIIIIIVVVVVVVVVVVVVVVVVVVVVIIII
" IHIOSTRB           ____

" ++++++ Image Memory Reads
" One byte transferred. HOSTREAD true. IHIOSTRB and LDIH are interlocked.
" This MACHs cycle is complete when byte is strobed into DOR by LDIH
"
" CLK50    |  |  |  |  |  |  |  |  |  |  |  |  |  |
" state    WFF    X RDX  WFF    -
" HEMDATA  ____--------__-_____
" XCVRIEN  _____--------------------_____
" INTIOEN  _____-_____
" IHIOSTRB _____------------------------
" INTIO    IIIIIIIIIIIIIIIIIIIIIIIII-IIIIVVVVVVVVVIIIIIIIII
" LDIH     _____-___----_____
"                                    ^
"                          INTIO data to DOR (RTEDA MACH)

" ++++++ GA Memory Writes
" Two bytes transferred. HOSTREAD false. No interlock between strobes.
"
" CLK50    |  |  |  |  |  |  |  |  |  |  |  |  |  |
" state    WFF    X 1 X 2 X 3 X 4 X 5 X 6 X 7 X WFF
" XCVRGLEN _____-----------------------_____
" XCVRGEEN _____-----------------------_____
" OUTHI    _____-------------_____
" INTIOEN  _____-----------------------_____
" INTIO    IIIIIIIIIIIIIIILLLLLLLLLLLLLXHHHHHHHHHHIIIII
" GAIOSTRB _____----_____----_____

" ++++++ GA Memory Reads
" Two bytes transferred. HOSTREAD true. GAIOSTRB and LDGA are interlocked.
" This MACHs cycle is complete when bytes are strobed into DOR by LDGA
"
" CLK50    |  |  |  |  -|  |  |  |  |  |  |  |  |  |
" state    WFF    X RDX - WFF
" HEMDATA  ____--------__-_____
" XCVRGLEN _____--  -------_____
" XCVRGEEN _____-_____--------_____
" (DGHEN)  _____-_____--------_____
" INTIOEN  _____-_____
" GAIOSTRB _____--  -------------------_____
" INTIO    ZZZZZZZZZZZZZZLL -LLLLLLZZZHHHHHHHHZZZZZZZZZZZZZZ
" LDGA     _____-_--------------_____
"                        ^            ^
"                 L then H byte INTIO data to DOR (RTEDA MACH)
"                 (timed from LDGA goes high).

XCVRDIR := HOSTREAD;
        DGHEN   := XCVRGHEN;

XCVRIEN.t = (IO_STATE == WRDATA_01) & !ADD11 & !XCVRIEN
                  # (IO_STATE == READ_DATA) & !ADD11 & !XCVRIEN
```

```
            # (IO_STATE == WRDATA_07) & XCVRIEN
            # LDIH & XCVRIEN
            # PURST & XCVRIEN;

XCVRGLEN.t = (IO_STATE == WRDATA_01) & ADD11 & !XCVRGLEN
           # (IO_STATE == READ_DATA) & ADD11 & !XCVRGLEN
           # (IO_STATE == WRDATA_07) & XCVRGLEN
           # LDGA & XCVRGLEN
           # PURST & XCVRGLEN;

XCVRGHEN.t = (IO_STATE == WRDATA_01) & ADD11 & !XCVRGHEN   "Wr
           # LDGA & !XCVRGLEN & !XCVRGHEN & GAIOSTRB        "Re
           # (IO_STATE == WRDATA_07) & XCVRGHEN
           # DGHEN & XCVRGHEN & HOSTREAD
           # PURST & XCVRGHEN;

INTIOEN.t  = (IO_STATE == WRDATA_01) & !INTIOEN
           # (IO_STATE == WRDATA_07) & INTIOEN;

IHIOSTRB.t = (IO_STATE == WRDATA_02) & !ADD11 & !IHIOSTRB
           # (IO_STATE == WRDATA_03) & IHIOSTRB
           # (IO_STATE == READ_DATA) & !ADD11 & !IHIOSTRB
           # LDIH & IHIOSTRB;

GAIOSTRB.t = (IO_STATE == WRDATA_02) & ADD11 & !GAIOSTRB
           # (IO_STATE == WRDATA_03) & GAIOSTRB
           # (IO_STATE == WRDATA_05) & ADD11 & !GAIOSTRB
           # (IO_STATE == WRDATA_06) & GAIOSTRB
           # (IO_STATE == READ_DATA) & ADD11 & !GAIOSTRB
           # LDGA & DGHEN & GAIOSTRB;

OUTHI.t    = (IO_STATE == WRDATA_04) & !OUTHI
           # (IO_STATE == WRDATA_07) & OUTHI;

Test_vectors(
[CLK50,RXC,RXD,RXCSTRB,RXDSTRB,CLK25PH,HHACC]
                                    ->[BUC,RX_STATE,RXCRST,RXDRST])

[.c., 0, 0, 0,   0,   0,   0] ->[0,WAIT_FOR_CMD,0,0];
[0,   1, 0, 1,   0,   1,   0] ->[1,WAIT_FOR_CMD,0,0];
[0,   1, 0, 1,   0,   0,   0] ->[1,WAIT_FOR_CMD,0,0];
[0,   1, 0, 1,   0,   1,   0] ->[1,WAIT_FOR_CMD,0,0];
[.c., 1, 0, 1,   0,   0,   0] ->[1,WAIT_FOR_CMD,1,0];
[.c., 1, 0, 0,   0,   1,   0] ->[1,WAIT_FOR_ADD,0,0];
[.c., 0, 0, 0,   0,   0,   0] ->[1,WAIT_FOR_ADD,0,0];

END
```

```
module rtectr title 'ALIGNMENT COUNTERS
      Ver. 0; 8/5/94'
      ElURO device 'I1032T08';

"inputs
      I1..I12 pin 35,80,84,68,90,87,36,83,22,40,30,81;
      DD1..DD12 pin 44,45,46,47,48,53,54,55,56,57,58,59;
      CGATE pin 93;
      FMHZ pin 62;
      SEL0,SEL1,SEL2,SEL3 pin 29,67,33,32;
      OE_,DIAG pin 78,69;
      TCLK pin 70;

"outputs
      O1..O12 pin 92,91,96,95,73,72,23,34,42,41,19,18 istype 'reg_D,buffer';
      S0..S8 pin 97,98,3,4,5,6,7,8,9 istype 'reg_D,buffer';

"nodes
      CA0..CA6 node istype 'reg_T,buffer';
      CB0..CB6 node istype 'reg_T,buffer';
      CC0..CC6 node istype 'reg_T,buffer';
      EA0..EA2 node istype 'reg_D,buffer';
      EB0..EB2 node istype 'reg_D,buffer';
      EC0..EC2 node istype 'reg_D,buffer';
      _I1.._I12 node istype 'reg_D,buffer';
      FSCY1,FSCY2,FSCY3,FSCY4,SCY1,SCY2,SCY3 node;
      FS0..FS7,V1..V12,SCLK node;
      CGATEL,CAOVF,CBOVF,CCOVF node istype 'reg_D,buffer';

PLSI PROPERTY 'TRY 3';
      PLSI PROPERTY 'ISP ON';
      PLSI PROPERTY 'PULLUP ON';
      PLSI PROPERTY 'STRONG_ROUTE EXTENDED';
      PLSI PROPERTY 'CLK SCLK CLK1';
      PLSI PROPERTY 'CLK FMHZ CLK2';

"constants
      H,L,X,C,Z = 1,0,.X.,.C.,.Z.;
      SEL = [SEL3..SEL0];
      S = [S8..S0];
      FS = [FS7..FS0];
      EA = [EA2..EA0];
      EB = [EB2..EB0];
      EC = [EC2..EC0];
      CA = [CA6..CA0];
      CB = [CB6..CB0];
      CC = [CC6..CC0];
      I = [I1..I12];
      IR = [I4..I1,I8..I5,I12..I9];
      O = [O1..O12];
      DD = [DD1..DD12];
      V = [V1..V12];
      FF = [V,EA,EB,EC,CA,CB,CC,O,_I,CGATEL,CAOVF,CBOVF,CCOVF];
      VA1 = [0,0,V1];
      VA2 = [0,0,V2];
      VA3 = [0,0,V3];
      VA4 = [0,0,V4];
      VB1 = [0,0,V5];
```

```
        VB2 = [0,0,V6];
        VB3 = [0,0,V7];
        VB4 = [0,0,V8];
        VC1 = [0,0,V9];
        VC2 = [0,0,V10];
        VC3 = [0,0,V11];
        VC4 = [0,0,V12];

ADD macro (Y,A,B,I,O)
            (?Y = ?A+?B+[0,?I];
             ?O = !?I&((?A==3)&(?B>=1) # (?A==2)&(?B>=2) # (?A==1)&(?B==3)) #
                  ?I&((?A==3) # (?A==2)&(?B>=1) # (?A==1)&(?B>=2) # (?B==3));}

RADD macro (Y,A,B,I,O)
            (?Y := ?A+?B+[0,?I];
             ?O = !?I&((?A==3)&(?B>=1) # (?A==2)&(?B>=2) # (?A==1)&(?B==3)) #
                  ?I&((?A==3) # (?A==2)&(?B>=1) # (?A==1)&(?B>=2) # (?B==3));}

RRADD macro (Y,A,B,I,O)
            (?Y := ?A+?B+[0,?I];
             ?O := !?I&((?A==3)&(?B>=1) # (?A==2)&(?B>=2) # (?A==1)&(?B==3)) #
                   ?I&((?A==3) # (?A==2)&(?B>=1) # (?A==1)&(?B>=2) # (?B==3));}

COUNT macro (C,E)
            (?C.t = CGATE&CGATEL&!?COVF&((?C$(?C+1))&(?E==1) #
                    (?C$(?C+2))&(?E==2) # (?C$(?C+3))&(?E==3) #
                    (?C$(?C+4))&(?E==4)) # ?C&CGATE&!CGATEL;
             ?COVF := (?C>=120)&CGATE&CGATEL&!(?E==0) #
                      ?COVF&!(SCLK);} equations
"CLOCK GENERATION

FF.clk = FMH3;
        SCLK = CGATE&!CGATEL;
        _I := I;
        O := (I$_I)&!DIAG # DD&DIAG&TCLK;
        V := O&([(SEL==0),(SEL==1),(SEL==2),(SEL==3),(SEL==4),(SEL==5),(SEL==6),
            (SEL==7),(SEL==8),(SEL==9),(SEL==10),(SEL==11)] # (SEL==15));

"ENCODES

EA0 := (VA1+VA2+VA3+VA4 == [0,0,1]) # (VA1+VA2+VA3+VA4 == [0,1,1]);
        EA1 := (VA1+VA2+VA3+VA4 == [0,1,0]) # (VA1+VA2+VA3+VA4 == [0,1,1]);
        EA2 := (VA1+VA2+VA3+VA4 == [1,0,0]);

EB0 := (VB1+VB2+VB3+VB4 == [0,0,1]) # (VB1+VB2+VB3+VB4 == [0,1,1]);
        EB1 := (VB1+VB2+VB3+VB4 == [0,1,0]) # (VB1+VB2+VB3+VB4 == [0,1,1]);
        EB2 := (VB1+VB2+VB3+VB4 == [1,0,0]);

EC0 := (VC1+VC2+VC3+VC4 == [0,0,1]) # (VC1+VC2+VC3+VC4 == [0,1,1]);
        EC1 := (VC1+VC2+VC3+VC4 == [0,1,0]) # (VC1+VC2+VC3+VC4 == [0,1,1]);
        EC2 := (VC1+VC2+VC3+VC4 == [1,0,0]);

"COUNTERS
        CGATEL := CGATE;
        COUNT (CA,EA);
        COUNT (CB,EB);
        COUNT (CC,EC);
```

```
"adder
    ADD ([FS1,FS0],[CA1,CA0],[CB1,CB0],0,FSCY1);
    ADD ([FS3,FS2],[CA3,CA2],[CB3,CB2],FSCY1,FSCY2);
    ADD ([FS5,FS4],[CA5,CA4],[CB5,CB4],FSCY2,FSCY3);
    ADD ([FS7,FS6],[0,CA6],[0,CB6],FSCY3,FSCY4);

RADD ([S1,S0],[CC1,CC0],[FS1,FS0],0,SCY1);
    RADD ([S3,S2],[CC3,CC2],[FS3,FS2],SCY1,SCY2);
    RADD ([S5,S4],[CC5,CC4],[FS5,FS4],SCY2,SCY3);
    RRADD ([S7,S6],[0,CC6],[FS7,FS6],SCY3,S8);
    S.oe = !OE_;
    S.clk = SCLK;

END
```

```
module rtegae title 'GAIN AND ALIGNMENT ENGINE
       Ver. 0; 8/11/94'
       R1U58R0 device 'MACH435A';

"inputs
    MAD,MAS,VSYNC_,HSYNC_,CGATE,CSYNC pin 3,4,6,7,41,8;
    SUM0..SUM2 pin 10,12,13;
    HACC,HRD,HSTB,ALNSEL,GACYC,DIAG,FSDIAG,VDIAG pin 15,17,18,24,25,27,28,29;
    FMHZ pin 65;
    EXTCLK pin 83;

"outputs
    BSY,WE_,OE_,CS1_,CS2_,!ALUENA,!ALUENB,ALUOE_,!ALUSB pin 31,34,35,36,37,70,69,71,73 istype 'reg_D,buffer';
    GOE0_,GOE1_,GOE2_,GOE3_,GOE4_,GOE5_,GOE6_,GOE7_ pin 75,76,77,78,79,80,81,82 istype 'reg_D,buffer';
    TCLK,LDGA pin 40,19 istype 'reg_D,buffer';
    TFMHZ pin 68 istype 'reg_D,buffer';
    SEL0..SEL3 pin 72,5,30,26;
    AC0..AC17 pin 45,46,47,48,49,50,51,52,54,55,56,57,58,59,60,61,66,67 istype 'reg_T,buffer';

"nodes
    DC0..DC4,T0,T1,TGC0..TGC4 node istype 'reg_T,buffer';
    HIGH,CNTACA,CNTACB,CNTACCD,RSTACAB,RSTACCD node istype 'reg_D,buffer';
    MCYCLE,LDSC,CNTSC,CNTDC,RSTDC,_FRAME node istype 'reg_D,buffer';
    FRAME pin 9 istype 'reg_D,buffer';
    SC0..SC1 pin 16,14 istype 'reg_T,buffer';
    SC2..SC6 node istype 'reg_T,buffer';
    _GACYC,_CGATE,_VSYNC_,_HSYNC_,_HSTB,_CSYNC node istype 'reg_D,buffer';
    CYB,CYC node;
    _CGLE2.._CGLE0 node istype 'reg_D,buffer';
    HOLDOFF node istype 'reg_D,buffer';

"constants
       H,L,X,C,Z = 1,0,.X.,.C.,.Z.;
       ACA = [AC2..AC0];
       ACB = [AC6..AC3];
       ACC = [AC12..AC7];
       ACD = [AC17..AC13];
       AC = [ACD,ACC,ACB,ACA];
       ACCS = [AC11..AC7,MAD];
       ACDS = [AC16..AC12];
       T = [T1,T0];
       SUM = [SUM2..SUM0];
       DC = [DC4..DC0];
       TGC = [TGC4..TGC0];
       GOE_ = [GOE0_,GOE1_,GOE2_,GOE3_,GOE4_,GOE5_,GOE6_,GOE7_];
       SEL = [SEL3..SEL0];
       SC = [SC6..SC0];
       _CGLE = [_CGLE2.._CGLE0];
       FF = [BSY,WE_,OE_,CS1_,CS2_,ALUENA,ALUENB,ALUOE_,ALUSB,GOE_,TCLK,LDGA,
             AC,DC,SC,T,TGC,HIGH,MCYCLE,CNTACA,CNTACB,CNTACCD,RSTACAB,
             RSTACCD,LDSC,CNTSC,CNTDC,RSTDC,_GACYC,_CGATE,_VSYNC_,_HSYNC_,
             _HSTB,_CSYNC,TFMHZ,FRAME,_FRAME,_CGLE,HOLDOFF];
       CGTE = !CGATE&_CGATE;
       CGLE = CGATE&!_CGATE;
       SBSY = GACYC&!_GACYC;
       FTE = !FRAME&_FRAME;
       FLE = FRAME&!_FRAME;
       HSTE = HSYNC_&!_HSYNC_;
```

```
VSTE = VSYNC_&!_VSYNC_;
HSLE = !HSYNC_&_HSYNC_;
VSLE = !VSYNC_&_VSYNC_;
HSTBTE = HACC&!HSTB&_HSTB;
CSTE = !CSYNC&_CSYNC;
V0   = [0,0,0,0,0,0,0];
V1   = [0,0,0,0,0,0,1];
V3   = [0,0,0,0,0,1,1];
V7   = [0,0,0,0,1,1,1];
V15  = [0,0,0,1,1,1,1];
V31  = [0,0,1,1,1,1,1];
V63  = [0,1,1,1,1,1,1];
V127 = [1,1,1,1,1,1,1];

"OVERALL ALIGNMENT CYCLE
"CGATE  __--__--__--__--        __--__--__--__--
"VSYNC  --_____--------_____--------____
"FRAME  ____------------_____------_____------
"SUM    11111111111111110000000000000000000000
"BSY    _--------------------------------_____

"OVERALL CALIBRATION CYCLE
"CGATE  __--__--__--__--            __--__--__--__--     __--__--__--
"BSY    _--------------------------------  ----------------
"CSYNC  ___--_____--___           __--
"FRAME  ____--------_____--------____           ____--------
"SUM    1111110000000000000000111111000000000    000001111110000000000
"SEL    0000000000000111111111111111111122222    1111111111111111
"                                                1111111111111112222

"FRAME TIMING
"FM3    ||||||||||||||||||||||||||||||||||||||||||||||||||
"TFM3   _-_-_-_-_-_-_-_-_-_-_-_-_-_-_-_-_-_-_-_-_-_-_-_-_
"TWM3   __--__--__--__--__--__--__--__--__--__--__--__--
"CGATE  -----_____------------------------------------_____
"_CGATE-----_____------------------------------------_____
"FRAME  ____--------------------------------------------_____
"MCYCLE ____--------------------------------------------_____
"T           001122001122001122001122001122001122001122001122
"OE          __  --__  --__  --__  --__  --__  --__  --__  --
"WE          _-    _-    _-    _-    _-    _-    _-    _-
"GOE0        ---
"GOE1             ---
"ENA/B       _-  _-  _-  _-  _-  _-  _-  _-
"ALUOE       --  --  --  --  --  --  --  --
"ADDRESS-----___0___---1---___2___---3---___4___---5---___6___---7---
"ACNT         _-  _-  _-  _-  _-  _-  _-  _-

"HOST READ/WRITE
"HAS    -----------_
"HAD    _19876543210---
"           0
"HHACC   _____--------------------____---------------_____
"HWRD    _____--------_____--------_____
"HSTB    _____------___---_____---------_____
"LDGA    _____--------_____
"HIGH    _____------------_____
"CS1     _____------_____----------_____
"CS2     _____------_____----------_____
```

```
"OE   ──────────────────────────  ──────────
"WE   ──────────────────  ──────  ──────────
"ACNT ────────────────────────────    ──  ──
``` equations

"CLOCK GENERATION

FF.clk = FMHZ;
    TFMHZ := !TFMHZ&!CGLE;

"TIMING CONTROL

_GACYC := GACYC;
    _CGATE := CGATE;
    _VSYNC_ := VSYNC_;
    _HSYNC_ := HSYNC_;
    _ESTB := ESTB;
    _FRAME := FRAME;
    _CSYNC := CSYNC;
" HOLDOFF holds off start of first FRAME until the start of a VSYNC_
    HOLDOFF := SBSY # HOLDOFF&!VSYNC_;
    BSY := GACYC&(SBSY # BSY&!(ALNSEL&FTE&(SC==0) # !ALNSEL&FTE&(ACB==11)));
    FRAME := BSY&(CGTE&ALNSEL&!VSYNC_&!HOLDOFF # !ALNSEL&CSTE #
              FRAME&!(CGTE&(ALNSEL&VSYNC_ # !ALNSEL&CGTE&(SC==0))));

"MEMORY CONTROL

MCYCLE := FRAME&(CGLE # MCYCLE& !((ACA==7)&!WE_) );
    T.t = (T$(T+1))&MCYCLE&TFMHZ # T&!MCYCLE;
    !OE_ := MCYCLE&(T==0) # HACC&HSTB&HRD;
    !WE_ := MCYCLE&(T==2)&!TFMHZ # HACC&HSTB&!HRD;
    !GOE0_ := FRAME&(CGLE # !GOE0_&!(ALUENA));
    !GOE1_ := MCYCLE&(!WE_&(ACA==0) # !GOE1_&!(ALUENA));
    !GOE2_ := MCYCLE&(!WE_&(ACA==1) # !GOE2_&!(ALUENA));
    !GOE3_ := MCYCLE&(!WE_&(ACA==2) # !GOE3_&!(ALUENA));
    !GOE4_ := MCYCLE&(!WE_&(ACA==3) # !GOE4_&!(ALUENA));
    !GOE5_ := MCYCLE&(!WE_&(ACA==4) # !GOE5_&!(ALUENA));
    !GOE6_ := MCYCLE&(!WE_&(ACA==5) # !GOE6_&!(ALUENA));
    !GOE7_ := MCYCLE&(!WE_&(ACA==6) # !GOE7_&!(ALUENA));
    ALUENA := MCYCLE&!OE_&!ALUENA;
    ALUENB := MCYCLE&!OE_&!ALUENA;
    !ALUOE_ := MCYCLE&((T==1)&TFMHZ # (T==2)&!TFMHZ);
    ALUSB := ALNSEL&(SBSY # ALUSB&!(FTE)) # !ALNSEL&(FLE # ALUSB&!(CGTE));
    !CS1_ := MCYCLE # HACC&HSTB&(HRD # !HRD&!HIGH);
    !CS2_ := MCYCLE # HACC&HSTB&(HRD # !HRD&HIGH);

LDCA := HACC & HRD & HSTB & !CS1_;

"ADDRESS COUNTER
" *** Gain Cycle
" *** Alignment Cycle
" least significant 3 bits count up during !CGATE so eight addresses are
" written each hole. Most significant bits count CGATEs. LSBs reset
" every CGATE. MSBs reset every frame.
" *** Host IO
" least significant 7 bits count up every read or write operation
" most significant 11 bits are loaded when strobed in by MAS ACA.t = (ACA$(ACA+1))&CNT&ACA&!RST&ACAB # ACA&RST&ACAB;

```
CNTACA := MCYCLE&!WE_ # !ERD&HSTM&&HIGH # ERD&HSTBTE;
ACB.t = (ACB$(ACB+1))&CNTACB&!RSTACAB # ACB&RSTACAB;
CNTACB := !ALNSEL&FTE # ALNSEL&FRAME&CGTE # HSTBTE&(ACA==7)&(!ERD&HIGH # ERD);
CYB = (ACB==15);
ACC.t = (ACC$(ACC+1))&CYB&CNTACCD&!RSTACCD # ACC&RSTACCD # (ACC$ACCS)&HAS;
CYC = (ACC==63);
ACD.t = (ACD$(ACD+1))&CYC&CYB&CNTACCD&!RSTACCD # ACD&RSTACCD # (ACD$ACDS)&HAS;
CNTACCD := ALNSEL&FRAME&CGTE;
RSTACAB := !ALNSEL&SBSY # ALNSEL&FLE # MAS;
RSTACCD := !ALNSEL&SBSY # ALNSEL&FLE;
HIGH := HSTBTE&!HRD&!HIGH # HIGH&!(!HRD&HSTBTE # MAS);

" SENSOR SELECTS

SEL = ACB&!ALNSEL # [1,1,1,1]&ALNSEL;

"SUM COUNTER

SC.t = (SC$(SC-1))&CNTSC # ((V0&(SUM==0)#V1&(SUM==1)#V3&(SUM==2)#
           V7&(SUM==3)#V15&(SUM==4)#V31&(SUM==5)#V63&(SUM==6)#
           V127&(SUM==7)}$SC)&LDSC;
    CNTSC := ALNSEL&FTE # !ALNSEL&FRAME&CGTE;
    LDSC := ALNSEL&SBSY # !ALNSEL&CSYNC;

"DIAGNOSTIC CONTROLLER

"OVERALL TIMING
    "VSYNC_  --_____----_____------
    "HSYNC_  --_-___-___-___-___------___-___-___-___----
    "CGATE         -_-_-_-_-_-_-_-_-_      -_-_-_-_-_-_-_-
    "VDIAG   _____-------------------------------
    "DC      00000011111122222233333    001111001111001111001111

CGATE TIMING
    "FME2   ||||||||||||||||||||||||||||||||||||||||||||||||||||||||||||
    "CGATE  _____---------------------_____
    "CGLE   _____-_____
    "TGC    xxxxxxxxxx3210
    "TGATE  _____---_____

" Delay CGLE so it doesn't occur during VSLE and HSLE resets
_CGLE0 := CGLE;
_CGLE1 := _CGLE0;
_CGLE2 := _CGLE1;
DC.t = (DC$(DC+1))&CNTDC # DC&RSTDC;
CNTDC := VDIAG&CGTE # !VDIAG&HSTE;
RSTDC := VSLE # VDIAG&HSLE;
TGC.t := (TGC$(TGC-1))&TCLK # (DC$TGC)&_CGLE1;
TCLK := EXTCLK # DIAG&FSDIAG&CGATE&(_CGLE2&!(DC==0) # TCLK&!(TGC==1));

END
```

```
module rtestr title 'STRING COUNTERS
      Ver. 0; 8/4/94'
        E1UR02 device 'I1032T08';

"inputs
        FMHZ pin 62;
        IA0..IA7 pin 67,68,69,70,71,72,73,78;
        IB0..IB7 pin 90,91,92,93,94,95,96,97;
        MOVE,CGATE,RST,CLR pin 29,54,8,9;
        CL1..CL8 pin 84,82,32,30,59,5,53,86;
        SELIN pin 7;
        SELIA,SELIB,SECOND pin 56,57,10;

"outputs
        POA0..POA7 pin 17,18,19,20,21,22,23,28 istype 'reg_D,buffer';
        POB0..POB7 pin 40,41,42,43,44,45,46,47 istype 'reg_D,buffer';
        SELOUT pin 33 istype 'reg_D,buffer';

"i/o's

"nodes
        CA0..CA6 node istype 'reg_T,buffer';
        CB0..CB6 node istype 'reg_T,buffer';
        CC0..CC6 node istype 'reg_T,buffer';
        CD0..CD6 node istype 'reg_T,buffer';
        CE0..CE6 node istype 'reg_T,buffer';
        CF0..CF6 node istype 'reg_T,buffer';
        CG0..CG6 node istype 'reg_T,buffer';
        CH0..CH6 node istype 'reg_T,buffer';
        PIA0..PIA6,PIB0..PIB6 node istype 'reg_D,buffer';
        CA7,CB7,CC7,CD7,CE7,CF7,CG7,CH7 node istype 'reg_T,buffer';
        PIA7,PIB7 node istype 'reg_D,buffer';
        _CLA,_CLB,_CLC,_CLD,_CLE,_CLF,_CLG,_CLH node istype 'reg_D,buffer';
        OVFA,OVFB,OVFC,OVFD,OVFE,OVFF,OVFG,OVFH node istype 'reg_D,buffer';
        SEL,T1,T2,_MOVE node istype 'reg_D,buffer';

PLSI PROPERTY 'TRY 3';
        PLSI PROPERTY 'Y1_AS_RESET OFF';
        PLSI PROPERTY 'ISP ON';
        PLSI PROPERTY 'PULLUP ON';
        PLSI PROPERTY 'STRONG_ROUTE EXTENDED';
        PLSI PROPERTY 'CLK FMHZ CLK2';

"constants
        H,L,X,C,Z = 1,0,.X.,.C.,.Z.;
        CA = [CA7..CA0];
        CB = [CB7..CB0];
        CC = [CC7..CC0];
        CD = [CD7..CD0];
        CE = [CE7..CE0];
        CF = [CF7..CF0];
        CG = [CG7..CG0];
        CH = [CH7..CH0];
        CAS = [CA6..CA0,PIA7];
        CBS = [CB6..CB0,CA7];
        CCS = [CC6..CC0,CB7];
        CDS = [CD6..CD0,CC7];
        CES = [CE6..CE0,PIB7];
```

```
         CFS = [CF6..CF0,CE7];
         CGS = [CG6..CG0,CF7];
         CHS = [CH6..CH0,CG7];
         PIA = [PIA7..PIA0];
         POA = [POA7..POA0];
         IA  = [IA7..IA0];
         IB  = [IB7..IB0];
         PIB = [PIB7..PIB0];
         POB = [POB7..POB0];
         PIAS = [PIA6..PIA0,0];
         POAS = [POA6..POA0,CD7];
         PIBS = [PIB6..PIB0,0];
         POBS = [POB6..POB0,CH7];
         CL = [CL1..CL8];
         _CL = [_CLA,_CLB,_CLC,_CLD,_CLE,_CLF,_CLG,_CLH];
         OVF = [OVFA,OVFB,OVFC,OVFD,OVFE,OVFF,OVFG,OVFH];
         FF = {CA,CB,CC,CD,CE,CF,CG,CH,PIA,PIB,POA,POB,OVF,SEL,_CL,T1,T2,SELOUT,_MOVE};

count MACRO (Q) {C?Q.t = (C?QS(C?Q+1))&_CL?Q&CGATE&!OVF?Q #
                                                (C?QSC?QS)&MOVE;
                    OVF?Q := (C?Q==254)&_CL?Q&CGATE # (C?Q==255) # OVF?Q&!(_MOVE);};

equations

"CLOCK GENERATION

FF.clk := FMHZ;

"COUNTERS

_CL := CL;
         _MOVE := MOVE;
         count (A);
         count (B);
         count (C);
         count (D);
         count (E);
         count (F);
         count (G);
         count (H);

"REGISTERS

"FMHZ  ||||||||||||||||||||||||||||||||||
"SECOND--------_____
"SELIN  -_____-----___
"SEL     ----___-----___
"SELOUT____-__
"T1       _-_
"T2       ___-___

SEL := SELIN # SECOND&SEL&!(SELOUT);
         T1 := SEL&!T1&!T2&!SELOUT;
         T2 := T1;
         SELOUT := T2;
         POA := POAS.fb&MOVE # POA.fb&!MOVE;
```

```
POA.oe = SEL;
POB := POBS.fb&MOVE # POB.fb&!MOVE;
POB.oe = SELIA;
PIA := IA&SELIA # PIAS&MOVE # PIA&!SELIA&!MOVE;
PIB := IB&SELIB # PIBS&MOVE # PIB&!SELIB&!MOVE;
PIA.AR = CLR;
PIB.AR = CLR;

END
```

```
module rteime title 'Real Time Eye Image Control
      Ver. 0;  9-14-94'
      R1U59R0 device 'MACH435A';
"     9/27/94 Changed OUTCNT so all bits reset when TOKEN
"     9/27/94 Fixed error in PARAD16 and PARAD17
"     9/28/94 Change to PIX488 so any length line can be sent
"     9/28/94 Changed HVAL to latch at 4 instead of 3
"     9/29/94 Added reset term to PARAD0
"     10/13/94 Changed OFIFS0 and OFIFS2 because sync scheme changed.
"     10/21/94 Removed sync bits at EOF "inputs
      CLK50_5 pin 65;
      SNGFRA,EMACC,MEMADD,IMHADS pin 3,4,5,6;
      VSYNC,HSYNC,CGATEO pin 8,41,83;
      EOSTREAD,IHIOSTRB pin 77,78;

"outputs
      IMBSY,!IHWE pin 45,82 istype 'reg_T,buffer';
      LDIH,OFIFS0,OFIFS2 pin 76,46,47 istype 'reg_D,buffer';
      !OFIFWE0,!OFIFWE1,!OFIFWE2 pin 48,49,50 istype 'reg_D,invert';
      SERAD0..SERAD6 pin 13..19 istype 'reg_T,buffer';
      SERAD7..SERAD17 pin 24..31,54,55,56 istype 'reg_D,buffer';
      PARAD0..PARAD8 pin 52,73,72,71,70,69,68,67,66 istype 'reg_T,buffer';
      PARAD9..PARAD17 pin 51,33..40 istype 'reg_T,buffer';
      !IHOE,!PRE,!PRES pin 81,79,80;

"nodes
      BSNGFRA,BCGATEO,BIHIOSTRB node istype 'reg_D,buffer';
      PX488,PIX488,TOKEN node istype 'reg_D,buffer';
      LINE0,LINE1 node istype 'reg_T,buffer';
      OUTCNT0..OUTCNT5 node istype 'reg_T,buffer';
      HVAL0,HVAL1,HVAL2 pin istype 'reg_T,buffer';
      VVAL0,VVAL1 node istype 'reg_T,buffer';

"constants
      H,L,X,C,Z = 1,0,.X.,.C.,.Z.;
      PARADR = [PARAD17..PARAD9];
      PARADC = [PARAD8..PARAD0];
      SERAD  = [SERAD17..SERAD0];
      LINE   = [LINE1..LINE0];
      HVAL   = [HVAL2..HVAL0];
      VVAL   = [VVAL1..VVAL0];
      OUTCNT = [OUTCNT5..OUTCNT0];

"macros
      PIX0 macro ( !PARAD8 & !PARAD7 & !PARAD6 & !PARAD5 & !PARAD4 &
                   !PARAD3 & !PARAD2 & !PARAD1 & !PARAD0 );
      LNE0 macro ( !PARAD17 & !PARAD16 & !PARAD15 & !PARAD14 &
                   !PARAD13 & !PARAD12 & !PARAD11 & !PARAD10 & !PARAD9 );
      LINE488 macro ( PARAD17 & PARAD16 & PARAD15 & PARAD14 & !PARAD13 &
                      PARAD12 & !PARAD11 & !PARAD10 & !PARAD9 );
      INCPIX macro ( LINE1 & OUTCNT1 & OUTCNT0 & !PIX488 );
      LASTPIX macro ( LINE1 & OUTCNT1 & OUTCNT0 & PIX488 );
      INCLINE macro ( (!LINE1 # LINE1&PIX488) & OUTCNT1 & OUTCNT0 );
      DECLINE macro ( LINE1 & OUTCNT1 & OUTCNT0 & !PIX488 );

AHDMACH property 'GROUP A HVAL2 HVAL1 HVAL0 VVAL1 VVAL0 BCGATEO BSNGFRA TOKEN';
```

```
AMDMACH property 'GROUP B BIHIOSTRB';
AMDMACH property 'GROUP D OUTCNT5 OUTCNT4 OUTCNT3 OUTCNT2 OUTCNT1 OUTCNT0';
AMDMACH property 'GROUP E LINE1 LINE0';
AMDMACH property 'GROUP G PIX488 PX488';

equations

BCGATE0.ar   = VSYNC & HSYNC & !CGATE0;
BCGATE0.ap   = 0;
BCGATE0.clk  = CLK50_5;

BIHIOSTRB.ar  = 0;
BIHIOSTRB.ap  = 0;
BIHIOSTRB.clk = CLK50_5;

BSNGFRA.ar   = VSYNC & HSYNC & !CGATE0;
BSNGFRA.ap   = 0;
BSNGFRA.clk  = CLK50_5;

HVAL.ar      = VSYNC & HSYNC & !CGATE0;
HVAL.ap      = 0;
HVAL.clk     = CLK50_5;

VVAL.ar      = VSYNC & HSYNC & !CGATE0;
VVAL.ap      = 0;
VVAL.clk     = CLK50_5;

PIX488.ar    = VSYNC & HSYNC & !CGATE0;
PIX488.ap    = 0;
PIX488.clk   = CLK50_5;

PX488.ar     = VSYNC & HSYNC & !CGATE0;
PX488.ap     = 0;
PX488.clk    = CLK50_5;

TOKEN.ar     = VSYNC & HSYNC & !CGATE0;
TOKEN.ap     = 0;
TOKEN.clk    = CLK50_5;

LINE.ar      = VSYNC & HSYNC & !CGATE0;
LINE.ap      = 0;
LINE.clk     = CLK50_5;

OUTCNT.ar    = VSYNC & HSYNC & !CGATE0;
OUTCNT.ap    = 0;
OUTCNT.clk   = CLK50_5;

IMWE.ar      = 0;
IMWE.ap      = 0;
IMWE.clk     = CLK50_5;

OFIFS0.ar    = VSYNC & HSYNC & !CGATE0;
OFIFS0.ap    = 0;
OFIFS0.clk   = CLK50_5;

OFIFS2.ar    = VSYNC & HSYNC & !CGATE0;
OFIFS2.ap    = 0;
OFIFS2.clk   = CLK50_5;
```

```
OFIFWE0.ar    = VSYNC & HSYNC & !CGATE0;
OFIFWE0.ap    = 0;
OFIFWE0.clk   = CLK50_5;

OFIFWE1.ar    = VSYNC & HSYNC & !CGATE0;
OFIFWE1.ap    = 0;
OFIFWE1.clk   = CLK50_5;

OFIFWE2.ar    = VSYNC & HSYNC & !CGATE0;
OFIFWE2.ap    = 0;
OFIFWE2.clk   = CLK50_5;

PARADR.ar     = VSYNC & HSYNC & !CGATE0;
PARADR.ap     = 0;
PARADR.clk    = CLK50_5;

PARADC.ar     = VSYNC & HSYNC & !CGATE0;
PARADC.ap     = 0;
PARADC.clk    = CLK50_5;

SERAD.ar      = 0;
SERAD.ap      = 0;
SERAD.clk     = CLK50_5;

IMBSY.ar      = VSYNC & HSYNC & !CGATE0;
IMBSY.ap      = 0;
IMBSY.clk     = CLK50_5;

LDIH.ar       = 0;
LDIH.ap       = 0;
LDIH.clk      = CLK50_5;
```

" Buffered signals for triggering on edges of signals.

```
BCGATE0   := CGATE0;
BIHIOSTRB := IHIOSTRB;
BSNGFRA   := SNGFRA;
```

" VVAL[0..1] counts the number of lines completed at the completion of
"   CGATE0 after HSYNC has become true. The count latches at 3 to allow data
"   storage.  VVAL is reset to zero at the end of each frame.

```
VVAL0.t = HSYNC & !CGATE0 & BCGATE0 & !(VVAL1 & VVAL0);
VVAL1.t = HSYNC & !CGATE0 & BCGATE0 & VVAL0 & !VVAL1;
```

" After VVAL[0..1] has latched at 3 it enables the HVAL[2..0] counter to count
"   the completion of the first three holes on each line and to latch at 4.
"   When VVAL is 3 and HVAL is 4, data is then stored in the image memory and
"   the output FIFO's. HVAL is reset to zero at the end of each line.

" HVAL0.t = VVAL0&VVAL1&!HSYNC&!CGATE0&BCGATE0&!(HVAL1&HVAL0) # LASTPIX&HVAL0;
" HVAL1.t = VVAL0&VVAL1&!HSYNC&!CGATE0&BCGATE0&!HVAL1&HVAL0 # LASTPIX&HVAL1;

HVAL.t=(HVAL$(HVAL+1))&VVAL0&VVAL1&!HSYNC&!CGATE0&BCGATE0&(HVAL<4)#LASTPIX&HVAL;

" During single frame mode IMBSY is set until the complete frame is stored.

IMBSY.t = SNGFRA&!BSNGFRA | IMBSY&LASTPIX&LINE488;

" The output of the scaling PROM is asynchronously disabled during a host
"    memory access.

PRES = 1;
PRE  = !HMACC;

" The 20 nsec TOKEN signal is generated at the beginning of each CGATEO
"    period for which valid data is to be stored, i.e when both VVAL and HVAL
"    are 3.

TOKEN := CGATEO&!BCGATEO & HVAL2;

" OUTCOUNT[0..5] counts in synchronism with OUTCOUNT in the RTEFIF MACH to
"    control the writing of nine bytes of data to the image memory and the
"    output FIFO's.

OUTCNT0.t = OUTCNT4 | OUTCNT5 | TOKEN & OUTCNT0;
OUTCNT1.t = ( OUTCNT4 | OUTCNT5) & OUTCNT0 | TOKEN & OUTCNT1;
OUTCNT2.t = ( OUTCNT4 | OUTCNT5) & OUTCNT0&OUTCNT1 | TOKEN&!OUTCNT2;
OUTCNT3.t = ( OUTCNT4 | OUTCNT5) & OUTCNT0&OUTCNT1&OUTCNT2 | TOKEN&!OUTCNT3;
OUTCNT4.t = ( OUTCNT4 | OUTCNT5) & OUTCNT0&OUTCNT1&OUTCNT2&OUTCNT3 |
                                                      TOKEN&!OUTCNT4;
OUTCNT5.t = OUTCNT0 & OUTCNT1 & OUTCNT2 & OUTCNT3 & OUTCNT4 | TOKEN&OUTCNT5;

" LINE[0..1] counts which of three lines, 0-2, each of the nine bytes is
"    associated with.

LINE0.t = !LINE1 & OUTCNT1 & OUTCNT0;
LINE1.t = (LINE1 | LINE0) & OUTCNT1 & OUTCNT0;

" The 20 nsec OFIFWEx signals enable the writing of bytes into the output
"    FIFO's on the clock pulse that occurs during the time when they are
"    asserted. The FIFO's are written even when HMACC is asserted, but the
"    data then is not from the string counters.

OFIFWE0 := !LINE1 & !LINE0 & OUTCNT1 & OUTCNT0;
OFIFWE1 := !LINE1 &  LINE0 & OUTCNT1 & OUTCNT0;
OFIFWE2 :=  LINE1 & OUTCNT1 & OUTCNT0;

" When HMACC is not asserted, the IMWE signal is generated whenever one of
"    the three OFIFWEx signals is present to write data into the image memory.
"    This signal is generated one clock ahead of the OFIFWEx signals because
"    data is written on the trailing edge of this 20 nsec pulse.

```
" When EMACC is asserted, the IHWE signal is generated by IHIOSTRB when in the
"    write mode. In a similar fashion LDIH is generated during a read mode to
"    strobe data into the TAXI interface. During a host read mode IHOE is
"    continuously asserted.

IHWE.t = !EMACC & OUTCNT1   & !OUTCNT0 & !IHWE  ;
         (EMACC&!SNGFRA) & !HOSTREAD & IHIOSTRB & !IHWE  ;
         IHWE;
LDIH  := (EMACC&!SNGFRA) & HOSTREAD & IHIOSTRB;
IHOE   = (EMACC & !SNGFRA & HOSTREAD) ; (EMACC & SNGFRA);

" There are two memory address counters in the MACH which have separate
"    output pins and are connected together externally. The parallel address
"    counter is used for loading the image memory from the string counters.
"    The serial address counter is used for host writes and reads to the image
"    memory. The parallel address counter is output enabled by /EMACC and the
"    serial address counter by EMACC.
" The 18-bit parallel address counter consists of two 9-bit sections. The
"    least significant bits, PARAD[0..8], count the number of pixels per line,
"    from 0 to 488. The most significant bits, PARAD[9..17], count the number
"    of lines per frame, 0 to 488. The least significant bits are incremented
"    after each three pixels are stored. The most significant bits are
"    incremented after the first and second pixels and decremented by two
"    after the third, except after the very last pixel on the group of three
"    lines where the counter is incremented by one to the next group of three
"    lines instead of decremented by two back to the first line of a group.

PARADC.oe = !EMACC ; EMACC & SNGFRA;
PARADR.oe = !EMACC ; EMACC & SNGFRA;
PARAD0.t = INCPIX ; LASTPIX&PARAD0;
PARAD1.t = INCPIX&PARAD0 ; LASTPIX&PARAD1;
PARAD2.t = INCPIX&PARAD0&PARAD1 ; LASTPIX&PARAD2;
PARAD3.t = INCPIX&PARAD0&PARAD1&PARAD2 ; LASTPIX&PARAD3;
PARAD4.t = INCPIX&PARAD0&PARAD1&PARAD2&PARAD3 ; LASTPIX&PARAD4;
PARAD5.t = INCPIX&PARAD0&PARAD1&PARAD2&PARAD3&PARAD4 ; LASTPIX&PARAD5;
PARAD6.t = INCPIX&PARAD0&PARAD1&PARAD2&PARAD3&PARAD4&PARAD5 ; LASTPIX&PARAD6;
PARAD7.t = INCPIX&PARAD0&PARAD1&PARAD2&PARAD3&PARAD4&PARAD5&PARAD6 ;
           LASTPIX&PARAD7;
PARAD8.t = INCPIX&PARAD0&PARAD1&PARAD2&PARAD3&PARAD4&PARAD5&PARAD6&PARAD7 ;
           LASTPIX&PARAD8;
PARAD9.t  = INCLINE;
PARAD10.t = INCLINE&PARAD9 ; DECLINE;
PARAD11.t = INCLINE&PARAD9&PARAD10 ; DECLINE&!PARAD10;
PARAD12.t = INCLINE&PARAD9&PARAD10&PARAD11 ; DECLINE&!PARAD10&!PARAD11;
PARAD13.t = INCLINE&PARAD9&PARAD10&PARAD11&PARAD12 ;
            DECLINE&!PARAD10&!PARAD11&!PARAD12;
PARAD14.t = INCLINE&PARAD9&PARAD10&PARAD11&PARAD12&PARAD13 ;
            DECLINE&!PARAD10&!PARAD11&!PARAD12&!PARAD13;
PARAD15.t = INCLINE&PARAD9&PARAD10&PARAD11&PARAD12&PARAD13&PARAD14 ;
            DECLINE&!PARAD10&!PARAD11&!PARAD12&!PARAD13&!PARAD14;
PARAD16.t = INCLINE&PARAD9&PARAD10&PARAD11&PARAD12&PARAD13&PARAD14&PARAD15 ;
            DECLINE&!PARAD10&!PARAD11&!PARAD12&!PARAD13&!PARAD14&!PARAD15;
PARAD17.t = INCLINE&PARAD9&PARAD10&PARAD11&PARAD12&PARAD13&PARAD14&PARAD15
            &PARAD16 ;
            DECLINE&!PARAD10&!PARAD11&!PARAD12&!PARAD13&!PARAD14&!PARAD15
            &!PARAD16;
```

```
" PIX488 is generated to indicate that the last group of three pixels is
"   being written.

" PIX488 := PARAD8&PARAD7&PARAD6&PARAD5&!PARAD4&PARAD3&!PARAD2&!PARAD1&!PARAD0;
" Decode OUTCNT so it is set and reset where it was set before
" This is to make the number of holes per line variable PX488 := HSYNC & CGATE0 & ([OUTCNT5..OUTCNT0] == 51 ) & LINE1
      # PX488 & ([OUTCNT5..OUTCNT0] != 63);
PIX488 := PX488;

" The sync scheme has been changed from the original.
" Now frame syncing is done by resetting all these FIFOs at the
" end of every VSYNC.
" Line syncing uses a sync bit in all three line FIFOs.
" The purpose of the change is to make the line and frame length variable
" One disadvantage, if data is not read out of the OFIFOs fast enough
" it could get lost, however there is the entire VSYNC period available
" to take out the last data.
"
" OFIFS0 and OFIFS2 are now identical, and we need an identical OFIFS1
" but it doesn't need its own pin, we can connect to either of the others.
" (only one signal is really necessary, but the board is already wired
" with these two connections)
" This puts a sync bit at the end of every line. This will cause a
" start of line message to be sent at the end of the line to
" the frame grabber.

"OFIFS0 := PIX0&LNE0;
"OFIFS2 := PIX488&LINE488;
OFIFS2 := PIX488 & !VSYNC;
OFIFS0 := PIX488;

"  The 18-bit serial address counter consists of a 7-bit low address section
"     and an 11-bit high address section. The high address section,
"     SERAD[7..17], is serially loaded by the host to specify which 128-byte
"     section of the image memory is to be used for the following read or write
"     operation. The low order section is cleared by this loading operation.
"     During host reads or writes, the low order section is incremented through
"     the 128 address following each read or write operation.

SERAD.oe = EMACC & !SNGFRA;
SERAD0.t = IMMADS&SERAD0 # BIMIOSTRB&!IMIOSTRB;
SERAD1.t = IMMADS&SERAD1 # BIMIOSTRB&!IMIOSTRB&SERAD0;
SERAD2.t = IMMADS&SERAD2 # BIMIOSTRB&!IMIOSTRB&SERAD0&SERAD1;
SERAD3.t = IMMADS&SERAD3 # BIMIOSTRB&!IMIOSTRB&SERAD0&SERAD1&SERAD2;
SERAD4.t = IMMADS&SERAD4 # BIMIOSTRB&!IMIOSTRB&SERAD0&SERAD1&SERAD2&SERAD3;
SERAD5.t = IMMADS&SERAD5 # BIMIOSTRB&!IMIOSTRB&SERAD0&SERAD1&SERAD2&SERAD3
              &SERAD4;
SERAD6.t = IMMADS&SERAD6 # BIMIOSTRB&!IMIOSTRB&SERAD0&SERAD1&SERAD2&SERAD3
              &SERAD4&SERAD5;
SERAD7  := IMMADS & HEMADD # !IMMADS & SERAD7;
SERAD8  := IMMADS & SERAD7 # !IMMADS & SERAD8;
SERAD9  := IMMADS & SERAD8 # !IMMADS & SERAD9;
SERAD10 := IMMADS & SERAD9 # !IMMADS & SERAD10;
```

```
SERAD11 := IMMADS & SERAD10 ; !IMMADS & SERAD11;
SERAD12 := IMMADS & SERAD11 ; !IMMADS & SERAD12;
SERAD13 := IMMADS & SERAD12 ; !IMMADS & SERAD13;
SERAD14 := IMMADS & SERAD13 ; !IMMADS & SERAD14;
SERAD15 := IMMADS & SERAD14 ; !IMMADS & SERAD15;
SERAD16 := IMMADS & SERAD15 ; !IMMADS & SERAD16;
SERAD17 := IMMADS & SERAD16 ; !IMMADS & SERAD17;

"---------------------------------- Simulation Segment ------------

"Test_Vectors

"------------------------------------------------------------------ end
```

```
module rtefif title 'Real Time Eye Line Buffer FIFO Controller
       Ver. 0;  9-14-94'
       21U42R0 device 'MACH435A';
"      9/26/94 Changed OUTCNT so all bits reset with STRTTKN
"      9/30/94 Changed the HOLE logic so the line FIFOs are written
"              after a delay of 4 holes instead of 1 at start of frame "inputs
       CLK50_5 pin 65;
       VSYNC,HSYNC,CGATE5,CLK12FB pin 70,71,72,34;

"outputs
       FIFCNT0,FIFCNT1,CLK25FB pin 8,9,33 istype 'reg_T,buffer';
       MOVE0..MOVE2 pin 19,18,17 istype 'reg_T,buffer';
       CLK12,CLK12PH,CLK25PH pin 35,36,37 istype 'reg_D,buffer';
       SELIN0,SELIN1 pin 4,5 istype 'reg_D,buffer';
       SELIA10,SELIA11,SELIA20,SELIA21 pin 75..78 istype 'reg_D,buffer';
       SELIB10,SELIB11,SELIB20,SELIB21 pin 79..82 istype 'reg_D,buffer';
       !FIFRE0..!FIFRE3 pin 45..48 istype 'reg_D,buffer';
       !FIFWE0..!FIFWE3 pin 49..52 istype 'reg_D,buffer';
       STRTTKN,RESET0..RESET2 pin 15,26,25,24 istype 'reg_D,buffer';
       IRCLR0..IRCLR2 pin 66..68 istype 'reg_D,buffer';
       !FIFWR,PRAD8,PRAD9 pin 73,58,57;

"nodes
       BVSYNC,BBVSYNC,BCGATE5,CLK12REF node istype 'reg_D,buffer';
       EOLE2..EOLE0,LINE1,MOVECNT0..MOVECNT2 node istype 'reg_T,buffer';
       OUTCNT0..OUTCNT5 node istype 'reg_T,buffer';

"constants
       H,L,X,C,Z = 1,0,.X.,.C.,.Z.;
       MOVECNT = [MOVECNT2..MOVECNT0];
       FIFCNT  = [FIFCNT1..FIFCNT0];
       OUTCNT  = [OUTCNT5..OUTCNT0];
       EOLE    = [EOLE2..EOLE0];
       FIFWE   = [FIFWE3..FIFWE0];
       FIFRE   = [FIFRE3..FIFRE0];
       FIF     = [FIFWE,FIFRE];
       SEL     = [SELIN0,SELIN1,SELIA10,SELIA11,SELIA20,SELIA21,
                  SELIB10,SELIB11,SELIB20,SELIB21];

AMDMACH property 'GROUP B MOVECNT0 MOVECNT1 MOVECNT2';
AMDMACH property 'GROUP D CLK12REF';
AMDMACH property 'GROUP E HOLE2 HOLE1 HOLE0 LINE1';
AMDMACH property 'GROUP F OUTCNT0 OUTCNT1 OUTCNT2 OUTCNT3 OUTCNT4 OUTCNT5';
AMDMACH property 'GROUP G BVSYNC BBVSYNC BCGATE5';

equations

BVSYNC.ar   = 0;
BVSYNC.ap   = 0;
BVSYNC.clk  = CLK50_5;

BBVSYNC.ar  = 0;
BBVSYNC.ap  = 0;
```

```
BBVSYNC.clk     = CLK50_5;

BCGATE5.ar      = 0;
BCGATE5.ap      = 0;
BCGATE5.clk     = CLK50_5;

EOLE.ar         = 0;
EOLE.ap         = 0;
EOLE.clk        = CLK50_5;

LINE1.ar        = 0;
LINE1.ap        = 0;
LINE1.clk       = CLK50_5;

CLK12REF.ar     = 0;
CLK12REF.ap     = 0;
CLK12REF.clk    = CLK50_5;

CLK12.ar        = 0;
CLK12.ap        = 0;
CLK12.clk       = CLK50_5;

CLK12PH.ar      = 0;
CLK12PH.ap      = 0;
CLK12PH.clk     = CLK50_5;

CLK25FB.ar      = 0;
CLK25FB.ap      = 0;
CLK25FB.clk     = CLK50_5;

CLK25PH.ar      = 0;
CLK25PH.ap      = 0;
CLK25PH.clk     = CLK50_5;

RESET0.ar       = 0;
RESET0.ap       = 0;
RESET0.clk      = CLK50_5;

RESET1.ar       = 0;
RESET1.ap       = 0;
RESET1.clk      = CLK50_5;

RESET2.ar       = 0;
RESET2.ap       = 0;
RESET2.clk      = CLK50_5;

IRCLR0.ar       = 0;
IRCLR0.ap       = 0;
IRCLR0.clk      = CLK50_5;

IRCLR1.ar       = 0;
IRCLR1.ap       = 0;
IRCLR1.clk      = CLK50_5;

IRCLR2.ar       = 0;
IRCLR2.ap       = 0;
IRCLR2.clk      = CLK50_5;

MOVE0.ar        = 0;
MOVE0.ap        = 0;
```

```
MOVE0.clk    = CLK50_5;

MOVE1.ar     = 0;
MOVE1.ap     = 0;
MOVE1.clk    = CLK50_5;

MOVE2.ar     = 0;
MOVE2.ap     = 0;
MOVE2.clk    = CLK50_5;

MOVECNT.ar   = 0;
MOVECNT.ap   = 0;
MOVECNT.clk  = CLK50_5;

STRTTKN.ar   = 0;
STRTTKN.ap   = 0;
STRTTKN.clk  = CLK50_5;

OUTCNT.ar    = 0;
OUTCNT.ap    = 0;
OUTCNT.clk   = CLK50_5;

SEL.ar       = 0;
SEL.ap       = 0;
SEL.clk      = CLK50_5;

FIFCNT.ar    = 0;
FIFCNT.ap    = 0;
FIFCNT.clk   = CLK50_5;

FIF.ar       = 0;
FIF.ap       = 0;
FIF.clk      = CLK50_5;

" RESET and Input Register CLeaR signals for the string counters are generated
"    during the vertical sync interval, but only after the last write to the
"    FIFO's has been finished at the beginning of the vertical sync period.

RESET0 := VSYNC&BSYNC&!CGATE5;
RESET1 := VSYNC&BSYNC&!CGATE5;
RESET2 := VSYNC&BSYNC&!CGATE5;
IRCLR0 := VSYNC&BSYNC&!CGATE5;
IRCLR1 := VSYNC&BSYNC&!CGATE5;
IRCLR2 := VSYNC&BSYNC&!CGATE5;

" Master reset for the FIFO's is set for two clock (40 nsec) periods by
"    double delaying the VSYNC input signal.

BVSYNC  := VSYNC;
BBVSYNC := BVSYNC;
FIFMR   = !VSYNC&BVSYNC # !BVSYNC&BBVSYNC;

" CLK25FB and CLK25PB are generated in phase with each other.

CLK25FB.t = 1;
```

```
CLK25PH    := !CLK25FB;

" CLK12 and CLK12PH are generated in phase with the CLK12FB input signal by
"    double delaying it using the internal CLK12REF signal.

CLK12REF := CLK12FB;
CLK12    := !CLK12REF;
CLK12PH  := !CLK12REF;

" During the 200 nsec interval when CGATE is not asserted after each hole has
"    been counted, 160 nsec MOVE SIGNALS are generated centered in the 200 nsec
"    interval for shifting the 8-bit data in the string counters.

BCGATE5 := CGATE5;
MOVECNT0.t = MOVE0;
MOVECNT1.t = MOVE0&MOVECNT0;
MOVECNT2.t = MOVE0&MOVECNT1&MOVECNT0;
MOVE0.t = !MOVE0&!CGATE5&BCGATE5 # MOVE0&MOVECNT2&MOVECNT1&MOVECNT0;
MOVE1.t = !MOVE1&!CGATE5&BCGATE5 # MOVE1&MOVECNT2&MOVECNT1&MOVECNT0;
MOVE2.t = !MOVE2&!CGATE5&BCGATE5 # MOVE2&MOVECNT2&MOVECNT1&MOVECNT0;

" A 20nsec STaRT ToKeN signal is generated at the begining of each 960 nsec
"    interval during which CGATE5 is high and the string counters are counting.
"    This signal passes through each of the nine string counters in the
"    sequence 1-4-7-2-5-8-3-6-9 enabling their output registers for 80 nsec
"    each to readout their data into the scaling PROM. The 2-bit portion of
"    the counter OUTCNT[0..1] counts four clock period to generate the 80 nsec
"    timing. The top four bits of this counter, OUTCNT[2..5], are set to 7 by
"    STRTTKN and count through 15. PRAD8 and PRAD9 are a 2-bit address into the
"    scaling PROM indicating whether 10, 11 or 12 detectors are counted. This
"    address is 0 for all even counts of OUTCNT[2..5] and is 1 for all odd
"    counts except 11, when it is 2. This address represents the least
"    significant digit of the number of detectors counted.

STRTTKN := CGATE5&!BCGATE5;
OUTCNT0.t = ( OUTCNT4 # OUTCNT5 ) # STRTTKN & OUTCNT0;
OUTCNT1.t = ( OUTCNT4 # OUTCNT5 )&OUTCNT0 # STRTTKN & OUTCNT1;
OUTCNT2.t = ( OUTCNT4 # OUTCNT5 )&OUTCNT1&OUTCNT0 # STRTTKN&!OUTCNT2;
OUTCNT3.t = ( OUTCNT4 # OUTCNT5 )&OUTCNT2&OUTCNT1&OUTCNT0 # STRTTKN&!OUTCNT3;
OUTCNT4.t = ( OUTCNT4 # OUTCNT5 )&OUTCNT3&OUTCNT2&OUTCNT1&OUTCNT0 #
               STRTTKN&!OUTCNT4;
OUTCNT5.t =   OUTCNT4&OUTCNT3&OUTCNT2&OUTCNT1&OUTCNT0 # STRTTKN&OUTCNT5;

PRAD8 = OUTCNT2 & !( OUTCNT5 & !OUTCNT4 & OUTCNT3 );
PRAD9 = OUTCNT5 & !OUTCNT4 & OUTCNT3 & OUTCNT2;

" FIFCNT[0..1] is a 2-bit counter counting the 80 nsec intervals of the
"    SELIAxx, SELIBxx and SELINx SIGNALS FIFCNT0.t = SELIA10 # SELIN0 # SELIA20 # VSYNC&FIFCNT0;
FIFCNT1.t = FIFCNT0 # VSYNC&FIFCNT1;
```

```
" The SELIAxx, SELIBxx, and SELINx signals are each asserted for 30 nsec for
"   controlling the loading and unloading of the string counters with their
"   associated FIFO's.

SELIA10 := STRTTKN # SELIA10 & !(FIFCNT1&FIFCNT0);
SELIA11 := STRTTKN # SELIA11 & !(FIFCNT1&FIFCNT0);
SELIB10 := STRTTKN # SELIB10 & !(FIFCNT1&FIFCNT0);
SELIB11 := STRTTKN # SELIB11 & !(FIFCNT1&FIFCNT0);

SELIN0  := SELIA10&FIFCNT1&FIFCNT0 # SELIN0 & !(FIFCNT1&FIFCNT0);
SELIN1  := SELIA10&FIFCNT1&FIFCNT0 # SELIN0 & !(FIFCNT1&FIFCNT0);
SELIB20 := SELIA10&FIFCNT1&FIFCNT0 # SELIB20 & !(FIFCNT1&FIFCNT0);
SELIB21 := SELIA10&FIFCNT1&FIFCNT0 # SELIB21 & !(FIFCNT1&FIFCNT0);

SELIA20 := SELIN0&FIFCNT1&FIFCNT0 # SELIA20 & !(FIFCNT1&FIFCNT0);
SELIA21 := SELIN0&FIFCNT1&FIFCNT0 # SELIA21 & !(FIFCNT1&FIFCNT0);

" The LINE1 signal is used to prevent reading the FIFO's during the first
"   line. All four FIFREx signals are identical.

LINE1.t = VSYNC&!CGATE5&!LINE1 # !VSYNC&BSYNC&LINE1;
FIFRE0 := ( STRTTKN # (SELIA10#SELIN0)&FIFCNT1&FIFCNT0 ) & !LINE1;
FIFRE1 := ( STRTTKN # (SELIA10#SELIN0)&FIFCNT1&FIFCNT0 ) & !LINE1;
FIFRE2 := ( STRTTKN # (SELIA10#SELIN0)&FIFCNT1&FIFCNT0 ) & !LINE1;
FIFRE3 := ( STRTTKN # (SELIA10#SELIN0)&FIFCNT1&FIFCNT0 ) & !LINE1;

" The EOLE counter is used to prevent writing the FIFO's during the first
" 4 holes of the frame. All four FIFWEx signals are identical.
" Reset count to 0 on VSYNC&!CGATE
" Count on BCGATE5 and !CGATE5 (CGATE trailing edge)
" Latch at 4 and gate FIFO write enables on EOLE=4
" We miss the first hole because there is not yet any output from the
"   counter
" We miss the next three holes to line up the output from the first
" counter with the input to the first counter when we take data out.

"EOLE0.t = VSYNC&!CGATE5&!EOLE0 # !VSYNC&!CGATE5&EOLE0;
"EOLE1.t = VSYNC&!CGATE5&!EOLE1 # CGATE5&BCGATE5&!EOLE0&EOLE1

EOLE.t = (EOLE$(EOLE+1))&!CGATE5&BCGATE5&(EOLE<4) # EOLE&VSYNC&!CGATE5;

FIFWE0 := ( SELIA10 # SELIN0 # SELIA20 ) & FIFCNT1 & !FIFCNT0 & (EOLE==4);
FIFWE1 := ( SELIA10 # SELIN0 # SELIA20 ) & FIFCNT1 & !FIFCNT0 & (EOLE==4);
FIFWE2 := ( SELIA10 # SELIN0 # SELIA20 ) & FIFCNT1 & !FIFCNT0 & (EOLE==4);
FIFWE3 := ( SELIA10 # SELIN0 # SELIA20 ) & FIFCNT1 & !FIFCNT0 & (EOLE==4);

"---------------------------------- Simulation Segment ------------

"Test_Vectors

"-----------------------------------------------------------------
```

```
module dtccnt title 'DETECTOR CONTROLLER CONTROL LOGIC
        Ver. 0; 1/9/95 1000';
        D1U14R0 device 'MACH435A';

"inputs
        SELECT_,BA1,BA2,BIOR_,BIOW_ pin 3,4,5,6,7;
        LRC0..LRC3,RRC0..RRC3 pin 24,25,26,27,45,46,47,48;
        LRCSTRB_,LRDSTRB_,RRCSTRB_,RRDSTRB_ pin 62,38,65,80;
        FMHZ pin 20;
        TWMHZ pin 67;
        TSEL pin 55;
        T0,LSEL,RSEL pin 28,41,83;
        BIG,EIG,EC0..EC3 pin 60,61,70,71,72,73;
        BC4 pin 23;

"outputs
        BUSY_,TEN_,SL,SH,AS,RX pin 8,9,17,18,19,54;
        LRCRSP,LRDRSP,RRCRSP,RRDRSP pin 40,39,82,81 istype 'reg_D,buffer';
        RSTRB,LSTRB pin 79,37 istype 'reg_D,buffer';
        DSEL0,DSEL1 pin 12,13 istype 'reg_D,buffer';
        LCFAULT,RCFAULT pin 29,50 istype 'reg_D,buffer';
        TC0..TC3 pin 75,76,77,78 istype 'reg_D,buffer';
        LVS,LHS,RVS,RHS pin 30,31,51,52 istype 'reg_D,buffer';
        TWMHZ0 pin 59;

"nodes
        STOP pin;
        _BIOW_,_BIOR_,_LRC0.._LRC3,_RRC0.._RRC3 node istype 'reg_D,buffer';
        _EC3.._EC0 node istype 'reg_D,buffer';
        ST0..ST2 pin istype 'reg_T,buffer';
        RRC15,LRC15,BEIGL,DSLL,DSLLL node istype 'reg_D,buffer';      "read,dsl
        TWMHZL,TWMHZLI node istype 'reg_D,buffer';
        INC,BUSY,TFMHZ,CYCLE pin istype 'reg_D,buffer';
        DSL,READ pin istype 'reg_D,buffer';

"constants
        H,L,X,C,Z = 1,0,.X.,.C.,.Z.;
        LRC = [LRC3..LRC0];
        _LRC = [_LRC3.._LRC0];
        RRC = [RRC3..RRC0];
        _RRC = [_RRC3.._RRC0];
        TC = [TC3..TC0];
        EC = [EC3..EC0];
        _EC = [_EC3.._EC0];
        DSEL = [DSEL1,DSEL0];
        DAT = !BA2&!BA1;
        ADD = !BA2&BA1;
        STAT = BA2&!BA1;
        ST = [ST2..ST0];
        FF = {TWMHZL,TFMHZ,TWMHZLI,_BIOW_,_BIOR_,DSEL,DSL,DSLL,DSLLL,
              CYCLE,BUSY,READ,ST,INC,TC,LSTRB,RSTRB,LRCRSP,LRDRSP,RRCRSP,
              RRDRSP,LRC15,LCFAULT,RRC15,RCFAULT,LVS,LHS,RVS,RHS,BEIGL};
        WR = !SELECT_&!_BIOW_;
        RD = !SELECT_&!_BIOR_;
        CLKEN = !TFMHZ&!TWMHZ;
        CLKEN_ = !TFMHZ&TWMHZ;

equations
```

```
"CLOCK GENERATION

FF.clk := FMHZ;
    TWMHZL := TWMHZ;
    TFMHZ := TWMHZ&TWMHZL # !TWMHZ&!TWMHZL;
    TWMHZLI := !TWMHZL;
    TWMHZO = TWMHZLI;

"R/W CONTROL

"R/W TIMING
    "50MHZ      ||||||||||||||||||||||||||||||||||||||||||||||||||||||
    "25MHZ      -_-_-_-_-_-_-_-_-_-_-_-_-_-_-_-_-_-_-_-_-_-_-_-_-_-_-_
    "12.5MHZ    -__--__--__--__--__--__--__--__--__--__--__--__--__--_
    "READ              _____
    "BUSY         _____  _____
    "ST          00000112233445566777700001122334444445555555556666666677
    "INC          -_ __-__-__-  _-_ _____ __-  _____   _    _
    "xSTRB            __-__-__-__-__      __-__-__
    "xTC         11111110000000000000022222200000000000000000000000000
    "xRCRSP                                       -__
    "xRDRSP                                                -     -_
    "SL/SH                                               -_____-_

_BIOW_ := BIOW_;
    _BIOR_ := BIOR_;
    _LRC := LRC;
    _LRC.clk = !LRCSTRB_;
    _RRC := RRC;
    _RRC.clk = !RRCSTRB_;
    !TEN_ = AS # !SELECT_&(LSEL#RSEL#TSEL)&(DAT&(!_BIOW_ # !_BIOR_) # !_BIOR_&STAT);
    AS = WR&ADD;
    SL = (ST==5)&READ&(LSEL&LRDRSP#RSEL&RRDRSP)&CYCLE # !_BIOW_&!SELECT_&DAT&TFMHZ;
    SH = (ST==6)&READ&(LSEL&LRDRSP#RSEL&RRDRSP)&CYCLE # !_BIOW_&!SELECT_&DAT&TFMHZ;
    DSEL := [1,0]&CYCLE&((ST==2)#(ST==3)) #
            [0,1]&CYCLE&READ&((ST==4)#(ST==5)#(ST==6)#(ST==7)) #
            [0,1]&CYCLE&!READ&((ST==6)#(ST==7)) #
            [1,1]&STAT&RD;
    DSL := DAT&(RD # WR);
    DSLL := DSL;
    DSLLL := DSLL;
    CYCLE := !TO&((LSEL # RSEL)&(!DSLL&DSLLL&!READ # READ&DSL&!DSLL) # CYCLE&!((ST==7)&!TFMHZ # !DSL&DSLLL));
    !BUSY_ = !_BIOR_&(LSEL#RSEL#TSEL)&(DSLL&!DSLLL # CYCLE);
    BUSY := CYCLE;
    READ := DAT&RD # READ&!(WR);
    ST.t = !TFMHZ&(ST$(ST+1))&!(SELECT_&DSL)&BUSY&INC # ST&(SELECT_&DSL # !BUSY);
    INC := (ST==0)&!TWMHZ&!STOP           # "WAIT FOR MARK
           (ST==1)                        # "SEND CONT/ (DATA)
           (ST==2)&!TWMHZ&!STOP           #
           (ST==3)                        # "SEND ADDR
           (ST==4)&!READ&!TWMHZ&!STOP     #
           (ST==4)&READ&LRCRSP&(_LRC==3)&LSEL #
           (ST==4)&READ&RRCRSP&(_RRC==3)&RSEL #
           (ST==5)&!READ                  # "SEND/READ DATA
           (ST==5)&READ&LRDRSP&LSEL       # "READ DATA
           (ST==5)&READ&RRDRSP&RSEL       # "READ DATA
           (ST==6)&!READ&!TWMHZ&!STOP     # "SEND/READ DATA
           (ST==6)&READ&LRDRSP&LSEL       # "READ DATA
           (ST==6)&READ&RRDRSP&RSEL;        "READ DATA
```

```
RX = READ&((ST==5)#(ST==6)#(ST==7));
_EC := EC;
_EC.clk = BC4;
TC := !STOP&([0,0,0,1]&!READ # [0,0,1,0]&READ)&((ST==0)#(ST==1)) #
       [0,1,1,1]&EIG # _EC&BIG;
LSTRB := LSEL&BUSY&CYCLE&!STOP&CLKEN&((ST==0)#(ST==2)#!READ&((ST==4)#(ST==6))) #
         (BIG#EIG)&CLKEN # LSTRB&!(!TFHHZ);
RSTRB := RSEL&BUSY&CYCLE&!STOP&CLKEN&((ST==0)#(ST==2)#!READ&((ST==4)#(ST==6))) #
         (BIG#EIG)&CLKEN # RSTRB&!(!TFHHZ);
LRCRSP := !LRCRSP&!LRCSTRB_&!TFHHZ;
LRDRSP := !LRDRSP&!LRDSTRB_&!TFHHZ;
RRCRSP := !RRCRSP&!RRCSTRB_&!TFHHZ;
RRDRSP := !RRDRSP&!RRDSTRB_&!TFHHZ;
```

"FAULT DETECTION

```
LRC15 := LRCRSP&(_LRC==15) # LRC15&!(LRCRSP&!(_LRC==15));
LCFAULT := LRC15&LRCRSP&(_LRC==15) # LCFAULT&!SELECT_&STAT&BIOR_&!_BIOR_;
RRC15 := RRCRSP&(_RRC==15) # RRC15&!(RRCRSP&!(_RRC==15));
RCFAULT := RRC15&RRCRSP&(_RRC==15) # RCFAULT&!SELECT_&STAT&BIOR_&!_BIOR_;
```

"SYNC TIMING

```
LVS := LRCRSP&(_LRC==13);
LHS := LRCRSP&(_LRC==14);
RVS := RRCRSP&(_LRC==13);
RHS := RRCRSP&(_LRC==14);
```

"BIGEIG TIMING

```
STOP = BIG # EIG # BEIGL;
BEIGL := (BIG#EIG)&CLKEN # BEIGL&!(CLKEN);
END
```

```
module DTCLDP title 'DETECTOR CONTROLLER LEFT DATA PATH
       Ver. 0; 1/5/95 1540'
       D1U5R0 device 'MACH435A';

"inputs
       LRD0..LRD7 pin 3,4,5,6,7,8,9,10;
       FMHZ,TWMHZ,LRDSTRB_ pin 20,23,62;
       SELECT_,BIOR_ pin 82,79;
       DSEL0,DSEL1,SL,SH,AS,BUSY_ pin 70,71,38,39,40,31;
       LCFAULT,RCFAULT,VS,HS,RX,LRDRSP pin 28,29,58,59,73,30;

"outputs
       LSEL,RSEL,TSEL pin 16,17,60;
       LRTSEL_ pin 37;
       TO pin 72 istype 'req_D,buffer';
       LTD0..LTD7 pin 24,25,26,27,33,34,35,36;
       ENR_,ENW_,MRST_ pin 12,13,14 istype 'req_D,buffer';
       VSYNC,DIGCLK,HSYNC pin 49,50,51 istype 'req_D,buffer';
       CGATE pin 52 istype 'req_D,buffer';

"i/o's
       B0..B7 pin 45,46,47,48,54,55,56,57 istype 'req_D,buffer';
       B8..B15 pin 66,67,68,69,75,76,77,78 istype 'req_D,buffer';

"nodes
       RCY node;
       AD0..AD7,TOS,STATENL,TFMHZ,LSH,FLINE,NLINE node istype 'req_D,buffer';
       _LRD7.._LRD0,RDL,DSYNC node istype 'req_D,buffer';
       TCNT4..TCNT0 node istype 'req_T,buffer';
       WCNT8..WCNT0,RCNT8..RCNT0 node istype 'req_T,buffer';

"constants
       H,L,X,C,Z = 1,0,.X.,.C.,.Z.;
       LTD = [LTD7..LTD0];
       WCNT = [WCNT8..WCNT0];
       RCNT = [RCNT8..RCNT0];
       B = [B15..B0];
       BL = [B7..B0];
       BH = [B15..B8];
       TCNT = [TCNT4..TCNT0];
       AD = [AD7..AD0];
       ADH = [AD7..AD4];
       DSEL = [DSEL1,DSEL0];
       LRD = [LRD7..LRD0];
       _LRD = [_LRD7.._LRD0];
       FF = [TFMHZ,STATENL,MRST_,FLINE,NLINE,ENW_,LSH,CGATE,RDL,DIGCLK,VSYNC,
             HSYNC,DSYNC,ENR_,WCNT,RCNT];
       STATEN = (DSEL==3);
       CLKEN = !TWMHZ&!TFMHZ;
       CLKEN_ = TWMHZ&!TFMHZ;

equations
"clock generation
       FF.clk = FMHZ;
       TFMHZ := !TFMHZ;

"data path latching and gating
       _LRD := LRD;
```

```
_LRD.clk = !LRDSTRB_;
STATENL := STATEN;
BL := BL.pin&(DSEL==0) # _LRD&(DSEL==1);
BH := BH.pin&(DSEL==0) # _LRD&(DSEL==1) #
      [TOS,LCFAULT,RCFAULT,0,0,0,0,0]&STATEN;
B.oe = !BIOR_&!SELECT_&(LSEL#STATEN#TSEL);
BL.clk = SL;
BH.clk = SH # STATEN&FMHZ;
LTD = BL.fb&(DSEL==0) # BH.fb&(DSEL==1) # AD&(DSEL==2);
AD := BL.pin;
AD.clk = !AS;
LSEL = (ADH==2);
RSEL = (ADH==3);
TSEL = (ADH==7);
!LRTSEL_ = !SELECT_&(LSEL # RSEL # TSEL);
```

"FRAME GRABBER TIMING
"FMHZ   ||||||||||||||||||||||||||||||||||||||||||||||||||||||||||||||||||||||
"25MHZ  - - - - - - - - - - - - - - - - - - - - - - - - - - - - - - - - - - -
"12.5MHZ-- -- -- -- -- -- -- -- -- -- -- -- -- -- -- -- -- -- -- -- -- -- --
"DIGCLK   _ _ _  _ _ _  _ _  _ _  _ _  _ _  _ _  _ _  _ _  _ _  _ _  _ _  _ _
"HRCRSP   _ _          _            _            _            _
"HRDRSP     _ _          _            _            _            _
"HRDL        ---------           ----                        -----------
"HRC     1111000000000000000000000000000000000001111000000000000000001111000000000000000011110
"       3333000000000000000003333000000000000000004444000000000000000004444000000000000000033330
"RX               --------                                     --------
"HRST         -
"FLINE        ----------------------------------------
"NLINE        ---                                   ---           ---
"ENW          ---------------------      ---------------------
"WCNT    xxxxxxxxxx00001111222222222222222222233333333333333333333333333333333
"RCNT    xxxxxxxxxxxxxxxxxxxxxxxxxxxxxxxxxxxxxxxxxxxxxxxxx33332222111100003333222211110000
"ENR                                      -----------          -----------
"VSYNC        ----------------------------------------
"HSYNC        --------                             --------             --------
"DSYNC                                                ----                 ----
"LSH                                           -----------------------------------

"FRAME GRABBER SYNCS AND CLOCK

```
    !HRST_ := VS&!LSH;
    FLINE := VS&!LSH # FLINE&!(VSYNC);
    NLINE := HS # NLINE&!(HSYNC # !HRST_);
    !ENW_ := !(RX&LSEL);
    LSH := HS # LSH&!(VS);
    CGATE := VS&LSH # CGATE&!(VSYNC);
    RDL := !(RX&LSEL)&LRDRSP&FLINE&!NLINE # RDL&!(CLKEN);
    DIGCLK := (HSYNC#CGATE#!ENR_#RDL)&CLKEN;
    VSYNC := FLINE&NLINE&ENR_&CLKEN_ # VSYNC&!(DSYNC&CLKEN_);
    HSYNC := NLINE&ENR_&CLKEN_ # HSYNC&!(DSYNC&CLKEN_);
    DSYNC := !DSYNC&HSYNC&CLKEN_ # DSYNC&!(CLKEN_);
    !ENR_ := HSYNC&CLKEN_ # !ENR_&!(RCY&CLKEN_);
    WCNT.t = (WCNT$(WCNT+1))&FLINE&!NLINE&!(RX&LSEL)&LRDRSP&HRST_ #
                                     WCNT&!HRST_;
    RCNT.t = (RCNT$(RCNT-1))&!ENR_&CLKEN_ #
                                 (WCNT$RCNT)&HSYNC&!DSYNC&CLKEN_;
    RCY = (RCNT==1);
```

"timeout counter

```
TCNT.t = (TCNT$(TCNT+1))&!BUSY_ # TCNT&BUSY_;
TCNT.clk = TWMHZ;
[TO,TOS] := [1,1];
TOS.ar = !STATEN&STATENL;
TO.ar = BUSY_;
TO.clk = !TCNT4;
TOS.clk = TO;
``` end

```
module DTCRDP title 'DETECTOR CONTROLLER RIGHT DATA PATH
       Ver. 0; 1/4/95 1210'
       D1U4R0 device 'MACH435A';

"inputs
       RRD0..RRD7 pin 3,4,5,6,7,8,9,10;
       FMHZ,TWMHZ,RRDSTRB_ pin 20,23,62;
       SELECT_,BIOR_ pin 82,79;
       DSEL0,DSEL1,SL,SH pin 70,71,38,39;
       VS,HS,RX,RRDRSP pin 58,59,17,30;
       RSEL pin 83;

"outputs
       RTD0..RTD7 pin 24,25,26,27,33,34,35,36;
       ENR_,ENW_,HRST_ pin 12,13,14 istype 'reg_D,buffer';
       VSYNC,DIGCLK,HSYNC pin 49,50,51 istype 'reg_D,buffer';
       CGATE pin 52 istype 'reg_D,buffer';

"i/o's
       B0..B7 pin 45,46,47,48,54,55,56,57 istype 'reg_D,buffer';
       B8..B15 pin 66,67,68,69,75,76,77,78 istype 'reg_D,buffer';

"nodes
       TFMHZ,LSH,FLINE,NLINE node istype 'reg_D,buffer';
       _RRD0.._RRD7,RDL,DSYNC node istype 'reg_D,buffer';
       WCNT0..WCNT8,RCNT0..RCNT8 node istype 'reg_T,buffer';
       RCY node;

"constants
       H,L,X,C,Z = 1,0,.X.,.C.,.Z.;
       RTD = [RTD7..RTD0];
       WCNT = [WCNT8..WCNT0];
       RCNT = [RCNT8..RCNT0];
       B = [B15..B0];
       BL = [B7..B0];
       BH = [B15..B8];
       DSEL = [DSEL1,DSEL0];
       RRD = [RRD7..RRD0];
       _RRD = [_RRD7.._RRD0];
       FF = [TFMHZ,MRST_,FLINE,NLINE,ENW_,LSH,CGATE,RDL,DIGCLK,VSYNC,HSYNC,
             DSYNC,ENR_,WCNT,RCNT];
       STATEN = (DSEL==3);
       CLKEN = !TWMHZ&!TFMHZ;
       CLKEN_ = TWMHZ&!TFMHZ;

equations
"clock generation
       FF.clk = FMHZ;
       TFMHZ := !TFMHZ;

"data path latching and gating
       _RRD := RRD;
       _RRD.clk = !RRDSTRB_;
       BL := BL.pin&(DSEL==0) # _RRD&(DSEL==1);
       BH := BH.pin&(DSEL==0) # _RRD&(DSEL==1);
       B.oe = !BIOR_&!SELECT_&RSEL&!(STATEN);
       BL.clk = SL;
       BH.clk = SH;
```

```
            RTD = BL.fb&(DSEL==0) # BE.fb$(DSEL==1);

"FRAME GRABBER TIMING
"FMHZ     ||||||||||||||||||||||||||||||||||||||||||||||||||||||||||||||||||||||||||
"25MHZ    - - - - - - - - - - - - - - - - - - - - - - - - - - - - - - - - - - - - -
"12.5MHZ  --  --  --  --  --  --  --  --  --  --  --  --  --  --  --  --  --  --
"DIGCLK    _   _   _   _____     _   _   _   _   _____     _   _   _   _   _____
"HRCRSP   __-_____-_____-_____
"HRDRSP   _____-_____-_____-_____
"HRDL     _____-------_____----_____----_____
"ERC       111100000000000000000000000000000000000000011110000000000000000011110000000000000000011110
"          333300000000000000000003333000000000000000000044440000000000000000044440000000000000000033330
"RX       _____--------_____
"HRST     __-_____
"FLINE    ___-----------------------------_____
"NLINE    ___---_____---_____---___
"ENW      ____-------------------_____--------------------_____
"WCNT      xxxxxxxxxx000011112222222222222222222233333333333333333333333333333333
"RCNT      xxxxxxxxxxxxxxxxxxxxxxxxxxxxxxxxxxxxxxxxxxxxxxxxxxx33332222111100003333222211110000
"ENR      _____-----------_____------------___
"VSYNC    ____-----------------------------------------------_____
"HSYNC    ____--------_____-------_____-------_____
"DSYNC    _____----_____---___
"LSH      _____-------------------------------------------

"FRAME GRABBER SYNCS AND CLOCK

!HRST_ := VS&!LSH;
     FLINE  := VS&!LSH # FLINE&!(VSYNC);
     NLINE  := HS # NLINE&!(HSYNC # !HRST_);
     !ENW_  := !(RX&RSEL);
     LSH    := HS # LSH&!(VS);
     CGATE  := VS&!LSH # CGATE&!(VSYNC);
     RDL    := !(RX&RSEL)&RRDRSP&FLINE&!NLINE # RDL&!(CLKEN);
     DIGCLK := (HSYNC#CGATE#!ENR_#RDL)&CLKEN;
     VSYNC  := FLINE&NLINE&ENR_&CLKEN_ # VSYNC&!(DSYNC&CLKEN_);
     HSYNC  := NLINE&ENR_&CLKEN_ # HSYNC&!(DSYNC&CLKEN_);
     DSYNC  := !DSYNC&HSYNC&CLKEN_ # DSYNC&!(CLKEN_);
     !ENR_  := HSYNC&CLKEN_ # !ENR_&!(RCY&CLKEN_);
     WCNT.t = (WCNT$(WCNT+1))&FLINE&!NLINE&!(RX&RSEL)&RRDRSP&HRST_ #
                                       WCNT&!HRST_;
     RCNT.t = (RCNT$(RCNT-1))&!ENR_&CLKEN_ #
                             (WCNT$RCNT)&HSYNC&!DSYNC&CLKEN_;
     RCY = (RCNT==1);

end
```

```
module tubcnt title 'TUBE CONTROLLER CONTROL LOGIN
       Ver. 0; 1/9/95 1410';
       T1U5R0 device 'MACH435A';

"inputs
      SELECT_,BA1,BA2,BIOW_ pin 3,4,5,7;
      BIOR_ pin 50;
      IRC0,IRC1,IRC2,IRC3 pin 54,55,56,57;
      IRCSTRB_,IRDSTRB_ pin 23,38;
      FMHZ,TWMHZ pin 20,65;
      D0,D1,D2,D3,D4,D5,D6,D7 pin 66,67,68,69,75,76,77,78;
      T0,BC4,IOS,SCS pin 15,52,41,83;
      LAST,HSTB,AD0..AD3,STHZ pin 18,58,33,34,35,36,37;

"outputs
      BUSY_,XENABLE pin 8,17;
      READ pin 14 istype 'reg_D,buffer';
      ISTRB,DSTRB,IRCRSP,IRDRSP pin 6,49,40,39 istype 'reg_D,buffer';
      SL,SH,AS,TEN_ pin 28,29,31,9;
      DSEL0,DSEL1,DOE pin 12,13,10 istype 'reg_D,buffer';
      REGCLKH,REGCLKL pin 81,82 istype 'reg_D,buffer';
      XON,ACTIVE pin 30,80 istype 'reg_D,buffer';
      PBIG,EIG,EC0..EC3,CFAULT pin 60,61,70,71,72,73,19 istype 'reg_D,buffer';
      CD0..CD3 pin 45,46,47,48 istype 'reg_D,buffer';
      ITC0..ITC3 pin 24,25,26,27 istype 'reg_D,buffer';
      BIG pin 59 istype 'reg_D,buffer';

"nodes
      _BIOW_,_BIOR_,_IRC0,_IRC1,_IRC2,_IRC3 node istype 'reg_D,buffer';
      TR0,TR1,TR2,TR3,TR4,TR5,TR6 node istype 'reg_D,buffer';
      HR0,HR1,HR2,HR3,HR4,HR5,HR6 node istype 'reg_D,buffer';
      TC0..TC6,FC0..FC5,ST0..ST2 node istype 'reg_T,buffer';
      QUIT,INC,XCONT,FR0..FR5 node istype 'reg_D,buffer';
      DONEL,DONE,EIGT,CSS,CSSL,TFMHZ,RAST,FTIHE,FTIHEL node istype 'reg_D,buffer';
      TWMHZL,STHZL,STHZLL,ICYCLE,SCYCLE,DSL,DSLL,DSLLL node istype 'reg_D,buffer';
      A68,A69,A70,TCCY,SACTIVE,FIRST node;
      FDONE,IRC15,CSTBE,BUSY,HOLDOFF,DFTIHE,XENABLER node istype 'reg_D,buffer';

"constants
      H,L,X,C,Z = 1,0,.X.,.C.,.Z.;
      D   = [D7..D0];
      AD  = [AD3..AD0];
      TC  = [TC6..TC0];
      FC  = [FC5..FC0];
      TR  = [TR6..TR0];
      HR  = [HR6..HR0];
      FR  = [FR5..FR0];
      CD  = [CD3..CD0];
      ITC = [ITC3..ITC0];
      EC  = [EC3..EC0];
      DSEL = [DSEL1,DSEL0];
      RD  = !SELECT_&!_BIOR_;
      WR  = !SELECT_&!_BIOW_;
      DAT = !BA2&!BA1;
      ADD = !BA2&BA1;
      STAT = BA2&!BA1;
      IRC = [IRC3..IRC0];
      _IRC = [_IRC3.._IRC0];
```

```
    ST = [ST2..ST0];
    FF = [TWMHZL,TFMHZ,STHZL,STHZLL,_BIOW_,_BIOR_,DOE,DSEL,DSL,DSLL,DSLLL,
         ICYCLE,SCYCLE,BUSY,READ,HOLDOFF,ST,INC,REGCLKL,REGCLKH,ITC,ISTRB,
         IRCRSP,IRDRSP,IRC15,CFAULT,TC,PBIG,BIG,EIG,EIGT,XCONT,ACTIVE,
         FTIHE,DFTIHE,FTIHEL,FC,FDONE,DONE,DONEL,QUIT,DSTRB,CD,CSS,CSSL,
         CSTBE,EC];
    CLKEN  = !TFMHZ&!TWMHZ;
    CLKEN_ = !TFMHZ&TWMHZ;

equations

"CLOCK GENERATION

FF.clk := FMHZ;
    TWMHZL := TWMHZ;
    TFMHZ  := TWMHZ&TWMHZL # !TWMHZ&!TWMHZL;
    STHZL  := STHZ&CLKEN # STHZL&!(CLKEN);
    STHZLL := STHZL&CLKEN # STHZLL&!(CLKEN);

"R/W CONTROL

"R/W TIMING
"FMHZ    ||||||||||||||||||||||||||||||||||||||||||||||||
"TFMHZ   _  _  _  _  _  _  _  _  _  _  _  _  _  _  _  _
"TWMHZ   __  __  __  __  __  __  __  __  __  __  __  __
"READ                      ------------------------------
"BUSY            -----------------   ----------------------
"ST      00000112233445566777700001122334444445555555556666666677
"INC     ___ _ ___ ___ _ ___ ___ _____ ___ ___ _____ ___
"ISTRB        __  __  __  __      __  __
"ISD     1111111000000000000002222220000000000000000000000
"IRCRSP                                   _
"IRDRSP                                              _  _
"SL/SH                                               -  -

_BIOW_ := BIOW_;
    _BIOR_ := BIOR_;
    _IRC   := IRC;
    _IRC.clk = !IRCSTRB_;
    !TEN_ = AS # !SELECT_&(IOS # SCS)&(DAT&(!_BIOW_ # !_BIOR_) # !_BIOR_&STAT);
    DOE = SCYCLE&!READ&!HOLDOFF;
    AS = WR&ADD;
    SL = (ST==5)&READ&IRDRSP&ICYCLE # READ&SCYCLE&!LAST&HSTB # !_BIOW_&!SELECT_&DAT&TFMHZ;
    SH = (ST==6)&READ&IRDRSP&ICYCLE # READ&SCYCLE&LAST&HSTB # !_BIOW_&!SELECT_&DAT&TFMHZ;
    DSEL := [1,1]&ICYCLE&((ST==2)#(ST==3)) #
            [0,1]&ICYCLE&READ&((ST==4)#(ST==5)#(ST==6)#(ST==7)) #
            [0,1]&ICYCLE&!READ&((ST==6)#(ST==7)) #
            [1,1]&STAT&RD #
            [1,0]&SCYCLE&READ #
            [0,1]&SCYCLE&!READ&((ST==5)#(ST==6)#(ST==7));
    DSL   := DAT&(RD # WR);
    DSLL  := DSL;
    DSLLL := DSLL;
    ICYCLE := !TO&(IOS&(!DSLL&DSLLL&!READ # READ&DSL&!DSLL) # ICYCLE&!((ST==7)&!TFMHZ # !DSL&DSLLL));
    SCYCLE := !TO&(SCS&(!DSLL&DSLLL&!READ # READ&DSL&!DSLL) # SCYCLE&!((ST==7)&!TFMHZ # !DSL&DSLLL));
    !BUSY_ = !_BIOR_&(DSLL&!DSLLL # (ICYCLE # SCYCLE));
    BUSY  := ICYCLE # SCYCLE;
    READ  := DAT&RD # READ&!(WR);
    HOLDOFF := ACTIVE&!LAST;
    ST.t = !TFMHZ&(ST$(ST+1))&!(SELECT_&DSL)&BUSY&INC # ST&(SELECT_&DSL # !BUSY);
```

```
       INC := (ST==0)&!TWMHZ&!(SCYCLE#HOLDOFF)    # "WAIT FOR MARK
              (ST==1)                              # "SEND CONT/ (DATA)
              (ST==2)                              #
              (ST==3)                              # "SEND ADDR
              (ST==4)&(!READ # SCYCLE)             #
              (ST==4)&IRCRSP&(_IRC==3)&READ        #
              (ST==5)&(!READ # SCYCLE)             # "SEND/READ DATA
              (ST==5)&IRDRSP&READ                  # "READ DATA
              (ST==6)&(!READ#SCYCLE)               # "SEND/READ DATA
              (ST==6)&IRDRSP&READ;                   "READ DATA
       REGCLKL := (ST==1)&SCYCLE;
       REGCLKH := (ST==6)&SCYCLE;
       A68 = (AD==4)&SCS;
       A69 = (AD==5)&SCS;
       A70 = (AD==6)&SCS;
       ITC := ([0,0,0,1]&!READ # [0,0,1,0]&READ)&((ST==0)#(ST==1));
       ISTRB := ICYCLE&((ST==0)#(ST==2)#!READ&((ST==4)#(ST==6)))&CLKEN #
                                             ISTRB&(!TFMHZ);
       IRCRSP := !IRCRSP&!IRCSTRB_&!TFMHZ;
       IRDRSP := !IRDRSP&!IRDSTRB_&!TFMHZ;
       IRC15 := IRCRSP&(_IRC==15) # IRC15&!(IRCRSP&!(_IRC==15));
       CFAULT := IRC15&IRCRSP&(_IRC==15) # CFAULT&!SELECT_&STAT&BIOR_&!_BIOR_;

"scan timing
       "TFMHZ  |||||||||||||||||||||||||||||||||||||||||||||||||||||||
       "TWMHZ  - - - - - - - - - - - - - - - - - - - - - - - - - -
       "ACTIVE ___-----------------------------------------------------
       "TCCY   1111111    1111     1111     1111     1111
       "       5555544 8 4 1005544 8 4 1005544 8 4 1005544 8 4 1005544 8 4 1
       "PBIG   _____--_____--___
       "EIG    _____--_____--_
       "BIG    _____--__
       "CGATE(in eye)_____--------___--------___--------

TR := [D6..D0];
       TR.clk = A68®CLKL&!XON;
       FR := [D5..D0];
       FR.clk = A69&!XON®CLKL;
       HR := [D6..D0];
       HR.clk = A68®CLKH&!XON;
       RAST := D0;
       RAST.clk = A69&!XON®CLKH;
       FIRST = !ACTIVE # FIRST&!(FTIMEL);
       TC.t = CLKEN&((TC$(TC-1))&!TCCY # (TC$TR)&TCCY);
       TCCY = (TC==0) # !ACTIVE;
       PBIG := (TC==8)&ACTIVE&CLKEN&!FTIMEL&!DONEL # PBIG&!(CLKEN);
       BIG  := (TC==HR)&ACTIVE&CLKEN&!FTIMEL&!FIRST # BIG&!(CLKEN);
       EIG  := TCCY&ACTIVE&CLKEN&!FTIMEL&!FIRST # EIG&!(CLKEN);
       EIGT := TCCY&ACTIVE&CLKEN # EIGT&!(CLKEN);
```

```
"FRAME TIMING
"CLKEN      |||||||||||||||||||||||||||||||||||||||||||||||||||||||||||||||||||||||||||||||||||||||||||||||
"ACTIVE     ------------------------------------------------------------------------------------------------
"PBIG       __-------_____
"HCYCLE     _-_____-----------_____-----------_____-----------_____-
"EIGT       _____-_____-_____-_____-_____-_____-
"EIG        _____-_____-_____-_____-_____-_____-_
"BIG        _____-_____-_____-_____-_____-_____-__
"CGATE      _____-----------_____-----------_____-----------_____-_
"XON        _____------------------------------------------------------------------------------_____-
"
"           note: XON will go low when D==5 or 6 with register 70 addressed.
"BC4        _____-_____-_____-_____-_____-_____-_____
"BCCY       _____-_____-_____-_____-_____-_____-_____
"D          xxxxxxx6666666666666666000000000000000000000000000000000000000000000044444444444444442222222222222222220000
"FIRST      ------------------------_____-----
"FTIME      _____-----------------------------_____
"DFTIME     _____-----------------_____
"FTIHEL     _____-----------------------------_____
"FDONE      _____-----------------_____
"FC         xxxxxx2222211111111111111111110000000000000000000xxxxx
"DONE       _____-------------------
"DONEL      _____-----------------_
"QUIT       _____----------------_

XON := ((D==1)#(D==2)) # XON&!((D==5)#(D==6));
    XON.clk = A70®CLKL;
    !XENABLE = BC4&!XENABLER;
    XENABLER := (D==3) # XENABLER&!((D==4) # (D==5));
    XENABLER.clk = A70®CLKL;
    XCONT := A70®CLKL&(D==2) # XCONT&!(!XON);
    SACTIVE = XON&!ACTIVE&(!XCONT&STH2L&!STH3LL # XCONT);
    ACTIVE := SACTIVE&CLKEN # ACTIVE&!(QUIT&EIGT&CLKEN);
    FTIME := ACTIVE&(!FTIHEL&BC4&CLKEN_&((D==6) # (D==2)&R1ST) #
                                        FTIME&!(FTIHEL&FDONE&EIGT&CLKEN));
    DFTIME := !FTIHEL&FTIME&EIGT&CLKEN # DFTIME&!(EIGT&CLKEN);
    FTIHEL := DFTIME&EIGT&CLKEN_ # FTIHEL&!(!FTIME&EIGT&CLKEN # SACTIVE);
    FC.t = (FC$(FC-1))&EIGT&FTIME&CLKEN # (FC$FR)&!FTIHEL&!FTIME&BC4&CLKEN_;
    FDONE := FTIME&((FC==1)&EIGT&CLKEN # FDONE);
    DONE := ACTIVE&(BC4&CLKEN_&(D==4) # A70®CLKL&(D==5) # DONE);
    DONEL := ACTIVE&(DONE&EIGT&CLKEN # DONEL);
    QUIT := ACTIVE&(EIGT&CLKEN&DONEL # QUIT);
    DSTRB := ACTIVE&CLKEN_&(PBIG # EIG # EIGT&FTIME&!FTIHEL # HSTB # CSTBE) # DSTRB&!(CLKEN);
    CD := [1,0,1,1]&PBIG # [1,1,0,0]&(EIG # EIGT&FTIME&!FTIHEL) # [1,1,1,1]&BIG&CSSL;
    CSS := ACTIVE&(BC4&CLKEN_&((D==12)#(D==13)) # CSS&!(CSTBE));
    CSSL := ACTIVE&(CSS&CLKEN&EIG # CSSL&!(CSTBE));
    CSTBE := ACTIVE&(CSSL&(TC==9)&CLKEN #CSTBE&!(CLKEN));
    EC := BC4&CLKEN&([0,1,1,0]&((D==0)#(D==1))    #
                     [0,1,0,0]&((D==2)#(D==3))    #
                     [1,0,0,0]&(D==4)             #
                     [0,1,0,1]&(D==6)             #
                     [1,0,1,0]&((D==8)#(D==9))    #
                     [1,1,1,1]&((D==10)#(D==11))) #
           EC&!(CLKEN&BC4);
END
```

```
module tubmem title 'TUBE CONTROLLER MEMORY CONTROLLER
       Ver. 0; 1/4/95 1230'
       T1U6R0 device 'MACH435A';

"inputs
       FMHZ pin 20;
       D0,D1,D2,D3,D4,D5,D6,D7 pin 3,4,5,6,12,13,14,15;
       REGCLKL,REGCLKH pin 62,23;
       PBIG,EIG,READ,XON pin 35,36,81,83;
       AD0..AD3,SCS pin 48,49,50,51,57;
       ACTIVE pin 41;

"outputs
       MA0,MA1,MA2,MA3,MA4,MA5,MA6,MA7,MA8,MA9,MA10 pin 45,46,47,54,55,56,66,67,68,75,76 istype 'reg_D,buffer';
       CAS_,RAS_ pin 77,78 istype 'reg_D,buffer';
       TWMHZ pin 39 istype 'reg_T,buffer';
       WE_ pin 79;
       MCYCLE,BC4,MSTB,LAST pin 80,69,16,82 istype 'reg_D,buffer';
       FBC0..FBC6 pin istype 'reg_T,buffer';

"nodes

A64,A65,A66,A71,PCLCY,PCHCY,BCCY,SMCYCLE node;
       FBR0..FBR6,PBR0..PBR6,SBR0..SBR6 node istype 'reg_D,buffer';
       PBC0..PBC6,SBC0..SBC6 node istype 'reg_T,buffer';
       PC0..PC12 node istype 'reg_T,buffer';
       BC0,BC1,BC2,BC3 node istype 'reg_T,buffer';
       DRAS,CAS,TFMHZ,OW,IPC node istype 'reg_D,buffer';
       ACTIVEL,ACTIVELE node istype 'reg_D,buffer';

"constants
       H,L,X,C,Z = 1,0,.X.,.C.,.Z.;
       D = [D7..D0];
       AD = [AD3..AD0];
       BC = [BC3..BC0];
       PC = [PC12..PC0];
       PCL = [PC7..PC0];
       PCH = [PC12..PC8];
       PBR = [PBR6..PBR0];
       FBR = [FBR6..FBR0];
       SBR = [SBR6..SBR0];
       PBC = [PBC6..PBC0];
       FBC = [FBC6..FBC0];
       SBC = [SBC6..SBC0];
       MA = [MA10..MA0];
       FF = {TFMHZ,TWMHZ,PC,PBC,FBC,SBC,ACTIVEL,ACTIVELE,MA,IPC,BC,BC4,
             MCYCLE,LAST,RAS_,DRAS,CAS_,CAS,MSTB};
       CLKEN = !TFMHZ&!TWMHZ;
       CLKEN_ = !TFMHZ&TWMHZ;

equations

"clock generation
       FF.clk = FMHZ;
       TFMHZ := !TFMHZ;
       TWMHZ.t = !TFMHZ;

"address decode
```

```
        A64 = (AD==0)&SCS;
        A65 = (AD==1)&SCS;
        A66 = (AD==2)&SCS;
        A71 = (AD==7)&SCS;

"MEMORY ADDRESSING
        PCL.t = (PCL$(PCL+1))&IPC # (PCL$[D7..D0])&A64®CLKL&!XON # PCL&ACTIVELE;
        PCLCY = (PCL==255);
        PCH.t = (PCH$(PCH+1))&PCLCY&IPC # (PCH$[D4..D0])&A64®CLKH&!ACTIVE;
        PCHCY = (PCH==31);
        PBC.t = (PBC$(PBC+1))&PCLCY&PCHCY&IPC # (PBR$PBC)&(A65®CLKL&!XON # ACTIVELE);
        FBC.t = (FBC$(FBC+1))&PCLCY&PCHCY&IPC # (FBR$FBC)&(A65®CLKH&!XON # ACTIVELE);
        SBC.t = (SBC$(SBC+1))&PCLCY&PCHCY&IPC # (SBR$SBC)&(A66®CLKL&!XON # ACTIVELE);
        ACTIVEL := ACTIVE;
        ACTIVELE := ACTIVE&!ACTIVEL;
        PBR := [D6..D0];
        FBR := [D6..D0];
        SBR := [D6..D0];
        PBR.clk = A65&!XON®CLKL;
        FBR.clk = A65&!XON®CLKH;
        SBR.clk = A66&!XON®CLKL;
        MA := [PC12..PC2]&RAS_ # [PC1,PC0,PBC6..PBC0,BC1,BC0]&(BC<4)&!RAS_ #
                                  [PC1,PC0,FBC6..FBC0,BC1,BC0]&(BC>3)&(BC<8)&!RAS_ #
                                  [PC1,PC0,SBC6..SBC0,BC1,BC0]&(BC>7)&(BC<12)&!RAS_;
        IPC := BCCY&CLKEN&ACTIVE # LAST&!MCYCLE&!ACTIVE&CLKEN;

"memory cycle
  "50MHZ   |||||||||||||||||||||||||||||||||||||||||||||||||||||||||||||||
  "25MHZ   - - - - - - - - - - - - - - - - - - - - - - - - - - - - - - -
  "12.5MHZ --  --  --  --  --  --  --  --  --  --  --  --  --  --  --  --
  "CLKEN   -   _   -   _   -   _   -   _   -   _   -   _   -   _   -   _

"for host data
  "SHCYCLE _____---_____
  "MCYCLE  _____----------_____
  "RAS_    ---     ----          ____          ----      ----     ---
  "DRAS    -   ____   -------------     ____     ----
  "CAS_    _____---------__-_____---____-____-----
  "LAST    _____---_____----

"for scan data
  "SHCYCLE _____-----_____
  "MCYCLE  _____-----------------------------------------
  "RAS_    ---     ----       --_____
  "DRAS    -   ____    -----------------------------------------
  "CAS_    ____---- ---- _  _  _  _  _  _  _  _  _  _  _  ----
  "LAST    _____----
  "DSTRB   --  --  --  --  --  --  --  --  --  --  --  --  --
  "BC      00000000000000001111222233334444555566667777888899991111111000
  "        00000000000000000000000000000000000000000000000000000001111000
  "PBIG    ----
  "EIG                                                    ----
  "BIG                                                               ----

BC.t = CLKEN&(BC$(BC+1))&MCYCLE&!EIG&!BCCY&ACTIVE # BC&!MCYCLE&ACTIVE #
                                    (BC$[1,0,OW,DRAS])&!ACTIVE;
        BCCY = (BC==11);
        BC4 := (BC==4)&CLKEN # BC4&!(CLKEN);
        OW := D0;
        OW.clk = A66&!XON®CLKH;
```

```
SHCYCLE = !XON&A71®CLKL # WIG # SHCYCLE&!(HCYCLE);
HCYCLE := SHCYCLE&CLKEN # HCYCLE&!(LAST&!TFMHZ);
LAST := HCYCLE&(BCCY&ACTIVE # DRAS&!ACTIVE)&CLKEN # LAST&!(!HCYCLE&CLKEN);
!RAS_ := CLKEN_&(HCYCLE # !HCYCLE&!SHCYCLE&!CAS_) # !RAS_&!(CLKEN_);
DRAS := !RAS_&CLKEN&!SHCYCLE # DRAS&!(CLKEN);
!CAS_ := HCYCLE&!RAS_&!(TFMHZ&!TWMHZ) #
         !HCYCLE&!SHCYCLE&(CAS_&RAS_&CLKEN # !CAS_&!(CLKEN));
CAS := !CAS_;
HSTB := HCYCLE&READ&!ACTIVE&!CAS_&!CAS # ACTIVE&HCYCLE&DRAS;
!WE_ = HCYCLE&!READ&!ACTIVE;

END
```

```
module tubdat title 'TUBE CONTROLLER DATA PATH
       Ver. 0; 1/4/95 1230'
       TIU7R0 device 'MACH435A';

"inputs
       IRD0,IRD1,IRD2,IRD3,IRD4,IRD5,IRD6,IRD7 pin 3,4,5,6,7,8,9,10;
       FMHZ,TWMHZ,IRDSTRB_ pin 20,23,62;
       SELECT_,BIOR_ pin 82,79;
       DSEL0,DSEL1,SL,SH,AS,BUSY_ pin 70,71,33,39,40,31;
       ACTIVE,CFAULT,DOE pin 30,29,83;

"outputs
       TO pin 73 istype 'reg_D,buffer';
       AD0..AD3 pin 12,13,14,15 istype 'reg_D,buffer';
       IOS,SCS pin 16,17;
       ISSEL_ pin 19;
       ITD0..ITD7 pin 24,25,26,27,33,34,35,36;

"i/o's
       D0,D1,D2,D3,D4,D5,D6,D7 pin 49,50,51,52,58,59,60,61;
       B0,B1,B2,B3,B4,B5,B6,B7 pin 45,46,47,48,54,55,56,57 istype 'reg_D,buffer';
       B8,B9,B10,B11,B12,B13,B14,B15 pin 66,67,68,69,75,76,77,78 istype 'reg_D,buffer';

"nodes
       AD4,AD5,AD6,AD7,STATENL,TOS,DOED node istype 'reg_D,buffer';
       _IRD0,_IRD1,_IRD2,_IRD3,_IRD4,_IRD5,_IRD6,_IRD7 node istype 'reg_D,buffer';
       TC0,TC1,TC2,TC3,TC4 node istype 'reg_T,buffer';

"constants
       H,L,X,C,Z = 1,0,.X.,.C.,.Z.;
       D = [D7..D0];
       ITD = [ITD7..ITD0];
       B = [B15..B0];
       BL = [B7..B0];
       BH = [B15..B8];
       AD = [AD7..AD0];
       ADH = [AD7..AD4];
       DSEL = [DSEL1,DSEL0];
       IRD = [IRD7..IRD0];
       _IRD = [_IRD7.._IRD0];
       TC = [TC4..TC0];
       STATEN = (DSEL==3);

equations
"data path latching and gating
       _IRD := IRD;
       _IRD.clk = !IRDSTRB_;
       STATENL := STATEN;
       STATENL.clk = FMHZ;
       BL := BL.pin&(DSEL==0) # _IRD&(DSEL==1) # D&(DSEL==2);
       BH := BH.pin&(DSEL==0) # _IRD&(DSEL==1) # D&(DSEL==2) #
             [TOS,ACTIVE,CFAULT,0,0,0,0,0]&STATEN;
       B.oe = !BIOR_&!SELECT_;
       BL.clk = SL;
       BH.clk = SH # STATEN&FMHZ;
       D = BL.fb&(DSEL==0) # BH.fb&(DSEL==1);
       D.oe = DOED;
```

```
    DOED := DOE;
    DOED.clk = FMHZ;
    ITD = BL.fb&(DSEL==0) # BH.fb&(DSEL==1) # AD&(DSEL==3);
    AD := BL.pin;
    AD.clk = !AS;
    IOS = (ADH==0);
    SCS = (ADH==4);
    !ISSEL_ = !SELECT_&(IOS # SCS);

"timeout counter

TC.t = (TCS(TC+1))&!BUSY_ # TC&BUSY_;
    TC.clk = TWHHZ;
    [TO,TOS] := [1,1];
    TOS.ar = !STATEN&STATENL;
    TO.ar = BUSY_;
    TO.clk = !TC+;
    TOS.clk = TO;
END
```

```
module bcicnt title 'Beam Controller Interface -- Beam Control
       Ver. 0; 12-29-94'
       B1U4R0 device 'MACH435A';

"inputs
       TFMHZ,TFMHZ0 pin 20,23;
       D0..D7 pin 12..19;
       C0..C3 pin 25..28;
       DSTRB,CSTRB pin 24,29;

"outputs
       TWMHZ0,BOR_ pin 3,4 istype 'reg_D,buffer';
       XSTEP_ pin 5;
       CSTRBS,CSSTRB pin 33,34;
       SDY,LTCHENY pin 38,40 istype 'reg_D,buffer';
       CLKY pin 39;
       LD1,LD2 pin 45,46;
       LD6..LD10 pin 50,51,52,54,55;
       LD11,LD12 pin 66,67;
       BCOK pin 82;

"nodes
       LD3,LD4,LD5,NDATA,DSTRBL,LDDAC,CSS,CS15 node;
       CS15L node istype 'reg_D,buffer';
       CLE,SHIFT,LDSR node istype 'reg_D,buffer';
       BCNT4..BCNT0 node istype 'reg_T,buffer';
       BCCY node;
       CBREG7..CBREG0 node istype 'reg_D,buffer';
       LDCNT3..LDCNT0 node istype 'reg_T,buffer';
       YD18..YD0 node istype 'reg_D,buffer';
       YS19..YS4 node istype 'reg_D,buffer';

"constants
       H,L,C,X,Z = 1,0,.C.,.X.,.Z.;
       DV    = [D7..D0];
       CV    = [C3..C0];
       CBREG = [CBREG7..CBREG0];
       LDCNT = [LDCNT3..LDCNT0];
       BCNT  = [BCNT4..BCNT0];
       YD    = [SDY,YD18..YD0];
       YSH   = [YS19..YS12];
       YSL   = [YS11..YS4];

TF = [CLE,LDSR,SHIFT,BCNT,LDCNT,CS15L];

"timing (normal operation)
```

211 212

```
               1      1      2      3      4      5      6      7      8      9      0      1      2
"iTFMHZ      - - - - - - - - - - - - - - - - - - - - - - - - - - - - - - - - - - - - - - - - - - - - -
"oTWMHZO     -- - - -- - - - - - - - - - - - - - - - - - - - - - - - - - - - - - - - - - - - - - - - -
"iCSTRB       B_____C_____B_____C_____B_____
"cNDATA      ----------------------------------------     ----------------------------------     ------
"+LDCNT      x000001111222233334444555566667777888899991111111110000001111222233334444555566667777888899991111111110000011112222333
"+LDCNT                                        0000111122                                    0000111122
"cLDDAC                                            -                                             -
"iDSTRB       - - - - - - - - - - - - - - - - - - - - - - - - - - - - - - - - - - - - - - - - - - -
"cDSTBL       - - - - - - - - - - - - - - - - - - - - - - - - - - - - - - - - - - - - - - - - - - -
"+CLE.d       - - - - - - - - - - - - - - - - - - - - - - - - - - - - - - - - - - - - - - - - - - -
"+CLE         - - - - - - - - - - - - - - - - - - - - - - - - - - - - - - - - - - - - - - - - - - -
"cCS_                                          _____                    _____
"cLDAC_      ----------------------------------                         -------------------          -
"cLD1           -                                                                             -
"cLD2             -                                                                             -
"cLD3               -                                                                             -
"cLD4                 -                                                                             -
"cLD5                   -                                                                             -
"cLD6                     -                                                                             -
"cLD7                       -                                                                             -
"cLD8                         -                                                                             -
"cLD9                           -                                                                             -
"cLD10                            -                                                                             -
"cLD11                              -                                                                             -
"cLD12                                -                                                                             -
"cLDSR.d                                --                                                          --
"+LDSR                                    -                                                           -
"iTFMHZ      - - - - - - - - - - - - - - - - - - - - - - - - - - - - - - - - - - - - - - - - - - -
"cSHIFT.d                                 ------------------------------                    -----------
"+SHIFT                                   ------------------------------                    -----------
"SDATA        know how many clocks I have sent x1111111111111111111111              11111111111111111111
 "                                             x99887766554433221100998877665544332211000000     998877665544332211009988776655443
"oCLKY        - - - - - - - - - - - - - - - - - - - - - - - - - - - -
"cLDDAC                                           -                                             -
"cLTCHRY.d   ----------------------------                  ----------                        ----------
"-LTCHRY     actually a low true signal        ---                                             ----------
"+BCNT       counts number of bits sent         00011223344556677889911111111111111111111222222222200001122334455667788991111111111111
 "                                                   0011223344556677889900112233344                  001122334455667
"cBCCY                                                                         --
``` equations

```
"CLOCK GENERATION
        TWMH20.clk = TFMHZO;
        TWMH20 := !TWMH20;
        TF.clk = TFMHZ;

"TIMING SIGNALS
        CSS = BCOK&((CSTRB&((CV==11) # (CV==15))) # CSS&!(DSTRB));
        NDATA = BCOK&(CSTRB&CSS # NDATA&!(LDCNT==12));
        LDCNT.t = (LDCNT$(LDCNT+1))&CLE # LDCNT&!NDATA;
        DSTRBL = NDATA&(DSTRB # DSTRBL&!(CLE));
        CLE.d = DSTRBL&NDATA;
        LD1 = NDATA&(DSTRB # DSTRBL)&(LDCNT==0);
        LD2 = NDATA&(DSTRB # DSTRBL)&(LDCNT==1);
        LD3 = NDATA&(DSTRB # DSTRBL)&(LDCNT==2);
        LD4 = NDATA&(DSTRB # DSTRBL)&(LDCNT==3);
        LD5 = NDATA&(DSTRB # DSTRBL)&(LDCNT==4);
        LD6 = NDATA&(DSTRB # DSTRBL)&(LDCNT==5);
        LD7 = NDATA&(DSTRB # DSTRBL)&(LDCNT==6);
        LD8 = NDATA&(DSTRB # DSTRBL)&(LDCNT==7);
        LD9 = NDATA&(DSTRB # DSTRBL)&(LDCNT==8);
        LD10 = NDATA&(DSTRB # DSTRBL)&(LDCNT==9);
        LD11 = NDATA&(DSTRB # DSTRBL)&(LDCNT==10);
        LD12 = NDATA&(DSTRB # DSTRBL)&(LDCNT==11);

!XSTEP_ = BCOK&(CSTRB&CSS # !XSTEP_&!(LD3));
        CSTRBS = BCOK&(CSTRB&(CV==12) # CSTRBS&!(DSTRB));
        CSSTRB = BCOK&(CSTRB&(CV==15) # CSSTRB&!(DSTRB));

"STORE CONTROL BYTE AND DETECT FAULT
        CBREG.ar = !BCOK;
        CBREG := DV&LD5;
        CBREG.clk = LD5&TFMHZ;
        BOR_.ap = !BCOK;
        !BOR_ := CBREG0;
        BOR_.clk = !LTCHENY;
        CS15 = CSTRB&(CV==15) # CS15&!(CSTRB&(CV!=15) # DSTRB);
        CS15L := CS15;
        BCOK = !CS15 # BCOK&!(CSTRB&CS15&CS15L);

"SHIFT DATA TO Y-DEFLECTION DAC
        YSH := DV&LD4;
        YSH.clk = LD4&TFMHZ;
        YSL := DV&LD3;
        YSL.clk = LD3&TFMHZ;

YD.ar = !BCOK;
        YD.d = SHIFT&[YD18..YD3,0,0,0,0] # LDSR&[!YS19,YS18..YS4,0,0,0,0];
        YD.clk = !TFMHZ&(SHIFT # LDSR);

LTCHENY.d = (BCNT==20)&SHIFT # LTCHENY&!(LDDAC);     "&SHIFT # !BCOK
        LTCHENY.clk = !TFMHZ;
        CLKY = TFMHZ&!LTCHENY&SHIFT;
        SHIFT.d = LDSR # SHIFT&!(BCNT==20);
        LDDAC = CSTRB&(CV==12) # !BCOK&(BCNT==24) # LDDAC&!(!LTCHENY);
        BCNT.t = (BCNT$(BCNT+1))&!LDSR&!BCCY # BCNT&(LDSR # BCCY);
        BCCY = (BCNT==24);
        LDSR.d = LD8 # !BCOK&(BCNT==24);
end
```

```
module bcixdef title 'Beam Controller Interface -- X-DEFL Control
       Ver. 0; 12-29-94'
       BIU6R0 device 'MACH435A';

"inputs
      TFMHZ pin 20;
      LD1,LD2,LD8 pin 3,4,5;
      D0..D7 pin 12..19;
      CSTRBS pin 25;
      BCOK pin 82;

"outputs
      XSCS_,XSWR_ pin 30,31;
      XSD0..XSD7 pin 33..40 istype 'reg_D,buffer';
      SDX,LTCHENX pin 45,47 istype 'reg_D,buffer';
      CLKX pin 46;

"nodes
      LDDAC,BCCY node;
      CLE,SHIFT,LDSR node istype 'reg_D,buffer';
      BCNT4..BCNT0 node istype 'reg_T,buffer';
      XD18..XD0 node istype 'reg_D,buffer';
      XS19..XS4 node istype 'reg_D,buffer';

"constants
      H,L,C,X,Z = 1,0,.C.,.X.,.Z.;
      DV    = [D7..D0];
      BCNT  = [BCNT4..BCNT0];
      XD    = [SDX,XD18..XD0];
      XSH   = [XS19..XS12];
      XSL   = [XS11..XS4];

TF = [CLE,LDSR,SHIFT,BCNT];

equations

"CLOCK GENERATION

TF.clk = TFMHZ;

"SHIFT DATA TO X-DEFLECTION DAC
      XSH := DV&LD2;
      XSH.clk = LD2&TFMHZ;
      XSL := DV&LD1;
      XSL.clk = LD1&TFMHZ;

XD.ar = !BCOK;
      XD.d = SHIFT&[XD18..XD3,0,0,0,0] # LDSR&[!XS19,XS18..XS4,0,0,0,0];
      XD.clk = !TFMHZ&(SHIFT # LDSR);

LTCHENX.d = (BCNT==20)&SHIFT # LTCHENX&!(LDDAC);
      LTCHENX.clk = !TFMHZ;
      CLKX = TFMHZ&!LTCHENX&SHIFT;
      SHIFT.d = LDSR # SHIFT&!(BCNT==20);
      LDDAC = CSTRBS # !BCOK&(BCNT==24) # LDDAC&!(!LTCHENX);
      BCNT.t = (BCNT$(BCNT+1))&!LDSR&!BCCY # BCNT&(LDSR # BCCY);
      BCCY = (BCNT==24);
      LDSR.d = LD8 # !BCOK&(BCNT==24);
```

```
module bcisdac title 'Beam Controller Interface -- Small DAC Control
       Ver. 0; 12-29-94'
       B1U33R0 device 'MACH435A';

"inputs
       TFMHZ pin 20;
       D0..D7 pin 3..10;
       LD6..LD10 pin 12..16;
       BCOK pin 82;

"outputs
       SDACD0..SDACD7 pin 45,46,47,48,66,67,68,69 istype 'reg_D,buffer';
       SDADR0..SDADR3 pin 54..57;
       LSDAC1_,LSDAC2_ pin 58,59;

"nodes
       CNTCY,OE6,OE7,OE8,OE9,OE10 node;
       SZD7..SZD0 node istype 'reg_D,buffer';
       SFFD7..SFFD0 node istype 'reg_D,buffer';
       XSSD7..XSSD0 node istype 'reg_D,buffer';
       XSAD7..XSAD0 node istype 'reg_D,buffer';
       DFD7..DFD0 node istype 'reg_D,buffer';
       CNT4..CNT0 node istype 'reg_T,buffer';

"constants
       H,L,C,X,Z = 1,0,.C.,.X.,.Z.;
       D7    = [D7..D0];
       SDACD = [SDACD7..SDACD0];
       SDA1  = [SDADR1,SDADR0];
       SDA2  = [SDADR3,SDADR2];
       SZD   = [SZD7..SZD0];
       SFFD  = [SFFD7..SFFD0];
       XSSD  = [XSSD7..XSSD0];
       XSAD  = [XSAD7..XSAD0];
       DFD   = [DFD7..DFD0];
       CNT   = [CNT4..CNT0];

"timing (normal operation)
"                 1        1        2        3        4        5        6        7        8        9        0        1        2
"iTFMHZ         - - - - - - - - - - - - - - - - - - - - - - - - - - - - - - - - - - - - - - - - - - - - - - - - - - - - - - - -
"oTWMHZO        -- -- -- -- -- -- -- -- -- -- -- -- -- -- -- -- -- -- -- -- -- -- -- -- -- -- -- -- -- -- -- --
"iCSTRB         _B_____C_____B_____C_____B_____
"cNDATA         ----------------------------------------------------------- -----------------------------------
"+LDCNT         X00000111122223333444455556666777788889999111111111100000011112222333344445555666677778888999911111111110000000111122223
"+LDCNT                                              0000111122                                           0000111122
"cLDDAC                                                  -                                                   -
"iDSTRB         - - - - - - - - - - - - - - - - - - - - - - - - - - - - - - - - - - - - - - - - - - - - - - - -
"cDSTBL         -- -- -- -- -- -- -- -- -- -- -- -- -- -- -- -- -- -- -- -- -- -- -- -- -- -- -- -- -- --
"+CLE.d         -- -- -- -- -- -- -- -- -- -- -- -- -- -- -- -- -- -- -- -- -- -- -- -- -- -- -- -- -- --
"+CLE           -- -- -- -- -- -- -- -- -- -- -- -- -- -- -- -- -- -- -- -- -- -- -- -- -- -- -- -- -- --

"iTFMHZ         - - - - - - - - - - - - - - - - - - - - - - - - - - - - - - - - - - - - - - - - - - - - - - - -
"cLSDAC1_       -----------------------------------                   --    -------------------------------
"
"                                                           DATA    777777    888888                    DATA      77777
"                                                           ADDR 77777777777 88888888888                ADDR 7777777777
"iTFMHZ         - - - - - - - - - - - - - - - - - - - - - - - - - - - - - - - - - - - - - - - - - - - - - - - -
"cLSDAC2_       _____                --    --     --  ------------------------------
"
"                                                  DATA        666666    000000    999999    DATA          666666
```

```
"iTFMHZ  _ _ _ _ _ _ _ _ _ _ _ _ _ _ _ _ _ _ _ _ _ _    ADDR    6666666666 000000000D  9999999999    ADDR    6666666666 0000
"CNT    00112233445566778899111100112233445566778899111111111111111111112222222222220011223344556677889911111111111111111222Z
                0011                            00112233445566778899001122334455                      00112233445566773399001I

"cLD6                              __                                                                  __
"cLD7   _____  _____  _____
"cLD8   _____  _____  _____
"cLD9   _____  _____  _____
"cLD10  _____  _____  _____ equations

"Load data into registers
        DFD.ar = !BCOK;
        DFD := DV&LD6;
        DFD.clk = LD6&TFMHZ;
        S2D.ar = !BCOK;
        S2D := DV&LD7;
        S2D.clk = LD7&TFMHZ;
        SFFD.ar = !BCOK;
        SFFD := DV&LD8;
        SFFD.clk = LD8&TFMHZ;
        XSAD.ar = !BCOK;
        XSAD := DV&LD9;
        XSAD.clk = LD9&TFMHZ;
        XSSD.ar = !BCOK;
        XSSD := DV&LD10;
        XSSD.clk = LD10&TFMHZ;

"Send data to DACs and create sync counter

CNT.ar = LD6&TFMHZ # CNTCY;
        CNT.t = CNT$(CNT + 1);
        CNTCY = (CNT==26)&!BCOK;
        CNT.clk = TFMHZ;
        !LSDAC1_ = (CNT==17)#(CNT==23) # !LSDAC1_&!((CNT==2)#(CNT==22));
        SDADR0 = 0;
        SDADR1 = !LSDAC1_&(CNT==23) # SDADR1&!(CNT==3);

!LSDAC2_ = (CNT==0)#(CNT==14)#(CNT==20) # !LSDAC2_&!((CNT==5)#(CNT==19)#(CNT==25));
        SDADR2 = !LSDAC2_&(CNT==0)  # SDADR2&!(CNT==6);
        SDADR3 = !LSDAC2_&(CNT==14) # SDADR3&!(CNT==20);

OE6  = !OE8&((CNT==16)           # OE6  &!((CNT==19)&!TFMHZ  # LD6&BCOK));
        OE7  = !OE8&((CNT==19)&!TFMHZ  # OE7  &!((CNT==22)&!TFMHZ  # LD6&BCOK));
        OE8  =      ((CNT==25)&!TFMHZ  # OE8  &!((CNT==2 )&!TFMHZ));
        OE9  =      ((CNT==2 )&!TFMHZ  # OE9  &!((CNT==5 )&!TFMHZ  # LD6&BCOK));
        OE10 = !OE8&((CNT==22)&!TFMHZ  # OE10&!((CNT==25)&!TFMHZ));

SDACD := DFD&OE6 # S2D&OE7 # SFFD&OE8 # XSAD&OE9 # XSSD&OE10;
        SDACD.clk = !TFMHZ;

end
```

```
module bciser title 'Bess Controller Interface -- Serial Control
       Ver. 0; 1-9-95 2330'
       B1U25R0 device 'MACH435A';

"inputs
       TFMHZ,OT1_ pin 20,40;
       SDIN pin 41;
       CSDATA,BCOK pin 10,83;
       SCLK pin 5;
       CSSHIFT,DONE pin 62,65;

"outputs
       SDOUT pin 24;
       CLKSF pin 45;
       LTCHEHSF,SDSF pin 47,48 istype 'reg_D,buffer';
       LGV,LCS,SCSIO pin 7,8,9;
       SD15..SD0 pin 15,16,17,18,55..61,12,13,14,19,54 istype 'reg_D,buffer';

"nodes
       CNTHL,SYNC,STOPCNT,SFCCY,LNKRST,CNTHCY,CNTLCY node;
       CNTH3..CNTH0,CNTL3..CNTL0 node istype 'reg_T,buffer';
       BCNT4..BCNT0 node istype 'reg_T,buffer';

SFD18..SFD0,LDSR,SHIFTSF,FIN node istype 'reg_D,buffer';
       SFCNT4..SFCNT0 node istype 'reg_T,buffer';

ZEROHOLD,ONEHOLD,START,SDOSYNC,ONE,ZERO,LOCKOUT,ECY,SDOS,HOLDOFF node;
       ECNT7..ECNT0,OCNT4..OCNT0 node istype 'reg_T,buffer';
       SDO15..SDO0,ECYL node istype 'reg_D,buffer';

"constants
       H,L,C,P,X,Z = 1,0,.C.,.P.,.X.,.Z.;
       CNTH  = [CNTH3..CNTH0];
       CNTL  = [CNTL3..CNTL0];
       SD    = [SD15..SD0];
       BCNT  = [BCNT4..BCNT0];
       FC    = [SD15..SD12];

SFD   = [SDSF,SFD18..SFD0];
       SFCNT = [SFCNT4..SFCNT0];

SDO   = [SDO15..SDO0];
       ECNT  = [ECNT7..ECNT0];
       OCNT  = [OCNT4..OCNT0];

TF    = [CNTH,CNTL,FIN,SHIFTSF,LDSR,SFCNT,ECNT,ECYL];

equations

"clock generation

TF.clk = TFMHZ;

"serial data control

CNTH.t = CNTH$(CNTH + 1)&SDIN # CNTH&(!SDIN # CNTHCY);
       CNTHCY = (CNTH==301);
       CNTHL  = (CNTH==200) # CNTHL&!((CNTH==1) # CNTHCY);         "+/-20%
```

```
        CNTL.ar = STOPCNT;
        CNTL.t = CNTL$(CNTL + 1)&!SDIN # CNTL&SDIN;
        CNTLCY = (CNTL==301);
        BCNT.ar = STOPCNT;
        BCNT.t = BCNT$(BCNT + 1);
        BCNT.clk = !SDIN&SYNC&!CNTHL # TFMHZ&FIN;

FIN := (BCNT==16) # FIN&!(BCNT==17);
        SYNC = CNTHL&(CNTL==200) # SYNC&!(FIN # !BCOK # LNKRST # CNTLCY);
        STOPCNT = (BCNT==17)&!FIN # CNTHCY # CNTLCY # LNKRST # !BCOK # STOPCNT&!(CNTH==200);

"store serial data in SD register

SD.ar = !BCOK # LNKRST;
        SD := [SD14..SD0,1]&SYNC&(CNTH==100) # [SD14..SD0,0]&SYNC&(CNTH==40);
        SD.clk = SYNC&!SDIN;

"detect and store function code

LCS    = FIN&(FC==1);
        SCSIO  = FIN&(FC==2);
        LGV    = FIN&(FC==3);
        LNKRST = FIN&(FC==15);

"FC==0000 Static focus DAC data

SFD.ar = !BCOK;
        SFD.d = SHIFTSF&[SFD18..SFD3,0,0,0,0] # !SHIFTSF&LDSR&[!SD11,SD10..SD0,0,0,0,0,0,0,0];
        SFD.clk = !TFMHZ&(SHIFTSF # LDSR);

LTCHENSF.d = (SFCNT==20)&SHIFTSF # LTCHENSF&!(SFCNT==24);
        LTCHENSF.clk = !TFMHZ;
        CLKSF = TFMHZ&!LTCHENSF&SHIFTSF;
        SHIFTSF.d = LDSR # SHIFTSF&!(SFCNT==20);
        SFCNT.t = SFCNT$(SFCNT + 1)&!LDSR&!SFCCY # SFCNT&(LDSR # SFCCY);
        SFCCY = (SFCNT==24);
        LDSR.d = FIN&(FC==0)&(BCNT==16) # !BCOK&(SFCNT==24);

"Store Current Sense Data

SDO := CSSHIFT&[0,0,0,!OT1_,SDO10..SDO0,CSDATA] # SDOS&[SD014..SD00,0];
        SDO.clk = CSSHIFT&SCLK # SDOS&!SDOUT;

"SDOUT Controls

SDOUT = SDOSYNC # ONE # ZERO;

START   = DONE # START&!(OCNT==16);
        SDOSYNC = DONE # SDOSYNC&!(ECYL);
        LOCKOUT = DONE # LOCKOUT&!(!SDOSYNC&ECY);
        HOLDOFF = DONE # HOLDOFF&!(!LOCKOUT&(ECNT==2));
        SDOS    = START&!HOLDOFF # SDOS&!(!START);

ZEROHOLD = !SDO15&(ECNT==1)&START&!LOCKOUT;
        ONEHOLD  = SDO15&(ECNT==1)&START&!LOCKOUT;

ONE  = ONEHOLD # ONE&!(ECNT==126);
        ZERO = ZEROHOLD # ZERO&!(ECNT==51);

"SDOUT counters
```

```
ECNT.ar = !START;
ECNT.t = START&(ECNT$(ECNT + 1)) # ECNT&(ECY);
ECY = (ECNT==250);
ECYL := ECY;

OCNT.ar = !START;
OCNT.t = START&(OCNT$(OCNT + 1));
OCNT.clk = SDOS&!SDOUT;
``` end

What is claimed is:

1. An x-ray grid assembly comprising
   a plurality of x-ray absorbent sheets, each comprising a plurality of x-ray transmissive areas arranged in a regular pattern;
   said plurality of x-ray absorbent sheets arranged one atop the other to form a substantially planar stack; said x-ray transmissive areas of each sheet aligned with the x-ray transmissive areas of the immediately adjacent sheets to form an x-ray transmissive passage through said stack; an axis of each of said x-ray transmissive passages forming an angle ranging from 40° to 90° with the plane of said stack and substantially converging at a single spot;
   a first endplate and a second endplate each comprised of an x-ray transmissive material; said first endplate arranged adjacent a first surface of said stack and said second endplate arranged adjacent a second surface of said stack;
   a target and a coolant chamber wherein said coolant chamber disposed between said first endplate and said target and said target is comprised of a target support and an x-ray emitting layer.

2. The grid assembly of claim 1 wherein said x-ray transmissive areas are formed by chemical etching of the sheets.

3. The grid assembly of claim 1 wherein the x-ray transmissive areas are cylindrically shaped.

4. The grid assembly of claim 1 wherein said sheets comprise at least one of the materials selected from the group consisting of: brass, tungsten, lead, molybdenum.

5. The grid assembly of claim 1 wherein said target support is beryllium and said x-ray emitting layer is comprised of tantalum or tungsten.

6. The grid assembly of claim 5 wherein an intermediate layer of a resilient material is deposited on said support between said support layer and said x-ray emitting layer.

7. The grid assembly of claim 6 wherein said resilient material is niobium.

8. An x-ray target assembly comprising
   a plurality of x-ray absorbent sheets, each comprising a plurality of x-ray transmissive apertures arranged in a regular pattern and alignment apertures precisely located in the same location on each of said sheets;
   said plurality of x-ray absorbent sheets arranged one atop the other in a frame to form a substantially planar stack, alignment pins occupying said alignment apertures; said x-ray transmissive apertures of each sheet aligned with the x-ray transmissive apertures of the immediately adjacent sheets to form an x-ray transmissive passage through said stack; an axis of each of said x-ray transmissive passages substantially converging at a single spot;
   a first endplate and a second endplate each comprised of an x-ray transmissive material; said first endplate arranged adjacent a first surface of said stack and said second endplate arranged adjacent a second surface of said stack;
   said stack and said endplates securely held in said frame;
   a target comprising a target support and an x-ray emitting layer secured to one end of said frame, and
   a coolant chamber arranged between said first endplate and said target support.

9. The target assembly of claim 8 wherein said x-ray transmissive areas are formed by chemical etching of the sheets.

10. The target assembly of claim 9 wherein said alignment apertures are formed by chemical etching to a diameter less than the diameter of the alignment pins and then mechanically enlarged to the final desired diameter.

11. The grid assembly of claim 8 wherein the x-ray transmissive areas are cylindrically shaped.

12. The target assembly of claim 8 wherein said sheets comprise at least one of the materials selected from the group consisting of: brass, tungsten, lead, molybdenum.

13. The target assembly of claim 8 wherein said target support is beryllium and said x-ray emitting layer is comprised of tungsten or tantalum.

14. The target assembly of claim 13 wherein an intermediate layer of resilient material is deposited on said support between said support and said emitting layer.

15. The target assembly of claim 14 wherein said resilient material is niobium.

16. An x-ray grid assembly comprising
    a first plurality of x-ray absorbent sheets, each comprising a plurality of x-ray transmissive areas arranged in a regular pattern, said first plurality of x-ray absorbent sheets comprised of a material having a high atomic number;
    a second plurality of x-ray absorbent sheets, each comprising a plurality of x-ray transmissive areas arranged in a regular pattern, said second plurality of x-ray absorbent sheets comprised of a material having a low atomic number;
    said first plurality and second plurality of x-ray absorbent sheets arranged one atop the other to form a substantially planar stack; said x-ray transmissive areas of each sheet aligned with the x-ray transmissive areas of the immediately adjacent sheets to form an x-ray transmissive passage through said stack; an axis of each of said x-ray transmissive passages forming an angle ranging from 40° to 90° with the plane of said stack and substantially converging at a single spot;
    a first endplate and a second endplate each comprised of an x-ray transmissive material; said first endplate arranged adjacent a first surface of said stack and said second endplate arranged adjacent a second surface of said stack;
    a target and a coolant chamber wherein said coolant chamber is disposed between said first endplate and said target and said target is comprised of a target support and an x-ray emitting layer and said first plurality of sheets are arranged adjacent said first endplate and said second plurality of sheets are arranged adjacent said second endplate.

17. The grid assembly of claim 16 wherein the x-ray transmissive areas are cylindrically shaped.

18. The grid assembly of claim 16 wherein said first plurality of sheets comprise at least one of the materials selected from the group consisting of: tungsten, lead, molybdenum.

19. The grid assembly of claim 16 wherein the material for said second plurality of sheets is brass.

20. The grid assembly of claim 16 wherein said target support is beryllium and said x-ray emitting layer is comprised of tantalum or tungsten.

21. The grid assembly of claim 20 wherein an intermediate layer of resilient material is deposited on said support between said support and said emitting layer.

22. The grid assembly of claim 21 wherein said resilient material is niobium.

23. An x-ray grid assembly comprising a plurality of x-ray absorbent sheets, each comprising a plurality of x-ray transmissive areas arranged in a regular pattern;

said plurality of x-ray absorbent sheets arranged one atop the other to form a substantially planar stack; said x-ray transmissive areas of each sheet aligned with the x-ray transmissive areas of the immediately adjacent sheets to form a first set and a second set of x-ray transmissive passages through said stack; the axis of each of said x-ray transmissive passages of said first set forming an angle ranging from 40° to 90° with the plane of said stack and substantially converging at a first spot, and the axis of each of said x-ray transmissive passages of said second set forming an angle ranging from 40° to 90° with the plane of said stack and substantially converging at a second spot;

a first endplate and a second endplate each comprised of an x-ray transmissive material; said first endplate arranged adjacent a first surface of said stack and said second endplate arranged adjacent a second surface of said stack; a target and a coolant chamber wherein said coolant chamber is disposed between said first endplate and said target and said target is comprised of a target support and an x-ray emitting layer.

24. The grid assembly of claim 23 wherein the x-ray transmissive areas of said first set and said second set are cylindrically shaped.

* * * * *

UNITED STATES PATENT AND TRADEMARK OFFICE
CERTIFICATE OF CORRECTION

PATENT NO. : 5,610,967
DATED : March 11, 1997
INVENTOR(S) : Jack W. Moorman, Brian Skillicorn, John Wilent, Virginia Wilent, Alan Abel It is certified that error appears in the above-indentified patent and that said Letters Patent is hereby corrected as shown below:

In column 10, line 39, please delete the text "25" and insert therefore --23--;

In column 10, line 40, please delete the text "25" and insert therefore --23--;

In column 10, line 47, please delete the text "Fig. 20 is" and insert therefore --Figs. 19 and 20 are--;

In column 10, line 50, please delete the text "21 and 22" and insert therefore --20 and 23--;

In column 10, line 53, please delete the text "23 and 24" and insert therefore --21 and 22--.

In column 30, line 67, please delete the text "67" and insert therefore --24--.

In column 31, line 34, please delete the text "68" and insert therefore --25--;

In column 31, line 64, please delete the text "68" and insert therefore --25--.

UNITED STATES PATENT AND TRADEMARK OFFICE
CERTIFICATE OF CORRECTION

PATENT NO. : 5,610,967

DATED : March 11, 1997

INVENTOR(S) : Jack W. Moorman, Brian Skillicorn, John Wilent, Virginia Wilent, Alan Abel It is certified that error appears in the above-identified patent and that said Letters Patent is hereby corrected as shown below:

In column 32, line 10, please delete the text "68" and insert therefore --25--;

In column 32, line 36, please delete the text "67" and insert therefore --24--;

In column 32, line 55, please delete the text "18-25" and insert therefore --18-23--;

In column 32, line 58, please delete the text "18-25" and insert therefore --18-23--.

In column 34, line 35, please delete the text "Fig. 19" and insert therefore --Figs. 18-19--;

In column 34, line 56, please delete the text "24" and insert therefore --18--.

Figure 21:
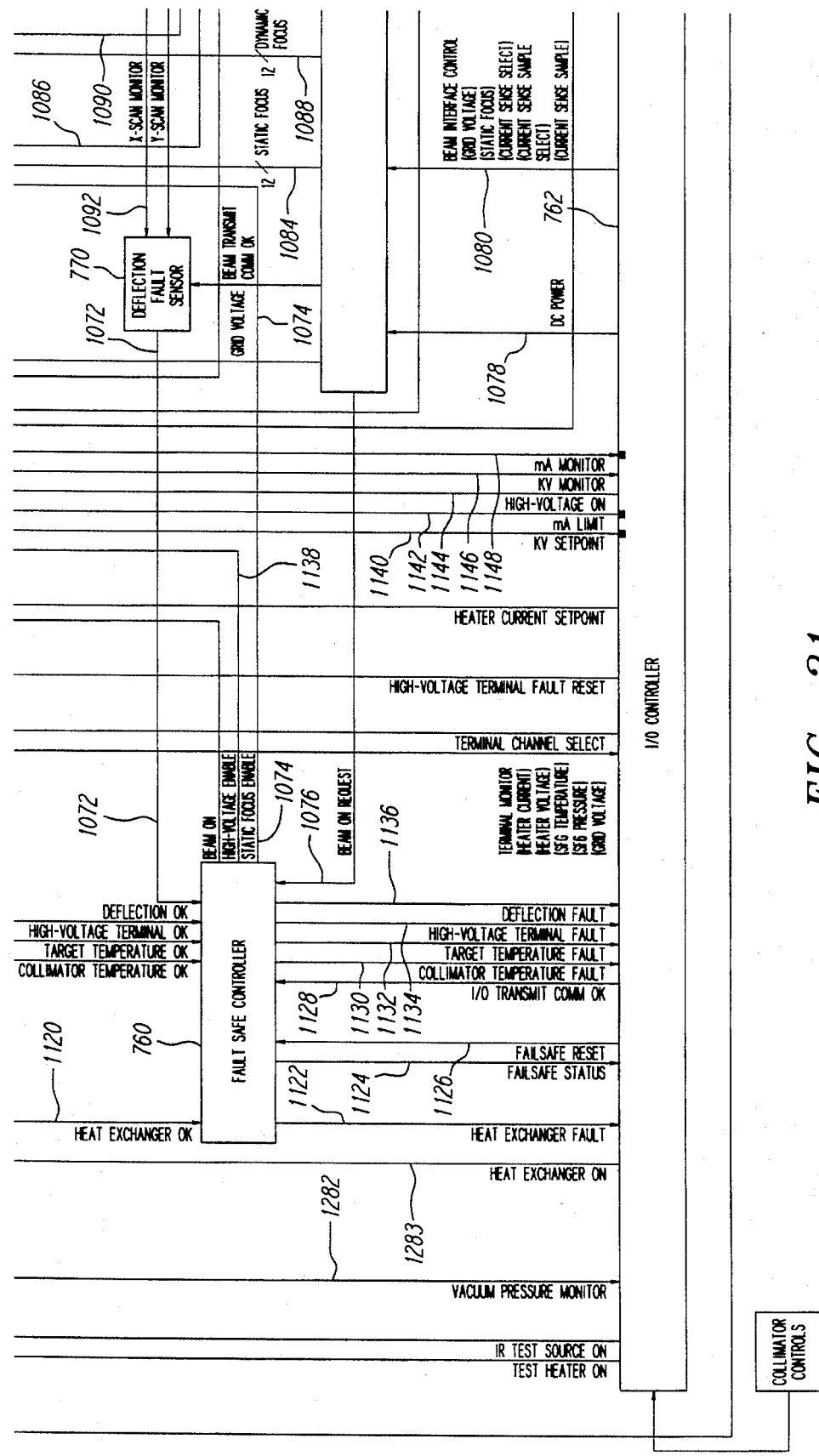

In column 35, line 3, please delete the text "Fig. 23 is" and insert therefore --Figs. 21 and 22 are--;

In column 35, line 50, please delete the text "Figs. 23 and 24" and insert therefore --Figs. 21 and 22--;

UNITED STATES PATENT AND TRADEMARK OFFICE
CERTIFICATE OF CORRECTION

PATENT NO. : 5,610,967
DATED : March 11, 1997
INVENTOR(S) : Jack W. Moorman, Brian Skillicorn, John Wilent, Virginia Wilent, Alan Abel It is certified that error appears in the above-indentified patent and that said Letters Patent is hereby corrected as shown below:

In column 35, line 56, please delete the text "23 and 24" and insert therefore --21 and 22--.

In column 36, line 24, please delete the text "20" and insert therefore --19--;

In column 36, line 28, please delete the text "22" and insert therefore --19--;

In column 36, line 30, please delete the text "diagram" and insert therefore --diagrams--;

In column 36, line 32, please delete the text "Fig. 20" and insert therefore --Figs. 19-20--.

In column 37, line 12, please delete the text "21" and insert therefore --20--;

UNITED STATES PATENT AND TRADEMARK OFFICE
CERTIFICATE OF CORRECTION

PATENT NO.   : 5,610,967
DATED        : March 11, 1997
INVENTOR(S)  : Jack W. Moorman, Brian Skillicorn, John Wilent
               Virginia Wilent, Alan Abel It is certified that error appears in the above-identified patent and that said Letters Patent is hereby corrected as shown below:

In column 37, line 34, please delete the text "25" and insert therefore --23--.

In column 54, line 26, please delete the text "21" and insert therefore --23--;

In column 54, line 43, please delete the text "25" and insert therefore --23--.

Signed and Sealed this

Ninth Day of June, 1998

BRUCE LEHMAN

*Attest:*

*Attesting Officer*    *Commissioner of Patents and Trademarks*